United States Patent
Charretier et al.

(10) Patent No.: US 9,506,932 B2
(45) Date of Patent: Nov. 29, 2016

(54) METHOD OF DETECTING AT LEAST ONE MECHANISM OF RESISTANCE TO CEPHALOSPORINS BY MASS SPECTROMETRY

(75) Inventors: Yannick Charretier, Courzieu (FR); Jean-Philippe Charrier, Tassin la demi-lune (FR); Christine Franceschi, Meximieux (FR); Gilles Zambardi, Chezeneuve (FR); Tiphaine Cecchini, Saint-Genis les Ollieres (FR); Elodie Degout-Charmette, Toussieux (FR)

(73) Assignee: BIOMERIEUX, INC., Durham, NC (US)

( * ) Notice: Subject to any disclaimer, the term of this patent is extended or adjusted under 35 U.S.C. 154(b) by 0 days.

(21) Appl. No.: 14/111,118

(22) PCT Filed: Apr. 20, 2012

(86) PCT No.: PCT/EP2012/057322
§ 371 (c)(1),
(2), (4) Date: Dec. 23, 2013

(87) PCT Pub. No.: WO2012/143534
PCT Pub. Date: Oct. 26, 2012

(65) Prior Publication Data
US 2014/0127734 A1    May 8, 2014

Related U.S. Application Data

(60) Provisional application No. 61/477,907, filed on Apr. 21, 2011.

(51) Int. Cl.
*C12Q 1/37* (2006.01)
*G01N 33/68* (2006.01)

(52) U.S. Cl.
CPC ...... *G01N 33/6893* (2013.01); *G01N 33/6851* (2013.01)

(58) Field of Classification Search
None
See application file for complete search history.

(56) References Cited

U.S. PATENT DOCUMENTS

| | | | |
|---|---|---|---|
| 2004/0229283 A1 | 11/2004 | Gygi et al. | |
| 2007/0006950 A1 | 1/2007 | Okada et al. | |
| 2007/0269895 A1* | 11/2007 | Aebersold | C12Q 1/34 436/56 |
| 2011/0245105 A1* | 10/2011 | Citri | C12Q 1/04 506/10 |
| 2012/0245128 A1* | 9/2012 | Haag | G01N 33/15 514/90 |
| 2012/0264156 A1 | 10/2012 | Beaulieu et al. | |

FOREIGN PATENT DOCUMENTS

| | | |
|---|---|---|
| WO | WO 2005/098071 A1 | 10/2005 |
| WO | WO 2006/128492 A1 | 12/2006 |
| WO | WO 2008/066629 A2 | 6/2008 |
| WO | WO 2008/145763 A1 | 12/2008 |
| WO | WO 2011/045544 A2 | 4/2011 |

OTHER PUBLICATIONS

Ahmet et al. Pyrolysis mass spsectormetry of cephalosporin-resistant Enterobacter cloacae. Journal Hospital Infection. 1995. vol. 31, pp. 99-104.*
Bush. Extended-spectrum beta-lactamases in North America, 1987-2006. Clin Microbiol Infect 2008. vol. 14 (Suppl 1), pp. 134-143.*
Hope et al. Efficacy of practised screening methods for detection of cephalosporin-resistant Enterobacteriaceae. J Antimicrob Chemotherapy 2007. vol. 59, pp. 110-113.*
Moosden. The Evolution of Resistance to Cephalosporins. CID 1997. pp. 487-493.*
Keshishian et al. Quantitative, Multiplexed Assays for Low Abundance Proteins in Plasma by Targeted Mass Spectrometry and Stable Isotope Dilution. MCP, 2007. vol. 6, No. 12, pp. 2212-2229.*
Anderson, L. et al. "Quantitative Mass Spectrometric Multiple Reaction Monitoring Assays for Major Plasma Proteins." Molecular & Cellular Proteomics, 2006, pp. 573-588, vol. 5, No. 4. The American Society for Biochemistry and Molecular Biology, Inc.
Anhalt, J. et al. "Identification of Bacteria Using Mass Spectrometry." Analytical Chemistry, Feb. 1975, pp. 219-225, vol. 47, No. 2.
Bernardo et al, "Identification and discrimination of *Staphylococcus aureus* strains using matrix-assisted laser desorption/ionization-time of flight mass spectrometry." Proteomics, 2002, pp. 747-753, 2(6).
Bernardo et al, "Identification of *Staphylococcus aureus* exotoxins by combined sodium dodecyl sulfate gel electrophoresis and matrix-assisted laser desorption/ionization-time of flight mass spectrometry." Proteomics, 2002, pp. 740-746, 2(6).
Brun, V. et al. "Isotope-labeled Protein Standards Toward Absolute Quantitative Proteomics." Molecular & Cellular Proteomics, 2007, pp. 2139-2149, vol. 6, No. 12, The American Society for Biochemistry and Molecular Biology, Inc.
Bundy, J. et al. "Lectin-Based Affinity Capture for MALDI-MS Analysis of Bacteria." Analytical Chemistry, Apr. 1999, pp. 1460-1463, vol. 71, No. 7, American Chemical Society.
Bush, K. et al. "Updated Classification of β-Lactamases." Antimicrobial Agents and Chemotherapy, Mar. 2010, pp. 969-976, vol. 54, No. 3, American Society for Microbiology.
Camara et al, "Discrimination between wild-type and ampicillin-resistant *Escherichia coli* by matrix-assisted laser desorption/ionization time-of-flight mass spectrometry." Analytical and Bioanal. Chemistry, 2007, pp. 1633-1638, 389(5).
Carbonnelle et al, "Rapid identification of *Staphylococci* isolated in clinical microbiology laboratories by matrix-assisted laser desorption ionization-time of flight mass spectrometry", Journal of Clinical Microbio., 2007, pp. 2156-2161, 45(7).

(Continued)

*Primary Examiner* — Marcela M Cordero Garcia
(74) *Attorney, Agent, or Firm* — Oliff PLC

(57) ABSTRACT

The present invention pertains to a method of detection, by mass spectrometry, of at least one marker of at least one mechanism of resistance to at least one antimicrobial, resistance of at least one microorganism contained in a sample, characterized in that the antimicrobial is a cephalosporin, and said resistance markers are proteins or peptides. Preferably, said proteins or peptides are proteins from said microorganism.

5 Claims, No Drawings

(56) References Cited

OTHER PUBLICATIONS

Chen, W. et al. "Functional Nanoparticle-Based Proteomic Strategies for Characterization of Pathogenic Bacteria." Analytical Chemistry, Dec. 2008, pp. 9612-9621, vol. 80, No. 24, American Chemical Society.
Claydon, M. et al. "The rapid identification of intact microorganisms using mass spectrometry." Nature Biotechnology, Nov. 1996, pp. 1584-1586, vol. 14.
Dare et al, "*Staphylococci* speciation and Panton-Valentine leukocidin detection by matrix assisted laser desorption ionisation time-of-flight mass spectrometry", Intern. Journal of Antimicrobial Agents, 2007, pp. 103-104, 29(2).
Desiere, F. et al. "The PeptideAtlas project." Nucleic Acids Research, 2006, pp. D655-D658, vol. 34, Database Issue, Oxford University Press, Oxford, UK.
Ding, D. et al. "Identification of protein components and quantitative immunoassay for SEC2 in staphylococcin injection." Journal of Pharmaceutical and Biomedical Analysis, 2009, pp. 79-85, vol. 50.
Ecker, D. et al. "Ibis T5000: a universal biosensor approach for microbiology." Nature Reviews Microbiology, Jun. 2008, pp. 553-558, vol. 6, No. 7, Nature Publishing Group.
Everley, R. et al. "Characterization of *Clostridium* species utilizing liquid chromatography/mass spectrometry of intact proteins." Journal of Microbiological Methods, pp. 152-158, Feb. 2009, vol. 77.
Fenselau, C. et al. "Identification of β-Lactamase in Antibiotic-Resistant *Bacillus cereus* Spores." Applied and Environmental Microbiology. Feb. 2008, pp. 904-906, vol. 74, No. 3, American Society for Microbiology.
Fortin, T. et al. "Clinical Quantitation of Prostate-specific Antigen Biomarker in the Low Nanogram/Milliliter Range by Conventional Bore Liquid Chromatography-Tandem Mass Spectrometry (Multiple Reaction Monitoring) Coupling and Correlation with ELISA Tests." Molecular & Cellular Proteomics, pp. 1006-1015, vol. 8, No. 5, The American Society for Biochemistry and Molecular Biology, Inc.
Fox, A. et al. ed., "Analytical Microbiology Methods: Chromatography and Mass Spectrometry." 1990, Plenum Press, New York, NY.
Fusaro, V. et al. "Prediction of high-responding peptides for targeted protein assays by mass spectrometry." Nature Biotechnology, Feb. 2009, pp. 190-198, vol. 27, No. 2, Nature America, Inc.
Gaskell, S. "Electrospray: Principles and Practice." Journal of Mass Spectrometry, 1997, pp. 677-688, vol. 32, John Wiley & Sons, Ltd.
Gröbner, S. et al. "Emergence of carbapenem-non-susceptible extended-spectrum β-lactamase-producing *Klebsiella pneumonia* isolates at the university hospital of Tübingen, Germany." Journal of Medical Microbiology, 2009, pp. 912-922, vol. 58, SGM.
Han, B. et al. "Proteomics: from hypothesis to quantitative assay on a single platform. Guidelines for developing MRM assays using ion trap mass spectrometers." Briefings in Functional Genomics and Proteomics, Jun. 2008, pp. 340-354, vol. 7, No. 5, Oxford University Press, Oxford, UK.
Hernychova, L. et al. "Detection and Identification of *Coxiella burnetii* Based on the Mass Spectrometric Analyses of the Extracted Proteins." Analytical Chemistry, Sep. 2008, pp. 7097-7104, vol. 80, No. 18, American Chemical Society.
Ho, K., et al, "Using Biofunctionalized Nanoparticles to Probe Pathogenic Bacteria", Anal. Chem., 2004, pp. 7162-7168, 76.
Iioestadler, S. et al. "TIGER: the universal biosensor." International Journal of Mass Spectrometry, 2005, pp. 23-41, vol. 242.
Keshishian, H. et al. "Quantitative, Multiplexed Assays for Low Abundance Proteins in Plasma by Targeted Mass Spectrometry and Stable Isotope Dilution." Molecular & Cellular Proteomics, 2007, pp. 2212-2229, vol. 6, No. 12, The American Society for Biochemistry and Molecular Biology, Inc.
Kondo, F., et al, "Identification of Shiga toxins in Shiga toxin-producing *Escherichia coli* using immunoprecipitation and high-performance liquid chromalography-electrospray ionization mass spectrometry." The Analyst, 2003, pp. 1360-1364, 128(11).
Krishnamurthy, T. et al. "Rapid Identification of Bacteria by Direct Matrix-assisted Laser Desorption/Ionization Mass Spectrometric Analysis of Whole Cells." Rapid Communications in Mass Spectrometry, 1996, pp. 1992-1996, vol. 18, John Wiley & Sons, Ltd.
Li, M., et al, "Comparative proteomic analysis to identification of extracellular virulence factors of enterohemorrhagic *Escherichia coli* (EHEC) and enteropathogenic *Escherichia coli* (EPEC)." Faseb Journal, 2005, A 1388, 19(5).
Lin, Y.C. et al. "Differences in carbapenem resistance genes among *Acinetobacter baumannii*, *Acinetobacter* genospecies 3 and *Acinetobacter* genospecies 13TU in Taiwan." International Journal of Antimicrobial Agents, 2010, pp. 439-443, vol. 35.
Lin, Y.S. et al. "Affinity Capture Using Vancomycin-Bound Magnetic Nanoparticles for the MALDI-MS Analysis of Bacteria." Analytical Chemistry, Mar. 2005, pp. 1753-1760, vol. 77, No. 6, American Chemical Society.
López-Ferrer, D. et al. "Ultra Fast Trypsin Digestion of Proteins by High Intensity Focused Ultrasound." Journal of Proteome Research, 2005, pp. 1569-1574, vol. 4, American Chemical Society.
López-Ferrer, D. et al. "On-line Digestion System for Protein Characterization and Proteome Analysis." Analytical Chemistry, Dec. 2008, pp. 8930-8936, vol. 80, No. 23, American Chemical Society.
Mainardi, J. et al, "Resistance to cefotaxime and peptidoglycan composition in *Enterococcus faecalis* are influenced by exogenous sodium chloride." Microbiology, 1998, pp. 2679-2685, vol. 144, SGM.
Majcherczyk P., et al, "The discriminatory power of MALDI-TOF mass spectrometry to differentiate between isogenic teicoplanin-susceptible and teicoplanin-resistant strains of methicillin-resistant *Staphylococcus aureus*", Ferns Microbiol Letters, 2006, pp. 233-239, 255(2).
Manes, N. et al. "Targeted Protein Degradation by *Salmonella* under Phagosome-mimicking Culture conditions Investigated Using Comparative Peptidomics." Molecular & Cellular Proteomics, Jan. 2007, pp. 717-727, vol. 6, No. 4, MCP Papers in Press.
Marinach, C. et al, "MALDI-TOF MS-based drug susceptibility testing of pathogens: The example of *Candida albicans* and fluconazole." Proteomics, 2009, pp. 4627-4631, 9(20).
Mazzeo, M., et al, "Matrix-assisted laser desorption ionization-time of flight mass spectrometry for the discrimination of food-home microorganisms", Applied and Env. Microbio., 2006, pp. 1180-1189,72(2).
Mead, J. et al. "MRMaid, the Web-based Tool for Designing Multiple Reaction Monitoring (MRM) Transitions." Molecular & Cellular Proteomics, 2009, pp. 696-705, vol. 8, No. 4, The American Society for Biochemistry and Molecular Biology, Inc.
Melanson, J., et al, "Targeted comparative proteomics by liquid chromatography/matrix-assisted laser desorption/ionization triple-quadruple mass spectrometry." Rapid Communications in Mass Spectrometry, 2006, pp. 904-910, 20(5).
Nandakumar, R. et al. "Proteomic analysis of endodontic infections by liquid chromatography-tandem mass spectrometry." Oral Microbiology and Immunology, 2009, pp. 347-352, vol. 24, John Wiley & Sons, Ltd.
Pratt, J. et al. "Multiplexed absolute quantification for proteomics using concatenated signature peptides encoded by QconCAT genes." Nature Protocols, 2006, pp. 1029-1043, vol. 1, No. 2, Nature Publishing Group.
Qian, J., et al, "MALDI-TOF mass signatures for differentiation of yeast species, strain grouping and monitoring of morphogenesis markers", Analytical and Bioanal. Chemistry, 2008, pp. 439-449, 392(3).
Savinova, T.A. et al, abstract of "A mass-spectrometric analysis of genetic markers of *S. pneumonia* resistance to β-lactam antibiotics." XP00268431, Database accession No. NLM20882772, Database Medline, 2010, US National Library of Medicine, Bethesda, MD.
Seng, P. et al. "Ongoing Revolution in Bacteriology: Routine Identification of Bacteria by Matrix-Assisted Laser Desorption Ionization Time-of-Flight Mass Spectrometry." Clinical Infectious Diseases, Aug. 2009, pp. 543-551, vol. 49, Infectious Diseases Society of America.

(56) References Cited

OTHER PUBLICATIONS

Stahl-Zeng, J. et al. "High Sensitivity Detection of Plasma Proteins by Multiple Reaction Monitoring of N-Glycosites." Molecular & Cellular Proteomics, Jul. 2007, pp. 1809-1817, vol. 6, No. 10, The American Society for Biochemistry and Molecular Biology, inc.
Takao, T., et al, "Identity of molecular structure of Shiga-like toxin I (VT1) from *Escherichia coli* 0157 : H7 with that of Shiga toxin." Microbial Pathogenesis, 1988, pp. 357-369, 5(5).
Teng, C.H. et al. "Gold Nanoparticles as Selective and Concentrating Probes for Samples in MALDI MS Analysis." Analytical Chemistry, Aug. 2004, pp. 4337-4342, vol. 76, No. 15, American Chemical Society.
Vaidyanathan, S. et al. "Discrimination of Aerobic Endospore-forming Bacteria via Electrospray-Ionization Mass Spectrometry of Whole Cell Suspensions." Analytical Chemistry, Sep. 2001, pp. 4134-4144, vol. 73, No. 17, American Chemical Society.
Wang, K.Y. et al. "Multiplexed Immunoassay: Quantitation and Profiling of Serum Biomarkers Using Magnetic Nanoprobes and MALDI-TOF MS." Analytical Chemistry, Aug. 2008, pp. 6159-6167, vol. 80, No. 16, American Chemical Society.
Wybo, I. et al. "Differentiation of *cfiA*-Negative and *cfiA*-Positive *Bacteroides fragilis* Isolates by Matrix-Assisted Laser Desorption Ionization-Time of Flight Mass Spectrometry." Journal of Clinical Microbiology, May 2011, pp. 1961-1964, vol. 49, No, 5, American Society for Microbiology.
Zheng, K. "Elucidation of peptide metabolism by on-line immunoaffinity liquid chromatography mass spectrometry." Rapid Communications in Mass Spectrometry, 2000, pp. 261-269, vol. 14, John Wiley & Sons, Ltd.
Written Opinion of the International Searching Authority for International Application No. PCT/EP2012/057323 (with English Translation).
Written Opinion of the International Searching Authority for International Application No. PCT/EP2012/057322 (with English Translation).
Written Opinion of the International Searching Authority for International Application No. PCT/FR2010/052181 (with English Translation).
U.S. Appl. No. 14/111,083 in the name of Charretier et al.
International Search Report issued in International Application No. PCT/EP2012/057322 (with English translation).
International Search Report issued in International Application No. PCT/EP2012/057323 (with English translation).
International Search Report issued in International Application No. PCT/FR2010/052181 (with English translation).
ExPaSy PeptideCutter for KPC-1, http://web.expasy.org/cgi-bin/peptide_cutter/peptidecutter.pl, Jun. 8, 2015, 2 pgs.
Savini et al. "Bacillus Cereus Heteroresistance to Carbapenems in a Cancer Patient," J. Hospital Infection, 2009, pp. 288-289.
Yigit et al. "Novel Carbapenem-Hydrolyzing Beta-Lactamase, KPC-1, from a Carbapenem-Resistant Strain of Klebsiella Pneumoniae," Antimicrobial Agents and Chemotherapy, 2001, vol. 45, No. 4, pp. 1151-1161.
Yigit et al. "Novel Carbapenem-Hydrolyzing Beta-Lactamase, KPC-1, from a Carbapenem-Resistant Strain of Klebsiella Pneumoniae," Author's Correction, Antimicrobial Agents and Chemotherapy, 2008, vol. 52, No. 2, p. 809.
Kulkarni et al. "Use of Imipenem to Detect KPC, NDM, OXA, IMP, and VIM Carbapenemase Activity from Gram-Negative Rods in 75 Minutes Using Liquid Chromatography-Tandem Mass Spectrometry," JCM, Jul. 2014, vol. 52, No. 7, pp. 2500-2505.
Jun. 11, 2015 Office Action issued in U.S. Appl. No. 14/111,083.
Jan. 3, 2014 Office Action issued in U.S. Appl. No. 13/502,020.
May 15, 2014 Office Action issued in U.S. Appl. No. 13/502,020.
Sauer, Sascha, et al., "Classification and Identification of Bacteria by Mass Spectrometry and Computational Analysis," vol. 3, Issue 7, Jul. 2008, pp. 1-10.
Dec. 5, 2014 Office Action issued in U.S. Appl. No. 14/111,083.
U.S. Appl. No. 13/502,020, filed Jun. 29, 2012 in the name of Beaulieu et al.
Mar. 11, 2016 Office Action issued in U.S. Appl. No. 14/111,083.
Beccerril et al., "Combination of Analytical and Microbiological Techniques to Study the Antimicrobial Activity of a New Active Food Packaging Containing Cinnamon or Oregano Against *E. coli* and *S. aureus*," Anal Bioanal Chem, vol. 388, pp. 1003-1011, 2007.
Kuhn et al., "Quantification of C-Reactive Protein in the Serum of Patients with Rheumatoid Arthritis Using Multiple Reaction Monitoring Mass Spectrometry and 13C-Labeled Peptide Standards," Proteomics, vol. 4, pp. 1175-1186, 2004.
Keller et al., "A Uniform Proteomics MS/MS Analysis Platform Utilizing Open XML File Formats," Molecular Systems Biology, vol. 1, pp. 1-8, 2005.
Sep. 23, 2015 Office Action issued in U.S. Appl. No. 13/502,020.

\* cited by examiner

METHOD OF DETECTING AT LEAST ONE MECHANISM OF RESISTANCE TO CEPHALOSPORINS BY MASS SPECTROMETRY

The present invention relates to the field of microbiology. More precisely, the invention relates to the detection of at least one mechanism of resistance to cephalosporins of at least one microorganism from a sample by using mass spectrometry.

Since Pasteur's discovery of microbes, microorganisms have been studied by microscopy and biochemical analyses. These conventional methods are often long and tedious, and analytical alternatives were sought very early on. This is why the analysis of bacteria by mass spectrometry was initiated from 1975 by J. Anhalt and C. Fenselau [1].

This preliminary work was followed by the study of fatty acids from the wall of the microorganisms using gas chromatography combined with mass spectrometry (GC-MS) [2]. This method was popularised under the English term FAME, standing for Fatty Acid Methyl Ester. It currently constitutes a reference method for taxonomic studies. However, its use remains limited to certain specialised laboratories dealing with the treatment of the sample by saponification, hydrolysis and derivation.

In 1996, the works by M. Claydon et al. [3] as well as by T. Krishnamurthy and P. Ross [4] demonstrated the possibility of identifying different bacterial species with a MALDI-TOF mass spectrometer (English acronym for Matrix Assisted Laser Desorption Ionization—Time Of Flight). The analysis combines the acquisition of a mass spectrum and the interpretation of expert software. It is extremely simple and can be carried out in a few minutes. However it has only been making it into medical analysis laboratories fairly recently [5]. Its clinical use is currently limited to the identification of bacteria and yeast species. It is not routinely used to identify resistances to antimicrobials.

Yet the identification of resistances to antimicrobials such as antibiotics is an essential element in ensuring optimal patient care.

Other mass spectrometry methods, particularly in tandem, have been proposed to meet these needs. By way of example, it is possible to cite the work of C. Fenselau et al. for identifying β-Lactamase with a quadripole-TOF (Q-TOF) [6].

However these research results are not applicable to routine clinical use. They were obtained with research instruments requiring highly qualified personnel. The analysis times, often greater than one hour per sample, are incompatible with the workload of a microbiological analysis laboratory.

More recently, S. Hofstadler et al. [7] proposed a method combining a microbial genome amplification by PCR to a detection of the PCR products by electrospray-TOF (ESI-TOF). This method is now fully automated [8]. However, it requires a PCR amplification with the flaws inherent in molecular biology, namely extraction yield, cost of the probes, etc.

In this context, the objective of the present invention is to propose a method of detecting mechanisms of resistance to cephalosporins which makes it possible to overcome the disadvantages of the prior art methods, namely providing an inexpensive method, without reagents specific to each species, particularly compared to molecular biology methods, which gives a result in a short amount of time, less than one hour, and which can be used in routine clinical work, without requiring highly qualified personnel.

To this end, the invention proposes a new method of detecting, by mass spectrometry, at least one mechanism of resistance to at least one antimicrobial of at least one microorganism from a sample, characterised in that the antimicrobial is a cephalosporin and in that proteins and/or peptides are detected as markers of said mechanism of resistance to at least one cephalosporin-class antibiotic.

Advantageously, markers of resistance to several different antimicrobials can be detected simultaneously.

As indicated in application PCT/FR2010/052181, markers of type and/or virulence of said microorganisms can be detected in the same way by mass spectrometry prior to or at the same time as the detection of the resistance mechanism markers.

Markers of resistance to at least one cephalosporin-class antimicrobial is understood to mean molecules of protein origin which are characteristic of said properties. Cephalosporins are antibiotics belonging to the beta-lactam family. They are usually classified in several subclasses:

first-generation cephalosporins, such as cefazolin, cephalothin, cefaclor, cephalexin, which are broken down by the beta-lactamases of groups 1 and 2b, 2br, 2be, 2ber second-generation cephalosporins, such as cefamandole, cefpodoxime, cefuroxime, which are broken down by the beta-lactamases of groups 1, 2be, 2ber third-generation cephalosporins, such as cefotaxime, ceftazidime, ceftriaxone, cefixime, which are broken down by the beta-lactamases of groups 1, 2be, 2ber, even though they are more stable than the first-generation and second-generation cephalosporins fourth-generation cephalosporins, such as cefepime and cefpirome, which are broken down by the beta-lactamases of groups 2be and 2ber cephalosporins exhibiting anti-MRSA activity such as ceftaroline and ceftobiprole, which are broken down by the beta-lactamases of groups 2be and 2ber cephamycins, such as cefoxitin, cefotetan, cefmetazole, which are broken down by the beta-lactamases of group 1

Determination of the resistance to at least one antimicrobial is understood to mean determining the susceptibility of a microorganism to being destroyed by an antimicrobial. The proteins involved in the resistance mechanisms will differ depending on the family and the species.

The nomenclature of the beta-lactamases, beta-lactam-resistant bacterial enzymes, is not standardised. They are either classified in four molecular classes (A to D) on the basis of their primary structure, or in functional groups on the basis of the target substrates and their resistance to inhibitors (for an overview, see [9] Bush and Jacoby, Antimicrobial Agents and Chemotherapy, 2010; 54 (3): 969-976). For molecular classification, sequencing techniques have made more precise classification possible: for example, 183 variants of the TEM protein have been described (labelled TEM-i, with i being between 1 and 183). For the functional classification, Bush and Jacoby (supra) have proposed new functional subgroups:

the group 1 enzymes are cephalosporinases belonging to the molecular class C. ACC, ACT, MIR, MOX, DHA, CMY and FOX are plasmid-borne enzymes, belonging to this subgroup.

the group 2 enzymes belong to molecular classes A and D. This group is itself subdivided into subgroups: 2a, 2b, 2be, 2br, 2ber, 2c, 2ce, 2d, 2de, 2df, 2f, etc. CTX-M (2be), SHV (2b, 2be or 2br), PER (2be), VEB (2be) and TEM (2b, 2be, 2br or 2ber) are enzymes belonging to this group.

The subgroup 2a corresponds to beta-lactamases which hydrolyse benzylpenicillin and penicillin derivatives, but which do not hydrolyse cephalosporins, carbapenems or monobactams.

The subgroup 2b corresponds to broad-spectrum beta-lactamases which hydrolyse first-generation penicillins and cephalosporins such as cephaloridine and cephalothin, and which are inhibited by clavulanic acid, sulfobactam, or tazobactam. The variants TEM-1, TEM-2 and SHV-1 belong to this subgroup.

The subgroup 2b corresponds to extended-spectrum beta-lactamases (ESBL) which are also inhibited by clavulanic acid, sulfobactam, or tazobactam. These enzymes, in addition to the properties of subgroup 2b, hydrolyse at least one oxyimino-beta-lactam such as cefotaxime or ceftazidime, and monobactams such as aztreonam. This subgroup contains numerous variants of TEM and SHV, variants of PER and VEB, as well as CTX-M, BEL-1, BES-1, SFO-1, TAL-1 and TAL-2.

The subgroup 2br corresponds to beta-lactamases from the subgroup 2b which are insensitive to inhibition by clavulanic acid, sulfobactam or tazobactam. This subgroup contains variants of the enzymes TEM and SHV.

The subgroup 2ber corresponds to beta-lactamases from the subgroup 2be which are insensitive to inhibition by clavulanic acid, sulfobactam or tazobactam. This subgroup contains TEM variants.

The subgroup 2ce is characterised by its ability to hydrolyse carbenicillin or ticarcillin, as well as cefepime and cefpirome. CARB-10 is part of this subgroup.

The subgroup 2d includes the OXA beta-lactamases capable of hydrolysing cloxacillin or oxacillin. The OXAs (or oxacillinases) correspond to class-D beta-lactamases, according to their primary sequence, and they can confer resistances to cephalosporins or to cephalosporins and to carbapenems (Poirel et al., 2010, Antimicrobio. Agents Chemother., 54:24-38).

The subgroup 2de includes OXAs having an extended spectrum extended to oxy-imino-beta-lactams, but not to carbapenems.

The subgroup 2df includes OXAs having a spectrum extended to carbapenems.

The subgroup 2e corresponds to extended-spectrum cephalosporinases, which are inhibited by clavulanic acid or tazobactam.

The subgroup 2f corresponds to carbapenemases such as SME, KPC or certain variants of GES. The first GES beta-lactamase was isolated in 1998 in French Guiana (Poirel et al., 2000, Antimicrobio. Agents Chemother., 43:622-632). This enzyme (GES-1) conferred an ESBL resistance (subgroup 2be). The second isolate from a bacterium bearing a GES beta-lactamase was achieved in 2000 in South Africa (Poirel et al., 2001, Antimicrobio. Agents Chemother., 45: 2598-2603). This enzyme (GES-2) conferred a resistance to cephalosporins and to carbapenems such as imipenem (subgroup 2f).

The group 3 enzymes are metallo-beta-lactamases known for hydrolysing carbapenem-class antibiotics. The enzymes IMP, VIM, CAU, GOB or FEZ are part of this group.

The method of the invention can be employed to detect mechanisms of resistance to cephalosporins in bacteria. Thus, for example, as bacteria in which it is possible to seek a mechanism of resistance to cephalosporins according to the method of the invention, non-exhaustive mention may be made of:
the Enterobacteriaceae, using group 1 and group 2 proteins and peptides as a resistance marker;
non-fermenting bacteria (*Pseudomonas aeruginosa, Acinetobacter baumannii*)
etc.

It should further be noted that the strains known to be resistant to carbapenems are also resistant to cephalosporins and to penicillins. Therefore, a method of detecting a mechanism of resistance to carbapenems also makes it possible to detect a mechanism of resistance to cephalosporins and to penicillins.

The sample on which the method of the invention can be employed is any sample susceptible of containing a target microorganism. The sample can be of biological origin, either animal, vegetable or human. In this case it may correspond to a specimen of biological fluid (whole blood, serum, plasma, urine, cerebrospinal fluid, organic secretion, for example), a tissue specimen or isolated cells. This specimen can be used such as it is insofar as the markers of mechanisms of bacterial resistance to beta-lactams are available in the sample tested, or it can, prior to the analysis, undergo preparation by enrichment, extraction, concentration, purification, culturing, in accordance with methods known to the person skilled in the art.

The sample can be of industrial origin, or, according to a non-exhaustive list, can be an air specimen, a water specimen, a surface specimen, a part or a manufactured product, or a food product. Amongst the food samples, non-exhaustive mention can be made of a sample of a dairy product (yogurts, cheeses), of meat, of fish, of egg, of fruit, of vegetable, of water, of a beverage (milk, fruit juice, soda, etc.). These food samples can also come from sauces or ready meals. Finally, a food sample can come from an animal feed, such as animal meals.

Upstream of the detection by mass spectrometry, the sample to be analysed is preferably pre-treated to produce peptides from the entirety of the proteins present in the sample to fragment these proteins into peptides, for example by digestion with a proteolytic enzyme (protease), or by the action of a chemical reagent. In fact, the cleaving of the protein can be performed by a physico-chemical treatment, by a biological treatment or by a combination of the two treatments. Amongst the useable treatments, mention can be made of treatment by hydroxyl radicals, in particular with $H_2O_2$. Treatment by hydroxyl radicals results in a cutting of the peptide bonds which takes place randomly on any of the protein's peptide bonds. The hydroxyl radical concentration determines the number of cleavages performed, and therefore the length of the peptide fragments obtained. Other chemical treatments can also be used such as, for example, cyanogen bromide (CNBr) treatment which specifically splits the peptide bonds at the carboxyl group of the methionyl residues. It is also possible to perform partial acid cleaving at the aspartyl residues by heating a solution of proteins in trifluoroacetic acid to 1000° C.

Treatment of the proteins by enzymatic digestion is nevertheless preferred over physico-chemical treatment because it preserves more of the structure of the protein, and is easier to control. "Enzymatic digestion" is understood to mean the single or combined action of one or more enzymes under appropriate reaction conditions. The enzymes carrying out the proteolysis, which are called proteases, cut the proteins at specific locations. Each protease generally recognises a sequence of amino acids within which it always makes the same cut. Certain proteases recognise a single amino acid or a sequence of two amino acids between which they perform a cleavage, whereas other proteases only recognise longer sequences. These proteases can be endoproteases or exoproteases. Amongst the known proteases, mention may be made of the following as described in WO20051098071:

specific enzymes such as trypsin which splits the peptide bond at the carboxyl group of the Arg and Lys residues, endolysin which cleaves the peptide bond of the —CO group of the lysines, chymotrypsin which hydrolyses the peptide bond at the carboxylic group of the aromatic residues (Phe, Tyr and Trp), pepsin which makes a cut at the $NH_2$ group of the aromatic residues (Phe, Tyr and Trp), the protease V8 from the V8 strain of Staphylococcus aureus which cleaves the peptide bond at the carboxylic group of the Glu residue;

the non-specific enzymes such as thermolysin from the bacteria Bacillus thermoproteolyticus which hydrolyses the peptide bond of the $NH_2$ group of hydrophobic amino acids (Xaa-The, Xaa-Ile, Xaa-Phe), subtilisin and pronase which are bacterial proteases which hydrolyse practically all the bonds and can transform the proteins into oligopeptides under controlled reaction conditions (enzyme concentration and duration of reaction).

Several proteases may be used simultaneously, if their modes of action are compatible, or they may be used successively. Within the framework of the invention, the digestion of the sample is preferably performed by the action of a protease enzyme, for example trypsin.

The generation of peptides using a chemical reagent or a protease can be obtained by means of a simple reaction in solution. It can also be performed with a microwave oven [10], or under pressure [11], or even with an ultrasound device [12]. In these three latter cases, the protocol will be much faster.

Amongst the peptides thus obtained, the peptides specific to the protein are referred to as proteotypic peptides. It is these which will be assayed by mass spectrometry. According to the invention, the markers of the mechanisms of bacterial resistance to cephalosporins are proteins from the bacterium in which the mechanisms of resistance to cephalosporins are to be sought. In particular, said proteins are digested into peptides, preferably by an enzyme, and more preferably by trypsin.

Similarly, the sample containing protein markers characterising mechanisms of bacterial resistance to cephalosporins can also be pre-treated for the purposes of purification. This purification pretreatment can be employed before or after the peptide production step as described above.

The sample purification pretreatment is widely known to the person skilled in the art and may in particular employ the techniques of centrifugation, filtration, electrophoresis or chromatography. These separating techniques can be used alone or in combination with one another to obtain a multidimensional separation. For example, multidimensional chromatography can be used by combining separation by ion exchange chromatography with reversed-phase chromatography, as described by T. Fortin et al. [13], or H. Keshishian et al. [14]. In these publications, the chromatography medium can be in a column or in a cartridge (solid-phase extraction).

The electrophoretic or chromatographic fraction (or the retention time in mono-dimensional or multidimensional chromatography) of the proteotypic peptides is characteristic of each peptide, and employing these techniques therefore makes it possible to select the proteotypic peptide or peptides to be assayed. Such a fractionation of the produced peptides makes it possible to increase the specificity of the subsequent assay by mass spectrometry.

An alternative to the electrophoresis or chromatography techniques for the fractionation of the peptides consists in specifically purifying the N-glycopeptides ([15] and patent application WO 2008/066629). However, such a purification only makes it possible to quantify the peptides which have undergone an N-glycosylation post-translational modification. Not all proteins are glycosylated though, which therefore limits its use.

The mass spectrometry to be employed in the method of the invention is widely known to the person skilled in the art as a powerful tool for analysing and detecting different types of molecules. Generally, any type of molecule able to be ionised can be detected according to its molecular mass with the aid of a mass spectrometer. According to the nature of the molecule to be detected, whether of protein or metabolic origin, certain mass spectrometry technologies can be more suitable. Nevertheless, whatever mass spectrometry method is used for the detection, this latter includes a step of ionising the target molecule into so-called molecular ions, in the present case a step of ionising the characterising markers, and a step of separating the molecular ions obtained according to their mass.

All mass spectrometers therefore comprise:

an ionising source intended to ionise the markers present in the sample to be analysed, i.e. to confer a positive or negative charge upon these markers;

a mass analyser intended to separate the ionised markers, or molecular ions, according to their mass-to-charge ratio (m/z);

a detector intended to measure the signal produced either directly by the molecular ions, or by ions produced from molecular ions as detailed hereafter.

The ionisation step necessary for employing mass spectrometry can be performed via any method known to the person skilled in the art. The ionising source makes it possible to transform the molecules to be assayed into a gaseous and ionised state. An ionising source can be used either in positive mode to study the positive ions, or in negative mode to study the negative ions. Several types of sources exist and will be used depending on the result sought and the molecules analysed. In particular, mention may be made of:

electron ionisation (EI), chemical ionisation (CI) and desorption chemical ionisation (DCI)

fast atom bombardment (FAB), metastable atom bombardment (MAB) or ion bombardment (SIMS, LSIMS)

inductively coupled plasma (ICP)

atmospheric-pressure chemical ionisation (APCI) and atmospheric-pressure photoionisation (APPI)

electronebulisation or electrospray (ESI)

matrix-assisted laser desorption/ionisation (MALDI), surface-activated laser desorption/ionisation (SELDI) or desorption/ionisation on silicon (DIOS)

ionisation/desorption by interaction with metastable species (DART)

In particular, ionisation can be employed as follows: the sample containing the target molecules is introduced into an ionisation source, where the molecules are ionised in gaseous state and thus transformed into molecular ions which correspond to the initial molecules. An electrospray ionisation (ESI) source makes it possible to ionise a molecule by making it pass from a liquid state into a gaseous state. The molecular ions obtained therefore correspond to the molecules present in liquid state, with, in positive mode, one, two, or even three or more additional protons and therefore carry one, two, or even three or more charges. For example, when the target molecule is a protein, an ionisation of the proteotypic peptides obtained after fractionation of the target protein, by means of an electrospray source functioning in positive mode, leads to polypeptide ions in gaseous state, with one, two, or even three or more additional protons and which therefore carry one, two, or even three or more charges, and makes it possible to move from a liquid state to a gaseous state [16]. This type of source is particularly well suited when the target molecules or proteotypic peptides obtained are separated beforehand by reversed-phase liquid chromatography. Nevertheless, the ionisation yield of the molecules present in the sample may vary depending on the concentration and the nature of the different species present. This phenomenon leads to a matrix effect well known to the person skilled in the art.

A MALDI ionisation source will allow ionisation of the molecules from a solid-state sample.

The mass analyser in which the step of separating the ionised markers according to their mass-to-charge ratio (m/z) is performed is any mass analyser known to the person skilled in the art. Mention can be made of low-resolution analysers, quadripole or quadrupole (Q), 3D ion trap (IT) or linear ion trap (LIT), also called ion trap, and high-resolution analysers which make it possible to measure the exact mass of the analytes and which in particular use the magnetic sector linked to an electric sector, the time of flight (TOF), Fourier transform ion cyclotron resonance (FT-ICR), orbitrap.

The separation of the molecular ions depending upon their m/z ratio can be employed just once (single mass spectrometry or MS), or several successive MS separations can be conducted. When two successive MS separations are carried out, the analysis is called MS/MS or $MS^2$. When three successive MS separations are carried out, the analysis is called MS/MS/MS or $MS^3$, and more generally, when n successive MS separations are carried out, the analysis is called $MS^n$.

Amongst the techniques which employ several successive separations, SRM (Selected Reaction Monitoring) mode when detecting or assaying a single target molecule, or MRM (Multiple Reaction Monitoring) mode when detecting or assaying several target molecules are particular uses of $MS^2$ separation. Similarly the $MRM^3$ mode is a particular use of MS/MS/MS separation. This is referred to as targeted mass spectrometry.

In the case of a detection in single MS mode, it is the mass-to-charge ratio of the molecular ions obtained which is correlated to the target molecule to be detected.

In the case of detection in MS/MS mode, essentially two steps are added, compared to an MS assay, which are:
  a fragmentation of the molecular ions, then called precursor ions, to give ions called $1^{st}$ generation fragment ions, and
  a separation of the ions called $1^{st}$ generation fragment ions according to their mass $(m/z)_2$, the ratio $(m/z)_1$ corresponding to the ratio (m/z) of the precursor ions.

It is therefore the mass-to-charge ratio of the $1^{st}$ generation fragment ions thus obtained which is correlated to the target molecule to be detected. First-generation fragment ion is understood to be an ion derived from the precursor ion, following a fragmentation step and of which the mass-to-charge ratio m/z is different from the precursor ion.

The $(m/z)_1$ and $(m/z)_2$ pairs are called transitions and are representative of the characteristic ions to be detected.

The choice of the characteristic ions which are detected to be correlated to the target molecule is made by the person skilled in the art in accordance with the standard methods. Their selection will advantageously lead to the most sensitive, specific and robust assays possible, in terms of reproducibility and reliability. In the methods developed for the selection of proteotypic peptides $(m/z)_1$, and of the first-generation fragment $(m/z)_2$, the choice is essentially based on the intensity of the response. For more details, it is possible to refer to V. Fusaro et al. [17]. Commercially available software, such as the MIDAS and MRM Pilot software from Applied Biosystems or MRMaid [18] can be used by the person skilled in the art to allow him to predict all the possible transition pairs. He can also make use of a database called PeptideAtlas constructed by F Desiere et al. [19] to compile all of the MRM transitions of peptides described by the scientific community. This database PeptideAtlas is freely available on the internet. For non-protein molecules, it is also possible to use databases, such as, for example, the one accessible through the Cliquid software from the company Applied Biosystems (United States of America).

An alternative approach to selecting the proteotypic peptides $(m/z)_1$ and $(m/z)_2$ consists in using MS/MS fragmentation spectra obtained during other work. This work can be, for example, the phases of biomarker discovery and identification by proteomic analysis. This approach was proposed by Thermo Scientific during user conferences [18]. It makes it possible to generate a list of candidate transitions from the peptides identified through testing by the SIEVE (Thermo Scientific) software. Certain criteria were detailed by J. Mead et al. [18] for the choice of the ions $(m/z)_1$ and $(m/z)_2$ and are detailed hereafter:
  peptides with internal cleavage sites, i.e. with internal Lysine or Arginine, must be avoided, unless the Lysine or Arginine is followed by Proline,
  peptides with Aspargine or Glutamine must be avoided because they may deaminate,
  peptides with Glutamine or Glutamic Acid at the N-terminal must be avoided because they may cyclise spontaneously,
  peptides with Methionine must be avoided because they may be oxidised,
  peptides with Cysteine must be avoided because they may be non-reproducibly modified during a potential step of denaturation, reduction and blocking of the thiol functions,
  peptides with Proline may be considered to be favourable because they generally produce intense fragments in MS/MS with a very strong single peak. However, a very strong single fragment does not make it possible to validate the identity of the transition in a complex mixture. Indeed, only the simultaneous presence of several characteristic fragments makes it possible to verify that the precursor ion sought has actually been detected,
  the peptides having a Proline adjacent to the C-terminal (Position n-1) or in second position relative to the C-terminal (position n-2) should be avoided because, in this case, the size of the first-generation peptide fragment is generally considered to be too small to be sufficiently specific,
  the selection of fragments having a mass greater than the precursor should be given preference in order to promote specificity. To this end, it is necessary to select a dicharged precursor ion and select the most intense first-generation ion fragment having a mass greater than the precursor, i.e. a monocharged first-generation fragment ion.

The fragmentation of the selected precursor ions is performed in a fragmentation cell such as the triple quadripole model [20], ion trap model [21], or time-of-flight (TOF) model [22], which also make it possible to separate ions. The fragmentation or fragmentations will be conventionally performed by collision with an inert gas such as argon or nitrogen, within an electrical field, by photo-excitation or photo-dissociation using an intense light source, collision with electrons or radical species, by applying a potential difference, for example in a time-of-flight tube, or by any other activation to mode. The characteristics of the electrical field determine the intensity and nature of the fragmentation. Thus, the electrical field applied in the presence of an inert gas, for example in a quadripole, determines the collision energy provided to the ions. This collision energy will be optimised, by the person skilled in the art, to increase the sensitivity of the transition to be assayed. By way of example, it is possible to vary the collision energy between 5 and 180 eV in q2 in an AB SCIEX QTRAP® 5500 mass spectrometer from the company Applied Biosystems (Foster City, United States of America). Similarly, the duration of the collision step and the excitation energy within, for example, an ion trap will be optimised by the person skilled in the art to lead to the most sensitive assay. By way of example, it is possible to vary this duration, called excitation time, between 0.010 and 50 ms and the excitation energy between 0 and 1 (arbitrary unit) in Q3 in an AB SCIEX QTRAP® 5500 mass spectrometer by the company Applied Biosystems.

Finally, the detection of the selected characteristic ions takes place in the conventional manner, particularly by means of a detector and a processing system. The detector collects the ions and produces an electrical signal whose intensity depends on the amount of ions collected. The signal obtained is then amplified such that it can be processed by computer. A computer data processing assembly makes it possible to transform the information received by the mass spectrum detector.

The principle of the SRM mode, or even of the MRM mode, is to specifically select a precursor ion, fragment it, and then specifically select one of its fragment ions. For such applications, triple quadripole or hybrid triple quadripole/ion trap devices are generally used.

In the case of a triple quadripole device (Q1q2Q3) used in $MS^2$ mode, with a view to assaying or detecting a target protein, the first quadripole (Q1) makes it possible to filter the molecular ions corresponding to the proteotypic peptides characteristic of the protein to be assayed and obtained during an earlier digestion step, depending on their mass-to-charge ratio (m/z). Only the peptides having the mass-to-charge ratio of the proteotypic peptide sought, which ratio is called $(m/z)_1$, are transmitted into the second quadripole (q2) and act as precursor ions for the subsequent fragmentation. The analyser q2 can fragment the peptides of mass-to-charge ratio $(m/z)_1$ into first-generation fragment ions. Fragmentation is generally obtained through collision of the precursor peptides with an inert gas, such as nitrogen or argon in q2. The first-generation fragment ions are transmitted into a third quadripole (Q3) which filters the first-generation fragment ions depending on a specific mass-to-charge ratio, called $(m/z)_2$. Only the first-generation fragment ions having the mass-to-charge ratio of a fragment characteristic of the sought proteotypic peptide $(m/z)_2$ are transmitted into the detector in order to be detected, or even quantified.

This mode of operation exhibits a double selectivity, with regard to the selection of the precursor ion on the one hand, and the selection of the first-generation fragment ion on the other hand. Mass spectrometry in SRM or MRM mode is therefore advantageous for quantification.

When the mass spectrometry employed in the method according to invention is tandem mass spectrometry ($MS^2$, $MS^3$, $MS^4$ or $MS^5$), several mass analysers can be linked to one another. For example, a first analyser separates the ions, a collision cell makes it possible to fragment the ions, and a second analyser separates the fragment ions. Certain analysers, such as the ion traps or the FT-ICR, constitute several analysers in one and make it possible to fragment the ions and analyse the fragments directly.

According to preferred embodiments of the invention, the method of the invention comprises one or more of the following characteristics:

the mass spectrometry employed for the properties of potential resistance to at least one antimicrobial is MS/MS spectrometry, which has the advantage of producing a fragment which is specific to the molecule to be detected or quantified, and thus of providing great specificity to the assaying method;

the MS/MS spectrometry is MRM which has the advantage of using an analysis cycle time in the mass spectrometer of several tens of milliseconds, which makes it possible to detect or quantify, with a high degree of sensitivity, a large number of different molecules in a multiplexed manner;

where applicable, the determination of the type properties and of the virulence factor is performed in the same mass spectrometry apparatus as the determination of the markers of resistance to at least one antimicrobial, preferably simultaneously, which has the advantage of reducing the analysis time and the cost of the instrument, which also facilitates the processing and the yielding of the results.

In addition to determining the resistance to an antibiotic, it is necessary to identify the microorganism or microorganisms present in the sample to be tested.

The methods of identifying microorganisms are widely known to the person skilled in the art, as described for example by Murray P. R. et al. in Manual of Clinical Microbiology, 2007, $9^{th}$ edition, and especially in Vol. I, Section III, chapters 15 and 16 for bacteria and yeasts, Vol. II, Section VI, chapter 82 for viruses, and Vol. II, Section X, chapter 135 for protozoa. As an example of conventional identification methods, mention can be made of the determination of the biological profile, by using the Vitek 2 (bioMerieux) identification cards, for example, or even by using molecular biology techniques with identification criteria based on the study of the presence of certain genes, and on the study of their sequence.

Identification can be performed directly from the sample in which the identification is made, or the microorganisms contained in the sample can be cultured using methods well known to the person skilled in the art with optimal culture media and culturing conditions tailored to the species of microorganisms to be sought, as described by Murray P. R. et al. in Manual of Clinical Microbiology, 2007, $9^{th}$ edition, Vol. I, Section III, chapter 14, and in particular in Vol. I, Section IV, chapter 21 for bacteria, and Vol. II, Section VI, chapter 81 for viruses, Vol. II, Section VIII, chapter 117 for yeasts, and Vol. II, Section X, chapter 134 for protozoa.

Thus, generally, in the case of an identification using a biochemical method of a bacterium in a specimen, it is first necessary to obtain it in a pure culture, for example after seeding on agar. Molecular biology (FOR) can in certain cases be applied directly to the sample to be analysed.

Instead of cultivating the microorganisms, they can be concentrated by capture directly in the sample by means of active surfaces. Such a method was described by W.-J. Chen et al. [11] who captured different bacterial species with the aid of magnetic beads with an $Fe_3O_4/TiO_2$-activated surface. Capture by other means is also possible, such as a capture by lectins [23], or by antibodies [24], or by Vancomycin [25]. The capture makes it possible to concentrate the microorganisms and thus to reduce or even eliminate the culture step. This results in a considerable time saving.

The identification may also be performed by mass spectrometry, in accordance with the techniques described previously, preferably by MS, by MS/MS, or even by MS followed by MS/MS spectrometry, which constitutes one embodiment of the invention. In this case too, the sample can be subjected to a culture step beforehand, such as seeding on agar.

The use of an MS identification method is advantageous in that it may be carried out in a few minutes, and in that it requires a mass spectrometer with a single analyser, i.e. a less complex instrument than a tandem mass spectrometer used in MS/MS.

The use of a method of identification by MS followed by MS/MS spectrometry is also advantageous. It makes it possible to check the identity of the ions observed by MS, which increases the specificity of the analysis.

The use of an MRM-type MS/MS identification method has the advantage of being more sensitive and simpler than the conventional MS followed by MS/MS approaches. This method requires neither a high-performance software to process the information between the acquisition of the MS spectrum and of the MS/MS spectrum, nor a change in the setting of the machine parameters for linking up MS then MS/MS spectra.

The method of identification by MS may be employed with an electrospray source on a raw sample, as described by S. Vaidyanathan et al. [26] or by R. Everley et al. [27] after chromatographic separation. Different m/z ranges thus make it possible to identify the microorganisms. S. Vaidyanathan et al. used a window of between 200 and 2000 Th, and R. Everley et al. used a window of between 620 and 2450 Th. The mass spectra may also be deconvoluted to access the mass of the proteins independently of their charge state. R. Everley et al. therefore used masses of between about 5,000 and 50,000 Da. Alternatively, the method of identification by MS can also be employed with the aid of a MALDI-TOF, as described by Claydon et al. [3] and T. Krishnamurthy and P. Ross [4]. The analysis combines acquisition of a mass spectrum and interpretation of expert software. It is extremely simple and can be carried out in a few minutes. This method of identification is currently becoming more widespread in medical analysis laboratories [28].

The identification of bacteria by MS followed by MS/MS via their proteins present in the sample has been applied widely by a number of teams. By way of example, mention can be made of the recent work of Manes N. et al. [29], who studied the peptidome of *Salmonella enterica*, or the work of R. Nandakumar et al. [30] or of L. Hernychova et al. [31] who have studied the proteome of bacteria after digestion of the proteins with trypsin. The conventional approach consists in i) acquiring an MS spectrum, ii) successively selecting each precursor ion observed on the MS spectrum with an intense signal, iii) successively fragmenting each precursor ion and acquiring its MS/MS spectrum, iv) interrogating protein databases such as SWISS-PROT or NCBI, through software such as Mascot (Matrix Science, London, United Kingdom) or SEQUEST (Thermo Scientific, Waltham, United States of America), to identify the peptide which has a strong probability of matching the MS/MS spectrum observed. This method may lead to the identification of a microorganism if a protein or a peptide characteristic of the species is identified.

One of the advantages of the use of the mass spectrometry lies in that it is particularly useful for quantifying molecules, in the present case the markers of the mechanisms of bacterial resistance to beta-lactams. To this end, the current intensity detected is used, which is proportional to the quantity of target molecule. The current intensity thus measured may serve as a quantitative measurement making it possible to determine the quantity of target molecule present, which is characterised by its expression in International System (SI) $mol/m^3$ or $kg/m^3$ units, or by multiples or sub-multiples of these units, or by the usual derivatives of the SI units, including multiples or sub-multiples thereof. As a non-limiting example, the units such as ng/ml or fmol/l are units characterising a quantitative measurement.

A calibration is nevertheless necessary in order to be able to correlate the measured area of the peak, which corresponds to the current intensity induced by the detected ions, to the quantity of target molecule to be assayed. For this purpose, the calibrations conventionally used in mass spectrometry may be employed, within the framework of the invention. MRM assays are conventionally calibrated with the aid of external standards or, preferably, with the aid of internal standards such as described by T. Fortin et al. [13]. If the target molecule is a proteotypic peptide which permits the assaying of a protein of interest, the correlation between the quantitative measurement and the quantity of target proteotypic peptide, and subsequently of protein of interest, is obtained by calibrating the measured signal relative to a standard signal for which the quantity to be assayed is known. The calibration may be performed using a calibration curve, for example obtained by successive injections of standard proteotypic peptide at different concentrations (external calibration), or preferably by internal calibration using a heavy peptide as an internal standard, for example in accordance with the AQUA, QconCAT or PSAQ methods detailed below. "Heavy peptide" is understood to mean a peptide corresponding to the proteotypic peptide, but in which one or more atoms of carbon 12 ($^{12}C$) is (are) replaced by carbon 13 ($^{13}C$), and/or one or more atoms of nitrogen 14 ($^{14}N$) is (are) replaced by nitrogen 15 ($^{15}N$).

The use of heavy peptides as internal standards (AQUA) was also proposed in US patent application 2004/0229283. The principle is to artificially synthesise proteotypic peptides with amino acids containing isotopes which are heavier than the usual natural isotopes. Such amino acids are obtained, for example, by replacing some of the atoms of carbon 12 ($^{12}C$) with carbon 13 ($^{13}C$), or by replacing some of the atoms of nitrogen 14 ($^{14}N$) with nitrogen 15 ($^{15}N$). The artificial peptide (AQUA) thus synthesised has strictly the same physicochemical properties as the natural peptide (with the exception of a higher mass). It is generally added, at a given concentration, to the sample, upstream of assaying by mass spectroscopy, for example between the treatment entailing the cleaving of the proteins in the sample of interest and the fractionation of the peptides obtained after the treatment step. Thus, the AQUA peptide is co-purified with the natural peptide to be assayed, during fractionation of the peptides. The two peptides are therefore injected simultaneously into the mass spectrometer, for assaying. They then undergo the same ionisation yield in the source. The comparison of the peak areas of the natural and AQUA peptides, whose concentration is known, makes it possible to calculate the concentration of the natural peptide and thus trace back the concentration of the protein to be assayed. A variation of the AQUA technique was proposed by J.-M. Pratt et al. [32] under the name QconCat. This variant is also described in patent application WO 2006/128492.

It consists in concatenating various AQUA peptides and producing the artificial polypeptide in the form of a heavy recombinant protein. The recombinant protein is synthesised with amino acids comprising heavy isotopes. In this way, it is possible to obtain a standard to calibrate the simultaneous assay of several proteins at lower cost. The QconCAT standard is added from the start, upstream of the treatment entailing the cleaving of the proteins and prior to the steps of protein fractionation, denaturation, reduction and blocking of the protein thiol functions, if these are present. The QconCAT standard therefore undergoes the same treatment cycle entailing the cleaving of the proteins as the natural protein, which makes it possible to take account of the yield from the treatment step which entails the cleaving of the proteins. In fact, the treatment, particularly by digestion, of the natural protein may not be complete. In this case, the use of an AQUA standard would lead to underestimating the quantity of natural protein. For full assaying, it may therefore be important to take into account the yields from treatment which entails the cleaving of the proteins. However, V. Brun et al. [33] have shown that the QconQAT standards sometimes do not exactly reproduce the treatment yield, particularly by digestion of the natural protein, undoubtedly due to a three-dimensional conformation different from the QconCAT protein.

V. Brun et al. [33] then proposed the use of a method dubbed PSAQ, and described in patent application WO 2008/145763. In this case, the internal standard is a recombinant protein having the same sequence as the natural protein but synthesised with heavy amino acids. The synthesis is performed ex-vivo with heavy amino acids. This standard has strictly the same physicochemical properties as the natural protein (with the exception of a higher mass). It is added from the start, before the protein fractionation step, when the latter is present. It is therefore co-purified with the native protein, during the protein fractionation step. It exhibits the same treatment yield, particularly by digestion, as the native protein. The heavy peptide obtained after cleaving is also co-purified with the natural peptide, if a peptide fractionation step is performed. The two peptides are therefore injected simultaneously into the mass spectrometer, to be quantitatively assayed. They then undergo the same ionisation yield in the source. Comparison of the peak areas of the natural and the reference peptides in the PSAQ method make it possible to calculate the concentration of the protein to be assayed taking into account all of the steps of the assay method.

All of these techniques, namely AQUA, QconCAT or PSAQ or any other calibration technique, used in the mass spectrometry assays and in particular in MRM or MS assays, may be employed to carry out calibration, within the framework of the invention.

Preferably, the mass spectrometry used in the detection method according to the invention is MS/MS. More preferably, the mass spectrometry is MRM.

The method of the invention makes it possible to detect resistances to cephalosporin, characterised by the detection of at least one peptide as a resistance marker. Said resistance marker peptide preferably belongs to the proteins TEM, CMY, CTX-M, SHV, FOX, ACC, ACT, GARB, DHA, MIR, MOX, PER, VEB, OXA or GES.

In particular, the detection of a mechanism of resistance to cephalosporins induced by the expression of the TEM protein is characterised by the detection of at least one peptide belonging to the TEM protein and its different sequence variants SEQ ID No. 1 to SEQ ID No. 165 and SEQ ID No. 1836 to SEQ ID No. 1843.

```
SEQ ID No. 1:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 2:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 3:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGASERGSRGIIAALGPDGKPSRIVVIYTTGSQATMDERNRQIAEIGASLIKHW

SEQ ID No. 4:
MSIQHFRVALIPFFAAFCFPVFAHPETLVKVKDAEDQLGARVGYIELDLNSGKILESF
RPEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGASERGSRGIIAALGPDGKPSRIVVIYMTGSQATMDERNRQIAEIGASLIKHW

SEQ ID No. 5:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDSWEPELNEAI
```

PNDERDTTMPAAMATTLRKLLTGELLTLASRQQLIDWMEADKVAGPLLRSALPAGW
FIADKSGTGKRGSRGIIAALGPDGKPSRIVVIYTTGSQATMDERNRQIAEIGASLIKHW

SEQ ID No. 6:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDHWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 7:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDSWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 8:
SIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDSWEPELNEAI
PNDERDTTMPAAMATTLRKLLTGELLTLASRQQLIDWMEADKVAGPLLRSALPAGW
FIADKSGASERGSRGIIAALGPDGKPSRIVVIYTTGSQATMDERNRQIAEIGASLIKHW

SEQ ID No. 9:
MSIQHFRVALIPFFAAFCFPVFAHPETLVKVKDAEDQLGARVGYIELDLNSGKILESF
RPEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDSWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYMTGSQATMDERNRQIAEIGASLIKHW

SEQ ID No. 10:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDSWEPELNEAI
PNDERDTTMPAAMATTLRKLLTGELLTLASRQQLIDWMEADKVAGPLLRSALPAGW
FIADKSGAGKRGSRGIIAALGPDGKPSRIVVIYTTGSQATMDERNRQIAEIGASLIKHW

SEQ ID No. 11:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDHWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 12:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDSWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 13:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYMTGSQATMDERNRQIAEIGASLIKHW

SEQ ID No. 14:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGASERGSRGIIAALGPDGKPSRIVVIYTTGSQATMDERNRQIAEIGASLIKHW

SEQ ID No. 15:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDHWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 16:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 17:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 18:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGASERGSRGIIAALGPDGKPSRIVVIYTTGSQATMDERNRQIAEIGASLIKHW

SEQ ID No. 19:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDRWEPELNEAI
PNDERDTTTPAAMATTLRKLLTGELLTLASRQQLIDWMEADKVAGPLLRSALPAGW
FIADKSGASERGSRGIIAALGPDGKPSRIVVIYTTGSQATMDERNRQIAEIGASLIKHW

SEQ ID No. 20:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVKYSPVTEKHLTDG
MTVRELCSAAITMSDNTAANLLLTTIGGPKELTAFLRNMGDHVTRLDRWEPELNEAI
PNDERDTTMPAAMATTLRKLLTGELLTLASRQQLIDWMEADKVAGPLLRSALPAGW
FIADKSGASERGSRGIIAALGPDGKPSRIVVIYTTGSQATMDERNRQIAEIGASLIKHW

SEQ ID No. 21:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGGSERGSRGIIAALGPDGKPSRIVVIYTTGSQATMDERNRQIAEIGASLIKH

SEQ ID No. 22:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDSWEPELNEAI
PNDERDTTMPAAMATTLRKLLTGELLTLASRQQLIDWMEADKVAGPLLRSALPAGW
FIADKSGTGKRGSRGIIAALGPDGKPSRIVVIYTTGSQATMDERNRQIAEIGASLIKHW

SEQ ID No. 23:
MSIQHFRVALIPFFAAFCFPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGASERGSRGIIAALGPDGKPSRIVVIYMTGSQATMDERNRQIAEIGASLIKHW

SEQ ID No. 24:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDSWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 25:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDHWEPELNEAI
PNDERDTTMPAAMATTLRKLLTGELLTLASRQQLIDWMEADKVAGPLIRSALPAGW
FIADKSGAGKRGSRGIIAALGPDGKPSRIVVIYMTGSQATMDERNRQIAEIGASLIKHW

SEQ ID No. 26:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDHWEPELNEAI
PNDERDTTMPAAMATTLRKLLTGELLTLASRQQLIDWMEADKVAGPLLRSALPAGW
FIADKSGAGKRGSRGIIAALGPDGKPSRIVVIYTTGSQATMDERNRQIAEIGASLIKHW

SEQ ID No. 27:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDHWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 28:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG

-continued
```
MTVRELCSAAITMSDNTAANLLLLTIGGPKELTAFLHNMGDHVTRLDRWEPELNEAI
PNDERDTTMPAAMATTLRKLLTGELLTLASRQQLIDWMEADKVAGPLLRSALPAGW
HADKSGAGERGSSGIIAALGPDGKPSRIVVIYTTGSQATMDERNRQIAEIGASLIKHW SEQ ID No. 29:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSCGIIAALGPDGKPSRIVVIYTTGSQATMDERNRQIAEIGASLIKHW SEQ ID No. 30:
MSIQHFRVALIPFFAAFCLPVFAHPETLVKVKDAEDQLGARVGYIELDLNSGKILESF
RPEERFPMISTFKVLLCGAVLSRVDAGQEQLGRRIHYSQNDLVEYSPVTEKHLTDG
MTVRELCSAAITMSDNTAANLLLLTIGGPKELTAFLHNMGDHVTRLDRWEPELNEAI
PNDERDTTTPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW SEQ ID No 31:
MSIQHFRVALIPFFAAFCLPVFAHPETLVKVKDAEDQLGARVGYIELDLNSGKILESF
RPEERFPMLSTFKVLLCGAVLSRVDAGQEQLGRRIHYSQNDLVEYSPVTEKHLTDG
MTVRELCSAAITMSDNTAANLLLLTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW SEQ ID No. 32:
MSIQHFRVALIPFFAAFCLPVFAHPETLVKVKDAEDQLGARVGYIELDLNSGKILESF
RPEERFPMVSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW SEQ ID No. 33:
MSIQHFRVALIPFFAAFCLPVFAHPETLVKVKDAEDQLGARVGYIELDLNSGKILESF
RPEERFPMLSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERDRQIAEIGASLIKHW SEQ ID No. 34:
MSIQHFRVALIPFFAAFCLPVFAHPETLVKVKDAEDQLGARVGYIELDLNSGKILESF
RPEERFPMVSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERDRQIAEIGASLIKHW SEQ ID No. 35:
MSIQHFRVALIPFFAAFCLPVFAHPETLVKVKDAEDQLGARVGYIELDLNSGKILESF
RPEERFPMISTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERDRQIAEIGASLIKHW SEQ ID No. 36:
MSIQHFRVALIPFFAAFCLPVFAHPETLVKVKDAEDQLGARVGYIELDLNSGKILESF
RPEERFPMVSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDELNRWEIGASLIKHW SEQ ID No. 37:
MSIQHFRVALIPFFAAFCLPVFAHPETLVKVKDAEDQLGARVGYIELDLNSGKILESF
RPEERFPMLSTFKVLLCGAVLSRVDAGQEQLGRRIHYSQNDLVEYSPVTEKHLTDG
MTVRELCSAAITMSDNTAANLLLITTIGGPKELTAFLHNMGDHVIRLDRREPELNEAIP
NDERDTTMPAAMATTLRKLLTGELLTLASRQQLIDWMEADKVAGPLLRSALPAGWF
IADKSGAGERGSRGIIAALGPDGKPSRIVVIYTTGSQATMDERDRQIAEIGASLIKHW SEQ ID No. 38:
MSIQHFRVALIPFFAAFCLPVFAHPETLVKVKDAEDQLGARVGYIELDLNSGKILESF
RPEERFPMISTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW SEQ ID No. 39:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSTGIIAALGPDGKPSRIVVIYTTGSQATMDERNRQIAEIGASLIKHW
```

-continued

SEQ ID No. 40:
MSIQHFRVALIPFFAAFCLPVFAHPETLVKVKDAEDKLGVRVGYIELDLNSGKILESFR
PEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGASKRGSRGIIAALGPDGKPSRIVVIYMTGSQATMDERNRQIAEIGASLIKHW

SEQ ID No. 41:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDHWEPELNEAI
PNDERDTTTPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 42:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSSGIIAALGPDGKPSRIVVIYTTGSQATMDERNRQIAEIGASLIKHW

SEQ ID No. 43:
MSIQHFRVALIPFFAAFCLPVFAHPETLVKVKDAEDQLGARVGYIELDLNSGKILESF
RPEERFPMLSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDEQNRQIAEIGASLIKHW

SEQ ID No. 44:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDSWEPELNEAI
PNDERDTTMPAAMATTLRKLLTGELLTLASRQQLIDWMEADKVAGPLLRSALPAGW
FlADKSGAGKRGSRGIIAALGPDGKPSRIVVIYTTGSQATMDERNRQIAEIGASLIKHW

SEQ ID No. 45:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGASKRGSRGIIAALGPDGKPSRIVVIYMTGSQATMDERNRQIAEIGASLIKHW

SEQ ID No. 46:
MSIQHFRVALIPFFAAFCFPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGASKRGSRGIIAALGPDGKPSRIVVIYMTGSQATMDERNRQIAEIGASLIKHW

SEQ ID No. 47:
MSIQHFRVALIPFFAAFCFPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGASKRGSRGIIAALGPDGKPSRIVVIYMTGGQATMDERNRQIAEIGASLIKHW

SEQ ID No. 48:
MSIQHFRVALIPFFAAFCLPVFAHPETLVKVKDAEDQLGARVGYIELDLNSGKILESF
RPEERFPMLSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGASERGSRGIIAALGPDGKPSRIVVIYTTGSQATMDERDRQIAEIGASLIKHW

SEQ ID No. 49:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSHGIIAALGPDGKPSRIVVIYTTGSQATMDERNRQIAEIGASLIKHW

SEQ ID No. 50:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDRWEPELNEAI
PNDERDTTTPAAMATTLRKLLTGELLTLASRQQLIDWMEADKVAGPLLRSALPAGW
FIADKSGASERGSRGIIAALGPDGKPSRIVVIYTTGSQATMDERNRQIAEIGASLIKHW

SEQ ID No. 51:
MSIQHFRVALIPFFAAFCFPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDSWEPELNEAI

-continued
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW SEQ ID No. 52:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSLGIIAALGPDGKPSRIVVIYTTGSQATMDERNRQIAEIGASLIKHW SEQ ID No. 53:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAEPLLRSALPAGW
FIADKSGAGERGSRGIIAALGPDGKPSRIVVIYTTGSQATMDERNRQIAEIGASLIKHW SEQ ID No. 54:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVKYSPVTEKHLTDG
MTVRELCSAAITMSDNTAANLLLTTIGGPKELTAFLRNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW SEQ ID No. 55:
MSIQHFRVALIPFFAAFCLPVFAHPETLVKVKDAEDQLGARVGYIELDLNSGKILESF
RPEERFPMMSTFKVLLCGAVLSRVDAGQEQLDRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW SEQ ID No. 56:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSSGIIAALGPDGKPSRIVVIYTTGSQATMDERNRQIAEIGASLIKHW SEQ ID No. 57:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVEYSPVTEKHLTDG
MTVRELCSAAITMGDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW SEQ ID No. 58:
MSIQHFRVALIPFFAAFCLPVFAHPETLVKVKDAEDKLGARVGYIELDPNSGKILESF
RPEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDSWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW SEQ ID No. 59:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDHWEPELNEAI
PNDERDTTMPAAMATTLRKLLTGELLTLASRQQLIDWMEADKVAGPLLRSALPAGW
FIADKSGAGKRGSRGIIAALGPDGKPSRIVVIYTTGSQATMDERNRQIAEIGASLIKHW SEQ ID No. 60:
MSIQHFRVALIPFFAAFCFPVFAHPETLVKVKDAEDQLGARVGYIELDLNSGKILESF
RPEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDSWEPELNEAI
PNDERDTTTPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW SEQ ID No. 61:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSCGIIAALGPDGKPSRIVVIYTTGSQATMDERNRQIAEIGASLIKHW SEQ ID No. 62:
MSIQHFRVALIPFFAAFCLPVFAHPETLVKVKDAEDKLGARVGYIELDLNSGKILESFR
PEERFPMMSTFKVLLCGAVLSRVDAGQEQLDRRIHYSQNDLVKYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGASERGSRGIIAALGPDGKPSRIVVIYTTGSQATMDERNRQIAEIGASLIKHW SEQ ID No. 63:
MSIQHFRVALIPFFAAFCIPVFAHPETLVKVKDAEDKLGARVGYIELDLNSGKILESFR
PEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSCGIIAALGPDGKPSRIVVIYTTGSQATMDERNRQIAEIGASLIKHW SEQ ID No. 64:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGASKRGSRGIIAALGPDGKPSRIVVIYMTGSQATMDELNRQIAEIGASLIKHW SEQ ID No. 65:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASQQQLIDWMEADKVAGPLLRSALPAGW
FIADKSGAGERGSRGIIAALGPDGKPSRIVVIYTTGSQATMDERNRQIAEIGASLIKHW SEQ ID No. 66:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGASKRGSRGIIAALGPDGKPSRIVVIYTTGSQATMDERNRQIAEIGASLIKHW SEQ ID No. 67:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTTPAAMATTLRKLLTGELLTLASRQQLIDWMEADKVAGPLLRSALPAGW
FIADKSGASKRGSRGIIAALGPDGKPSRIVVIYTTGSQATMDERNRQIAEIGASLIKHW SEQ ID No. 68:
MSIQHFRVALIPFFAAFCFPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSCGIIAALGPDGKPSRIVVIYMTGSQATMDERNRQIAEIGASLIKHW SEQ ID No. 69:
MSIQHFRVALIPFFAAFCFPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSSGIIAALGPDGKPSRAIVVIYMTGSQATMDERNRQIAEIGASLIKHW SEQ ID No. 70:
MSIQHFRVALIPFFAAFCFPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDHWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYMTGSQATMDERNRQIAEIGASLIKHW SEQ ID No. 71:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMGDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW SEQ ID No. 72:
MSIQHFRVALIPFFAAFCLPVFAHPETLVKVKDAEDQLGARVGYIELDLNSGKILESF
RPEERFPMLSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSSGIIAALGPDGKPSRIVVIYTTGSQATMDERNRQIAEIGASLIKHW SEQ ID No. 73:
MSIQHFRVALIPFFAAFCLPVFAHPETLVKVKDAEDQLGARVGYIELDLNSGKILESF
RPEERFPMVSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRREPELNEAIP
NDERDTTMPAAMATTLRKLLTGELLTLASRQQLIDWMEADKVAGPLLRSALPAGWF
IADKSGAGERGSRGIIAALGPDGKPSRIVVIYTTGSQATMDERDRQIAEIGASLIKHW SEQ ID No. 74:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG

```
SEQ ID No. 75:
MSIQHFRVALIPFFAAFCLPVFAHPETLVKVKDAEDQLGARVGYIELDLNSGKILESF
RPEERFPMLSTFKVLLCGAVLSRVDAGQEQLGRRIHYSQNDLVEYSPVTEKHLTDG
MTVRELCSAAVTMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDER DRQIAEIGASLIKHW

SEQ ID No. 76:
MSIQHFRVALIPFFAAFCLPVFAHPETLVKVKDAEDQLGARVGYIELDLNSGKIESF
RPEERFPMLSTFKVLLCGAVLSRVDAGQEQLGRRIHYSQNDLVEYSPVTEKHLTDG
MTVRELCSAAVTMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 77:
MSIQHFRVALIPFFAAFCLPVFAHPETLVKVKDAEDQLGARVGYIELDLNSGKIESF
RPEERFPMVSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDEQNRQIAEIGASLIKHW

SEQ ID No. 78:
MSIQHFRVALIPFFAAFCLPVFAHPETLVKVKDAEDQLGARVGYIELDLNSGKILESF
RPEERFPMLSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRCEPELNEAIP
NDERDTTMPAAMATTLRKLLTGELLTLASRQQLIDWMEADKVAGPLLRSALPAGWF
IADKSGAGERGSRGIIAALGPDGKPSRIVVIYTTGSQATMDEQNRQIAEIGASLIKHW

SEQ ID No. 79:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERDRQIAEIGASLIKHW

SEQ ID No. 80:
MSIQHFRVALIPFFAAFCFPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDSWEPELNEAI
PNDERDTTMPAAMATTLRKLLTGELLTLASRQQLIDWMEADKVAGPLLRSALPAGW
FIADKSGAGKRGSRGIIAALGPDGKPSRIVVIYMTGSQATMDERNRQIAEIGASLIKHW

SEQ ID No. 81:
MSIQHFRVALIPFFAAFCFPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDSWEPELNEAI
PNDERDTTMPAAMATTLRKLLTGELLTLASRQQLIDWMEADKVAGPLLRSALPAGW
FIADKSGTGKRGSRGIIAALGPDGKPSRIVVIYMTGSQATMDERNRQIAEIGASLIKHW

SEQ ID No. 82:
MSIKHFRVALIPFFAAFCLPVFAHPETLVKVKDAEDQLGARVGYIELDLNSGKILESFR
PEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLHCWEPELNEAI
PNDERDTTTPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 83:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDRWEPELNEAI
PNDERDTTTPAAMATTLRKLLTDELLTLASRQQLIDWMEADKVAGPLLRSALPAGW
FIADKSGASERGSRGIIAALGPDGKPSRIVVIYTTGSQATMDERNRQIAEIGASLIKHW

SEQ ID No. 84:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVKYSPVTEKHLTDG
MTVRELCSAAITMGDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGASERGSRGIIAALGPDGKPSRIVVIYTTGSQATMDERNRQIAEIGASLIKHW

SEQ ID No. 85:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTG
GMTVRELCSAAITMSDNTAANLLLTTIGGPKELTAFLHNMGDHVTRLDRWEPELNE
AIPNDERDTTMPAAMATTLRKLLTGELLTLASRQQLIDWMEADKVAGPLLRSALPAG
WFIADKSGAGERGSRGIIAALGPDGKPSRIVVIYTTGSQATMDERNRQIAEIGASLIK
HW
```

```
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSGGIIAALGPDGKPSRIVVIYTTGSQATMDERNRQIAEIGASLIKHW
```

SEQ ID No. 86:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDCWEPELNEAI
PNDERDTTTPAAMATTLRKLLTGELLTLASRQQLIDWMEADKVAGPLLRSALPAGW
FIADKSGAGKRGSRGIIAALGPDGKPSRIVVIYTTGSQATMDERNRQIAEIGASLIKHW

SEQ ID No. 87:
MSIKHFRVALIPFFAAFCLPVFAHPETLVKVKDAEDQLGARVGYIELDLNSGKILESFR
PEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDRWEPELNEAI
PNDERDTTTPAAMATTLRKLLTGELLTLASRQQLIDWMEADKVAGPLLRSALPAGW
FIADKSGASERGSRGIIAALGPDGKPSRIVVIYTTGSQATMDERNRQIAEIGASLIKHW

SEQ ID No. 88:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDRWEPELNEAI
PNDERDTTTPAAMATTLRKLLTGELLTLASRQQLIDWMEADKVAGPLLRSALPAGW
FIADKSGASKRGSRGIIAALGPDGKPSRIVVIYTTGSQATMDERNRQIAEIGASLIKHW

SEQ ID No. 89:
MSIQHFRVALIPFFAAFCFPVFAHPETLVKVKDAEDQLGARVGYIELDLNSGKILESF
RPEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDRWEPELNEAI
PNDERDTTTPAAMATTLRKLLTGELLTLASRQQLIDWMEADKVAGPLLRSALPAGW
FIADKSGASERGSRGIIAALGPDGKPSRIVVIYMTGSQATMDERNRQIAEIGASLIKHW

SEQ ID No. 90:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGAKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 91:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLGRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 92:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGASKRGSRGIIAALGPDGKPSRIVVIYTTGSQATMDERNRQIVEIGASLIKHW

SEQ ID No. 93:
MSIQHFRVALIPFFAAFCFPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDSWEPELNEAI
PNDERDTIMPAAMATTLRKLLTGELLTLASRQQLIDWMEADKVAGPLLRSALPAGW
FIADKSGAGERGSRGIIAALGPDGKPSRIVVIYMTGSQATMDERNRQIAEIGASLIKHW

SEQ ID No. 94:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDELNRQIAEIGASLIKHW

SEQ ID No. 95:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIVEIGASLIKHW

SEQ ID No. 96:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCNAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 97:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVKYSPVTEKHLTDG

-continued
```
MTVRELCSAAITMSDNTAANLLLTTIGGPKELTAFLHNMGDHVTRLDRWEPELNEAI
PNDERDTTTPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW SEQ ID No. 98:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDHWEPELNEAI
PNDERDTTTPAAMATTLRKLLTGELLTLASRQQLIDWMEADKVAGPLLRSALPAGW
FIADKSGASERGSRGIIAALGPDGKPSRIVVIYTTGSQATMDERNRQIAEIGASLIKHW SEQ ID No. 99:
MSIQHFRVALIPFFAAFCLPVFAHPETLVKVKDAEDQLGARVGYIELDLNSGKILESF
RPEERFPMMSTFKVLLCGAELSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTSELLTLASRQQLIDWMEADKVAGPLLRSALPAGW
FIADKSGAGERGSRGIIAALGPDGKPSRIVVIYTTGSQATMDERSRQIAEIGASLIKHW SEQ ID No. 100:
MSIQHFRVALIPFFAAFCLPVFAHPETLVKVKDAEDQLGARVGYIELDLNSGKILESF
RPEERFPMLSTFKVLLCGAVLSRVDAGQEQLGRRHYSQNDLVKYSPVTEKHLTDG
MTVRELCSAAITMSDNTAANLLLTTIGGPKELTAFLHNMGDHVTRLDHWEPELNEAI
PNDERDTIMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW SEQ ID No. 101:
MSIQHFRVALIPFFAAFCFPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYMTGSQATMDERNRQIAEIGASLIKHW SEQ ID No. 102:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGADERGSRGIIAALGPDGKPSRIVVIYMTGSQATMDERNRQIAEIGASLIKHW SEQ ID No. 103:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLRNMGDHVTRLDRWEPELNEAI
PNDERDTTMPAAMATTLRKLLTGELLTLASRQQLIDWMEADKVAGPLLRSALPAGW
FIADKSGASERGSRGIIAALGPDGKPSRIVVIYTTGSQATMDERNRQIAEIGASLIKHW SEQ ID No. 104:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDRWEPELNEAI
PNDERDTTTPAAMATTLRKLLTGELLTLASRQQLIDWMEADKVAGPLLRSALPAGW
FIADKSGASERGSRGIIAALGPDGKPSRIVVIYTTGSQATMDERNRQIAEIGASLIKHW SEQ ID No. 105:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDSWEPELNEAI
PNDERDTTMPAAMATTLRKLLTGELLTLASRQQLIDWMEADKVAGPLLRSALPAGW
FIADKSGTGKRGSRGIIAALGPDGKPSRIVVIYTTGSQATMDERNRQIAEIGASLIKHW SEQ ID No. 106:
MSIQHFRVALIPFFAAFCFPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDHWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW SEQ ID No. 107:
MSIQHFRVALIPFFAAFCLPVFAHPETLVKVKDAEDQLGARVGYIELDLNSGKILESF
RPEERFPMMSTFKVLLCGAVLSRIDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPVAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW SEQ ID No. 108:
MSIQHFRVALIPFFAAFCFPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW
```

SEQ ID No. 109:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDHWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYMTGSQATMDERNRQIAEIGASLIKHW

SEQ ID No. 110:
MSIQHFRVALIPFFAAFCFPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGASERGSRGIIAALGPDGKPSRIVVIYTTGSQATMDERNRQIAEIGASLIKHW

SEQ ID No. 111:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDSWEPELNEAI
PNDERDTIMPAAMATTLRKLLTGELLTLASRQQLIDWMEADKVAGPLLRSALPAGW
FIADKSGTGKRGSSGIIAALGPDGKPSRIVVIYTTGSQATMDERNRQIAEIGASLIKHW

SEQ ID No. 112:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDEQNRQIAEIGASLIKHW

SEQ ID No. 113:
MSIKHFRVALIPFFAAFCLPVFAHPETLVKVKDAEDQLGARVGYIELDLNSGKILESFR
PEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGASERGSRGIIAALGPDGKPSRIVVIYTTGSQATMDERNRQIAEIGASLIKHW

SEQ ID No. 114:
MSIKHFRVALIPFFAAFCLPVFAHPETLVKVKDAEDQLGARVGYIELDLNSGKILESFR
PEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDRWEPELNEAI
PNDERDTTTPAAMATTLRKLLTGELLTLASRQQLIDWMEADKVAGPLLRSALPAGW
FIADKSGAGERGSRGIIAALGPDGKPSRIVVYTTGSQATMDERNRQIAEIGASLIKHW

SEQ ID No. 115:
MSIQHFRVALIPFLAAFCLPVFAHPETLVKVKDAEDQLGARVGYIELDLNSGKILESF
RPEERFPMLSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDSREPELNEAIP
NDERDTTMPAAMATTLRKLLTGELLTLASRQQLIDWMEADKVAGPLLRSALPAGWF
IADKSGAGERGSRGIIAALGPDGKPSRIVVIYTTGSQATMDERDRQIAEIGASLIKHW

SEQ ID No. 116:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERETTTPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 117:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDNVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 118:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGEHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 119:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDSWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 120:
MSIQHFRVALIPFFAAFCLPVFAHPETLVKVKPAEDKLGARVGYIELDLNSGKILESFR
PEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDSWEPELNEAI

```
SEQ ID No. 121:
MSIQHFRVALIPFFAAFCFPVFAHPETLVKVKDAEDQLGARVGYIELDLNSGKILESF
RPEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDSWEPELNEAI
PNDERDTTTPAAMATTLRKLLTGELLTLASRQQLIDWMEADKVAGPLLRSALPAGW
FIADKSGTGERGSRGIIAALGPDGKPSRIVVIYTTGSQATMDERNRQIAEIGASLIKHW

SEQ ID No. 122:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDHWEPELNEAV
PNDERDTTMPAAMATTLRKLLTGELLTLASRQQLIDWMEADKVAGPLLRSALPAGW
FIADKSGAGKRGSRGIIAALGPDGKPSRIVVIYTTGSQATMDERNRQIAEIGASLIKHW

SEQ ID No. 123:
MSIQHFRVALIPFFAAFCFPVFAHPETLVKVKDAEDQLGARVGYIELDLNSGKILESF
RPEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDSWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 124:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDHWEPELNEAI
PNDERDTTMPAAMATTLRKLLTGELLTLASRQQLIDWMEADKVAGPLLRSALPAGW
FIADKSGASERGSRGIIAALGPDGKPSRIVVIYTTGSQATMDERNRQIAEIGASLIKHW

SEQ ID No. 125:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTTPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 126:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDSWEPELNEAI
PNDERDTTMPAAMATTLRKLLTGELLTLASRQQLIDWMEADKVAGPLLRSALPAGW
FIADKSGTGKRGSRGIIAALGPDGKPSRIVVIYTTGGQATMDERNRQIAEIGASLIKHW

SEQ ID No. 127:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDSWEPELNEAI
PNDERDTTMPAAMATTLRKLLTGELLTLASRQQLIDWMEADKVAGPLLRSALPAGW
FIADKSGAGRRGSRGIIAALGPDGKPSRIVVIYTTGSQATMDERNRQIAEIGASLIKHW

SEQ ID No. 128:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDRWEPELNEAI
PIDERDTTMPAAMATTLRKLLTGELLTLASRQQLIDWMEADKVAGPLLRSALPAGWF
IADKSGASERGSRGIIAALGPDGKPSRIVVIYTTGSQATMDERNRQIAEIGASLIKHW

SEQ ID No. 129:
MSIQHFRVALIPFFAAFCLPVFAHPETLVKVKDAEDKLGARVGYIEMDLNSGKILESF
RPEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGASERGSRGIIAALGPDGKPSRIVVIYTTGSQATMDERNRQIAEIGASLIKHW

SEQ ID No. 130:
MSIQHFRVALIPFFAAFCLPVFAHPETLVKVEDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 131:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGANERGSRGIIAALGPDGKPSRIVVIYMTGSQATMDERNRQIAEIGASLIKHW
```

-continued

SEQ ID No. 132:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDCWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 133:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDCWEPELNEAI
PNDERDTTMPAAMATTLRKLLTGELLTLASRQQLIDWMEADKVAGPLLRSALPAGW
FIADKSGAGKRGSRGIIAALGPDGKPSRIVVIYTTGSQATMDERNRQIAEIGASLIKHW

SEQ ID No. 134:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLMRSALPAG
WFIADKSGAGERGSHGIIAALGPDGKPSRIVVIYTTGSQATMDERNRQIAEIGASLIK
HW

SEQ ID No. 135:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLPD
GMTVRELCSAAITMSDNTAANLLLTTIGGPKELTAFLHNMGDHVTRLDRWEPELNE
AIPNDERDTTMPAAMATTLRKLLTGELLTLASRQQLIDWMEADKVAGPLLRSALPAG
WFIADKSGAGERGSHGIIAALGPDGKPSRIVVIYTTGSQATMDERNRQIAEIGASLIK
HW

SEQ ID No. 136:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDHWEPELNEAI
PNDERDTTMPAAMATTLRKLLTGELLTLASRQQLIDWMEADKVAGPLLRSVLPAGW
FIADKSGAGERGSRGIIAALGPDGKPSRIVVIYTTGSQATMDERNRQIAEIGASLIKHW

SEQ ID No. 137:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATKLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 138:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDSWEPELNEAI
PNDERDTTTPAAMATTLRKLLTGELLTLASRQQLIDWMEADKVAGPLLRSALPAGW
FIADKSGAGVRGSRGIIAALGPDGKPSRIVVIYTTGSQATMDERNRQIAEIGASLIKHW

SEQ ID No. 139:
MSIQHFRVALIPFFAAFCLPVFAHPDTLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 140:
MSIQHFRVALIPFFAAFCLPVFAHPETLVKVKDAEDQLGARVGYIELDLNSGKILESF
RPEERFPMVSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDHWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERDRQIAEIGGSLIKHW

SEQ ID No. 141:
MSIQHFRVALIPFFAAFCLPVFAHPETLVKVKDAEDQLGARVGYIELDLNSGKILESF
RPEERFPMVSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDHWEPELNEAI
PNDERDTIMPAAMATTLRKLLTGELLTLASRQQLIDWMEADKVAGPLLRSALPAGW
FIADKSGAGKRGSRGIIAALGPDGKPSRIVVIYTTGSQATMDERDRQIAEIGASLIKHW

SEQ ID No. 142:
MSIQHFRVALIPFFAAFCLPVFAHPETLVKVKDAEDQLGARVGYIELDLNSGKILESF
RPEERFPMLSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDSWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

-continued

SEQ ID No. 143:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDSWEPELNEAI
PNDERDTTMPAAMATTLRKLLTGELLTLASRQQLIDWMEADKVAGPLLRSALPAGW
FIADKSGAGKRGSRGIIAALGPDGKPSRIVVIYTTGSQATMDERNRQIAEIGASLIKHW

SEQ ID No. 144:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNIGDHVTRLDRWEPELNEAIP
NDERDTTMPAAMATTLRKLLTGELLTLASRQQLIDWMEADKVAGPLLRSALPAGWF
IADKSGAGERGSRGIIAALGPDGKPSRIVVIYTTGSQATMDERNRQIAEIGASLIKHW

SEQ ID No. 145:
MSIQHFRVALIPFFAAFCLPVFAHPETLVKVKDAEDQLGARVGYIELDLNSGKILESF
RPEERFPMMSTFKVLLCGAVLSRIDAGQEQLGRRIHYSQSDLVEYSPVTEKHLTDG
MTVRELCSAAITMSDNTAANLLLTTIGGPKELTAFLHNMGDHVTRLDRWEPELNEAI
PNDERDTTMPVAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 146:
MSIQHFRVALIPFFAAFCLPVFAHPETLVKVKDAEDQLGARVGYIELDLNSGKILESF
RPEERFPMLSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDSWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERDRQIAEIGASLIKHW

SEQ ID No. 147:
MSIQHFRVALIPFFAAFCFPVFAHPETLVKVKDAEDQLGARVGYIELDLNSGKILESF
RPEERFPMISTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTTPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 148:
MSIQHFRVALIPFFAAFCLPVFAHPETLVKVKDAEDKLGARVGYIELDLNSGKILESFR
PEERFPMVSTFKVLLCGAVLSRVDAGQEQLGRRIHYSQNDLVEYSPVTEKHLTDGM
TVRELCSAAITMSDNTAANLLLTTIGGPKELTAFLHNMGDHVTRLDRWEPELNEAIP
NDERDTTMPAAMATTLRKLLTGELLTLASRQQLIDWMEADKVAGPLLRSALPAGWF
IADKSGAGERGSRGIIAALGPDGKPSRIVVIYTTGSQATMDERNRQIAEIGASLIKHW

SEQ ID No. 149:
MSIKHFRVALIPFFAAFCLPVFAHPETLVKVKDAEDQLGARVGYIELDLNSGKILESFR
PEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDHWEPELNEAI
PNDERDTTTPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 150:
MSIQHFRVALIPFFAAFCLPVFAHPKTLVKVKDAENQLGARVGYIELDLNSGKILESF
RPEKRFPMMSTFKVLLCGAVLSRIDAGQEQLGRRIHYSQSDVVEYSPVTEKHLTDG
MTVRELCSAAITMSDNTAANLLLTTIGGPKELTAFLHNMGDHVTRLDRWEPELNEAI
PNDERDTTMPVAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 151:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDEQNRQIAEIGASLIKLW

SEQ ID No. 152:
MSIQHFRVALIPFFAAFCLPVFAHPETLVKVKDAEDQVGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQTAEIGASUKHW

SEQ ID No. 153:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDSWEPELNEAI
PNDERDTTTPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW

SEQ ID No. 154:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG

-continued
MTVGELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW SEQ ID No. 155:
MSIQHFRVALIPFFAAFCFPVFAHPETLVKVKDAEDQLGARVGYIELDLNSGKILESF
RPEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSVLPAGW
FIADKSGASERGSRGIIAALGPDGKPSRIVVIYMTGSQATMDERNRQIAEIGASLIKHW SEQ ID No. 156:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYMTGSQATMDERNRQIAEIGASLIKHW SEQ ID No. 157:
MSIQHFRVALIPFFAAFCLPVFAHPETLVKVKDAEDQLGARVGYIELDLNSGKILESF
RPEERFPMLSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRGEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW SEQ ID No. 158:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDVVMEADKVAGPLLRSALPAGW
FIADKSGAGERGSRGIIAALGPDGKPSRIVVIYTTGSQATMDERNRQIAEICASLIKHW SEQ ID No. 159:
MSIQHFRVALIPFFAAFCLPVFAHPETLVKVKDAEDQLGARVGYIELDLNSGKILESF
RPEERFPMMSTFKVLLCGAVLSRIDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW SEQ ID No. 160:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEVDKVAGPLLRSALPAGW
FIADKSGAGERGSSGIIAALGPDGKPSRIVIIYTTGSQATMDERNRQIAEIGASLIKHW SEQ ID No. 161:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEVDKVAGPLLRSALPAGW
FIADKSGAGERGSSGIIAALGPDGKPSRIVVIYTTGSQATMDERKRQIAEIGASLIKHW SEQ ID No. 162:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEVDKVAGPLLRSALPAGW
FIADKSGAGERGSRGIIAALGPDGKPSRIVVIYTTGSQATMDERNRQIAEIGASLIKHW SEQ ID No. 163:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSVLPAGW
FIADKSGAGERGSRGIIAALGPDGKPSRIVVIYTTGSQATMDERNRQIAEIGASLIKHW SEQ ID No. 164:
MSIKHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVKYSPVTEKHLTDG
MTVRELCSAAITMSDNTAANLLLTTIGGPKELTAFLHNMGDHVTRLDSWEPELNEAI
PNDERDTTTPAAMATTLRKLLTGELLTLASRQQLIDWMEADKVAGPLLRSALPAGW
FIADKSGTGKRGSRGIIAALGPDGKPSRIVVIYTTGSQATMDERNRQIAEIGASLIKHW SEQ ID No. 165:
MSIQHFRVALIPFFAAFCLPVFAHPETLVKVKDAEDQLGSTSGYIELDLNSGKILESFR
PEERFPMMSTFKVLLCGAVLSRVDAGQEQLGRRIHYSQNDLVEYSPVTEKHLTDG
MTVRELCSAAITMSDNTAANLLLTTIGGSQELTAFLHNMGDHVTRLDRVVEPELNEAI
PNDEADTTMPAAMATTLRKLLTGELLTLASRQQLIDWMADKVAGPLLRSALPAGWFI
ADKSGARERGSRGIIAALGPDGKPSRIVVIYTTGSQATMDERNRQIAEIGASUKHW -continued SEQ ID No. 1836:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW SEQ ID No. 1837:
MSIQHFRVALIPFFAAFCLPVFAHPETLVKVKDAEDQLGARVGYIELDLNSGKILESF
RPEERFPMLSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRVVEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW SEQ ID No. 1838:
MSIQHFRVALIPFFAAFCLPVFAHPETLVKVKDAEDKLGARVGYIELDLNSGKILESFR
PEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW SEQ ID No. 1839:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGASKRGSRGIIAALGPDGKPSRIVVIYMTGSQATMDERNRQIAEIGASLIKHW SEQ ID No. 1840:
MSIQHFRVALIPFFAAFCFPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGASKRGSRGIIAALGPDGKPSRIVVIYMTGSQATMDERNRQIAEIGASLIKHW SEQ ID No. 1841:
MSIQHFRVALIPFFAAFCFPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDRWEPELNEAI
PNDERDTTMPAAMATTLRKLLTGELLTLASRQQLIDWMEADKVAGPLLRSALPAGW
FIADKSGASKRGSRGIIAALGPDGKPSRIVVIYMTGGQATMDERNRQIAEIGASLIKHW SEQ ID No. 1842:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVTRLDHWEPELNEAI
PNDERDTTMPAAMATTLRKLLTGELLTLASRQQLIDWMEADKVAGPLLRSALPAGW
FIADKSGAGERGSRGIIAALGPDGKPSRIVVIYTTGSQATMDERNRQIAEIGASLIKHW SEQ ID No. 1843:
MSIQHFRVALIPFFAAFCLPVFAHPETLVKVKDAEDQLGARVGYIELDLNSGKILESF
RPEERFPMMSTFKVLLCGAVLSRVDAGQEQLGRRIHYSQNDLVEYSPVTEKHLTDG
MTVRELCSAAITMSDNTAANLLLTTIGGPKELTAFLHNMGDHVIRLDRWEPELNEAI
PNDERDTTMPAAMATTLRKLLTGELLTLASRQQLIDWMEADKVAGPLLRSALPAGW
FIADKSGAGERGSSGIIAALGPDGKPSRIVVIYTTGSQATMDERNRQIAEIGASLIKHW said peptides being chosen, preferably, from the peptides of sequence SEQ ID No. 166 to SEQ ID 261 and SEQ ID No. 1923 to SEQ ID 1928 as defined hereafter:

| Peptide SEQ ID No. | Amino acid sequence | Position of the peptide in the TEM protein(s) | Clinical interest |
|---|---|---|---|
| SEQ ID No. 166 | CEPELNEAIPNDER | 163-176 for the protein of SEQ No. 78 | 2br |
| SEQ ID No. 167 | DAENQLGAR | 33-41 for the proteins of SEQ No. 1, 4, 5, 6, 9, 10, 12, 14, 16, 18, 19, 23, 24, 25, 26, 27, 28, 29, 30, 31, 32, 33, 34, 35, 36, 37, 38, 39, 41, 43, 45, 46, 47, 48, 49, 50, 51, 52, 53, 55, 56, 60, 64, 65, 66, 68, 69, 70, 71, 72, 73, 74, 75, 76, 77, 78, 79, 80, 81, 82, 83, 85, 86, 87, 88, 89, 90, 91, 93, 94, 95, 96, 97, 98, 99, 100, 101, 102, 103, 106, 107, 108, 109, 110, 112, 113, 114, 115, 116, 117, 118, 121, 122, 123, 125, 126, 127, 128, 130, 131, 132, 133, 134, | TEM |

| Peptide SEQ ID No. | Amino acid sequence | Position of the peptide in the TEM protein(s) | Clinical interest |
|---|---|---|---|
| | | 135, 136, 137, 138, 139, 140, 141, 142, 144, 145, 146, 147, 149, 151, 153, 154, 155, 156, 157, 158, 159, 160, 161, 162, 163, 1837, 1838, 1840, 1841, 1842, 1843, 1844 | |
| SEQ ID No. 168 | DAEDQLGSTSGYIELDLNSGK | 33-53 for the protein of SEQ No. 165 | 2be |
| SEQ ID No. 169 | DAEDQVGAR | 33-41 for the protein of SEQ No. 152 | 2be |
| SEQ ID No. 170 | DAENQLGAR | 33-41 for the protein of SEQ No. 150 | TEM |
| SEQ ID No. 171 | DTTMPAAMATK | 177-187 for the protein of SEQ No. 137 | TEM |
| SEQ ID No. 172 | DTTMPAAMATTLR | 177-189 for the proteins of SEQ No. 1, 2, 3, 4, 5, 6, 7, 8, 9, 10, 11, 12, 13, 14, 15, 16, 17, 18, 20, 21, 22, 23, 24, 25, 26, 27, 28, 29, 31, 32, 33, 34, 35, 36, 37, 38, 39, 40, 42, 43, 44, 45, 46, 47, 48, 49, 51, 52, 53, 54, 55, 56, 57, 58, 59, 61, 62, 63, 64, 65, 66, 68, 69, 70, 71, 72, 73, 74, 75, 76, 77, 78, 79, 80, 81, 84, 85, 90, 91, 92, 93, 94, 95, 96, 99, 100, 101, 102, 103, 105, 106, 108, 109, 110, 111, 112, 113, 115, 117, 118, 119, 120, 122, 123, 124, 126, 127, 128, 129, 130, 131, 132, 133, 134, 135, 136, 139, 140, 141, 142, 143, 144, 146, 148, 151, 152, 164, 155, 156, 157, 158, 159, 160, 161, 162, 163, 165, 1837, 1838, 1839, 1840, 1841, 1842, 1843, 1844 | TEM |
| SEQ ID No. 173 | DTTMPVAMATTLR | 177-189 for the proteins of SEQ No. 107, 145, 150 | TEM |
| SEQ ID No. 174 | DTTMPAAMATTLR | 177-189 for the proteins of SEQ No. 19, 30, 41, 50, 60, 67, 82, 83, 86, 87, 88, 89, 97, 98, 104, 114, 121, 125, 138, 147, 149, 153, 164 | TEM |
| SEQ ID No. 175 | ELTAFLHNIGDHVTR | 145-159 for the protein of SEQ No. 144 | TEM |
| SEQ ID No. 176 | ELTAFLHNMGDHVTR | 145-159 for the proteins of SEQ No. 1, 2, 3, 4, 5, 6, 7, 8, 9, 10, 11, 12, 13, 14, 15, 16, 17, 18, 19, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 104, 105, 106, 107, 108, 109, 110, 111, 112, 113, 114, 115, 116, 119, 120, 121, 122, 123, 124, 125, 126, 127, 128, 129, 130, 131, 132, 133, 134, 135, 136, 137, 138, 139, 140, 141, 142, 143, 145, 146, 147, 148, 149, 150, 151, 152, 153, 154, 155, 156, 157, 158, 159, 160, 161, 162, 163, 164, 165, 1837, 1838, 1839, 1840, 1841, 1842, 1843, 1844 | TEM |
| SEQ ID No. 177 | ELTAFLHNMGDNVTR | 145-159 for the protein of SEQ No. 117 | 2b |
| SEQ ID No. 178 | ELTAFLHNMGEHVTR | 145-159 for the protein of SEQ No. 118 | 2b |
| SEQ ID No. 179 | ELTAFLR | 145-151 for the proteins of SEQ No. 20, 54, 103 | 2be |

-continued

| Peptide SEQ ID No. | Amino acid sequence | Position of the peptide in the TEM protein(s) | Clinical interest |
|---|---|---|---|
| SEQ ID No. 180 | EPELNEAIPNDER | 164-176 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 123, 124, 125, 126, 127, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 1837, 1838, 1839, 1840, 1841, 1842, 1843, 1844 | TEM |
| SEQ ID No. 181 | ETTTPAAMATTLR | 177-189 for the protein of SEQ No. 116 | 2be |
| SEQ ID No. 182 | FPMISTFK | 64-71 for the proteins of SEQ No. 30, 35, 38, 147 | 2br |
| SEQ ID No. 183 | FPMLSTFK | 64-71 for the proteins of SEQ No. 31, 33, 37, 43, 48, 72, 76, 78, 100, 115, 142, 146, 157, 1838 | TEM |
| SEQ ID No. 184 | FPMMSTFK | 64-71 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 39, 40, 41, 42, 44, 45, 46, 47, 49, 50, 51, 52, 53, 54, 55, 56, 57, 58, 59, 60, 61, 62, 63, 64, 65, 66, 67, 68, 69, 70, 71, 74, 79, 80, 81, 82, 83, 84, 85, 86, 87, 88, 89, 90, 91, 92, 93, 94, 95, 96, 97, 98, 99, 101, 102, 103, 104, 105, 106, 107, 108, 109, 110, 111, 112, 113, 114, 116, 117, 118, 119, 120, 121, 122, 123, 124, 125, 126, 127, 128, 129, 130, 131, 132, 133, 134, 135, 136, 137, 138, 139, 143, 144, 145, 149, 150, 151, 152, 153, 154, 155, 156, 158, 159, 160, 161, 162, 163, 164, 165, 1837, 1839, 1840, 1841, 1842, 1843, 1844 | TEM |
| SEQ ID No. 185 | FPMVSTFK | 64-71 for the proteins of SEQ No. 32, 34, 36, 73, 77, 140, 141, 148 | TEM |
| SEQ ID No. 186 | GEPELNEAIPNDER | 163-176 for the protein of SEQ No. 157 | 2be |
| SEQ ID No. 187 | GIIAALGPDGKPSR | 242-255 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, | TEM |

-continued

| Peptide SEQ ID No. | Amino acid sequence | Position of the peptide in the TEM protein(s) | Clinical interest |
|---|---|---|---|
| | | 159, 160, 161, 162, 163, 164, 1837, 1838, 1839, 1840, 1841, 1842, 1843, 1844; 241-254 for the protein of sequence SEQ ID No. 165 | |
| SEQ ID No. 188 | GSCGIIAALGPDGKPSR | 239-255 for the proteins of SEQ No. 29, 61, 63, 68 | 2br |
| SEQ ID No. 189 | GSGGIIAALGPDGKPSR | 239-255 for the protein of SEQ No. 74 | 2br |
| SEQ ID No. 190 | GSHGIIAALGPDGKPSR | 239-265 for the proteins of SEQ No. 49, 134, 135 | 2br |
| SEQ ID No. 191 | GSLGIIAALGPDGKPSR | 239-255 for the protein of SEQ No. 52 | 2br |
| SEQ ID No. 192 | GSSGIIAALGPDGKPSR | 239-255 for the proteins of SEQ No. 28, 42, 56, 69, 72, 111, 160, 161, 1844 | TEM |
| SEQ ID No. 193 | GSTGIIAALGPDGKPSR | 239-255 for the protein of SEQ No. 39 | TEM |
| SEQ ID No. 194 | HLPDGMTVR | 110-118 for the protein of SEQ No. 135 | TEM |
| SEQ ID No. 195 | HLTDGMTVR | 110-118 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 136, 137, 138, 139, 140, 141, 142, 143, 144, 145, 146, 147, 148, 149, 150, 151, 152, 153, 155, 156, 157, 158, 159, 160, 161, 162, 163, 164, 165, 1837, 1838, 1839, 1840, 1841, 1842, 1843, 1844 | TEM |
| SEQ ID No. 196 | HLTGGMTVR | 110-118 for the protein of SEQ No. 85 | 2b |
| SEQ ID No. 197 | IDAGQEQLGR | 82-91 for the proteins of SEQ No. 107, 146, 150, 159 | TEM |
| SEQ ID No. 198 | IHYSQNDLVEYSPVTEK | 93-109 for the proteins of SEQ No. 1, 2, 5, 7, 10, 11, 12, 13, 18, 19, 23, 25, 26, 27, 28, 29, 30, 31, 32, 33, 34, 35, 36, 37, 38, 39, 40, 42, 43, 45, 46, 47, 49, 51, 52, 53, 55, 56, 57, 59, 61, 63, 64, 65, 66, 67, 68, 69, 70, 71, 72, 73, 74, 75, 76, 77, 78, 79, 80, 81, 85, 86, 88, 90, 91, 92, 93, 94, 95, 96, 99, 101, 103, 105, 106, 107, 108, 109, 110, 112, 115, 116, 117, 118, 122, 125, 126, 127, 130, 132, 133, 134, 135, 136, 137, 139, 140, 141, 142, 143, 144, 146, 147, 148, 151, 152, 153, 154, 156, 157, 158, 159, 160, 161, 162, 163, 165, 1837, 1838, 1839, 1840, 1841, 1842, 1843, 1844 | TEM |
| SEQ ID No. 199 | IHYSQNDLVK | 93-102 for the proteins of SEQ No. 3, 4, 6, 8, 9, 14, 15, 16, 17, 20, 21, 22, 24, 41, 44, 48, 50, 54, 58, 60, 62, 82, 83, 84, 87, 89, 97, 98, 100, 102, 104, 111, 113, 114, 119, 120, 121, 123, 124, 128, 129, 131, 138, 149, 155, 164 | 2be |

-continued

| Peptide SEQ ID No. | Amino acid sequence | Position of the peptide in the TEM protein(s) | Clinical interest |
|---|---|---|---|
| SEQ ID No. 200 | IHYSQSDLVEYSPVTEK | 93-109 for the protein of SEQ No. 145 | 2be |
| SEQ ID No. 201 | IHYSQSDVVEYSPVTEK | 93-109 for the protein of SEQ No. 150 | TEM |
| SEQ ID No. 202 | ILESFRPEER | 54-63 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 151, 152, 153, 154, 155, 156, 157, 158, 159, 160, 161, 162, 163, 164, 165, 1837, 1838, 1839, 1840, 1841, 1842, 1843, 1844 | TEM |
| SEQ ID No. 203 | ILESFRPEK | 54-62 for the protein of SEQ No. 150 | TEM |
| SEQ ID No. 204 | IVIIYTTGSQATMDER | 256-271 for the proteins of SEQ Na. 56, 160 | 2br |
| SEQ ID No. 205 | IVVIYMTGGQATMDER | 256-271 for the proteins of SEQ No. 47, 1842 | 2be |
| SEQ ID No. 206 | IVVIYMTGSQATMDELNR | 256-273 for the protein of SEQ No. 64 | 2be |
| SEQ ID No. 207 | IVVIYMTGSQATMDER | 256-271 for the proteins of SEQ No. 4, 9, 13, 23, 25, 40, 45, 46, 68, 69, 70, 80, 81, 89, 93, 101, 102, 109, 131, 155, 156, 1840, 1841 | TEM |
| SEQ ID No. 208 | IVVIYTTGGQATMDER | 256-271 for the protein of SEQ No, 126 | 2be |
| SEQ ID No. 209 | IVVIYTTGSQATMDELNR | 256-273 for the proteins of SEQ No. 36, 94 | 2br |
| SEQ ID No. 210 | IVVIYTTGSQATMDEQNR | 256-273 for the proteins of SEQ No. 43, 77, 78, 112, 151 | 2br |
| SEQ ID No. 211 | IVVIYTTGSQATMDER | 256-271 for the proteins of SEQ No. 1, 2, 3, 5, 6, 7, 8, 10, 11, 12, 14, 15, 16, 17, 18, 19, 20, 21, 22, 24, 26, 27, 28, 29, 30, 31, 32, 33, 34, 35, 37, 38, 39, 41, 42, 44, 48, 49, 50, 51, 52, 53, 54, 55, 57, 58, 59, 60, 61, 62, 63, 65, 66, 67, 71, 72, 73, 74, 75, 76, 79, 82, 83, 84, 85, 86, 87, 88, 90, 91, 92, 95, 96, 97, 98, 99, 100, 103, 104, 105, 106, 107, 108, 110, 111, 113, 114, 115, 116, 117, 118, 119, 120, 121, 122, 123, 124, 125, 127, 128, 129, 130, 132, 133, 134, 135, 136, 137, 138, 139, 140, 141, 142, 143, 144, 145, 146, 147, 148, 149, 150, 152, 153, 154, 157, 158, 159, 161, 162, 163, 164, 1837, 1838, 1839, 1843, 1844 | TEM |
| SEQ ID No. 212 | LDCWEPELNEAIPNDER | 160-176 for the proteins of SEQ No. 86, 132, 133 | 2be |
| SEQ ID No. 213 | LDHWEPELNEAIPNDER | 160-176 for the proteins of SEQ No. 6, 11, 15, 25, 26, 27, 41, 59, 70, 98, 100, 106, 109, 124, 136, 140, 141, 149, 1843 | 2be |

-continued

| Peptide SEQ ID No. | Amino acid sequence | Position of the peptide in the TEM protein(s) | Clinical interest |
|---|---|---|---|
| SEQ ID No. 214 | LDHWEPELNEAVPNDER | 160-176 for the protein of SEQ No. 122 | 2be |
| SEQ ID No. 215 | LDSWEPELNEAIPNDER | 160-176 for the proteins of SEQ No. 5, 7, 8, 9, 10, 12, 22, 24, 44, 51, 58, 60, 80, 81, 93, 105, 111, 119, 120, 121, 123, 126, 127, 138, 142, 143, 146, 153, 164 | 2be |
| SEQ ID No 216 | LHCWEPELNEAIPNDER | 160-176 for the protein of SEQ No. 82 | 2be |
| SEQ ID No. 217 | LLTDELLTLASR | 191-202 for the protein of SEQ No. 83 | 2be |
| SEQ ID No. 218 | LLTGELLTLASQQQLIDWMEADK | 191-213 for the protein of SEQ No. 65 | TEM |
| SEQ ID No. 219 | LLTGELLTLASR | 191-202 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 66, 67, 68, 69, 70, 71, 72, 73, 74, 75, 76, 77, 78, 79, 80, 81, 82, 84, 85, 86, 87, 88, 89, 90, 91, 92, 93, 94, 95, 96, 97, 98, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 1837, 1838, 1839, 1840, 1841, 1842, 1843, 1844 | TEM |
| SEQ ID No. 220 | LLTSELLTLASR | 191-202 for the protein of SEQ No. 99 | TEM |
| SEQ ID No. 221 | MSIQHFR | 1-7 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 83, 84, 85, 86, 88, 89, 90, 91, 92, 93, 94, 95, 96, 97, 98, 99, 100, 101, 102, 103, 104, 105, 106, 107, 108, 109, 110, 111, 112, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 150, 151, 152, 153, 154, 155, 156, 157, 158, 159, 160, 161, 162, 163, 165, 1837, 1838, 1839, 1840, 1841, 1842, 1843, 1844 | TEM |
| SEQ ID No. 222 | NMGDHVTR | 152-159 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 119, 120, 121, 122, 123, 124, 125, 126, 127, 128, 129, 130, 131, 132, 133, 134, 135, 136, | 2be |

-continued

| Peptide SEQ ID No. | Amino acid sequence | Position of the peptide in the TEM protein(s) | Clinical interest |
|---|---|---|---|
| | | 137, 138, 139, 140, 141, 142, 143, 145, 146, 147, 148, 149, 150, 151, 152, 153, 154, 155, 156, 157, 158, 159, 160, 161, 162, 163, 164, 165, 1837, 1838, 1839, 1840, 1841, 1842, 1843, 1844 | |
| SEQ ID No. 223 | QIAEICASLIK | 274-284 for the protein of SEQ No. 158 | TEM |
| SEQ ID No. 224 | QIAEIGASLIK | 274-284 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 93, 94, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 141, 142, 143, 144, 145, 146, 147, 148, 149, 150, 151, 153, 154, 155, 156, 157, 159, 160, 161, 162, 163, 164, 1837, 1838, 1839, 1840, 1841, 1842, 1843, 1844; 273-283 for the protein of sequence SEQ ID No. 165 | TEM |
| SEQ ID No. 225 | QIAEIGGSLIK | 274-284 for the protein of SEQ No. 140 | 2be |
| SEQ ID No. 226 | QIVEIGASLIK | 274-284 for the proteins of SEQ No 92, 95 | 2be |
| SEQ ID No. 227 | QQLIDWMADK | 203-212 for the protein of SEQ No. 165 | 2be |
| SEQ ID No. 228 | QQLIDWMEADK | 203-213 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 163, 164, 1837, 1838, 1839, 1840, 1841, 1842, 1843, 1844 | TEM |
| SEQ ID No. 229 | QQLIDWMEVDK | 203-213 for the proteins of SEQ No. 160, 161, 162 | TEM |
| SEQ ID No. 230 | QTAEIGASLIK | 274-284 for the protein of SEQ No. 152 | 2be |
| SEQ ID No. 231 | SALPAGWFIADK | 221-232 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, | TEM |

| Peptide SEQ ID No. | Amino acid sequence | Position of the peptide in the TEM protein(s) | Clinical interest |
|---|---|---|---|
| | | 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 137, 138, 139, 140, 141, 142, 143, 144, 145, 146, 147, 148, 149, 150, 151, 152, 153, 154, 156, 157, 158, 159, 160, 161, 162, 164, 1837, 1838, 1839, 1840, 1841, 1842, 1843, 1844; 220-231 for the protein of sequence SEQ ID No. 165 | |
| SEQ ID No. 232 | SGADER | 233-238 for the protein of SEQ No. 102 | TEM |
| SEQ ID No. 233 | SGAGER | 233-238 for the proteins of SEQ No. 1, 2, 6, 7, 9, 11, 12, 13, 15, 16, 17, 24, 27, 28, 29, 30, 31, 32, 33, 34, 35, 36, 37, 38, 39, 41, 42, 43, 49, 51, 52, 53, 54, 55, 56, 57, 58, 60, 61, 63, 65, 68, 69, 70, 71, 72, 73, 74, 75, 76, 77, 78, 79, 82, 85, 90, 91, 93, 94, 95, 96, 97, 99, 100, 101, 106, 107, 108, 109, 112, 114, 115, 116, 117, 118, 119, 123, 125, 130, 132, 134, 135, 136, 137, 139, 140, 142, 144, 145, 146, 147, 148, 149, 150, 151, 152, 153, 154, 156, 157, 158, 159, 160, 161, 162, 163, 1837, 1838, 1839, 1843, 1844 | TEM |
| SEQ ID No. 234 | SGAGVR | 233-238 for the protein of SEQ No. 138 | 2be |
| SEQ ID No 235 | SGANER | 233-238 for the protein of SEQ No. 131 | TEM |
| SEQ ID No. 236 | SGASER | 233-238 for the proteins of SEQ No. 3, 4, 8, 14, 18, 19, 20, 23, 48, 50, 62, 83, 84, 87, 89, 98, 103, 104, 110, 113, 124, 128, 129, 155 | 2be |
| SEQ ID No. 237 | SGASK | 233-237 for the proteins of SEQ No. 40, 45, 46, 47, 64, 66, 67, 88, 92, 1840, 1841, 1842 | 2be |
| SEQ ID No. 238 | SGGSER | 233-238 for the protein of SEQ No. 21 | 2be |
| SEQ ID No. 239 | SGTGER | 233-238 for the proteins of SEQ No. 120, 121 | 2be |
| SEQ ID No. 240 | SVLPAGWFIADK | 221-232 for the proteins of SEQ No. 136, 155, 163 | 2be |
| SEQ ID No. 241 | VAEPLLR | 214-220 for the protein of SEQ No. 53 | 2b |
| SEQ ID No. 242 | VAGPLLR | 214-220 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 135, 136, 137, 138, 139, 140, 141, 142, 143, 144, 145, 146, 147, 148, 149, 150, 151, 152, 153, 154, 155, 156, 157, 158, 159, 160, | TEM |

-continued

| Peptide SEQ ID No. | Amino acid sequence | Position of the peptide in the TEM protein(s) | Clinical interest |
|---|---|---|---|
| | | 161, 162, 163, 164, 1837, 1838, 1839, 1840, 1841, 1842, 1843, 1844; 213-219 for the protein of sequence SEQ ID No. 165 | |
| SEQ ID No. 243 | VAGPLMR | 214-220 for the protein of SEQ No. 134 | 2br |
| SEQ ID No. 244 | VALIPFFAAFCFPVFAHPETLVK | 8-30 for the proteins of SEQ No. 4, 9, 23, 46, 47, 51, 60, 68, 69, 70, 80, 81, 89, 93, 101, 106, 108, 110, 121, 123, 147, 155, 1841, 1842 | TEM |
| SEQ ID No. 245 | VALIPFFAAFCIPVFAHPETLVK | 8-30 for the protein of SEQ No. 63 | 2br |
| SEQ ID No. 246 | VALIPFFAAFCLPVFAHPDTLVK | 8-30 for the protein of SEQ No. 139 | TEM |
| SEQ ID No. 247 | VALIPFFAAFCLPVFAHPETLVK | 8-30 for the proteins of SEQ No. 1, 2, 3, 5, 6, 7, 8, 10, 11, 12, 13, 14, 15, 16, 17, 18, 19, 20, 21, 22, 24, 25, 26, 27, 28, 29, 30, 31, 32, 33, 34, 35, 36, 37, 38, 39, 40, 41, 42, 43, 44, 45, 48, 49, 50, 52, 53, 54, 55, 56, 57, 58, 59, 61, 62, 64, 65, 66, 67, 71, 72, 73, 74, 75, 76, 77, 78, 79, 82, 83, 84, 85, 86, 87, 88, 90, 91, 92, 94, 95, 96, 97, 98, 99, 100, 102, 103, 104, 105, 107, 109, 111, 112, 113, 114, 116, 117, 118, 119, 120, 122, 124, 125, 126, 127, 128, 129, 130, 131, 132, 133, 134, 135, 136, 137, 138, 140, 141, 142, 143, 144, 145, 146, 148, 149, 151, 152, 153, 154, 156, 157, 158, 159, 160, 161, 162, 163, 164, 165, 1837, 1838, 1839, 1840, 1843, 1844 | TEM |
| SEQ ID No. 248 | VALIPFFAAFCLPVFAHPK | 8-26 for the protein of SEQ No. 150 | TEM |
| SEQ ID No. 249 | VALIPFLAAFCLPVFAHPETLVK | 8-30 for the protein of SEQ No. 115 | 2be |
| SEQ ID No. 250 | VDAGQEQLDR | 82-91 for the proteins of SEQ No. 55, 62 | TEM |
| SEQ ID No. 251 | VDAGQEQLGR | 82-91 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 56, 57, 58, 59, 60, 61, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 146, 147, 148, 149, 151, 152, 153, 154, 155, 156, 157, 158, 160, 161, 162, 163, 164, 165, 1837, 1838, 1839, 1840, 1841, 1842, 1843, 1844 | TEM |
| SEQ ID No. 252 | VEDAEDQLGAR | 31-41 for the protein of SEQ No. 130 | 2b |
| SEQ ID No. 253 | VGYIELDLNSGK | 42-53 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 59, 60, 61, 62, 63, 64, 65, 66, 67, 68, 69, 70, 71, | TEM |

-continued

| Peptide SEQ ID No. | Amino acid sequence | Position of the peptide in the TEM protein(s) | Clinical interest |
|---|---|---|---|
| | | 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 1837, 1838, 1839, 1840, 1841, 1842, 1843, 1844 | |
| SEQ ID No. 254 | VGYIELDPNSGK | 42-53 for the protein of SEQ No. 58 | 2be |
| SEQ ID No. 255 | VGYIEMDLNSGK | 42-53 for the protein of SEQ No. 129 | 2be |
| SEQ ID No. 256 | VKPAEDK | 31-37 for the protein of SEQ No. 120 | 2be |
| SEQ ID No. 257 | VLLCGAELSR | 72-81 for the protein of SEQ No. 99 | TEM |
| SEQ ID No. 258 | VLLCGAVLSR | 72-81 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 1837, 1838, 1839, 1840, 1841, 1842, 1843, 1844 | TEM |
| SEQ ID No. 259 | WEPELNEAIPIDER | 163-176 for the protein of SEQ No. 128 | 2be |
| SEQ ID No. 260 | WEPELNEAIPNDER | 163-176 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 74, 75, 76, 77, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 116, 117, 118, 119, 120, 121, 123, 124, 125, 126, 127, 129, 130, 131, 132, 133, 134, 135, 136, 137, 138, 139, 140, 141, 142, 143, 144, 145, 146, 147, 148, 149, 150, 151, 152, 153, 154, 155, 156, 158, 159, 160, 161, 162, 163, 164, 1837, 1838, 1839, 1840, 1841, 1842, 1843, 1844 | TEM |
| SEQ ID No. 261 | YSPVTEK | 103-109 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, | 2be |

-continued

| Peptide SEQ ID No. | Amino acid sequence | Position of the peptide in the TEM protein(s) | Clinical interest |
|---|---|---|---|
| | | 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 1837, 1838, 1839, 1840, 1841, 1842, 1843, 1844 | |
| SEQ ID No. 1923 | DAEDK | 33-37 for the proteins of SEQ No. 2, 3, 7, 8, 11, 13, 15, 17, 20, 21, 22, 40, 42, 44, 54, 57, 58, 59, 61, 62, 63, 67, 84, 92, 104, 105, 111, 119, 124, 129, 143, 148, 164, 1839 | TEM |
| SEQ ID No. 1924 | GIIAALGPDGK | 242-252 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 1837, 1838, 1839, 1840, 1841, 1842, 1843, 1844; 241-251 for the protein of sequence SEQ ID No. 165 | TEM |
| SEQ ID No. 1925 | GSSGIIAALGPDGK | 239-252 for the proteins of SEQ No. 28, 42, 56, 69, 72, 111, 160, 161, 1844 | TEM |
| SEQ ID No. 1926 | ILESFR | 54-59 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 1837, 1838, 1839, 1840, 1841, 1842, 1843, 1844 | TEM |
| SEQ ID No. 1927 | SGAGK | 233-237 for the proteins of SEQ No. 10, 25, 26, 44, 59, 80, 86, 122, 133, 141, 143 | 2be |
| SEQ ID No. 1928 | SGTGK | 233-237 for the proteins of SEQ No. 5, 22, 81, 105, 111, 126, 164 | 2be |

In the clinical interest column, the entries 2b, 2br, 2be and 2ber correspond to the functional subgroups of TEM beta-lactamases which the corresponding peptide makes it possible to detect. Thus, the detection of a 2be peptide indicates the presence of a beta-lactamase with an extended spectrum (ESBL) capable of hydrolysing penicillins, first-generation cephalosporins such as cephaloridine and cefalotin, and at least one antibiotic from the oxyimino-beta-lactam class such as cefotaxime, ceftazidime or monobactams such as aztreonam.

The entry TEM indicates a common peptide between at least two of the subgroups 2b, 2br and 2be or 2ber. The corresponding peptide indicates the presence of a TEM beta-lactamase and the presence of a mechanism of resistance to at least penicillins and first-generation cephalosporins.

The detection of a mechanism of resistance to ESBL (extended-spectrum beta-lactamase) cephalosporins, induced by the TEM protein, is characterised by the detection of at least one resistance-marking 2be peptide, chosen from the sequences SEQ ID No. 168, SEQ ID No. 169, SEQ ID No. 179, SEQ ID No. 181, SEQ ID No. 186, SEQ ID No. 199, SEQ ID No. 200, SEQ ID No. 205, SEQ ID No. 206, SEQ ID No. 208, SEQ ID No. 212, SEQ ID No. 213, SEQ ID No. 214, SEQ ID No. 215, SEQ ID No. 216, SEQ ID No. 217, SEQ ID No. 222, SEQ ID No. 225, SEQ ID No. 226, SEQ ID No. 227, SEQ ID No. 230, SEQ ID No. 234, SEQ ID No. 236, SEQ ID No. 237, SEQ ID No. 238, SEQ ID No. 239, SEQ ID No. 240, SEQ ID No. 249, SEQ ID No. 254, SEQ ID No. 255, SEQ ID No. 256, SEQ ID No. 259, SEQ ID No. 261, SEQ ID No. 1927, SEQ ID No. 1928.

The detection of a mechanism of resistance to cephalosporins induced by the expression of the CMY protein is characterised by the detection of at least one peptide belonging to the CMY protein and to its different sequence variants SEQ ID No. 262 to SEQ ID No. 311 and SEQ ID No. 1844 to SEQ ID No. 1870.

```
SEQ ID No. 262:
MQQRQSILWGAVATLMWAGLAHAGEASPVDPLRPVVDASIQPLLKEHRIPGMAVAV
LKDGKAHYFNYGVANRESGASVSEQTLFEIGSVSKTLTATLGAYAVVKGAMQLDDK
ASRHAPWLKGSVFDSITMGELATYSAGGLPLQFPEEVDSSEKMRAYYRQWAPVYS
PGSHRQYSNPSIGLFGHLAASSLKQPFAQLMEQTLLPGLGMHHTYVNVPKQAMAS
YAYGYSKEDKPIRVNPGMLADEAYGIKTSSADLLAFVKANIGGVDDKALQQAISLTH
KGHYSVGGMTQGLGWESYAYPVTEQTLLAGNSAKVILEANPTAAPRESGSQVLFN
KTGSTNGFGAYVAFVPARGIGIVMLANRNYPIPARVKAAHAILAQLAG

SEQ ID No. 263:
MQQRQSILWGAVATLMWAGLAHAGEASPVDPLRPVVDASIQPLLKEHRIPGMAVAV
LKDGKAHYFNYGVANRESGAGVSEQTLFEIGSVSKTLTATLGAYAVVKGAMQLDDK
ASRHAPWLKGSAFDSITMGELATYSAGGLPLQFPEEVDSSEKMRAYYRQWAPVYS
PGSHRQYSNPSIGLFGHLAASSLKQPFAPLMEQTLLPGLGMHHTYVNVPKQAMAS
YAYGYSKEDKPIRVNPGMLADEAYGIKTSSADLLRFVKANIGGVDDKALQQAISLTH
QGHYSVGGMTQGLGWESYAYPVTEQTLLAGNSAKVILEANPTAAPRESGSQVLFN
KTGSTNGFGAYVAFVPARGIGIVMLANRNYPIEARIKAAHAILAQLAG

SEQ ID No. 264:
MQQRQSILWGAVATLMWAGLAHAGEASPVDPLRPVVDASIQPLLKEHRIPGMAVAV
LKDGKAHYFNYGVANRESGAGVSEQTLFEIGSVSKTLTATLGAYAVVKGAMQLDDK
ASRHAPWLKGSAFDSITMGELATYSAGGLPLQFPEEVDSSEKMRAYYRQWAPVYS
PGSHRQYSNPSIGLFGHLAASSLKQPFAPLMEQTLLPGLGMHHTYVNVPKQAMAS
YAYGYSKEDKPIRVNPGMLADEAYGIKTSSADLLRFVKANIGGVDDKALQQAISLTH
QGHYSVGGMTQGLGWESYAYPVTEQTLLAGNSAKVSLEANPTAAPRESGSQVLFN
KTGSTNGFGAYVAFVPARGIGIVMLANRNYP1EARIKAAHAILAQLAG

SEQ ID No. 265:
MMKKSLCCALLLTASFSTFASAKTEQQIADIVNRTITPLMQEQAIPGMAVAIIYQGKPY
YFTWGKADIANNHPVTQQTLFELGSVSKTFNGVLGGDAIARGEIKLSDPVTKYWPEL
TGKQWQGISLLHLATYTAGGLPLQIPDDVTDKAALLRFYQNWQPQWAPGAKRLYA
NSSIGLFGALAVKPSGMSYEEAMTRRVLQPLKLAHTWITVPQNEQKDYAWGYREG
KPVHVSPGQLDAEAYGVKSNVTDMARWVQVNMDASRVQEKTLQQGIALAQSRYW
RIGDMYQGLGWEMLNWPLKADSIINGSDSKVALAALPAVEVNPPAPAVKASWVHKT
GSTGGFGSYVAFVPEKNLGIVMLANKSYPNPVRVEAAWRILEKLQ

SEQ ID No. 266:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYAWGYR
EGKPVHVSPGQLDAEAYGVKSSVIDMARWVQANMDASHVQEKTLQQGIALAQSRY
WRIGDMYQGLGWEMLNWPLKADSIINGSDSKVAFAALPAVEVNPPAPAVKASWVH
KTGSTGGFGSYVAFVPEKNLGIVMLANKSYPNPVRVEAAWRILEKLQ

SEQ ID No. 267:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYAWGYR
EGKPVHVSPGQLDAEAYGVKSSVIDMARWVQANMDASHVQEKTLQQGIALAQSRY
WRIGDMYQGLGWEMLNWPLKADSIINGNGSDSKVALAALPAVEVNPPAPAVKASW
VHKTGSTGGFGSYVAFVPEKNLGIVMLANKSYPNPVRVEAAWRILEKLQ

SEQ ID No. 268:
MKKSLCCALLLTASFSTFAAAKTEQQIADIVNRTITPLMQEQAIPGMAVAVIYQGKPY
YFTWGKADIANNHPVTQQTLFELGSVSKTFNGVLGGDAIARGEIKLSDPVTKYWPEL
```

-continued

TGKQWQGISLLHLATYTAGGLPLQIPDDVTDKAALLHFYQNWQPQWTPGAKRLYA
NSSIGLFGALAVKPSGMSYEEAMTRRVLQPLKLAHTWITVPQNEQKDYAWGYREG
KPVHVSPGQLDAEAYGVKSSVIDMARWVQANMDASHVQEKTLQQGIALAQSRYW
RIGDMYQGLGWEMLNWPLKADSIINGSDNKVALAALPAVEVNPPAPAVKASWVHKT
GSTGGFGSYVAFVPEKNLGIVMLANKSYPNPVRVEAAWRILEKLQ

SEQ ID No. 269:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGELAVKPSGMSYEEAMTRRVLQPLKLAHTWITVPQNEQKDYAWGYR
EGKPVHVSPGKLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ

SEQ ID No. 270:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYAWGYR
EGKPVHVSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAYWRILEKLQ

SEQ ID No. 271:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYAWGYR
EGKPVHVSPGQLDAGAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ

SEQ ID No. 272:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGISLLHLATYTAGGLPLQIPDDVTDKAALLHFYQNWQPQWTPGAKRLY
ANSSIGLFGALAVKPSGMSYEEAMTRRVLQPLKLAHTWITVPQNEQKDYAWGYRE
GKPVHVSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ

SEQ ID No. 273:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYAWGYR
EGKAVHVSPGQLDAEAYGVKSSVIDMARWVQVNMDASRVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ

SEQ ID No. 274:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYAWGYR
EGKPVYVSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ

SEQ ID No. 275:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGELAVKPSGMSYEEAMTRRVLQPLKLAHTINITVPQNEQKDYAWGYR
EGKPVHVSPGQLDAEAYGVKSSVIDMARWVQANMDASHVQEKTLQQGIALAQSRY
WRIGDMYQGLGWEMLNWPLKADSIINGSDNKVALAALPAVEVNPPAPAVKASWVH
KTGSTGGFGSYVAFVPEKNLGIVMLANKSYPNPVRVEAAWRILEKLQ

SEQ ID No. 276:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYAWGYR
EGKPVHVSPGRLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ

SEQ ID No. 277:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP

ELTGKQWQGIRLLHLATYTAGGLPLQFPDDVRDKAALLHFYQNWQPQWTPGAKRL
YANSSIGLFGELAVKPSGMSYEEAMTRRVLQPLKLAHTWITVPQNEQKDYAWGYR
EGKPVHVSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ

SEQ ID No. 278:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYAWGYR
EGKPVHGSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ

SEQ ID No. 279:
MMKKSLCCALLLTASFSTFAAAKTEQQIADIVNRTITPLMQEQAIPGMAVAVIYQGKP
YYFTVWGKADIANNHPVTQQTLFELGSVSKTFNGVLGGDCIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPENEQKDYAWGYRE
GKPVHVSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ

SEQ ID No. 280:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVTDKAALLHFYQNWQPQINTPGAKRLY
ANSSIGLFGALAVKPSGMSYEEAMTRRVLQPLKLAHTWITVPQNEQKDYAWGYRE
GKPVHVSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ

SEQ ID No. 281:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYACGYRE
GKPVHVSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ

SEQ ID No. 282:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGISLLHLATYTAGGLPLQIPDDVTDKAALLRFYQNWQPQWTPGAKRLY
ANSSIGLFGTLAVKPSGMSYEEAMTRRVLQPLKLAHTWITVPQSEQKDYAWGYRE
GKPVHVSPGQLDAEAYGVKSSVIDMAHWVQANMDASHVQEKTLQQGIELAQSRY
WRIGDMYQGLGWEMLNWPLKADSIINGSDSKVALAALPAVEVNPPAPAVKASWVH
KTGYTGGFGSYVAFVPEKNLGIVMLANKSYPNPVRVEAAWRILEKLQ

SEQ ID No. 283:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYAWGYR
EGKPVHVSPEQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ

SEQ ID No. 284:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYAWGYR
EGKPVHVSPGQLDAEAYGVKSSVIDMARWVQANMDASHVQEKTLQQGIALAQSRY
WRIGDMYQGLGWEMLNWPLKADSIINGSDSKVAALPAVEVNPPAPAVKASWVHKT
GSTGGFGSYVAFVPEKNLGIVMLANKSYPNPVRVEAAWRILEKLQ

SEQ ID No. 285:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFAALAVKPSGMSYEEAMTRRVLQPLKLAHTWITVPQNEQKDYAWGYRE
GKPVHVSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ

SEQ ID No. 286:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP

-continued

ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYAWGYR
EGKPVHVSPGQLDAEAYGVKSSVIDMARWVQANMDASHVQEKTLQQGIALAQSRY
WRIGDMYQGLGWEMLNWPLKADSIINGSDSKVAPAVEVNPPAPAVKASWVHKTGS
TGGFGSYVAFVPEKNLGIVMLANKSYPNPVRVEAAWRILEKLQ

SEQ ID No. 287:
MMKKSLCCALLLTASFSTFAAAKTEQQIADIVNRTITPLMQEQAIPGMAVAIIYQGKPY
YFTWGKADIANNHPVTQQTLFELGSVSKTFNGVLGGDAIARGEIKLSDPVTKYWPEL
TGKQWQGISLLHLATYTAGGLPLQIPDDVTDKAALLRFYQNWQPQWTPGAKRLYA
NSSIGLFGALAVKPSGMSYEEAMTRRVLQPLKLAHTWITVPQNEQKDYAWGYREG
KPVHVTPGQLDAEAYGVKSNVTDMARWIQVNMDASRVQEKTLQQGIALAQSRYW
RIGDMYQGLGWEMLNWPLKADSIINGSDSKVALAALHTVEVNPPAPAVKASWVHKT
GSTGGFGSYVAFIPEKNLGIVMLANKSYPNPVRVEAAWRILEKLQ

SEQ ID No. 288:
MMKKSICCALLLTASFSTFAAAKTEQQIADIVNRTITPLMQEQAIPGMAVAl1YEGKPY
YFTWGKADIANNHPVTQQTLFELGSVSKTFNGVLGGDAIARGEIKLSDPVFKYWPEL
TGKQWRGISLLHLATYTAGGLPLQIPDEVTDKAELLRFYQNWQPQWTPGAKRLYAN
SSIGLFGALVVKPSGMSYEEAMTRRVLQPLKLAHTWITVPQSEQKNYAWGYREGK
PVHVSPGQLDAEAYGVKSSVIDMARWVQANMDASHVQEKTLQQGIELAQSRYWRI
GDMYQGLGWEMLNWPLKADSIINGSDSKVALAALPAVEVNPPAPAVKASWVHKTG
STGGFGSYVAFVPEKNLGIVMLANKSYPNPARVEAAWRILEKLQ

SEQ ID No. 289:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYAWGYR
EGKPVHVSPGQLELDAEAYGVKSSVIDMARWVQANMDASHVQEKTLQQGIALAQS
RYWRIGDMYQGLGWEMLNWPLKADSIINGSDSKVALAALPAVEVNPPAPAVKASW
VHKTGSTGGFGSYVAFVPEKNLGIVMLANKSYPNPVRVEAAWRILEKLQ

SEQ ID No. 290:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGEAIARGEIKLSDPVTKYWPE
LTGKQWQGIRLLHLATYTAGGLPLQIPDDVRDKAALLHFYQNWQPQWTPGAKRLY
ANSSIGLFGALAVKPSGMSYEEAMTRRVLQPLKLAHTWITVPQNEQKDYAWGYRE
GKPVHVSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ

SEQ ID No. 291:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYAWGYR
EGKPVHVSPGQFDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ

SEQ ID No. 292:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYAWGYR
EGKPVHVSPGQLDAEAYGVKSSVIDMARWVQANMDASHVQEKTLQQGIALAQSRY
WRIGDMYQGLGWEMLNWPLKTDSIINGSDSKVALAALPAVEVNPPAPAVKASWVH
KTGSTGGFGSYVAFVPEKNLGIVMLANKSYPNPVRVEAAWRILEKLQ

SEQ ID No. 293:
MQQRQSILWGAVATLMWAGLAHAGEASPVDPLRPVVDASIQPLLKEHRIPGMAVAV
LKDGKAHYFNYGVANRESGASVSEQTLFDIGSVSKTLTATLGAYAVVKGAMQLDDK
ASRHAPWLKGSVFDSITMGELATYSAGGLPLQFPEEVDSSEKMRAYYRQWAPVYS
PGSHRQYSNPSIGLFGHLAASSLKQPFAQLMEQTLLPGLGMHHTYVNVPKQAMAS
YAYGYSKEDKPIRVNPGMLADEAYGIKTSSADLLAFVKANIGGVDDKALQQAISLTH
KGHYSVGGMTQGLGWESYAYPVTEQTLLAGNSAKVILEANPTAAPRESGSQVLFN
KTGSTNGFGAYVAFVPARGIGIVMLANRNYPIPARVKAAHAILAQLAG

SEQ ID No. 294:
MQQRQSILWGAVATLMWAGLAHAGEASPVDPLRPVVDASIQPLLKEHRIPGMAVAV
LKDGKAHYFNYGVANRESGASVSEQTLFDIGSVSKTLTATLGAYANNKGAMQLDDK
ASRHAPWLKGSVFDSITMGELATYSAGGLPLQFPEEVDSSEKMRAYYRQWAPVYS
PGSHRQYSNPSIGLFGHLAASSLKQPFAQLMEQTLLPGLGMHHTYVNVPKQAMAS
YAYGYSKEDKPIRVNPGMLADEAYGIKTSSADLLAFVKANIGGVDDKALQQAISLTH
KGHYSVGGMTQGLGWESYAYPVTEQTLLAGNSAKVSLEANPTAAPRESGSQVLFN
KTGSTNGFGAYVAFVPARGIGIVMLANRNYPIPARVKAAHAILAQLAG

SEQ ID No. 295:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWS

-continued
ELTGKQWQGISLLHLATYTAGGLPLQIPDDVTDKTALLHFYQNWQPQWAPGAKRLY
ANSSIGLFGALAVKPSGMSYEEAMTRRVLQPLKLAHTWITVPQSEQKDYAWGYRE
GKPVHVSPGQLDAEAYGVKSSVIDMARWVQANMDASRVQEKTLQQGIALAQSRY
WRIGDMYQGLGWEMLNWPLKADSIINGSDSKVALAAIPAVEVNPPAPAVKASWVHK
TGSTGGFGSYVAFVPEKNLGIVMLANKSYPNPIRVEAAWRILEKLQ SEQ ID No. 296:
MMKKSLCCALLLTASFSTFASAKTEQQIADIVNRTITPLMQEQAIPGMAVAVIYQGKT
YYFTWGKADIANNHPVTQQTLFELGSVSKTFNGVLGGDAIARGEIKLSDPVTKYWP
ELTGKQWQDISLLHLATYTAGGLPLQIPDDVTDKTALLHFYQNWQPQWAPGAKRLY
ANSSIGLFGALAVKPSGMSYEEAMTRRVLQPLKLAHTWITVPQSEQKDYAWGYRE
GKPVHVSPGQLDAEAYGVKSNVTDMARWVQVNMDASRVQEKTLQQGIALAQSRY
WRIGDMYQGLGWEMLNWPLKADSIINGSDSKVALAALPAVEVNPPAPAVKASVVVH
KTGSTGGFGSYVAFVPEKNLGIVMLANKSYPNPVRVEAAWRILEKLQ SEQ ID No. 297:
MMKKSLCCALLLTAPLSTFAAAKTEQQIADIVNRTITPLMQEQAIPGMAVAVIYQGKP
YYFTWGKADITNNHPVTQQTLFELGSVSKTFNGVLGGDAIARGEIKLSDPVTKYWPE
LTGKQWQGISLLHLATYTAGGLPLQIPDDVTDKAALLRFYQNWQPQWAPGAKRLYA
NSSIGLFGALAVKPSGMSYEEAMTRRVLQPLKLAHTWIKVPQSEQKDYAWGYREG
KAVHVSPGQLDAEAYGVKSSVIDMARWVQVNMDASRVQEKTLQQGIALAQSRYW
RIGDMYQGLGWEMLNWPLKADSIINGSDSKVALAALPAVEVNPPAPAVKASWVHKT
GSTGGFGSYVAFVPEKNLGIVMLANKSYPNPVRVEAAWRILEKLQ SEQ ID No. 298:
MMKKSICCALLLTASFSTFAATKTEQQIADIVNRTITPLMQEQAIPGMAVAIIYEEKPY
YFTWGKADIANNHPVTQQTLFELGSVSKTFNGVLGGDAIARGEIKLSDPVTKYWPEL
TGKQWRGISLLHLATYTAGGLPLQIPDEVTDKAALLRFYQNWQPQWTPGAKRLYAN
SSIGLFGALAVKPSGMSYEEAMTRRVLQPLKLAHTWITVPQSEQKNYAWGYREGK
PVHVSPGQLDAEAYGVKSSVIDMARWVQANMDASHVQEKTLQQGIELAQSRYWRI
GDMYQGLGWEMLNWPLKADSIINGSDSKVALAALPAVEVNPPAPAVKASWVHKTG
STGGFGSYVAFVPEKNLGIVMLANKSYPNPARVEAAWRILEKLQ SEQ ID No. 299:
GPGHLFAFNYGTDFMMKKSLCCALLLTASFSTFAAAKTEQQIADIVNRTITPLMQEQ
AIPGMAVAVIYQGKPYYFTWGKADIANNHPVTQQTLFELGSVSKTFNGVLGGDAIAR
GEIKLSDPVTKYWPELTGKQWQGIRLLHLATYTAGGLPLQIPDDVRDKAALLHFYQN
WQPQWTPGAKRLYANSSIGLFGALAVKPSGMSYEEAMTRRVLQPLKLAHTWITVP
QNEQKDYAWGYREGKPVHASPGQLDAEAYGVKSSVIDMARWVQANMDASHVQE
KTLQQGIALAQSRYWRIGDMYQGLGWEMLNWPLKADSIINGSDSKVALAALPAVEV
NPPAPAVKASWVHKTGSTGGFGSYVAFVPEKNLGIVMLANKSYPNPVRVEAAWRIL
EKLQ SEQ ID No. 300:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQVUTPGAKRL
YANSSIGLFGALAVKPSGMSYEEAMTRRVLQPLKLAHTWITVPQNEQKDYAWGYR
EGKPVHVSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ SEQ ID No. 301:
MQQRQSILWGAVATLMWAGLAHAGEASPVDPLRPVVDASIQPLLKEHRIPGMAVAV
LKDGKAHYFNYGVANRESGAGVSEQTLFEIGSVSKTLTATLGAYAVVKGAMQLDDK
ASRHAPWLKGSAFDSITMGELATYSAGGLPLQFPEEVDSSEKMRAYYRQWAPVYS
PGSHRQYSNPSIGLFGHLAASSLKQPFAPLMEQTLLPGLGMHHTYVNVPKQAMAS
YAYGYSKEDKPIRVNPGMLADEAYGIKTSSADLLRFVKANIGGVDDKALQQAISLTH
QGHYSVGGMTQGLGWESYAYPVTEQTLLAGNSAKVILEANPTAAPRESGSQVLFN
KTGSTNGFGAYVAFVPARGIGIVMLANRNYPNEARIKAAHAILAQLAG SEQ ID No. 302:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYARGYRE
GKPVHVSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ SEQ ID No. 303:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYARGYRE
GKPVHVSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWNH
KTGSTGGFGSYVAFVPEKNLGIVMLANKSYPNPVRVEAAWRILEKLQ SEQ ID No. 304:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YSNSSIGLFGALAVKPSGMSYEEAMTRRVLQPLKLAHTWITVPQNEQKDYARGYRE
GKPVHVSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKNYPNPVRVEAAWRILEKLQ SEQ ID No. 305:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGELAVKPSGMSYEEAMTRRVLQPLKLAHTWITVPQNEQKDYAWGYR
EGKPVHVSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ SEQ ID No. 306:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYALGYRE
GKPVHVSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ SEQ ID No. 307:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKFSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYAWGYR
EGKPVHVSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ SEQ ID No. 308:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYARGYRE
GKPVHVSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKNYPNPVRVEAAWRILEKLQ SEQ ID No. 309:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYARGYRE
GKPVHVSPGQLDAEAYGVKSSVIDMARWVQANMDASHVQEKTLQQGIALAQSRY
WRIGDMYQGLGWEMLNWPLKADSIINGSDSKVALAALPAVEINPPAPAVKASWVHK
TGSTGGFGSYVAFVPEKNLGIVMLANKSYPNPVRVEAAWRILEKLQ SEQ ID No. 310:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YSNSSIGLFGALAVKPSGMSYEEAMTRRVLQPLKLAHTWITVPQNEQKDYARGYRE
GKPVHVSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ SEQ ID No. 311:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYARGYRE
GKPVHVSPGQLNAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKNYPNPVRVEAAWRILEKLQ SEQ ID No. 1844:
MQQRQSILWGAVATLMWAGLAHAGEASPVDPLRPVVDASIQPLLKEHRIPGMAVAV
LKDGKAHYFNYGVANRESGAGVSEQTLFEIGSVSKTLTATLGAYAVVKGAMQLDDK
ASRHAPWLKGSAFDSITMGELATYSAGGLPLQFPEEVDSSEKMRAYYRQWAPVYS
PGSHRQYSNPSIGLFGHLAASSLKQPFAPLMEQTLLPGLGMHHTYVNVPKQAMAS
YAYGYSKEDKPIRVNPGMLADEAYGIKTSSADLLRFVKANIGGVDDKALQQAISLTH
QGHYSVGGMTQGLGWESYAYPVTEQTLLAGNSAKVILEANPTAAPRESGSQVLFN
KTGSTNGFGAYVAFVPARGIGIVMLANRNYPIEARIKAAHAILAQLAG SEQ ID No. 1845:
MQQRQSILWGAVATLMINAGLAHAGEASPVDPLRPVVDASIQPLLKEHRIPGMAVAV
LKDGKAHYFNYGVANRESGAGVSEQTLFEIGSVSKTLTATLGAYAVVKGAMQLDDK
ASRHAPWLKGSAFDSITMGELATYSAGGLPLQFPEEVDSSEKMRAYYRQWAPVYS
PGSHRQYSNPSIGLFGHLAASSLKQPFAPLMEQTLLPGLGMMHHTYVNVPKQAMAS
YAYGYSKEDKPIRVNPGMLADEAYGIKTSSADLLRFVKANIGGVDDKALQQAISLTH
QGHYSVGGMTQGLGWESYAYPVTEQTLLAGNSAKVSLEANPTAAPRESGSQVLFN
KTGSTNGFGAYVAFVPARGIGIVMLANRNYPIEARIKAAHAILAQLAG SEQ ID No. 1846:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYAWGYR
EGKPVHVSPGQLDAEAYGVKSSVIDMARWVQANMDASHVQEKTLQQGIALAQSRY
WRIGDMYQGLGWEMLNWPLKADSIINGSDSKVAFAALPAVEVNPPAPAVKASWVH
KTGSTGGFGSYVAFVPEKNLGIVMLANKSYPNPVRVEAAWRILEKLQ SEQ ID No. 1847:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYAWGYR
EGKPVHVSPGQLDAEAYGVKSSVIDMARWVQANMDASHVQEKTLQQGIALAQSRY
WRIGDMYQGLGWEMLNWPLKADSIINGNGSDSKVALAALPAVEVNPPAPAVKASW
VHKTGSTGGFGSYVAFVPEKNLGIVMLANKSYPNPVRVEAAWRILEKLQ SEQ ID No. 1848:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYAWGYR
EGKPVHVSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAYWRILEKLQ SEQ ID No. 1849:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGELAVKPSGMSYEEAMTRRVLQPLKLAHTWITVPQNEQKDYAWGYR
EGKPVHVSPGQLDAEAYGVKSSVIDMARWVQANMDASHVQEKTLQQGIALAQSRY
WRIGDMYQGLGWEMLNWPLKADSIINGSDNKVALAALPAVEVNPPAPAVKASWVH
KTGSTGGFGSYVAFVPEKNLGIVMLANKSYPNPVRVEAAWRILEKLQ SEQ ID No. 1850:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYAWGYR
EGKPVHVSPGQLDAEAYGVKSSVIDMARWVQANMDASHVQEKTLQQGIALAQSRY
WRIGDMYQGLGWEMLNWPLKADSIINGSDSKVAALPAVEVNPPAPAVKASWVHKT
GSTGGFGSYVAFVPEKNLGIVMLANKSYPNPVRVEAAWRILEKLQ SEQ ID No. 1851:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYAWGYR
EGKPVHVSPGQLDAEAYGVKSSVIDMARWVQANMDASHVQEKTLQQGIALAQSRY
WRIGDMYQGLGWEMLNWPLKADSIINGSDSKVAPAVEVNPPAPAVKASWVHKTGS
TGGFGSYVAFVPEKNLGIVMLANKSYPNPVRVEAAWRILEKLQ SEQ ID No. 1852:
MMKKSLCCALLLTASFSTFAAAKTEQQIADIVNRTITPLMQEQAIPGMAVAVLYQGKP
YYFTWGKADIANNHPVTQQTLFELGSVSKTFNGVLGGDAIARGEIKLSDPVTKYLPE
LTGKQWQGISLLHLATYTAGGLPLQIPDDVTDKAALLRFYQNWQPQWTPGAKRLYA
NSSIGLFGALAVKPSGMSYEEAMTRRVLQPLKLAHTWITVPQNEQKDYAWGYREG
KPVHVTPGQLDAEAYGVKSNVTDMARWIQVNMDASRVQEKTLQQGIALAQSRYW
RIGDMYQGLGWEMLNWPLKADSIINGSDSKVALAALPTVEVNPPAPAVKASWVHKT
GSTGGFGSYVAFVPEKNLGIVMLANKSYPNPVRVEAAWRILEKLQ SEQ ID No. 1853:
MMKKSICCALLLTASFSTFAAAKTEQQIADIVNRTITPLMQEQAIPGMAVAIIYEGKPY
YFTWGKADIANNHPVTQQTLFELGSVSKTFNGVLGGDAIARGEIKLSDPVTKYWPEL
TGKQWRGISLLHLATYTAGGLPLQIPDDVTDKAALLRFYQNWQPQWTPGAKRLYAN
SSIGLFGALAVKPSGMSYEEAMTRRVLQPLKLAHTWITVPQSEQKNYAWGYREGK
PVHVSPGQLDAEAYGVKSSVIDMARWVQANMDASHVQEKTLQQGIELAQSRYWRI
GDMYQGLGWEMLNWPLKADSIINGSDSKVALAALPAVEVNPPAPAVKASWVHKTG
STGGFGSYVAFVPEKNLGIVMLANKSYPNPARVEAAWRILEKLQ SEQ ID No. 1854:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYAWGYR
EGKPVHVSPGQLDAEAYGVKSSVIDMARWVQANMDASHVQEKTLQQGIALAQSRY
WRIGDMYQGLGWEMLNWPLKTDSIINGSDSKVALAALPAVEVNPPAPAVKASWVH
KTGSTGGFGSYVAFVPEKNLGIVMLANKSYPNPVRVEAAWRILEKLQ SEQ ID No. 1855:
MMKKSLCCALLLTASLSTFAAAKTEQQIADIVNRTITPLMQEQAIPGMAIAVIYQGKPY
YFTWGKADITNNHPVTQQTLFELGSVSKTFNGVLGGDAIARGEIKLSDPVTKYWPEL
TGKQWQGISLLHLATYTAGGLPLQIPDDVTDKAALLRFYQNWQPQWAPGAKRLYA
NSSIGLFGALAVKPSGMSYEEAMTRRVLQPLKLAHTWITVPQNEQKDYAWGYREG
KAVHVSPGQLDAEAYGVKSSVIDMARWVQVNMDASRVQEKTLQQGIALAQSRYVV
RIGDMYQGLGWEMLNWPLKADSIINGSDSKVALAALPAVEVNPPAPAVKASWVHKT
GSTGGFGSYVAFVPEKNLGIVMLANKSYPNPVRVEAAWRILEKLQ SEQ ID No. 1856:
MMKKSLCCALLLTASFSTFAAAKTEQQIADIVNRTITPLMQEQAIPGMAVAVIYQGKP
YYFTVVGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYAWGYR
EGKPVHVSPGQLDAEAYCVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ SEQ ID No. 1857:
MMKKSLCCALLLTASFSTFAAAKTEQQIADIVNRTITPLMQEQAIPGMAVAVIYQGKP
YYFTWGKADIANNHPVTQQTLFELGSVSKTFIGVLGGDAIARGEIKLSDPVTKYWPE
LTGKQWQGIRLLHLATYTAGGLPLQIPDDVRDKAALLHFYQNWQPQWTPGAKRLY
ANSSIGLFGALAVKPSGMSYEEAMTRRVLQPLKLAHTWITVPQNEQKDYAWGYRE
GKPVHVSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ SEQ ID No. 1858:
MMNRYAAALLLTASFSTFAAAKTEQQIADIVNRTITPLMQEQAIPGMAVAVIYQGKPY
YFTWGKADIANNHPVTQQTLFELGSVSKTFNGVLGGDAIARGEIKLSDPVTKYWPEL
TGKQWQGIRLLHLATYTAGGLPLQIPDDVRDKAALLHFYQNWQPQWTPGAKRLYA
NSSIGLFGALAVKPSGMSYEEAMTRRVLQPLKLAHTWITVPQNEQKDYAWGYREG
KPVHVSPGQLDAEAYGVKSSVIDMARWVQANMDASHVQEKTLQQGIALAQSRYW
RIGDMYQGLGWEMLNWPLKADSIINGSDSKVALAALPAVEVNPPAPAVKASWVHKT
GSTGGFGSYVAFVPEKNLGIVMLANKSYPNPVRVEAAWRILEKLQ SEQ ID No. 1859:
MMKKSLCCALLLTASFSTFAAAKTEQQIADIVNRTITPLMQEQAIPGMAVAVIYQGKP
YYFTVVGKADIANNHPVTQQTLFELGSVSKTFNGVLGGDA1ARGEIKLSDPVTKYWP
ELTGKQWQGIRLLHLATYTAGGLPLQIPDDVRDKAALLHFYQNWQPQWTPGAKRL
YANSSIGLFSALAVKPSGMSYEEAMTRRVLQPLKLAHTWITVPQNEQKDYAWGYRE
GKPVHVSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ SEQ ID No. 1860:
MQQRQSILWGAVATLMWAGLAHAGEASPVDPLRPVVDASIQPLLKEHRIPGMAVAV
LKDGKAHYFNYGVANRESGASVSEQTLFDIGSVSKTLTATLGAYAVVKGAMQLDDK
ASRHAPWLKGSVFDSITMGELATYSAGGLPLQFPEEVDSSEKMRAYYRQWAPVYS
PGSHRQYSNPSIGLFGHLAASSLKQPFAQLMEQTLLPGLGMHHTYVNVPKQAMAS
YAYGYSKEDKPIRVNPGMLADEAYGIKTSSADLLAFVKANIGGVDDKALQQAISLTH
KGHYSVGGMTQGLGWESYAYPVTEQTLLAGNSAKVILEANPTAAPRESGSQVLFN
KTGSTNGFGAYVAFVPARGIGIVMLANRNYPIPARVKAAHAILAQLAG SEQ ID No. 1861:
MQQRQSILWGAVATLMWAGLAHAGEASPVDPLRPVVDASIQPLLKEHRIPGMAVAV
LKDGKAHYFNYGVANRESGASVSEQTLFDIGSVSKTLTATLGAYAWKGAMQLDDK
ASRHAPWLKGSVFDSITMGELATYSAGGLPLQFPEEVDSSEKMRAYYRQWAPVYS
PGSHRQYSNPSIGLFGHLAASSLKQPFAQLMEQTLLPGLGMHHTYVNVPKQAMAS
YAYGYSKEDKPIRVNPGMLADEAYGIKTSSADLLAFVKANIGGVDDKALQQAISLTH
KGHYSVGGMTQGLGWESYAYPVTEQTLLAGNSAKVSLEANPTAAPRESGSQVLFN
KTGSTNGFGAYVAFVPARGIGIVMLANRNYPIPARVKAAHAILAQLAG SEQ ID No. 1862:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYAWGYR
EGKPVHVSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ SEQ ID No. 1863:
MQQRQSILWGAVATLMWAGLAHAGEASPVDPLRPWDASIQPLLKEHRIPGMAVAV
LKDGKAHYFNYGVANRESGAGVSEQTLFEIGSVSKTLTATLGAYAVVKGAMQLDDK
ASRHAPWLKGSAFDSITMGELATYSAGGLPLQFPEEVDSSEKMRAYYRQWAPVYS
PGSHRQYSNPSIGLFGHLAASSLKQPFAPLMEQTLLPGLGMHHTYVNVPKQAMAS
YAYGYSKEDKPIRVNPGMLADEAYGIKTSSADLLRFVKANIGGVDDKALQQAISLTH
QGHYSVGGMTQGLGWESYAYPVTEQTLLAGNSAKVILEANPTAAPRESGSQVLFN
KTGSTNGFGAYVAFVPARGIGIVMLANRNYPNEARIKAAHAILAQLAG SEQ ID No. 1864:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYARGYRE
GKPVHVSPGQLDAEAYGVKSSVIDMARINVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ SEQ ID No. 1865:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YSNSSIGLFGALAVKPSGMSYEEAMTRRVLQPLKLAHTWITVPQNEQKDYARGYRE
GKPVHVSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKNYPNPVRVEAAWRILEKLQ SEQ ID No. 1866:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGELAVKPSGMSYEEAMTRRVLQPLKLAHTWITVPQNEQKDYAWGYR
EGKPVHVSPGQLDAEAYGVKSSVIDMARINVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ SEQ ID No. 1867:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYINP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYARGYRE
GKPVHVSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKNYPNPVRVEAAWRILEKLQ SEQ ID No. 1868:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIPDDVRDKAALLHFYQNWQPQWTPGAKRL
YANSSIGLFGALAVKPSGMSYEEAMTRRVLQPLKLAHTWITVPQNEQKDYARGYRE
GKPVHVSPGQLDAEAYGVKSSVIDMARWVQANMDASHVQEKTLQQGIALAQSRY
WRIGDMYQGLGWEMLNWPLKADSIINGSDSKVALAALPAVEINPPAPAVKASWVHK
TGSTGGFGSYVAFVPEKNLGIVMLANKSYPNPVRVEAAWRILEKLQ SEQ ID No. 1869:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLQIIDDDVRDKAALLHFYQNWQPQWTPGAKRL
YSNSSIGLFGALAVKPSGMSYEEAMTRRVLQPLKLAHTWITVPQNEQKDYARGYRE
GKPVHVSPGQLDAEAYGVKSSVIDMARWVQANMDASHVQEKTLQQGIALAQSRY
WRIGDMYQGLGWEMLNWPLKADSIINGSDSKVALAALPAVEVNPPAPAVKASWVH
KTGSTGGFGSYVAFVPEKNLGIVMLANKSYPNPVRVEAAWRILEKLQ SEQ ID No. 1870:
MMKKSLCCALLLTASFSTFAAAKTEQQIADIVNRTITPLMQEQAIPGMAVAVIYQGKP
YYFTWGKADIANNHPVTQQTLFELGSVSKTFNGVLGGDAIARGEIKLSDPVTKYWP
ELTGKQWQGIRLLHLATYTAGGLPLKIPDDVRDKAALLHFYQNWQPQWTPGAKRLY
SNSSIGLFGALAVKPSGMSYEEAMTRRVLQPLKLAHTWITVPQNEQKDYARGYREG
KPVHVSPGQLDAEAYGVKSSVIDMARWVQANMDASHVQEKTLQQGIALAQSRYW
RIGDMYQGLGWEMLNWPLKADSIINGSDSKVALAALPAVEVNPPAPAVKASWVHKT
GSTVGFGSYVAFVPEKNLGIVMLANKSYPNPVRVEAAWRILEKLQ said peptides being chosen, preferably, from the peptides of sequence SEQ ID No. 312 to SEQ ID No. 350, SEQ ID No. 734, SEQ ID No. 735 and SEQ ID No. 1929 to SEQ ID No. 2007, as defined hereafter:

| Peptide SEQ ID No. | Amino acid sequence | Position of the peptide in the CMY protein |
|---|---|---|
| SEQ ID No. 312 | AALLHFYQNWQPQWTPGAK | 149-167 for the proteins of SEQ No. 266, 267, 269, 270, 271, 272, 273, 274, 275, 276, 277, 278, 279, 280, 281, 283, 284, 285, 286, 289, 290, 291, 292, 300, 302, 303, 304, 305, 306, 307, 308, 309, 310, 311, 1846, 1847, 1848, 1849, 1850, 1851, 1854, 1856, 1857, 1859, 1862, 1864, 1865, 1866, 1867, 1868, 1869, 1870; 148-166 for the protein of sequence SEQ ID No. 268; 163-181 for the protein of sequence SEQ ID No. 299; 148-166 for the protein of sequence SEQ ID No. 1858 |
| SEQ ID No. 313 | ADIANNHPVTQQTLFEL-GSVSK | 66-87 for the proteins of SEQ No. 265, 266, 267, 269, 270, 271, 272, 273, 274, 275, 276, 277, 278, 279, 280, 281, 282, 283, 284, 285, 286, 287, 288, 289, 290, 291, 292, 295, 296, 298, 300, 302, 303, 304, 305, 306, 307, 308, 309, 310, 311, 1846, 1847, 1848, 1849, 1850, 1851, 1852, 1853, 1854, 1856, 1857, 1859, 1862, 1864, 1865, 1866, 1867, 1868, 1869, 1870; 65-86 for the protein of sequence SEQ ID No. 268; 80-101 for the protein of sequence SEQ ID No. 299; 65-86 for the protein of sequence SEQ ID No. 1858 |
| SEQ ID No. 314 | ADSIINGSDSK | 300-310 for the proteins of SEQ No. 265, 266, 269, 270, 271, 272, 273, 274, 276, 277, 278, 279, 280, 281, 282, 283, 284, 285, 286, 287, 288, 290, 291, 295, 296, 297, 298, 300, 302, 303, 304, 305, 306, 307, 308, 309, 310, 311, 1846, 1848, 1850, 1851, 1852, 1853, 1855, 1856, 1857, 1859, 1862, 1864, 1865, 1866, 1867, 1868, 1869, 1870; 302-312 for the protein of sequence SEQ ID No. 289; 314-324 for the protein of sequence SEQ ID No. 299; 299-309 for the protein of sequence SEQ ID No. 1858 |
| SEQ ID No. 315 | ASWVHK | 330-335 for the proteins of SEQ No. 265, 266, 269, 270, 271, 272, 273, 274, 275, 276, 277, 278, 279, 280, 281, 282, 283, 285, 287, 288, 290, 291, 292, 295, 296, 297, 298, 300, 302, 303, 304, 305, 306, 307, 308, 309, 310, 311, 1846, 1848, 1849, 1852, 1853, 1854, 1855, 1856, 1857, 1859, 1862, 1864, 1865, 1866, 1867, 1868, 1869, 1870; 332-337 for the protein of sequence SEQ ID No. 267; 329-334 for the protein of sequence SEQ ID No. 268; 328-333 for the protein of sequence SEQ ID No. 284; 326-331 for the protein of sequence SEQ ID No. 286; 332-337 for the protein of sequence SEQ ID No. 289; 344-349 for the protein of sequence SEQ ID No. 299; 332-337 for the protein of sequence SEQ ID No. 1847; 328-333 for the protein of sequence SEQ ID No. 1850; 326-331 for the protein of sequence SEQ ID No. 1851; 329-334 for the protein of sequence SEQ ID No. 1858 |
| SEQ ID No. 316 | DYAWGYR | 218-224 for the proteins of SEQ No. 265, 266, 267, 269, 270, 271, 272, 273, 274, 275, 276, 277, 278, 279, 280, 282, 283, 284, 285, 286, 287, 289, 290, 291, 292, 295, 296, 297, 300, 305, 307, 1846, 1847, 1848, 1849, 1850, 1851, 1852, 1854, 1855, 1856, 1857, 1859, 1862, 1866; 217-223 for the protein of sequence SEQ ID No. 268; 232-238 for the protein of sequence SEQ ID No. 299; 217-223 for the protein of sequence SEQ ID No. 1858 |
| SEQ ID No. 317 | IGDMYQGLGWEMLNWPLK | 282-299 for the proteins of SEQ No. 265, 266, 267, 269, 270, 271, 272, 273, 274, 275, 276, 277, 278, 279, 280, 281, 282, 283, 284, 285, 286, 287, 288, 290, 291, 292, 295, 296, 297, 298, 300, 302, 303, 304, 305, 306, 307, 308, 309, 310, 311, 1846, 1847, 1848, 1849, 1850, 1851, 1852, 1853, 1854, 1855, 1856, 1857, 1859, 1862, 1864, 1865, 1866, 1867, 1868, 1869, 1870; 281-298 for the protein of sequence SEQ ID No. 268; 284-301 for the protein of sequence SEQ ID No. 289; 296-313 for the protein of sequence SEQ ID No. 299; 281-298 for the protein of sequence SEQ ID No. 1858 |
| SEQ ID No. 318 | LAHTWITVPQNEQK | 204-217 for the proteins of SEQ No. 265, 266, 267, 269, 270, 271, 272, 273, 274, 275, 276, 277, 278, 280, 281, 283, 284, 285, 286, 287, 289, 290, 291, 292, 300, 302, 303, 304, 305, 306, 307, 308, 309, 310, 311, 1846, 1847, 1848, 1849, 1850, 1851, 1852, 1854, 1855, 1856, 1857, 1859, 1862, 1864, 1865, 1866, 1867, 1868, 1869, 1870; 203-216 for the protein of sequence SEQ ID No. 268; 218-231 for the protein of sequence SEQ ID No. 299; 203-216 for the protein of sequence SEQ ID No. 1858 |
| SEQ ID No. 319 | LLHLATYTAGGLPLQI-PDDVR | 126-146 for the proteins of SEQ No. 266, 267, 269, 270, 271, 273, 274, 275, 276, 278, 279, 281, 283, 284, 285, 286, 289, 290, 291, 292, 300, 302, 303, 304, 305, 306, 307, 308, 309, 310, 311, |

| Peptide SEQ ID No. | Amino acid sequence | Position of the peptide in the CMY protein |
|---|---|---|
| | | 1846, 1847, 1848, 1849, 1850, 1851, 1854, 1856, 1857, 1859, 1862, 1864, 1865, 1866, 1867, 1868, 1869; 140-160 for the protein of sequence SEQ ID No. 299; 125-145 for the protein of sequence SEQ ID No. 1858 |
| SEQ ID No. 320 | LSDPVTK | 105-111 for the proteins of SEQ No. 265, 266, 267, 269, 270, 271, 272, 273, 274, 275, 276, 277, 278, 279, 280, 281, 282, 283, 284, 285, 286, 287, 288, 289, 290, 291, 292, 295, 296, 297, 298, 300, 302, 303, 304, 305, 306, 308, 309, 310, 311, 1846, 1847, 1848, 1849, 1850, 1851, 1852, 1853, 1854, 1855, 1856, 1857, 1859, 1862, 1864, 1865, 1866, 1867, 1868, 1869, 1870; 104-110 for the protein of sequence SEQ ID No. 268; 119-125 for the protein of sequence SEQ ID No. 299; 104-110 for the protein of sequence SEQ ID No. 1858 |
| SEQ ID No. 321 | LYANSSIGLFGALAVK | 169-184 for the proteins of SEQ No. 265, 266, 267, 270, 271, 272, 273, 274, 276, 278, 279, 280, 281, 283, 284, 286, 287, 289, 290, 291, 292, 295, 296, 297, 298, 300, 302, 303, 306, 307, 308, 309, 311, 1846, 1847, 1848, 1850, 1851, 1852, 1853, 1854, 1855, 1856, 1857, 1862, 1864, 1867, 1868; 168-183 for the protein of sequence SEQ ID No. 268; 183-198 for the protein of sequence SEQ ID No. 299; 168-183 for the protein of sequence SEQ ID No. 1858 |
| SEQ ID No. 322 | NLGIVMLANK | 353-362 for the proteins of SEQ No. 265, 266, 269, 270, 271, 272, 273, 274, 275, 276, 277, 278, 279, 280, 281, 282, 283, 285, 287, 288, 290, 291, 292, 295, 296, 297, 298, 300, 302, 303, 304, 305, 306, 307, 308, 309, 310, 311, 1846, 1848, 1849, 1852, 1853, 1854, 1855, 1856, 1857, 1859, 1862, 1864, 1865, 1866, 1867, 1868, 1869, 1870; 355-364 for the protein of sequence SEQ ID No. 267; 352-361 for the protein of sequence SEQ ID No. 268; 351-360 for the protein of sequence SEQ ID No. 284; 349-358 for the protein of sequence SEQ ID No. 286; 355-364 for the protein of sequence SEQ ID No. 289; 367-376 for the protein of sequence SEQ ID No. 299; 355-364 for the protein of sequence SEQ ID No. 1847; 351-360 for the protein of sequence SEQ ID No. 1850; 349-358 for the protein of sequence SEQ ID No. 1851; 352-361 for the protein of sequence SEQ ID No. 1858 |
| SEQ ID No. 323 | QWQGIR | 120-125 for the proteins of SEQ No. 266, 267, 269, 270, 271, 273, 274, 275, 276, 277, 278, 279, 280, 281, 283, 284, 285, 286, 289, 290, 291, 292, 300, 302, 303, 304, 305, 306, 307, 308, 309, 310, 311, 1846, 1847, 1848, 1849, 1850, 1851, 1854, 1856, 1857, 1859, 1862, 1864, 1865, 1866, 1867, 1868, 1869, 1870; 134-139 for the protein of sequence SEQ ID No. 299; 119-124 for the protein of sequence SEQ ID No. 1858 |
| SEQ ID No. 324 | SLCCALLLTASFSTFAAAK | 5-23 for the proteins of SEQ No. 266, 267, 269, 270, 271, 272, 273, 274, 275, 276, 277, 278, 279, 280, 281, 282, 283, 284, 285, 286, 287, 289, 290, 291, 292, 295, 300, 302, 303, 304, 305, 306, 307, 308, 309, 310, 311, 1846, 1847, 1848, 1849, 1850, 1851, 1852, 1854, 1856, 1857, 1859, 1862, 1864, 1865, 1866, 1867, 1868, 1869, 1870; 4-22 for the protein of sequence SEQ ID No. 268; 19-37 for the protein of sequence SEQ ID No. 299 |
| SEQ ID No. 325 | SSVIDMAR | 245-252 for the proteins of SEQ No. 266, 267, 269, 270, 271, 272, 273, 274, 275, 276, 277, 278, 279, 280, 281, 283, 284, 285, 286, 288, 290, 291, 292, 295, 297, 298, 300, 302, 303, 304, 305, 306, 307, 308, 309, 310, 311, 1846, 1847, 1848, 1849, 1850, 1851, 1853, 1854, 1855, 1856, 1857, 1859, 1862, 1864, 1865, 1866, 1867, 1868, 1869, 1870; 244-251 for the protein of sequence SEQ ID No. 268; 247-254 for the protein of sequence SEQ ID No. 289; 259-266 for the protein of sequence SEQ ID No. 299; 244-251 for the protein of sequence SEQ ID No. 1858 |
| SEQ ID No. 326 | SYPNPVR | 363-369 for the proteins of SEQ No. 265, 266, 269, 270, 271, 272, 273, 274, 275, 276, 277, 278, 279, 280, 281, 282, 283, 285, 287, 290, 291, 292, 296, 297, 300, 302, 303, 305, 306, 307, 309, 310, 1846, 1848, 1849, 1852, 1854, 1855, 1856, 1857, 1859, 1862, 1864, 1866, 1868, 1869, 1870; 365-371 for the protein of sequence SEQ ID No. 267; 362-368 for the protein of sequence SEQ ID No. 268; 361-367 for the protein of sequence SEQ ID No. 284; 359-365 for the protein of sequence SEQ ID No. 286; 365-371 for the protein of sequence SEQ ID No. 289; 377-383 for the protein of sequence SEQ ID No. 299; 365-371 for the |

-continued

| Peptide SEQ ID No. | Amino acid sequence | Position of the peptide in the CMY protein |
|---|---|---|
| | | protein of sequence SEQ ID No. 1847; 361-367 for the protein of sequence SEQ ID No. 1850; 359-365 for the protein of sequence SEQ ID No. 1851; 362-368 for the protein of sequence SEQ ID No. 1858 |
| SEQ ID No. 327 | TEQQIADIVNR | 24-34 for the proteins of SEQ No. 265, 266, 267, 269, 270, 271, 272, 273, 274, 275, 276, 277, 278, 279, 280, 281, 282, 283, 284, 285, 286, 287, 288, 289, 290, 291, 292, 295, 296, 297, 298, 300, 302, 303, 304, 305, 306, 307, 308, 309, 310, 311, 1846, 1847, 1848, 1849, 1850, 1851, 1852, 1853, 1854, 1855, 1856, 1857, 1859, 1862, 1864, 1865, 1866, 1867, 1868, 1869, 1870; 23-33 for the protein of sequence SEQ ID No. 268; 38-48 for the protein of sequence SEQ ID No. 299; 23-33 for the protein of sequence SEQ ID No. 1858 |
| SEQ ID No. 328 | TFNGVLGGDAIAR | 88-100 for the proteins of SEQ No. 265, 266, 267, 269, 270, 271, 272, 273, 274, 275, 276, 277, 278, 280, 281, 282, 283, 284, 285, 286, 287, 288, 289, 291, 292, 295, 296, 297, 298, 300, 302, 303, 304, 305, 306, 307, 308, 309, 310, 311, 1846, 1847, 1848, 1849, 1850, 1851, 1852, 1853, 1854, 1855, 1856, 1859, 1862, 1864, 1865, 1866, 1867, 1868, 1869, 1870; 87-99 for the protein of sequence SEQ ID No. 268; 102-114 for the protein of sequence SEQ ID No. 299; 87-99 for the protein of sequence SEQ ID No. 1858 |
| SEQ ID No. 329 | TGSTGGFGSYVAFVPEK | 336-352 for the proteins of SEQ No. 265, 266, 269, 270, 271, 272, 273, 274, 275, 276, 277, 278, 279, 280, 281, 282, 283, 285, 288, 290, 291, 292, 295, 296, 297, 298, 300, 302, 303, 304, 305, 306, 307, 308, 309, 310, 311, 1846, 1848, 1849, 1852, 1853, 1854, 1855, 1856, 1857, 1859, 1862, 1864, 1865, 1866, 1867, 1868, 1869; 338-354 for the protein of sequence SEQ ID No. 267; 335-351 for the protein of sequence SEQ ID No. 268; 334-350 for the protein of sequence SEQ ID No. 284; 332-348 for the protein of sequence SEQ ID No. 286; 338-354 for the protein of sequence SEQ ID No. 289; 350-366 for the protein of sequence SEQ ID No. 299; 338-354 for the protein of sequence SEQ ID No. 1847; 334-350 for the protein of sequence SEQ ID No. 1850; 332-348 for the protein of sequence SEQ ID No. 1851; 335-351 for the protein of sequence SEQ ID No. 1858 |
| SEQ ID No. 330 | TITPLMQEQAIPGMAVAVIYQGK | 35-57 for the proteins of SEQ No. 266, 267, 269, 270, 271, 272, 273, 274, 275, 276, 277, 278, 279, 280, 281, 282, 283, 284, 285, 286, 289, 290, 291, 292, 295, 296, 297, 300, 302, 303, 304, 305, 306, 307, 308, 309, 310, 311, 1846, 1847, 1848, 1849, 1850, 1851, 1854, 1856, 1857, 1859, 1862, 1864, 1865, 1866, 1867, 1868, 1869, 1870; 34-56 for the protein of sequence SEQ ID No. 268; 49-71 for the protein of sequence SEQ ID No. 299; 34-56 for the protein of sequence SEQ ID No. 1858 |
| SEQ ID No. 331 | TLQQGIALAQSR | 267-278 for the proteins of SEQ No. 265, 266, 267, 269, 270, 271, 272, 273, 274, 275, 276, 277, 278, 279, 280, 281, 283, 284, 285, 286, 287, 290, 291, 292, 295, 296, 297, 300, 302, 303, 304, 305, 306, 307, 308, 309, 310, 311, 1846, 1847, 1848, 1849, 1850, 1851, 1852, 1854, 1855, 1856, 1857, 1859, 1862, 1864, 1865, 1866, 1867, 1868, 1869, 1870; 266-277 for the protein of sequence SEQ ID No. 268; 269-280 for the protein of sequence SEQ ID No. 289; 281-292 for the protein of sequence SEQ ID No. 299; 266-277 for the protein of sequence SEQ ID No. 1858 |
| SEQ ID No. 332 | VALAALPAVEVNPPAPAVK | 311-329 for the proteins of SEQ No. 265, 269, 270, 271, 272, 273, 274, 275, 276, 277, 278, 279, 280, 281, 282, 283, 285, 288, 290, 291, 292, 296, 297, 298, 300, 302, 303, 304, 305, 306, 307, 308, 310, 311, 1848, 1849, 1853, 1854, 1855, 1856, 1857, 1859, 1862, 1864, 1865, 1866, 1867, 1869, 1870; 313-331 for the protein of sequence SEQ ID No. 267; 310-328 for the protein of sequence SEQ ID No. 268; 313-331 for the protein of sequence SEQ ID No. 289; 325-343 for the protein of sequence SEQ ID No. 299; 313-331 for the protein of sequence SEQ ID No. 1847; 310-328 for the protein of sequence SEQ ID No. 1858 |
| SEQ ID No. 333 | VEAAWR | 370-375 for the proteins of SEQ No. 265, 266, 269, 271, 272, 273, 274, 275, 276, 277, 278, 279, 280, 281, 282, 283, 285, 287, 288, 290, 291, 292, 295, 296, 297, 298, 300, 302, 303, 304, 305, 306, 307, 308, 309, 310, 311, 1846, 1849, 1852, 1853, 1854, 1855, 1856, 1857, 1859, 1862, 1864, 1865, 1866, 1867, 1868, 1869, 1870; 372-377 for the protein of sequence SEQ ID No. |

-continued

| Peptide SEQ ID No. | Amino acid sequence | Position of the peptide in the CMY protein |
|---|---|---|
| | | 267; 369-374 for the protein of sequence SEQ ID No. 268; 368-373 for the protein of sequence SEQ ID No. 284; 366-371 for the protein of sequence SEQ ID No. 286; 372-377 for the protein of sequence SEQ ID No. 289; 384-389 for the protein of sequence SEQ ID No. 299; 372-377 for the protein of sequence SEQ ID No. 1847; 368-373 for the protein of sequence SEQ ID No. 1850; 366-371 for the protein of sequence SEQ ID No. 1851; 369-374 for the protein of sequence SEQ ID No. 1858 |
| SEQ ID No. 334 | VLQPLK | 198-203 for the proteins of SEQ No. 265, 266, 267, 269, 270, 271, 272, 273, 274, 275, 276, 277, 278, 279, 280, 281, 282, 283, 284, 285, 286, 287, 288, 289, 290, 291, 292, 295, 296, 297, 298, 300, 302, 303, 304, 305, 306, 307, 308, 309, 310, 311, 1846, 1847, 1848, 1849, 1850, 1851, 1852, 1853, 1854, 1855, 1856, 1857, 1859, 1862, 1864, 1865, 1866, 1867, 1868, 1869, 1870; 197-202 for the protein of sequence SEQ ID No. 268; 212-217 for the protein of sequence SEQ ID No. 299; 197-202 for the protein of sequence SEQ ID No. 1858 |
| SEQ ID No. 335 | WVQANMDASHVQEK | 253-266 for the proteins of SEQ No. 266, 267, 269, 270, 271, 272, 274, 275, 276, 277, 278, 279, 280, 281, 282, 283, 284, 285, 286, 288, 290, 291, 292, 298, 300, 302, 303, 304, 305, 306, 307, 308, 309, 310, 311, 1846, 1847, 1848, 1849, 1850, 1851, 1853, 1854, 1856, 1857, 1859, 1862, 1864, 1865, 1866, 1867, 1868, 1869, 1870; 252-265 for the protein of sequence SEQ ID No. 268; 255-268 for the protein of sequence SEQ ID No. 289; 267-280 for the protein of sequence SEQ ID No. 299; 252-265 for the protein of sequence SEQ ID No. 1858 |
| SEQ ID No. 336 | YWPELTGK | 112-119 for the proteins of SEQ No. 265, 266, 267, 269, 270, 271, 272, 273, 274, 275, 276, 277, 278, 279, 280, 281, 282, 283, 284, 285, 286, 287, 288, 289, 290, 291, 292, 296, 297, 298, 300, 302, 303, 304, 305, 306, 307, 308, 309, 310, 311, 1846, 1847, 1848, 1849, 1850, 1851, 1853, 1854, 1855, 1856, 1857, 1859, 1862, 1864, 1865, 1866, 1867, 1868, 1869, 1870; 111-118 for the protein of sequence SEQ ID No. 268; 126-133 for the protein of sequence SEQ ID No. 299; 111-118 for the protein of sequence SEQ ID No. 1858 |
| SEQ ID No. 337 | AHYFNYGVANR | 62-72 for the proteins of SEQ No. 262, 263, 264, 293, 294, 301, 1844, 1845, 1860, 1861, 1863 |
| SEQ ID No. 338 | ANIGGVDDK | 261-269 for the proteins of SEQ No. 262, 263, 264, 293, 294, 301, 1844, 1845, 1860, 1861, 1863 |
| SEQ ID No. 339 | ESGSQVLFNK | 326-335 for the proteins of SEQ No. 262, 263, 264, 293, 294, 301, 1844, 1845, 1860, 1861, 1863 |
| SEQ ID No. 340 | GAMQLDDK | 105-112 for the proteins of SEQ No. 262, 263, 264, 293, 294, 301, 1844, 1845, 1860, 1861, 1863 |
| SEQ ID No. 341 | GIGIVMLANR | 353-362 for the proteins of SEQ No. 262, 263, 264, 293, 294, 301, 1844, 1845, 1860, 1861, 1863 |
| SEQ ID No. 342 | HAPWLK | 116-121 for the proteins of SEQ No. 262, 263, 264, 293, 294, 301, 1844, 1845, 1860, 1861, 1863 |
| SEQ ID No. 343 | IPGMAVAVLK | 49-58 for the proteins of SEQ No. 262, 263, 264, 293, 294, 301, 1844, 1845, 1860, 1861, 1863 |
| SEQ ID No. 344 | PVVDASIQPLLK | 34-45 for the proteins of SEQ No. 262, 263, 264, 293, 294, 301, 1844, 1845, 1860, 1861, 1863 |
| SEQ ID No. 345 | QAMASYAYGYSK | 218-229 for the proteins of SEQ No. 262, 263, 264, 293, 294, 301, 1844, 1845, 1860, 1861, 1863 |
| SEQ ID No. 346 | QWAPVYSPGSHR | 161-172 for the proteins of SEQ No. 262, 263, 264, 293, 294, 301, 1844, 1845, 1860, 1861, 1863 |
| SEQ ID No. 347 | QYSNPSIGLFGHLAASSLK | 173-191 for the proteins of SEQ No. 262, 263, 264, 293, 294, 301, 1844, 1845, 1860, 1861, 1863 |
| SEQ ID No. 348 | TGSTNGFGAYVAFVPAR | 336-352 for the proteins of SEQ No. 262, 263, 264, 293, 294, 301, 1844, 1845, 1860, 1861, 1863 |

-continued

| Peptide SEQ ID No. | Amino acid sequence | Position of the peptide in the CMY protein |
|---|---|---|
| SEQ ID No. 349 | TLTATLGAYAVVK | 92-104 for the proteins of SEQ No. 262, 263, 264, 293, 294, 301, 1844, 1845, 1860, 1861, 1863 |
| SEQ ID No. 350 | VNPGMLADEAYGIK | 236-249 for the proteins of SEQ No. 262, 263, 264, 293, 294, 301, 1844, 1845, 1860, 1861, 1863 |
| SEQ ID No. 734 | PSGMSYEEAMTR | 185-196 for the proteins of SEQ No. 265, 266, 267, 269, 270, 271, 272, 273, 274, 275, 276, 277, 278, 279, 280, 281, 282, 283, 284, 285, 286, 287, 288, 289, 290, 291, 292, 295, 296, 297, 298, 300, 302, 303, 304, 305, 306, 307, 308, 309, 310, 311, 1846, 1847, 1848, 1849, 1850, 1851, 1852, 1853, 1854, 1855, 1856, 1857, 1859, 1862, 1864, 1865, 1866, 1867, 1868, 1869, 1870; 184-195 for the protein of sequence SEQ ID No. 268; 199-210 for the protein of sequence SEQ ID No. 299; 184-195 for the protein of sequence SEQ ID No. 1858 |
| SEQ ID No. 735 | PYYFTWGK | 58-65 for the proteins of SEQ No. 265, 266, 267, 269, 270, 271, 272, 273, 274, 275, 276, 277, 278, 279, 280, 281, 282, 283, 284, 285, 286, 287, 288, 289, 290, 291, 292, 295, 297, 298, 300, 302, 303, 304, 305, 306, 307, 308, 309, 310, 311, 1846, 1847, 1848, 1849, 1850, 1851, 1852, 1853, 1854, 1855, 1856, 1857, 1859, 1862, 1864, 1865, 1866, 1867, 1868, 1869, 1870; 57-64 for the protein of sequence SEQ ID No. 268; 72-79 for the protein of sequence SEQ ID No. 299; 57-64 for the protein of sequence SEQ ID No. 1858 |
| SEQ ID No. 1929 | AALLR | 149-153 for the proteins of SEQ No. 265, 282, 287, 297, 298, 1852, 1853, 1855 |
| SEQ ID No. 1930 | ADSIINGNGSDSK | 300-312 for the proteins of SEQ No. 267, 1847 |
| SEQ ID No. 1931 | ADSIINGSDNK | 300-310 for the proteins of SEQ No. 275, 1849; 299-309 for the protein of sequence SEQ ID No. 268 |
| SEQ ID No. 1932 | AELLR | 149-153 for the protein of SEQ No. 288 |
| SEQ ID No. 1933 | ALQQAISLTHK | 270-280 for the proteins of SEQ No. 262, 293, 294, 1860, 1861 |
| SEQ ID No. 1934 | AVHVSPGQLDAEAYGVK | 228-244 for the proteins of SEQ No. 273, 297, 1855 |
| SEQ ID No. 1935 | DYACGYR | 218-224 for the protein of SEQ No. 281 |
| SEQ ID No. 1936 | DYALGYR | 218-224 for the protein of SEQ No. 306 |
| SEQ ID No. 1937 | EDKPIR | 230-235 for the proteins of SEQ No. 262, 263, 264, 293, 294, 301, 1844, 1845, 1860, 1861, 1863 |
| SEQ ID No. 1938 | EGKPVHASPGQLDAEAYGVK | 239-258 for the protein of SEQ No. 299 |
| SEQ ID No. 1939 | EGKPVHGSPGQLDAEAYGVK | 225-244 for the protein of SEQ No. 278 |
| SEQ ID No. 1940 | EGKPVHVSPEQLDAEAYGVK | 225-244 for the protein of SEQ No. 283 |

| Peptide SEQ ID No. | Amino acid sequence | Position of the peptide in the CMY protein |
|---|---|---|
| SEQ ID No. 1941 | EGKPVHVSPGK | 225-235 for the protein of SEQ No. 269 |
| SEQ ID No. 1942 | EGKPVHVSPGQFDAEAYGVK | 225-244 for the protein of SEQ No. 291 |
| SEQ ID No. 1943 | EGKPVHVSPGQLDAEAYCVK | 225-244 for the proteins of SEQ No. 1856 |
| SEQ ID No. 1944 | EGKPVHVSPGQLDAEAYGVK | 225-244 for the proteins of SEQ No. 265, 266, 267, 270, 272, 275, 277, 279, 280, 281, 282, 284, 285, 286, 288, 290, 292, 295, 296, 298, 300, 302, 303, 304, 305, 306, 307, 308, 309, 310, 1846, 1847, 1848, 1849, 1850, 1851, 1853, 1854, 1857, 1859, 1862, 1864, 1865, 1866, 1867, 1868, 1869, 1870; 224-243 for the protein of sequence SEQ ID No. 268; 224-243 for the protein of sequence SEQ ID No. 1858 |
| SEQ ID No. 1945 | EGKPVHVSPGQLDAGAYGVK | 225-244 for the protein of SEQ No. 271 |
| SEQ ID No. 1946 | EGKPVHVSPGQLNAEAYGVK | 225-244 for the protein of SEQ No. 311 |
| SEQ ID No. 1947 | EGKPVHVSPGR | 225-235 for the protein of SEQ No. 276 |
| SEQ ID No. 1948 | EGKPVHVTPGQLDAEAYGVK | 225-244 for the proteins of SEQ No. 287, 1852 |
| SEQ ID No. 1949 | EGKPVYVSPGQLDAEAYGVK | 225-244 for the protein of SEQ No. 274 |
| SEQ ID No. 1950 | ESGAGVSEQTLFEIGSVSK | 73-91 for the proteins of SEQ No. 263, 264, 301, 1844, 1845, 1863 |
| SEQ ID No. 1951 | ESGASVSEQTLFD1GSVSK | 73-91 for the proteins of SEQ No. 293, 294, 1860, 1861 |
| SEQ ID No. 1952 | ESGAGVSEQTLFEIGSVSK | 73-91 for the protein of SEQ No. 262 |
| SEQ ID No. 1953 | FSDPVTK | 105-111 for the protein of SEQ No. 307 |
| SEQ ID No. 1954 | FYQNWQPQWAPGAK | 154-167 for the proteins of SEQ No. 265, 295, 296, 297, 1855 |
| SEQ ID No. 1955 | FYQNWQPQWTPGAK | 154-167 for the proteins of SEQ No. 266, 267, 269, 270, 271, 272, 273, 274, 275, 276, 277, 278, 279, 280, 281, 282, 283, 284, 285, 286, 287, 288, 289, 290, 291, 292, 298, 300, 302, 303, 304, 305, 306, 307, 308, 309, 310, 311, 1846, 1847, 1848, 1849, 1850, 1851, 1852, 1853, 1854, 1856, 1857, 1859, 1862, 1864, 1865, 1866, 1867, 1868, 1869, 1870; 153-166 for the protein of sequence SEQ ID No. 268; 168-181 for the protein of sequence SEQ ID No. 299; 153-166 for the protein of sequence SEQ ID No. 1858 |
| SEQ ID No. 1956 | IPDDVR | 141-146 for the proteins of SEQ No. 266, 267, 269, 270, 271, 273, 274, 275, 276, 278, 279, 281, 283, 284, 285, 286, 289, 290, 291, 292, 300, 302, 303, 304, 305, 306, 307, 308, 309, 310, 311, 1846, 1847, 1848, 1849, 1850, 1851, 1854, 1856, 1857, 1859, 1862, 1864, 1865, 1866, 1867, 1868, 1869, 1870; 155-160 for |

| Peptide SEQ ID No. | Amino acid sequence | Position of the peptide in the CMY protein |
|---|---|---|
| | | the protein of sequence SEQ ID No. 299; 140-145 for the protein of sequence SEQ ID No. 1858 |
| SEQ ID No. 1957 | LAHTWIK | 204-210 for the protein of SEQ No. 297 |
| SEQ ID No. 1958 | LAHTWITVPENEQK | 204-217 for the protein of SEQ No. 279 |
| SEQ ID No. 1959 | LAHTWITVPQSEQK | 204-217 for the proteins of SEQ No. 282, 288, 295, 296, 298, 1853 |
| SEQ ID No. 1960 | LDAEAYGVK | 236-244 for the proteins of SEQ No. 265, 266, 267, 269, 270, 272, 273, 274, 275, 276, 277, 278, 279, 280, 281, 282, 283, 284, 285, 286, 287, 288, 290, 292, 295, 296, 297, 298, 300, 302, 303, 304, 305, 306, 307, 308, 309, 310, 1846, 1847, 1848, 1849, 1850, 1851, 1852, 1853, 1854, 1855, 1857, 1859, 1862, 1864, 1865, 1866, 1867, 1868, 1869, 1870; 235-243 for the protein of sequence SEQ ID No. 268; 238-246 for the protein of sequence SEQ ID No. 289; 250-258 for the protein of sequence SEQ ID No. 299; 235-243 for the protein of sequence SEQ ID No. 1858 |
| SEQ ID No. 1961 | LLHLATYTAGGLPLK | 126-140 for the proteins of SEQ No. 1870 |
| SEQ ID No. 1962 | LLHLATYTAGGLPLQFPDDVR | 126-146 for the protein of SEQ No. 277 |
| SEQ ID No. 1963 | LYANSSIGLFAALAVK | 169-184 for the protein of SEQ No. 285 |
| SEQ ID No. 1964 | LYANSSIGLFGALVVK | 169-184 for the protein of SEQ No. 288 |
| SEQ ID No. 1965 | LYANSSIGLFGELAVK | 169-184 for the proteins of SEQ No. 269, 275, 277, 305, 1849, 1866 |
| SEQ ID No. 1966 | LYANSSIGLFGTLAVK | 169-184 for the protein of SEQ No. 282 |
| SEQ ID No. 1967 | LYANSSIGLFSALAVK | 169-184 for the proteins of SEQ No. 1859 |
| SEQ ID No. 1968 | LYSNSSIGLFGALAVK | 169-184 for the proteins of SEQ No. 304, 310, 1865, 1869, 1870 |
| SEQ ID No. 1969 | NYAWGYR | 218-224 for the proteins of SEQ No. 288, 298, 1853 |
| SEQ ID No. 1970 | NYPIPAR | 363-369 for the proteins of SEQ No. 262, 293, 294, 1860, 1861 |
| SEQ ID No. 1971 | NYPNEAR | 363-369 for the proteins of SEQ No. 301, 1863 |
| SEQ ID No. 1972 | NYPNPVR | 363-369 for the proteins of SEQ No. 304, 308, 311, 1865, 1867 |
| SEQ ID No. 1973 | SICCALLLTASFSTFAAAK | 5-23 for the proteins of SEQ No. 288, 1853 |

| Peptide SEQ ID No. | Amino acid sequence | Position of the peptide in the CMY protein |
|---|---|---|
| SEQ ID No. 1974 | SICCALLLTASFSTFAATK | 5-23 for the protein of SEQ No. 298 |
| SEQ ID No. 1975 | SLCCALLLTAPLSTFAAAK | 5-23 for the protein of SEQ No. 297 |
| SEQ ID No. 1976 | SLCCALLLTASFSTFASAK | 5-23 for the proteins of SEQ No. 265, 296 |
| SEQ ID No. 1977 | SLCCALLLTASLSTFAAAK | 5-23 for the proteins of SEQ No. 1855 |
| SEQ ID No. 1978 | SNVTDMAR | 245-252 for the proteins of SEQ No. 265, 287, 296, 1852 |
| SEQ ID No. 1979 | SYPNPIR | 363-369 for the protein of SEQ No. 295 |
| SEQ ID No. 1980 | TALLHFYQNWQPQWAPGAK | 149-167 for the proteins of SEQ No. 295, 296 |
| SEQ ID No. 1981 | TDSIINGSDSK | 300-310 for the proteins of SEQ No. 292, 1854 |
| SEQ ID No. 1982 | TFIGVLGGDAIAR | 88-100 for the proteins of SEQ No. 1857 |
| SEQ ID No. 1983 | TFNGVEGGDCIAR | 88-100 for the protein of SEQ No. 279 |
| SEQ ID No. 1984 | TFNGVLGGEAIAR | 88-100 for the protein of SEQ No. 290 |
| SEQ ID No. 1985 | TGSTVGFGSYVAFVPEK | 336-352 for the proteins of SEQ No. 1870 |
| SEQ ID No. 1986 | TGYTGGFGSYVAFVPEK | 336-352 for the protein of SEQ No. 282 |
| SEQ ID No. 1987 | TLQQGIELAQSR | 267-278 for the proteins of SEQ No. 282, 288, 298, 1853 |
| SEQ ID No. 1988 | TSSADLLAFVK | 250-260 for the proteins of SEQ No. 262, 293, 294, 1860, 1861 |
| SEQ ID No. 1989 | TSSADLLR | 250-257 for the proteins of SEQ No. 263, 264, 301, 1844, 1845, 1863 |
| SEQ ID No. 1990 | TYYFTWGK | 58-65 for the protein of SEQ No. 296 |
| SEQ ID No. 1991 | VAALPAVEVNPPAPAVK | 311-327 for the proteins of SEQ No. 284, 1850 |
| SEQ ID No. 1992 | VAFAALPAVEVNPPAPAVK | 311-329 for the proteins of SEQ No. 266, 1846 |

| Peptide SEQ ID No. | Amino acid sequence | Position of the peptide in the CMY protein |
|---|---|---|
| SEQ ID No. 1993 | VALAAIPAVEVNPPAPAVK | 311-329 for the protein of SEQ No. 295 |
| SEQ ID No. 1994 | VALAALHTVEVNPPAPAVK | 311-329 for the protein of SEQ No. 287 |
| SEQ ID No. 1995 | VALAALPAVEINPPAPAVK | 311-329 for the proteins of SEQ No. 309, 1868 |
| SEQ ID No. 1996 | VALAALPTVEVNPPAPAVK | 311-329 for the proteins of SEQ No. 1852 |
| SEQ ID No. 1997 | VAPAVEVNPPAPAVK | 311-325 for the proteins of SEQ No. 286, 1851 |
| SEQ ID No. 1998 | VEAYWR | 370-375 for the proteins of SEQ No. 270, 1848 |
| SEQ ID No. 1999 | VILEANPTAAPR | 314-325 for the proteins of SEQ No. 262, 263, 293, 301, 1844, 1860, 1863 |
| SEQ ID No. 2000 | VPQSEQK | 211-217 for the proteins of SEQ No. 282, 288, 295, 296, 297, 298, 1853 |
| SEQ ID No. 2001 | VSLEANPTAAPR | 314-325 for the proteins of SEQ No. 264, 294, 1845, 1861 |
| SEQ ID No. 2002 | WIQVNMDASR | 253-262 for the proteins of SEQ No. 287, 1852 |
| SEQ ID No. 2003 | WVQANMDASR | 253-262 for the protein of SEQ No. 295 |
| SEQ ID No. 2004 | WVQVNMDASR | 253-262 for the proteins of SEQ No. 265, 273, 296, 297, 1855 |
| SEQ ID No. 2005 | YAAALLLTASFSTFAAAK | 5-22 for the proteins of SEQ No. 1858 |
| SEQ ID No. 2006 | YLPELTGK | 112-119 for the proteins of SEQ No. 1852 |
| SEQ ID No. 2007 | YWSELTGK | 112-119 for the protein of SEQ No. 295 |

The detection of a mechanism of resistance to cephalosporins induced by the expression of the CTX-M protein is characterised by the detection of at least one peptide belonging to the CTX-M protein and to its different sequence variants SEQ ID No. 351 to SEQ ID No. 445 and SEQ ID No. 1871 to SEQ ID No. 1908.

SEQ ID No. 351:
MMTQSIRRSMLTVMATLPLLFSSATLHAQTNSVQQQLEALEKSSGGRLGVALINTAD
NSQILYRADERFAMCSTSKVMAAAAVLKQSESDKHLLNQRVEIKKSDLVNYNPIAEK
HVNGTMTLAELGAAALQYSDNTAMNKLIAHLGGPDKVTAFARSLGDETFRLDRTEP
TLNTAIPGDPRDTTTPLAMAQTLKNLTLGKALAETQRAQLVTWLKGNTTGSASIRAG
LPKSWGVGDKTGSGDYGTTNDIAVIWPANHAPLVLVTYFTQPEQKAESRRDVLAAA
AKIVTHGF

SEQ ID No. 352:
MMRHRVKRMMLMTTACISLLLGSAPLYAQANDVQQKLAALEKSSGGRLGVALIDTA
DNAQTLYRADERFAMCSTSKVMAAAAVLKQSETQKKVLSQKVEIKSSDLINYNPITE
KHVNGTMTLAELSAAALQYSDNTAMNKLIAHLGGPDKVTAFARAIGDNTFRLDRTEP
TLNTAIPGDPRDTTTPLAMAQTLRNLTLGSALGETQRAQLVTWLKGNTTGAASIQAG
LPTSWVVGDKTGSGDYGTTNDIAVIWPEGRAPLILVTYFTQPEQKAESRRDVLAAAA
KIVTDGY

SEQ ID No. 353:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTAGDKTGSGDYGTTNDIAVIWPQGRAPLVLVTYFTQPQQNAESRRDV
LASAARIIAEGL

SEQ ID No. 354:
MVKKSLRQFTLMATATVTLLLGSVPLYAQTVDVQQKLAELEQQSGGRLGVALINTA
DNSQILYRADERFAMCSTSKVMAAAAVLKKSESEPNLLNQRVEIKKSDLVNYNPIAE
KHVNGTMSLAELSAAALQYSDNVAMNKLIAHVGGPASVTAFARQLGDETFRLDRTE
PTLNTAIPGDPRDTTSPRAMAQTLRNLTLGKALGDSQRAQLVTWMKGNTTGAASIQ
AGLPASWVVGDKTGSGDYGTTNDIAVIWPKDRAPLILVTYFTQPQPKAESRRDVLA
SAAKIVTDGL

SEQ ID No. 355:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAESRRDV
LASAARIIAEGL

SEQ ID No. 356:
MVTKRMQRMMFAAAACIPLLLGSAPLYAQTSAVQQKLAALEKSSGGRLGVALIDTK
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFAREIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAESRRDV
LASAARIIAEGL

SEQ ID No. 357:
MVKKSLRQFTLMATATVTLLLGSVPLYAQTADVQQKLAGLERQSGGRLGVALINTA
DNSQILYRADERFAMCSTSKVMAAAAVLKKSESEPNLLNQRVEIKKSDLVNYNPIAE
KHVNGTMSPAELSAAALQYSDNVAMNKLIAHVGGPASVTAFARQLGDETFRLDRTE
PTLNTAIPGDPRDTTSPRAMAQTLRNLTLGKALGDSQRAQLVTVVMKGNTTGAASIQ
AGLPASWVVGDKTGSGDYGTTNDIAVIWPKDRAPLILVTYFTQPQPKAESRRHVLAS

SEQ ID No. 358:
MVKKSLRQFTLMATAAVTLLLGSVPLYAQTADVQQKLAELERQSGGRLGVALINTA
DNSQILYRADERFAMCSTSKVMAAAAVLKKSESEPSLLNQRVEIKKSDLVNYNPIAE
KHVNGTMSLAELSAAALQYSDNVAMNKLIAHVGGPASVTAFARQLGDETFRLDRTE
PTLNTAIPGDPRDTTSPRAMAQTLRNLTLGKALGDSQRAQLVTWMKGNTTGAASIQ
AGLPASWVVGDKTGSGDYGTTNDIAVIWPKDRAPLILVTYFTQPQPKAESRRDILAS
AAKIVTDGL

SEQ ID No. 359:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTAGDKTGSGGYGTTNDIAVIWPQGRAPLVLVTYFTQPQQNAESRRDV
LASAARIIAEGL

SEQ ID No. 360:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAESRRDV
LASAARIIAEGL

SEQ ID No. 361:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
ESTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAESRRDV
LASAARIIAEGL

-continued

SEQ ID No. 362:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAESRRDV
LASAARIIAKGL

SEQ ID No. 363:
MVKKSLRQFTLMATATVTLLLGSVPLYAQTADVQQKLAELERQSGGRLGVALINTAD
NSQILYRADERFAMCSTSKVMAAAAVLKKSESEPNLLNQRVEIKKSDLVNYNPIAEK
HVNGTMSLAELSAAALQYSDNVAMNKLIAHVGGPASVTAFARQLGDETFRLDRTEP
TLNTAIPGDPRDTTSPRAMAQTLRNLTLGKALGDSQRAQLVTWMKGNTTGAASIQA
GLPASWVVGDKTGSGGYGTTNDIAVIWPKDRAPLILVTYFTQPQPKAESRRDVLAS
AAKIVTDGL

SEQ ID No. 364:
MVKKSLRQFTLMATATVTLLLGSVPLYAQTADVQQKLAELERQSGGRLGVALINTAD
NSQILYRADERFAMCSTSKVMAAAAVLKKSESEPNLLNQRVEIKKSDLVNYNPIAEK
HVNGTMSLAELSAAALQYSDNVAMNKLIAHVGGPASVTAFARQLGDETFRLDRTEP
TLNTAIPGDPRDTTSPRAMAQTLRNLTLGKALGDSQRAQLVTWMKGNTTGAASIQA
GLPASWVVGDKTGSGDYGTTNDIAVIWPKDRAPLILVTYFTQPQPKAESRRDVLAS
AAKIVTNGL

SEQ ID No. 365:
MVKKSLRQFTLMATATVTLLLGSVPLYAQTADVQQKLAELERQSGGRLGVALINTAD
NSQILYRADERFAMCSTSKVMAVAAVLKKSESEPNLLNQRVEIKKSDLVNYNPIAEK
HVNGTMSLAELSAAALQYSDNVAMNKLIAHVGGPASVTAFARQLGDETFRLDRTET
TLNTAIPGDPRDTTSPRAMAQTLRNLTLGKALGDSQRAQLVTWMKGNTTGAASIQA
GLPASWVVGDKTGSGDYGTTNDIAVIWPKDRAPLILVTYFTQPQPKAESRRDVLAS
AAKIVTNGL

SEQ ID No. 366:
MMRKSVRRAMLMTTACVSLLLASVPLCAQANDVQQKLAALEKSSGGRLGVALINTA
DNTQTLYRADERFAMCSTSKVMAVAAVLKQSETQKGLLSQRVEIKPSDLINYNPIAE
KHVNGTMTFGELSAAALQYSDNTAMNKLIAHLGGPDKVTAFARTIGDDTFRLDRTE
PTLNTAIPGDPRDTTTPLAMAQALRNLTLGNALGDTQRAQLVMWLKGNTTGAASIQ
AGLPTSWVVGDKTGSGGYGTTNDIAVIWPEGRAPLVLVTYFTQSEPKAESRRDVLA
AAARIVTDGY

SEQ ID No. 367:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAERRRDV
LASAARIIAEGL

SEQ ID No. 368:
MMRKSVRRAMLMTTACVSLLLASVPLCAQANDVQQKLAALEKSSGGRLGVALINTA
DNTQTLYRADERFAMCSTSKVMAAAAVLKQSETQKGLLSQRVEIKPSDLINYNPIAE
KHVNGTMTFGELSAAALQYSDNTAMNKLIAHLGGPDKVTAFARTIGDDTFRLDRTE
PTLNTAIPGDPRDTTTPLAMAQALRNLTLGNALGDTQRAQLVMWLKGNTTGAASIR
AGLPTSWVVGDKTGSDYGTTNDIAVIWPEGRAPLVLVTYFTQSEPKAESRRDVLA
AAARIVTDGY

SEQ ID No. 369:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGGYGTTNDIAVIWPQGRAPLVLVTYFTQPQQNAESRRDV
LASAARIIAEGL

SEQ ID No. 370:
MVKKSLRQFTLMATATVTLLLGSVPLYAQTADVQQKLAELERQSGGRLGVALINTAD
NSQILYRADERFAMCSTSKVMAAAAVLKKSESEPNLLNQRVEIKKSDLVNYSPIAEK
HVNGTMSLAELSAAALQYSDNVAMNKLIAHVGGPASVTAFARQLGDETFRLDRTEP
TLNTAIPGDPRDTTSPRAMAQTLRNLTLGKALGDSQRAQLVTWMKGNTTGAASIQA
GLPASWVVGDKTGSGGYGTTNDIAVIWPKDRAPLILVTYFTQPQPKAESRRDVLAS
AAKIVTDGL

SEQ ID No. 371:
MVKKSLRQFTLMATAAVTLLLGSVPLYAQTADVQQKLAELERQSGGRLGVALINTA
DNSQILYRADERFAMCSTSKVMAAAAVLKKSESEPNLLNQRVEIKKSDLVNYNPIAE
KHVDGTMSLAELSAAALQYSDNVAMNKLIAHVGGPASVTAFARQLGDETFRLDRTE
PTLNTAIPGDPRDTTSPRAMAQTLRNLTLGKALGDSQRAQLVTWMKGNTTGAASIQ
AGLPASWVVGDKTGSGGYGTTNDIAVIWPKDRAPLILVTYFTQPQPKAESRRDVLA
SAAKIVTNGL

SEQ ID No. 372:
MVKKSLRQFTLMATAAVTLLLGSVPLYAQTADVQQKLAELERQSGGRLGVALINTA
DNSQILYRADERFAMCSTSKVMAAAAVLKKSESEPNLLNQRVEIKKSDLVNYNPIAE
KHVDGTMSLAELSAAALQYSDNVAMNKLIAHVGGPASVTAFARQLGDETFRLDRTE
PTLNTAIPGDPRDTTSPRAMAQTLRNLTLGKALGDSQRAQLVTWMKGNTTGAASIQ
AGLPASWVVGDKTGSGDYGTTNDIAVIWPKDRAPLILVTYFTQPQPKAESRRDVLA
SAAKIVTDGL

SEQ ID No. 373:
MVKKSLRQFTLMATATVTLLLGSVPLYAQTVDVQQKLAELEQQSGGRLGVALINTA
DNSQILYRADERFAMCSTSKVMAAAAVLKKSESEPNLLNQRVEIKKSDLVNYNPIAE
KHVNGTMSLAELSAAALQYSDNVAMNKLIAHVGGPASVTAFARQLGDETFRLDRTE
PTLNTAIPGDPRDTTSPRAMAQTLRNLTLGKALGDSQRAQLVTWMKGNTTGAASIQ
AGLPASWVVGDKTGSCDYGTTNDIAVIWPKDRAPLILVTYFTQPQPKAESRRDVLA
SAAKIVTDGL

SEQ ID No. 374:
MVKKSLRQFTLMATATVTLLLGSVPLHAQTADVQQKLAELEQQSGGRLGVALINTA
DNSQILYRADERFAMCSTSKVMAAAAVLKKSESEPNLLNQRVEIKKSDLVNYNPIAE
KHVDGTMSLAELSAAALQYSDNVAMNKLIAHVGGPASVTAFARQLGDETFRLDRTE
PTLNTAIPGDPRDTTSPRAMAQTLRNLTLGKALGDSQRAQLVTWMKGNTTGAASIQ
AGLPASWVVGDKTGSGDYGTTNDIAVIWPKDRAPLILVTYFTQPQPKAESRRDVLA
SAAKIVTDGL

SEQ ID No. 375:
MRHRVKRMMLMTTACISLLLGSAPLYAQANDVQQKLAALEKSSGGRLGVALIDTAD
NAQTLYRADERFAMCSTSKVMAAAAVLKQSETQKNVLSQKVEIKSSDLINYNPIAEK
HVNGTMTLAELSAAALQYSDNTAMNKLIAHLGGPDKVTAFARAIGDDTFRLDRTEPT
LNTAIPGDPRDTTTPLAMAQTLRHLTLGSALGETQRAQLVTWLKGNTTGAASIQAGL
PTSWVVGDKTGSGDYGTTNDIAVIWPEGRAPLILVTYFTQPEQKAESRRDVLAAAA
KIVTDGY

SEQ ID No. 376:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAARI
RAGLPTSWTVGDKTGSGDYGTTNDIAVIWPQGRAPLVLVTYFTQPQQNAESRRDV
LASAARIIAEGL

SEQ ID No. 377:
MVTKRVQRMMFAAAACIPLLLGSAPLYAQTSAVQQKLAALEKSSGRRLGVALIDTAD
NTQVLYRGDERFPMCSTSKVMAAAAVLKQSETQKQLLNQPVEIKPADLVNYNPIAE
KHVNGTMTLAELSAAALQYSDNTAMNKLIAQLGGPGGVTAFARAIGDETFRLDRTE
PTLNTAIPGDPRDTTTPRAMAQTLRQLTLGHALGETQRAQLVTWLKGNTTGAASIR
AGLPTSWTVGDKTGSGDYGTTNDIAVIWPQGRAPLVLVTYFTQPQQNAESRRDVL
ASAARIIAEGL

SEQ ID No. 378:
MVTKRVQRMMFAAAACIPLLLGSAPLYAQTNAVQQKLAALEKSSGGRLGVALIDTA
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAESRRDV
LASAARIIAEGL

SEQ ID No. 379:
MVTKRVQRMMFAAAACIPLLLGSAPLYAQTSAVQQKLAALEKSSGRRLGVPLIDTAD
NTQVLYRGDERFPMCSTSKVMAAAAVLKQSETQKQLLNQPVEIKPADLVNYNPIAE
KHVNGTMTLAELSAAALQYSDNTAMNKLIAQLGGPGGVTAFARAIGDETFRLDRTE
PTLNTAIPGDPRDTTTPRAMAQTLRQLTLGHALGETQRAQLVTWLKGNTTGAASIR
AGLPTSWTVGDKTGSGDYGTTNDIAVIWPQGRAPLVLVTYFTQPQQNAESRRDVL
ASAARIIAEGL

SEQ ID No. 380:
MVTKRVQRMMFAAAACIPLLLGSAPLYAQTSAVQQKLAALEKSSGGRLGVPLIDTA
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAESRRDV
LASAARIIAEGL

SEQ ID No. 381:
MVTKRVQRMMFAAAACIPLLLGSAPLYAQTNAVQQKLAALEKSSGGRLGVPLIDTA
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAESRRDV
LASAARIIAEGL

SEQ ID No. 382:
MVKKSLRQFTLMATATVTLLLGSVPLYAQTADVQQKLAELERQSGGRLGVALINTAD
NSQILYRADERFAMCSTSKVMAAAAVLKKSESEPNLLNQRVEIKKSDLVNYNPIAEK
HVNGTMSLAELSAAALQYSDNVAMNKLIAHVGGPASVTAFARQLGDETFRLDGTEP
TLNTAIPGDPRDTTSPRAMAQTLRNLTLGKALGDSQRAQLVTWMKGNTTGAASIQA
GLPASWVVGDKTGSGDYGTTNDIAVIWPKDRAPLILVTYFTQPQPKAESRRDVLAS
AAKIVTDGL

SEQ ID No. 383:
MMRKSVRRAMLMTTACVSLLLASVPLCAQANDVQQKLAALEKSSGGRLGVALINTA
DNTQTLYRADERFAMCSTSKVMAAAAVLKQSETQKGLLSQRVEIKPSDLINYNPIAE
KHVNGTMTFGELSAAALQYSDNTAMNKLIAHLGGPDKVTAFARTIGDDTFRLDRTE
PTLNTAIPGDPRDITTPLAMAQALRNLTLGNALGDTQRAQLVMWLKGNTTGAASIQ
AGLPTSWVVGDKTGSGDYGTTNDIAVIWPEGRAPLVLVTYFTQSEPKAESRRDVLA
AAARIVTDGY

SEQ ID No. 384:
MMRKSVRRAMLMTTACVSLLLASVPLCAQANDVQQKLAALEKSSGGRLGVALINTA
DNTQTLYRADERFAMCSTSKVMAAAAVLKQSETQKGLLSQRVEIKPSDLVNYNPIA
EKHVNGTMTFGELIAAALQYSDNTAMNKLIAHLGGPDKVTAFARTIGDDTFRLDRTE
PTLNTAIPGDPRDTTTPLAMAQALRNLTLGNALGDTQRAQLVMWLKGNTTGAASIQ
AGLPTSWVVGDKTGSGGYGTTNDIAVIWPEGRAPLVLVTYFTQSEPKAESRRDVLA
AAARIVTDGY

SEQ ID No. 385:
MVKKSLRQFTLMATATVTLLLGSVPLYAQTADVQQKLAELERQSGGRLGVALINTAD
NSQILYRADERFAMCSTSKVMAAAAVLKKSESEPNLLNQRVEIKKSDLVNYNPIAEK
HVNGTMSLAELSAAALQYSDNVAMNKLIAHVGGPASVTAFARQLGDETFRLDRTET
TLNTAIPGDPRDTTSPRAMAQTLRNLTLGKALGDSQRAQLVTWMKGNTTGAASIQA
GLPASWVVGDKTGSGDYGTTNDIAVIWPKDRAPLILVTYFTQPQPKAESRRDVLAS
AAKIVTDGL

SEQ ID No. 386:
MMTQSIRRSMLTVMATLPLLFSSATLHAQANSVQQQLEALEKSSGGRLGVALINTA
DNSQILYRADERFAMCSTSKVMAAAAVLKQSESDKHLLNQRVEIKKSDLVNYNPIAE
KHVNGTMTLAELGAAALQYSDNTAMNKLIAHLGGPDKVTAFARSLGDETFRLDRTE
PTLNTAIPGDPRDTTTPLAMAQTLKNLTLGKALAETQRAQLVTWLKGNTTGSASIRA
GLPKSWVVGDKTGSGGYGTTNDIAVIWPENHAPLVLVTYFTQPEQKAERRRDILAA
AAKIVTHGF

SEQ ID No. 387:
MVTKRVQRMMFAAAACIPLLLGSAPLYAQTSAVQQKLAALEKSSGGRLGVALIDTA
DNTQVLYRGDERFPMCSTSKVMAVAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTAGDKTGSGDYGTTNDIAVIWPQGRAPLVLVTYFTQPQQNAESRRDV
LASAARIIAEGL

SEQ ID No. 388:
MVKKSLRQFTLMATATVTLLLGSVPLYAQTADVQQKLAELERQSGGRLGVALINTAD
NSQILYRADERFAMCSTSKVMAVAAVLKKSESEPNLLNQRVEIKKSDLVNYNPIAEK
HVNGTMSLAELSAAALQYSDNVAMNKLIAHVGGPASVTAFARQLGDETFRLDRTES
TLNTAIPGDPRDTTSPRAMAQTLRNLTLGKALGDSQRAQLVTWMKGNTTGAASIQA
GLPASWVVGDKTGSGDYGTTNDIAVIWPKDRAPLILVTYFTQPQPKAESRRDVLAS
AAKIVTDGL

SEQ ID No. 389:
MVKKSLRQFTLMATATVTLLLGSVPLYAQTADVQQKLAELERQSGGRLGVALINTAD
NSQILYRADERFPMCSTSKVMAAAAVLKKSESEPNLLNQRVEIKKSDLVNYNPIAEK
HVNGTMSLAELSAAALQYSDNVAMNKLIAHVGGPASVTAFARQLGDETFRLDRTEP
TLNTAIPGDPRDTTSPRAMAQTLRNLTLGKALGDSQRAQLVTWMKGNTTGAASIQA
GLPASWVVGDKTGSGGYGTTNDIAVIWPKDRAPLILVTYFTQPQPKAESRRDVLAS
AAKIVTDGL

SEQ ID No. 390:
MVKKSLRQFTLMATATVTLLLGSVPLYAQTVDVQQKLAELEQQSGGRLGVALINTA
DNSQILYRADERFAMCSTSKVMAVAAVLKKSESEPNLLNQRVEIKKSDLVNYNPIAE
KHVNGTMSLAELSAAALQYSDNVAMNKLIAHVGGPASVTAFARQLGDETFRLDRTE
PTLNTAIPGDPRDTTSPRAMAQTLRNLTLGKALGDSQRAQLVTWMKGNTTGAASIQ
AGLPASWVVGDKTGSGGYGTTNDIAVIWPKDRAPLILVIYFTQPQPKAESRRDVLAS
AAKIVTDGL

SEQ ID No. 391:
MVKKSLRQFTLMATATVTLLLGSVPLYAQTADVQQKLAELERQSGGRLGVALINTAD
NSQILYRADERFAMCSTSKVMAAAAVLKKSESEPNLLNQRVEIKKSDLVNYNPIAEK
HVNGTMSLAELSAAALQYSDNVAMNKLIAHVGGPASVTAFARQLGDETFRLDRTEQ
TLNTAIPGDPRDTTSPRAMAQTLRNLTLGKALGDSQRAQLVTWMKGNTTGAASIQA
GLPASWVVGDKTGSGDYGTTNDIAVIWPKDRAPLILVTYFTQPQPKAESRRDVLAS
AAKIVTDGL

SEQ ID No. 392:
MMTQSIRRSMLTVMATLPLLFSSATLHAQANSVQQQLEALEKSSGGRLGVALINTA
DNSQILYRADERFAMCSTSKVMAAAAVLKQSESDKLLLNQRVEIKKSDLVNYNPIAE
KHVNGTMTLAELGAAALQYSDNTAMNKLIAHLGGPDKVTAFARSLGDETFRLDRTE
PTLNTAIPGDPRDTTTPLAMAQTLKNLTLGKALAETQRAQLVTVVLKGNTTGSASIRA
GLPKSWVVGDKTGSGDYGTTNDIAVIWPENHAPLVLVTYFTQPEQKAESRRDILAA
AAKIVTHGF

SEQ ID No. 393:
MVKKSLRQFTLMATATVTLLLGSVPLYAQTADVQQKLAELERQSGGRLGVALINTAD
NSQILYRADERFAMCSTSKVMAVAAVLKKSESEPNLLNQRVEIKKSDLVNYNPIAEK
HVNGTMSLAELSAAALQYSDNVAMNKLIAHVGGPASVTAFARQLGDETFRLDRTEP
TLNTAIPGDPRDTTSPRAMAQTLRNLTLGKALGDSQRAQLVTWMKGNTTGAASIQA
GLPASWVVGDKTGSGGYGTTNDIAVIWPKDRAPLILVTYFTQPQPKAESRRDVLAS
AAKIVTDGL

SEQ ID No. 394:
MVKKSLRQFTLMATATVTLLLGSVPLYAQTADVQQKLAELERQSGGRLGVALINTAD
NSQILYRADERFAMCSTSKVMAVAAVLKKSESEPNLLNQRVEIKKSDLVNYNPIAEK
HVNGTMSLAELSAAALQYSDNVAMNKLIAHVGGPASVTAFARQLGDETFRLDRTEP
TLNTAIPGDPRDTTSPRAMAQTLRNLTLGKALGDSQRAQLVTWMKGNTTGAASIQA
GLPASWVVGDKTGSGGYGTTNDIAVIWPKDRAPLILVTYFTQPQPKAESRRDVLAS
AAKIVTDGL

SEQ ID No. 395:
MVKKSLRQFTLMATATVTLLLGSVPLYAQTADVQQKLAELERQSGGRLGVALINTAD
NSQILYRADERFAMCSTSKVMAVAAVLKKSESEPNLLNQRVEIKKSDLVNYNPIAEK
HVDGTMSLAELSAAALQYSDNVAMNKLISHVGGPASVTAFARQLGDETFRLDRTET
TLNTAIPGDPRDTTSPRAMAQTLRNLTLGKALGDSQRAQLVTWMKGNTTGAASIQA
GLPASWVVGDKTGSDYGTTNDIAVIWPKDRAPLILVTYFTQPQPKAESRRDVLAS
AAKIVTNGL

SEQ ID No. 396:
MVKKSLRQFTLMATATVTLLLGSVPLYAQTADVQQKLAELERQSGGRLGVALINTAD
NSQILYRADERFAMCSTSKVMAVAAVLKKSESEPNLLNQRVEIKKSDLVNYNPIAEK
HVDGTMSLAELSAAALQYSDNVAMNKLISHVGGPASVTAFARQLGDETFRLDRTEP
TLNTAIPGDPRDTTSPRAMAQTLRNLTLGKALGDSQRAQLVTWMKGNTTGAASIQA
GLPASWVVGDKTGSDYGTTNDIAVIWPKDRAPLILVTYFTQPQPKAESRRDVLAS
AAKIVTDGL

SEQ ID No. 397:
MMTQSIRRSMLTVMATLPLLFSSATLHAQANSVQQQLEALEKSSGGRLGVALINTA
DNSQILYRADERFAMCSTSKVMAAAAVLKQSESDKHLLNQRVEIKKSDLVNYNPIAE
KHVNGTMTLAELGAAALQYSDNTAMNKLIAHLGGPDKVTAFARSLGDETFRLDRTE
PTLNTAIPGDPRDTTTPLAMAQTLKNLTLGKALAETQRAQLVTWLKGNTTGSASIRA
GLPKSWVVGDKTGSGDYGTTNDIAVIWPENHAPLVLVTYFTQPEQKAENRRDILAA
AAKIVTHGF

SEQ ID No. 398:
MVTKRVQRMMFAAAACIPLLLGSAPLYAQTSAVQQKLAALEKSSGGRLGVALIDTA
DNTQVLYRGDERFPMCSTSKVMAVAAVLKQSETQKQLLNQPVEIKPADLVNYNPIA
EKHVNGTMLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAERRRDV
LASAARIIAEGL

SEQ ID No. 399:
MVKKSLRQFTLMATATVTLLLGSVPLYAQTADVQQKLAELERQSGGRLGVALINTAD
NSQILYRADERFAMCSTSKVMAVAAVLKKSESEPNLLNQRVEIKKSDLVNYNPIAEK
HVNGTMSLAELSAAALQYSDNVAMNKLIAHVGGPASVTAFARQLGDETFRLDRTEP
TLNTAIPGDPRDTTSPRAMAQTLRNLTLGKALGDSQRAQLVTWMKGNTTGAASIQA
GLPASWVVGDKTGSGGYGTTNDIAVIWPKDRAPLILVTYFTQPQPKAESRRDVLAS
AAKIVTNGL

SEQ ID No. 400:
MVKKSLRQFTLMATATVTLLLGSVPLYAQTADVQQKLAELERQSGGRLGVALINTAD
NSQILYRADERFAMCSTSKVMAAAAVLKKSESEPNLLNQRVEIKKSDLVNYNPIAEK
HVNGTMSLAELSAAALQYSDNVAMNKLIAHVGGPASVTAFARQLGDETFRLDRTES
TLNTAIPGDPRDTTSPRAMAQTLRNLTLGKALGDSQRAQLVTWMKGNTTGAASIQA
GLPASWVVGDKTGSGDYGTTNDIAVIWPKDRAPLILVTYFTQPQPKAESRRDVLAS
AAKIVTDGL

SEQ ID No. 401:
MVKKSLRQFTLMATATVTLLLGNVPLYAQTADVQQKLAELERQSGGRLGVALINTA
DNSQILYRADERFAMCSTSKVMAAAAVLKKSESEPNLLNQRVEIKKSDLVNYNPIAE
KHVNGTMSLAELSAAALQYSDNVAMNKLIAHVGGPASVTAFARQLGDETFRLDRTE
PTLNTAIPGDPRDTTSPRAMAQTLRNLTLGKALGDSQRAQLVTWMKGNTTGAASIQ
AGLPASWVVGDKTGSGDYGTTNDIAVIWPKDRAPLILVTYFTQPQPKAESRRDVLA
SAAKIVTDGL

SEQ ID No. 402:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYSPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAESRRDV
LASAARIIAEGL

SEQ ID No. 403:
MVTKRVQRMMFAAAACIPLLLGSAPLYAQTSAVQQKLAALEKSSGGRLGVALIDTA
DNTQVLYRGDERFPMCSTSKVMAAAAVLEQSETQKQLLNQPVEIQPADLVNYNPIA
EKHVNGTMTLAELSAAALQYSDHTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAESRRDV
LASAARIIAEGL

SEQ ID No. 404:
MVKKSLRQFTLMATATVTLLLGSVPLHAQTVDVQQKLAELERQSGGRLGVALINTA
DNSQILYRADERFAMCSTSKVMAAAAVLKKSESEPNLLNQRVEIKKSDLVNYNPIAE
KHVNGTMSLAELSAAALQYSDNVAMNKLIAHVGGPASVTAFARQLGDDTFRLDRTE
PTLNTAIPGDPRDTTSPRAMAQTLRNLTLGKALGDSQRAQLVTWMKGNTTGAASIQ
AGLPASWVVGDKTGSGDYGTTNDIAVIWPKDRAPLILVTYFTQPQPKAESRRDVLA
SAAKIVTDGL

SEQ ID No. 405:
MVKKSLRQFTLMATATVTLLLGSVPLYAQTVDVQQKLAELERQSGGRLGVALINTAD
NSQILYRADERFAMCSTSKVMAAAAVLKKSESEPNLLNQRVEIKKSDLVNYNPIAEK
HVNGTMSLAELSAAALQYSDNVAMNKLIAHVGGPASVTAFARQLGDETFRLDRTEP
TLNTAIPGDPRDTTSPRAMAQTLRNLTLGKALGDSQRAQLVTWMKGNTTGAASIQA
GLPASWVVGDKTGSGDYGTTNDIAVIWPKDRAPLILVTYFTQPQPKAESRRDVLAS
AAKIVTDGL

SEQ ID No. 406:
MVKKSLRQFTLMATATVTLLLGSVPLYAQTADVQQKLAELERQSGGRLGVALINTAD
NSQILYRADERFAMCSTSKVMAVAAVLKKSESEPNLLNQRVEIKKSDLVNYNPIAEK
HVNGTMSLAELSAAALQYSDNVAMNKLIAHVGGPASVTAFARQLGDETFRLDRTEP
TLNTAIPGDPRDTTSPRAMAQTLRNLTLGKALGDSQRAQLVTWMKGNTTGAASIQA
GLPASWVVGDKTGSGGYGTTNDIAVIWPKDRAPLILVTYFTQPQPNAESRRDVLAS
AAKIVTNGL

SEQ ID No. 407:
MVTKRVQRMMFAAAACIPLLLGSAPLYAQTSAVQQKLAALEKSSGGRLGVALIDTA
DNTQVLYRGDERFPMCSTSKVMAVAAVLKQSETQKQLLNQPVEIKPADLVNYNPIA
EKHVNGTMTLAELSAAALQYSDNTAMNKLIAQLGGPGGVTAFARAIGDETFRLDRT
ELTLNTAIPGDPRDTTTPRAMAQTLRQLTLGHALGETQRAQLVTWLKGNTTGAASIR
AGLPTSWTVGDKTGSGDYGTTNDIAVIWPQGRAPLVLVTYFTQPQQNAESRRDVL
ASAARIIAEGL

SEQ ID No. 408:
MVTKRVQRMMFAAAACIPLLLGSAPLYAQTSAVQQKLAALEKSSGGRLGVALIDTA
DNTHVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAESRRDV
LASAARIIAEGL

SEQ ID No. 409:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVAWLKGNTTGAASI
RAGLPTSWTVGDKTGSGDYGTTNDIAVIWPQGRAPLVLVTYFTQPQQNAESRRDV
LASAARIIAEGL

SEQ ID No. 410:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYNPIA
EKHVNGTMTPAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAESRRDV
LASAARIIAEGL

SEQ ID No. 411:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYNPFA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAESRRDV
LASAARIIAEGL

SEQ ID No. 412:
MVKKSLRQFTLMATATVILLLGSVPLYAQTADVQQKLAELERQSGGRLGVALINTAD
NSQILYRADERFAMCSTSKVMAAAAVLKKSESEPNLLNQRVEIKKSDLVNYNPIAEK
HVNGTMSLAELSAAALQYSDNVAMNKLIAHVGGPASVTAFARQLGDETFRLDRTEP
TLNTAIPGDPRDTTSPRAMAQTLRNLTLGKALGDSQRAQLVTWMKGNTTGAASIQA
GLPASWVVGDKTGSGGYGTTNDIAVIWPKDRAPLILVTYFTQPQPKAESRHDVLAS
AAKIVTDGL

SEQ ID No. 413:
MVTKRVQRMMFAAAACIPLLLGSAPLYAQTSAVQQKLAALEKSSGGRLGVALIDTA
DNTQVLYRGDERFPMCSTSKVMAVAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAESRRDV
LASAARIIAEGL

SEQ ID No. 414:
MMRKSVRRAMLMTTACVSLLLASVPLCAQANDVQQKLAALEKSSGGRLGVALINTA
DNTQTLYRADERFAMCSTSKVMAVAAVLKQSETQKGLLSQRVEIKPSDLINYNPIAE
KHVNGTMTFGELSAAALQYSDNTAMNKLIAHLGGPDKVTAFARTIGDDTFRLDRTE
PTLNTAIPGDPRDTTTPLAMAQALRNLTLGNALGDTQRAQLVMWLKGNTTGAASIQ
AGLPTSWVVGDKTGSGDYGTTNDIAVIWPEGRAPLVLVTYFTQSEPKAESRRDVLA
AAARIVTDGY

SEQ ID No. 415:
MMTQSIRRSMLTVMATLPLLFSSATLHAQANSVQQQLEALEKSSGGRLGVALINTA
DNSQILYRADERFAMCSTSKVMAAAAVLKQSESDKHLLNQRVEIKKSDLVNYNPIAE
KHVNGTMTLAELGAAALQYSDNTAMNKLIAHLGGPDKVTAFARSLGDETFRLDRTE
TTLNTAIPGDPRDTTTPLAMAQTLKNLTLGKALAETQRAQLVTWLKGNTGSASIRA
GLPKSWVVGDKTGSGDYGTTNDIAVIWPENHAPLVLVTYFTQPEQKAESRRDILAA
AAKIVTHGF

SEQ ID No. 416:
MMTQSIRRSMLTVMATLSLLFSSATLHAQANSVQQQLEALEKSSGGRLGVALINTA
DNSQILYRADERFAMCSTSKVMAAAAVLKQSESDKHLLNQRVEIKKSDLVNYNPIAE
KHVNGTMTLAELGAAALQYSDNTAMNKLIAHLGGPDKVTAFARSLGDETFRLDRTE
PTLNTAIPGDPRDTTTPLAMAQTLKNLTLGKALAETQRAQLVTWLKGNTIGSASIRA
GLPKSWVVGDKTGSGDYGTTNDIAVIWPENHAPLVLVTYFTQPEQKAESRRDILAA
AAKIVTHGF

SEQ ID No. 417:
MVKKSLRQFTLMATATVTLLLGSVPLYAQTADVQQKLAELERQSGGRLGVALINTAD
NSQILYRADERFAMCSTSKVMAAAAVLKKSESEPNLLNQRVEIKKSDLVNYNPIAEK
HVNGTMSLAELSAAALQYSDNVAMNKLIAHVGGPASVTAFARQLGDETFRLDRTEP
TLNTAIPGDPRDTTSPRAMAQTLRNLTLGKALGDSQRAQLVTWMKGNTTGAASIQA
GLPASWVVGDKTGSCGYGTTNDIAVIWPKDRAPLILVTYFTQPQPKAESRRDVLAS
AAKIVTDGL

SEQ ID No. 418:
MMRKSVRRAMLMTTACVSLLLASVPLCAQANDVQQKLAALEKSSGGRLGVALINTA
DNTQTLYRADERFAMCSTSKVMAVAAVLKQSETQKGLLSQRVEIKPSDLINYNPIAE
KHVNGTMTFGELSAAALQYSDNTAMNKLIAHLGGPDKVTAFARTIGDDTFRLDRTE
PTLNTAIPGDPRDTTTPLAMAQSLRNLTLGNALGDTQRAQLVMWLKGNTTGAASIQ
AGLPTSWVVGDKTGSGDYGTTNDIAVIWPEGRAPLVLVTYFTQSEPKAESRRDVLA
AAARIVTDGY

SEQ ID No. 419:
MMTQSIRRSMLTVMATLPLLFSSATLHAQANSVQQQLEALEKSSGGRLGVALINTA
DNSQILYRADERFAMCSTSKVMAAAAVLKQSESDKHLLNQRVEIKKSDLVNYNPIAE
KHVNGTMTLAELGAAALQYSDNTAMNKLIAHLGGPDKVTAFARSLGDETFRLDRTE
PTLNTAIPGDPRDTTTPLAMAQTLKNLTLGKALAETQRTQLVTWLKGNTTGSASIRA
GLPKSWVVGDKTGSGDYGTTNDIAVIWPENHAPLVLVTYFTQPEQKAESRRDILAA
AAKIVTHGF

SEQ ID No. 420:
MMRKSVRRAMLMTTACVSLLLASVPLCAQANDVQQKLAALEKSSGGRLGVALINTA
DNTQTLYRADERFAMCSTSKVMAAAAVLKQSETQKGLLSQRVEIKPSDLINYNPIAE
KHVNGTMTLGELSAAALQYSDNTAMNKLIAHGGPDKVTAFARTIGDDTFRLDRTEP
TLNTAIPGDPRDITTPLAMAQALRNLTLGNALGDTQRAQLVMWLKGNTTGAASIQA
GLPTSWVVGDKTGSGGYGTTNDIAVIWPEGRAPLVLVTYFTQSEPKAESRRDVLAA
AARIVTDGY

SEQ ID No. 421:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
ESTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAERRRDV
LASAARIIAEGL

SEQ ID No. 422:
MMTQSIGRSMLTVMATLPLLFSSATLHAQANSVQQQLEALEKSSGGRLGVALINTA
DNSQILYRADERFAMCSTSKVMAAAAVLKQSESDKHLLNQRVEIKKSDLVNYNPIAE
KHVNGTMTLAELGAAALQYSDNTAMNKLIAHLGGPDKVTAFARSLGDETFRLDRTE
PTLNTAIPGDPRDTTTPLAMAQTLKNLTLGKALAETQRAQLVTWLKGNTTGSASIRA
GLPKSWVVGDKTGSGDYGTTNDIAVIWPENHAPLVLVTYFTQPEQKAESRRDILAA
AAKIVTHGF

SEQ ID No. 423:
MVTKRVQRMMFAAAACIPLLLGSAPLYAQTSAVQQKLAALEKSSGGRLGVALIDTA
DNTQVLYRGDERFPMCSTSKVMAVAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGGYGTTNDIAVIWPQGRAPLVLVTYFTQPQQNAESRRDV
LASAARIIAEGL

SEQ ID No. 424:
MMTQSIRRSMLTVMATLPLLFSSATLHAQANSVQQQLEALEKSSGGRLGVALINTA
DNSQILYRADERFAMCSTSKVMAAAAVLKQSESDKHLLNQRVEIKKSDLVNYNPIAE
KHVNGTMTLAELGAAALQYSDNTAMNKLIAHLGGPDKVTAFARSLGDETFRLDRTE
PTLNTAIPGDPRDTTTPLAMAQTLKNLTLGKALAETQRAQLVTWLKGNTTGSASIRA
GLPKSWVVGDKTGSGDYGTTNDIAVIWPENHAPLVLVTYFTQPEQKAERRRDILAA
AAKIVTHGF

SEQ ID No. 425:
MVTKRVQRMMSAAAACIPLLLGSPTLYAQTSAVQQKLAALEKSSGGRLGVALIDTA
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTARAGADVASLRWVMRWAKPSGAVGDVAQRQYDRAAGIR
AGLPTSWTVGDKTGSGDYGTTNDIAVIWPQGRAPLVLVTYFTQPQQNAESRRDVL
ASAARIIAEGL

SEQ ID No. 426:
MVKKSLRQFTLMATATVTLLLGSVPLYAQTADVQQKLAELERQSGGRLGVALINTAD
NSQILYRADERFAMCSTSKVMAAAAVLKKSESEPNLLNQRVEIKKSDLVNYNPIAEK
HVDGTMSLAELSAAALQYSDNVAMNKLISHVGGPASVTAFARQLGDETFRLDRTEP
TLNTAIPGDPRDTTSPRAMAQTLRNLTLGKALGDSQRAQLVTWMKGNTTGAASIQA
GLPASWVVGDKTGSGDYGTTNDIAVIWPKDRAPLILVTYFTQPQPKAESRRDVLAS
AAKIVTNGL

SEQ ID No. 427:
MRHRVKRMMLMTTACISLLLGSAPLYAQANDVQQKLAALEKSSGGRLGVALIDTAD
NAQTLYRADERFAMCSTSKVMAAAAVLKQSETQKNVLSQKVEIKSSDLINYNPIAEK
HVNGTMTLAELSAAALQYSDNTAMNKLIAHLGGPDKVTAFARAIGDDTFRLDRTEPT
LNTAIPGDPRDTTTPLAMAQTLRHLTLGSALGETQRAQLVTWLKGNTTGAASIQAGL
PTSWVVGDKTGSGDYGTTNDIAVIWPEGRAPLILVTYFTQPEQKAENRRDVLAAAA
KIVTDGY

SEQ ID No. 428:
MVKKSLRQFTLMATATVTLLLGSVPLYAQTADVQQKLAELERQSGGRLGVALINTAD
NSQILYRADERFPMCSTSKVMAAAAVLKQSETQKQLLNQPVEIKPADLVNYNPIAEK
HVNGTMTLAELSAAALQYSDNTAMNKLIAQLGGPGGVTAFARAIGDETFRLDRTEP
TLNTAIPGDPRDTTTPRAMAQTLRQLTLGHALGETQRAQLVTWLKGNTTGAASIRA
GLPASWVVGDKTGSGGYGTTNDIAVIWPKDRAPLILVTYFTQPQPKAESRRDVLAS
AAKIVTDGL

SEQ ID No. 429:
MMTQSIRRSMLTVMATLPLLFSSATLHAQANSVQQQLEALEKSSGGRLGVALINTA
DNSQILYLADERFAMCSTSKVMAAAAVLKQSESDKHLLNQRVEIKASDLVNYNPIAE
KHVNGTMTLAELGAGALQYSDNTAMNKLIAHLGGPDKVTAFARSLGDETFRLDRTE
PTLNSAIPGDPRDTTTPLAMAQTLKNLTLGKALAETQRAQLVTWLKGNTTGSASIRA
GLPKCWVVGDKTGSGDYGTTNDIAVIWPENHAPLVLVTYFTQPEQKAESRRDVLAA
AAKIVTHGF

SEQ ID No. 430:
MMTQSIRRSMLTVMATLPLLFSSATLHAQANSVQQQLEALEKSSGGRLGVALINTA
DNSQILYVADERFAMCSTSKVMAAAAVLKQSESDKHLLNQRVEIRASDLVNYNPIAE
KHVNGTMTLAQLGAGALQYSDNTAMNKLIAHLGGPDKVTAFARSLGDETFRLDRTE
PTLNSAIPGDPRDTTTPLAMAQTLKNLTLGKALAETQRAQLVTWLKGNTTGSASIRA
GLPKSWGVGDKTGSGDYGTTNDIAVIWPENHAPLVLVTYFTQPEQKAESRRDVLAA
AAKIVTHGF

SEQ ID No. 431:
MVKKSLRQFTLMATATVTLLLGSVPLYAQTADVQQKLAELERQSGGRLGVALINTAD
NSQILYRADERFAMCSTSKVMAVAAVLKKSESEPNLLNQRVEIKKSDLVNYNPIAEK
HVDGTMSLAELSAAALQYSDNVAMNKLISHVGGPASVTAFARQLGDETFRLDRTEP
TLNTAIPGDPRDTTSPRAMAQTLRNLTLGKALGDSQRAQLVTWMKGNITGAASIQA
GLPASWVVGDKTGSGDYGTTNDIAVIWPKDRAPLILVTYFTQPQPKAESRRDVLAS
AAKIVTNGL

SEQ ID No. 432:
MMTQSIRRSMLTVMATLPLLFSSATLHAQANSVQQQLEALEKSSGGRLGVALINTA
DNSQILYRADERFAMCSTSKVMAAAAVLKQSESDKHLLNQRVEIKKSDLVNYNPIAE
KHVNGTMTLAELGAAALQYSDNTAMNKLIAHLGGPDKVTAFARSLGDETFRLDRTE
PTLNTAIPGDPRDTTTPLAMAQTLKNLTLGKALAETQRAQLVTWLKGNTTGSASIRA
GLPKSWVVGDKTGSGDYGTTNDIAVIWPENHAPLVLVTYFTQPEQKAESRRDILAA
AAKIVTHGF

SEQ ID No. 433:
MVKKSLRQFTLMATATVTLLLGSVPLYAQTADVQQKLAELERQSGGRLGVALINTAD
NSQILYRADERFAMCSTSKVMAAAAVLKKSESEPNLLNQRVEIKKSDLVNYNPIAEK
HVNGTMSLAELSAAALQYSDNVAMNKLIAHVGGPASVTAFARQLGDETFRLDRTEP
TLNTAIPGDPRDTTSPRAMAQTLRNLTLGKALGDSQRAQLVTWMKGNTTGAASIQA
GLPASWVVGDKTGSGDYGTTNDIAVIWPKDRAPLILVTYFTQPQPKAESRRDVLAS
AAKIVTDGL

SEQ ID No. 434:
MMTQSIRRSMLTVMATLPLLFSSATLHAQANSVQQQLEALEKSSGGRLGVAQINTA
DNSQILYVADERFAMCSTSKVMAAAAVLKQSESDKHLLNQRVEIRASDLVNYNPIAE
KHVNGTMTLAELGAGALQYSDNTAMNKLIAHLGGPDKVTAFARSLGDETFRLDRTE
PTLNSAIPGDPRDTTTPLAMAQTLKNLTLGKALAETQRAQLVTWLKGNITTGSASIRA
GMPKSWGVGDKTGSGDYGTTNDIAVIWPENHAPLVLVTYFTQPEQKAESRRDILAA
AAKIVTHGF

SEQ ID No. 435:
MMTQSIRRSMLTVMATLPLLFSSATLHAQANSVQQQLEALEKSSGGRLGVALINTA
DNSQILYRADERFAMCSTSKVMAAAAVLKQSESDKHLLNQRVEIKKSDLVNYNPIAE
KHVNGTMTLAELGAAALQYSDNTAMNKLIAHLGGPDKVTAFARSLGDETFRLDRTE
PTLNTAIPGDPRDTTTPLAMAQTLKNLTLGKALAETQRAQLVTWLKGNTTGSASIRA
GLPKSWVVGDKTGSGDYGTTNDIAVIWPENHAPLVLVTYFTQPEQKAESRRDFLAA
AAKIVTHGF

SEQ ID No. 436:
MVTKRVQRMMFAGGAGIPLLLGSAPFYAQTSAGGQQKLAALEKSSGGRLGVALIDTA
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAESRRDV
LASAARIIAEGL

SEQ ID No. 437:
MVKKSLRQFTLMATATVTLLLGSVPLYAQTADVQQKLAELERQSGGRLGVALINTAD
NSQILYRADERFAMCSTSKVMAAAAVLKKSESEPNLLNQRVEIKKSDLVNYNPIAEK
HVNGTMSLAELSAAALQYSDNVAMNKLIAHVGGPASVTAFARQLGDETFRLDRTEP
TLNTAIPGDPRDTTSPRAMAQTLRNLTLGKALGDSQRAQLVTWMKGNTTGAASIQA
GLPASWVVGDKTGSGGYGTTNDIAVIWPKDRAPLILVTYFTQPQPKAESRRDVLAS
AAKIVTNGL

SEQ ID No. 438:
MVKKSLRQFTLMATATVTLLLGSVPLYAQTADVQQKLAELERQSGGRLGVALINTAD
NSQILYRADERFAMCSTSKVMAVAAVLKKSESEPNLLNQRVEIKKSDLVNYNPIAEK
HVDGTMSLAELSAAALQYSDNVAMNKLISHVGGPASVTAFARQLGDETFRLDRTEP
TLNTAIPGDPRDTTSPRAMAQTLRNLTLGKALGDSQRAQLVTWMKGNTTGAASIQA
GLPASWVVGDKTGSGGYGTTNDIAVIWPKDRAPLILVTYFTQPQPKAESRRDVLAS
AAKIVTNGL

SEQ ID No. 439:
MMTQSIRRSMLTVMATLPLLFSSATLHAQANSVQQQLEALEKSSGGRLGVALINTA
DNSQILYRADERFAMCSTSKVMAAAAVLKQSESDKHLLNQRVEIKKSDLVNYNPIAE
KHVNGTMTLAELGAAALQYSDNTAMNKLIAHLGGPDKVTAFARSLGDESFRLDRTE
PTLNTAIPGDPRDTTTPLAMAQTLKNLTLGKALAETQRAQLVTWLKGNTTGSASIRA
GLPKSWVVGDKTGSGDYGTTNDIAVIWPENHAPLVLVTYFTQPEQKAESRRDILAA
AAKIVTHGF

SEQ ID No. 440:
MVKKSLRQFTLMATAAVTLLLGSVPLYAQTADVQQKLAELERQSGGRLGVALINTA
DNSQILYRADERFAMCSTSKVMAAAAVLKKSESEPSLLNQRVEIKKSDLVNYNPIAE
KHVNGTMSLAELSAAALQYSDNVAMNKLIAHVGGPASVTAFARQLGDETFRLDRTE
PTLNTAIPGDPRDTTSPRAMAQTLRNLTLGKALGDSQRAQLVTWMKGNTTGAASIQ
AGLPASWVVGDKTGSGGYGTTNDIAVIWPKDRAPLILVTYFTQPQPKAESRRDILAS
AAKIVTDGL

SEQ ID No. 441:
MVKKSLRQFTLMATAAVTLLLGSVPLYAQTADVQQKLAELERQSGGRLGVALINTA
DNSQILYRADERFAMCSTSKVMAVAAVLKKSESEPSLLNQRVEIKKSDLVNYNPIAE
KHVNGTMSLAELSAAALQYSDNVAMNKLIAHVGGPASVTAFARQLGDETFRLDRTE
PTLNTAIPGDPRDTTSPRAMAQTLRNLTLGKALGDSQRAQLVTWMKGNTTGAASIQ
AGLPASWVVGDKTGSGDYGTTNDIAVIWPKDRAPLILVTYFTQPQPKAESRRDILAS
AAKIVTDGL

SEQ ID No. 442:
MMTQSIRRSMLTVMATLPLLFSSATLHAQTNSVQQQLKALEKSSGGRLGVALINTAD
NSQILYRADERFAMCSTSKVMAAAAVLKQSESDKHLLNQRVEIKKSDLVNYNPIAEK
HVNGTMTLAELGAAALQYSDNTAMNKLIAHLGGPDKVTAFARSLGDETFRLDRTEP
TLNTAIPGDPRDTTTPLAMAQTLKNLTLGKALAETQRAQLVTWLKGNTTGSASIQAG
LPKSWVVGDKTGSGDYGTTNDIAIIWPENHAPLVLVTYFTQPEQKAESRRDVLAAAA
KIVTRGF

SEQ ID No. 443:
MMRKSVRRAILMTTACVSLLLASVPLYAQANDIQQKLAALEKSSGGRLGVALINTAD
NTQTLYRADERFAMCSTSKVMAAAAVLKQSETQKDLLSQRVEIKSSDLINYNPIAEK
HVNGTMTLGELSAAALQYSDNTAMNKLIAHLGGPGKVTAFARVIGDDTFRLDRTEP
TLNTAIPGDPRDTTTPLAMAQTLRNLTLGNALGDTQRAQLVTWLKGNTTGAASIQA
GLPTSWVVGDKTGSGDYGTTNDIAVIWPEGRAPLVLVTYFTQPEPKAESRRDVLAA
AARIVTDGY

SEQ ID No. 444:
MMTQSIRRSMLTVMATLPLLFSSATLHAQTNSVQQQLEALEKSSGGRLGVALINTAD
NSQILYRADERFAMCSTSKVMAAAAVLKQSESDKHLLNQRVEIKKSDLVNYNPIAEK
HVNGTMTLAELGAAALQYSDNTAMNKLIAHLGGPDKVTAFARSLGDETFRLDRTEP
TLNTAIPGDPRDTTTPLAMAQTLKNLTLGKALAETQRAQLVTWLKGNTTGSASIRAG
LPKSWGVGDKTGSGDYGTTNDIAVIWPENHAPLVLVTYFTQPEQKAESRRDVLAAA
AKIVTHGF

SEQ ID No. 445:
MMTQSIRRSMLTVMATLPLLFSSATLHAQTNSVQQQLEALEKSSGGRLGVALINTAD
NSQILYRADERFAMCSTSKVMAAAALLKQSESDKHLLNQRVEIKKSDLVNYNPIAEK
HVNGTMTLAELGAAALQYSDNTAMNKLIAHLGGPDKVTAFARSLGDETFRLDRTEP
TLNTAIPGDPRDTTTPLAMAQTLKNLTLGKALAETQRAQLVTWLKGNTTGSASIQAG
LPKSWVVGDKTGSGDYGTTNDIAVIWPENHAPLVLVTYFTQPEQKAESRRDVLAAA
AKIVTHGF

SEQ ID No. 1871:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAESRRDV
LASAARIIAEGL

SEQ ID No. 1872:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
ESTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAESRRDV
LASAARIIAEGL

SEQ ID No. 1873:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAESRRDV
LASAARIIAKGL

SEQ ID No. 1874:
MVKKSLRQFTLMATATVTLLLGSVPLYAQTADVQQKLAELERQSGGRLGVALINTAD
NSQILYRADERFAMCSTSKVMAAAAVLKKSESEPNLLNQRVEIKKSDLVNYNPIAEK
HVNGTMSLAELSAAALQYSDNVAMNKLIAHVGGPASVTAFARQLGDETFRLDRTEP
TLNTAIPGDPRDTTSPRAMAQTLRNLTLGKALGDSQRAQLVTWMKGNTTGAASIQA
GLPASWVVGDKTGSGGYGTTNDIAVIWPKDRAPLILVTYFTQPQPKAESRRDVLAS
AAKIVTDGL

SEQ ID No. 1875:
MVKKSLRQFTLMATATVTLLLGSVPLYAQTADVQQKLAELERQSGGRLGVALINTAD
NSQILYRADERFAMCSTSKVMAAAAVLKKSESEPNLLNQRVEIKKSDLVNYNPIAEK
HVNGTMSLAELSAAALQYSDNVAMNKLIAHVGGPASVTAFARQLGDETFRLDRTEP
TLNTAIPGDPRDTTSPRAMAQTLRNLTLGKALGDSQRAQLVTWMKGNTTGAASIQA
GLPASWVVGDKTGSDYGTTNDIAVIWPKDRAPLILVTYFTQPQPKAESRRDVLAS
AAKIVTNGL

SEQ ID No. 1876:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAERRRDV
LASAARIIAEGL

SEQ ID No. 1877:
MRHRVKRMMLMTTACISLLLGSAPLYAQANDVQQKLAALEKSSGGRLGVALIDTAD
NAQTLYRADERFAMCSTSKVMAAAAVLKQSETQKNVLSQKVEIKSSDLINYNPIAEK
HVNGTMTLAELSAAALQYSDNTAMNKLIAHLGGPDKVTAFARAIGDDTFRLDRTEPT
LNTAIPGDPRDTTTPLAMAQTLRHLTGSALGETQRAQLVTWLKGNTTGAASIQAGL
PTSWVVGDKTGSGDYGTTNDIAVIWPEGRAPLILVTYFTQPEQKAESRRDVLAAAA
KIVTDGY

SEQ ID No. 1878:
MVKKSLRQFTLMATATVTLLLGSVPLYAQTADVQQKLAELERQSGGRLGVALINTAD
NSQILYRADERFAMCSTSKVMAVAAVLKKSESEPNLLNQRVEIKKSDLVNYNPIAEK
HVNGTMSLAELSAAALQYSDNVAMNKLIAHVGGPASVTAFARQLGDETFRLDRTEP
TLNTAIPGDPRDTTSPRAMAQTLRNLTGKALGDSQRAQLVTWMKGNTTGAASIQA
GLPASWVVGDKTGSGGYGTTNDIAVIWPKDRAPLILVTYFTQPQPKAESRRDVLAS
AAKIVTDGL

SEQ ID No. 1879:
MVKKSLRQFTLMATATVTLLLGSVPLYAQTADVQQKLAELERQSGGRLGVALINTAD
NSQILYRADERFAMCSTSKVMAVAAVLKKSESEPNLLNQRVEIKKSDLVNYNPIAEK
HVDGTMSLAELSAAALQYSDNVAMNKLISHVGGPASVTAFARQLGDETFRLDRTEP
TLNTAIPGDPRDTTSPRAMAQTLRNLTGKALGDSQRAQLVTWMKGNTTGAASIQA
GLPASWVVGDKTGSDYGTTNDIAVIWPKDRAPLILVTYFTQPQPKAESRRDVLAS
AAKIVTDGL

SEQ ID No. 1880:
MMTQSIRRSMLTVMATLPLLFSSATLHAQANSVQQQLEALEKSSGGRLGVALINTA
DNSQILYRADERFAMCSTSKVMAAAAVLKQSESDKHLLNQRVEIKKSDLVNYNPIAE
KHVNGTMTLAELGAAALQYSDNTAMNKLIAHLGGPDKVTAFARSLGDETFRLDRTE
PTLNTAIPGDPRDTTTPLAMAQTLKNLTLGKALAETQRAQLVTWLKGNTTGSASIRA
GLPKSWVVGDKTGSGDYGTTNDIAVIWPENHAPLVLVTYFTQPEQKAENRRDILAA
AAKIVTHGF

SEQ ID No. 1881:
MVTKRVQRMMFAAAACIPLLLGSAPLYAQTSAVQQKLAALEKSSGGRLGVALIDTA
DNTQVLYRGDERFPMCSTSKVMAVAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAERRRDV
LASAARIIAEGL

SEQ ID No. 1882:
MVKKSLRQFTLMATATVTLLLGSVPLYAQTADVQQKLAELERQSGGRLGVALINTAD
NSQILYRADERFAMCSTSKVMAVAAVLKKSESEPNLLNQRVEIKKSDLVNYNPIAEK
HVNGTMSLAELSAAALQYSDNVAMNKLIAHVGGPASVTAFARQLGDETFRLDRTEP
TLNTAIPGDPRDTTSPRAMAQTLRNLTGKALGDSQRAQLVTWMKGNTTGAASIQA
GLPASWVVGDKTGSGGYGTTNDIAVIWPKDRAPLILVTYFTQPQPKAESRRDVLAS
AAKIVINGL

SEQ ID No. 1883:
MVKKSLRQFTLMATATVTLLLGSVPLYAQTADVQQKLAELERQSGGRLGVALINTAD
NSQILYRADERFAMCSTSKVMAVAAVLKKSESEPNLLNQRVEIKKSDLVNYNPIAEK
HVNGTMSLAELSAAALQYSDNVAMNKLIAHVGGPASVTAFARQLGDETFRLDRTEP
TLNTAIPGDPRDTTSPRAMAQTLRNLTGKALGDSQRAQLVTWMKGNTTGAASIQA
GLPASWVVGDKTGSGGYGTTNDIAVIWPKDRAPLILVTYFTQPQPNAESRRDVLAS
AAKIVTNGL

SEQ ID No. 1884:
MVKKSLRQFTLMATATVTLLLGSVPLYAQTADVQQKLAELERQSGGRLGVALINTAD
NSQILYRADERFAMCSTSKVMAAAAVLKKSESEPNLLNQRVEIKKSDLVNYNPIAEK
HVNGTMSLAELSAAALQYSDNVAMNKLIAHVGGPASVTAFARQLGDETFRLDRTEP
TLNTAIPGDPRDTTSPRAMAQTLRNLTGKALGDSQRAQLVTWMKGNTTGAASIQA
GLPASWVVGDKTGSGGYGTTNDIAVIWPKDRAPLILVTYFTQPQPKAESRHDVLAS
AAKIVTDGL

SEQ ID No. 1885:
MVTKRVQRMMFAAAACIPLLLGSAPLYAQTSAVQQKLAALEKSSGGRLGVALIDTA
DNTQVLYRGDERFPMCSTSKVMAVAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAESRRDV
LASAARIIAEGL

SEQ ID No. 1886:
MVKKSLRQFTLMATATVTLLLGSVPLYAQTADVQQKLAELERQSGGRLGVALINTAD
NSQILYRADERFAMCSTSKAMAVAAVLKKSESEPNLLNQRVEIKKSDLVNYNPIAEK
HVNGTMSLAELSAAALQYSDNVAMNKLIAHVGGPASVTAFARQLGDETFRLDRTEP
TLNTAIPGDPRDTTSPRAMAQTLRNLTGKALGDSQRAQLVTWMKGNTTGAASIQA
GLPASWVVGDKTGSGGYGTTNDIAVIWPKDRAPLILVTYFTQPQPKAESRRDVLAS
AAKIVTDGL

SEQ ID No. 1887:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
ESTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAERRRDV
LASAARIIAEGL

SEQ ID No. 1888:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
EPTQNTAIPGDPRDTTTPRAMAQTLRQLTLGHALGETQRAQLVTWLKGNTTGAASI
RAGLPTSVVTVGDKTGSGGYGTTNDIAVIWPQGRAPLVLVTYFTQPQQNAESRRDV
LASAARIIAEGL

SEQ ID No. 1889:
MVKKSLRQFTLMATATVTLLLGSVPLYAQTADVQQKLAELERQSGGRLGVALINTAD
NSQILYRADERFAMCSTSKVMAAAAVLKKSESEPNLLNQRVEIKKSDLVNYNPIAEK
HVNGTMSLAELIAAALQYSDNVAMNKLIAHVGGPASVTAFARQLGDETFRLDRTEPT
LNTAIPGDPRDTTSPRAMAQTLRNLTLGKALGDSQRAQLVTWMKGNTTGAASIQAG
LPASWVVGDKTGSGGYGTTNDIAVIWPKDRAPLILVTYFTQPQPKAESRRDVLASA
AKIVTDGL

SEQ ID No. 1890:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQREQLVTWLKGNTTGAASI
RAGLPTSWTVGDKTGSGGYGTTNDIAVIWPQGRAPLVLVTYFTQPQQNAESRRDV
LASAARIIAEGL

SEQ ID No. 1891:
MVTKRVQRMMFAAAACIPLLLGSAPLYAQTSAVQQKLAALEKSSGGRLGVALIDTA
DNTQVLYRGDERFPMCSTSKVMAVAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQREQLVTWLKGNTTGAASI
RAGLPTSWTVGDKTGSGGYGTTNDIAVIWPQGRAPLVLVTYFTQPQQNAESRRDV
LASAARIIAEGL

SEQ ID No. 1892:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAENRRDV
LASAARIIAEGL

SEQ ID No. 1893:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDRTGSGDYGTTNDIAVIWPQGRAPLVLVTYFTQPQQNAESRHDV
LASAARIIAEG

SEQ ID No. 1894:
MVKKSLRQFTLMATATVTLLLGSVPLYAQTADVQQKLAELERQSGGRLGVALINTAD
NSQILYRADERFAMCSTSKVMAVAAVLKKSESEPNLLNQRVEIKKSDLVNYNPIAEK
HVNGTMSLAELSAAALQYSDNVAMNKLIAHVGGPASVTAFARQLGDETFRLDRTEP
TLNTAIPGDPRDTTSPRAMAQTLRNLTLGKALGDSQRAQLVTWMKGNTTGAASIQA
GLPASWVVGDKTGSGDYGTTNDIAVIWPKDRAPLILVTYFTQPQPKAESRRDVLAS
AAKIVTNGL

SEQ ID No. 1895:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYNPIA
EEHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAESRRDV
LASAARIIAEGNL

SEQ ID No. 1896:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYNPIA
EEHVNGTMTLAELSAAALQYSDNTAMNKLIAQLGGQGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAESRRDV
LASAARIIAEGL

SEQ ID No. 1897:
VKKSLRQFTLMATATVTLLLGSVPLYAQTADVQQKLAELERQSGGRLGVALINTADN
SQILYRADERFAMCSTSKVMAAAAVLKKSESEPNLLNQRVEIKKSDLVNYNPIAEKH
VNGTMSLAELSAAALQYSDNVAMNKLIAHVGGPASVTAFARQLGDETFRLDRTEPT
LNTAIPGDPRDTTSPRAMAQTLRNLTLGKALGDSQRAQLVTWMKGNTTGAASIQAG
LPASWVVGDRTGSGGYGTTNDIAVIWPKDRAPLILVTYFTQPQPKAESRRDVLASA
AKIVT

SEQ ID No. 1898:
VKKSLRQFTLMATATVTLLLGSVPLYAQTADVQQKLAELERQSGGRLGVALINTADN
SQILYRADERFAMCSTSKVMAAAAVLKKSESEPNLLNQRAEIKKSDLVNYNPIAEKH
VNGTMSLAELSAAALQYSDNVAMNKLIAHVGGPASVTAFARQLGDETFRLDRTEPT
LNTAIPGDPRDTTSPRAMAQTLRNLTLGKALGDSQRAQLVTWMKGNTTGAASIQAG
LPASWVVGDKTGSGGYGTTNDIAVIWPKDRAPLILVTYFTQPQPKAESRRDVLASA
AKIVT

SEQ ID No. 1899:
MVTKRVQRMMFAAAACIPLLLGSAPLYAQTSAVQQKLAALEKSSGGRLGVALIDTA
DNTQVLYRGDERFPMCSTSKVMAAAAVLKQSETQKQLLNQPVEIKPADLVNYNPIA
EKHVNGTMTLAELGAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAESRRDV
LASAARIIAEGL

SEQ ID No. 1900:
MVTKRVQRMMFAAAACIPLLLGSAPLYAQTSAVQQKLAALEKSSGGRLGVALIDTA
DNTQVLYRGDERFPMCSTSKVMAAAAVLKRSETQKQLLNQPVEIKPADLVNYNPIA
EKHVNGTMTLAELSAAALQYSDNTAMNKLIAQLGGPGGVTAFARAIGDETFRLDRT
EPTLNTAIPGDPRDTTTPRAMAQTLRQLTLGHALGETQRAQLVTWLKGNTTGAASI
RAGLPTSWTVGDKTGSGDYGTTNDIAVIWPQGRAPLVLVTYFTQPQQNAESRRDV
LASAARIIAEGL

SEQ ID No. 1901:
VKKSLRQFTLMATATVTLLLGSVPLYAQTADVQQKLAELERQSGGRLGVALINTADN
SRILYRADERFAMCSTSKVMAAAAVLKKSESEPNLLNQRVEIKKSDLVNYNPIAEKH
VNGTMSLAELSAAALQYSDNVAMNKLIAHVGGPASVTAFARQLGDETFRLDRTEPT
LNTAIPGDPRDTTSPRAMAQTLRNLTLGKALGDSQRAQLVTWMKGNTTGAASIQAG
LPASWVVGDKTGSGGYGTTNDIAVIWPKDRAPLILVTYFTQPQPKAESRRDVLASA
AKIVTK

SEQ ID No. 1902:
MMTQSIRRSMLTVMATLPLLFSSATLHAQANSVQQQLEALEKSSGGRLGVALINTA
DNSQILYRADERFAMCSTSKVMAAAAVLKQSESDKHLLNQRVEIKKSDLVNYNPIAE
KHVNGTMTLAELGAAALQYSDNTAMNKLIAHLGGPDKVTAFARSLGDETFRLDRTE
PTLNTAIPGDPRDTTTPLAMAQTLKNLTLGKALAETQRAQLVTWLKGNTTGSASIRA
GLPKSWVVGDKTGSGDYGTTNDIAVIWPENHAPLVLVTYFTQPEQKAERRRDILAA
AAKIVTHGF

SEQ ID No. 1903:
MRHRVKRMMLMTTACISLLLGSAPLYAQANDVQQKLAALEKSSGGRLGVALIDTAD
NAQTLYRADERFAMCSTSKVMAAAAVLKQSETQKNVLSQKVEIKSSDLINYNPIAEK
HVNGTMTLAELSAAALQYSDNTAMNKLIAHLGGPDKVTAFARAIGDDTFRLDRTEPT
LNTAIPGDPRDTTTPLAMAQTLRHLTLGSALGETQRAQLVTWLKGNTTGAASIQAGL
PTSWVVGDKTGSGDYGTTNDIAVIWPEGRAPLILVTYFTQPEQKAENRRDVLAAAA
KIVTDGY

SEQ ID No. 1904:
MVKKSLRQFTLMATATVTLLLGSVPLYAQTADVQQKLAELERQSGGRLGVALINTAD
NSQILYRADERFAMCSTSKVMAVAAVLKKSESEPNLLNQRVEIKKSDLVNYNPIAEK
HVDGTMSLAELSAAALQYSDNVAMNKLISHVGGPASVTAFARQLGDETFRLDRTEP
TLNTAIPGDPRDTTSPRAMAQTLRNLTLGKALGDSQRAQLVTWMKGNTTGAASIQA
GLPASWVVGDKTGSGDYGTTNDIAVIWPKDRAPLILVTYFTQPQPKAESRRDVLAS
AAKIVTNGL

SEQ ID No. 1905:
MMTQSIRRSMLTVMATLPLLFSSATLHAQANSVQQQLEALEKSSGGRLGVALINTA
DNSQILYRADERFAMCSTSKVMAAAAVLKQSESDKHLLNQRVEIKKSDLVNYNPIAE
KHVNGTMTLAELGAAALQYSDNTAMNKLIAHLGGPDKVTAFARSLGDETFRLDRTE
PTLNTAIPGDPRDTTTPLAMAQTLKNLTLGKALAETQRAQLVTWLKGNTTGSASIRA
GLPKSWVVGDKTGSGDYGTTNDIAVIWPENHAPLVLVTYFTQPEQKAESRRDILAA
AAKIVTHGF

SEQ ID No. 1906:
MVKKSLRQFTLMATATVTLLLGSVPLYAQTADVQQKLAELERQSGGRLGVALINTAD
NSQILYRADERFAMCSTSKVMAAAAVLKKSESEPNLLNQRVEIKKSDLVNYNPIAEK
HVNGTMSLAELSAAALQYSDNVAMNKLIAHVGGPASVTAFARQLGDETFRLDRTEP
TLNTAIPGDPRDTTSPRAMAQTLRNLTLGKALGDSQRAQLVTWMKGNTTGAASIQA
GLPASWVVGDKTGSGDYGTTNDIAVIWPKDRAPLILVTYFTQPQPKAESRRDVLAS
AAKIVTDGL

-continued

SEQ ID No. 1907:
MMTQSIRRSMLTVMATLPLLFSSATLHAQANSVQQQLEALEKSSGGRLGVALINTA
DNSQILYRADERFAMCSTSKVMAAAAVLKQSESDKHLLNQRVEIKKSDLVNYNPIAE
KHVNGTMTLAELGAAALQYSDNTAMNKLIAHLGGPDKVTAFARSLGDETFRLDRTE
PTLNTAIPGDPRDTTTPLAMAQTLKNLTLGKALAETQRAQLVTWLKGNTTGSASIRA
GLPKSWVVGDKTGSGDYGTTNDIAVIWPENHAPLVLVTYFTQPEQKAESRRDFLAA
AAKIVTHGF

SEQ ID No. 1908:
MVKKSLRQFTLMATATVTLLLGSVPLYAQTADVQQKLAELERQSGGRLGVALINTAD
NSQILYRADERFAMCSTSKVMAAAAVLKKSESEPNLLNQRVEIKKSDLVNYNPIAEK
HVNGTMSLAELSAAALQYSDNVAMNKLIAHVGGPASVTAFARQLGDETFRLDRTEP
TLNTAIPGDPRDTTSPRAMAQTLRNLTLGKALGDSQRAQLVTWMKGNTTGAASIQA
GLPASWVVGDKTGSGGYGTTNDIAVIWPKDRAPLILVTYFTQPQPKAESRRDVLAS
AAKIVTNGL said peptides being chosen, preferably, from the peptides of sequence SEQ ID No. 446 to SEQ ID 495 and SEQ ID No. 2008 to SEQ ID No. 2092 as defined hereafter:

| Peptide SEQ ID No. | Amino acid sequence | Position of the peptide in the CTX-M protein | Clinical interest |
|---|---|---|---|
| SEQ ID No. 446 | AGLPK | 226-230 for the proteins of SEQ No. 351, 386, 392, 397, 415, 416, 419, 422, 424, 429, 430, 432, 435, 439, 442, 444, 445, 1881, 1903, 1906, 1908 | 2be |
| SEQ ID No. 447 | AGLPTSWTVGDK | 226-237 for the proteins of SEQ No. 355, 356, 360, 361, 362, 367, 369, 376, 377, 378, 379, 380, 381, 398, 402, 403, 407, 408, 409, 410, 411, 413, 421, 423, 436, 1872, 1873, 1874, 1877, 1882, 1886, 1888, 1889, 1891, 1892, 1893, 1896, 1897, 1900, 1901; 224-235 for the protein of sequence SEQ ID No. 425 | 2be |
| SEQ ID No. 448 | AIGDETFR | 157-164 for the proteins of SEQ No. 353, 355, 359, 360, 361, 362, 367, 369, 376, 377, 378, 379, 380, 381, 387, 398, 402, 403, 407, 408, 409, 410, 411, 413, 421, 423, 425, 428, 436, 1872, 1873, 1874, 1877, 1882, 1886, 1888, 1889, 1891, 1892, 1893, 1894, 1896, 1897, 1900, 1901 | 2be |
| SEQ ID No. 449 | ALAETQR | 201-207 for the proteins of SEQ No. 351, 386, 392, 397, 415, 416, 419, 422, 424, 429, 430, 432, 434, 435, 439, 442, 444, 445, 1881, 1903, 1906, 1908 | 2be |
| SEQ ID No. 450 | ALGDSQR | 201-207 for the proteins of SEQ No. 354, 357, 358, 363, 364, 365, 370, 371, 372, 373, 374, 382, 385, 388, 389, 390, 391, 393, 394, 395, 396, 399, 400, 401, 404, 405, 406, 412, 417, 426, 431, 433, 437, 438, 440, 441, 1875, 1876, 1879, 1880, 1883, 1884, 1885, 1887, 1890, 1895, 1905, 1907, 1909; 200-206 for the protein of sequence SEQ ID No. 1898; 200-206 for the protein of sequence SEQ ID No. 1899; 200-206 for the protein of sequence SEQ ID No. 1902 | 2be |
| SEQ ID No. 451 | AMAQTLR | 188-194 for the proteins of SEQ No. 352, 353, 354, 355, 356, 357, 358, 359, 360, 361, 362, 363, 364, 365, 367, 369, 370, 371, 372, 373, 374, 376, 377, 378, 379, 380, 381, 382, 385, 387, 388, 389, 390, 391, 393, 394, 395, 396, 398, 399, 400, 401, 402, 403, 404, 405, 406, 407, 408, 409, 410, 411, 412, 413, 417, 421, 423, 426, 428, 431, 433, 436, 437, 438, 440, 441, 443, 1872, 1873, 1874, 1875, 1876, 1877, 1879, 1880, 1882, 1883, 1884, 1885, 1886, 1887, 1888, 1889, 1890, 1891, 1892, 1893, 1894, 1895, 1896, 1897, 1900, 1901, 1905, 1907, 1909; 187-193 for the protein of sequence SEQ ID No. 375; 187-193 for the protein of sequence SEQ ID No. 427; 187-193 for the protein of sequence SEQ ID No. 1878; 187-193 for the protein of sequence SEQ ID No. 1898; 187-193 for the protein of sequence SEQ ID No. 1899; 187-193 for the protein of sequence SEQ ID No. 1902; 187-193 for the protein of sequence SEQ ID No. 1904 | 2be |
| SEQ ID No. 452 | APLILVTYFTQPQPK | 258-272 for the proteins of SEQ No. 354, 357, 358, 363, 364, 365, 370, 371, 372, 373, 374, 382, 385, 388, 389, 391, 393, 394, 395, 396, 399, 400, 401, 404, 405, 412, 417, 426, 428, 431, 433, 437, 438, 440, 441, 1875, 1876, | 2be |

-continued

| Peptide SEQ ID No. | Amino acid sequence | Position of the peptide in the CTX-M protein | Clinical interest |
|---|---|---|---|
| | | 1879, 1880, 1883, 1885, 1887, 1890, 1895, 1905, 1907, 1909; 257-271 for the protein of sequence SEQ ID No. 1898; 257-271 for the protein of sequence SEQ ID No. 1899; 257-271 for the protein of sequence SEQ ID No. 1902 | |
| SEQ ID No. 453 | APLVLVTYFTQPQQNAESR | 258-276 for the proteins of SEQ No. 353, 355, 356, 359, 360, 361, 362, 369, 376, 377, 378, 379, 380, 381, 387, 402, 403, 407, 408, 409, 410, 411, 413, 423, 436, 1872, 1873, 1874, 1886, 1889, 1891, 1892, 1894, 1896, 1897, 1900, 1901; 256-274 for the protein of sequence SEQ ID No. 425 | 2be |
| SEQ ID No. 454 | AQLVTWLK | 208-215 for the proteins of SEQ No. 351, 352, 353, 355, 356, 359, 360, 361, 362, 367, 369, 376, 377, 378, 379, 380, 381, 386, 387, 392, 397, 398, 402, 403, 407, 408, 410, 411, 413, 415, 416, 421, 422, 423, 424, 428, 429, 430, 432, 434, 435, 436, 439, 442, 443, 444, 445, 1872, 1873, 1874, 1877, 1881, 1882, 1886, 1888, 1889, 1893, 1894, 1896, 1897, 1900, 1901, 1903, 1906, 1908; 207-214 for the protein of sequence SEQ ID No. 375; 207-214 for the protein of sequence SEQ ID No. 427; 207-214 for the protein of sequence SEQ ID No. 1878; 207-214 for the protein of sequence SEQ ID No. 1904 | 2be |
| SEQ ID No. 455 | AQLVTWMK | 208-215 for the proteins of SEQ No. 354, 357, 358, 363, 364, 365, 370, 371, 372, 373, 374, 382, 385, 388, 389, 390, 391, 393, 394, 395, 396, 399, 400, 401, 404, 405, 406, 412, 417, 426, 431, 433, 437, 438, 440, 441, 1875, 1876, 1879, 1880, 1883, 1884, 1885, 1887, 1890, 1895, 1905, 1907, 1909; 207-214 for the protein of sequence SEQ ID No. 1898; 207-214 for the protein of sequence SEQ ID No. 1899; 207-214 for the protein of sequence SEQ ID No. 1902 | 2be |
| SEQ ID No. 456 | DILAAAAK | 278-285 for the proteins of SEQ No. 386, 392, 397, 415, 416, 419, 422, 424, 432, 434, 439, 1881, 1903, 1906 | 2be |
| SEQ ID No. 457 | DTTSPR | 182-187 for the proteins of SEQ No. 354, 357, 358, 363, 364, 365, 370, 371, 372, 373, 374, 382, 385, 388, 389, 390, 391, 393, 394, 395, 396, 399, 400, 401, 404, 405, 406, 412, 417, 426, 431, 433, 437, 438, 440, 441, 1875, 1876, 1879, 1880, 1883, 1884, 1885, 1887, 1890, 1895, 1905, 1907, 1909; 181-186 for the protein of sequence SEQ ID No. 1898; 181-186 for the protein of sequence SEQ ID No. 1899; 181-186 for the protein of sequence SEQ ID No. 1902 | 2be |
| SEQ ID No. 458 | DTTTPLAMAQTLK | 182-194 for the proteins of SEQ No. 351, 386, 392, 397, 415, 416, 419, 422, 424, 429, 430, 432, 434, 435, 439, 442, 444, 445, 1881, 1903, 1906, 1908 | 2be |
| SEQ ID No. 459 | DTTTPR | 182-187 for the proteins of SEQ No. 353, 355, 356, 359, 360, 361, 362, 367, 369, 376, 377, 378, 379, 380, 381, 387, 398, 402, 403, 407, 408, 409, 410, 411, 413, 421, 423, 428, 436, 1872, 1873, 1874, 1877, 1882, 1886, 1888, 1889, 1891, 1892, 1893, 1894, 1896, 1897, 1900, 1901 | 2be |
| SEQ ID No. 460 | DVLAAAAK | 277-284 for the proteins of SEQ No. 375, 427, 1878, 1904; 278-285 for the protein of sequence SEQ ID No. 351; 278-285 for the protein of sequence SEQ ID No. 352; 278-285 for the protein of sequence SEQ ID No. 429; 278-285 for the protein of sequence SEQ ID No. 430; 278-285 for the protein of sequence SEQ ID No. 442; 278-285 for the protein of sequence SEQ ID No. 444; 278-285 for the protein of sequence SEQ ID No. 445 | 2be |
| SEQ ID No. 461 | DVLASAAK | 278-285 for the proteins of SEQ No. 354, 363, 364, 365, 370, 371, 372, 373, 374, 382, 385, 388, 389, 390, 391, 393, 394, 395, 396, 399, 400, 401, 404, 405, 406, 412, 417, 426, 428, 431, 433, 437, 438, 1875, 1876, 1879, 1880, 1883, 1884, 1885, 1887, 1890, 1895, 1905, 1907, | 2be |

-continued

| Peptide SEQ ID No. | Amino acid sequence | Position of the peptide in the CTX-M protein | Clinical interest |
|---|---|---|---|
| | | 1909; 277-284 for the protein of sequence SEQ ID No. 1898; 277-284 for the protein of sequence SEQ ID No. 1899; 277-284 for the protein of sequence SEQ ID No. 1902 | |
| SEQ ID No. 462 | DVLASAAR | 278-285 for the proteins of SEQ No. 353, 355, 356, 359, 360, 361, 362, 367, 369, 376, 377, 378, 379, 380, 381, 387, 398, 402, 403, 407, 408, 409, 410, 411, 413, 421, 423, 436, 1872, 1873, 1874, 1877, 1882, 1886, 1888, 1889, 1891, 1892, 1893, 1894, 1896, 1897, 1900, 1901; 276-283 for the protein of sequence SEQ ID No. 425 | 2be |
| SEQ ID No. 463 | FAMCSTSK | 69-76 for the proteins of SEQ No. 351, 352, 354, 357, 358, 363, 364, 365, 366, 368, 370, 371, 372, 373, 374, 382, 383, 384, 385, 386, 388, 390, 391, 392, 393, 394, 395, 396, 397, 399, 400, 401, 404, 405, 406, 412, 414, 415, 416, 417, 418, 419, 420, 422, 424, 426, 429, 430, 431, 432, 433, 434, 435, 437, 438, 439, 440, 441, 442, 443, 444, 445, 1875, 1876, 1879, 1880, 1881, 1883, 1884, 1885, 1887, 1890, 1895, 1903, 1905, 1906, 1907, 1908, 1909; 68-75 for the protein of sequence SEQ ID No. 375; 68-75 for the protein of sequence SEQ ID No. 427; 68-75 for the protein of sequence SEQ ID No. 1878; 68-75 for the protein of sequence SEQ ID No. 1898; 68-75 for the protein of sequence SEQ ID No. 1899; 68-75 for the protein of sequence SEQ ID No. 1902; 68-75 for the protein of sequence SEQ ID No. 1904 | 2be |
| SEQ ID No. 464 | FPMCSTSK | 69-76 for the proteins of SEQ No. 353, 355, 356, 359, 360, 361, 362, 367, 369, 376, 377, 378, 379, 380, 381, 387, 389, 398, 402, 403, 407, 408, 409, 410, 411, 413, 421, 423, 425, 428, 436, 1872, 1873, 1874, 1877, 1882, 1886, 1888, 1889, 1891, 1892, 1893, 1894, 1896, 1897, 1900, 1901 | 2be |
| SEQ ID No. 465 | GNTTGAASIQAGLPASWVVGDK | 216-237 for the proteins of SEQ No. 354, 357, 358, 363, 364, 365, 370, 371, 372, 373, 374, 382, 385, 388, 389, 390, 391, 393, 394, 395, 396, 399, 400, 401, 404, 405, 406, 412, 417, 426, 431, 433, 437, 438, 440, 441, 1875, 1876, 1879, 1880, 1883, 1884, 1885, 1887, 1890, 1895, 1905, 1907, 1909; 215-236 for the protein of sequence SEQ ID No. 1899; 215-236 for the protein of sequence SEQ ID No. 1902 | 2be |
| SEQ ID No. 466 | GNTTGAASIQAGLPTSWVVGDK | 215-236 for the proteins of SEQ ID No. 375, 427, 1878, 1904; 216-237 for the protein of sequence SEQ ID No. 352; 216-237 for the protein of sequence SEQ ID No. 366; 216-237 for the protein of sequence SEQ ID No. 383; 216-237 for the protein of sequence SEQ ID No. 384; 216-237 for the protein of sequence SEQ ID No. 414; 216-237 for the protein of sequence SEQ ID No. 418; 216-237 for the protein of sequence SEQ ID No. 420; 216-237 for the protein of sequence SEQ ID No. 443 | 2be |
| SEQ ID No. 467 | GNTTGAASIR | 216-225 for the proteins of SEQ No. 353, 355, 356, 359, 360, 361, 362, 367, 368, 369, 377, 378, 379, 380, 381, 387, 398, 402, 403, 407, 408, 409, 410, 411, 413, 421, 423, 428, 436, 1872, 1873, 1874, 1877, 1882, 1886, 1888, 1889, 1891, 1892, 1893, 1894, 1896, 1897, 1900, 1901 | 2be |
| SEQ ID No. 468 | GNTTGSASIR | 216-225 for the proteins of SEQ No. 351, 386, 392, 397, 416, 419, 422, 424, 429, 430, 432, 434, 435, 439, 44-4, 1881, 1903, 1906, 1908 | 2be |
| SEQ ID No. 469 | HLLNQR | 92-97 for the proteins of SEQ No. 351, 386, 397, 415, 416, 419, 422, 424, 429, 430, 432, 434, 435, 439, 442, 444, 445, 1881, 1903, 1906, 1908 | 2be |
| SEQ ID No. 470 | LAALEK | 36-41 for the proteins of SEQ No. 375, 427, 1878, 1904; 37-42 for the proteins of sequence SEQ ID No. 352, 353, 355, 356, 359, 360, 361, 362, 366, 367, 368, 369, 376, 377, 378, 379, 380, 381, 383, 384, 387, 398, 402, 403, 407, 408, 409, 410, 411, 413, 414, 418, 420, 421, 423, 425, 436, 443, 1872, 1873, 1874, 1877, 1882, 1886, 1888, 1889, 1891, 1892, 1893, 1894, 1896, 1897, 1900, 1901 | 2be |

-continued

| Peptide SEQ ID No. | Amino acid sequence | Position of the peptide in the CTX-M protein | Clinical interest |
|---|---|---|---|
| SEQ ID No. 471 | LAELER | 37-42 for the proteins of SEQ No. 358, 363, 364, 365, 370, 371, 372, 382, 385, 388, 389, 391, 393, 394, 395, 396, 399, 400, 401, 404, 405, 406, 412, 417, 426, 428, 431, 433, 437, 438, 440, 441, 1875, 1876, 1879, 1880, 1883, 1884, 1885, 1887, 1890, 1895, 1905, 1907, 1909; 36-41 for the protein of sequence SEQ ID No. 1898; 36-41 for the protein of sequence SEQ ID No. 1899; 36-41 for the protein of sequence SEQ ID No. 1902 | 2be |
| SEQ ID No. 472 | LGVALIDTADNTQVLYR | 48-64 for the proteins of SEQ No. 353, 355, 359, 360, 361, 362, 367, 369, 376, 377, 378, 387, 398, 402, 403, 407, 409, 410, 411, 413, 421, 423, 425, 436, 1872, 1873, 1874, 1877, 1882, 1886, 1888, 1889, 1891, 1892, 1893, 1894, 1896, 1897, 1900, 1901 | 2be |
| SEQ ID No. 473 | LGVALINTADNSQILYR | 48-64 for the proteins of SEQ No. 351, 354, 357, 358, 363, 364, 365, 370, 371, 372, 373, 374, 382, 385, 386, 388, 389, 390, 391, 392, 393, 394, 395, 396, 397, 399, 400, 401, 404, 405, 406, 412, 415, 416, 417, 419, 422, 424, 426, 428, 431, 432, 433, 435, 437, 438, 439, 440, 441, 442, 444, 445, 1875, 1876, 1879, 1880, 1881, 1883, 1884, 1885, 1887, 1890, 1895, 1903, 1905, 1906, 1907, 1908, 1909; 47-63 for the protein of sequence SEQ ID No. 1898; 47-63 for the protein of sequence SEQ ID No. 1899 | 2be |
| SEQ ID No. 474 | LIAHLGGPDK | 141-150 for the proteins of SEQ No. 351, 352, 366, 368, 383, 384, 386, 392, 397, 414, 415, 416, 418, 419, 420, 422, 424, 429, 430, 432, 434, 435, 439, 444, 445, 1881, 1903, 1906, 1908; 140-149 for the protein of sequence SEQ ID No. 375; 140-149 for the protein of sequence SEQ ID No. 427; 140-149 for the protein of sequence SEQ ID No. 1878; 140-149 for the protein of sequence SEQ ID No. 1904 | 2be |
| SEQ ID No. 475 | LIAHVGGPASVTAFAR | 141-156 for the proteins of SEQ No. 354, 357, 358, 363, 364, 365, 370, 371, 372, 373, 374, 382, 385, 388, 389, 390, 391, 393, 394, 399, 400, 401, 404, 405, 406, 412, 417, 433, 437, 440, 441, 1875, 1876, 1879, 1883, 1884, 1885, 1887, 1890, 1895, 1907, 1909; 140-155 for the protein of sequence SEQ ID No. 1898; 140-155 for the protein of sequence SEQ ID No. 1899; 140-155 for the protein of sequence SEQ ID No. 1902 | 2be |
| SEQ ID No. 476 | LIAQLGGPGGVTAFAR | 141-156 for the proteins of SEQ No. 353, 355, 356, 359, 360, 361, 362, 367, 369, 376, 377, 378, 379, 380, 381, 387, 398, 402, 403, 407, 408, 409, 410, 411, 413, 421, 423, 425, 428, 436, 1872, 1873, 1874, 1877, 1882, 1886, 1888, 1889, 1891, 1892, 1893, 1894, 1896, 1900, 1901 | 2be |
| SEQ ID No. 477 | NLTLGK | 195-200 for the proteins of SEQ No. 351, 354, 357, 358, 363, 364, 365, 370, 371, 372, 373, 374, 382, 385, 386, 388, 389, 390, 391, 392, 393, 394, 395, 396, 397, 399, 400, 401, 404, 405, 406, 412, 415, 416, 417, 419, 422, 424, 426, 429, 430, 431, 432, 433, 434, 435, 437, 438, 439, 440, 441, 442, 444, 445, 1875, 1876, 1879, 1880, 1881, 1883, 1884, 1885, 1887, 1890, 1895, 1903, 1905, 1906, 1907, 1908, 1909; 194-199 for the protein of sequence SEQ ID No. 1898; 194-199 for the protein of sequence SEQ ID No. 1899; 194-199 for the protein of sequence SEQ ID No. 1902 | 2be |
| SEQ ID No. 478 | QLGDETFR | 157-164 for the proteins of SEQ No. 354, 357, 358, 363, 364, 365, 370, 371, 372, 373, 374, 382, 385, 388, 389, 390, 391, 393, 394, 395, 396, 399, 400, 401, 405, 406, 412, 417, 426, 431, 433, 437, 438, 440, 441, 1875, 1876, 1879, 1880, 1883, 1884, 1885, 1887, 1890, 1895, 1905, 1907, 1909; 156-163 for the protein of sequence SEQ ID No. 1898; 156-163 for the protein of sequence SEQ ID No. 1899; 156-163 for the protein of sequence SEQ ID No. 1902 | 2be |
| SEQ ID No. 479 | QLLNQPVEIK | 92-101 for the proteins of SEQ No. 353, 355, 356, 359, 360, 361, 362, 367, 369, 376, 377, 378, 379, 380, 381, | 2be |

| Peptide SEQ ID No. | Amino acid sequence | Position of the peptide in the CTX-M protein | Clinical interest |
|---|---|---|---|
| | | 387, 398, 402, 407, 408, 409, 410, 411, 413, 421, 423, 425, 428, 436, 1872, 1873, 1874, 1877, 1882, 1886, 1888, 1889, 1891, 1892, 1893, 1894, 1896, 1897, 1900, 1901 | |
| SEQ ID No. 480 | QLTLGHALGETQR | 195-207 for the proteins of SEQ No. 353, 355, 356, 359, 360, 361, 362, 367, 369, 376, 377, 378, 379, 380, 381, 387, 398, 402, 403, 407, 408, 409, 410, 411, 413, 421, 423, 428, 436, 1872, 1873, 1874, 1877, 1882, 1886, 1888, 1889, 1891, 1892, 1893, 1894, 1896, 1897, 1900, 1901 | 2be |
| SEQ ID No. 481 | QSESDK | 86-91 for the proteins of SEQ No. 351, 386, 392, 397, 415, 416, 419, 422, 424, 429, 430, 432, 434, 435, 439, 442, 444, 445, 1881, 1903, 1906, 1908 | 2be |
| SEQ ID No. 482 | QSETQK | 85-90 for the proteins of SEQ No. 375, 427, 1878, 1904; 86-91 for the protein of sequence SEQ ID No. 352; 86-91 for the protein of sequence SEQ ID No. 353; 86-91 for the protein of sequence SEQ ID No. 355; 86-91 for the protein of sequence SEQ ID No. 356; 86-91 for the protein of sequence SEQ ID No. 359; 86-91 for the protein of sequence SEQ ID No. 360; 86-91 for the protein of sequence SEQ ID No. 361; 86-91 for the protein of sequence SEQ ID No. 362; 86-91 for the protein of sequence SEQ ID No. 366; 86-91 for the protein of sequence SEQ ID No. 367; 86-91 for the protein of sequence SEQ ID No. 368; 86-91 for the protein of sequence SEQ ID No. 369; 86-91 for the protein of sequence SEQ ID No. 376; 86-91 for the protein of sequence SEQ ID No. 377; 86-91 for the protein of sequence SEQ ID No. 378; 86-91 for the protein of sequence SEQ ID No. 379; 86-91 for the protein of sequence SEQ ID No. 380; 86-91 for the protein of sequence SEQ ID No. 381; 86-91 for the protein of sequence SEQ ID No. 383; 86-91 for the protein of sequence SEQ ID No. 384; 86-91 for the protein of sequence SEQ ID No. 387; 86-91 for the protein of sequence SEQ ID No. 398; 86-91 for the protein of sequence SEQ ID No. 402; 86-91 for the protein of sequence SEQ ID No. 403; 86-91 for the protein of sequence SEQ ID No. 407; 86-91 for the protein of sequence SEQ ID No. 408; 86-91 for the protein of sequence SEQ ID No. 409; 86-91 for the protein of sequence SEQ ID No. 410; 86-91 for the protein of sequence SEQ ID No. 411; 86-91 for the protein of sequence SEQ ID No. 413; 86-91 for the protein of sequence SEQ ID No. 414; 86-91 for the protein of sequence SEQ ID No. 418; 86-91 for the protein of sequence SEQ ID No. 420; 86-91 for the protein of sequence SEQ ID No. 421; 86-91 for the protein of sequence SEQ ID No. 423; 86-91 for the protein of sequence SEQ ID No. 425; 86-91 for the protein of sequence SEQ ID No. 428; 86-91 for the protein of sequence SEQ ID No. 436; 86-91 for the protein of sequence SEQ ID No. 443; 86-91 for the protein of sequence SEQ ID No. 1872; 86-91 for the protein of sequence SEQ ID No. 1873; 86-91 for the protein of sequence SEQ ID No. 1874; 86-91 for the protein of sequence SEQ ID No. 1877; 86-91 for the protein of sequence SEQ ID No. 1882; 86-91 for the protein of sequence SEQ ID No. 1886; 86-91 for the protein of sequence SEQ ID No. 1888; 86-91 for the protein of sequence SEQ ID No. 1889; 86-91 for the protein of sequence SEQ ID No. 1891; 86-91 for the protein of sequence SEQ ID No. 1892; 86-91 for the protein of sequence SEQ ID No. 1893; 86-91 for the protein of sequence SEQ ID No. 1894; 86-91 for the protein of sequence SEQ ID No. 1896; 86-91 for the protein of sequence SEQ ID No. 1897; 86-91 for the protein of sequence SEQ ID No. 1900 | 2be |
| SEQ ID No. 483 | QSGGR | 43-47 for the proteins of SEQ No. 354, 357, 358, 363, 364, 365, 370, 371, 372, 373, 374, 382, 385, 388, 389, 390, 391, 393, 394, 395, 396, 399, 400, 401, 404, 405, 406, 412, 417, 426, 428, 431, 433, 437, 438, 440, 441, 1875, 1876, 1879, 1880, 1883, 1884, 1885, 1887, 1890, | 2be |

| Peptide SEQ ID No. | Amino acid sequence | Position of the peptide in the CTX-M protein | Clinical interest |
|---|---|---|---|
| | | 1895, 1905, 1907, 1909; 42-46 for the protein of sequence SEQ ID No. 1898; 42-46 for the protein of sequence SEQ ID No. 1899; 42-46 for the protein of sequence SEQ ID No. 1902 | |
| SEQ ID No. 484 | SDLVNYNPIAEK | 103-114 for the proteins of SEQ No. 351, 354, 357, 358, 363, 364, 365, 371, 372, 373, 374, 382, 384, 385, 386, 388, 389, 390, 391, 392, 393, 394, 395, 396, 397, 399, 400, 401, 404, 405, 406, 412, 415, 416, 417, 419, 422, 424, 426, 429, 430, 431, 432, 433, 434, 435, 437, 438, 439, 440, 441, 442, 444, 445, 1875, 1876, 1879, 1880, 1881, 1883, 1884, 1885, 1887, 1890, 1895, 1903, 1905, 1906, 1907, 1908, 1909; 102-113 for the protein of sequence SEQ ID No. 1898; 102-113 for the protein of sequence SEQ ID No. 1899; 102-113 for the protein of sequence SEQ ID No. 1902 | 2be |
| SEQ ID No. 485 | SESEPNLLNQR | 87-97 for the proteins of SEQ No. 354, 357, 363, 364, 365, 370, 371, 372, 373, 374, 382, 385, 388, 389, 390, 391, 393, 394, 395, 396, 399, 400, 401, 404, 405, 406, 412, 417, 426, 431, 433, 437, 438, 1875, 1876, 1879, 1880, 1883, 1884, 1885, 1887, 1890, 1895, 1905, 1907, 1909; 86-96 for the protein of sequence SEQ ID No. 1898; 86-96 for the protein of sequence SEQ ID No. 1899; 86-96 for the protein of sequence SEQ ID No. 1902 | 2be |
| SEQ ID No 486. | SLGDETFR | 157-164 for the proteins of SEQ No. 351, 386, 392, 397, 415, 416, 419, 422, 424, 429, 430, 432, 434, 435, 442, 444, 445, 1881, 1903, 1906, 1908 | 2be |
| SEQ ID No. 487 | SSGGR | 43-47 for the proteins of SEQ No. 351, 352, 353, 355, 356, 359, 360, 361, 362, 366, 367, 368, 369, 376, 378, 380, 381, 383, 384, 386, 387, 392, 397, 398, 402, 403, 407, 408, 409, 410, 411, 413, 414, 415, 416, 418, 419, 420, 421, 422, 423, 424, 425, 429, 430, 432, 434, 435, 436, 439, 442, 443, 444, 445, 1872, 1873, 1874, 1877, 1881, 1882, 1886, 1888, 1889, 1891, 1892, 1893, 1894, 1896, 1897, 1900, 1901, 1903, 1906, 1908; 42-46 for the protein of sequence SEQ ID No. 375; 42-46 for the protein of sequence SEQ ID No. 427; 42-46 for the protein of sequence SEQ ID No. 1878; 42-46 for the protein of sequence SEQ ID No. 1904 | 2be |
| SEQ ID No. 488 | SWVVGDK | 231-237 for the proteins of SEQ No. 352, 354, 357, 358, 363, 364, 365, 366, 368, 370, 371, 372, 373, 374, 382, 383, 384, 385, 386, 388, 389, 390, 391, 392, 393, 394, 395, 396, 397, 399, 400, 401, 404, 405, 406, 412, 414, 415, 416, 417, 418, 419, 420, 422, 424, 426, 428, 431, 432, 433, 435, 437, 438, 439, 440, 441, 442, 443, 445, 1875, 1876, 1879, 1880, 1881, 1883, 1884, 1885, 1887, 1890, 1895, 1903, 1905, 1906, 1907, 1908, 1909; 230-236 for the protein of sequence SEQ ID No. 375; 230-236 for the protein of sequence SEQ ID No. 427; 230-236 for the protein of sequence SEQ ID No. 1878; 230-236 for the protein of sequence SEQ ID No. 1899; 230-236 for the protein of sequence SEQ ID No. 1902; 230-236 for the protein of sequence SEQ ID No. 1904 | 2be |
| SEQ ID No. 489 | TEPTLNTAIPGDPR | 168-181 for the proteins of SEQ No. 351, 352, 353, 354, 355, 356, 357, 358, 359, 360, 362, 363, 364, 366, 367, 368, 369, 370, 371, 372, 373, 374, 376, 377, 378, 379, 380, 381, 382, 383, 384, 386, 387, 389, 390, 392, 393, 394, 396, 397, 398, 399, 401, 402, 403, 404, 405, 406, 408, 409, 410, 411, 412, 413, 414, 416, 417, 418, 419, 420, 422, 423, 424, 425, 426, 428, 431, 432, 433, 435, 436, 437, 438, 439, 440, 441, 442, 443, 444, 445, 1872, 1874, 1875, 1876, 1877, 1879, 1880, 1881, 1882, 1883, 1884, 1885, 1886, 1887, 1890, 1891, 1892, 1893, 1894, 1895, 1896, 1897, 1900, 1901, 1903, 1905, 1906, 1907, 1908, 1909; 167-180 for the protein of sequence SEQ ID No. 375; 167-180 for the protein of sequence SEQ ID No. 427; 167-180 for the protein of sequence SEQ ID No. 1878; 167-180 for the protein of sequence SEQ ID No. 1898; 167-180 for the protein of sequence SEQ ID No. 1899; 167-180 for the protein of sequence SEQ ID No. | 2be |

| Peptide SEQ ID No. | Amino acid sequence | Position of the peptide in the CTX-M protein | Clinical interest |
|---|---|---|---|
| | | 1902; 167-180 for the protein of sequence SEQ ID No. 1904 | |
| SEQ ID No. 490 | TGSGDYGTTNDIAVIWPK | 238-255 for the proteins of SEQ No. 354, 357, 358, 364, 365, 372, 374, 382, 385, 388, 391, 395, 396, 400, 401, 404, 405, 426, 431, 433, 441, 1876, 1880, 1895, 1905, 1907 | 2be |
| SEQ ID No. 491 | TGSGDYGTTNDIAVIWPQGR | 238-257 for the proteins of SEQ No. 353, 355, 356, 360, 361, 362, 367, 376, 377, 378, 379, 380, 381, 387, 398, 402, 403, 407, 408, 409, 410, 411, 413, 421, 436, 1872, 1873, 1874, 1877, 1882, 1886, 1888, 1893, 1894, 1896, 1897, 1900, 1901; 236-255 for the protein of sequence SEQ ID No. 425 | 2be |
| SEQ ID No. 492 | TGSGGYGTTNDIAVIWPK | 238-255 for the proteins of SEQ No. 363, 370, 371, 389, 390, 393, 394, 399, 406, 412, 428, 437, 438, 440, 1875, 1879, 1883, 1884, 1885, 1887, 1890; 237-254 for the protein of sequence SEQ ID No. 1898; 237-254 for the protein of sequence SEQ ID No. 1899; 237-254 for the protein of sequence SEQ ID No. 1902 | 2be |
| SEQ ID No. 493 | VMAAAAVLK | 77-85 for the proteins of SEQ No. 351, 352, 353, 354, 355, 356, 357, 358, 359, 360, 361, 362, 363, 364, 367, 368, 369, 370, 371, 372, 373, 374, 376, 377, 378, 379, 380, 381, 382, 383, 384, 385, 386, 389, 391, 392, 397, 400, 401, 402, 404, 405, 408, 409, 410, 411, 412, 415, 416, 417, 419, 420, 421, 422, 424, 425, 426, 428, 429, 430, 432, 433, 434, 435, 436, 437, 439, 440, 442, 443, 444, 1872, 1873, 1874, 1875, 1876, 1877, 1881, 1885, 1888, 1889, 1890, 1891, 1893, 1894, 1896, 1897, 1900, 1901, 1903, 1906, 1907, 1908, 1909; 76-84 for the protein of sequence SEQ ID No. 375; 76-84 for the protein of sequence SEQ ID No. 427; 76-84 for the protein of sequence SEQ ID No. 1878; 76-84 for the protein of sequence SEQ ID No. 1898; 76-84 for the protein of sequence SEQ ID No. 1899; 76-84 for the protein of sequence SEQ ID No. 1902; 76-84 for the protein of sequence SEQ ID No. 1904 | 2be |
| SEQ ID No. 494 | VMAVAAVLK | 77-85 for the proteins of SEQ No. 365, 366, 387, 388, 390, 393, 394, 395, 396, 398, 399, 406, 407, 413, 414, 418, 423, 431, 438, 441, 1879, 1880, 1882, 1883, 1884, 1886, 1892, 1895, 1905 | 2be |
| SEQ ID No. 495 | VTAFAR | 151-156 for the proteins of SEQ No. 351, 352, 353, 354, 355, 356, 357, 358, 359, 360, 361, 362, 363, 364, 365, 366, 367, 368, 369, 370, 371, 372, 373, 374, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 428, 429, 430, 431, 432, 433, 434, 435, 436, 437, 438, 439, 440, 441, 442, 443, 444, 445, 1872, 1873, 1874, 1875, 1876, 1877, 1879, 1880, 1881, 1882, 1883, 1884, 1885, 1886, 1887, 1888, 1889, 1890, 1891, 1892, 1893, 1894, 1895, 1896, 1897, 1900, 1901, 1903, 1905, 1906, 1907, 1908, 1909; 150-155 for the protein of sequence SEQ ID No. 375; 150-155 for the protein of sequence SEQ ID No. 427; 150-155 for the protein of sequence SEQ ID No. 1878; 150-155 for the protein of sequence SEQ ID No. 1898; 150-155 for the protein of sequence SEQ ID No. 1899; 150-155 for the protein of sequence SEQ ID No. 1902; 150-155 for the protein of sequence SEQ ID No. 1904 | 2be |
| SEQ ID No. 2008 | AAGIR | 219-223 for the protein of SEQ No. 425 | 2be |
| SEQ ID No. 2009 | AGADVASLR | 188-196 for the protein of SEQ No. 425 | 2be |
| SEQ ID No. 2010 | AGLPASWVVGDK | 226-237 for the proteins of SEQ No. 354, 357, 358, 363, 364, 365, 370, 371, 372, 373, 374, 382, 385, 388, 389, 390, 391, 393, 394, 395, 396, 399, 400, 401, 404, 405, | 2be |

-continued

| Peptide SEQ ID No. | Amino acid sequence | Position of the peptide in the CTX-M protein | Clinical interest |
|---|---|---|---|
| | | 406, 412, 417, 426, 428, 431, 433, 437, 438, 440, 441, 1875, 1876, 1879, 1880, 1883, 1884, 1885, 1887, 1890, 1895, 1905, 1907, 1909; 225-236 for the protein of sequence SEQ ID No. 1899; 225-236 for the protein of sequence SEQ ID No. 1902 | |
| SEQ ID No. 2011 | AGLPTSWTAGDK | 226-237 for the proteins of SEQ No. 353, 359, 387 | 2be |
| SEQ ID No. 2012 | AGLPTSWTVGDR | 226-237 for the proteins of SEQ No. 1894 | 2be |
| SEQ ID No. 2013 | AGLPTSWVVGDK | 225-236 for the proteins of SEQ No. 375, 427, 1878, 1904; 226-237 for the protein of sequence SEQ ID No. 352; 226-237 for the protein of sequence SEQ ID No. 366; 226-237 for the protein of sequence SEQ ID No. 368; 226-237 for the protein of sequence SEQ ID No. 383; 226-237 for the protein of sequence SEQ ID No. 384; 226-237 for the protein of sequence SEQ ID No. 414; 226-237 for the protein of sequence SEQ ID No. 418; 226-237 for the protein of sequence SEQ ID No. 420; 226-237 for the protein of sequence SEQ ID No. 443 | 2be |
| SEQ ID No. 2014 | AGMPK | 226-230 for the protein of SEQ No. 434 | 2be |
| SEQ ID No. 2015 | AIGDDTFR | 156-163 for the proteins of SEQ No. 375, 427, 1878, 1904 | 2be |
| SEQ ID No. 2016 | AIGDNTFR | 157-164 for the protein of SEQ No. 352 | 2be |
| SEQ ID No. 2017 | AMAVAAVLK | 77-85 for the proteins of SEQ No. 1887 | 2be |
| SEQ ID No. 2018 | APLILVIYFTQPQPK | 258-272 for the protein of SEQ No. 390 | 2be |
| SEQ ID No. 2019 | APLILVTYFTQPEQK | 257-271 for the proteins of SEQ No. 375, 427, 1878, 1904; 258-272 for the protein of sequence SEQ ID No. 352 | 2be |
| SEQ ID No. 2020 | APLILVTYFTQPQPNAESR | 258-276 for the proteins of SEQ No. 406, 1884 | 2be |
| SEQ ID No. 2021 | APLVLVTYFTQPEPK | 258-272 for the protein of SEQ No. 443 | 2be |
| SEQ ID No. 2022 | APLVLVTYFTQPQQNAENR | 258-276 for the proteins of SEQ No. 1893 | 2be |
| SEQ ID No. 2023 | APLVLVTYFTQPQQNAER | 258-275 for the proteins of SEQ No. 367, 398, 421, 1877, 1882, 1888 | 2be |
| SEQ ID No. 2024 | APLVLVTYFTQSEPK | 258-272 for the proteins of SEQ No. 366, 368, 383, 384, 414, 418, 420 | 2be |
| SEQ ID No. 2025 | AQLVAWLK | 208-215 for the protein of SEQ No. 409 | 2be |
| SEQ ID No. 2026 | AQLVMWLK | 208-215 for the proteins of SEQ No. 366, 368, 383, 384, 414, 418, 420 | 2be |
| SEQ ID No. 2027 | ASDLVNYNPIAEK | 102-114 for the proteins of SEQ No. 429, 430, 434 | 2be |
| SEQ ID No. 2028 | CWVVGDK | 231-237 for the protein of SEQ No. 429 | 2be |
| SEQ ID No. 2029 | DFLAAAAK | 278-285 for the proteins of SEQ No. 435, 1908 | 2be |
| SEQ ID No. 2030 | DILASAAK | 278-285 for the proteins of SEQ No. 358, 440, 441 | 2be |

| Peptide SEQ ID No. | Amino acid sequence | Position of the peptide in the CTX-M protein | Clinical interest |
|---|---|---|---|
| SEQ ID No. 2031 | DLLSQR | 92-97 for the protein of SEQ No. 443 | 2be |
| SEQ ID No. 2032 | DNTQVLYR | 57-64 for the proteins of SEQ No. 353, 355, 356, 359, 360, 361, 362, 367, 369, 376, 377, 378, 379, 380, 381, 387, 398, 402, 403, 407, 409, 410, 411, 413, 421, 423, 425, 436, 1872, 1873, 1874, 1877, 1882, 1886, 1888, 1889, 1891, 1892, 1893, 1894, 1896, 1897, 1900, 1901 | 2be |
| SEQ ID No. 2033 | DTTTAR | 182-187 for the protein of SEQ No. 425 | 2be |
| SEQ ID No. 2034 | DTTTPLAMAQALR | 182-194 for the proteins of SEQ No. 366, 368, 383, 384, 414, 420 | 2be |
| SEQ ID No. 2035 | DTTTPLAMAQSLR | 182-194 for the protein of SEQ No. 418 | 2be |
| SEQ ID No. 2036 | DTTTPLAMAQTLR | 181-193 for the proteins of SEQ No. 375, 427, 1878, 1904; 182-194 for the protein of sequence SEQ ID No. 352; 182-194 for the protein of sequence SEQ ID No. 443 | 2be |
| SEQ ID No. 2037 | DVLAAAAR | 278-285 for the proteins of SEQ No. 366, 368, 383, 384, 414, 418, 420, 443 | 2be |
| SEQ ID No. 2038 | EIGDETFR | 157-164 for the protein of SEQ No. 356 | 2be |
| SEQ ID No. 2039 | EQLVTWLK | 208-215 for the proteins of SEQ No. 1891, 1892 | 2be |
| SEQ ID No. 2040 | GLLSQR | 92-97 for the proteins of SEQ No. 366, 368, 383, 384, 414, 418, 420 | 2be |
| SEQ ID No. 2041 | GNTTGAAR | 216-223 for the protein of SEQ No. 376 | 2be |
| SEQ ID No. 2042 | GNTTGSASIQAGLPK | 216-230 for the proteins of SEQ No. 442, 445 | 2be |
| SEQ ID No. 2043 | HDVLASAAK | 277-285 for the proteins of SEQ No. 412, 1885 | 2be |
| SEQ ID No. 2044 | HDVLASAAR | 277-285 for the protein of SEQ No. 1894 | 2be |
| SEQ ID No. 2045 | HLTLGSALGETQR | 194-206 for the proteins of SEQ No. 375, 427, 1878, 1904 | 2be |
| SEQ ID No. 2046 | LAELEQQSGGR | 37-47 for the proteins of SEQ No. 354, 373, 374, 390 | 2be |
| SEQ ID No. 2047 | LAGLER | 37-42 for the protein of SEQ No. 357 | 2be |
| SEQ ID No. 2048 | LDGTEPTLNTAIPGDPR | 165-181 for the protein of SEQ No. 382 | 2be |
| SEQ ID No. 2049 | LGVALIDTADNAQTLYR | 47-63 for the proteins of SEQ No. 375, 427, 1878, 1904; 48-64 for the protein of sequence SEQ ID No. 352 | 2be |
| SEQ ID No. 2050 | LGVALIDTADNTHVLYR | 48-64 for the protein of SEQ No. 408 | 2be |
| SEQ ID No. 2051 | LGVALIDTK | 48-56 for the protein of SEQ No. 356 | 2be |
| SEQ ID No. 2052 | LGVALINTADNSQILYLADER | 48-68 for the protein of SEQ No. 429 | 2be |
| SEQ ID No. 2053 | LGVALINTADNSQILYVADER | 48-68 for the protein of SEQ No. 430 | 2be |
| SEQ ID No. 2054 | LGVALINTADNSR | 47-59 for the proteins of SEQ No. 1902 | 2be |

-continued

| Peptide SEQ ID No. | Amino acid sequence | Position of the peptide in the CTX-M protein | Clinical interest |
|---|---|---|---|
| SEQ ID No. 2055 | LGVALINTADNTQTLYR | 48-64 for the proteins of SEQ No. 366, 368, 383, 384, 414, 418, 420, 443 | 2be |
| SEQ ID No. 2056 | LGVAQINTADNSQILYVADER | 48-68 for the protein of SEQ No. 434 | 2be |
| SEQ ID No. 2057 | LGVPLIDTADNTQVLYR | 48-64 for the proteins of SEQ No. 379, 380, 381 | 2be |
| SEQ ID No. 2058 | LIAHLGGPGK | 141-150 for the protein of SEQ No. 443 | 2be |
| SEQ ID No. 2059 | LIAQLGGQGGVTAFAR | 141-156 for the proteins of SEQ No. 1897 | 2be |
| SEQ ID No. 2060 | LISHVGGPASVTAFAR | 141-156 for the proteins of SEQ No. 395, 396, 426, 431 438, 1880, 1905 | 2be |
| SEQ ID No. 2061 | LLLNQR | 92-97 for the protein of SEQ No. 392 | 2be |
| SEQ ID No. 2062 | NLTLGNALGDTQR | 195-207 for the proteins of SEQ No. 366, 368, 383, 384, 414, 418, 420, 443 | 2be |
| SEQ ID No. 2063 | NLTLGSALGETQR | 195-207 for the protein of SEQ No. 352 | 2be |
| SEQ ID No. 2064 | NVLSQK | 91-96 for the proteins of SEQ No. 375, 427, 1878, 1904 | 2be |
| SEQ ID No. 2065 | QLGDDTFR | 157-164 for the protein of SEQ No. 404 | 2be |
| SEQ ID No. 2066 | SDLVNYSPIAEK | 103-114 for the protein of SEQ No. 370 | 2be |
| SEQ ID No. 2067 | SESEPSLLNQR | 87-97 for the proteins of SEQ No. 358, 440, 441 | 2be |
| SEQ ID No. 2068 | SETQK | 86-90 for the proteins of SEQ No. 375, 427, 1878, 1904; 87-91 for the protein of sequence SEQ ID No. 352; 87-91 for the protein of sequence SEQ ID No. 353; 87-91 for the protein of sequence SEQ ID No. 355; 87-91 for the protein of sequence SEQ ID No. 356; 87-91 for the protein of sequence SEQ ID No. 359; 87-91 for the protein of sequence SEQ ID No. 360; 87-91 for the protein of sequence SEQ ID No. 361; 87-91 for the protein of sequence SEQ ID No. 362; 87-91 for the protein of sequence SEQ ID No. 366; 87-91 for the protein of sequence SEQ ID No. 367; 87-91 for the protein of sequence SEQ ID No. 368; 87-91 for the protein of sequence SEQ ID No. 369; 87-91 for the protein of sequence SEQ ID No. 376; 87-91 for the protein of sequence SEQ ID No. 377; 87-91 for the protein of sequence SEQ ID No. 378; 87-91 for the protein of sequence SEQ ID No. 379; 87-91 for the protein of sequence SEQ ID No. 380; 87-91 for the protein of sequence SEQ ID No. 381; 87-91 for the protein of sequence SEQ ID No. 383; 87-91 for the protein of sequence SEQ ID No. 384; 87-91 for the protein of sequence SEQ ID No. 387; 87-91 for the protein of sequence SEQ ID No. 398; 87-91 for the protein of sequence SEQ ID No. 402; 87-91 for the protein of sequence SEQ ID No. 403; 87-91 for the protein of sequence SEQ ID No. 407; 87-91 for the protein of sequence SEQ ID No. 408; 87-91 for the protein of sequence SEQ ID No. 409; 87-91 for the protein of sequence SEQ ID No. 410; 87-91 for the protein of sequence SEQ ID No. 411; 87-91 for the protein of sequence SEQ ID No. 413; 87-91 for the protein of sequence SEQ ID No. 414; 87-91 for the protein of sequence SEQ ID No. 418; 87-91 for the protein of sequence SEQ ID No. 420; 87-91 for the protein of sequence SEQ ID No. 421; 87-91 for the | 2be |

| Peptide SEQ ID No. | Amino acid sequence | Position of the peptide in the CTX-M protein | Clinical interest |
|---|---|---|---|
| | | protein of sequence SEQ ID No. 423; 87-91 for the protein of sequence SEQ ID No. 425; 87-91 for the protein of sequence SEQ ID No. 428; 87-91 for the protein of sequence SEQ ID No. 436; 87-91 for the protein of sequence SEQ ID No. 443; 87-91 for the protein of sequence SEQ ID No. 1872; 87-91 for the protein of sequence SEQ ID No. 1873; 87-91 for the protein of sequence SEQ ID No. 1874; 87-91 for the protein of sequence SEQ ID No. 1877; 87-91 for the protein of sequence SEQ ID No. 1882; 87-91 for the protein of sequence SEQ ID No. 1886; 87-91 for the protein of sequence SEQ ID No. 1888; 87-91 for the protein of sequence SEQ ID No. 1889; 87-91 for the protein of sequence SEQ ID No. 1891; 87-91 for the protein of sequence SEQ ID No. 1892; 87-91 for the protein of sequence SEQ ID No. 1893; 87-91 for the protein of sequence SEQ ID No. 1894; 87-91 for the protein of sequence SEQ ID No. 1896; 87-91 for the protein of sequence SEQ ID No. 1897; 87-91 for the protein of sequence SEQ ID No. 1900; 87-91 for the protein of sequence SEQ ID No. 1901 | |
| SEQ ID No. 2069 | SLGDESFR | 157-164 for the protein of SEQ No. 439 | 2be |
| SEQ ID No. 2070 | SSDLINYNPIAEK | 101-113 for the proteins of SEQ No. 375, 427, 1878, 1904; 102-114 for the protein of sequence SEQ ID No. 443 | 2be |
| SEQ ID No. 2071 | SSDLINYNPITEK | 102-114 for the protein of SEQ No. 352 | 2be |
| SEQ ID No. 2072 | SWGVGDK | 231-237 for the proteins of SEQ No. 351, 430, 434, 444 | 2be |
| SEQ ID No. 2073 | TELTLNTAIPGDPR | 168-181 for the protein of SEQ No. 407 | 2be |
| SEQ ID No. 2074 | TEPTLNSAIPGDPR | 168-181 for the proteins of SEQ No. 429, 430, 434 | 2be |
| SEQ ID No. 2075 | TEPTQNTAIPGDPR | 168-181 for the proteins of SEQ No. 1889 | 2be |
| SEQ ID No. 2076 | TEQTLNTAIPGDPR | 168-181 for the protein of SEQ No. 391 | 2be |
| SEQ ID No. 2077 | TESTLNTAIPGDPR | 168-181 for the proteins of SEQ No. 361, 388, 400, 421, 1873, 1888 | 2be |
| SEQ ID No. 2078 | TETTLNTAIPGDPR | 168-181 for the proteins of SEQ No. 365, 385, 395, 415 | 2be |
| SEQ ID No. 2079 | TGSCDYGTTNDIAVIWPK | 238-255 for the protein of SEQ No. 373 | 2be |
| SEQ ID No. 2080 | TGSCGYGTTNDIAVIWPK | 238-255 for the protein of SEQ No. 417 | 2be |
| SEQ ID No. 2081 | TGSGDYGTTNDIAVIWPEGR | 237-256 for the proteins of SEQ No. 375, 427, 1878, 1904; 238-257 for the protein of sequence SEQ ID No. 352; 238-257 for the protein of sequence SEQ ID No. 368; 238-257 for the protein of sequence SEQ ID No. 383; 238-257 for the protein of sequence SEQ ID No. 414; 238-257 for the protein of sequence SEQ ID No. 418; 238-257 for the protein of sequence SEQ ID No. 443 | 2be |
| SEQ ID No. 2082 | TGSGGYGTTNDIAVIWPEGR | 238-257 for the proteins of SEQ No. 366, 384, 420 | 2be |
| SEQ ID No. 2083 | TGSGGYGTTNDIAVIWPQGR | 238-257 for the proteins of SEQ No. 359, 369, 423, 1889, 1891, 1892 | 2be |
| SEQ ID No. 2084 | TIGDDTFR | 157-164 for the proteins of SEQ No. 366, 368, 383, 384, 414, 418, 420 | 2be |

| Peptide SEQ ID No. | Amino acid sequence | Position of the peptide in the CTX-M protein | Clinical interest |
|---|---|---|---|
| SEQ ID No. 2085 | TQLVTWLK | 208-215 for the protein of SEQ No. 419 | 2be |
| SEQ ID No. 2086 | VEIKPSDLINYNPIAEK | 98-114 for the proteins of SEQ No. 366, 368, 383, 414, 418, 420 | 2be |
| SEQ ID No. 2087 | VEIKPSDLVNYNPIAEK | 98-114 for the protein of SEQ No. 384 | 2be |
| SEQ ID No. 2088 | VIGDDTFR | 157-164 for the protein of SEQ No. 443 | 2be |
| SEQ ID No. 2089 | VLSQK | 92-96 for the proteins of SEQ No. 375, 427, 1878, 1904; 93-97 for the protein of sequence SEQ ID No. 352 | 2be |
| SEQ ID No. 2090 | VMAAAALLK | 77-85 for the protein of SEQ No. 445 | 2be |
| SEQ ID No. 2091 | VMAAAAVLEQSETQK | 77-91 for the protein of SEQ No. 403 | 2be |
| SEQ ID No. 2092 | WAKPSGAVGDVAQR | 201-214 for the protein of SEQ No. 425 | 2be |

In the clinical interest column, the entry 2be indicates that all of the CTX-M peptides indicates the presence of a beta-lactamase with an extended spectrum (ESBL) capable of hydrolysing penicillins, first-generation cephalosporins such as cephaloridine and cefalotin, and at least one antibiotic from the oxyimino-beta-lactam class such as cefotaxime, ceftazidime or monobactams such as aztreonam.

The detection of a mechanism of resistance to ESBL (extended-spectrum beta-lactamase) cephalosporins, induced by the CTX-M protein is characterised by the detection of at least one resistance-marking 2be peptide chosen from the sequences SEQ ID No. 446 to SEQ ID No. 478, SEQ ID No. 480 to SEQ ID No. 495 and SEQ ID No. 2008 to SEQ ID No. 2092.

The detection of a mechanism of resistance to cephalosporins induced by the expression of the SHV protein is characterised by the detection of at least one peptide belonging to the SHV protein and to its different sequence variants SEQ ID No. 496 to SEQ ID No. 613 and SEQ ID No. 1909 to SEQ ID No. 1919.

SEQ ID No. 496:
KRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 497:
LRYIRLCIISLLATLPLAVHASPQPLEQIKLSESQLSGRVGMIEMDLASGRTLTAWRAD
ERFPMMSTFKVVLCGAVLARVDAGDEQLERKIHYRQQDLVDYSPVSEKHLADGMT
VGELCAAAITMSDNSAANLLLATVGGPAGLTAFLRQIGDNVTRLDRWETELNEALPG
DARDTTTPASMAATLRKLLTSQRLSASSQRQLLQWMVDDRVAGPLIRSVLPAGWFI
ADKTGAGERGARGIVALLGPNNKAERIVVIYLRDTPASMAERNQQIAGIGAALIEHW
QR

SEQ ID No. 498:
MRFIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 499:
MRFIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNAERMVVIYLRDTPASMAERNQQIAGIGAALIEH
WQR

-continued

SEQ ID No. 500:
MRFIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGASKRGARGIVALLGPNNKAERIVVIYLRDTPASMAERNQQIAGIGAALIEH
DWQR

SEQ ID No. 501:
MRIRLCIISLLATLPLAVHASPQPLEQIKLSESQLSGRVGMIEMDLASGRTLTAWRAD
ERFPMMSTFKVVLCGAVLARVDAGDEQLERKIHYRQQDLVDYSPVSEKHLADGMT
VGELCAAAITMSDNSAANLLLATVGGPVGLTAFLRQIGDNVTRLDRWETELNEALPG
DARDTTTPASMAATLRKLLTSQRLSARSQRQLLQWMVDDRVAGPLIRSVLPAGWFI
ADRTGAGERGARGIVALLGPNNKAERIVVIYLRDTPASMAERNQQIAGIGAALIEHW
QR

SEQ ID No. 502:
MRYARLCIISLLATLPLVVHASPQPLEQIKQSESQLSGRVGMIEMDLASGRTLTAWR
ADERFPMMSTFKVVLCGAVLARVDAGDEQLERKIHYRQQDLVDYSPVSEKHLADG
MTVGELCAAAITVSDNSAANLLLATVGGPAGLTAFLRQIGDNVTRLDRWETELNEAL
PGDARDTTTPASMAATLRKLLTSQRLSARSQRQLLQWMVDDRVAGPLIRSVLPAG
WFIADKTGAGERGARGIVALLGPNNKAERIVVIYLRDTPASMAERNQQIAGIGAALIE
HWQR

SEQ ID No. 503:
MRYFRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGASERGARGIVALLGPNNKAERIVVIYLRDTPASMAERNQQIAGIGAALIEH
WQR

SEQ ID No. 504:
MRYFRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPVGLTAFLRQIGDNVTRLDRWETELNEALP
GDARDTTTPASMAATLRKLLTSQRLSARSQRQLLQWMVDDRVAGPLIRSVLPAGW
FIADRTGAGERGARGIVALLGPNNKAERIVVIYLRDTPASMAERNQQIAGIGAALIEH
WQR

SEQ ID No. 505:
MRYFRLCIISLLATLPLAVHASPQPLEQIKLSESQLSGSVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIDDNVTRLDRWETELNEALP
GDARDTTTPASMAATLRKLLTSQRLSARSQRQLLQWMVDDRVAGPLIRSVLPAGW
FIADKTGASKRGARGIVALLGPNNKAERIVVIYLRDTPASMAERNQQIAGIGAALIEH
WQR

SEQ ID No. 506:
MRYFRLCIISLLATLPLAVHASPQPLEQIKLSESQLSGSVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAAKRGARGIVALLGPNNKAERIVVIYLRDTPASMAERNQQIAGIGAALIEH
WQR

SEQ ID No. 507:
MRYFRLCIISLLATLPLAVHASPQPLEQIKLSESQLSGSVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 508:
MRYFRLCIISLLATLPLAVHASPQPLEQIKLSESQLSGSVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGASERGARGIVALLGPNNKAERIVVIYLRDTPASMAERNQQIAGIGAALIEH
WQR

SEQ ID No. 509:
MRYFRLCIISLLATLPLAVHASPQPLEQIKLSESQLSGSVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGASKRGARGIVALLGPNNKAERIVVIYLRDTPASMAERNQQIAGIGAALIEH
WQR

SEQ ID No. 510:
MRYFRLCIISLLATLPLAVHASPQPLEQIKLSESQLSGSVGMIEMDLASGRTLTAWRA
DGRFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGASERGARGIVALLGPNNKAERIVVIYLRDTPASMAERNQQIAGIGAALIEH
WQR

SEQ ID No. 511:
MRYIRLCIISLLAALPLAVHASPQPLEQIKQSESQLSGRVGMIEMDLASGRTLTAWRA
DERFPMISTFKVVLCGAVLARVDAGDEQLERKIHYRQQDLVDYSPVSEKHLADGMT
VGELCAAAITMSDNSAANLLLAIVGGPAGLTAFLRQIGDNVTRLDRWETELNEALPG
DARDTTTPASMAATLRKLLTSQRLSARSQRQLLQWMVDDRVAGPLIRSVLPAGWFI
ADKTGAGERGARGIVALLGPNNKAERIVVIYLRDTPASMAERNQQIAGIGAALIEHW
QR

SEQ ID No. 512:
MRYIRLCIISLLAALPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVEDRVAGPLIRSVLPAGW
FIADKTGAGERGARGIVALLGPNNKAERIVVIYLRDTPASMAERNQQIAGIGAALIEH
WQR

SEQ ID No. 513:
MRYIRLCIISLLAALPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITVSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQHIAGIGAALIEH
WQR

SEQ ID No. 514:
MRYIRLCIISLLAALPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITVSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 515:
MRYIRLCIISLLATLPLAVHASPQPLDQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGASKRGARGIVALLGPNNKAERIVVIYLRDTPASMAERNQQIAGIGAALIEH
WQR

SEQ ID No. 516:
MRYIRLCIISLLATLPLAVHASPQPLEQIKLSESQLSGRVGMIEMDLASGRTLTAWHA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 517:
MRYIRLCIISLLATLPLAVHASPQPLEQIKLSESQLSGRVGMIEMDLASGRTLTAWHA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGKRGARGIVALLGPNNKAERIVVIYLRDTPASMAKRNQQIAGIGAALIEH
WQR

SEQ ID No. 518:
MRYIRLCIISLLATLPLAVHASPQPLEQIKLSESQLSGRVGMIEMDLASGRTLTAWRA
DERFPMISTFKVVLCGAVLARVDAGDEQLERKIHYRQQDLVDYSPVSEKHLADGMT
VGELCAAAITMSDNSAANLLLATVGGPAGLTAFLRQIGDNVTRLDRWETELNEALPG
DARDTTTPASMAATLRKLLTSQRLSARSQRQLLQWMVDDRVAGPLIRSVLPAGWFI
ADKTGAGERGARGIVALLGPNNKAERIVVIYLRDTPASMAERNQQIAGIGAALIEHW
QR

SEQ ID No. 519:
MRYIRLCIISLLATLPLAVHASPQPLEQIKLSESQLSGRVGMIEMDLASGRTLTAWRA
DERFPMMSTFKVVLCGAVLARVDAGDEQLERKIHYLQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 520:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHFADGM
TVGELCAAAITMSDNSAANLLLATVGGPAGLSAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 521:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TIGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 522:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGEFCAAAITMSDNSAANLLLATVGGPAGLTAFLRQIGDNVTRLDRVVETELNEAFP
GDARDTTTPASMAATLRKLLTSQRLSARSQRQLLQWMVDDRVAGPLIRSVLPAGW
FIADKTGASERGARGIVALLGPNNKAERIVVIYLRDTPASMAERNQQIAGIGAALIEH
WQR

SEQ ID No. 523:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGEFCAAAITMSDNSAANLLLATVGGPAGLTAFLRQIGDNVTRLDRWETELNEALP
GDARDTTTPASMAGTLRKLLTSQRLSARSQRQLLQWMVDDRVAGPLIRSVLPAGW
FIADKTGASKRGARGIVALLGPNNKAERIVVIYLRDTPASMAERNQQIAGIGAALIEH
WQR

SEQ ID No. 524:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAAKLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 525:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATFGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 526:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGLAGLTAFLRQIGDNVTRLDRWETELNEALP
ADARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 527:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIDDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 528:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIDDNVTRLDRWETELNEALP
GDARDTTTPASMAATLRKLLTSQRLSARSQRQLLQWMVDDRVAGPLIRSVLPAGW
FIADKTGASKRGARGIVALLGPNNKAERIVVIYLRDTPASMAERNQQIAGIGAALIEH
WQR

SEQ ID No. 529:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDKVTRLDRWETELNEALP
GDARDTTTPASMAATLRKLLTSQRLSARSQRQLLQWMVDDRVAGPLIRSVLPAGW
FIADKTGASKRGARGIVALLGPNNKAERIVVIYLRDTPASMAERNQQIAGIGAALIEH
WQR

-continued

SEQ ID No. 530:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETDRWETE
LNEALPGDARDTTTPASMAATLRKLLTSQRLSARSQRQLLQWMVDDRVAGPLIRSV
LPAGWFIADKTGAGERGARGIVALLGPNNKAERIVVIYLRDTPASMAERNQQIAGIG
AALIEHWQR

SEQ ID No. 531:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEAFP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 532:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEAFP
GDARDTTTPASMAATLRKLLTSQRLSARSQRQLLQWMVDDRVAGPLIRSVLPAGW
FIADKTGASERGARGIVALLGPNNKAERIVVIYLRDTPASMAERNQQIAGIGAALIEN
WQR

SEQ ID No. 533:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARATTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 534:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLNSQRLSARSQRQLLQWMVDDRVAGPLIRSVLPAGW
FIADKTGASKRGARGIVALLGPNNKAERIVVIYLRDTPASMAERNQQIAGIGAALIEH
WQR

SEQ ID No. 535:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARLQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 536:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQLQLLQWMVDDRVAGPLIRSVLPAGW
FIADKTGAGERGARGIVALLGPNNKAERIVVIYLRDTPASMAERNQQIAGIGAALIEH
WQR

SEQ ID No. 537:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQLQLLQWMVDDRVAGPLIRSVLPAGW
FIADKTGASERGARGIVALLGPNNKAERIVVIYLRDTPASMAERNQQIAGIGAALIEH
WQR

SEQ ID No. 538:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQLQLLQWMVDDRVAGPLIRSVLPAGW
FIADKTGASKRGARGIVALLGPNNKAERIVVIYLRDTPASMAERNQQIAGIGAALIEH
WQR

SEQ ID No. 539:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDGVAGPLIRSVLPAGW
FIADKTGAGERGARGIVALLGPNNKAERIVVIYLRDTPASMAERNQQIAGIGAALIEH
WQR

SEQ ID No. 540:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAAERGARGIVALLGPNNKAERIVVIYLRDTPASMAERNQQIAGIGAALIEH
WQR

SEQ ID No. 541:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPDNKAERIVVIYLRDTPASMAERNQQIAGIGAALIEH
WQR

SEQ ID No. 542:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNHKAERIVVIYLRDTPASMAERNQQIAGIGAALIEH
WQR

SEQ ID No. 543:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 544:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALRGPNNKAERIVVIYLRDTPASMAERNQQIAGIGAALIEH
WQR

SEQ ID No. 545:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGKRGARGIVALLGPNNKAERIVVIYLRDSPASMAERNQQIAGIGAALIEH
WQR

SEQ ID No. 546:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGKRGARGIVALLGPNNKAERTVVIYLRDTPASMAERNQQIAGIGAALIEH
WQR

SEQ ID No. 547:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGASERGARGIVALLGPNNKAERIVVIYLRDSPASMAERNQQIAGIGAALIEH
WQR

SEQ ID No. 548:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGASERGARGIVALLGPNNKAERIVVIYLRDTPASMAERNQQIAGIGAALIEH
WQR

SEQ ID No. 549:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGASKRGARGIVALLGPNNKAERIVVIYLRDTPASMAERNQQIAGIGAALIEH
WQR

SEQ ID No. 550:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGASKRGARGIVALLGPNNKAERIVVIYLRDTPASMAERNQQIAGLGAALIEH
WQR

SEQ ID No. 551:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADRTGAGERGARGIVALLGPNNKAERIVVIYLRDTPASMAERNQQIAGIGAALIEH
WQR

SEQ ID No. 552:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLSAGW
FIADKTGAGERGARGIVALLGPNNKAERIVVIYLRDTPASMAERNQQIAGIGAALIEH
WQR

SEQ ID No. 553:
MRYIRLCIISLLATLPLAVHASPQPLEQIKLSESQLSGRVGMIEMDLASGRILTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDGRVAGPLIRSVLPAGW
FIADKTGAGERGARGIVALLGPNNKAERIVVIYLRDTPASMAERNQQIAGIGAALIEH
WQR

SEQ ID No. 554:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMTATLRKLLTSQRLSARSQRHLLQWMVDDRVAGPLIRSVLPAGW
FIADKTGAGERGARGIVALLGPNNKAERIVVIYLRDTPASMAERNQQIAGIGAALIEH
WQR

SEQ ID No. 555:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMTATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 556:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMTATLRKLLTSQRLSARSQRQLLQWMVDDRVAGPLIRSVLPAGW
FIADKTGAGKRGARGIVALLGPNNKAERIVVIYLRDTPASMAERNQQIAGIGAALIEH
WQR

SEQ ID No. 557:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMTATLRKLLTSQRLSARSQRQLLQWMVDDRVAGPLIRSVLPAGW
FIADKTGASKRGARGIVALLGPNNKAERIVVIYLRDTPASMAERNQQIAGIGAALIEH
WQR

SEQ ID No. 558:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARGTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 559:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARNTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 560:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALS
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 561:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETERNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 562:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGENVTRLDRWETELNEALP
GDARDTTTPASMAATLRKLLTNQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 563:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPVGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 564:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSVANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTLASMAERNQQIAGIGAALIEH
WQR

SEQ ID No. 565:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAVITMSDNSAANLLLATVGGPAGLTAFLRQIDDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 566:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCTAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 567:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKYLADGM
TVGELCAAAITMSDNSAANLLLATVGGPVGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 568:
MRYIRLCIISLLATLPLAVHASPQPLEQIKLSESQLSGRVGMIEMDLASRTLTAWRAD
ERFPMMSTFKVVLCGAVLARVDAGDEQLERKIHYRQQDLVDYSPVSEKHLADGMT
VGELCAAAITMGDNSAANLLLRTVGGPAGLTAFLRQIGDNVTRLDRWETELNEALP
GDARDTTTPASMAATLRNVLTSQRLSARSQRQLLQWMVDDRVAGPLIRSVLPAGW
FIADKTGASKRGARGIVALLGPNNKAERIVVIYLRDTPASMAERNQQIAGIGAALIEH
WQR

SEQ ID No. 569:
MRYIRLCIISLLATLPLAVHASPQPLEQIKLSESQLSGRVGMIEMDLASRTLTAWRAD
ERFPMMSTFKVVLCGAVLARVDAGDEQLERKIHYRQQDLVDYSPVSEKHLADGMT
VGELCAAAITMSDNSAANLLLRTVGGPAGLTAFLRQIGDNVTRLDRWETELNEALPG
DARDTTTPASMAATLRNVLTSQRLSARSQRQLLQWMVDDRVAGPLIRSVLPAGWFI
ADKTGASKRGARGIVALLGPNNKAERIVVIYLRDTPASMAERNQQIAGIGAALIEHW
QR

SEQ ID No. 570:
MRYIRLCIISLLATLPLAVHASPQPLEQIKLSESQLSGRVGMIEMDLASSRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 571:
MRYIRLCIISLLATLPLAVHASPQPLEQIKQSESQLSGRVGMIEMDLASGRTLTAWCA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 572:
MRYIRLCIISLLATLPLAVHASPQPLEQIKQSESQLSGRVGMIEMDLASGRTLTAWRA
DERFPMISTFKVVLCGAVLARVDAGDEQLERKIHYRQQDLVDYSPVSEKHLADGMT
VGELCAAAITMSDNSAANLLLAIVGGPAGLTAFLRQIGDNVTRLDRWETELNEALPG
DARDTTTPASMAATLRKLLTSQRLSARSQRQLLQWMVDDRVAGPLIRSVLPAGWFI
ADKTGAGERGARGIVALLGPNNKAERIVVIYLRDTPASMAERNQQIAGIGAALIEHW
QR

SEQ ID No. 573:
MRYIRLCIISLLATLPLAVHASPQPLEQIKQSESQLSGRVGMIEMDLASGRTLTAWRA
DERFPMMSTFKVALCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 574:
MRYIRLCIISLLATLPLAVHASPQPLEQIKQSESQLSGRVGMIEMDLASGRTLTAWRA
DERFPMMSTFKVLLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGASKRGARGIVALLGPNNKAERIVVIYLRDTPASMAERNQQIAGIGAALIEH
WQR

SEQ ID No. 575:
MRYIRLCIISLLATLPLAVHASPQPLEQIKQSESQLSGRVGMIEMDLASGRTLTAWRA
DERFPMMSTFKVVLCGAMLARVDAGDKQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGASKRGARGIVALLGPNNKAERIVVIYLRDTPASMAERNQQIAGIGAALIEH
WQR

SEQ ID No. 576:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLAIVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 577:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIDDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 578:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLISQRLSARSQRQLLQWMVDDRVAGPLIRSVLPAGWF
IADKTGAGERGARGIVALLGPNNKAERIWIYLRDTPASMAERNQQIAGIGAALIEHW
QR

SEQ ID No. 579:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDARVAGPLIRSVLPAGW
FIADKTGAGERGARGIVALLGPNNKAERIWIYLRDTPASMAERNQQIAGIGAALIEH
WQR

SEQ ID No. 580:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKAGAGERGARGIVALLGPNNKAERIVVIYLRDTPASMAERNQQIAGIGAALIEH
WQR

SEQ ID No. 581:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGVV
FIADKTGAAERGARGIVALLGPNNKAERIVVIYLRDTPASMAERNQQIAGIGAALIEH
WQR

SEQ ID No 582:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 583:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGGRGIVALLGPNNKAERIVVIYLRDTPASMAERNQQIAGIGAALIEH
WQR

SEQ ID No. 584:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGKRGARGIVALLGPNNKAERIVVIYLRDTPASMAERNQQIAGIGAALIEH
WQR

SEQ ID No. 585:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGASERGARGIVALLGPNNKAERIVVIYLRDTPASMAERNQQIAGIGAALIEH
WQR

SEQ ID No. 586:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGASKRGARGIVALLGGNIKAERIVVIYLRDTPASMAERNQQIAGIGAALIEHW
QR

SEQ ID No. 587:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGASKRGARGIVALLGPNNKAERIVVIYLRDTPASMAELDQQIAGIGAALIEHW
QR

SEQ ID No. 588:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGASKRGARGIVALLGPNNKAERIVVIYLRDTPASMAERNQQIAGIGAALIEH
WQR

SEQ ID No. 589:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGASRRGARGIVALLGPNNKAERIVVIYLRDTPASMAERNQQIAGIGAALIEH
WQR

SEQ ID No. 590:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRRVAGPLIRSVLPAGW
FIADRTGAGERGARGIVALLGPNNKAERIVVIYLRDTPASMAERNQQIAGIGAALIEH
WQR

SEQ ID No. 591:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMTATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 592:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEVLP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 593:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGVTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 594:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPTGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 595:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGSPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 596:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITVSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 597:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLTDGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 598:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKYLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 599:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQHLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

-continued

SEQ ID No. 600:
MRYIRLCIISLLATLPLAVHASPQPLEQIKQSESQLSGRVGMIEMDLASGRTLTAWRA
DERFPMMSTFKVVLCGAVLARVDAGDKQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGGRGIVALLGPNNKAERIVVIYLRDTPASMAERNQQIAGIGAALIEH
WQR

SEQ ID No. 601:
MRYIRLCIISLLATLPLAVHASPQPLEQIKQSESQLSGRVGMIEMDLASGRTLTAWRA
DERFPMMSTFKVVLCGTVLARVDAGDEQLERKIHYRQQDLVDYSPVSEKHLADGM
TVGELCAAAITMSDNSAANLLLATVGGPAGLTAFLRQIDDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 602:
MRYIRLCIISLLATLPLAVHASPQPLEQIKQSESQLSGRVGMIEMDLASGRTLTAWRA
DQRFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGASKRGARGIVALLGPNNKAERIVVIYLRDTPASMAERNQQIAGIGAALIEH
WQR

SEQ ID No. 603:
MRYIRLCIISLLATLPLAVHASPQPLEQIKQSESQLSGSVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAAERGARGIVALLGPNNKAERIVVIYLRDTPASMAERNQQIAGIGAALIEH
WQR

SEQ ID No. 604:
MRYIRLCIISLLATLPLAVHSSPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITVSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 605:
MRYIRLCIISLLATLPLTVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 606:
MRYIRLCIISLLATLSLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGKRGARGIVALLGPNNKAERIVVIYLRDTPASMAERNQQIAGIGAALIEH
WQR

SEQ ID No. 607:
MRYIRLCIISLLATMPLAVHASPQPLEQIKQSESQLSGRVGMIEMDLASGRTLTAWR
ADERFPMMSTFKVVLCGAVLARVDAGDEQLERKIHYRQQDLVDYSPVSEKHLADG
MTVGELCAAAITMSDNSAANLLLATVGGPAGLTAFLRQIGDNVTRLDRWETELNEAL
PGDARDTTTPASMAATLRKLLTSQRLSARSQRQLLQWMVDDRVAGPLIRSVLPAG
WFIADKTGAGERGARGIVALLGPNNKAERIVVIYLRDTPASMAERNQQIAGIGAALIE
HWQR

SEQ ID No. 608:
MRYIRLCIISLLAVLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITVSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 609:
MRYIRLNIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 610:
MRYIRRCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDMPASMAERNQQIAGIGAALIEH
WQR

SEQ ID No. 611:
MRYIRRCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 612:
MRYVRLCIISLLATLPLAVHASPQPLEQIKQSESQLSGRVGMIEMDLASGRTLTAWR
ADERFPMMSTFKVVLCGAVLARVDAGDEQLERKIHYRQQDLVDYSPVSEKHLADG
MTVGELCAAAITMSDNSAANLLLATVGGPAGLTAFLRQIGDNVTRLDRWETELNEAL
PGDARDTTTPASMAATLRKLLTSQRLSARSQRQLLQWMVDDRVAGPLIRSVLPAG
WFIADKTGAGERGARGIVALLGPNNKAERIVVIYLRDTPASMAERNQQIAGIGAALIE
HWQR

SEQ ID No. 613:
MRYVRLCIISLLATLPLAVHTSPQPLEQIKQSESQLSGRVGMIEMDLASGRTLTAWR
ADERFPMMSTFKVVLCGAVLARVDAGDEQLERKIHYRQQDLVDYSPVSEKHLADG
MTVGELCAAAITMSDNSAANLLLATVGGPAGLTAFLRQIGDNVTRLDRWETELNEAL
PGDARDTTTPASMAATLRKLLTSQRLSARSQRQLLQWMVDDRVAGPLIRSVLPAG
WFIADKTGAGERGARGIVALLGPNNKAERIVVIYLRDTPASMAERNQQIAGIGAALIE
HWQR

SEQ ID No. 1909:
MRYIRLCIISLLAALPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITVSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQHIAGIGAALIEH
WQR

SEQ ID No. 1910:
ALPGDARDTTTPASMAATLRKLLTSQRLSARSQRQLLQWMVDDRVAGPLIRSVLPA
GWFIADKTGASERGARGIVALLGPNNKAERIVVIYLRDS

SEQ ID No. 1911:
MRYIRLCIISLLAALPLVVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITVSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 1912:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGASKRGARGIVALLGPNNKAERIVVIYLRDTPASMAELDQQIAGIGAALIEHW
QR

SEQ ID No. 1913:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELRAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGASKRGARGIVALLGPNNKAERIVVIYLRDTPASMAERNQQIAGTGAAPIEH
WQR

SEQ ID No. 1914:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLREIGDNVTRLDRWETELNEALP
GDARDTTTPASMAATLRKLLTSQRLSARSQRQLLQWMVDDRVAGPLIRSVLPAGW
FIADKTGASKRGARGIVALLGPNNKAERIVVIYLRDTPASMAERNQQIAGIGAALIEH
WQR

SEQ ID No. 1915:
MRYIRLCIISLLATLPLAVHASPQPLKQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMTATLRKLLTSQRLSARSQRQLLQWMVDDRVAGPLIRSVLPAGW

-continued

FIADKTGAGERGARGIVALLGPNNKAERIVVIYLRDTPASMAERNQQIAGIGAALIEH
WQR

SEQ ID No. 1916:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAALTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPHNKAERIVVIYLRDTPASMAERNQQIAGIGAALIEH
WQR

SEQ ID No. 1917:
KRYIRLCIISLLATLPLAVHASPQPLEQIKLSESQLSGRVGMIEMDLASGRTLTAWRA
DERFPMMSTFKVVLCGAVLARVDAGDEQLERKIHYSQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 1918:
MRYIRLCIISLLATLPLAVHASPQPLEQIKLSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGASKRGARGIVALLGPNNKAERIVVIYLRDTPASMAERNQQIAGIGAALIEH
WQR

SEQ ID No. 1919:
MRYIRLCIISLLATLPLAVHASPQPLEQIKQSESQLSGRVGMIEMDLASGRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGASKRGARGIVALLGPNNKAERIVVIYLRDTPASMAERNQQIAGIGAA said peptides being chosen, preferably, from the peptides of sequence SEQ ID No. 614 to SEQ ID No. 711 and SEQ ID No. 2093 to SEQ ID No. 2096 as defined hereafter:

| Peptide SEQ ID No. | Amino acid sequence | Position of the peptide in the SHV protein | Clinical interest |
|---|---|---|---|
| SEQ ID No. 614 | AGAGER | 231-236 for the protein of SEQ No. 580 | SHV |
| SEQ ID No. 615 | ATTTPASMAATLR | 175-187 for the protein of SEQ No. 533 | 2be |
| SEQ ID No. 616 | CIISLLATLPLAVH ASPQPLEQIK | 7-30 for the proteins of SEQ No. 496, 497, 498, 499, 500, 503, 504, 505, 506, 507, 508, 509, 510, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 610, 611, 612, 1913, 1914, 1915, 1917, 1918, 1919, 1920; 6-29 for the protein of sequence SEQ ID No. 501 | SHV |
| SEQ ID No. 617 | DMPASMAER | 261-269 for the protein of SEQ No. 610 | 2b |
| SEQ ID No. 618 | DSPASMAER | 261-269 for the proteins of SEQ No. 545, 547 | SHV |
| SEQ ID No. 619 | DTLASMAER | 261-269 for the protein of SEQ No. 564 | SHV |
| SEQ ID No. 620 | DTPASMAER | 261-269 for the proteins of SEQ No. 496, 497, 498, 499, 500, 502, 503, 504, 505, 506, 507, 508, 509, 510, 511, 512, 513, 514, 515, 516, 518, 519, 520, 521, 522, 523, 524, 525, 526, 527, 528, 529, 531, 532, 533, 534, 535, 536, 537, 538, 539, 540, 541, 542, 543, 544, 546, 548, 549, 550, 551, 552, 553, 554, 555, 556, 557, 558, 559, 560, 561, 562, 563, 565, 566, 567, 570, 571, 572, 573, 574, 575, 576, 577, 578, 579, 580, 581, 582, 583, 584, 585, 586, 588, 589, 590, 591, 592, 593, 594, 595, 596, 597, 598, 599, 600, 601, 602, 603, 604, 605, | SHV |

| Peptide SEQ ID No. | Amino acid sequence | Position of the peptide in the SHV protein | Clinical interest |
|---|---|---|---|
| | | 606, 607, 608, 609, 611, 612, 613, 1910, 1912, 1914, 1915, 1916, 1917, 1918, 1919, 1920; 260-268 for the protein of sequence SEQ ID No. 501; 266-274 for the protein of sequence SEQ ID No. 530; 260-268 for the protein of sequence SEQ ID No. 568; 260-268 for the protein of sequence SEQ ID No. 569 | |
| SEQ ID No. 621 | DTPASMAK | 261-268 for the protein of SEQ No. 517 | SHV |
| SEQ ID No. 622 | DTTTPASMAATLR | 175-187 for the proteins of SEQ No. 496, 497, 498, 499, 500, 502, 503, 504, 505, 506, 507, 508, 509, 510, 511, 512, 513, 514, 515, 516, 517, 518, 519, 520, 521, 522, 524, 525, 526, 527, 528, 529, 531, 532, 534, 535, 536, 537, 538, 539, 540, 541, 542, 543, 544, 545, 546, 547, 548, 549, 550, 551, 552, 553, 560, 561, 562, 563, 564, 565, 566, 567, 570, 571, 572, 573, 574, 575, 576, 577, 578, 579, 580, 581, 582, 583, 584, 585, 586, 587, 588, 589, 590, 592, 593, 594, 595, 596, 597, 598, 599, 600, 601, 602, 603, 604, 605, 606, 607, 608, 609, 610, 611, 612, 613, 1910, 1912, 1913, 1914, 1915, 1917, 1918, 1919, 1920; 174-186 for the protein of sequence SEQ ID No. 501; 180-192 for the protein of sequence SEQ ID No. 530; 174-186 for the protein of sequence SEQ ID No. 568; 174-186 for the protein of sequence SEQ ID No. 569; 8-20 for the protein of sequence SEQ ID No. 1911 | SHV |
| SEQ ID No 623 | DTTTPASMAGTLR | 175-187 for the protein of SEQ No. 523 | 2b |
| SEQ ID No. 624 | DTTTPASMTATLR | 175-187 for the proteins of SEQ No. 554, 555, 556, 557, 591, 1916 | SHV |
| SEQ ID No. 625 | FPMISTFK | 62-69 for the proteins of SEQ No. 511, 518, 572 | 2br |
| SEQ ID No. 626 | FPMMSTFK | 62-69 for the proteins of SEQ No. 496, 497, 498, 499, 500, 502, 503, 504, 505, 506, 507, 508, 509, 510, 512, 513, 514, 515, 516, 517, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 570, 571, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 1910, 1912, 1913, 1914, 1915, 1916, 1917, 1918, 1919, 1920; 61-68 for the protein of sequence SEQ ID No. 501; 61-68 for the protein of sequence SEQ ID No. 568; 61-68 for the protein of sequence SEQ ID No. 569 | SHV |
| SEQ ID No. 627 | GIVALLGGNIK | 240-250 for the protein of SEQ No. 586 | 2b |
| SEQ ID No. 628 | GIVALLGPDNK | 240-250 for the protein of SEQ No. 541 | SHV |
| SEQ ID No. 629 | GIVALLGPNHK | 240-250 for the protein of SEQ No. 542 | SHV |
| SEQ ID No. 630 | GIVALLGPNNK | 240-250 for the proteins of SEQ No. 496, 497, 498, 500, 502, 503, 504, 505, 506, 507, 508, 509, 510, 511, 512, 513, 514, 515, 516, 517, 518, 519, 520, 521, 522, 523, 524, 525, 526, 527, 528, 529, 531, 532, 533, 534, 535, 536, 537, 538, 539, 540, 543, 545, 546, 547, 548, 549, 550, 551, 552, 553, 554, 555, 556, 557, 558, 559, 560, 561, 562, 563, 564, 565, 566, 567, 570, 571, 572, 573, 574, 575, 576, 577, 578, 579, 580, 581, 582, 583, 584, 585, 587, 588, 589, 590, 591, 592, 593, 594, 595, 596, 597, 598, 599, 600, 601, 602, 603, 604, 605, 606, 607, 608, 609, 610, 611, 612, 613, 1910, 1912, 1913, 1914, 1915, 1916, 1918, 1919, 1920; 239-249 for the protein of sequence SEQ ID No. 501; 245-255 for the protein of sequence SEQ ID No. 530; 239-249 for the protein of sequence SEQ ID No. 568; 239-249 for the protein of sequence SEQ ID No. 569; 73-83 for the protein of sequence SEQ ID No. 1911 | SHV |

-continued

| Peptide SEQ ID No. | Amino acid sequence | Position of the peptide in the SHV protein | Clinical interest |
|---|---|---|---|
| SEQ ID No. 631 | GIVALLGPNNNAER | 240-253 for the protein of SEQ No. 499 | 2b |
| SEQ ID No. 632 | GIVALR | 240-245 for the protein of SEQ No. 544 | SHV |
| SEQ ID No. 633 | GPNNK | 246-250 for the proteins of SEQ No. 496, 497, 498, 500, 502, 503, 504, 505, 506, 507, 508, 509, 510, 511, 512, 513, 514, 515, 516, 517, 518, 519, 520, 521, 522, 523, 524, 525, 526, 527, 528, 529, 531, 532, 533, 534, 535, 536, 537, 538, 539, 540, 543, 544, 545, 546, 547, 548, 549, 550, 551, 552, 553, 554, 555, 556, 557, 558, 559, 560, 561, 562, 563, 564, 565, 566, 567, 570, 571, 572, 573, 574, 575, 576, 577, 578, 579, 580, 581, 582, 583, 584, 585, 587, 588, 589, 590, 591, 592, 593, 594, 595, 596, 597, 598, 599, 600, 601, 602, 603, 604, 605, 606, 607, 608, 609, 610, 611, 612, 613, 1910, 1912, 1913, 1914, 1915, 1916, 1918, 1919, 1920; 245-249 for the protein of sequence SEQ ID No. 501; 251-255 for the protein of sequence SEQ ID No. 530; 245-249 for the protein of sequence SEQ ID No. 568; 245-249 for the protein of sequence SEQ ID No. 569; 79-83 for the protein of sequence SEQ ID No. 1911 | SHV |
| SEQ ID No. 634 | GTTTPASMAATLR | 175-187 for the protein of SEQ No. 558 | 2be |
| SEQ ID No. 635 | HLADGMTVGELCAAAITMSDNSAAK | 108-132 for the protein of SEQ No. 524 | SHV |
| SEQ ID No. 636 | HLLQWMVDDR | 202-211 for the protein of SEQ No. 554 | SHV |
| SEQ ID No. 637 | IHYLQQDLVDYSPVSEK | 91-107 for the protein of SEQ No. 519 | SHV |
| SEQ ID No. 638 | IVVIYLR | 254-260 for the proteins of SEQ No. 496, 497, 498, 500, 502, 503, 504, 505, 506, 507, 508, 509, 510, 511, 512, 513, 514, 515, 516, 517, 518, 519, 520, 521, 522, 523, 524, 525, 526, 527, 528, 529, 531, 532, 533, 534, 535, 536, 537, 538, 539, 540, 541, 542, 543, 544, 545, 547, 548, 549, 550, 551, 552, 553, 554, 555, 556, 557, 558, 559, 560, 561, 562, 563, 564, 565, 566, 567, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 1910, 1912, 1913, 1914, 1915, 1916, 1917, 1918, 1919, 1920; 253-259 for the protein of sequence SEQ ID No. 501; 259-265 for the protein of sequence SEQ ID No. 530; 253-259 for the protein of sequence SEQ ID No. 568; 253-259 for the protein of sequence SEQ ID No. 569; 87-93 for the protein of sequence SEQ ID No. 1911 | SHV |
| SEQ ID No. 639 | LCIISLLAALPLAVHASPQPLEQIK | 6-30 for the proteins of SEQ No. 511, 512, 513, 514, 1910 | 2b |
| SEQ ID No. 640 | LCIISLLATLPLAVHASPQPLDQIK | 6-30 for the protein of SEQ No. 515 | 2b |
| SEQ ID No. 641 | LCIISLLATLPLAVHASPQPLEQIK | 6-30 for the proteins of SEQ No. 496, 497, 498, 499, 500, 503, 504, 505, 506, 507, 508, 509, 510, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 612, 1913, 1914, 1915, 1917, 1918, 1919, 1920; 5-29 for the protein of sequence SEQ ID No. 501 | SHV |
| SEQ ID No. 642 | LCIISLLATLPLAVHSSPQPLEQIK | 6-30 for the protein of SEQ No. 604 | SHV |
| SEQ ID No. 643 | LCIISLLATLPLAVHTSPQPLEQIK | 6-30 for the protein of SEQ No. 613 | SHV |

-continued

| Peptide SEQ ID No. | Amino acid sequence | Position of the peptide in the SHV protein | Clinical interest |
|---|---|---|---|
| SEQ ID No. 644 | LCIISLLATLPLTV HASPQPLEQIK | 6-30 for the protein of SEQ No. 605 | 2b |
| SEQ ID No. 645 | LCIISLLATLPLVV HASPQPLEQIK | 6-30 for the protein of SEQ No. 502 | 2b |
| SEQ ID No. 646 | LCIISLLATLPLAV HASPQPLEQIK | 6-30 for the protein of SEQ No. 606 | 2be |
| SEQ ID No. 647 | LCIISLLATMPLAV HASPQPLEQIK | 6-30 for the protein of SEQ No. 607 | SHV |
| SEQ ID No. 648 | LCIISLLAVLPLAV HASPQPLEQIK | 6-30 for the protein of SEQ No. 608 | 2b |
| SEQ ID No. 649 | LLISQR | 189-194 for the protein of SEQ No. 578 | SHV |
| SEQ ID No. 650 | LLLATVGGPAGLT AFLR | 133-149 for the proteins of SEQ No. 496, 497, 498, 499, 500, 502, 503, 505, 506, 507, 508, 509, 510, 512, 513, 514, 515, 516, 517, 518, 519, 521, 522, 523, 524, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 564, 565, 566, 570, 571, 573, 574, 575, 577, 578, 579, 580, 581, 582, 583, 584, 585, 586, 587, 588, 589, 590, 591, 592, 596, 597, 598, 599, 600, 601, 602, 603, 604, 605, 606, 607, 608, 609, 610, 611, 612, 613, 1910, 1912, 1913, 1914, 1915, 1916, 1918, 1919, 1920 | SHV |
| SEQ ID No. 651 | LLNSQR | 189-194 for the protein of SEQ No. 534 | 2be |
| SEQ ID No. 652 | LLTNQR | 189-194 for the protein of SEQ No. 562 | SHV |
| SEQ ID No. 653 | LLTSQR | 189-194 for the proteins of SEQ No. 496, 497, 498, 499, 500, 502, 503, 504, 505, 506, 507, 508, 509, 510, 511, 512, 513, 514, 515, 516, 517, 518, 519, 520, 521, 522, 523, 524, 525, 526, 527, 528, 529, 531, 532, 533, 535, 536, 537, 538, 539, 540, 541, 542, 543, 544, 545, 546, 547, 548, 549, 550, 551, 552, 553, 554, 555, 556, 557, 558, 559, 560, 561, 563, 564, 565, 566, 567, 570, 571, 572, 573, 574, 575, 576, 577, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 1910, 1912, 1913, 1914, 1915, 1916, 1917, 1918, 1919, 1920; 188-193 for the protein of sequence SEQ ID No. 501; 194-199 for the protein of sequence SEQ ID No. 530; 22-27 for the protein of sequence SEQ ID No. 1911 | SHV |
| SEQ ID No. 654 | LNIISLLATLPLAV HASPQPLEQIK | 6-30 for the protein of SEQ No. 609 | 2b |
| SEQ ID No. 655 | LSASSQR | 195-201 for the protein of SEQ No. 497 | SHV |
| SEQ ID No. 656 | LSESQLSGR | 31-39 for the proteins of SEQ No. 496, 497, 498, 499, 500, 503, 504, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 604, 606, 609, 1917, 1918, 1919; 30-38 for the protein of sequence SEQ ID No. 501 | SHV |
| SEQ ID No. 657 | LSESQLSGSVGM IEMDLASGR | 31-51 for the proteins of SEQ No. 505, 506, 507, 508, 509, 510 | SHV |
| SEQ ID No. 658 | MVVIYLR | 254-260 for the protein of SEQ No. 499 | 2b |
| SEQ ID No. 659 | NEALPGDAR | 166-174 for the proteins of SEQ No. 496, 497, 498, 499, 500, 502, 503, 504, 505, 506, 507, 508, 509, 510, 511, 512, 513, | 2be |

-continued

| Peptide SEQ ID No. | Amino acid sequence | Position of the peptide in the SHV protein | Clinical interest |
|---|---|---|---|
| | | 514, 515, 516, 517, 518, 519, 520, 521, 523, 524, 525, 527, 528, 529, 533, 534, 535, 536, 537, 538, 539, 540, 541, 542, 543, 544, 545, 546, 547, 548, 549, 550, 551, 552, 553, 554, 555, 556, 557, 558, 559, 561, 562, 563, 564, 565, 566, 567, 570, 571, 572, 573, 574, 575, 576, 577, 578, 579, 580, 581, 582, 583, 584, 585, 586, 587, 588, 589, 590, 591, 593, 594, 595, 596, 597, 598, 599, 600, 601, 602, 603, 604, 605, 606, 607, 608, 609, 610, 611, 612, 613, 1910, 1912, 1913, 1914, 1915, 1916, 1917, 1918, 1919, 1920; 165-173 for the protein of sequence SEQ ID No. 501; 171-179 for the protein of sequence SEQ ID No. 530; 165-173 for the protein of sequence SEQ ID No. 568; 165-173 for the protein of sequence SEQ ID No. 569 | |
| SEQ ID No. 660 | NQHIAGIGAALIEHWQR | 270-286 for the proteins of SEQ No. 513, 1910 | SHV |
| SEQ ID No. 661 | NQQIAGIGAALIEHWQR | 270-286 for the proteins of SEQ No. 496, 497, 498, 499, 500, 502, 503, 504, 505, 506, 507, 508, 509, 510, 511, 512, 514, 515, 516, 517, 518, 519, 520, 521, 522, 523, 524, 525, 526, 527, 528, 529, 531, 532, 533, 534, 535, 536, 537, 538, 539, 540, 541, 542, 543, 544, 545, 546, 547, 548, 549, 551, 552, 553, 554, 555, 556, 557, 558, 559, 560, 561, 562, 563, 564, 565, 566, 567, 570, 571, 572, 573, 574, 575, 576, 577, 578, 579, 580, 581, 582, 583, 584, 585, 586, 588, 589, 590, 591, 592, 593, 594, 595, 596, 597, 598, 599, 600, 601, 602, 603, 604, 605, 606, 607, 608, 609, 610, 611, 612, 613, 1912, 1915, 1916, 1917, 1918, 1919; 269-285 for the protein of sequence SEQ ID No. 501; 275-291 for the protein of sequence SEQ ID No. 530; 269-285 for the protein of sequence SEQ ID No. 568; 269-285 for the protein of sequence SEQ ID No. 569 | SHV |
| SEQ ID No. 662 | NQQIAGLGAALIEHWQR | 270-286 for the protein of SEQ No. 550 | SHV |
| SEQ ID No. 663 | NTTTPASMAATLR | 175-187 for the protein of SEQ No. 559 | 2be |
| SEQ ID No 664 | NVLTSQR | 187-193 for the proteins of SEQ No. 568, 569 | SHV |
| SEQ ID No. 665 | QIDDNVTR | 150-157 for the proteins of SEQ No. 505, 527, 528, 565, 577, 601 | 2be |
| SEQ ID No. 666 | QIGDK | 150-154 for the protein of SEQ No. 529 | 2b |
| SEQ ID No. 667 | QIGDNVTR | 150-157 for the proteins of SEQ No. 496, 497, 498, 499, 500, 502, 503, 504, 506, 507, 508, 509, 510, 511, 512, 513, 514, 515, 516, 517, 518, 519, 520, 521, 522, 523, 524, 525, 526, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 563, 564, 566, 567, 570, 571, 572, 573, 574, 575, 576, 578, 579, 580, 581, 582, 583, 584, 585, 586, 587, 588, 589, 590, 591, 592, 593, 594, 595, 596, 597, 598, 599, 600, 602, 603, 604, 605, 606, 607, 608, 609, 610, 611, 612, 613, 1910, 1912, 1913, 1914, 1916, 1917, 1918, 1919, 1920; 149-156 for the protein of sequence SEQ ID No. 501; 149-156 for the protein of sequence SEQ ID No. 568; 149-156 for the protein of sequence SEQ ID No. 569 | SHV |
| SEQ ID No. 668 | QIGENVTR | 150-157 for the protein of SEQ No. 562 | 2b |
| SEQ ID No. 669 | QLLQWMVDAR | 202-211 for the protein of SEQ No. 579 | SHV |
| SEQ ID No. 670 | QLLQWMVDDGVAGPLIR | 202-218 for the protein of SEQ No. 539 | SHV |
| SEQ ID No. 671 | QLLQWMVDDR | 202-211 for the proteins of SEQ No. 496, 497, 498, 499, 500, 502, 503, 504, 505, 506, 507, 508, 509, 510, 511, 513, 514, 515, 516, 517, 518, 519, 520, 521, 522, 523, 524, 525, 526, 527, 528, 529, 531, 532, 533, 534, 535, 536, 537, 538, 540, 541, 542, 543, 544, 545, 546, 547, 548, 549, 550, 551, 552, 555, 556, 557, 558, 559, 560, 561, 562, 563, 564, 565, 566, | SHV |

| Peptide SEQ ID No. | Amino acid sequence | Position of the peptide in the SHV protein | Clinical interest |
|---|---|---|---|
| | | 567, 570, 571, 572, 573, 574, 575, 576, 577, 578, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 1910, 1912, 1913, 1914, 1915, 1916, 1917, 1918, 1919, 1920; 201-210 for the protein of sequence SEQ ID No. 501; 207-216 for the protein of sequence SEQ ID No. 530; 201-210 for the protein of sequence SEQ ID No. 568; 201-210 for the protein of sequence SEQ ID No. 569; 35-44 for the protein of sequence SEQ ID No. 1911 | |
| SEQ ID No. 672 | QLLQWMVDGR | 202-211 for the protein of SEQ No. 553 | 2b |
| SEQ ID No. 673 | QLLQWMVEDR | 202-211 for the protein of SEQ No. 512 | SHV |
| SEQ ID No. 674 | QQDLVDYSPVSEK | 95-107 for the proteins of SEQ No. 496, 497, 498, 499, 500, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 570, 571, 572, 573, 574, 575, 576, 577, 578, 579, 580, 581, 582, 583, 584, 585, 586, 587, 588, 589, 590, 591, 592, 593, 594, 595, 596, 597, 598, 600, 601, 602, 603, 604, 605, 606, 607, 608, 609, 610, 611, 612, 613, 1910, 1912, 1913, 1914, 1915, 1916, 1917, 1918, 1919, 1920; 94-106 for the protein of sequence SEQ ID No. 501; 94-106 for the protein of sequence SEQ ID No. 568; 94-106 for the protein of sequence SEQ ID No. 569 | SHV |
| SEQ ID No. 675 | QQHLVDYSPVSEK | 95-107 for the protein of SEQ No. 599 | 2b |
| SEQ ID No. 676 | QSESQLSGR | 31-39 for the proteins of SEQ No. 502, 511, 512, 513, 514, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 605, 607, 608, 610, 611, 612, 613, 1910, 1912, 1913, 1914, 1915, 1916, 1920 | SHV |
| SEQ ID No. 677 | QSESQLSGSVGMIEMDLASGR | 31-51 for the protein of SEQ No. 603 | 2b |
| SEQ ID No. 678 | SQLQLLQWMVDDR | 199-211 for The proteins of SEQ No. 536, 537, 538 | 2be |
| SEQ ID No. 679 | SVLPAGWFIADK | 219-230 for the proteins of SEQ No. 496, 497, 498, 499, 500, 502, 503, 505, 506, 507, 508, 509, 510, 511, 512, 513, 514, 515, 516, 517, 518, 519, 520, 521, 522, 523, 524, 525, 526, 527, 528, 529, 531, 532, 533, 534, 535, 536, 537, 538, 539, 540, 541, 542, 543, 544, 545, 546, 547, 548, 549, 550, 553, 554, 555, 556, 557, 558, 559, 560, 561, 562, 563, 564, 565, 566, 567, 570, 571, 572, 573, 574, 575, 576, 577, 578, 579, 580, 581, 582, 583, 584, 585, 586, 587, 588, 589, 591, 592, 593, 594, 595, 596, 597, 598, 599, 600, 601, 602, 603, 604, 605, 606, 607, 608, 609, 610, 611, 612, 613, 1910, 1912, 1913, 1914, 1915, 1916, 1917, 1918, 1919, 1920; 224-235 for the protein of sequence SEQ ID No. 530; 218-229 for the protein of sequence SEQ ID No. 568; 218-229 for the protein of sequence SEQ ID No. 569; 52-63 for the protein of sequence SEQ ID No. 1911 | SHV |
| SEQ ID No. 680 | SVLPAGWFIADR | 219-230 for the proteins of SEQ No, 504, 551, 590; 218-229 for the protein of sequence SEQ ID No. 501 | SHV |
| SEQ ID No. 681 | SVLSAGWFIADK | 219-230 for the protein of SEQ No. 552 | 2b |
| SEQ ID No. 682 | TGAAER | 231-236 for the proteins of SEQ No. 540, 581, 603 | SHV |
| SEQ ID No. 683 | TGAAK | 231-235 for the protein of SEQ No, 506 | 2be |

-continued

| Peptide SEQ ID No. | Amino acid sequence | Position of the peptide in the SHV protein | Clinical interest |
|---|---|---|---|
| SEQ ID No. 684 | TGAGER | 231-236 for the proteins of SEQ No. 496, 497, 498, 499, 502, 504, 507, 511, 512, 513, 514, 516, 518, 519, 520, 521, 524, 525, 526, 527, 531, 533, 535, 536, 539, 541, 542, 543, 544, 551, 552, 553, 554, 555, 558, 559, 560, 561, 562, 563, 564, 565, 566, 567, 570, 571, 572, 573, 576, 577, 578, 579, 582, 583, 590, 591, 592, 593, 594, 595, 596, 597, 598, 599, 600, 601, 604, 605, 607, 608, 609, 610, 611, 612, 613, 1910, 1912, 1916, 1917, 1918; 230-235 for the protein of sequence SEQ ID No. 501; 236-241 for the protein of sequence SEQ ID No. 530 | SHV |
| SEQ ID No. 685 | TGAAK | 231-235 for the proteins of SEQ No. 517, 545, 546, 556, 584, 606 | SHV |
| SEQ ID No. 686 | TGASER | 64-69 for the proteins of SEQ No. 1911; 231-236 for the protein of sequence SEQ ID No. 503; 231-236 for the protein of sequence SEQ ID No. 508; 231-236 for the protein of sequence SEQ ID No. 510; 231-236 for the protein of sequence SEQ ID No. 522; 231-236 for the protein of sequence SEQ ID No. 532; 231-236 for the protein of sequence SEQ ID No. 537; 231-236 for the protein of sequence SEQ ID No, 547; 231-236 for the protein of sequence SEQ ID No. 548; 231-236 for the protein of sequence SEQ ID No. 585 | 2be |
| SEQ ID No. 687 | TGASK | 231-235 for the proteins of SEQ No. 500, 505, 509, 515, 523, 528, 529, 534, 538, 549, 550, 557, 574, 575, 586, 587, 588, 602, 1913, 1914, 1915, 1919, 1920; 230-234 for the protein of sequence SEQ ID No. 568; 230-234 for the protein of sequence SEQ ID No. 569 | SHV |
| SEQ ID No. 688 | TGASR | 231-235 for the protein of SEQ No. 589 | SHV |
| SEQ ID No. 689 | TLTAWCADER | 52-61 for the protein of SEQ No. 571 | SHV |
| SEQ ID No. 690 | TLTAWHADER | 52-61 for the proteins of SEQ No. 516, 517 | 2be |
| SEQ ID No. 691 | TLTAWR | 52-57 for the proteins of SEQ No, 496, 497, 498, 499, 500, 502, 503, 504, 505, 506, 507, 508, 509, 510, 511, 512, 513, 514, 515, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 570, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 1910, 1912, 1913, 1914, 1915, 1916, 1917, 1918, 1919, 1920; 51-56 for the protein of sequence SEQ ID No. 501; 51-56 for the protein of sequence SEQ ID No. 568; 51-56 for the protein of sequence SEQ ID No. 569 | SHV |
| SEQ ID No. 692 | TVGGPAGLTAFLR | 137-149 for the proteins of SEQ No. 496, 497, 498, 499, 500, 502, 503, 505, 506, 507, 508, 509, 510, 512, 513, 514, 515, 516, 517, 518, 519, 521, 522, 523, 524, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 564, 565, 566, 570, 571, 573, 574, 575, 577, 578, 579, 580, 581, 582, 583, 584, 585, 586, 587, 588, 589, 590, 591, 592, 596, 597, 598, 599, 600, 601, 602, 603, 604, 605, 606, 607, 608, 609, 610, 611, 612, 613, 1910, 1912, 1913, 1914, 1915, 1916, 1918, 1919, 1920; 136-148 for the protein of sequence SEQ ID No. 568; 136-148 for the protein of sequence SEQ ID No. 569 | SHV |
| SEQ ID No. 693 | TVVIYLR | 254-260 for the protein of SEQ No. 546 | SHV |
| SEQ ID No. 694 | VAGPLIR | 212-218 for the proteins of SEQ No. 496, 497, 498, 499, 500, 502, 503, 504, 505, 506, 507, 508, 509, 510, 511, 512, 513, 514, 515, 516, 517, 518, 519, 520, 521, 522, 523, 524, 525, 526, 527, 528, 529, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, | SHV |

| Peptide SEQ ID No. | Amino acid sequence | Position of the peptide in the SHV protein | Clinical interest |
|---|---|---|---|
| | | 563, 564, 565, 566, 567, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 1910, 1912, 1913, 1914, 1915, 1916, 1917, 1918, 1919, 1920; 211-217 for the protein of sequence SEQ ID No. 501; 217-223 for the protein of sequence SEQ ID No. 530; 211-217 for the protein of sequence SEQ ID No. 568; 211-217 for the protein of sequence SEQ ID No. 569; 45-51 for the protein of sequence SEQ ID No. 1911 | |
| SEQ ID No. 695 | VALCGAVLAR | 70-79 for the protein of SEQ No. 573 | 2b |
| SEQ ID No. 696 | VDAGDEQLER | 80-89 for the proteins of SEQ No. 496, 497, 498, 499, 500, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 570, 571, 572, 573, 574, 576, 577, 578, 579, 580, 581, 582, 583, 584, 585, 586, 587, 588, 589, 590, 591, 592, 593, 594, 595, 596, 597, 598, 599, 601, 602, 603, 604, 605, 606, 607, 608, 609, 610, 611, 612, 613, 1910, 1912, 1913, 1914, 1915, 1916, 1917, 1918, 1919, 1920; 79-88 for the protein of sequence SEQ ID No. 501; 79-88 for the protein of sequence SEQ ID No. 568; 79-88 for the protein of sequence SEQ ID No. 569 | SHV |
| SEQ ID No. 697 | VDAGDK | 80-85 for the proteins of SEQ No. 575, 600 | SHV |
| SEQ ID No. 698 | VGMIEMDLASGR | 40-51 for the proteins of SEQ No. 496, 497, 498, 499, 500, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 1910, 1912, 1913, 1914, 1915, 1916, 1917, 1918, 1919, 1920; 39-50 for the protein of sequence SEQ ID No. 501 | SHV |
| SEQ ID No. 699 | VGMIEMDLASR | 40-50 for the proteins of SEQ No. 568, 569 | SHV |
| SEQ ID No. 700 | VGMIEMDLASSR | 40-51 for the protein of SEQ No, 570 | SHV |
| SEQ ID No. 701 | VLLCGAVLAR | 70-79 for the protein of SEQ No. 574 | SHV |
| SEQ ID No. 702 | VVLCGAMLAR | 70-79 for the protein of SEQ No. 575 | 2be |
| SEQ ID No. 703 | VVLCGAVLAR | 70-79 for the proteins of SEQ No. 496, 497, 498, 499, 500, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 570, 571, 572, 576, 577, 578, 579, 580, 581, 582, 583, 584, 585, 586, 587, 588, 589, 590, 591, 592, 593, 594, 595, 596, 597, 598, 599, 602, 603, 604, 605, 606, 607, 608, 609, 610, 611, 612, 613, 1910, 1912, 1913, 1914, 1915, 1916, 1917, 1918, 1919, 1920; 69-78 for the protein of sequence SEQ ID No. 501; 69-78 for the protein of sequence SEQ ID No. 568; 69-78 for the protein of sequence SEQ ID No. 569 | SHV |
| SEQ ID No. 704 | VVLCGTVLAR | 70-79 for the protein of SEQ No. 601 | 2b |

| Peptide SEQ ID No. | Amino acid sequence | Position of the peptide in the SHV protein | Clinical interest |
|---|---|---|---|
| SEQ ID No. 705 | WETDR | 161-165 for the protein of SEQ No. 530 | 2be |
| SEQ ID No. 706 | WETELNEALPGDAR | 161-174 for the proteins of SEQ No. 522, 531, 532 | SHV |
| SEQ ID No. 707 | WETELNEALPADAR | 161-174 for the protein of SEQ No. 526 | 2b |
| SEQ ID No. 708 | WETELNEALPGDAR | 161-174 for the proteins of SEQ No. 496, 497, 498, 499, 500, 502, 503, 504, 505, 506, 507, 508, 509, 510, 511, 512, 513, 514, 515, 516, 517, 518, 519, 520, 521, 523, 524, 525, 527, 528, 529, 533, 534, 535, 536, 537, 538, 539, 540, 541, 542, 543, 544, 545, 546, 547, 548, 549, 550, 551, 552, 553, 554, 555, 556, 557, 558, 559, 562, 563, 564, 565, 566, 567, 570, 571, 572, 573, 574, 575, 576, 577, 578, 579, 580, 581, 582, 583, 584, 585, 586, 587, 588, 589, 590, 591, 593, 594, 595, 596, 597, 598, 599, 600, 601, 602, 603, 604, 605, 606, 607, 608, 609, 610, 611, 612, 613, 1910, 1912, 1913, 1914, 1915, 1916, 1917, 1918, 1919, 1920; 160-173 for the protein of sequence SEQ ID No. 501; 166-179 for the protein of sequence SEQ ID No. 530; 160-173 for the protein of sequence SEQ ID No. 568; 160-173 for the protein of sequence SEQ ID No. 569 | SHV |
| SEQ ID No. 709 | WETELNEALSGDAR | 161-174 for the protein of SEQ No. 560 | 2b |
| SEQ ID No. 710 | WETELNEALPGDAR | 161-174 for the protein of SEQ No. 592 | SHV |
| SEQ ID No. 711 | WETER | 161-165 for the protein of SEQ No. 561 | SHV |
| SEQ ID No. 2093 | EIGDNVTR | 150-157 for the proteins of SEQ No. 1915 | SHV |
| SEQ ID No. 2094 | GIVALLGPHNK | 240-250 for the proteins of SEQ No. 1917 | SHV |
| SEQ ID No. 2095 | HLADGMTVGELR | 108-119 for the proteins of SEQ No. 1914 | 2be |
| SEQ ID No. 2096 | IHYSQQDLVDYSPVSEK | 91-107 for the proteins of SEQ No. 1918 | SHV |

In the clinical interest column, the entries 2b, 2br, 2be and 2ber correspond to the functional subgroups of the SHV beta-lactamases which the corresponding peptide makes it possible to detect. Thus, the detection of a 2be peptide will indicate the presence of a beta-lactamase with an extended spectrum (ESBL) capable of hydrolysing penicillins, first-generation cephalosporins such as cephaloridine and cefalotin, and at least one antibiotic from the oxyimino-beta-lactam class such as cefotaxime, ceftazidime or monobactams such as aztreonam.

The entry SHV indicates a common peptide between at least two of the subgroups 2b, 2br and 2be or 2ber. The corresponding peptide indicates the presence of an SHV beta-lactamase and the presence of a mechanism of resistance at least to penicillins and to first-generation cephalosporins.

The detection of a mechanism of resistance to ESBL (extended-spectrum beta-lactamase) cephalosporins, induced by the SHV protein, is characterised by the detection of at least one resistance-marking 2be peptide, chosen from the sequences SEQ ID No. 616, SEQ ID No. 617, SEQ ID No. 627, SEQ ID No. 629, SEQ ID No. 634, SEQ ID No. 647, SEQ ID No. 648, SEQ ID No. 653, SEQ ID No. 654, SEQ ID No. 656, SEQ ID No. 660, SEQ ID No. 661, SEQ ID No. 662, SEQ ID No. 663, SEQ ID No. 664, SEQ ID No. 665, SEQ ID No. 670, SEQ ID No. 673, SEQ ID No, 674, SEQ ID No. 675, SEQ ID No. 678, SEQ ID No. 682, SEQ ID No. 684, SEQ ID No. 685, SEQ ID No. 686, SEQ ID No. 687, SEQ ID No. 688, SEQ ID No. 697, SEQ ID No. 702, SEQ ID No. 703, SEQ ID No. 704, SEQ ID No. 707, SEQ ID No. 708, SEQ ID No. 709, SEQ ID No. 711, SEQ ID No. 2095.

The detection of a mechanism of resistance to cephalosporins induced by the expression of the FOX protein is characterised by the detection of at least one peptide belonging to the FOX protein and to its different sequence variants SEQ ID No. 712 to SEQ ID No. 718 and SEQ ID No. 1920 to SEQ ID No. 1922.

SEQ ID No. 712:
MQQRRAFALLTLGSLLLAPCTYASGEAPLTAAVDGIIQPMLKAYRIPGMAVAVLKDG
KAHYFNYGVANRESGQRVSEQTLFEIGSVSKTLTATLGAYAAVKGGFELDDKVSQH

```
APWLKGSALDGVTMAELATYSAGGLPLQFPDEVDSNDKMRTYYRSWSPVYPAGT
HRQYSNPSIGLFGHLAANSLGQPFEQLMSQTLLPKLGLHHTYIQVPESAMVNYAYG
YSKEDKPVRVTPGVLAAEAYGIKTGSADLLKFAEANMGYQGDAAVKSAIALTHTGFY
SVGDMTQGLGWESYAYPVTEQTLLAGNAPAVSFQANPVTRFAVPKAMGEQRLYN
KTGSTGGFGAYVAFVPARGIAIVMLANRNYPIEARVKAAHAILSQLAE

SEQ ID No. 713:
MQQRRAFALLTLGSLLLAPCTYASGEAPLTAAVDGIIQPMLKAYRIPGMAVAVLKDG
KAHYFNYGVANRESGQRVSEQTLFEIGSVSKTLTATLGAYAAVKGGFELDDKVSQH
APWLKGSALDGVTMAELATYSAGGLPLQFPDEVDSNDKMRTYYRSWSPVYPAGT
HRQYSNPSIGLFGHLAANSLGQPFEQLMSQTLLPKLGLHHTYIQVPESAMVNYAYG
YSKEDKPVRVTPGVLAAEAYGIKTGSADLLKFAEANMGYQGDAAVKSAIALTHTGFY
SVGDMTQGLGWESYAYPVTEQTLLAGNAPAVSFQANPVTRFAVPKAMGEQRLYN
KTGSTGGFGAYVAFVPARGIAIVMLANRNYPIEARVKAAHAILSQLAE

SEQ ID No. 14:
MQQRRAFALLTLGSLLLAPCTYARGEAPLTAAVDGIIQPMLKEYRIPGMAVAVLKDG
KAHYFNYGVANRESGQRVSEQTLFEIGSVSKTLTATLGAYAAVKGGFELDDKVSQH
APWLKGSAFDGVTMAELATYSAGGLPLQFPDEVDSNDKMRTYYRHWSPVYPAGT
HRQYSNPSIGLFGHLAANSLGQPFEQLMSQTLLPKLGLHHTYIQVPESAIANYAYGY
SKEDKPVRVTPGVLAAEAYGIKTGSADLLKFTEANMGYQGDAALKTRIALTHTGFYS
VGDMTQGLGWESYAYPLTEQALLAGNSPAVSFQANPVTRFAVPKAMGEQRLYNKT
GSTGGFGAYVAFVPARGIAIVMLANRNYPIEARVKAAHAILSQLAE

SEQ ID No. 715:
MQQRRALALLTLGSLLLAPCTYASGEAPLTAAVDGIIQPMLKEYRIPGMAVAVLKDG
KAHYFNYGVANRESGQRVSEQTLFEIGSVSKTLTATLGAYAAVKGGFELDDKVSHH
APWLKGSAFDGVTMAELATYSAGGLPLQFPDEVDSNDKMQTYYRSWSPVYPAGT
HRQYSNPSIGLFGHLAANSLGQPFEKLMSQTLLPKLGLHHTYIQVPESAMANYAYG
YSKEDKPIRVTPGVLAAEAYGIKTGSADLLKFVEANMGYQGDAALKSAIALTHTGFY
SVGDMTQGLGWESYAYPVTEQALLAGNSPAVSFQANPVTRFAVPKAMGEQRLYN
KTGSTGGFGAYVAFVPARGIAIVMLANRNYPIEARVKAAHAILSQLAE

SEQ ID No. 716:
MQQRRAFALLTLGSLLLAPCTYASGEAPLTATVDGIIQPMLKEYRIPGIAVAVLKDGK
ARYFNYGVANRESGQRVSEQTLFEIGSVSKTLTATLGAYAAVKGGFVLDDKVSQHA
PWLKGSALDGVTMAELATYSAGGLPLQFPDKVDSNDKMQTYYRSWSPVYPAGTH
RQYSNPSIGLFGHLAANSLGQPFEQLMSQTLLPKLGLHHTYIQVPESAMANYAYGY
SKEDKPIRVTPGVLAAEAYGIKTGSADLLKFAEANMGYQGDAVKSAIALTHTGFYS
VGEMTQGLGWESYDYPVTEQVLLAGNSPAVSFQANPVTRFAVPKAMGEQRLYNK
TGSTGGFGAYVAFVPARGIAIVMLANRNYPIEARVKAAHAILSQLAE

SEQ ID No. 717:
MQQRRALALLMLGSLLLAPCTYASGEAPLTATVDGIIQPMLKAYRIPGMAVAVLKDG
KAHYFNYGVANRESGQRVSEQTLFEIGSVSKTLTATLGAYAAVKGGFELDDKVSQH
APWLKGSAFDGVTMAELATYSAGGLPLQFPDEVDSNDKMQTYYRSWSPVYPAGT
HRQYSNPSIGLFGHLAANSLGQPFEQLMSQTLLPKLGLHHTYIQVPESAMANYAYG
YSKEDKPIRATPGVLAAEAYGIKTGSADLLKFVEANMGYQGDAALKSAIALTHTGFH
SVGEMTQGLGWESYDYPVTEQVLLAGNSPAVSFQANPVTRFAVPKAMGEQRLYN
KTGSTGGFGAYVAFVPARGIAIVMLANRNYPIEARVKAAHAILSQLAE

SEQ ID No. 718:
MQQRRAFALLTLGSLLLAPCTYARGEAPLTAAVDGIIQPMLKEYRIPGMAVAVLKDG
KAHYFNYGVANRESGQRVSEQTLFEIGSVSKTLTATLGAYAAVKGGFELDDKVSQH
APWLKGSAFDGVTMAELATYSAGGLPLQFPDEVDSNDKMRTYYRHWSPVYPAGT
HRQYSNPSIGLFGHLAANSLGQPFEQLMSQTLLPKLGLHHTYIQVPESAIANYAYGY
SKEDKPVRATPGVLAAEAYGIKTGSADLLKFTEANMGYQGDAALKSAIALTHTGFYS
VGDMTQGLGWESYAYPLTEQALLAGNSPAVSFQANPVTRFAVPKAMGEQRLYNKT
GSTGGFGAYVAFVPARGIAIVMLANRNYPIEARVKAAHAILSQLAE

SEQ ID No. 1920:
MQQRRAFALLTLGSLLLAPCTYASGEAPLTATVDGIIQPMLKEYRIPGIAVAVLKDGK
AHYFNYGVANRESGQRVSEQTLFEIGSVSKTLTATLGAYAAVKGGFVLDDKVSQHA
PWLKGSALDGVTMAELATYSAGGLPLQFPDKVDSNDKMQTYYRSWSPVYPAGTH
RQYSNPSIGLFGHLAANSLGQPFEQLMSQTLLPKLGLHHTYIQVPESAMANYAYGY
SKEDKPIRVTPGVLAAEAYGIKTGSADLLKFAEANMGYQGDALVKSAIALTHTGFYS
VGEMTQGLGWESYDYPVTEQVLLAGNSPAVSLQANPVTRFAVPKAMGEQRLYNKT
GSTGGFGAYVAFVPARGIAIVMLANRNYPIEARVKAAHAILSQLAE

SEQ ID No. 1921:
MQQRRAFALLTLGSLLLAPCTYASGEAPLTVTVDGIIQPMLKAYRIPGMAVAVLKDG
KAHYFNYGVANRESGQRVSEQTLFEIGSVSKTLTATLGAYAAVKGGFELDDKVSQH
APWLKGSAFDGVTMAELATYSAGGLPLQFPEEVDSNDKMRTYYRSWSPVYPAGT
HRQYANTSIGLFGYLAANSLGQSFEQLMSQTLLPKLGLHHTYIQVPESAMANYAYG
YSKEEKPIRVTPGMLAAEAYGIKTGSADLLKFAEANMGYQGDAAVKSAIALTHTGFY
SVGDMTQGLGWESYDYPVTEQVLLADNSPAVSFQANPVTRFAVPKAMGEQRLYN
KTGSTGGFGAYVAFVPARGIAIVMLANRNYPIEARVKAAHAILSQLAE

SEQ ID No. 1922:
MQQRRAFALLTLGSLLLAPCTYASGEAPLTATVDGIIQPMLKEYRIPGIAVAVLKDGK
AHYFNYGVANRESGQRVSEQTLFEIGSVSKTLTATLGAYAAVKGGFVLDDKVSQHA
```

```
-continued
PWLKGSALDGVTMAELATYSAGGLPLQFPDKVDSNDKMQTYYRSWSPVYPAGTH
RQYSNPSIGLFGHLAANSLGQPFEQLMSQTLLPKLGLHHTYIQVPESAMANYAYGY
SKEDKPIRVTPGVLAAEAYGIKTGSADLLKFAEANMGYQGDALVKSAIALTHTGFYS
VGEMTQGLGWESYDYPVTEQVLLAGNSPAVSFQANPVTRFAVPKAMGEQRLYNK
TGSTGGFGAYVAFVPARGIAIVMLANRNYPIEARVKAAHAILSQLAE
``` said peptides being chosen, preferably, from the peptides of sequence SEQ ID No. 719 to SEQ ID No. 733 and SEQ ID No. 2097 to SEQ ID No. 2113 as defined hereafter:

| Peptide SEQ ID No. | Amino acid sequence | Position of the peptide in the FOX protein |
|---|---|---|
| SEQ ID No. 719 | AHYFNYGVANR | 59-69 for the proteins of SEQ No. 712, 713, 714, 715, 716, 717, 718, 1920, 1921, 1922 |
| SEQ ID No. 720 | AMGEQR | 326-331 for the proteins of SEQ No. 712, 713, 714, 715, 716, 717, 718, 1920, 1921, 1922 |
| SEQ ID No. 721 | ESGQR | 70-74 for the proteins of SEQ No. 712, 713, 714, 715, 716, 717, 718, 1920, 1921, 1922 |
| SEQ ID No. 722 | FAVPK | 321-325 for the proteins of SEQ No. 712, 713, 714, 715, 716, 717, 718, 1920, 1921, 1922 |
| SEQ ID No. 723 | GGFELDDK | 102-109 for the proteins of SEQ No. 712, 713, 714, 715, 717, 718, 1921 |
| SEQ ID No. 724 | GIAIVMLANR | 353-362 for the proteins of SEQ No. 712, 713, 714, 715, 716, 717, 718, 1920, 1921, 1922 |
| SEQ ID No. 725 | IPGMAVAVLK | 46-55 for the proteins of SEQ No. 712, 713, 714, 715, 717, 718, 1921 |
| SEQ ID No. 726 | NYPIEAR | 363-369 for the proteins of SEQ No. 712, 713, 714, 715, 716, 717, 718, 1920, 1921, 1922 |
| SEQ ID No. 727 | SWSPVYPAGTHR | 158-169 for the proteins of SEQ No. 712, 713, 715, 716, 717, 1920, 1921, 1922 |
| SEQ ID No. 728 | TGSADLLK | 247-254 for the proteins of SEQ No. 712, 713, 714, 715, 716, 717, 718, 1920, 1921, 1922 |
| SEQ ID No. 729 | TGSTGGFGAYVAFVPAR | 336-352 for the proteins of SEQ No. 712, 713, 714, 715, 716, 717, 718, 1920, 1921, 1922 |
| SEQ ID No. 730 | TLTATLGAYAAVK | 89-101 for the proteins of SEQ No. 712, 713, 714, 715, 716, 717, 718, 1920, 1921, 1922 |
| SEQ ID No. 731 | VSEQTLFEIGSVSK | 75-88 for the proteins of SEQ No. 712, 713, 714, 715, 716, 717, 718, 1920, 1921, 1922 |
| SEQ ID No. 732 | VSQHAPWLK | 110-118 for the proteins of SEQ No. 712, 713, 714, 716, 717, 718, 1920, 1921, 1922 |
| SEQ ID No. 733 | VTPGVLAAEAYGIK | 233-246 for the proteins of SEQ No. 712, 713, 714, 715, 716, 1920, 1922 |
| SEQ ID No. 2097 | AFALLTLGSLLLAPCTYAR | 6-24 for the proteins of SEQ No. 714, 718 |
| SEQ ID No. 2098 | ATPGVLAAEAYGIK | 233-246 for the proteins of SEQ No. 717, 718 |
| SEQ ID No. 2099 | EDKPVR | 227-232 for the proteins of SEQ No. 712, 713, 714, 718 |
| SEQ ID No. 2100 | EEKPIR | 227-232 for the proteins of SEQ No. 1921 |
| SEQ ID No. 2101 | FAEANMGYQGDAAVK | 255-269 for the proteins of SEQ No. 712, 713, 1921 |
| SEQ ID No. 2102 | FAEANMGYQGDALVK | 255-269 for the proteins of SEQ No. 716, 1920, 1922 |
| SEQ ID No. 2103 | FTEANMGYQGDAALK | 255-269 for the proteins of SEQ No. 714, 718 |

| Peptide SEQ ID No. | Amino acid sequence | Position of the peptide in the FOX protein |
|---|---|---|
| SEQ ID No. 2104 | FVEANMGYQGDAALK | 255-269 for the proteins of SEQ No. 715, 717 |
| SEQ ID No. 2105 | GEAPLTAAVDGIIQPMLK | 25-42 for the proteins of SEQ No. 712, 713, 714, 715, 718 |
| SEQ ID No. 2106 | GGFVLDDK | 102-109 for the proteins of SEQ No. 716, 1920, 1922 |
| SEQ ID No. 2107 | HWSPVYPAGTHR | 158-169 for the proteins of SEQ No. 714, 718 |
| SEQ ID No. 2108 | IPGIAVAVLK | 46-55 for the proteins of SEQ No. 716, 1920, 1922 |
| SEQ ID No. 2109 | LMSQTLLPK | 194-202 for the proteins of SEQ No. 712, 713, 714, 715, 716, 717, 718, 1920, 1921, 1922 |
| SEQ ID No. 2110 | MQTYYR | 152-157 for the proteins of SEQ No. 715, 716, 717, 1920, 1922 |
| SEQ ID No. 2111 | VDSNDK | 146-151 for the proteins of SEQ No. 712, 713, 714, 715, 716, 717, 718, 1920, 1921, 1922 |
| SEQ ID No. 2112 | VSHHAPWLK | 110-118 for the protein of SEQ No. 715 |
| SEQ ID No. 2113 | VTPGMLAAEAYGIK | 233-246 for the proteins of SEQ No. 1921 |

The detection of a mechanism of resistance to cephalosporins induced by the expression of the ACC protein is characterised by the detection of at least one peptide belonging to the ACC protein and to its different sequence variants SEQ ID No. 736 to SEQ ID No. 739.

SEQ ID No. 736:
MRKKMQNTLKLLSVITCLAATAQGAMAANIDESKIKDTVDGLIQPLMQKNNIPGMSV
AVTIRGRNYIYNYGLAAKQPQQPVTENTLFEVGSLSKTFAAILASYAQASGKLSLEQS
VSHYVPELRGSSFDHVSVLNVGTHTSGLQLFMPEDIKNTTQLMTYLKAWKPADAAG
THRVYSNIGTGLLGMIAAKSLGVSYEDAIEQTILPLLGMNQTYLKVPADQMENYAWG
YNKKDEPVHVNMEILGNEAYGIKTTSSDLLRYVQANMGQLKLDGNAKIQHALTATHT
GYFKSGEITQDLMWEQLPYPVSLPNLLTGNDMAMTKSVATPIVPPLPPQENVWINK
TGSTNGFGAYIAFVPAKKMGIVMLANKNYSIDQRVTVAYKILSSLEVNK

SEQ ID No. 737:
MRKKMQNTLKMLSVITCLALTAQGAMASEMDQAKIKDTVDSLIQPLMQKNNIPGMS
VAVTLNGKNYIYNYGLASKQPQQPVTDNTLFEVGSLSKTFAATLASYAQVSGKLSLD
KSISHYVPELRGSSFDHISVLNAGTHTTGLALFMPEEVKNTDQLMAYLKAWKPADPA
GTHRVYSNIGTGLLGMIAAQSMGMTYEDAIEKTLLPKLGMTHTYLNVPADQAENYA
WGYNKKNEPIHVNMEVLGNEAYGIRTNASDLIRYVQANMGQLKLDGNSTLQKALTD
THIGYFKSGKITQDLMWEQLPYPVSLPDLLTGNDMAMTKSVATPIVPPLPPQENVWI
NKTGSTNGFGAYIAFVPAKKMGIVMLANKNYSIDQRVT

SEQ ID No. 738:
MQNTLKLLSVITCLAATVQGALAANIDESKIKDTVDDLIQPLMQKNNIPGMSVAVTVN
GKNYIYNYGLAAKQPQQPVTENTLFEVGSLSKTFAATLASYAQVSGKLSLDQSVSH
YVPELRGSSFDHVSVLNVGTHTSGLQLFMPEDIKNTTQLMAYLKAWKPADAAGTHR
VYSNIGTGLLGMIAAKSLGVSYEDAIEKTLLPQLGMHHSYLKVPADQMENYAWGYN
KKDEPVHGNMEILGNEAYGIKTTSSDLLRYVQANMGQLKLDANAKMQQALTATHTG
YFKSGEITQDLMWEQLPYPVSLPNLLTGNDMAMTKSVATPIVPPLPPQENVWINKT
GSTNGFGAYIAFVPAKKMGIVMLANKNYSIDQRVTVAYKILSSLEGNK

SEQ ID No. 739:
MQNTLKLLSVITCLAATVQGALAANIDESKIKDTVDDLIQPLMQKNNIPGMSVAVTVN
GKNYIYNYGLAAKQPQQPVTENTLFEVGSLSKTFAATLASYAQVSGKLSLDQSVSH
YVPELRGSSFDHVSVLNVGTHTSGLQLFMPEDIKNTTQLMAYLKAWKPADAAGTHR
VYSNIGTGLLGMIAAKSLGVSYEDAIEKTLLPQLGMHHSYLKVPADQMENYAWGYN
KKDEPVHVNMEILGNEAYGIKTTSSDLLRYVQANMGQLKLDANAKMQQALTATHTG
YFKSGEITQDLMWEQLPYPVSLPNLLTGNDMAMTKSVATPIVPPLPPQENVWINKT
GSTNGFGAYIAFVPAKKMGIVMLANKNYSIDQRVTVAYKILSSLEGNK said peptides being chosen, preferably, from the peptides of sequence SEQ ID No. 740 to SEQ ID No. 787 as defined hereafter:

| Peptide SEQ ID No. | Amino acid sequence | Position of the peptide in the ACC protein(s) |
|---|---|---|
| SEQ ID No. 740 | ALTDTHIGYFK | 279-289 for the protein of SEQ No. 737 |
| SEQ ID No. 741 | AWKPADAAGTHR | 159-170 for the proteins of SEQ No. 738, 739; 163-174 for the protein of sequence SEQ ID No. 736 |
| SEQ ID No. 742 | AWKPADPAGTHR | 163-174 for the protein of SEQ No. 737 |
| SEQ ID No. 743 | DEPVHGNMEILGNEAYGIK | 229-247 for the protein of SEQ No. 738 |
| SEQ ID No. 744 | DEPVHVNMEILGNEAYGIK | 229-247 for the protein of SEQ No. 739; 233-251 for the protein of sequence SEQ ID No. 736 |
| SEQ ID No. 745 | DTVDDLIQPLMQK | 33-45 for the proteins of SEQ No. 738, 739 |
| SEQ ID No. 746 | DTVDGLIQPLMQK | 37-49 for the protein of SEQ No. 736 |
| SEQ ID No. 747 | DTVDSLIQPLMQK | 37-49 for the protein of SEQ No. 737 |
| SEQ ID No. 748 | IQHALTATHTGYFK | 276-289 for the protein of SEQ No. 736 |
| SEQ ID No. 749 | LDANAK | 266-271 for the proteins of SEQ No. 738, 739 |
| SEQ ID No. 750 | LDGNAK | 270-275 for the protein of SEQ No. 736 |
| SEQ ID No. 751 | LDGNSTLQK | 270-278 for the protein of SEQ No. 737 |
| SEQ ID No. 752 | LGMTHTYLNVPADQAENYAWGYNK | 208-231 for the protein of SEQ No. 737 |
| SEQ ID No. 753 | LLSVITCLAATAQGAMAANIDESK | 11-34 for the protein of SEQ No. 736 |
| SEQ ID No. 754 | LLSVITCLAATVQGALAANIDESK | 7-30 for the proteins of SEQ No. 738, 739 |
| SEQ ID No. 755 | LSLDK | 110-114 for the protein of SEQ No. 737 |
| SEQ ID No. 756 | LSLDQSVSHYVPELR | 106-120 for the proteins of SEQ No. 738, 739 |
| SEQ ID No. 757 | LSLEQSVSHYVPELR | 110-124 for the protein of SEQ No. 736 |
| SEQ ID No. 758 | MGIVMLANK | 356-364 for the proteins of SEQ No. 738, 739; 360-368 for the proteins of sequence SEQ ID No. 736, 737 |
| SEQ ID No. 759 | MLSVITCLALTAQGAMASEMDQAK | 11-34 for the protein of SEQ No. 737 |
| SEQ ID No. 760 | MQNTLK | 1-6 for the proteins of SEQ No. 738, 739; 5-10 10 for the proteins of sequence SEQ ID No. 736, 737 |
| SEQ ID No. 761 | MQQALTATHTGYFK | 272-285 for the proteins of SEQ No. 738, 739 |
| SEQ ID No. 762 | NEPIHVNMEVLGNEAYGIR | 233-251 for the protein of SEQ No. 737 |

-continued

| Peptide SEQ ID No. | Amino acid sequence | Position of the peptide in the ACC protein(s) |
|---|---|---|
| SEQ ID No. 763 | NNIPGMSVAVTIR | 50-62 for the protein of SEQ No. 736 |
| SEQ ID No. 764 | NNIPGMSVAVTLNGK | 50-64 for the protein of SEQ No. 737 |
| SEQ ID No. 765 | NNIPGMSVAVTVNGK | 46-60 for the proteins of SEQ No. 738, 739 |
| SEQ ID No. 766 | NTDQLMAYLK | 153-162 for the protein of SEQ No. 737 |
| SEQ ID No. 767 | NTTQLMAYLK | 149-158 for the proteins of SEQ No. 738, 739 |
| SEQ ID No. 768 | NTTQLMTYLK | 153-162 for the protein of SEQ No. 736 |
| SEQ ID No. 769 | NYIYNYGLAAK | 61-71 for the proteins of SEQ No. 738, 739; 65-75 for the protein of sequence SEQ ID No. 736 |
| SEQ ID No. 770 | NYIYNYGLASK | 65-75 for the protein of SEQ No. 737 |
| SEQ ID No. 771 | NYSIDQR | 365-371 for the proteins of SEQ No. 738, 739; 369-375 for the protein of sequence SEQ ID No. 736, 737 |
| SEQ ID No. 772 | QPQQPVTDNTLFEVGSLSK | 76-94 for the protein of SEQ No. 737 |
| SEQ ID No. 773 | QPQQPVTENTLFEVGSLSK | 72-90 for the proteins of SEQ No. 738, 739; 76-94 for the protein of sequence SEQ ID No. 736 |
| SEQ ID No. 774 | SISHYVPELR | 115-124 for the protein of SEQ No. 737 |
| SEQ ID No. 775 | SLGVSYEDAIEK | 187-198 for the proteins of SEQ No. 738, 739 |
| SEQ ID No. 776 | SVATPIVPPLPPQENVWINK | 318-337 for the proteins of SEQ No. 738, 739; 322-341 for the protein of sequence SEQ ID No. 736, 737 |
| SEQ ID No. 777 | TFAAILASYAQASGK | 95-109 for the protein of SEQ No. 736 |
| SEQ ID No. 778 | TFAATLASYAQVSGK | 91-105 for the proteins of SEQ No. 738, 739; 95-109 for the protein of sequence SEQ ID No. 737 |
| SEQ ID No. 779 | TGSTNGFGAYIAFVPAK | 338-354 for the proteins of SEQ No. 738, 739; 342-358 for the protein of sequence SEQ ID No. 736, 737 |
| SEQ ID No. 780 | TLLPK | 203-207 for the protein of SEQ No. 737 |
| SEQ ID No. 781 | TLLPQLGMHHSYLK | 199-212 for the proteins of SEQ No. 738, 739 |
| SEQ ID No. 782 | TNASDLIR | 252-259 for the protein of SEQ No. 737 |
| SEQ ID No. 783 | TTSSDLLR | 248-255 for the proteins of SEQ No. 738, 739; 252-259 for the protein of sequence SEQ ID No. 736 |
| SEQ ID No. 784 | VPADQMENYAWGYNK | 213-227 for the proteins of SEQ No. 738, 739; 217-231 for the protein of sequence SEQ ID No. 736 |

-continued

| Peptide SEQ ID No. | Amino acid sequence | Position of the peptide in the ACC protein(s) |
|---|---|---|
| SEQ ID No. 785 | VTVAYK | 372-377 for the proteins of SEQ No. 738, 739; 376-381 for the protein of sequence SEQ ID No. 736 |
| SEQ ID No. 786 | VYSNIGTGLLGMIAAK | 171-186 for the proteins of SEQ No. 738, 739; 175-190 for the protein of sequence SEQ ID No. 736 |
| SEQ ID No. 787 | YVQANMGQLK | 256-265 for the proteins of SEQ No. 738, 739; 260-269 for the protein of sequence SEQ ID No. 736, 737 |

The detection of a mechanism of resistance to cephalosporins induced by the expression of the ACT protein is characterised by the detection of at least one peptide belonging to the ACT protein and to its different sequence variants SEQ ID No. 788 to SEQ ID No. 794.

SEQ ID No. 788:
MMMTKSLCCALLLSTSCSVLATPMSEKQLAEVVERTVTPLMKAQAIPGMAVAVIYE
GQPHYFTFGKADVAANKPVTPQTLFELGSISKTFTGVLGGDAIARGEISLGDPVTKY
WPELTGKQWQGIRMLDLATYTAGGLPLQVPDEVKDNASLLRFYQNWQPQWKPGT
TRLYANASIGLFGALAVKPSGMSYEQAITTRVFKPLKLDHTWINVPKAEEAHYAWGY
RDGKAVHVSPGMLDAEAYGVKTNVQDMASWVMVNMKPDSLQDNSLRKGLTLAQS
RYWRVGAMYQGLGWEMLNWPVDAKTVVEGSDNKVALAPLPAREVNPPAPPVNAS
WVHKTGSTGGFGSYVAFIPEKQLGIVMLANKSYPNPARVEAAYRILSAL

SEQ ID No. 789:
MMMTKSLCCALLLSTSCSVLATPMSEKQLAEVVERTVTPLMKAQAIPGMAVAVIYE
GQPHYFTFGKADVAANKPVTPQTLFELGSISKTFTGVLGGDAIARGEISLGDPVTKY
WPELTGKQWQGIRMLDLATYTAGGLPLQVPDEVTDNASLLRFYQNWQPQWKPGT
TRLYANASIGLFGALAVKPSGMSYEQAITTRVFKPLKLDHTWINVPKAEEAHYAWGY
RDGKAIHVSPGMLDAEAYGVKTNVQDMASWVMVNMKPDSLQDNSLRKGLTLAQS
RYWRVGAMYQGLGWEMLNWPVDAKTVVEGSDNKVALAPLPAREVNPPAPPVNAS
WVHKTGSTGGFGSYVAFIPEKQLGIVMLANKSYPNPARVEAAYRILSAL

SEQ ID No. 790:
MMTKSLCCALLLSTSCSVLAAPMSEKQLAEVVERTVTPLMKAQAIPGMAVAVIYQG
QPHYFTFGKADVAANKPVTPQTLFELGSISKTFTGVLGGDAIARGEISLGDPVTKYW
PELTGKQWQGIRMLDLATYTAGGLPLQVPDEVADNASLLRFYQNWQPQWKPGTT
RLYANTSIGLFGALAVKPSGMSYEQAITTRVFKPLKLDHTWINVPKAEEAHYAWGYR
DGKAVHVSPGMLDAEAYGVKTNVQDMASWVMVNMKPDSLQDNSLRQGIALAQSR
YWRVGAMYQGLGWEMLNWPVDAKTVVEGSDNKVALAPLPAREVNPPAPPVNAS
WVHKTGSTGGFGSYVAFIPEKQLGIVMLANKSYPNPARVEAAYRILSAL

SEQ ID No. 791:
MMTKSLCCALLLSTSCSVLAAPMSEKQLAEVVERTVTPLMKAQAIPGMAVAVIYQG
QPHYFTFGKADVAANKPVTPQTLFELGSISKTFTGVLGGDAIARGEISLGDPVTKYW
PELTGKQWQGIRMLDLATYTAGGLPLQVPDEVTDNASLLRFYQNWQPQWKPGTTR
LYANASIGLFGALAVKPSGMSYEQAITTRVFKPLKLDHTWINVPKAEEAHYAWGYRD
GKAVHVSPGMLDAEAYGVKTNVKDMANWVMVNMKPDSLQDSSLKEGITLAQSRY
WRVGAMYQGLGWEMLNWPVDAKTVVEGSDNKVALAPLPAREVNPPAPPVNASW
VHKTGSTGGFGSYVAFIPEKQLGIVMLANKSYPNPARVEAAYRILDALQ

SEQ ID No. 792:
MMRKSLCCALLLGISCSALATPVSEKQLAEVVANTVTPLMKAQSVPGMAVAVIYQG
KPHYYTFGKADIAANKPVTPQTLFELGSISKTFTGVLGGDAIARGEISLDDPVTRYWP
QLTGKQWQGIRMLDLATYTAGGLPLQVPDEVTDNASLLRFYQNWQPQWKPGTTRL
YANASIGLFGALAVKPSGMPYEQAMTTRVLKPLKLDHTWINVPKAEEAHYAWGYRD
GKAVRVSPGMLDAQAYGVKTNVQDMANWVMANMAPENVADASLKQGIALAQSRY
WRIGSMYQGLGWEMLNWPVEANTVVEGSDSKVALAPLPVAEVNPPAPPVKASWV
HKTGSTGGFGSYVAFIPEKQIGIVMLANTSYPNPARVEAAYHILEALQ

SEQ ID No. 793:
MMKKSLCCALLLGISCSALAAPVSEKQLAEVVANTVTPLMKAQSIPGMAVAVIYQGK
PHYYTFGKADIAASKPVTPQTLFELGSISKTFTGVLGGDAIARGEISLDDPVTRYWPQ
LTGKQWQGIRMLDLATYTAGGLPLQVPDEVTDNAALLRFYQNWQPQWKPGTTRLY
ANASIGLFGALAVKPSGMPFEQAMTTRVLKPLKLDHTWINVPKAEEAHYAWGYRDG
KAVRVSPGMLDAQAYGMKTNVQDMANWVMANMAPENVADASLKQGISLAQSRY
WRIGSMYQGLGWEMLNWPVEANTVIEGSDSKVALAPLPVAEVNPPAPPVKASWVH
KTGSTGGFGSYVAFIPEKQIGIVMLANKSYPNPARVEAAYPILDALQ

-continued

SEQ ID No. 794:
MMMTKSLCCALLLSTSCSVLATPMSEKQLAEVVERTVTPLMKAQAIPGMAVAVIYE
GQPHYFTFGKADVAANKPVTPQTLFELGSISKTFTGVLGGDAIARGEISLGDPVTKY
WPELTGKQWQGIRMLDLATYTAGGLPLQVPDEVTDNASLLRFYQNWQPQWKPGT
TRLYANASIGLFGALAVKPSGMSYEQAITTRVFKPLKLDHTWINVPKAEEAHYAWGY
RDGKAVHVSPGMLDAEAYGVKTNVQDMASWVMVNMKPDSLQDNSLRKGLTLAQS
RYWRVGAMYQGLGWEMLNWPVDAKTVVEGSDNKVALAPLPAREVNPPAPPVNAS
WVHKTGSTGGFGSYVAFIPEKQLGIVMLANKSYPNPARVEAAYRILSAL said peptides being chosen, preferably, from the peptides of sequence SEQ ID No. 795 to SEQ ID No. 841 as defined hereafter:

| Peptide SEQ ID No. | Amino acid sequence | Position of the peptide in the ACT protein(s) |
|---|---|---|
| SEQ ID No. 795 | ADIAANK | 66-72 for the protein of SEQ No. 792 |
| SEQ ID No. 796 | ADIAASK | 66-72 for the protein of SEQ No. 793 |
| SEQ ID No. 797 | ADVAANK | 67-73 for the proteins of SEQ No. 788, 789, 794; 66-72 for the protein of sequence SEQ ID No. 790, 791 |
| SEQ ID No. 798 | AEEAHYAWGYR | 215-225 for the proteins of SEQ No. 788, 789, 794; 214-224 for the proteins of sequence SEQ ID No. 790, 791, 792, 793 |
| SEQ ID No. 799 | AIHVSPGMLDAEAYGVK | 229-245 for the protein of SEQ No. 789 |
| SEQ ID No. 800 | AQSIPGMAVAVIYQGK | 42-57 for the protein of SEQ No. 793 |
| SEQ ID No. 801 | AQSVPGMAVAVIYQGK | 42-57 for the protein of SEQ No. 792 |
| SEQ ID No. 802 | AVHVSPGMLDAEAYGVK | 229-245 for the proteins of SEQ No. 788, 794; 228-244 for the proteins of sequence SEQ ID No. 790, 791 |
| SEQ ID No. 803 | DMANWVMVNMK | 249-259 for the protein of SEQ No. 791 |
| SEQ ID No. 804 | DMANWVMVNMKPDSLQDSSLK | 249-269 for the protein of SEQ No. 791 |
| SEQ ID No. 805 | DNASLLR | 148-154 for the proteins of SEQ No. 788, 789, 794; 147-153 for the proteins of sequence SEQ ID No. 790, 791, 792 |
| SEQ ID No. 806 | EGITLAQSR | 270-278 for the protein of SEQ No. 791 |
| SEQ ID No. 807 | EVNPPAPPVNASWVHK | 321-336 for the proteins of SEQ No. 788, 789, 794; 320-335 for the proteins of sequence SEQ ID No. 790, 791 |
| SEQ ID No. 808 | FYQNWQPQWK | 155-164 for the proteins of SEQ No. 788, 789, 794; 154-163 for the proteins of sequence SEQ ID No. 790, 791, 792, 793 |
| SEQ ID No. 809 | FYQNWQPQWKPGTTR | 155-169 for the proteins of SEQ No. 788, 789, 794; 154-168 for the proteins of sequence SEQ ID No. 790, 791, 792, 793 |
| SEQ ID No. 810 | GEISLDDPVTR | 101-111 for the proteins of SEQ No. 792, 793 |
| SEQ ID No. 811 | GEISLGDPVTK | 102-112 for the proteins of SEQ No. 788, 789, 794; 101-111 for the proteins of sequence SEQ ID No. 790, 791 |

-continued

| Peptide SEQ ID No. | Amino acid sequence | Position of the peptide in the ACT protein(s) |
|---|---|---|
| SEQ ID No. 812 | GLTLAQSR | 272-279 for the proteins of SEQ No. 788, 789, 794 |
| SEQ ID No. 813 | LDHTWINVPK | 205-214 for the proteins of SEQ No. 788, 789, 794; 204-213 the proteins of sequence SEQ ID No. 791, 792, 793 |
| SEQ ID No. 814 | LYANASIGLFGALAVK | 170-185 for the proteins of SEQ No. 788, 789, 794; 169-184 for the proteins of sequence SEQ ID No. 791, 792, 793 |
| SEQ ID No. 815 | LYANTSIGLFGALAVK | 169-184 for the protein of SEQ No. 790 |
| SEQ ID No. 816 | MLDLATYTAGGLPLQVPDEVK | 127-147 for the protein of SEQ No. 788 |
| SEQ ID No. 817 | QGIALAQSR | 270-278 for the proteins of SEQ No. 790, 792 |
| SEQ ID No. 818 | QGISLAQSR | 270-278 for the proteins of SEQ No. 793 |
| SEQ ID No. 819 | QIGIVMLANK | 353-362 for the protein of SEQ No. 793 |
| SEQ ID No. 820 | QIGIVMLANTSYPNPAR | 353-369 for the protein of SEQ No. 792 |
| SEQ ID No. 821 | QLAEVVANTVTPLMK | 27-41 for the proteins of SEQ No. 792, 793 |
| SEQ ID No. 822 | QLAEVVER | 28-35 for the proteins of SEQ No. 788, 789, 794; 27-34 for the proteins of sequence SEQ ID No. 790, 791 |
| SEQ ID No. 823 | QLGIVMLANK | 354-363 for the proteins of SEQ No. 788, 789, 794; 353-362 for the proteins of sequence SEQ ID No. 790, 791 |
| SEQ ID No. 824 | SYPNPAR | 364-370 for the proteins of SEQ No. 788, 789, 794; 363-369 for the proteins of sequence SEQ ID No. 790, 791, 792, 793 |
| SEQ ID No. 825 | TFTGVLGGDAIAR | 89-101 for the proteins of SEQ No. 788, 789, 794; 88-100 for the proteins of sequence SEQ ID No. 790, 791, 792, 793 |
| SEQ ID No. 826 | TGSTGGFGSYVAFIPEK | 337-353 for the proteins of SEQ No. 788, 789, 794; 336-352 for the proteins of sequence SEQ ID No. 790, 791, 792, 793 |
| SEQ ID No. 827 | TNVQDMASWVMVNMK | 246-260 for the proteins of SEQ No. 788, 789, 794; 245-259 for the protein of sequence SEQ ID No. 790 |
| SEQ ID No. 828 | TVTPLMK | 36-42 for the proteins of SEQ No. 788, 789, 794; 35-41 for the proteins of sequence SEQ ID No. 790, 791, 792, 793 |
| SEQ ID No. 829 | TVVEGSDNK | 303-311 for the proteins of SEQ No. 788, 789, 794; 302-310 for the proteins of sequence SEQ ID No. 790, 791 |
| SEQ ID No. 830 | VALAPLPAR | 312-320 for the proteins of SEQ No. 788, 789, 794; 311-319 for the proteins of sequence SEQ ID No. 790, 791 |
| SEQ ID No. 831 | VALAPLPVAEVNPPAPPVK | 311-329 for the proteins of SEQ No. 792, 793 |
| SEQ ID No. 832 | VEAAYR | 371-376 for the proteins of SEQ No. 788, 789, 794; 370-375 for the proteins of sequence SEQ ID No. 790, 791 |

| Peptide SEQ ID No. | Amino acid sequence | Position of the peptide in the ACT protein(s) |
|---|---|---|
| SEQ ID No. 833 | VFKPLK | 199-204 for the proteins of SEQ No. 788, 789, 794; 198-203 for the proteins of sequence SEQ ID No. 790, 791 |
| SEQ ID No. 834 | VGAMYQGLGWEMLNWPVDAK | 283-302 for the proteins of SEQ No. 788, 789, 794; 282-301 for the proteins of sequence SEQ ID No. 790, 791 |
| SEQ ID No. 835 | VLKPLK | 198-203 for the proteins of SEQ No. 792, 793 |
| SEQ ID No. 836 | VSPGMLDAQAYGMK | 231-244 for the protein of SEQ No. 793 |
| SEQ ID No. 837 | VSPGMLDAQAYGVK | 231-244 for the protein of SEQ No. 792 |
| SEQ ID No. 838 | YWPQLTGK | 112-119 for the proteins of SEQ No. 792, 793 |
| SEQ ID No. 839 | ASWVHK | 331-336 for the proteins of SEQ No. 788, 789, 794; 330-335 for the proteins of sequence SEQ ID No. 790, 791, 792, 793 |
| SEQ ID No. 840 | QWQGIR | 121-126 for the proteins of SEQ No. 788, 789, 794; 120-125 for the proteins of sequence SEQ ID No. 790, 791, 792, 793 |
| SEQ ID No. 841 | YWPELTGK | 113-120 for the proteins of SEQ No. 788, 789, 794; 112-119 for the proteins of sequence SEQ ID No. 790, 791 |

The detection of a mechanism of resistance to cephalosporins induced by the expression of the CARB protein is characterised by the detection of at least one peptide belonging to the GARB protein and to its different sequence variants SEQ ID No. 842 to SEQ ID No. 852.

SEQ ID No. 842:
MLLYKMCDNQNYGVTYMKFLLAFSLLIPSVVFASSSKFQQVEQDVKAIEVSLSARIG
VSVLDTQNGEYWDYNGNQRFPLTSTFKTIACAKLLYDAEQGKVNPNSTVEIKKADL
VTYSPVIEKQVGQAITLDDACFATMTTSDNTAANIILSAVGGPKGVTDFLRQIGDKET
RLDRIEPDLNEGKLGDLRDTTTPKAIASTLNKFLFGSALSEMNQKKLESWMVNNQVT
GNLLRSVLPAGWNIADRSGAGGFGARSITAVVWSEHQAPIIVSIYLAQTQASMAERN
DAIVKIGHSIFDVYTSQSR

SEQ ID No. 843:
MLLYKMCDNQNYGVTYMKFLLAFSLLIPSVVFASSSKFQQVEQDVKAIEVSLSARIG
VSVLDTQNGEYWDYNGNQRFPLTSTFKTIACAKLLYDAEQGKVNPNSTVEIKKADL
VTYSPVIEKQVGQAITLDDACFATMTTSDNTAANIILSAVGGPKGVTDFLRQIGDKET
RLDRIEPDLNEGKLGDLRDTTTPKAIASTLNKLLFGSALSEMNQKKLESWMVNNQVT
GNLLRSVLPAGWNIADRSGAGGFGARSITAVVWSEHQAPIIVSIYLAQTQASMAERN
DAIVKIGHSIFDVYTSQSR

SEQ ID No. 844:
MKLLLVFSLLIPSMVFANSSKFQQVEQDAKVIEASLSAHIGISVLDTQTGEYWDYNG
NQRFPLTSTFKTIACAKLLYDAEQGEINPKSTIEIKKADLVTYSPVIEKQVGQAITLDDA
CFATMTTSDNAAANIILNALGGPESVTDFLRQIGDKETRLDRIEPELNEGKLGDLRDT
TTPNAIVNTLNELLFGSTLSQDGQKKLEYWMVNNQVTGNLLRSVLPEGWNIADRSG
AGGFGARSITAVVWSEAQSPIIVSIYLAQTEASIADRNDAIVKIGRSIFEVYSSQSR

SEQ ID No. 845:
MKFLLAFSLLIPSVVFASSSKFQQVEQDVKAIEVSLSARIGVSVLDTQNGEYWDYNG
NQRFPLTSTEKTIACAKLLYDAEQGKVNPNSTVEIKKADLVTYSPVIEKQVGQAITLD
DACFATMTTSDNTAANIILSAVGGPKGVTDFLRQIGDKETRLDRIEPDLNEGKLGDLR
DTTTPKAIASTLNQLLFGSTLSEASQKKLESWMVNNQVTGNLLRSVLPVKWSIADRS
GAGGFGARSITAIVWSEEKKTIIVSIYLAQTEASMAERNDAIVKIGRSIFEVYTSQSR

SEQ ID No. 846:
MNVRKHKASFFSVVITFLCLTLSLNANATDSVLEAVTNAETELGARIGLAVHDLETGK
RWEHKSNERFPLSSTFKTLACANVLQRVDLGKERIDRVVRFSESNLVTYSPVTEKH

-continued

```
VGKKGMSLAELCQATLSTSDNSAANFILQAIGGPKALTKFLRSIGDDTTRLDRWETE
LNEAVPGDKRDTTTPIAMVTTLEKLLIDETLSIKSRQQLESWLKGNEVGDALFRKGV
PSDWIVADRTGAGGYGSRAITAVMWPPNRKPIVAALYITETDASFEERNAVIAKIGE
QIAKTVLMENSRN

SEQ ID No. 847:
MKFLLAFSLLIPSVVFASSSKFQQVEQDVKAIEVSLSARIGVSVLDTQNGEYWDYNG
NQRFPLTSTFKTIACAKLLYDAEQGKVNSNSTVEIKKADLVTYSPVIEKQVGQAITLD
DACFATMTTSDNTAANIILSAVGGPKGVTDFLRQIGDKETRLDRIEPDLNEGKLGDLR
DTTTPKAIASTLNKFLFGSALSEMNQKKLESWMVNNQVTGNLLRSVLPAGWNIADR
SGAGGFGARSITAVVWSEHQAPIIVSIYLAQTQASMAERNDAIVKIGHSIFDVYTSQSR

SEQ ID No. 848:
MKFLLAFSLLIPSVVFASSSKFQQVEQDVKAIEVSLSARIGVSVLDTQNGEYWDYNG
NQRFPLTSTFKTIACAKLLYDAEQGKVNPNSTVEIKKADLVTYSPVIEKQVGQAITLD
DACFATMTTSDNTAANIILSAVGGPKGVTDFLRQIGDKETRLDRIEPDLNEGKLGDLR
DTTTPKAIASTLNKFLFGSALSEMNQKKLESWMVNNQVTGNLLRSVLPAGWNIADR
SGAGGFGARSITAVVWSEHQAPIIVSIYLAQTQASMEERNDAIVKIGHSIFDVYTSQSR

SEQ ID No. 849:
MKSLLVFALLMPSVVFASSSKFQSVEQEIKGIESSLSARIGVAILDTQNGESWDYNG
DQRFPLTSTFKTIACAKLLYDAEHGKVNLNSTVEIKKADLVTYSPVLEKQVGKPITLS
DACLATMTTSDNTAANIVINAVGDPKSITDFLRQIGDKETRLDRVEPELNEGKLGDLR
DTTTPNAITSTLNQLLFGSTLSEASQKKLESWMVNNQVTGNLLRSVLPVKWSIADRS
GAGGFGARSITAIVWSEEKKPIIVSIYLAQTEASMAERNDAIVKIGRSIFEVYTSQSR

SEQ ID No. 850:
MDVRKHKASFFSWITFLCLTLSLNANATDSVLEAVTNAETELGARIGLAVHDLETGK
RWEHKSNERFPLSSTFKTLACANVLQRVDLGKERIDRVVRFSESNLVTYSPVTEKH
VGKKGMSLAELCQATLSTSDNSAANFILQAIGGPKALTKFLRSIGDDTTRLDRWETE
LNEAVPGDKRDTTTPIAMVTTLEKLLIDETLSIKSRQQLESWLKGNEVGDALFRKGV
PSDWIVADRTGAGGYGSRAITAVMWPPNRKPIVAALYITETDASFEERNAVIAKIGE
QIAKTILMENSRN

SEQ ID No. 851:
MKSLLVFALLMPSVVFASSSKFQSVEQEIKGIESSLSARIGVAILDTQNGESWDYNG
DQRFPLTSTFKTIACAKLLYDAEHGKVNLNSTVEVKKADLVTYSPVLEKQVGKPITLS
DACFATMTTSDNTAANIVINAVGDPKSITDFLRQIGDKETRLDRVEPELNEGKLGDLR
DTTTPNAITSTLNQLLFGSTLSEASQKKLESWMVNNQVTGNLLRSVLPVTWSIADRS
GAGGFGARSITAIVWSEEKKPIIVSIYLAQTEASMAERNDAIVKIGRSIFEVYTSQSR

SEQ ID No. 852:
MKFLLVFSLLIPSVVFASSSKFRQVEQDVKAIEVSLSARIGVSVLDTQNGEYWDYNG
NQRFPLTSTFKTIACAKLLYDAEQGKVNPNSTVEIKKADLVTYSPVIEKQVGQAITLD
DACFATMTTSDNTAANIILSAVGGSKGVTDFLRQIGDKETRLDRIEPDLNEGKLGDLR
DTTTPKAIASTLNKFLFGSALSEMNKKKLESWMVNNQVTGNLLRSVLPAGWNIADR
SGAGGFGARSITAVVWSEHQAPIIVSIYLAQTQASMAERNDAIVKIGRSIFDVYTSQSR
``` said peptides being chosen, preferably, from the peptides of sequence SEQ ID No. 853 to SEQ ID No. 921 as defined hereafter:

| Peptide SEQ ID No. | Amino acid sequence | Position of the peptide in the CARB protein(s) |
|---|---|---|
| SEQ ID No. 853 | ADLVTYSPVIEK | 95-106 for the proteins of SEQ No. 844, 845, 847, 848, 852; 111-122 for the protein of sequence SEQ ID No. 842; 111-122 for the protein of sequence SEQ ID No. 843 |
| SEQ ID No. 854 | ADLVTYSPVLEK | 95-106 for the proteins of SEQ No. 849, 851 |
| SEQ ID No. 855 | AIASTLNK | 180-187 for the proteins of SEQ No. 847, 848, 852; 196-203 for the protein of sequence SEQ ID No. 842; 196-203 for the protein of sequence SEQ ID No. 843 |
| SEQ ID No. 856 | AIASTLNQLLFGSTLSEASQK | 180-200 for the protein of SEQ No. 845 |
| SEQ ID No. 857 | AIEVSLSAR | 31-39 for the proteins of SEQ No. 845, 847, 848, 852; 47-55 for the protein of sequence SEQ ID No. 842; 47-55 for the protein of sequence SEQ ID No. 843 |

-continued

| Peptide SEQ ID No. | Amino acid sequence | Position of the peptide in the CARB protein(s) |
|---|---|---|
| SEQ ID No. 858 | AITAVMWPPNR | 247-257 for the proteins of SEQ No. 846, 850 |
| SEQ ID No. 859 | DTTTPIAMVTTLEK | 182-195 for the proteins of SEQ No. 846, 850 |
| SEQ ID No. 860 | DTTTPK | 174-179 for the proteins of SEQ No. 845, 847, 848, 852; 190-195 for the protein of sequence SEQ ID No. 842; 190-195 for the protein of sequence SEQ ID No. 843 |
| SEQ ID No. 861 | FLFGSALSEMNK | 188-199 for the protein of SEQ No. 852 |
| SEQ ID No. 862 | FLFGSALSEMNQK | 188-200 for the proteins of SEQ No. 847, 848; 204-216 for the protein of sequence SEQ ID No. 842 |
| SEQ ID No. 863 | FLLAFSLLIPSVVFASSSK | 3-21 for the proteins of SEQ No. 845, 847, 848; 19-37 for the protein of sequence SEQ ID No. 842; 19-37 for the protein of sequence SEQ ID No. 843 |
| SEQ ID No. 864 | FLLVFSLLIPSVVFASSSK | 3-21 for the protein of SEQ No. 852 |
| SEQ ID No. 865 | FPLSSTFK | 68-75 for the proteins of SEQ No. 846, 850 |
| SEQ ID No. 866 | FPLTSTFK | 61-68 for the proteins of SEQ No. 844, 845, 847, 848, 849, 851, 852; 77-84 for the protein of sequence SEQ ID No. 842; 77-84 for the protein of sequence SEQ ID No. 843 |
| SEQ ID No. 867 | FQQVEQDAK | 22-30 for the protein of SEQ No. 844 |
| SEQ ID No. 868 | FQQVEQDAK | 22-30 for the proteins of SEQ No. 845, 847, 848; 38-46 for the protein of sequence SEQ ID No. 842; 38-46 for the protein of sequence SEQ ID No. 843 |
| SEQ ID No. 869 | FQSVEQEIK | 22-30 for the proteins of SEQ No. 849, 851 |
| SEQ ID No. 870 | FSESNLVTYSPVTEK | 99-113 for the proteins of SEQ No. 846, 850 |
| SEQ ID No. 871 | GIESSLSAR | 31-39 for the proteins of SEQ No. 849, 851 |
| SEQ ID No. 872 | GNEVGDALFR | 216-225 for the proteins of SEQ No. 846, 850 |
| SEQ ID No. 873 | GVPSDWIVADR | 227-237 for the proteins of SEQ No. 846, 850 |
| SEQ ID No. 874 | GVTDFLR | 142-148 for the proteins of SEQ No. 845, 847, 848, 852; 158-164 for the protein of sequence SEQ ID No. 842; 158-164 for the protein of sequence SEQ ID No. 843 |
| SEQ ID No. 875 | IEPDLNEGK | 160-168 for the proteins of SEQ No. 845, 847, 848, 852; 176-184 for the protein of sequence SEQ ID No. 842; 176-184 for the protein of sequence SEQ ID No. 843 |
| SEQ ID No. 876 | IEPELNEGK | 160-168 for the protein of SEQ No. 844 |
| SEQ ID No. 877 | IGEQIAK | 283-289 for the proteins of SEQ No. 846, 850 |

-continued

| Peptide SEQ ID No. | Amino acid sequence | Position of the peptide in the CARB protein(s) |
|---|---|---|
| SEQ ID No. 878 | IGLAVHDLETGK | 47-58 for the proteins of SEQ No. 846, 850 |
| SEQ ID No. 879 | IGVAILDTQNGESWDYNGDQR | 40-60 for the proteins of SEQ No. 849, 851 |
| SEQ ID No. 880 | IGVSVLDTQNGEYWDYNGNQR | 40-60 for the proteins of SEQ No. 845, 847, 848, 852; 56-76 for the protein of sequence SEQ ID No. 842; 56-76 for the protein of sequence SEQ ID No. 843 |
| SEQ ID No. 881 | KPIIVSIYLAQTEASMAER | 250-268 for the proteins of SEQ No. 849, 851 |
| SEQ ID No. 882 | KPIVAALYITETDASFEER | 258-276 for the proteins of SEQ No. 846, 850 |
| SEQ ID No. 883 | LESWMVNNQVTGNLLR | 202-217 for the proteins of SEQ No. 845, 847, 848, 849, 851, 852; 218-233 for the protein of sequence SEQ ID No. 842; 218-233 for the protein of sequence SEQ ID No. 843 |
| SEQ ID No. 884 | LEYWMVNNQVTGNLLR | 202-217 for the protein of SEQ No. 844 |
| SEQ ID No. 885 | LGDLR | 169-173 for the proteins of SEQ No. 844, 845, 847, 848, 849, 851, 852; 185-189 for the protein of sequence SEQ ID No. 842; 185-189 for the protein of sequence SEQ ID No. 843 |
| SEQ ID No. 886 | LLFGSALSEMNQK | 204-216 for the protein of SEQ No. 843 |
| SEQ ID No. 887 | LLIDETLSIK | 196-205 for the proteins of SEQ No. 846, 850 |
| SEQ ID No. 888 | LLLVFSLLIPSMVFANSSK | 3-21 for the protein of SEQ No. 844 |
| SEQ ID No. 889 | LLYDAEHGK | 75-83 for the proteins of SEQ No. 849, 851 |
| SEQ ID No. 890 | LLYDAEQGEINPK | 75-87 for the protein of SEQ No. 844 |
| SEQ ID No. 891 | LLYDAEQGK | 75-83 for the proteins of SEQ No. 845, 847, 848, 852; 91-99 for the protein of sequence SEQ ID No. 842; 91-99 for the protein of sequence SEQ ID No. 843 |
| SEQ ID No. 892 | MCDNQNYGVTYMK | 6-18 for the proteins of SEQ No. 842, 843 |
| SEQ ID No. 893 | NAVIAK | 277-282 for the proteins of SEQ No. 846, 850 |
| SEQ ID No. 894 | NDAIVK | 269-274 for the proteins of SEQ No. 844, 845, 847, 848, 849, 851, 852; 285-290 for the protein of sequence SEQ ID No. 842; 285-290 for the protein of sequence SEQ ID No. 843 |
| SEQ ID No. 895 | QIGDK | 149-153 for the proteins of SEQ No. 844, 845, 847, 848, 849, 851, 852; 165-169 for the protein of sequence SEQ ID No. 842; 165-169 for the protein of sequence SEQ ID No. 843 |
| SEQ ID No. 896 | QQLESWLK | 208-215 for the proteins of SEQ No. 846, 850 |

-continued

| Peptide SEQ ID No. | Amino acid sequence | Position of the peptide in the CARB protein(s) |
|---|---|---|
| SEQ ID No. 897 | QVEQDVK | 24-30 for the proteins of SEQ No. 845, 847, 848, 852; 40-46 for the protein of sequence SEQ ID No. 842; 40-46 for the protein of sequence SEQ ID No. 843 |
| SEQ ID No. 898 | SGAGGFGAR | 230-238 for the proteins of SEQ No. 844, 845, 847, 848, 849, 851, 852; 246-254 for the protein of sequence SEQ ID No. 842; 246-254 for the protein of sequence SEQ ID No. 843 |
| SEQ ID No. 899 | SIGDDTTR | 157-164 for the proteins of SEQ No. 846, 850 |
| SEQ ID No. 900 | SITAIVWSEEK | 239-249 for the proteins of SEQ No. 845, 849, 851 |
| SEQ ID No. 901 | SITDFLR | 142-148 for the proteins of SEQ No. 849, 851 |
| SEQ ID No. 902 | SLLVFALLMPSVVFASSSK | 3-21 for the proteins of SEQ No. 849, 851 |
| SEQ ID No. 903 | STIEIK | 88-93 for the protein of SEQ No. 844 |
| SEQ ID No. 904 | SVLPAGWNIADR | 218-229 for the proteins of SEQ No. 847, 848, 852; 234-245 for the protein of sequence SEQ ID No. 842; 234-245 for the protein of sequence SEQ ID No. 843 |
| SEQ ID No. 905 | SVLPEGWNIADR | 218-229 for the protein of SEQ No. 844 |
| SEQ ID No. 906 | SVLPVK | 218-223 for the proteins of SEQ No. 845, 849 |
| SEQ ID No. 907 | SVLPVTWSIADR | 218-229 for the protein of SEQ No. 851 |
| SEQ ID No. 908 | TGAGGYGSR | 238-246 for the proteins of SEQ No. 846, 850 |
| SEQ ID No. 909 | TIACAK | 69-74 for the proteins of SEQ No. 844, 845, 847, 848, 849, 851, 852; 85-90 for the protein of sequence SEQ ID No. 842; 85-90 for the protein of sequence SEQ ID No. 843 |
| SEQ ID No. 910 | TIIVSIYLAQTEASMAER | 251-268 for the protein of SEQ No. 845 |
| SEQ ID No. 911 | TILMENSR | 290-297 for the protein of SEQ No. 850 |
| SEQ ID No. 912 | TLACANVLQR | 76-85 for the proteins of SEQ No. 846, 850 |
| SEQ ID No. 913 | TVLMENSR | 290-297 for the protein of SEQ No. 846 |
| SEQ ID No. 914 | VDLGK | 86-90 for the proteins of SEQ No. 846, 850 |
| SEQ ID No. 915 | VEPELNEGK | 160-168 for the proteins of SEQ No. 849, 851 |
| SEQ ID No. 916 | VNLNSTVEIK | 84-93 for the protein of SEQ No. 849 |
| SEQ ID No. 917 | VNLNSTVEVK | 84-93 for the protein of SEQ No. 851 |
| SEQ ID No. 918 | VNPNSTVEIK | 84-93 for the proteins of SEQ No. 845, 848, 852; 100-109 for the protein of sequence |

| Peptide SEQ ID No. | Amino acid sequence | Position of the peptide in the CARB protein(s) |
|---|---|---|
| | | SEQ ID No. 842; 100-109 for the protein of sequence SEQ ID No. 843 |
| SEQ ID No. 919 | VNSNSTVEIK | 84-93 for the protein of SEQ No. 847 |
| SEQ ID No. 920 | WETELNEAVPGDK | 168-180 for the proteins of SEQ No. 846, 850 |
| SEQ ID No. 921 | WSIADR | 224-229 for the proteins of SEQ No. 845, 849, 851 |

The detection of a mechanism of resistance to cephalosporins induced by the expression of the DHA protein is characterised by the detection of at least one peptide belonging to the DHA protein and to its different sequence variants SEQ ID No. 922 to SEQ ID No. 927.

SEQ ID No. 922:
MKKSLSATLISALLAFSAPGFSAADNVAAVVDSTIKPLMAQQDIPGMAVAVSVKGKP
YYFNYGFADVQAKQPVTENTLFELGSVSKTFTGVLGAVSVAKKEMMLNDPAEKYQ
PELALPQWKGITLLDLATYTTGGLPLQVPDAVKNRAELLHFYQQWQPSRKPGDMRL
YANSSIGLFGALTANAAGMPYEQLLTARILAPLGLSHTFITVPESAQSQYAYGYKNKK
PVRVSPGQLDAESYGVKSASKDMLRWAEMNMEPSRAGNADLEMAMYLAQTRYYK
TAAINQGLGWEMYDWPQQKDMIINGVTNEVALQPHPVTDNQVQPYNRASWVHKT
GATTGFGAYVAFIPEKQVAIVILANKNYPNTERVKAAQAILSALE

SEQ ID No. 923:
MKKSLSATLISALLAFSAPGFSAADNVAAVVDSTIKPLMAQQDIPGMAVAVSVKGKP
YYFNYGFADIQAKQPVTENTLFELGSVSKTFTGVLGAVSVAKKEMALNDPAAKYQP
ELALPQWKGITLLDLATYTAGGLPLQVPDAVKSRADLLNFYQQWQPSRKPGDMRLY
ANSSIGLFGALTANAAGMPYEQLLTARILAPLGLSHTFITVPDSAQSQYAYGYKNKKP
VRVSPGQLDAESYGVKSASKDMLRWAEMNIEPSRAGNADLEMAMYLAQTRYYKTA
AINQGLGWEMYDWPQQKDMIINGVTNEVALQPHPVTDNQVQPYNRASWVHKTGA
TTGFGAYVAFIPEKQVAIVILANKNYPNTERVKAAQAILSALE

SEQ ID No. 924:
MKKSLSATLISALLAFSAPGFSAADNVAAVVDSTIKPLMAQQDIPGMAVAVSVKGKP
YYFNYGFADIQAKQPVTENTLFELGSVSKTFTGVLGAVSVAKKEMALNDPAAKYQP
ELALPQWKGITLLDLATYTAGGLPLQVPDAVKSRADLLNFYQQWQPSRKPGDMRLY
ANSSIGLFGALTANAAGMPYEQLLTARILAPLGLSHTFITVPESAQSQYAYGYKNKKP
VRVSPGQLDAESYGVKSASKDMLRWAEMNMEPSRAGNADLEMAMYLAQTRYYKT
AAINQGLGWEMYDWPQQKDMIINGVTNEVALQPHPVTDNQVQPYNRASWVHKTG
ATTGSGAYVAFIPEKQVAIVILANKNYPNTERVKAAQAILSALE

SEQ ID No. 925:
MKKSLSATLISALLAFSAPGFSAADNVAAVVDSTIKPLMAQQDIPGMAVAVSVKGKP
YYFNYGFADIQAKQPVTENTLFELGSVSKTFTGVLGAVSVAKKEMALNDPAAKYQP
ELALPQWKGITLLDLATYTAGGLPLQVPDAVKSRADLLNFYQQWQPSRKPGDMRLY
ANSSIGLFGALTANAAGMPYEQLLTARILAPLGLSHTFITVPESAQSQYAYGYKNKKP
VRVSPGQLDAESYGVKSTSKDMLRWAEMNMEPSRAGNADLEMAMYLAQTRYYKT
AAINQGLGWEMYDWPQQKDMIINGVTNEVALQPHPVTDNQVQPYNRASWVHKTG
ATTGFGAYVAFIPEKQVAIVILANKNYPNTERVKAAQAILSALE

SEQ ID No. 926:
MKKSLSATLISALLAFSAPGFSAADNVAAVVDSTIKPLMAQQDIPGMAVAVSVKGRP
YYFNYGFADVQAKQPVTENTLFELGSVSKTFTGVLGAVSVAKKEMALNDPAAKYQP
ELALPQWKGITLLDLATYTAGGLPLQVPDAVKSRADLLHFYQQWQPSRKPGDMRLY
ANSSIGLFGALTANAAGMPYEQLLTARILAPLGLSHTFITVPESAQSQYAYGYKNKKP
VRVSPGQLDAESYGVKSASKDMLRWAEMNMEPSRAGNADLEMAMYLAQTRYYKT
AAINQGLGWEMYDWPQQKDMIINGVTNEVALQPHPVTDNQVQPYNRASWVHKTG
ATTGFGAYVAFIPEKQVAIVILANKNYPNTERVKAAQAILSALE

SEQ ID No. 927:
MKKSLSATLISALLAFSAPGFSAADNVAAVVDSTIKPLMAQQDIPGMAVAVSVKGKP
YYFNYGFADIQAKQPVTENTLFELGSVSKTFTGVLGAVSVAKKEMALNDPAAKYQP
ELALPQWKGITLLDLATYTAGGLPLQVPDAVKSRADLLNFYQQWQPSRKPGDMRLY
ANSSIGLFGALTANAAGMPYEQLLTARILAPLGLSHTFITVPESAQSQYAYGYKNKKP
VRVSPGQLDAESYGVKSASKDMLRWAEMNMEPSRAGNADLEMAMYLAQTRYYKT
AAINQGLGWEMYDWPQQKDMIINGVTNEVALQPHPVTDNQVQPYNRASWVHKTG
ATTGFGAYVAFIPEKQVAIVILANKNYPNTERVKAAQAILSALE said peptides being chosen, preferably, from the peptides of sequence SEQ ID No. 928 to SEQ ID No. 948 as defined hereafter:

| Peptide SEQ ID No. | Amino acid sequence | Position of the peptide in the DHA protein(s) |
|---|---|---|
| SEQ ID No. 928 | ADLLHFYQQWQPSR | 148-161 for the protein of SEQ No. 926 |
| SEQ ID No. 929 | ADLLNFYQQWQPSR | 148-161 for the proteins of SEQ No. 923, 924, 925, 927 |
| SEQ ID No. 930 | AELLHFYQQWQPSR | 148-161 for the protein of SEQ No. 922 |
| SEQ ID No. 931 | AGNADLEMAMYLAQTR | 262-277 for the proteins of SEQ No. 922, 923, 924, 925, 926, 927 |
| SEQ ID No. 932 | EMALNDPAAK | 101-110 for the proteins of SEQ No. 923, 924, 925, 926, 927 |
| SEQ ID No. 933 | EMMLNDPAEK | 101-110 for the protein of SEQ No. 922 |
| SEQ ID No. 934 | GKPYYFNYGFADIQAK | 55-70 for the proteins of SEQ No. 923, 924, 925, 927 |
| SEQ ID No. 935 | GKPYYFNYGFADVQAK | 55-70 for the protein of SEQ No. 922 |
| SEQ ID No. 936 | KPGDMR | 162-167 for the proteins of SEQ No. 922, 923, 924, 925, 926 |
| SEQ ID No. 937 | NYPNTER | 361-367 for the proteins of SEQ No. 922, 923, 924, 925, 926, 927 |
| SEQ ID No. 938 | QPVTENTLFELGSVSK | 71-86 for the proteins of SEQ No. 922, 923, 924, 925, 926, 927 |
| SEQ ID No. 939 | QVAIVILANK | 351-360 for the proteins of SEQ No. 922, 923, 924, 925, 926, 927 |
| SEQ ID No. 940 | TAAINQGLGWEMYDWPQQK | 281-299 for the proteins of SEQ No. 922, 923, 924, 925, 926, 927 |
| SEQ ID No. 941 | TFTGVLGAVSVAK | 87-99 for the proteins of SEQ No. 922, 923, 924, 925, 926, 927 |
| SEQ ID No. 942 | TGATTGFGAYVAFIPEK | 334-350 for the proteins of SEQ No. 922, 923, 925, 926, 927 |
| SEQ ID No. 943 | TGATTGSGAYVAFIPEK | 334-350 for the protein of SEQ No. 924 |
| SEQ ID No. 944 | VSPGQLDAESYGVK | 230-243 for the proteins of SEQ No. 922, 923, 924, 925, 926, 927 |
| SEQ ID No. 945 | WAEMNIEPSR | 252-261 for the protein of SEQ No. 923 |
| SEQ ID No. 946 | WAEMNMEPSR | 252-261 for the proteins of SEQ No. 922, 924, 925, 926, 927 |
| SEQ ID No. 947 | YQPELALPQWK | 111-121 for the proteins of SEQ No. 922, 923, 924, 925, 926, 927 |
| SEQ ID No. 948 | ASWVHK | 328-333 for the proteins of SEQ No. 922, 923, 924, 925, 926, 927 |

The detection of a mechanism of resistance to cephalosporins induced by the expression of the MIR protein is characterised by the detection of at least one peptide belonging to the MIR protein and to its different sequence variants SEQ ID No. 949 to SEQ ID No. 953.

SEQ ID No. 949:
MMTKSLSCALLLSVASSAFAAPMSEKQLAEVVERTVTPLMNAQAIPGMA
VAVIYQGQPHYFTFGKADVAANKPVTPQTLFELGSISKTFTGVLGGDAI

-continued

```
ARGEIALGDPVAKYWPELTGKQWQGIRMLDLATYTAGGLPLQVPDEVTD
TASLLRFYQNWQPQWKPGTTRLYANASIGLFGALAVKPSGMSYEQAMTT
RVFKPLKLDHTWINVPKAEEAHFAWGYREGKAVHVSPGMLDAEAYGVKT
NVKDMASWLIANMKPDSLQAPSLKQGIALAQSRYWRVGAMYQGLGWEML
NWPVDAKTVVGGSDNKVALAPLPVAEVNPPAPPVKASWVHKTGSTGGFG
SYVAFIPEKQLGIVMLANKSYPNPARVEAAYRILDALQ

SEQ ID No. 950:
MMTKSLSCALLLSVASAAFAAPMSETQLAEVVERTVTPLMNAQAIPGMAG
VAVIYQQPHYFTFGKADVAANKPVTPQTLFELGSISKTFTGVLGGDAIA
RGEIALGDPVAKYWPELTGKQWQGIRMLDLATYTAGGLPLQVPDEVTDT
ASLLRFYQNWQPQWKPGTTRLYANASIGLFGALAVKPSGMSYEQAMTTR
VFKPLKLDHTWINVPKAEEAHYAWGYREGKAVHVSPGMLDAEAYGVKTN
VKDMASWVIANMKPDSLQAPSLKQGIALAQSRYWRVGAMYQGLGWEMLN
WPVDAKTVVGGSDNKVALAPLPVAEVNPPAPPVKASWVHKTGSTGGFGS
YVAFIPEKQLGIVMLANKSYPNPARVEAAYHILDALQ

SEQ ID No. 951:
MMTKSLSCALLLSVASAAFAAPMSEKQLAEVVERTVTPLMNAQAIPGMA
VAVIYQGQPHYFTFGKADVAANKPVTPQTLFELGSISKTFTGVLGGDAI
ARGEIALGDPVAKYWPELTGKQWQGIRMLDLATYTAGGLPLQVPDEVTD
TASLLRFYQNWQPQWKPGTTRLYANASIGLFGALAVKPSGMSYEQAMT
TRVFKPLKLDHTWINVPKAEEAHYAWGYREGKAVHVSPGMLDAEAYGVK
TNVKDMASWLIANMKPDSLHAPSLKQGIALAQSRYWRVGAMYQGLGWEM
LNWPVDAKTVVGGSDNKVALAPLPVAEVNPPAPPVKASWVHKTGSTGGF
GSYVAFIPEKQLGIVMLANKSYPNPARVEAAYRILDALQ

SEQ ID No. 952:
MMTKSLSCALLLSVASAAFAAPMFEKQLAEVVERTVTPLMNAQAIPGMA
VAVIYQGQPHYFTFGKADVAANKPVTPQTLFELGSISKTFTGVLGGDAI
ARGEIALGDPVAKYWPELTGKQWQGIRMLDLATYTAGGLPLQVPDEVTD
TASLLRFYQNWQPQWKPGTTRLYANASIGLFGALAVKPSGMSYEQAMTT
RVFKPLKLDHTWINVPKAEEAHYAWGYREGKAVHVSPGMLDAEAYGVKT
NVKDMASWLIANMKPDSLHAPSLKQGIALAQSRYWRVGAMYQGLGWEML
NWPVDAKTVVGGSDNKVALAPLPVAEVNPPAPPVKASWVHKTGSTGGFG
SYVAFIPEKQLGIVMLANKSYPNPARVEAAYRILDALQ

SEQ ID No. 953:
MMTKSLSCALLLSVASSAFAAPMSEKQLAEVVERTVTPLMNAQAIPGMA
VAVIYQGQPHYFTFGKADVAANKPVTPQTLFELGSISKTFTGVLGGDAI
ARGEIALGDPVAKYWPELTGKQWQGIRMLDLATYTAGGLPLQVPDEVTD
TASLLRFYQNWQPQWKPGTTRLYANASIGLFGALAVKPSGMSYEQAMTT
RVFKPLKLDHTWINVPKAEEAHYAWGYREGKAVHVSPGMLDAEAYGVKT
NVKDMASWLIANMKPDSLQAPSLKQGIALAQSRYWRVGAMYQGLGWEML
NWPVDAKTVVGGSDNKVALAPLPVAEVNPPAPPVKASWVHKTGSTGGFG
SYVAFIPEKQLGIVMLANKSYPNPARVEAAYRILDALQ
``` said peptides being chosen, preferably, from the peptides of sequence SEQ ID No. 954 to SEQ ID No. 981 as defined hereafter:

| Peptide SEQ ID No. | Amino acid sequence | Position of the peptide in the MIR protein(s) |
|---|---|---|
| SEQ ID No. 954 | AEEAHFAWGYR | 214-224 for the protein of SEQ No. 949 |
| SEQ ID No. 955 | DMASWLIANMK | 249-259 for the proteins of SEQ No. 949, 951, 952, 953 |
| SEQ ID No. 956 | DMASWLIANMKPDSLHAPSLK | 249-269 for the proteins of SEQ No. 951, 952 |
| SEQ ID No. 957 | DMASWLIANMKPDSLQAPSLK | 249-269 for the proteins of SEQ No. 949, 953 |
| SEQ ID No. 958 | DMASWVIANMK | 249-259 for the protein of SEQ No. 950 |
| SEQ ID No. 959 | DMASWVIANMKPDSLQAPSLK | 249-269 for the protein of SEQ No. 950 |
| SEQ ID No. 960 | GEIALGDPVAK | 101-111 for the proteins of SEQ No. 949, 950, 951, 952, 953 |
| SEQ ID No. 961 | TVVGGSDNK | 302-310 for the proteins of SEQ No. 949, 950, 951, 952, 953 |
| SEQ ID No. 962 | ADVAANK | 66-72 for the proteins of SEQ No. 949, 950, 951, 952, 953 |
| SEQ ID No. 963 | AEEAHYAWGYR | 214-224 for the proteins of SEQ No. 950, 951, 952, 953 |
| SEQ ID No. 964 | AVHVSPGMLDAEAYGVK | 228-244 for the proteins of SEQ No. 949, 950, 951, 952, 953 |
| SEQ ID No. 965 | FYQNWQPQWK | 154-163 for the proteins of SEQ No. 949, 950, 951, 952, 953 |
| SEQ ID No. 966 | FYQNWQPQWKPGTTR | 154-168 for the proteins of SEQ No. 949, 950, 951, 952, 953 |
| SEQ ID No. 967 | LDHTWINVPK | 204-213 for the proteins of SEQ No. 949, 950, 951, 952, 953 |
| SEQ ID No. 968 | LYANASIGLFGALAVK | 169-184 for the proteins of SEQ No. 949, 950, 951, 952, 953 |
| SEQ ID No. 969 | QGIALAQSR | 270-278 for the proteins of SEQ No. 949, 950, 951, 952, 953 |

| Peptide SEQ ID No. | Amino acid sequence | Position of the peptide in the MIR protein(s) |
|---|---|---|
| SEQ ID No. 970 | QLAEWER | 27-34 for the proteins of SEQ No. 949, 950, 951, 952, 953 |
| SEQ ID No. 971 | QLGIVMLANK | 353-362 for the proteins of SEQ No. 949, 950, 951, 952, 953 |
| SEQ ID No. 972 | SYPNPAR | 363-369 for the proteins of SEQ No. 949, 950, 951, 952, 953 |
| SEQ ID No. 973 | TFTGVLGGDAIAR | 88-100 for the proteins of SEQ No. 949, 950, 951, 952, 953 |
| SEQ ID No. 974 | TGSTGGFGSYVAFIPEK | 336-352 for the proteins of SEQ No. 949, 950, 951, 952, 953 |
| SEQ ID No. 975 | VALAPLPVAEVNPPAPPVK | 311-329 for the proteins of SEQ No. 949, 950, 951, 952, 953 |
| SEQ ID No. 976 | VEAAYR | 370-375 for the proteins of SEQ No. 949, 951, 952, 953 |
| SEQ ID No. 977 | VFKPLK | 198-203 for the proteins of SEQ No. 949, 950, 951, 952, 953 |
| SEQ ID No. 978 | VGAMYQGLGWEMLNWPVDAK | 282-301 for the proteins of SEQ No. 949, 950, 951, 952, 953 |
| SEQ ID No. 979 | ASWVHK | 330-335 for the proteins of SEQ No. 949, 950, 951, 952, 953 |
| SEQ ID No. 980 | QWQGIR | 120-125 for the proteins of SEQ No. 949, 950, 951, 952, 953 |
| SEQ ID No. 981 | YWPELTGK | 112-119 for the proteins of SEQ No. 949, 950, 951, 952, 953 |

The detection of a mechanism of resistance to cephalosporins induced by the expression of the MOX protein is characterised by the detection of at least one peptide belonging to the MOX protein and to its different sequence variants SEQ ID No. 982 to SEQ ID No. 988.

SEQ ID No. 982:
MQQRQSILWGAVATLMWAGLAHAGETSPVDPLRPVVDASIQPLLKEHRIPGMAVAV
LKDGKAHYFNYGVADRERAVGVSEQTLFEIGSVSKPLTATLGAYAVVKGAMQLDDK
ASRHAPWLKGSAFDSITMGELATYSAGGLPLQFPEEVDSLEKMQAYYRQWTPAYS
PGSHRQYSNPSIGLFGHLAASSLKQPFAQLMEQTLLPGLGLHHTYVNVPKQAMASY
AYGYSKEDKPIRVSPGMLADEAYGIKTSSADLLRFVKANISGVDDKALQQAISLTHK
GHYSVGGMTQGLGWERYAYPVSEQTLLAGNSAKVILEANPTAAPRESGSQMLFNK
TGSTSGFGAYVAFVPAKGIGIVMLANRNYPIPARVKAAHAILTQLAR

SEQ ID No. 983:
MQQRQSILWGALATLMWAGLAHAGDTSAVDPLRPVVDASIRPLLKEHRIPGMAVAV
LKDGKAHYFNYGVADRERAVGVSEQTLFEIGSVSKPLTATLGAYAVVKGAMQLDDK
ASRHAPWLKGSAFDSITMGELATYSAGGLPLQFPEEVDSLEKMQAYYRQWTPAYS
PGSHRQYSNPSIGLFGHLAASSMKQPFAQLMEQTLLPGLGLHHTYVNVPKQAMAS
YAYGYSKEDKPIRVSPGMLADEAYGIKTSSADLLRFVKANISGVDDKALQQAISLTHK
GHYSVGGMTQGLGWESYAYPVSEQTLLAGNSAEVILEANPTAAPRESGNLMLFNK
TGSTSGFGAYVAFVPAKGIGIVMLANRNYPIPARVKAAHAILTQLAR

SEQ ID No. 984:
MQQRQSILWGALATLMWAGLAHAGDKAATDPLRPVVDASIRPLLKEHRIPGMAVAV
LKDGKAHYFNYGVADRERAVGVSEQTLFEIGSVSKTLTATLGAYAVVQGGFELDDK
ASLFAPWLKGSAFDNITMGELATYSAGGLPLQFPEEVDSLEKMQAYYRQWTPAYS
RGSHRQYANPSIGLFGYLAASSMKQPFDRLMEQTMLPGLGLYHTYLNVPEQPMGH
YAYGYWKEDKPFRVTPAMLAEEPYGIKTSSADLLRFVKANISGVDNAAMQQAIDLTH
QGQYAVGEMTQGLGWERYPYPVSEQTLLAGNSPAMIYNANPAAPAPAAAGHPVLF
KKTGSTNGFGAYVAFVPAKGIGVVMLANRNYPNEGTLKAGHAILTQLAR

-continued

SEQ ID No. 985:
MQQRQSILWGVLPTLMWAGLAHAGDRAATDPLRPVVDASIRPLLKEHRIPGMAVAV
LKDGKAHYFNYGVADRERAVGVSEQTLFEIGSVSKTLTATLGAYAVVQGSFELDDK
ASLFAPWLKGSVFDNITMGELATYSAGGLPLQFPEEVDSLEKMQAYYRQWTPAYS
PGSHRQYANPSIGLFGYLAASSMKQPFDRLMEQTILPGLGLYHTYLNVPEQAMGHY
AYGYSKEDKPIRVTPGMLADEAYGIKTSSADLLRFVKANISGVDNAAMQQAIDLTHQ
GQYAVGEMTQGLGWERYAYPVSEQTLLAGNSAAMIYNANPAAPAPAARGHPVLFN
KTGSTNGFGAYVAFVPAKGIGIVMLANRNSPIEGTLKAGHAILTQLAR

SEQ ID No. 986:
MQQRQSILWGALATLMWAGLVHAGDKAATDPLRPVVDASIRPLLKEHRIPGMAVAV
LKDGKAHYFNYGVADRERAVGVSEQTLFEIGSVSKTLTATLGAYAVVQGSFELDDK
ASLFAPWLKGSVFDNITMGELATYSAGGLPLQFPEEVDSLEKMQAYYRQWTPAYS
PGSHRQYANPSIGLFGYLAASSMKQPFDRLMEQTMLPGLGLYHTYLTVPEQAMGH
YAYGYSKEDKPIRVTPGMLADEAYGIKTSSADLLRFVKANIGGVDNAAMQQAIDLTH
QGQYAVGEMTQGLGWERYAYPVSEQTLLAGNSPAMIYNAIPAVPAPAAAGHPVLF
NKTGSTNGFGAYVAFVPAKGIGIVMLANRNSPIEARIKAAHAILTQLAR

SEQ ID No. 987:
MQQRQSILWGAVATLMWAGLAHAGEASPVDPLRPVVDASIQPLLKEHRIPGMAVAV
LKDGKAHYFNYGVANRESGASVSEQTLFEIGSVSKTLTATLGAYAVVKGAMQLDDK
ASRHAPWLKGSVFDSITMGELATYSAGGLPLQFPEEVDSSEKMRAYYRQWAPVYS
PGSHRQYSNPSIGLFGHLAASSLKQPFAQLMEQTLLPGLGMHHTYVNVPKQAMAS
YAYGYSKEDKPIRVNPGMLADEAYGIKTSSADLLAFVKANIGGVDDKALQQAISLTH
KGHYSVGGMTQGLGWESYAYPVTEQTLLAGNSAKVILEANPTAAPRESGSQVLFN
KTGSSNGFGAYVAFVPARGIGIVMLANRNYPIPARVKAAHAILAQLAG

SEQ ID No. 988:
MQQRQSILWGALATLMWAGLAHAGETSPVDPLRPVVDASIRPLLKEHRIPGMAVAV
LKDGKAHYFNYGVADRERAVGVSEQTLFEIGSVSKPLTATLGAYAVVKGAMQLDDK
ASRHAPWLKGSAFDSITMGELATYSAGGLPLQFPEEVDSLEKMQAYYRQWTPAYS
PGSHRQYSNPSIGLFGHLAASSMKQPFAQLMEQTLLPGLGLHHTYVNVPKQAMAS
YAYGYSKEDKPIRVSPGMLADEAYGIKTSSADLLRFVKANISGVHDKALQQAISLTHK
GHYSVGGMTQGLGWESYAYPVSEQTLLAGNSAKVILEANPTAAPRESGSQMLFNK
TGSTSGFGAYVAFVPAKGIGIVMLANRNYPIPARVKAAHAILTQLAR said peptides being chosen, preferably, from the peptides of sequence SEQ ID No. 989 to SEQ ID No. 1037 as defined hereafter:

| Peptide SEQ ID No. | Amino acid sequence | Position of the peptide in the MOX protein(s) |
|---|---|---|
| SEQ ID No. 989 | AATDPLR | 27-33 for the proteins of SEQ No. 984, 985, 986 |
| SEQ ID No. 990 | AHYFNYGVADR | 62-72 for the proteins of SEQ No. 982, 983, 984, 985, 986, 988 |
| SEQ ID No. 991 | ANISGVDDK | 261-269 for the proteins of SEQ No. 982, 983 |
| SEQ ID No. 992 | ANISGVHDK | 261-269 for the protein of SEQ No. 988 |
| SEQ ID No. 993 | ASLFAPWLK | 113-121 for the proteins of SEQ No. 984, 985, 986 |
| SEQ ID No. 994 | AVGVSEQTLFEIGSVSK | 75-91 for the proteins of SEQ No. 982, 983, 984, 985, 986, 988 |
| SEQ ID No. 995 | EDKPFR | 230-235 for the protein of SEQ No. 984 |
| SEQ ID No. 996 | ESGNLMLFNK | 326-335 for the protein of SEQ No. 983 |
| SEQ ID No. 997 | ESGSQMLFNK | 326-335 for the proteins of SEQ No. 982, 988 |
| SEQ ID No. 998 | GHPVLFNK | 329-336 for the proteins of SEQ No. 985, 986 |
| SEQ ID No. 999 | GHYSVGGMTQGLGWER | 281-296 for the protein of SEQ No. 982 |

-continued

| Peptide SEQ ID No. | Amino acid sequence | Position of the peptide in the MOX protein(s) |
|---|---|---|
| SEQ ID No. 1000 | GIGVVMLANR | 354-363 for the protein of SEQ No. 984 |
| SEQ ID No. 1001 | MQAYYR | 155-160 for the proteins of SEQ No. 982, 983, 984, 985, 986, 988 |
| SEQ ID No. 1002 | NSPIEAR | 364-370 for the protein of SEQ No. 986 |
| SEQ ID No. 1003 | NSPIEGTLK | 364-372 for the protein of SEQ No. 985 |
| SEQ ID No. 1004 | NYPNEGTLK | 364-372 for the protein of SEQ No. 984 |
| SEQ ID No. 1005 | QPFDR | 192-196 for the proteins of SEQ No. 984, 985, 986 |
| SEQ ID No. 1006 | QWTPAYSPGSHR | 161-172 for the proteins of SEQ No. 982, 983, 985, 986, 988 |
| SEQ ID No. 1007 | QWTPAYSR | 161-168 for the protein of SEQ No. 984 |
| SEQ ID No. 1008 | QYANPSIGLFGYLAASSMK | 173-191 for the proteins of SEQ No. 984, 985, 986 |
| SEQ ID No. 1009 | QYSNPSIGLFGHLAASSMK | 173-191 for the proteins of SEQ No. 983, 988 |
| SEQ ID No. 1010 | TGSSNGFGAYVAFVPAR | 336-352 for the protein of SEQ No. 987 |
| SEQ ID No. 1011 | TGSTNGFGAYVAFVPAK | 337-353 for the proteins of SEQ No. 984, 985, 986 |
| SEQ ID No. 1012 | TGSTSGFGAYVAFVPAK | 336-352 for the proteins of SEQ No. 982, 983, 988 |
| SEQ ID No. 1013 | TLTATLGAYAVVQGGFELDDK | 92-112 for the protein of SEQ No. 984 |
| SEQ ID No. 1014 | TLTATLGAYAVVQGSFELDDK | 92-112 for the proteins of SEQ No. 985, 986 |
| SEQ ID No. 1015 | VSPGMLADEAYGIK | 236-249 for the proteins of SEQ No. 982, 983, 988 |
| SEQ ID No. 1016 | VTPAMLAEEPYGIK | 236-249 for the protein of SEQ No. 984 |
| SEQ ID No. 1017 | VTPGMLADEAYGIK | 236-249 for the proteins of SEQ No. 985, 986 |
| SEQ ID No. 1018 | YAYPVSEQTLLAGNSAK | 297-313 for the proteins of SEQ No. 982, 988 |

| Peptide SEQ ID No. | Amino acid sequence | Position of the peptide in the MOX protein(s) |
|---|---|---|
| SEQ ID No. 1019 | ALQQAISLTHK | 270-280 for the proteins of SEQ No. 982, 983, 987, 988 |
| SEQ ID No. 1020 | ANIGGVDDK | 261-269 for the protein of SEQ No. 987 |
| SEQ ID No. 1021 | EDKPIR | 230-235 for the proteins of SEQ No. 982, 983, 985, 986, 987, 988 |
| SEQ ID No. 1022 | ESGASVSEQTLFEIGSVSK | 73-91 for the protein of SEQ No. 987 |
| SEQ ID No. 1023 | ESGSQVLFNK | 326-335 for the protein of SEQ No. 987 |
| SEQ ID No. 1024 | GAMQLDDK | 105-112 for the proteins of SEQ No. 982, 983, 987, 988 |
| SEQ ID No. 1025 | GIGIVMLANR | 353-362 for the proteins of SEQ No. 982, 983, 987, 988; 354-363 for the proteins of sequence SEQ ID No. 985, 986 |
| SEQ ID No. 1026 | HAPWLK | 116-121 for the proteins of SEQ No. 982, 983, 987, 988 |
| SEQ ID No. 1027 | NYPIPAR | 363-369 for the proteins of SEQ No. 982, 983, 987, 988 |
| SEQ ID No. 1028 | QAMASYAYGYSK | 218-229 for the proteins of SEQ No. 982, 983, 987, 988 |
| SEQ ID No. 1029 | QWAPVYSPGSHR | 161-172 for the protein of SEQ No. 987 |
| SEQ ID No. 1030 | QYSNPSIGLFGHLAASSLK | 173-191 for the proteins of SEQ No. 982, 987 |
| SEQ ID No. 1031 | TLTATLGAYAVVK | 92-104 for the protein of SEQ No. 987 |
| SEQ ID No. 1032 | TSSADLLAFVK | 250-260 for the protein of SEQ No. 987 |
| SEQ ID No. 1033 | TSSADLLR | 250-257 for the proteins of SEQ No. 982, 983, 984, 985, 986, 988 |
| SEQ ID No. 1034 | VILEANPTAAPR | 314-325 for the proteins of SEQ No. 982, 983, 987, 988 |
| SEQ ID No. 1035 | VNPGMLADEAYGIK | 236-249 for the protein of SEQ No. 987 |
| SEQ ID No. 1036 | AHYFNYGVANR | 62-72 for the protein of SEQ No. 987 |

| Peptide SEQ ID No. | Amino acid sequence | Position of the peptide in the MOX protein(s) |
|---|---|---|
| SEQ ID No. 1037 | IPGMAVAVLK | 49-58 for the proteins of SEQ No. 982, 983, 984, 985, 986, 987, 988 |

The detection of a mechanism of resistance to cephalosporins induced by the expression of the PER protein is characterised by the detection of at least one peptide belonging to the PER protein and to its different sequence variants SEQ ID No. 1038 to SEQ ID No. 1044.

SEQ ID No. 1038:
MNVIIKAVVTASTLLMVSFSSFETSAQSPLLKEQIESIVIGKKATVGVAVWGPDDLEPL
LINPFEKFPMQSVFKLHLAMLVLHQVDQGKLDLNQTVIVNRAKVLQNTWAPIMKAYQ
GDEFSVPVQQLLQYSVSLSDNVACDLLFELVGGPAALHDYIQSMGIKETAVVANEA
QMHADDQVQYQNWTSMKGAAEILKKFEQKTQLSETSQALLWKWMVETTTGPERL
KGLLPAGTVVAHKTGTSGIKAGKTAATNDLGIILLPDGRPLLVAVFVKDSAESSRTNE
AIIAQVAQTAYQFELKKLSALSPN

SEQ ID No. 1039:
MNVIIKAVVTASTLLMVSFSSFETSAQSPLLKEQIESIVIGKKATVGVAVWGPDDLEPL
LINPFEKFPMQSVFKLHLAMLVLHQVDQGKLDLNQTVIVNRAKVLQNTWAPIMKAYQ
GDEFSVPVQQLLQYSVSHTDNVACDLLFELVGGPAALHDYIQSMGIKETAVVANEA
QMHADDQVQYQNWTSMKGAAEILKKFEQKTQLSETSQALLWKWMVETTTGPERL
KGLLPAGTVVAHKTGTSGIKAGKTAATNDLGIILLPDGRPLLVAVFVKDSAESSRTNE
AIIAQVAQTAYQFELKKLSALSPN

SEQ ID No. 1040:
MNVIIKAVVTASTLLMVSFSSFETSAQSPLLKGQIESIVIGKKATVGVAVWGPDDLEP
LLINPFEKFPMQSVFKLHLAMLVLHQVDQGKLDLNQTVIVNRAKVLQNTWAPIMKAY
QGDEFSVPVQQLLQYSVSHSDNVACDLLFELVGGPAALHDYIQSMGIKETAVVANE
AQMHADDQVQYQNWTSMKGAAEILKKFEQKTQLSETSQALLWKWMVETTTGPER
LKGLLPAGTVVAHKTGTSGIKAGKTAATNDLGIILLPDGRPLLVAVFVKDSAESSRTN
EAIIAQVAQTAYQFELKKLSALSPN

SEQ ID No. 1041:
MNVIAKGVFTTTALLMLSLSSWVVSAQSPLLKEQIETIVTGKKATVGVAVWGPDDLE
PLLVNPFEKFPMQSVFKMHLAMLVLHQVDQGKLDLNKTVAVNRAAVLQNTWSPMM
KDHQGDEFTVTVQQLLQYSVSHSDNVACDLLFELVGGPAALHAYIQSLGIKETEVVA
NEAQMHADDQVQYKNWTSMKAAAQLLRKFEQKKQLSETSQALLWKWMVETTTGP
QRLKGLLPAGTVVAHKTGTSGVRAGKTAATNDIGVIMLPDGRPLLVAVFVKDSAESA
RTNEAIIAQVAQAAYQFELKKLSAVSPD

SEQ ID No. 1042:
MNVIIKAVVTASTLLMVSFSSFETSAQSPLLKEQIESIVIGKKATVGVAVWGPDDLEPL
LINPFEKFPMQSVFKLHLAMLVLHQVDQGKLDLNQTVIVNRAKVLQNTWAPIMKAYQ
GDQFSVPVQQLLQYSVSHSDNVACDLLFELVGGPAALHDYIQSMGIKETAVVANEA
QMHADDQVQYQNWTSMKGAAEILKKFEQKTQLSETSQALLWKWMVETTTGPERL
KGLLPAGTVVAHKTGTSGVRAGKTAATNDLGIILLPDGRPLLVAVFVKDSAESSRTN
EAIIAQVAQAAYQFELKKLSALSPN

SEQ ID No. 1043:
MNVITKCVFTASALLMLGLSSFVVSAQSPLLKEQIETIVTGKKATVGVAVWGPDDLE
PLLLNPFEKFPMQSVFKLHLAMLVLHQVDQGKLDLNQSVTVNRAAVLQNTWSPMM
KDHQGDEFTVAVQQLLQYSVSHSDNVACDLLFELVGGPQALHAYIQSLGVKEAAVV
ANEAQMHADDQVQYQNWTSMKAAAQVLQKFEQKKQLSETSQALLWKWMVETTT
GPQRLKGLLPAGTIVAHKTGTSGVRAGKTAATNDAGVIMLPDGRPLLVAVFVKDSA
ESERTNEAIIAQVAQAAYQFELKKLSAVSPD

SEQ ID No. 1044:
MNVIIKAVVTASTLLMVSFSSFETSAQSPLLKEQIESIVIGKKATVGVAVWGPDDLEPL
LINPFEKFPMQSVFKLHLAMLVLHQVDQGKLDLNQTVIVNRAKVLQNTWAPIMKAYQ
GDEFSVPVQQLLQYSVSHSDNVACDLLFELVGGPAALHDYIQSMGIKETAVVANEA

-continued

```
QMHADDQVQYQNWTSMKGAAEILKKFEQKTQLSETSQALLWKWMVETTTGPERL
KGLLPAGTVVAHKTGTSGIKAGKTAATNDLGIILLPDGRPLLVAVFVKDSAESSRTNE
AIIAQVAQTAYQFELKKLSALSPN
```

5. said peptides being chosen, preferably, from the peptides of sequence SEQ ID No. 1045 to SEQ ID No. 1077 as defined hereafter:

| Peptide SEQ ID No. | Amino acid sequence | Position of the peptide in the PER protein(s) |
|---|---|---|
| SEQ ID No. 1045 | AAAQLLR | 190-196 for the proteins of SEQ No. 1041 |
| SEQ ID No. 1046 | AAAQVLQK | 190-197 for the proteins of SEQ No. 1043 |
| SEQ ID No. 1047 | AAVLQNTWSPMMK | 101-113 for the proteins of SEQ No. 1041, 1043 |
| SEQ ID No. 1048 | DSAESAR | 275-281 for the proteins of SEQ No. 1041 |
| SEQ ID No. 1049 | DSAESER | 275-281 for the proteins of SEQ No. 1043 |
| SEQ ID No. 1050 | DSAESAR | 275-281 for the proteins of SEQ No. 1038, 1039, 1040, 1042, 1044 |
| SEQ ID No. 1051 | EQIESIVIGK | 33-42 for the proteins of SEQ No. 1038, 1039, 1042, 1044 |
| SEQ ID No. 1052 | EQIETIVTGK | 33-42 for the proteins of SEQ No. 1041, 1043 |
| SEQ ID No. 1053 | ETEVVANEAQMHADDQVQYK | 164-183 for the proteins of SEQ No. 1041 |
| SEQ ID No. 1054 | FPMQSVFK | 67-74 for the proteins of SEQ No. 1038, 1039, 1040, 1041, 1042, 1043, 1044 |
| SEQ ID No. 1055 | GAAEILK | 190-196 for the proteins of SEQ No. 1038, 1039, 1040, 1042, 1044 |
| SEQ ID No. 1056 | GLLPAGTIVAHK | 228-239 for the proteins of SEQ No. 1043 |
| SEQ ID No. 1057 | GLLPAGTVVAHK | 228-239 for the proteins of SEQ No. 1038, 1039, 1040, 1041, 1042, 1044 |
| SEQ ID No. 1058 | GQIESIVIGK | 33-42 for the proteins of SEQ No. 1040 |
| SEQ ID No. 1059 | LDLNK | 90-94 for the proteins of SEQ No. 1041 |
| SEQ ID No. 1060 | LDLNQSVTVNR | 90-100 for the proteins of SEQ No. 1043 |

| Peptide SEQ ID No. | Amino acid sequence | Position of the peptide in the PER protein(s) |
|---|---|---|
| SEQ ID No. 1061 | LDLNQTVIVNR | 90-100 for the proteins of SEQ No. 1038, 1039, 1040, 1042, 1044 |
| SEQ ID No. 1062 | LHLAMLVLHQVDQGK | 75-89 for the proteins of SEQ No. 1038, 1039, 1040, 1042, 1043, 1044 |
| SEQ ID No. 1063 | MHLAMLVLHQVDQGK | 75-89 for the proteins of SEQ No. 1041 |
| SEQ ID No. 1064 | NWTSMK | 184-189 for the proteins of SEQ No. 1038, 1039, 1040, 1041, 1042, 1043, 1044 |
| SEQ ID No. 1065 | QLSETSQALLWK | 203-214 for the proteins of SEQ No. 1038, 1039, 1040, 1041, 1042, 1043, 1044 |
| SEQ ID No. 1066 | TAATNDAGVIMLPDGR | 250-265 for the proteins of SEQ No. 1043 |
| SEQ ID No. 1067 | TAATNDIGVIMLPDGR | 250-265 for the proteins of SEQ No. 1041 |
| SEQ ID No. 1068 | TAATNDLGIILLPDGR | 250-265 for the proteins of SEQ No. 1038, 1039, 1040, 1042, 1044 |
| SEQ ID No. 1069 | TGTSGIK | 240-246 for the proteins of SEQ No. 1038, 1039, 1040, 1044 |
| SEQ ID No. 1070 | TGTSGVR | 240-246 for the proteins of SEQ No. 1041, 1042, 1043 |
| SEQ ID No. 1071 | TNEAIIAQVAQAAYQFELK | 282-300 for the proteins of SEQ No. 1041, 1042, 1043 |
| SEQ ID No. 1072 | TNEAIIAQVAQTAYQFELK | 282-300 for the proteins of SEQ No. 1038, 1039, 1040, 1044 |
| SEQ ID No. 1073 | TQLSETSQALLWK | 202-214 for the proteins of SEQ No. 1038, 1039, 1040, 1042, 1044 |
| SEQ ID No. 1074 | TVAVNR | 95-100 for the proteins of SEQ No. 1041 |
| SEQ ID No. 1075 | VLQNTWAPIMK | 103-113 for the proteins of SEQ No. 1038, 1039, 1040, 1042, 1044 |
| SEQ ID No. 1076 | WMVETTTGPER | 215-225 for the proteins of SEQ No. 1038, 1039, 1040, 1042, 1044 |
| SEQ ID No. 1077 | WMVETTTGPQR | 215-225 for the proteins of SEQ No. 1041, 1043 |

The detection of a mechanism of resistance to cephalosporins induced by the expression of the PER protein indicates an ESBL resistance. It is preferably detected with the aid of SEQ ID No. 1045 to SEQ ID No. 1065 and SEQ ID No. 1069 to SEQ ID No. 1077.

The detection of a mechanism of resistance to cephalosporins induced by the expression of the VEB protein is characterised by the detection of at least one peptide belonging to the VEB protein and to its different sequence variants SEQ ID No. 1078 to SEQ ID No. 1084.

SEQ ID No. 1078:
MKIVKRILLVLLSLFFTIVYSNAQTDNLTLKIENVLKAKNARIGVAIFNSNEKDTLKINND
FHFPMQSVMKFPIALAVLSEIDKGNLSFEQKIEITPQDLLPKTWSPIKEEFPNGTTLTI
EQILNYTVSESDNIGCDILLKLIGGTDSVQKFLNANHFTDISIKANEEQMHKDWNTQY
QNWATPTAMNKLLIDTYNNKNQLLSKKSYDFIWKIMRETTTGSNRLKGQLPKNTIVA
HKTGTSGINNGIAAATNDVGVITLPNGQLIFISVFVAESKETSEINEKIISDIAKITWNYY
LNK

SEQ ID No. 1079:
MKIVKRILLVLLSLFFTIVYSNAQADNLTLKIENVLKAKNARIGVAIFNSNEKDTLKINND
FHFPMQSVMKFPIALAVLSEIDKGNLSFEQKIEITPQDLLPKTWSPIKEEFPNGTTLTI
EQILNYTVSESDNIGCDILLKLIGGTDSVQKFLNANHFTDISIKANEEQMHKDWNTQY
QNWATPTAMNKLLIDTYNNKNQLLSKKSYDFIWKIMRETTTGSNRLKGQLPKNTIVA
HKTGTSGINNGIAAATNDVGVITLPNGQLIFISVFVAESKETSEINEKIISDIAKITWNYY
LNK

SEQ ID No. 1080:
MKIVKRILLVLLSLFFTVVYSNAQTDNLTLKIENVLKAKNARIGVAIFNSNEKDTFKINN
DFHFPMQSVMKFPIALAVLSEIDKGNLSFEQKIEITPQDLLPKTWSPIKEEFPNGTTLT
IEQILNYTVSESDNIGCDILLKLIGGTDSVQKFLNANHFTDISIKANEEQMHKDWNTQY
QNWATPTAMNKLLIDTYNNKNQLLSKKSYDFIWKIMRETTTGSNRLKGQLPKNTIVA
HKTGTSGINNGIAAATNDVGVITLPNGQLIFISVFVAESKETSEINEKIISDIAKITWNYY
LNK

SEQ ID No. 1081:
MKIVKRILLVLLSLFFTIVYSNAQADNLTLKIENVLKAKNARIGVAIFNSNEKDTLKINND
FHFPMQSVMKFPIALAVLSEIDKGNLSFEQKIEITPQDLLPKMWSPIKEEFPNGTTLTI
EQILNYTVSESDNIGCDILLKLIGGTDSVQKFLNANHFTDISIKANEEQMHKDWNTQY
QNWATPTAMNKLLIDTYNNKNQLLSKKSYDFIWKIMRETTTGSNRLKGQLPKNTIVA
HKTGTSGINNGIAAATNDVGVITLPNGQLIFISVFVAESKETSEINEKIISDIAKITWNYY
LNK
SIEQ ID No. 1082:
MKIVKRILLVLLSLFFTVEYSNAQTDNLTLKIENVLKAKNARIGVAIFNSNEKDTLKINN
DFHFPMQSVMKFPIALAVLSEIDKGNLSFEQKIEITPQDLLPKMWSPIKEEFPNGTTL
TIEQILNYTVSESDNIGCDILLKLIGGTDSVQKFLNANHFTDISIKANEEQMHKDWNTQ
YQNWATPTAMNKLLIDTYNNKNQLLSKKSYDFIWKIMRETTTGSNRLKGQLPKNTIV
AHKTGTSGINNGIAAATNDVGVITLPNGQLIFISVFVAESKETSEINEKIISDIAKITWNY
YLNK

SEQ ID No. 1083:
MKIVKRILLVLLSLFFTVVYSNAQADNLTLKIENVLKAKNARIGVAIFNSNEKDTLKINN
DFHFPMQSVMKFPIALAVLSEIDKGNLSFEQKIEITPQDLLPKMWSPIKEEFPNGTTL
TIEQILNYTVSESDNIGCDILLKLIGGTDSVQKFLNANHFTDISIKANEEQMHKDWNTQ
YQNWATPTAMNKLLIDTYNNKNQLLSKKSYDFIWKIMRETTTGSNRLKGQLPKNTIV
AHKTGTSGINNGIAAATNDVGVITLPNGQLIFISVFVAESKETSEINEKIISDIAKITWNY
YLNK

SEQ ID No. 1084:
MKIVKRILLVLLSLFFTVEYSNAQTDNLTLKIENVLKAKNARIGVAIFNSNEKDTLKINN
DFHFPMQSVMKFPIALAVLSEIDKGNLSFEQKIEITPQDLLPKTWSPIKEEFPNGTTLT
IEQILNYTVSESDNIGCDILLKLIGGTDSVQKFLNANHFTDISIKANEEQMHKDWNTQY
QNWATPTAMNKLLIDTYNNKNQLLSKKSYDFIWKIMRETTTGSNRLKGQLPKNTIVA
HKTGTSGINNGITAATNDVGVITLPNGQLIFISVFVAESKETSEINEKIISDIAKITWNYY
LNK said peptides being chosen, preferably, from the peptides of sequence SEQ ID No. 1085 to SEQ ID No. 1104 as defined hereafter:

| Peptide SEQ ID No. | Amino acid sequence | Position of the peptide in the VEB protein(s) |
|---|---|---|
| SEQ ID No. 1085 | ANEEQMHK | 165-172 for the proteins of SEQ No. 1078, 1079, 1080, 1081, 1082, 1083, 1084 |
| SEQ ID No. 1086 | DWNTQYQNWATPTAMNK | 173-189 for the proteins of SEQ No. 1078, 1079, 1080, 1081, 1082, 1083, 1084 |
| SEQ ID No. 1087 | ETSEINEK | 276-283 for the proteins of SEQ No. 1078, 1079, 1080, 1081, 1082, 1083, 1084 |
| SEQ ID No. 1088 | ETTTGSNR | 216-223 for the proteins of SEQ No. 1078, 1079, 1080, 1081, 1082, 1083, 1084 |

-continued

| Peptide SEQ ID No. | Amino acid sequence | Position of the peptide in the VEB protein(s) |
|---|---|---|
| SEQ ID No. 1089 | FLNANHFTDISIK | 152-164 for the proteins of SEQ No. 1078, 1079, 1080, 1081, 1082, 1083, 1084 |
| SEQ ID No. 1090 | FPIALAVLSEIDK | 72-84 for the proteins of SEQ No. 1078, 1079, 1080, 1081, 1082, 1083, 1084 |
| SEQ ID No. 1091 | GNLSFEQK | 85-92 for the proteins of SEQ No. 1078, 1079, 1080, 1081, 1082, 1083, 1084 |
| SEQ ID No. 1092 | GQLPK | 226-230 for the proteins of SEQ No. 1078, 1079, 1080, 1081, 1082, 1083, 1084 |
| SEQ ID No. 1093 | IEITPQDLLPK | 93-103 for the proteins of SEQ No. 1078, 1079, 1080, 1081, 1082, 1083, 1084 |
| SEQ ID No. 1094 | IENVLK | 32-37 for the proteins of SEQ No. 1078, 1079, 1080, 1081, 1082, 1083, 1084 |
| SEQ ID No. 1095 | IGVAIFNSNEK | 43-53 for the proteins of SEQ No. 1078, 1079, 1080, 1081, 1082, 1083, 1084 |
| SEQ ID No. 1096 | IISDIAK | 284-290 for the proteins of SEQ No. 1078, 1079, 1080, 1081, 1082, 1083, 1084 |
| SEQ ID No. 1097 | INNDFHFPMQSVMK | 58-71 for the proteins of SEQ No. 1078, 1079, 1080, 1081, 1082, 1083, 1084 |
| SEQ ID No. 1098 | LIGGTDSVQK | 142-151 for the proteins of SEQ No. 1078, 1079, 1080, 1081, 1082, 1083, 1084 |
| SEQ ID No. 1099 | LLIDTYNNK | 190-198 for the proteins of SEQ No. 1078, 1079, 1080, 1081, 1082, 1083, 1084 |
| SEQ ID No. 1100 | MWSPIK | 104-109 for the proteins of SEQ No. 1081, 1082, 1083 |
| SEQ ID No. 1101 | NQLLSK | 199-204 for the proteins of SEQ No. 1078, 1079, 1080, 1081, 1082, 1083, 1084 |
| SEQ ID No. 1102 | NTIVAHK | 231-237 for the proteins of SEQ No. 1078, 1079, 1080, 1081, 1082, 1083, 1084 |
| SEQ ID No. 1103 | SYDFIWK | 206-212 for the proteins of SEQ No. 1078, 1079, 1080, 1081, 1082, 1083, 1084 |
| SEQ ID No. 1104 | TWSPIK | 104-109 for the proteins of SEQ No. 1078, 1079, 1080, 1084 |

The detection of a mechanism of resistance to cephalosporins induced by the expression of the VEB protein indicates an ESBL resistance.

The detection of a mechanism of resistance to cephalosporins or to carbapenems induced by the expression of the OXA protein is characterised by the detection of at least one peptide belonging to the OXA protein and to its different sequence variants SEQ ID No. 1105 to SEQ ID No. 1266:

SEQ. ID. No. 1105:
MSRLLLSGLLATGLLCAVPASAASGCFLYADGNGQTLSSEGDCSSQLPPASTFKIPL
ALMGYDSGFLVNEEHPALPYKPSYDGWLPAWRETTTPRRWETYSVVWFSQQITE
WLGMERFQQYVDRFDYGNRDLSGNPGKHDGLTQAWLSSSLAISPEEQARFLGKM
VSGKLPVSAQTLQYTANILKVSEVEGWQIHGKTGMGYPKKLDGSLNRDQQIGWFV
GWASKPGKQLIFVHTVVQKPGKQFASIKAKEEVLAALPAQLKKL

SEQ ID No. 1106:
IACLSSTALAGSITENTSWNKEFSAEAVNGVFVLCKSSSKSCATNDLARASKEYLPA
STFKIPNAIIGLETGVIKNEHQVFKWDGKPRAMKQWERDLTLRGAIQVSAVPVFQQI
AREVGEVRMQKYLKKFSYGNQNISGGIDKFWLEDQLRISAVNQVEFLESLYLNKLSA
SKENQLIVKEALVTEAAPEYLVHSKTGFSGVGTESNPGVAWWVGWVEKETEVYFF
AFNMDIDNESKLPLRKSIPTKIMESEGIIGG

SEQ ID No. 1107:
MKKILLLHMLVFVSATLPISSVASDEVETLKCTIIADAITGNTLYETGECARRVSPCSS
FKLPLAIMGFDSGILQSPKSPTWELKPEYNPSPRDRTYKQVYPALWQSDSVVWFSQ
QLTSRLGVDRFTEYVKKFEYGNQDVSGDSGKHNGLTQSWLMSSLTISPKEQIQFLL
RFVAHKLPVSEAAYDMAYATIPQYQAAEGWAVHGKSGSGWLRDNNGKINESRPQ
GWFVGWAEKNGRQWFARLEIGKEKSDIPGGSKAREDILVELPVLMGNK

SEQ ID No. 1108:
MAIRIFAILFSIFSLATFAHAQEGTLERSDWRKFFSEFQAKGTIVVADERQADRAMLV
FDPVRSKKRYSPASTFKIPHTLFALDAGAVRDEFQIFRWDGVNRGFAGHNQDQDLR
SAMRNSTVWVYELFAKEIGDDKARRYLKKIDYGNAGPSTSNGDYWIEGSLAISAQE
QIAFLRKLYRNELPFRVEHQRLVKDLMIVEAGRNWILRAKTGWEGRMGWWVGWVE
WPTGSVFFALNIDTPNRMDDLFKREAIVRAILRSIEALPPNPAVNSDAAR

SEQ ID No. 1109:
MQRSLSMSGKRHFIFAVSFVISTVCLTFSPANAAQKLSCTLVIDEASGDLLHREGSC
DKAFAPMSTFKLPLAIMGYDADILLDATTPRWDYKPEFNGYKSQQKPTDPTIWLKDS
IVWYSQELTRRLGESRFSDYVQRFDYGNKDVSGDPGKHNGLTHAWLASSLKISPEE
QVRFLRRFLRGELPVSEDALEMTKAWPHFEAGDWDVQGKTGTGSLSDAKGGKAP
IGWFIGWATRDDRRWFARLTVGARKGEQPAGPAARDEFLNTLPALSENF

SEQ ID No. 1110:
MKTFAAYVIIACLSSTALAGSITENTSWNKEFSAEAVNGVFVLCKSSSKSCATNDLAR
ASKEYLPASTFKIPNAIIGLETGVIKNEHQVFKWDGKPRAMKQWERDLTLRGAIQVS
AVPVFQQIAREVGEVRMQKYLKKFSYGNQNISGGIDKFWLEGQLRISAVNQVEFLE
SLYLNKLSASKENQLIVKEALVTEAAPEYLVHSKTGFSGVGTESNPGVAWWVGWVE
KETEVYFFAFNMDIDNESKLPLRKSIPTKIMESEGIIGG

SEQ ID No. 1111:
IACLSSTALAGSITENTSWNKEFSAEAVNGVFVLCKSSSKSCATNDLARASKEYLPA
STFKIPNAIIGLETGVIKNEHQVFKWDGKPRAMKQWERDLTLRGAIQVSAVPVFQQIT
REVGEVRMQKYLKKFSYGNQNISGGIDKFWLEDQLRISAVNQVEFLESLYLNKLSAS
KENQLIVKEALVTEAAPEYLVHSKTGFSGVGTESNPGVAWWVGWVEKETEVYFFA
FNMDIDNESKLPLRKSIPTKIMESEGIIGG

SEQ ID No. 1112:
IACLSSTALAGSITENTSWNKEFSAEAVNGVFVLCKSSSKSCATNDLARASKEYLPA
STFKIPSAIIGLETGVIKNEHQVFKWDGKPRAMKQWERDLTLRGAIQVSAVPVFQQIA
REVGEVRMQKYLKKFSYGNQNISGGIDKFWLEGQLRISAVNQVEFLESLYLNKLSAS
KENQLIVKEALVTEAAPEYLVHSKTGFSGVGTESNPGVAWWVGWVEKETEVYFFA
FNMDIDNESKLPLRKSIPTKIMESEGIIGG

SEQ ID No. 1113:
MIIRFLALLFSAWLVSLGHAQEKTHESSNWGKYFSDFNAKGTIVVVDERTNGNSTS
VYNESRAQQRYSPASTFKIPHTLFALDAGAVRDEFHVFRWDGAKRSFAGHNQDQN
LRSAMRNSTVWVYQLFAKEIGENKARSYLEKLNYGNADPSTKSGDYWIDGNLAISA
NEQISILKKLYRNELPFRVEHQRLVKDLMIVEAKRDWILRAKTGWDGQMGWWVGW
VEWPTGPVFFALNIDTPNRMEDLHKREAIARAILQSVNALPPN

SEQ ID No. 1114:
MAIRIFAILFSTFVFGTFAHAQEGMRERSDWRKFFSEFQAKGTIVVADERQTDRVILV
FDQVRSEKRYSPASTFKIPHTLFALDAGAARDEFQVFRWDGIKRSFAAHNQDQDLR
SAMRNSTVWIYELFAKEIGEDKARRYLKQIDYGNADPSTSNGDYWIDGNLAIAAQEQ
IAFLRKLYHNELPFRVEHQRLVKDLMIVEAGRNWILRAKTGWEGRIGWWVGWVEW
PTGPVFFALNIDTPNRMDDLFKREAIVRAILRSIEALPPNPAVNSDAAR

SEQ ID No. 1115:
MKTFAAYVITACLSSTALASSITENTSWNKEFSAEAVNGVFVLCKSSSKSCATNNLA
RASKEYLPASTFKIPSAIIGLETGVIKNEHQVFKWDGKPRAMKQWERDLSLRGAIQV
SAVPVFQQIAREVGEVRMQKYLKKFSYGNQNISGGIDKFWLEGQLRISAVNQVEFL
ESLFLNKLSASKENQLIVKEALVTEAAPEYLVHSKTGFSGVGTESNPGVAWWVGWV
EKGTEVYFFAFNMDIDNENKLPLRKSIPTKIMASEGIIGG

SEQ ID No. 1116:
MKTFAAYVITACLSSTALASSITENTSWNKEFSAEAVNGVFVLCKSSSKSCATNNLA
RASKEYLPASTFKIPNAIIGLETGVIKNEHQVFKWDGKPRAMKQWERDLSLRGAIQV
SAVPVFQQIAREVGEVRMQKYLKKFSYGNQNISGGIDKFWLEDQLRISAVNQVEFLE
SLFLNKLSASKENQLIVKEALVTEAAPEYLVHSKTGFSGVGTESNPGVAWWVGWVE
KGTEVYFFAFNMDIDNENKLPLRKSIPTKIMASEGIIGG

SEQ ID No. 1117:
MKTFAAYVITACLSSTALASSITENTSWNKEFSAEAVNGVFVLCKSSSKSCATNNLA
RASKEYLPASTFKIPNAIIGLETGVIKNEHQVFKWDGKPRAMKQWERDLSLRGAIQV
SAVPVFQQIAREVGEVRMQKYLKKFSYGNQNISGGIDKFGLEGQLRISAVNQVEFLE
SLFLNKLSASKENQLIVKEALVTEAAPEYLVHSKTGFSGVGTESNPGVAWWVGWVE
KGTEVYFFAFNMDIDNENKLPLRKSIPTKIMASEGIIGG

SEQ ID No. 1118:
MKNTIHINFAIFLIIANIIYSSASASTDISTVASPLFEGTEGCFLLYDASTNAEIAQFNKA
KCATQMAPDSTFKIALSLMAFDAEIIDQKTIFKWDKTPKGMEIWNSNHTPKTWMQFS
VVWVSQEITQKIGLNKIKNYLKDFDYGNQDFSGDKERNNGLTEAWLESSLKISPEEQ
IQFLRKIINHNLPVKNSAIENTIENMYLQDLDNSTKLYGKTGAGFTANRTLQNGWFEG
FIISKSGHKYVFVSALTGNLGSNLTSSIKAKKNAITILNTLNL

SEQ ID No. 1119:
ANIIYSSASASTDISTVASPLFEGTEGCFLLYDVSTNAEIAQFNKAKCATQMAPDSTF
KIALSLMAFDAEIIDQKTIFKWDKTPKGMEIWNSNHTPKTWMQFSWWVSQEITQKI
GLNKIKNYLKDFDYGNQDFSGDKERNNGLTEAWLESSLKISPEEQIQFLRKIINHNLP
VKNSAIENTIENMYLQDLENSTKLYGKTGAGFTANRTLQNGWFEGFIISKSGHKYVF
VSALTGNLGSNLTSSIKAKKNAITIL

SEQ ID No. 1120:
IFSLATFAHAQEGTLERSDWRKFFSEFQAKGTIVVADERQADRAMLVFDPVRSKKR
YSPASTFKIPHTLFALDAGAVRDEFQIFRWDGVNRGFAGHNQDQDLRSAMRNSTV
WVYELFAKEIGDDKARRYLKKIDYGNAYPSTSNGDYWIEGSLAISAQEQIAFLRKLYR
NELPFRVEHQRLVKDLMIVEAGRNWILRAKTGWEGRMGWWVGWVEWPTGSVFFA
LNIDTPNRMDDLFKREAIVRAIL

SEQ ID No. 1121:
MIIRFLALLFSAVVLVSLGHAQDKTHESSNWGKYFSDFNAKGTIVVVDERTNGNSTS
VYNESRAQQRYSPASTFKIPHTLFALDAGAVRDEFHVFRWDGAKRSFAGHNQDQN
LRSAMRNSTVWVYQLFAKEIGENKARSYLEKLNYGNADPSTKSGDYWIDGNLAISA
NEQISILKKLYRNELPFRVEHQRLVKDLMIVEAKRDWILRAKTGWDGMGWWVGW
VEWPTGPVFFALNIDTPNRMEDLHKREAIARAILQSVNALPPN

SEQ ID No. 1122:
MKKFILPIFSISILVSLSACSSIKTKSEDNFHISSQQHEKAIKSYFDEAQTQGVIIIKEGK
NLSTYGNALARANKEYVPASTFKMLNALIGLENHKATTNEIFKWDGKKRTYPMWEK
DMTLGEAMALSAVPVYQELARRTGLELMQKEVKRVNFGNTNIGTQVDNFWLVGPL
KITPVQEVNFADDLAHNRLPFKLETQEEVEKMLLIKEVNGSKIYAKSGWGMGVTPQV
GWLTGWVEQANGKKIPFSLNLEMKEGMSGSIRNEITYKLLENLGII

SEQ ID No. 1123:
MKKFILPIFSISILVSLSACSSIKTKSEDNFHISSQQHEKAIKSYFDEAQTQGVIIIKEGK
NLSTYGNALARANKEYVPASTFKMLNALIGLENHKATTNEIFKWDGKKRTYPMWEK
DMTLGEAMALSAVPVYQELARRTGLELMQKEVKRVNFGNTNIGTQVDNFWLVGPL
KITPVQEVNFADDLAHNRLPFKLETQEEVKKMLLIKEVNGSKIYAKSGWGMGVTPQV
GWLTGWVEQANGKKIPFSLNLEMKEGMTGSIRNEITYKSLENLGII

SEQ ID No. 1124:
MNKYFTCYVVASLFLSGCTVQHNLINETPSQIVQGHNQVIHQYFDEKNTSGVLVIQT
DKKINLYGNALSRANTEYVPASTFKMLNALIGLENQKADINEIFKWKGEKRSFTAWE
KDMTLGEAMKLSAVPVYQELARRIGLDLMQKEVKRIGFGNAEIGQQVDNFWLVGPL
KVTPIQEVEFVSQLAHTQLPFSEKVQANVKNMLLLEESNGYKIFGKTGWAMDIKPQV
GWLTGWVEQPDGKIVAFALKMEMRSEMPASIRNELLMKSLKQLNII

SEQ ID No. 1125:
MAIRIFAILFSIFSLATFAHAQEGTLERSDWRKFFSEFQAKGTIVVADERQADRAMLV
FDPVRSKKRYSPASTFKIPHTLFALDAGAVRDEFQIFRWDGVNRGFAGHNQDQDLR
SAMRNSTVWVYELFAKEIGDDKARRYLKKIDYGNADPSTSNGDYCIEGSLAISAQEQ
IAFLRKLYRNELPFRVEHQRLVKDLMIVEAGRNWILRAKTGWEGRMGWWVGWVE
WPTGSVFFALNIDTPNRMDDLFKREAIVRAIL

SEQ ID No. 1126:
MKTFAAYVITACLSSTALASSITENTSWNKEFSAEAVNGVFVLCKSSSKSCATNNLA
RASKEYLPASTFKIPNAIIGLETGVIKNEHQVFKWDGKPRAMKQWERDLSLRGAIQV

-continued

SAVPVFQQIAREVGEVRMQKYLKKFSYGNQNISGGIDKFWLEGQLRISAVNQVEFL
ESLFLNKLSASKENQLIVKEALVTEAAPEYLVHSKTGFSGVGTESNPGVAWWVGWV
EKGTEVYFFAFNMDIDNENKLPLRKSIPTKIMASEGIIGG

SEQ ID No. 1127:
MAIRFLTILLSTFFLTSFVHAQEHVLERSDWKKFFSDLRAEGAIVISDERQAEHALLVF
GQERAAKRYSPASTFKLPHTLFALDADAVRDEFQVFRWDGVKRSFAGHNQDQDLR
SAMRNSAVWVYELFAKEIGKDKARHYLKQIDYGNADPSTIKGDYWIDGNLEISAHEQ
ISFLRKLYRNQLPFQVEHQRLVKDLMITEAGRNWILRAKTGWEGRFGWWVGWVE
WPTGPVFFALNIDTPNRTDDLFKREAIARAILRSIDALPPN

SEQ ID No. 1128:
MAIRIFAILFSIFSLATFAHAQEGTLERSDWRKFFSEFQAKGTIVVADERQADRAMLV
FDPVRSKKRYSPASTFKIPHTLFALDAGAVRDEFQIFRWDGVNRGFAGHNQDQDLR
SAMRNSTVWVYELFAKEIGDDKARRYLKKIDYGNADPSTSNGDYWIEGSIAISAQEQ
IAFLRKLYRNELPFRVEHQRLVKDLMIVEAGRNWILRAKTGWEGRMGWWVGWVE
WPTGSVFFALNIDTPNRMDDLFKREAIVRAILRSIEALPPNPAVNSDAAR

SEQ ID No. 1129:
MKKFILPIFSISILVSLSACSSIKTKSEDNFHISSQQHEKAIKSYFDEAQTQGVIIIKEGK
NLSTYGNALARANKEYVPASTFKMLNALIGLENHKATTNEIFKWDGKKRTYPMWEK
DMTLGEAMALSAVPVYQELARRTGLELMQKEVKRVNFGNTNIGTQVDNFWLVGPL
KITPVQEVNFADDLAHNRLPFKLETQEEVKKMLLIKEVNGSKIYAKSGWGMGVTPQV
GWLTGWVEQANGKKIPFSLNLEMKEGMSGSIRNEITYKSLENLGII

SEQ ID No. 1130:
MAIRFLTILLSTFFLTSFVHAQEHVLERSDWKKFFSDLRAEGAIVISDERQAEHALLVF
GQERAAKRYSPASTFKLPHTLFALDADAVRDEFQVFRWDGVKRSFAGHNQDQDLR
SAMRNSAVWVYELFAKEIGEDKARRYLKQIDYGNADPSTIKGDYWIDGNLEISAHEQ
ISFLRKLYRNQLPFQVEHQRLVKDLMITEAGRNWILRAKTGWEGRFGWWVGWVE
WPTGPVFFALNIDTPNRTDDLFKREAIARAILRSIDALPPN

SEQ ID No. 1131:
MAIRFFTILLSTFFLTSFVYAQEHVVIRSDWKKFFSDLQAEGAIVIADERQAKHTLSVF
DQERAAKRYSPASTFKIPHTLFALDADAVRDEFQVFRWDGVNRSFAGHNQDQDLR
SAMRNSTVWVYELFAKDIGEDKARRYLKQIDYGNVDPSTIKGDYWIDGNLKISAHEQ
ILFLRKLYRNQLPFKVEHQRLVKDLMITEAGRSWILRAKTGWEGRFGWWVGWIEW
PTGPVFFALNIDTPNRTDDLFKREAIARAILRSIDALPPN

SEQ ID No. 1132:
MNKYFTCYVVASLFLSGCTVQHNLINETPSQIVQGHNQVIHQYFDEKNTSGVLVIQT
DKKINLYGNALSRANTEYVPASTFKMLNALIGLENQKTDINEIFKWKGEKRSFTAWE
KDMTLGEAMKLSAVPVYQELARRIGLDLMQKEVERIGFGNAEIGQQVDNFWLVGPL
KVTPIQEVEFVSQLAHTQLPFSEKVQANVKNMLLLEESNGYKIFGKTGWAAMDIKPQ
VGWLTGWVEQPDGKIVAFALNMEMRSEMPASIRNELLMKSLKQLNII

SEQ ID No. 1133:
MAIQIFAILFSTFVLATFAHAQDGTLERSDWGKFFSDFQAKGTIWADERQADHAILV
FDQARSMKRYSPASTFKIPHTLFALDAGAVRDEFQIFRWDGVKRSFAGHNKDQDLR
SAMRNSTVWVYELFAKEIGDGKARRYLKQIGYGNADPSTSHGDYWIEGSLAISAQE
QIAFLRKLYQNDLPFRVEHQRLVKDLMIVEAGRNWILRAKTGWEGSMGWWVGWV
EWPTGPVFFALNIDTPNRMDDLFKREAIARAILLSIEALPPNPAVHSDAAR

SEQ ID No. 1134:
MKNTIHINFAIFLIIANIIYSSASASTDISTVASQLFEGTEGCFLLYDASTNAEIAQFNKA
KCAAQMAPDSTFKIALSLMAFDAEIIDQKTIFKWDKIPKGMEIWNSNHTPKTWMQFS
VVWVSQEITQKIGLNKIKNYLKDFDYGNQDFSGDKERNNGLTEAWLESSLKISPEEQ
IQFLRKIINHNLPVRNSAIENTIDNMYLQDLENSTKLYGKTGAGFTANRTLQNGWFEG
FIISKSGHKYVFVSALTGSLGSNLTSSIKAKKNAITILNTLNL

SEQ ID No. 1135:
MLLFMFSIISFGNENQFMKEIFERKGLNGTFWYDLKNDKIDYYNLDRANERFYPASS
FKIFNTLIGLENGIVKNVDEMFYYYDGSKVFLDSWAKDSNLRYAIKVSQVPAYKKLAR
ELGKERMQEGLNKLNYGNKEIGSEIDKFWLEGPLKISAMEQVKLLNLLSQSKLPFKL
ENQEQVKDITILEKKDDFILHGKTGWATDNIVVPIGWFVGWIETSDNIYSFAINLDISD
SKFLPKREEIVREYFKNINVIK

SEQ ID No. 1136:
MRVLALSAVFLVASIIGMPAVAKEWQENKSWNAHFTEHKSQGVVVLWNENKQQGF
TNNLKRANQAFLPASTFKIPNSLIALDLGWKDEHQVFKWDGQTRDIATWNRDHNLI
TAMKYSVVPVYQEFARQIGEARMSKMLHAFDYGNEDISGNVDSFWLDGGIRISATE
QISFLRKLYHNKLHVSERSQRIVKQAMLTEANGDYIIRAKTGYSTRIEPKIGWWVGW
VELDDNVWFFAMNMDMPTSDGLGLRQAITKEVLKQEKIIP

SEQ ID No. 1137:
MLSRYSKTLAFAVVACTLAISTATAHAELVVRNDLKRVFDDAGVSGTFVLMDITADR
TYWDPARAARSIHPASTFKIPNSLIAFDTGAVRDDQEVLPYGGKPQPYEQWEHDM
ALPEAIRLSAVPIYQEVARRVGFERMQAYVDAFDYGNRQLGSAIDQFWLRGPLEISA
FEEEARFTSRMALKQLPVKPRTWDMVQRMLLIEQQGDAALYAKTGVATEYQPEIGW
WAGWVERAGHVYAFALNIDMPREGDMAKRIPLGKQLMRALEVWPAP

-continued

SEQ ID No. 1138:
MRPLLFSALLLLSGHTQASEWNDSQAVDKLFGAAGVKGTFVLYDVQRQRYVGHDR
ERAETRFVPASTYKVANSLIGLSTGAVRSADEVLPYGGKPQRFKAWEHDMSLRDAI
KASNVPVYQELARRIGLERMRANVSRLGYGNAEIGQVVDNFWLVGPLKISAMEQTR
FLLRLAQGELPFPAPVQSTVRAMTLLESGPGWELHGKTGWCFDCTPELGWWVGW
VKRNERLYGFALNIDMPGGEADIGKRVELGKASLKALGILP

SEQ ID No. 1139:
MNKGLHRKRLSKRLLLPMLLCLLAQQTQAVAAEQTKVSDVCSEVTAEGWQEVRRW
DKLFESAGVKGSLLLWDQKRSLGLSNNLSRAAEGFIPASTFKLPSSLIALETGAVRD
ETSRFSWDGKVREIAVWNRDQSFRTAMKYSVVPVYQQLAREIGPKVMAAMVRQLE
YGNQDIGGQADSFWLDGQLRITAFQQVDFLRQLHDNKLPVSERSQRIVKQMMLTE
ASTDYIIRAKTGYGVRRTPAIGWWVGWLELDDNTVYFAVNLDLASASQLPLRQQLV
KQVLKQEQLLP

SEQ ID No. 1140:
MNTIISRRWRAGLWRRLVGAVVLPATLAATPAAYAADVPKAALGRITERADWGKLF
AAEGVKGTIWLDARTQTYQAYDAARAEKRMSPASTYKIFNSLLALDSGALDNERAII
PWDGKPRRIKNWNAAMDLRTAFRVSCLPCYQVVSHKIGRRYAQAKLNEVGYGNRT
IGGAPDAYWVDDSLQISAREQVDFVQRLARGTLPFSARSQDIVRQMSIVEATPDYVL
HGKTGWFVDKKPDIGWWVGWIERDGNITSVAINIDMLSEADAPKRARIVKAVLKDLK
LI

SEQ ID No. 1141:
MKTFAAYVITACLSSTALASSITENTFWNKEFSAEAVNGVFVLCKSSSKSCATNNLA
RASKEYLPASTFKIPNAIIGLETGVIKNEHQIFKWDGKPRAMKQWERDLSLRGAIQVS
AVPVFQQIAREVGEVRMQKYLKKFSYGNQNISGGIDKFWLEGQLRISAVNQVEFLE
SLFLNKLSASKENQLIVKEALVTEAAPEYLVHSKTGFSGVGTESNPGVAWWVGWVE
KGAEVYFFAFNMDIDNENKLPLRKSIPTKIMASEGIIGG

SEQ ID No. 1142:
MRVLALSAVLVVASIVGMPAMANEWQEKPSWNTHFSEHKAQGVIVLWNENKQQGF
TNNLKRANQAFLPASTFKIPNSLIALDLGWKDEHQVFKWDGQTRDIAAWNRDHDLI
TAMKYSWPVYQEFARQIGQARMSKMLHAFDYGNEDISGNLDSFWLDGGIRISATE
QVAFLRKLYHNKLHVSERSQRIVKQAMLTEANSDYIIRAKTGYSTRIEPQIGWWVGW
VELDDNVWFFAMNMDMPTADGLGLRQAITKEVLKQEKIIP

SEQ ID No. 1143:
MKKITLFLLFLNLVFGQDKILNNWFKEYNTSGTFVFYDGKTWASNDFSRAMETFSPA
STFKIFNALIALDSGVIKTKKEIFYHYRGEKVFLSSWAQDMNLSSAIKYSNVLAFKEVA
RRIGIKTMQEYLNKLHYGNAKISKIDTFWLDNSLKISAKEQAILLFRLSQNSLPFSQEA
MNSVKEMIYLKNMENLELFGKTGFNDGQKIAWIVGFVYLKDENKYKAFALNLDIDKF
EDLYKREKILEKYLDELVKKVKNDG

SEQ ID No. 1144:
MSKKNFILIFIFVILISCKNTEKISNETTLIDNIFTNSNAEGTLVIYNLNDDKYIIHNKERAE
QRFYPASTFKIYNSLIGLNEKAVKDVDEVFYKLMAKSFLESWAKDSNLRYAIKNSQV
PAYKELARRIGIKKMKENIEKLDFGNKSIGDSVDTFWLEGPLEISAMEQVKLLTKLAQ
NELQYPIEIQKAISDITITRANLHITLHGKTGLADSKNMTTEPIGWFVGWLEENDNIYV
FALNIDNINSDDLAKRINIVKESLKALNLLK

SEQ ID No. 1145:
MNKYFTCYVVASLFLSGCTVQHNLINETPSQIVQGHNQVIHQYFDEKNTSGVLVIQT
DKKINLYGNALSRANTEYVPASTFKMLNALIGLENQKTDINEIFKWKGEKRSFTAWE
KDMTLGEAMKLSAVPVYQELARRIGLDLMQKEVKRIGFGNAEIGQQVDNFWLVGPL
KVTPIQEVEFVSQLAHTQLPFSEKVQANVKNMLLLEESNGYKIFGKTGWAMDIKPQV
GWLTGWVEQPDGKIVAFALKMEMRSEMPASIRNELLMKSLKQLNII

SEQ ID No. 1146:
MNIQALLLITSAIFISACSPYIVTANPNYSASKSDEKAEKIKNLFNEAHTTGVLVIQQGQ
TQQSYGNDLARASTEYVPASTFKMLNALIGLEHHKATTTEVFKWDGQKRLFPEWEK
NMTLGDAMKASAIPVYQDLARRIGLELMSNEVKRIGYGNADIGTQVDNFWLVGPLKI
TPQQEAQFAYKLANKTLPFSQKVQDEVQSMLFIEEKNGNKIYAKSGWGWDVNPQV
GWLTGWVVQPGNIVAFSLNLEMKKGISSSVRKEITYRGLEQLGIL

SEQ ID No. 1147:
MNIKALLLITSAIFISACSPYIVTANPNHSASKSDEKGEKIKNLFNEAHTTGVLVIQQGQ
TQQSYGNDLARASTEYVPASTFKMLNALIGLEHHKATTTEVFKWDGQKRLFPEWEK
DMTLGDAMKASAIPVYQDLARRIGLELMSKEVKRVGYGNADIGTQVDNFWLVGPLK
ITPQQEAQFAYKLANKTLPFSPKVQDEVQSMLFIEEKNGNKIYAKSGWGWDVDPQV
GWLTGWVVQPQGNIVAFSLNLEMKKGIPSSVRKEITYKSLEQLGIL

SEQ ID No. 1148:
MNIKALLLITSAIFISACSPYIVTANPNHSASKSDEKAEKIKNLFNEAHTTGVLVIQQGQ
TQQSYGNDLARASTEYVPASTFKMLNALIGLEHHKATTTEVFKWDGKKRLFPEWEK
DMTLGDAMKASAIPVYQDLARRIGLELMSKEVKRVGYGNADIGTQVDNFWLVGPLK
ITPQQEAQFAYKLANKTLPFSQKVQDEVQSMLFIEEKNGNKIYAKSGWGWDVNPQV
GWLTGWVVQPQGNIVAFSLNLEMKKGIPSSVRKEITYKSLEQLGIL

SEQ ID No. 1149:
MNIKALLLITSAIFISACSPYIVTANPNHSASKSDVKAEKIKNLFNEAHTTGVLVIQQGQ
TQQSYGNDLARASTEYVPASTFKMLNALIGLEHHKATTTEVFKWDGKKRLFPEWEK
DMTLGDAMKASAIPVYQDLARRIGLELMSKEVKRVGYGNADIGTQVDNFWLVGPLK
ITPQQEAQFAYKLANKTLPFSQKVQDEVQSMLFIEEKNGNKIYAKSGWGWDVNPQV
GWLTGWVVQPQGNIVAFSLNLEMKKGIPSSVRKEITYKSLEQLGIL

SEQ ID No. 1150:
MNIKALLLITSAIFISACSPYIVSANPNHSASKSDEKAEKIKNLFNEAHTTGVLVIQQGQ
TQQSYGNDLARASTEYVPASTFKMLNALIGLEHHKATTTEVFKWDGQKRLFPEWEK
NMTLGDAMKASAIPVYQDLARRIGLELMSNEVKRVGYGNADIGTQVDNFWLVGPLK
ITPQQEAQFAYKLANKTLPFSQEVQDEVQSMLFIEEKNGNKIYAKSGWGWDVNPQV
GWLTGWVVQPQGNIVAFSLNLEMKKGIPSSVRKEITYKSLEQLGIL

SEQ ID No. 1151:
MNIKALLLITSAIFISACSPYIVTANPNHSASKSDDKAEKIKNLFNEAHTTGVLVIHQGQ
TQQSYGNDLARASTEYVPASTFKMLNALIGLEHHKATTTEVFKWDGEKRLFPEWEK
NMTLGDAMKASAIPVYQDLARRIGLELMSKEVKRVGYGNADIGTQVDNFWLVGPLK
ITPQQEAQFAYKLANKTLPFSQKVQDEVQSMLFIEEKNGNKIYAKSGWGWDVNPQV
GWLTGWVVQPQGNIVAFSLNLEMKKGIPSSVRKEITYKSLEQLGIL

SEQ ID No. 1152:
MNIKALLLITSAIFISACSPYIVTANPNHSASKSDKKAEKIKNLFNEAHTTGVLVIQQGQ
TQQSYGNDLARASTEYVPASTFKMLNALIGLEHHKATTTEVFKWNGQKRLFPEWEK
DMTLGDAMKASAIPVYQDLARRIGLELMSNEVKRVGYGNADIGTQVDNFWLVGPLK
ITPQQEAQFAYKLANKTLPFSQKVQHEVQSMLFIEEKNGNKIYAKSGWGWDVDPQV
GWLTGWVVQPQGNIVAFSLNLEMKKGIPSSVRKEITYKSLEQLGIL

SEQ ID No. 1153:
MNIKALLLITSAIFISACSPYIVTANPNHSASKSDEKAEKIKNLFNEAHTTGVLVIQQGQ
TQQSYGNDLARASTEYVPASTFKMLNALIGLEHHKTTTEVFKWDGQKRLFPEWEK
DMTLGDAMKASAIPVYQDLARRIGLELMSKEVKRVGYGNADIGTQVDNFWLVGPLK
ITPQQEAQFAYKLANKTLPFSPKVQDEVQSMLFIEEKNGNKIYAKSGWGWDVDPQV
GWLTGWVVQPQGNIVAFSLNLEMKKGIPSSVRKEITYKSLEQLGIL

SEQ ID No. 1154:
MNIKALLLITSAIFISACSPYIVSANPNHSASKSDEKAEKIKNLFNEAHTTGVLVIQQGQ
TQQSYGNDLARASTEYVPASTFKMLNALIGLEHHKATTTAVFKWDGQKRLFPEWEK
NMTLGDAMKASAIPVYQDLARRIGLELMSNEVKRVGYGNADIGTQVDNFWLVGPLK
ITPQQEAQFAYKLANKTLPFSQKVQDEVQSMLFIEEKNGNKIYAKSGWGWDVNPQV
GWLTGWVVQPQGNIVAFSLNLEMKKGTPSSVRKEITYKSLEQLGIL

SEQ ID No. 1155:
MNIKALLLITSAIFISACSPYIVSANPNHSASKSDEKAEKIKNLFNEAHTTGVLVIQQGQ
TQQSYGNDLARASTEYVPASTFKMLNALIGLEHHKATTTEVFKWDGQKRLFPEWEK
NMTLGDAMKASAIPVYQDLPRRIGLELMSNEVKRVGYGNADIGTQVDNFWLVGPLK
ITPQQEAQFAYKLANKTLPFSQKVQDEVQSMLFIEEKNGNKIYAKSGWGWDVNPQV
GWLTGWVVQPQGNIVAFSLNLEMKKGIPSSVRKEITYKSLEQLGIL

SEQ ID No. 1156:
MNIKALLLITSAIFISACSPYIVTANPNHSASKSDVKAEKIKNLFNEAHTTGVLVIQQGQ
TQQSYGNDLARASTEYVPASTFKMLNALIGLEHHKATTTEVFKWDGKKRLFPEWEK
DMTLGDAMKASAIPVYQDLARRIGLELMSKEVKRVGYGNADIGTQVDNFWLVGPLK
ITPQQEAQFAYKLANKTLPFSQKVQDEVQSMLFIEEKNGNKIYAKSGWGWDVNPQV
GWLTGWVVQPQGNIVAFSLNLEMKKGIPSSVRKEITYKSLEKLGIL

SEQ ID No. 1157:
MNIKTLLLITSTIFISACSPYIVTANPNHSTSKSDEKAEKIKNLFNEAHTTGVLVIQQGQ
TQQSYGNDLARASIEYVPASTFKMLNALIGLEHHKATTTEIFKWDGQKRLFPEWEKD
MTLGDAMKASAIPVYQDLARRIGLELMSKEVKRVGYGNADIGTQVDNFWLVGPLKIT
PQQEAQFAYKLANKTLPFSLKVQDEVQSMLFIEEKNGNKIYAKSGWGWDVDPQVG
WLTGWVVQPQGNIVAFSLNLEMKKGIPSSVRKEITYKSLEQLGIL

SEQ ID No. 1158:
MNIKALLLITSAIFISACSPYIVTANPNHSASKSDVKAEKIKNLFNEAHTTGVLVIQQGQ
TQQSYGNDLARASTEYVPASTFKMLNALIGLEHHKATTTEVFKWDGKKRLFPEWEK
DMTLGDAMKASAISVYQDLARRIGLELMSKEVKRVGYGNADIGTQVDNFWLAGPLK
ITPQQEAQFAYKLANKTLPFSQKVQDEVQSMLFIEEKNGNKIYAKSGWGWDVNPQV
GWLTGWVVQPQGNIVAFSLNLEMKKGIPSSVRKEITYKSLEQLGIL

SEQ ID No. 1159:
MNIKALLLITSAIFISACSPYIVTANPNHSASKSDVKAEKIKNLFNEAHTTGVLVIQQGQ
TQQSYGNDLARASTEYVPASTFKMLNALIGLEHHKATTTEVFKWDGKKRLFPEWEK
DMTLGDAMKASALPVYQDLARRIGLELMSKEVKRVGYGNADIGTQVDNFWLVGPL
KITPQQEAQFAYKLANKTLPFSQKVQDEVQSMLFIEEKNGNKIYAKSGWGWDVNPQ
VGWLTGWVVQPQGNIVAFSLNLEMKKGIPSSVRKEITYKSLEQLGIL

SEQ ID No. 1160:
MNIKALLLITSAIFISACSPYIVTANPNHSASKSDDKAEKIKNLFNEAHTTGVLVIHQGQ
TQQSYGNDLARASTEYVPASTFKMLNALIGLEHHKATTTEVFKWDGEKRLFPEWEK

-continued
NMTLGDAMKASAIPVYQDLARRIGLELMSKEVKRVGYGNADIGTQVDNFWLVGPLK
ITPQQEAQFAYKLANKTLPFSQKVQDEVQSMLFIEEKNGNKIYAKSGWGWDVNPQV
GWLTGSVVQPQGNIVAFSLNLEMKKGIPSSVRKEITYKSLEQLGIL SEQ ID No. 1161:
MNIKTLLLITSTIFISACSPYIVTANPNHSTSKSDEKAEKIKNLFNEAHTTGVLVIQQGQ
TQQSYGNDLARASIEYVPASTFKMLNALIGLEHHKATTTEIFKWDGQKRLFPEWEKD
MTLGDAMKASAIPVYQDLARRIGLELMSKEVKRVGYGNADIGTQVDNFWLVGPLKIT
PQQEAQFAYKLANKTLPFSLKAQDEVQSMLFIEEKNGNKIYAKSGWGWDVDPQVG
WLTGWVVQPQGNIVAFSLNLEMKKGIPSSVRKEITYKSLEQLGIL SEQ ID No. 1162:
MNIKALLLITSAIFISACSPYIVTANPNHSASKSDKKAEKIKNLFNEAHTTGVLVIQQGQ
TQQSYGNDLARASTEYVPASTFKMLNALIGLEHHKATTTEVFKWDGKKRLFPEWEK
DMTLGDAMKASAIPVYQDLARRIGLELMSKEVKRVGYGNADIGTQVDNFWLVGPLK
ITPQQEAQFAYKLANKTLPFSQKVQDEVQSMLFIEEKNGNKIYAKSGWGWDVNPQV
GWLTGWVVQPQGNIVAFSLNLEMKKGIPSSVRKEITYKSLEQLGIL SEQ ID No. 1163:
MNIKTLLLITSAIFISACSHYIVSANPNHSASKSDEKAEKIKNLFNEAHTTGVLVIQQGQ
TQQSYGNDLARASTEYVPASTFKMLNALIGLEHHKATTTEVFKWDGQKRLFPEWEK
NMTLGDAMKASAIPVYQDLARRIGLELMSNEVKRVGYGNADIGTQVDNFWLVGPLK
ITPQQEAQFTYKLANKTLPFSQKVQDEVQSMLFIEEKNGNKIYAKSGWGWDVNPQV
GWLTGWVVQPQGNIVAFSLNLEMKKGIPSSVRKEITYKSLEQLGIL SEQ ID No. 1164:
MNIKALLLITSAIFISACSPYIVSANPNHSASKSDEKAEKIKNLFNEAHTTGVLVIQQGQ
TQQSYGNDLARASTEYVPASTFKMLNALIGLEHHKATTTEVFKWDGQKRLFPEWEK
NMTLGDAMKASAIPVYQDLARRIGLELMSNEVKRVGYGNADIGTQVDNFWLVGPLK
ITPQQEAQFAYKLANKTLPFSQKVQDEVQSMLFIEEKNGNKIYAKSGWGWDVDPQV
GWLTGWVVQPQGNIVAFSLNLEMKKGIPSSVRKEITYKSLEQLGIL SEQ ID No. 1165:
MNIKALLLITSTIFISACSPYIVTANPNHSASKSDEKAEKIKNLFNEAHTTGVLVIQQGQ
TQQSYGNDLARASTEYVPASTFKMLNALISLEHHKATTTEVFKWDGQKRLFPEWEK
DMTLGDAMKASAIPVYQDLARRIGLELMSNEVKRVGYGNADIGTQVDNFWLVGPLK
ITPQQEAQFAYKLANKTLPFSQKVQDEVQSMLFIEEKNGNKIYAKSGWGWDVNPQV
GWLTGWVVQPQGNIVAFSLNLEMKKGIPSSVRKEITYKSLEQLGIL SEQ ID No. 1166:
MNIQALLLITSAIFISACSPYIVSANPNHSASKSDEKAEKIKNLFNEAHTTGVLVIQQGQ
TQQSYGNDLARASTEYVPASTFKMLNALIGLEHHKATTTEVFKWDGKKRLFPEWEK
DMTLGDAMKASAIPVYQDLARRIGLELMSKEVKRVGYGNADIGTQVDNFWLVGPLK
ITPQQEAQFAYKLANKTLPFSQKVQDEVQSMLFIEEKNGNKIYAKSGWGWDVNPQV
GWVVQPHGNIVAFSLNLEMKKGIPSSVRKEITYKSLEQLGIL SEQ ID No. 1167:
MNIKALFLITSAIFISACSPYIVTANPNHSASKSDEKAEKIKNLFNEAHTTGVLVIQQGQ
TQQSYGNDLARASTEYVPASTFKMLNALIGLEHHKATTTEVFKWDGKKRLFPEWEK
DMTLGDAMKASAIPVYQDLARRIGLELMSKEVKRVGYGNADIGTQVDNFWLVGPLK
ITPQQEAQFAYKLANKTLPFSQKVQDEVQSMLFIEEKNGNKIYAKSGWGWDVDPQV
GWLTGWVVQPQGNIVAFSLNLEMKKGIPSSVRKEITYKSLEQLGIL SEQ ID No. 1168:
MKLLKILSLVCLSISIGACAEHSMSRAKTSTIPQVNNSIIDQNVQALFNEISADAVFVTY
DGQNIKKYGTHLDRAKTAYIPASTFKIANALIGLENHKATSTEIFKWDGKPRFFKAWD
KDFTLGEAMQASTVPVYQELARRIGPSLMQSELQRIGYGNMQMGTEVDQFWLKGP
LTITPIQEVKFVYDLAQGQLPFKPEVQQQVKEMLYVERRGENRLYAKSGWGMAVD
PQVGWYVGFVEKADGQVVAFALNMQMKAGDDIALRKQLSLDVLDKLGVFHYL SEQ ID No. 1169:
MNIKALLLITSTIFISACSPYIVTANPNHSTSKSDEKAEKIKNLFNEAHTTGVLVIQQGQ
TQQSYGNDLARASTEYVPASTFKMLNALIGLEHHKATTTEIFKWDGQKRLFPEWEK
DMTLGDAMKASAIPVYQDLARRIGLELMSKEVKRVGYGNADIGTQVDNFWLVGPLK
ITPQQEAQFAYKLANKTLPFSLKVQDEVQSMLFIEEKNGNKIYAKSGWGWDVDPQV
GWLTGWWQPQGNIVAFSLNLEMKKGIPSSVRKEITYKSLEQLGIL SEQ ID No. 1170:
MNIKTLLLITSAIFISACSPYIVTANPNHSASKSDEKAEKIKNLFNEVHTTGVLVIRQGQ
TQQSYGNDLARASTEYVPASTFKMLNALIGLEHHKATTTEVFKWDGQKRLFPEWEK
DMTLGDAMKASAIPVYQDLARRIGLELMSKEVKRVGYGNADIGTQVDNFWLVGPLK
ITPQQEAQFAYKLANKTLPFSPKVQDEVQSMLFIEEMNGNKIYAKSGWGWDVDPQV
GWLTGWVVQPQGNIVAFSLNLEMKKGIPSSVRKEITYKSLEQLGIL SEQ ID No. 1171:
MKLLKILSLVCLSISIGACAEHSMSRAKTSTIPQVNNSIIDQNVQALFNEISGDAVFVTY
DGQNIKKYGTHLDRAKTAYIPASTFKIANALIGLENHKATSTEIFKWDGKPRFFKAWD
KDFTLGEAMQASTVPVYQELARRIGPSLMQSELQRIGYGNMQIGTEVDQFWLKGPL
TITPIQEVKFVYDLAQGQLPFKPEVQQQVKEMLYVERRGENRLYAKSGWGMAVDP
QVGWYVGFVEKADGQVVAFALNMQMKAGDDIALRKQLSLDVLDKLGVFHYL SEQ ID No. 1172:
MKKFILPIFSISILVSLSACSSIKTKSEDNFHISSQQHEKAIKSYFDEAQTQGVIIIKEGK
NLSTYGNALARANKEYVPASTFKMLNALIGLENHKATTNEIFKWDGKKRTYPMWEK
DMTLGEAMALSAVPVYQELARRTGLELMQKEVKRVNFGNTNIGTQVDNFWLVGPL
KITPVQEVNFADDLAHNRLPFKLETQEEVKKMLLIKEVNGSKIYAKSGWGMDVTPQV
GWLTGWVEQANGKKIPFSLNLEMKEGMSGSIRNEITYKSLENLGII SEQ ID No. 1173:
MAIRIFAILFSIFSLATFAHAQEGTLERSDWRKFFSEFQAKGTIVVADERQADRAMLV
FDPVRSKKRYSPASTFKIPHTLFALDAGAVRDEFQIFRWDGVNRGFAGHNQDQDLR
SAMRNSTVVVVYELFAKEIGDDKARRYLKKIDYGNADPSTSNGDYWIESSLAISAQE
QIAFLRKLYRNELPFRVEHQRLVKDLMIVEAGRNWILRAKTGWEGRMGWWVGWVE
WPTGSVFFALNIDTPNRMDDLFKREAIVRAILRSIEALPPNPAVNSDAAR SEQ ID No. 1174:
MNIKALLLITSAIFISACSPYIVTANPNHSASKSDEKAEKIKNLFNEAHTTGVLVIQQGQ
TQQSYGNDLARASTEYVPASTFKMLNALIGLEHHKATTTEVFKWDGKKRLFPEWEK
NMTLGDAMKASAIPVYQDLARRIGLELMSNEVKRVGYGNADIGTQVDNFWLVGPLK
ITPQQEAQFAYKLANKTLPFSQKVQDEVQSMLFIEEKNGNKIYAKSGWGWDVDPQV
GWLTGWVVQPQGNIVAFSLNLEMKKGIPSSVRKEITYKSLEQLGIL SEQ ID No. 1175:
MNIKALLLITSAIFISACSPYIVTANPNHSASKSDVKAEKIKNLFNEAHTTGVLVIQQGQ
TQQSYGNDLARASTEYVPASTFKMLNALIGLEHHKATTTEVFKWDGKKRLFPEWEK
DMTLGDAMKASAILVYQDLARRIGLELMSKEVKRVGYGNADIGTQVDNFWWGPLK
ITPQQEAQFAYKLANKTLPFSQKVQDEVQSMLFIEEKNGNKIYAKSGWGWDVNPQV
GWLTGWVVQPQGNIVAFSLNLEMKKGIPSSVRKEITYKSLEQLGIL SEQ ID No. 1176:
MNIKALLLITSAIFISACSPYIVTANPNHSASKSDKKAEKIKNLFNEAHTTGVLVIQQGQ
TQQSYGNDLARASTEYVPASTFKMLNALIGLEHHKATTTEVFKWNGQKRLFPEWEK
DMTLGDAMKASAIPVYQDLARRIGLELMSNEVKRVGYGNADIGTQVDNFWLVGPLK
ITPQQEAQFAYKLANKTLPFSQKVQDEVQSMLFIEEKNGNKIYAKSGWGWDVDPQV
GWLTGWVVQPQGNIVAFSLNLEMKKGIPSSVRKEITYKSLEQLGIL SEQ ID No. 1177:
MNIKALLLITSAIFISACSPYIVTANPNHSASKSDDKAEKIKNLFNEAHTTGVLVIHQGQ
TQQSYGNDLARASTEYVPASTFKMLNALIGLEHHKATTTEVFKWDGEKRLFPEWEK
NMTLGDAMKASAIPVYQDLARRIGLELMSKEVKRVGYGNADIGTQVDNFWWGPLK
ITPQQEAQFAYKLANKTLPFSQKVQDEVQSMLFIEEKNGNKIYAKSGWGWDVNPQV
GWLTGWVVQPQGNIVAFSLNLEMKKGIPSSVRKEITYKSLEQLGIL SEQ ID No. 1178:
MNIKALLLITSAIFISACSPYIVTTNPNHSASKSDEKAEKIKNLFNEAHTTGVLVIQQGQ
TQQSYGNDLARASTEYVPASTFKMLNALIGLEHHKATTTEVFKWDGKKRLFPEWEK
DMTLGDAMKASAIPVYQDLARRIGLELMSKEVKRVGYGNTDIGTQVDNFWVVGPLK
ITPQQEAQFAYKLANKTLPFSQKVQDEVQSMLFIEEKNGNKIYAKSGWGWDVDPQV
GWLTGWVVQPQGNIVAFSLNLEMKKGIPSSVRKEITYKSLEQLGIL SEQ ID No. 1179:
MNIKALLLITSAIFISACSPYIVTANPNHSASKSDVKAEKIKNLFNEAHTTGVLVIQQGQ
TQQSYGNDLARASTEYVPASTFKMLNALIGLEHHKATTTEVFKWDGKKRLFPEWEK
DMTLGDAMKASAIQVYQDLARRIGLELMSKEVKRVGYGNADIGTQVDNFWLVGPLK
ITPQQEAQFAYKLANKTLPFSQKVQDEVQSMLFIEEKNGNKIYAKSGWGWDVNPQV
GWLTGWVVQPQGNIVAFSLNLEMKKGIPSSVRKEITYKSLEQLGIL SEQ ID No. 1180:
MNIKALLLITSAIFISACSPYIVTANPNHSASKSDDKAEKIKNLFNEAHTTGVLVIHQGQ
TQQSYGNDLARASTEYVPASTFKMLNALIGLEHHKATTTEVFKWDGEKRLFPEWEK
NMTLGDAMKASALPVYQDLARRIGLELMSKEVKRVGYGNADIGTQVDNFWLVGPL
KITPQQEAQFAYKLANKTLPFSQKVQDEVQSMLFIEEKNGNKIYAKSGWGWDVNPQ
VGWLTGWVVQPQGNIVAFSLNLEMKKGIPSSVRKEITYKSLEQLGIL SEQ ID No. 1181:
MNIKTLLLITSAIFISACSPYIVSANPNHSASKSDEKAEKIKNLFNEAHTTGVLVIQQGQ
TQQSYGNDLARASTEYVPASTFKMLNALIGLEHHKATTTEVFKWDGQKRLFPEWEK
DMTLGDAMKASAIPVYQDLARRIGLELMSKEVKRVGYGNADIGTQVDNFWLVGPLK
ITPQQEAQFAYKLANKTLPFSPKVQDEVQSMLFIEEMNGNKIYAKSGWGWDVDPQV
GWLTGWVVQPQGNIVAFSLNLEMKKGIPSSVRKEITYKSLEQLGIL SEQ ID No. 1182:
MNIKALLLITSAIFISACSPYIVTANPNHSASKSDDKAEKIKNLFNEAHTTGVLVIHQGQ
TQQSYGNDLARASTEYVPASTFKMLNALIGLEHHKATTTEVFKWDGEKRLFPEWEK
NMTLGDAMKASAIPVYQDLARRIGLELMSKEVKRVGYGNADIGTQVDNFWLVGPLK
ITPQQEAQFAYKLANKTLPFSQKVQDEVQSMLFIEEKNGNKIYAKSGWGWDVNPQV
GWLTGWVVQPQGNIVAFPLNLEMKKGIPSSVRKEITYKSLEQLGIL SEQ ID No. 1183:
MNIKALLLITSAIFISACSPYIVTANPNHSASKSDVKAEKIKNLFNEAHTTGVLVIQQGQ
TQQSYGNDLARASTEYVPASTFKMLNALIGLEHHKATTTEVFKWDGKKRLFPEWEK
DMTLGDAMKASAIPVYQDLARRIGLELMSKEVKRVGYGNADIGTQVDNFWLVGPLK

```
ITPQQEAQFAYKLANKTLPFSQKVQDEVQSMLFIEEKNGNKIYAKSGWGGDVNPQV
GWLTGWVVQPQGNIVAFSLNLEMKKGIPSSVRKEITYKSLEQLGIL

SEQ ID No. 1184:
MNIKALLLITSAIFISACSPYIVTANPNHSASKSDVKAEKIKNLFNEAHTTGVLVIQQGQ
TQQSYGNDLARASTEYVPASTFKMLNALIGLEHHKATTTEVFKWDGKKRLFPEWEK
DMTLGDAMKASAILVYQDLARRIGLELMSKEVKRVGYGNADIGTQVDNFWLVGPLKI
TPQQEAQFAYKLANKTLPFSQKVQDEVQSMLFIEEKNGNKIYAKSGWGWDVNPQV
GWLTGWVVQPQGNIVAFSLNLEMKKGIPSSVRKEITYKSLEQLGIL

SEQ ID No. 1185:
MNIKALLLITSAIFISACSPYIVTANPNHSASKSDVKAEKIKNLFNEAHTTGVLVIQQGQ
TQQSYGNDLARASTEYVPASTFKMLNALIGLEHHKATTTEVFKWDGKKRLFPEWEK
DMTLGDAMKASAIPVYQDLARRIGLELMSKEVKRVGYGNADIGTQVDNFWWGPLK
ITPQQEAQFAYKLANKTLPFSQKVQDEVQSMLFIEEKNGNKIYAKSGWGWDVNPQV
GWLTGWVVQPQGNIVAFSLNLEMKKGIPSSVRKEITYKSLEQLGIL

SEQ ID No. 1186:
MNIKALLLITSAIFISACSPYIVTANPNHSASKSDEKAEKIKNLFNEAHTTGVLVIQQGQ
TQQSYGNDLARASTEYVPASTFKMLNALIGLEHHKTTTTEVFKWDGQKRLFPEWEK
DMTLGDAMKASAIPVYQDLARRIGLELMSKEVKRVGYGNADIGTQVDNFWWGPLK
ITPQQEAQFAYKLANKTLPFSPKVQDEVQSMLFIEEKNGNKIYAKSGWGWDVDPQV
GWLTGWVVQPQGNIVAFSLNLEMKKGIPSSVRKEITYKSLEQLGIL

SEQ ID No. 1187:
MSKKNFILIFIFVILISCKNTEKISNETTLIDNIFTNSNAEGTLVIYNLNDDKYIIHNKERAE
QRFYPASTFKIYNSLIGLNEKAVKDVDEVFYKYNGEKVFLESWAKDSNLRYAIKNSQ
VPAYKELARRIGLKKMKENIEKLDFGNKSIGDSVDTFWLEGPLEISAMEQVKLLTKLA
QNELPYPIEIQKAVSDITILEQTYNYTLHGKTGLADSKNMTTEPIGWFVGWLEENDNI
YVFALNIDNINSDDLAKRINIVKESLKALNLLK

SEQ ID No. 1188:
MSKKNFILIFIFVILTSCKNTEKISNETTLIDNIFTNSNAEGTLVIYNLNDDKYIIHNKERA
EQRFYPASTFKIYNSLIGLNEKAVKDVDEVFYKYNGEKVFLESWAKDSNLRYAIKNS
QVPAYKELARRIGLKKMKENIEKLDFGNKSIGDSVDTFWLEGPLEISAMEQIKLLTKL
AQNELPYPIEIQKAVSDITILEQTYNYTLHGKTGLADSKNMTTEPIGWFVGWLEENDN
IYVFALNIDNINSDDLAKRINIVKESLKALNLLK

SEQ ID No. 1189:
LLITSAIFISACSPYIVSANPNHSASKSDDKAEKIKNLFNEAHTTGVLVIQQGQTQQSY
GNDLARASTEYVPASTFKMLNALIGLEHHKATTTEVFKWDGQKRLFPEWEKNMTLG
DAMKASAIPVYQDLARRIGLELMSNEVKRVGYGNADIGTQVDNFWLVGPLKITPQQ
EAQFAYKLANKTLPFSQKVQDEVQSMLFIEEKNGNKIYAKSGWGWDVDPQVGWLT
GWVVQPQGNIVAFSLNLEMKKGIPSSVRKEITYKSL

SEQ ID No. 1190:
LLITSAIFISACSPYIVSANPNHSASKSDEKAEKIKNLFNEAHTTGVLVIQQGQTQQSY
GNDLARASTEYVPASTFKMLNALIGLEHHKATTTEVFKWDGQKRLFPEWEKNMTLG
DAMKASAIPVYQDLARRIGLELMSNEVKRVGYGNADIGTQVDNFWLVGPLKITPQQ
EAQFAYKLANKTLPFSQKVQDEVQSMLFIEEKNGNKIYAKSGWGWDVNPQVGWLT
EWVVQPQGNIVAFSLNLEMKKGIPSSVRKEITYKSL

SEQ ID No. 1191:
MTVRRLSCALGAALSLSALGGGPVQAAVLCTVVADAADGRILFQQGTQQACAERYT
PASTFKLAIALMGADAGILQGPHEPVWNYQPAYPDWGGDAWRQPTDPARWIKYSV
VWYSQLTAKALGQDRFQRYTSAFGYGNADVSGEPGKHNGTDGAWIISSLRISPLEQ
LAFLRKLVNRQLPVKAAAYELAENLFEAGQADGWRLYGKTGTGSPGSNGVYTAAN
AYGWFVGWARKDGRQLVYARLLQDERATRPNAGLRARDELVRDWPAMAGAWRP

SEQ ID No. 1192:
MNIKALLLITSAIFISACSPYIVSANPNHSASKSDEKAEKIKNLFNEAHTTGVLVIQQGQ
TQQSYGNVLARASTEYVPASTFKMLNALIGLEHHKATTTEVFKWDGQKRLFPEWEK
NMTLGDAMKASAIPVYQDLARRIGLELMSNEVKRVGYGNADIGTQVDNFWLVGPLK
ITPQQEAQFAYKLANKTLPFSQEVQDEVQSMLFIEEKNGNKIYAKSGWGWDVNPQV
GWLTGWVVQPQGNIVAFSLNLEMKKGIPSSVRKEITYKSLEQLGIL

SEQ ID No. 1193:
MKTFAAYVIIACLSSTALAGSITENTSWNKEFSAEAVNGVFVLCKSSSKSCATNDLAR
ASKEYLPASTFKIPSAIIGLETGVIKNEHQVFKWDGKPRAMKQWERDLTLRGAIQVS
AVPVFQQIAREVGEVRMQKYLKKFSYGNQNISGGIDKFWLEDQLRISAVNQVEFLES
LYLNKLSASKENQLIVKEALVTEAAPEYLVHSKTGFSGVGTESNPGVAWWVGWEK
ETEVYFFAFNMDIDNESKLPLRKSIPTKIMESEGIIGG

SEQ ID No. 1194:
MNIKTLLLITSAIFISACSPYIVTANPNHSASKSDVKAEKIKNLFNEAHTTGVLVIQQGQ
TQQSYGNDLARASTEYVPASTFKMLNALIGLEHHKATTTEVFKWDGKKRLFPEWEK
DMTLGDAMKASAIPVYQDLARRIGLELMSKEVKRVGYGNADIGTQVDNFWVGPLK
ITPQQEAQFAYKLANKTLPFSQKVQDEVQSMLFIEEKNGNKIYAKSGWGWDVNPQV
GWLTGWVVQPQGNIVAFSLNLEMKKGIPSSVRKEITYKSLEQLGIL
```

SEQ ID No. 1195:
MNIKALLLITSAIFISACSPYIVTTNPNHSASKSDEKAEKIKNLFNEAHTTGVLVIQQGQ
TQQSYGNDLARASTEYVPASTFKMLNALIGLEHHKATTTEVFKWDGKKRLFPEWEK
DMTLGDAMKASAIPVYQDLARRIGLELMSKEVKRVGYGNTDIGTQVDNFWLVGPLKI
TPQQEAQFAYKLANKTLPFSQKVQDEVQSMLFIEEKNGNKIYAKSGWGWDVDPQV
GWLTGWVVQPQGNIVAFSLNLEMKKGIPSSVRKEITYKSLEQLGIL

SEQ ID No. 1196:
MNIKALLLITSAIFISACSPYIVTANPNHSASKSDVKAEKIKNLFNEAHTTGVLVIQQGQ
TQQSYGNDLARASTEYVPASTFKMLNALIGLEHHKATTTEVFKWDGKKRLFPEWEK
DMTLGDAMKASAVPVYQDLARRIGLELMSKEVKRVGYGNADIGTQVDNFWLVGPL
KITPQQEAQFAYKLANKTLPFSQKVQDEVQSMLFIEEKNGNKIYAKSGWGWDVNQ
QVGWLTGWVVQPQGNIVAFSLNLEMKKGIPSSVRKEITYKSLEQLGIL

SEQ ID No. 1197:
MNIKTLLLITSAIFISACSPYIVTANPNHSASKSDEKAEKIKNLFNEVHTTGVLVIQQGQ
TQQSYGNDLARASTEYVPASTFKMLNALIGLEHHKATTTEVFKWDGQKRLFPEWEK
DMTLGDAMKASAIPVYQDLARRIGLELMSKEVKRVGYGNADIGTQVDNFWLVGPLK
ITPQQEAQFAYKLANKTLPFSPKVQDEVQSMLFIEEKNGNKIYAKSGWGWDVDPQV
GWLTGWVVQPQGNIVAFSLNLEMKKGIPSSVRKEMTYKSLEQLGIL

SEQ ID No. 1198:
MNKYFTCYVVASLFFSGCTVQHNLINETQSQIVQGHNQVIHQYFDEKNTSGVLVIQT
DKKINLYGNALSRANTEYVPASTFKMLNALIGLENQKTDINEIFKWKGEKRSFTTWE
KDMTLGEAMKLSAVPVYQELARRIGLDLMQKEVERIDFGNAEIGQQVDNFWLIGPLK
VTPIQEVEFVSQLAHTQLPFSEKVQANVKNMLLLEENNGYKIFGKTGWAMDIKPQV
GWLTGWVEQPDGKIVAFALNMEMRSEMPASIRNELLMKSLKQLNII

SEQ ID No. 1199:
MNKYFTCYVVASLFLSGCTVQHNLINETPSQIVQGHNQVIHQYFDEKNTSGVLVIQT
DKKINLYGNALSRANTEYVPASTFKMLNALIGLENQKTDINEIFKWKGEKRSFTAWE
KDMTLGEAMKLSAVPVYQELARRIGLDLMQKEVKRIGFGNAEIGQQVDNFWLVGPL
KVTPIQEVEFVSQLAHTQLPFSEKVQANVKNMLLLEESNGYKIFGKTGWAAMDIKPQ
VGWLTGWVEQPDGKIVAFALNMEMRSEMPASIRNELLMKSLKQLNII

SEQ ID No. 1200:
MKTFAAYVITACLSSTALASSITENTSWNKEFSAEAVNGVFVLCKSSSKSCATNNLA
RASKEYLPASTFKIPNAIIGLETGVIKNEHQVFKWDGKPRAMKQWERDLSLRGAIQV
SAVPVFQQIAREVGEVRMQKYLKKFSYGNQNISSGIDKFLLEGQLRISAVNQVEFLE
SLFLNKLSASKENQLIVKEALVTEAAPEYLVHSKTGFSGVGTESNPGVAWWVGWVE
KGTEVYFFAFNMDIDNENKLPLRKSIPTKIMASEGIIGG

SEQ ID No. 1201:
MAIRIFAILFSIFSLATFAHAQEGTLERSDWRKFFSEFQAKGTIVVADERQADRAMLV
FDPVRSKKRYSPASTFKIPHTLFALDAGAVRDEFQIFRWDGVNRGFAGHNQDQDLR
SAMRNSTVWVYELFAKEIGDDKARRYLKKIDYGDADPSTSNGDYVVIEGSLAISAQE
QIAFLRKLYRNELPFRVEHQRLVKDLMIVEAGRNWILRAKTGWEGRMGWWVGWVE
WPTGSVFFALNIDTPNRMDDLFKREAIVRAILRSIEALPPNPAVNSDAAR

SEQ ID No. 1202:
MNIKALLLITSAIFISACSPYIVTANPNHSASKSDKKAEKIKNLFNEAHTTGVLVIQQGQ
TQQSYGNDLARASTEYVPASTFKMLNALIGLEHHKASTTEVFKWNGQKRLFPEWEK
DMTLGDAMKASAIPVYQDLARRIGLELMSNEVKRVGYGNADIGTQVDNFWLVGPLK
ITPQQEAQFAYKLANKTLPFSQKVQDEVKSMLFIEEKNGNKIYAKSGWGWDVDPQV
GWLTGWVVQPQGNIVAFSLNLEMKKGIPSSVRKEITYKSLEQLGIL

SEQ ID No. 1203:
MNIKALLLITSAIFISACSPYIVSANPNHSASKSDEKAEKIKNLFNEAHTTGVLVIQQGQ
TQQSYGNDLARASTEYVPASTFKMLNALIGLEHHKATTTEVFKWDGQKRLFPEWEK
NMTLGDAMKASAIPVYQDLARRIGLELMSNEVKHVGYGNADIGTQVDNFWLVGPLK
ITPQQEAQFAYKLANKTLPFSPKVQDEVQSMLFIEEKNGNKIYAKSGWGWDVNPQV
GWLTGWVVQPQGNIVAFSLNLEMKKGIPSSVRKEITYKSLEQLGIL

SEQ ID No. 1204:
MNIKALLLITSAIFISACSPYIVSANPNHSASKSDEKAEKIKNLFNEAHTTGVLVIQQGQ
TQQSYGNDLARASTEYVPASTFKMLNALIGLEHHKATTTEVFKWDGQKRLFPEWEK
NMTLGDAMKASAIPVYQDLARRIGLELMSNEVKHVGYGNADIGTQVDNFWLVGPLK
ITPQQEAQFAYKLANKTLPFSQKVQDEVQSMLFIEEKNGNKIYAKSGWGWDVNPQV
GWLTGWVVQPQGNIVAFSLNLEMKKGIPSSVRKEITYKSLEQLGIL

SEQ ID No. 1205:
MKKFILPILSISTLLSVSACSSIQTKFEDTFHTSNQQHEKAIKSYFDEAQTQGVIIIKKG
KNISTYGNNLTRAHTEYVPASTFKMLNALIGLENHKATTTEIFKWDGKKRSYPMWEK
DMTLGDAMALSAVPVYQELARRTGLDLMQKEVKRVGFGNMNIGTQVDNFWLGPL
KITPIQEVNFADDFANNRLPFKLETQEEVKKMLLIKEFNGSKIYAKSGWGMDVTPQV
GWLTGWVEKSNGEKVAFSLNIEMKQGMPGSIRNEITYKSLENLGII

SEQ ID No. 1206:
MNIKALLLITSAIFISACSPYIVSANPNHSASKSDEKAEKIKNLFNEAHTTGVLVIQQGQ
TQQSYGNDLARASTEYVPASTFKMLNALIGLEHHKATTTEVFKWDGQKRLFPEWEK

-continued
NMTLGDAMKASAIPVYQDLARRIGLELMSNEVKRVGYGNADIGTQVDNFWLVGPLK
ITPQQEAQFAYKLANKTLPFSQEVQDEVQSILFIEEKNGNKIYAKSGWGWDVNPQV
GWLTGWVVQPQGNIVAFSLNLEMKKGIPSSVRKEITYKSLEQLGIL SEQ ID No. 1207:
MKKFILPIFSISILVSLSACSSIKTKSEDNFHISSQQHEKAIKSYFDEAQTQGVIIIKEGK
NLSTYGNALARANKEYVPASTFKMLNALIGLENHKATTNEIFKWDGKKRTYPMWEK
DMTLGEAMALSAVPVYQELARRTGLELMQKEVKRVNFGNTNIGTQVDNFWLVGPL
KITPVQEVNFADDLAHNRLPFKLETQEEVKKMLLIKEVNGSKIYAKSGWGMGVTSQV
GWLTGWVEQANGKKIPFSLNLEMKEGMSGSIRNEITYKSLENLGII SEQ ID No. 1208:
MRVLALSAVFLVASIIGMPAVAKEWQENKSWNAHFTEHKSQGVVVLWNENKQQGF
TNNLKRANQAFLPASTFKIPNSLIALDLGWKDEHQVFKWDGQTRDIATWNRDHNLI
TAMKYSWPVYQEFARQIGEARMSKMLHAFDYGNEDISGNVDSFWLDGGIRISATE
QISFLRKLYHNKLHVSERSQRIVKQAMLTEANGDYIIRAKTGYSARIEPKIGWWVGW
VELDDNVWFFAMNMDMPTSDGLGLRQAITKEVLKQEKIIP SEQ ID No. 1209:
MNIKALLLITSAIFISACSPYIVTANPNHSASKSDVKAEKIKNLFNEAHTTGVLVIQQGQ
TQQSYGNDLARASTEYVPASTFKMLNALIGLEHHKATTTEVFKWDGKKRLFPEWEK
DMTLGDAMKASAVPVYQDLARRIGLELMSKEVKRVGYGNADIGTQVDNFWLVGPL
KITPQQEAQFAYKLANKTLPFSQKVQDEVQSMLFIEEKNGNKIYAKSGWGLDVNPQ
VGWLTGWVVQPQGNIVAFSLNLEMKKGIPSSVRKEITYKSLEQLGIL SEQ ID No. 1210:
MNIKALLLITSAIFISACSPYIVTANPNHSASKSDVKAEKIKNLFNEAHTTGVLVIQQGQ
TQQSYGNDLARASTEYVPASTFKMLNALIGLEHHKATTTEVFKWDGKKRLFPEWEK
DMTLGDAMKASAVPVYQDLARRIGLELMSKEVKRVGYGNADIGTQVDNFWLVGPL
KITPQQEAQFAYKLANKTLPFSQKVQDEVQSMLFIEEKNGNKIYAKSGWGLDVNLQ
VGWLTGWVVQPQGNIVAFSLNLEMKKGIPSSVRKEITYKSLEQLGIL SEQ ID No. 1211:
MNIKALLLITSAIFISACSPYIVTANPNHSASKSDVKAEKIKNLFNEAHTTGVLVIQQGQ
TQQSYGNDLARASTEYVPASTFKMLNALIGLEHHKATTTEVFKWDGKKRLFPEWEK
DMTLGDAMKASAIPVYQDLARRIGLELMSKEVKRVGYGNADIGTQVDNFWWGPLK
ITPQQEAQFAYKLANKTLPFSQKVQDEVQSMLFIEEKNGNKIYAKSGWGWDVNPQV
GWLTGWVVQPQGNIVAFSLNLEMKKGIPSSVRKEITYKSLEKLGIL SEQ ID No. 1212:
MNIKALLLITSAIFISACSPYIVTANPNHSASKSDVKAEKIRNLFNEAHTTGVLVIQQGQ
TQQSYGNDLARASTEYVPASTFKMLNALIGLEHHKATTTEVFKWDGKKRLFPEWEK
DMTLGDAMKASAIPVYQDLARRIGLELMSKEVKRVGYGNADIGTQVDNFWVVPLK
ITPQQEAQFAYKLANKTLPFSQKVQDEVQSMLFIEEKNGNKIYAKSGWGWDVNPQV
GWLTGWVVQPQGNIVAFSLNLEMKKGIPSSVRKEITYKSLEQLGIL SEQ ID No. 1213:
MNIKALLLITSAIFISACSPYIVTANPNHSASKSDVKAEKIKNLFNEAHTTGVLVIQQGQ
TQQSYGNDLARASTEYVPASTFKMLNALIGLEHHKATTTEVFKWDSKKRLFPEWEK
DMTLGDAMKASAIPVYQDLARRIGLELMSKEVKRVGYGNADIGTQVDNFWWGPLK
ITPQQEAQFAYKLANKTLPFSQKVQDEVQSMLFIEEKNGNKIYAKSGWGWDVNPQV
GWLTGWVVQPQGNIVAFSLNLEMKKGIPSSVRKEITYKSLEQLGIL SEQ ID No. 1214:
MNIKALLLITSAIFISACSPYIVTANPNHSASKSDVKAEKIKNLFNEAHTTGVLVIQQGQ
TQQSYGNDLARASTEYVPASTFKMLNALIGLEHHKATTTEVFKWDGKKRLFPEWEK
DMTLGDAMKASAIPVYQDLARRIGLELMSKEVKRVGYGNADIGTQVDNFWVVGPLK
ITPQQEAQFAYKLANKTLPFSQKVQDGVQSMLFIEEKNGNKIYAKSGWGWDVNPQ
VGWLTGWVVQPQGNIVAFSLNLEMKKGIPSSVRKEITYKSLEQLGIL SEQ ID No. 1215:
MNIKALLLITSAIFISACSPYIVTANPNHSASKSDVKAEKIKNLFNEAHTTGVLVIQQGQ
TQQSYGNDLARASTEYVPASTFKMLNALIGLEHHKATTTEVFKWDSKKRLFPEWEK
DMTLGDAMKASAILVYQDLARRIGLELMSKEVKRVGYGNADIGTQVDNFWLVGPLKI
TPQQEAQFAYKLANKTLPFSQKVQDEVQSMLFIEEKNGNKIYAKSGWGWDVNPQV
GWLTGWVVQPQGNIVAFSLNLEMKKGIPSSVRKEITYKSLEQLGIL SEQ ID No. 1216:
MKLLKILSLVCLSISIGACAEHSMSRAKTSTIPQVNNSIIDQNVQALFNEISADAVFVTY
DGQNIKKYGTHLDRAKTAYIPASTFKIANALIGLENHKATSTEIFKWDGKPRFLKAWD
KDFTLGEAMQASTVPVYQELARRIGPSLMQSELQRIGYGNMQIGTEVDQFWLKGPL
TITPIQEVKFVYDLAQGQLPFKPEVQQQVKEMLYVERRGENRLYAKSGWGMAVDP
QVGWYVGFVEKADGQVVAFALNMQMKAGDDIALRKQLSLDVLDKLGVFHYL SEQ ID No. 1217:
MNKYFTCYVVASLFLSGCTVQHNLINETPSQIVQGHNQVIHQYFDEKNTSGVLVIQT
DKKINLYGNALSRANTEYVPASTFKMLNALIGLENQKTDINEIFKWKGEKRSFTAWE
KDMTLGEAMKLSAVPVYQELARRIGLDLMQKEVKRIGFGNAEIGQQVDNFWLVGPL
KVTPIQEVEFVSQLAHTQLPFSEKVQANVKNMLLLEESNGYKIFGKTGWAMDVKPQ
VGWLTGWVEQPDGKIVAFALNMEMRSEMPASIRNELLMKSLKQLNII -continued SEQ ID No. 1218:
MNKYFTCYVVASLFLSGCTVQHNLINETPSQIVQGHNQVIHQYFDEKNTSGALVIQT
DKKINLYGNALSRANTEYVPASTFKMLNALIGLENQKTDINEIFKWKGEKRSFTAWE
KDMTLGEAMKLSAVPVYQELARRIGLDLMQKEVKRIGFGNAEIGQQVDNFWLVGPL
KVTPIQEVEFVSQLAHTQLPFSEKVQANVKNMLLLEESNGYKIFGKTGWAMDIKPQV
GWLTGWVEQPDGKIVAFALNMEMRSEMPASIRNELLMKSLKQLNII SEQ ID No. 1219:
MNKYFTCYVVASLFLSGCTVQHNLINETPSQIVQGHNQVIHQYFDEKNTSGVLVIQT
DKKINLYGNALSRANTEYVPASTFKMLNALIGLENQKTDINEIFKWKGEKRSFTAWE
KDMTLGEAMKLSAVPVYQELARRIGLDLMQKEVKRIGFGNAEIGQQVDNFWLVGPL
KVTPIQEVEFVSQLAHTQLPFSEKVQANVKNMLLLEESNGYKIFGKTGWAMDIKPQV
GWLTGWVEQPDGKIVAFALNMEMRSEMPASIRNELMMKSLKQLNII SEQ ID No. 1220:
MNKYFTCYVVASLFLSGCTVQHNLINETPSQIVQGHNQVIHQYFDEKNTSGVLVIQT
DKKINLYGNALSRANTEYVPASTFKMLNALIGLENQKTDINEIFKWKGEKRSFTAWE
KDMTLGEAMKLSAVPVYQELARRIGLDLMQKEVKRIGFGNAEIGQQVDNFWLVGPL
KVTPIQEVEFVSQLAHTQLPFSEKVQANVKNMLLLEESNGYKIFGKTGWAMDIKPQV
GWLAGWVEQPDGKIVAFALNMEMRSEMPASIRNELLMKSLKQLNII SEQ ID No. 1221:
MNKYFTCYVVASLFLSGCTVQHNLINETPSQIVQGHNQVIHQYFDERNTSGVLVIQT
DKKINLYGNALSRANTEYVPASTFKMLNALIGLENQKTDINEIFKWKGEKRSFTAWE
KDMTLGEAMKLSAVPVYQELARRIGLDLMQKEVKRIGFGNAEIGQQVDNFWLVGPL
KVTPIQEVEFVSQLAHTQLPFSEKVQANVKNMLLLEESNGYKIFGKTGWAMDIKPQV
GWLTGWVEQPDGKIVAFALNMEMRSEMPASIRNELLMKSLKQLNII SEQ ID No. 1222:
MNKYFTCYVVASLFLSGCTVQHNLINETPSQIVQGHNQVIHQYFDEKNTSGVLVIQT
DKKINLYGNALSRANTEYVPASTFKMLNALIGLENQKTDINEIFKWKGEKRSFTAWE
KDMTLGEAMKLSAVPVYQELARRIGLDLMQKEVKRIGFGNAEIGQQVDNFWLVGPL
KVTPIQEVEFVSQLAHTQLPFSEKVQANVKNMLLLEKSNGYKIFGKTGWAMDIKPQV
GWLTGWVEQPDGKIVAFALNMEMRSEMPASIRNELLMKSLKQLNII SEQ ID No. 1223:
MNKYFTCYVVASLFLSGCTVQHNLINETPSQIVQGHNQVIHQYFDEKNTSGVLVIQT
DKKINLYGNALSRANTEYVPASTFKMLNALIGLENQKTDINEIFKWKGEKRSFTAWE
KDMTLGEAMKLSAVPVYQELARRIGLDLMQKEVKRIGFGNAEIGQQVDNFWLVGPL
KVTPIQEVEFVSQLAHTQLPFSEKVQANVKNMLLLEESNGYKIFGKTGWAMDIKPQV
GWLTGWVEQPDGKIVAFALNMEMRSEMPASTRNELLMKSLKQLNII SEQ ID No. 1224:
MKKFILPIFSISILLSLSACSSIQTKFEDTFHISNQKHEKAIKSYFDEAQTQGVIIIKEGKN
ISSYGNNLVRAHTEYVPASTFKMLNALIGLENHKATTNEIFKWDGKKRSYPMWEKD
MTLGEAMALSAVPVYQDLARRIGLNLMQKEVKRVGFGNMNIGTQVDNFWLIGPLKI
TPIQEVNFADDLANNRLPFKLETQEEVKKMLLIKEVNGSKIYAKSGWGMDVSPQVG
WLTGWVEKSNGEKVSFSLNIEMKQGMSGSIRNEITYKSLENLGII SEQ ID No. 1225:
MNIKALLLITSAIFISACSPYIVTANPNHSASKSDEKAEKIKNLFNEAHTTGVLVIQQGQ
TQQSYGNDLARASTEYVPASTFKMLNALIGLEHHKATTTEVFKWDGQKRLFPEWEK
DMTLGDAMKASAIAVYQDLARRIGLELMSKEVKRVGYGNADIGTQVDNFWLVGPLK
ITPQQEAQFAYKLANKTLPFSPKVQDEVQSMLFIEEKNGNKIYAKSGWGWDVDPQV
GWLTGWVVQPQGNIVAFSLNLEMKKGIPSSVRKEITYKSLEQLGIL SEQ ID No. 1226:
MNIKALLLITSAIFISACSPYIVTANPNHSASKSDEKAEKIKNLFNEAHTTGVLVIQQGQ
TQQSYGNDLARASTEYVPASTFKMLNALIGLEHHKATTTEVFKWDGQKRLFPEWEK
DMTLGDAIKASAIPVYQDLARRIGLELMSKEVKRVGYGNADIGTQVDNFWLVGPLKI
TPQQEAQFAYKLANKTLPFSQKVQDEVQSMLFIEEKNGNKIYAKSGWGWDVDPQV
GWLTGWVVQPQGNIVAFSLNLEMKKGIPSSVRKEITYKSLEQLGIL SEQ ID No. 1227:
MKILIFLPLLSCLGLTACSLPVSSLPSQSISTQAIASLFDQAQSSGVLVIQRDQQVQVY
GNDLNRANTEYVPASTFKMLNALIGLQHGKATTNEIFKWDGKKRSFTAWEKDMTLG
QAMQASAVPVYQELARRIGLELMQQEVQRIQFGNQQIGQQVDNFWLVGPLKVTPK
QEVQFVSALAREQLAFDPQVQQQVKAMLFLQERKAYRLYVKSGWGMDVEPQVGW
LTGWVETPQAEIVAFSLNMQMQNGIDPAIRLEILQQALAELGLYPKAEG SEQ ID No. 1228:
MHKHMSKLFIAFLAFLLSVPAAAEDQTLAELFAQQGIDGTIVISSLHNGKTFIHNDPRA
KQRFSTASTFKILNTLISLEEKAISGKDDVLKWDGHIYDFPDWNRDQTLESAFKVSCV
WCYQALARQVGAEKYRNYLRKSVYGELREPFEETTFWLDGSLQISAIEQVNFLKKV
HLRTLPFSASSYETLRQIMLIEQTPAFTLRAKTGWATRVKPQVGWYVGHVETPTDV
WFFATNIEVRDEKDLPLRQKLTRKALQAKGIIE SEQ ID No. 1229:
MKTFAAYVITACLSSTALASSITENTSWNKEFSAEAVNGVFVLCKSSSKSCATNNLA
RASKEYLPASTFKIPNAIIGLETGVIKNEHQVFKWDGKPRAMKQWERDLSLRGAIQV
SAVPVFQQIAREVGEVRMQKYLKKFSYGNQNISGGTDKFWLEDQLRISAVNQVEFL -continued
ESLFLNKLSASKENQLIVKEALVTEAAPEYLVHSKTGFSGVGTESNPGVAWWVGWV
EKGTEVYFFAFNMDIDNENKLPLRKSIPTKIMASEGIIGG SEQ ID No. 1230:
MNIKALLLITSAIFISACSPYIVTANPNHSASKSDEKAEKIKNLFNEAHTTGVLVIQQGQ
TQQSYGNDLARASTEYVPASTFKMLNALIGLEHHKATTTEVFKWDGKKRLFPEWEK
DMTLGDAMKASAILVYQDLARRIGLELMSKEVKRVGYGNADIGTQVDNFWLVGPLKI
TPQQEAQFAYKLANKTLPFSQKVQDEVQSMLFIEEKNGNKIYAKSGWGLDVDPQV
GWLTGWVVQPQGNIVAFSLNLEMKKGIPSSVRKEITYKSLEQLGIL SEQ ID No. 1231:
MNIKALLLITSAIFISACSPYIVTANPNHSASKSDVKAEKIKNLFNEAHTTGVLVIQQGQ
TQQSYGNDLARASTEYVPASTFKMLNALIGLEHHKATTTEVFKWDGKKRLFPEWEK
DMTLGDAMKASAIQVYQDLARRIGLELMSKEVKRVGYGNADIGTQVDNFWVVGPLK
ITPQQEAQFAYKLANKTLPFSQKVQDEVQSMLFIEEKNGNKIYAKSGWGWDVNPQV
GWLTGWVVQPQGNIVAFSLNLEMKKGIPSSVRKEITYKSLEQLGIL SEQ ID No. 1232:
MNIKALLLITSAIFISACSPYIVTANPNHSASKSDVKAEKIKNLFNEAHTTGVLVIQQGQ
TQQSYGNDLARASTEYVPASTFKMLNALIGLEHHKATTTEVFKWDGKKRLFPEWEK
DMTLGDAMKASAMPVYQDLARRIGLELMSKEVKRVGYGNADIGTQVDNFWLVGPL
KITPQQEAQFAYKLANKTLPFSQKVQDEVQSMLFIEEKNGNKIYAKSGWGWDVNPQ
VGWLTGWVVQPQGNIVAFSLNLEMKKGIPSSVRKEITYKSLEQLGIL SEQ ID No. 1233:
MNIKALLLITSAIFISACSPYIVTANPNHSASKSDEKAEKIKNLFNEVHTTGVLVIQQGQ
TQQSYGNDLARASTEYVPASTFKMLNALIGLEHHKATTTEVFKWDGKKRLFPEWEK
NMTLGDAMKASAIPVYQDLARRIGLELMSNEVKRVGYGNADIGTQVDNFWLVGPLK
ITPQQEAQFAYKLANKTLPFSQKVQDEVQSMLFIEEKNGNKIYAKSGWGWDVDPQV
GWLTGWVVQPQGNIVAFSLNLEMKKGIPSSVRKEITYKSLEQLGIL SEQ ID No. 1234:
MRVLALSAVFLVASIIGMPAVAKEWQENKSWNAHFTEHKSQGVVVLWNENKQQGF
TNNLKRANQAFLPASTFKIPNSLIALDLGWKDEHQVFKWDGQTRDIATWNRDHNLI
TAMKYSWPVYQEFARQIGEARMSKMLHAFDYGNEDISGNVDSFWLDGGIRISATE
QISFLRKLYHNKLHVSERSQRIVKQAMLTEANGDYIIRAKTGYDTKIGWWVGWVELD
DNVWFFAMNMDMPTSDGLGLRQAITKEVLKQEKIIP SEQ ID No. 1235:
MSKKNFILIFIFVILISCKNTEKTSNETTLIDNIFTNSNAEGTLVIYNLNDDKYIIHNKERA
EQRFYPASTFKIYNSLIGLNEKAVKDVDEVFYKYNGEKVFLESWAKDSNLRYAIKNS
QVPAYKELARRIGLEKMKENIEKLDFGNKNIGDSVDTFWLEGPLEISAMEQVKLLTKL
AQNELPYPIEIQKAVSDITILEQTDNYTLHGKTGLADSENMTTEPIGWLVGWLEENNN
IYVFALNIDNINSDDLAKRINIVKESLKALNLLK SEQ ID No. 1236:
MNIKALFLITSAIFISACSPYIVTANPNHSASKSDVKAEKIKNLFNEAHTTGVLVIQQGQ
TQQSYGNDLARASTEYVPASTFKMLNALIGLEHHKATTTEVFKWDGKKRLFPEWEK
DMTLGDAMKASAIPVYQDLARRIGLELMSKEVKRVGYGNADIGTQVDNFWVVGPLK
ITPQQEAQFAYKLANKTLPFSQKVQDEVQSMLFIEEKNGNKIYAKSGWGWDVNPQV
GWLTGWVVQPQGNIVAFSLNLEMKKGIPSSVRKEITYKSLEQLGIL SEQ ID No. 1237:
MNIKALFLITSAIFISACSPYIVTANPNHSASKSDVKAEKIKNLFNEAHTTGVLVIQQGQ
TQQSYGNDLARASTEYVPASTFKMLNALIGLEHHKATTTEVFKWDGKKRLFPEWEK
DMTLGDAMKASAIPVYQDLARRIGLELMSKEVKRVGYGNADIGTQVDNFWVVGPLK
ITPQQEAQFAYKLANKTLPSSQKVQDEVQSMLFIEEKNGNKMYAKSGWGWDVNPQ
VGWLTGWVVQPQGNIVAFSLNLEMKKGIPSSVRKEITYKSLEQLGIL SEQ ID No. 1238:
MNIKALFLITSAIFISACSPYIVTANPNHSASKSDVKAEKIKNLFNEAHTTGVLVIQQGQ
TQQSYGNDLARASTEYVPASTFKMLNALIGLEHHKATTTEVFKWDGKKRLFPEWEK
DMTLGDAMKASAIPVYQDLARRIGLELMSKEVKRVGYGNADIGTQVDNFWVVGPLK
ITPQQEAQFAYKLANKTLPFSQKVQDEVQSMLFIEEKNGNKIYAKSGWGWDVNPQV
GWLTGWVVQPQGNIVAFSLNLEMKKGIPSSVRKEIAYKSLEQLGIL SEQ ID No. 1239:
MAIRIFAILFSIFSLATFAHAQEGTLERSDWRKFFSEFQAKGTIWADERQADRAMLV
FDPVRSKKRYSPASTFKIPHTLFALDAGAVRDEFQIFRWDGVNRGFAGHNQDQDLR
SAMRNSTWVVYELFAKEIGDDKARRYLKKIDYGNADPSTSNGDCWIEGSLAISAQE
QIAFLRKLYRNELPFRVEHQRLVKDLMIVEAGRNWILRAKTGWEGRMGWWVGWVE
WPTGSVFFALNIDTPNRMDDLFKREAIVRAILRSIEALPPNPAVNSDAAR SEQ ID No. 1240:
MNIKTLLLITSAIFISACSPYIVTANPNHSASKSDEKAEKIKNLFNEVHTTGVLVIQQGQ
TQQSYGNDLARASTEYVPASTFKMLNALIGLEHHKATTTEVFKWDGQKRLFPEWEK
DMTLGDAMKASAIPVYQDLARRIGLELMSKEVKRVGYGNADIGTQVDNFWVVGPLK
ITPQQEAQFAYKLANKTLPFSPKVQDEVQSMLFIEEKNGNKIYAKSGWGWDVDPQV
GWLTGWVVQPQGNIVAFSLNLEMKKGIPSSVRKEITYKSLEQLGIL SEQ ID No. 1241:
MNIKTLLLITSAIFISACSPYIVTANPNHSASKSDEKAEKIKNLFNEVHTTGVLVIQQGQ
TQQSYGNDLARASTEYVPASTFKMLNALIGLEYHKATTTEVFKWDGQKRLFPEWEK
DMTLGDAMKASAIPVYQDLARRIGLELMSKEVKRVGYGNADIGTQVDNFWLVGPLK
ITPQQEAQFAYKLANKTLPFSPKVQDEVQSMLFIEEKNGNKIYAKSGWGWDVNPQV
GWLTGWVVQPQGNIVAFSLNLEMKKGIPSSVRKEITYKSLEQLGIL SEQ ID No. 1242:
MAIRFLTILLSTFFLTSFVHAQEHVWRSDWKKFFSDLQAEGAIVIADERQAEHALLV
FGQERAAKRYSPASTFKLPHTLFALDAGAVRDEFQVFRWDGVKRSFAGHNQDQDL
RSAMRNSAVWVYELFAKEIGEDNARRYLKQIDYGNADPSTIKGNYWIDGNLEISAHE
QISFLRKLYRNQLPFQVEHQRLVKYLMITEAGRNWILRAKTGWEGRFGWWIGWVE
WPTGPVFFALNIDTPNRTDDLFKREAIARAILRSIDALPPN SEQ ID No. 1243:
MRVLALSAVFLVASIIGMPAVAKEWQENKSWNAHFTEHKSQGVVVLWNENKQQGF
TNNLKRANQAFLPASTFKIPNSLIALDLGVVKDEHQVFKWDGTRDIAAWNRDHDLI
TAMKYSVVPVYQEFARQIGEARMSKMLHAFDYGNEDISGNVDSFWLDGGIRISATQ
QIAFLRKLYHNKLHVSERSQRIVKQAMLTEANGDYIIRAKTGYSTRIEPKIGWWVGW
VELDDNVWFFAMNMDMPTSDGLGLRQAITKEVLKQEKIIP SEQ ID No. 1244:
MNKYFTCYVVASLFLSGCTVQHNLINETPSQIVQGHNQVIHQYFDEKNTSGVLVIQT
DKKINLYGNALSRANTEYVPASTFKMLNALIGLENQKTDINEIFKWKGEKRSFTAWE
KDMTLGEAMKLSAVPVYQELARRIGLDLMQKEVKRIGFGNAEIGQQVDNFWLVGPL
KVTPIQEVEFVSQLAHTQLPFSEKVQANVKNMLLLEESNGYKIFGKTGWAMDIKSQV
GWLTGWVEQPDGKIVAFALNMEMRSEMPASIRNELLMKSLKQLNII SEQ ID No. 1245:
MNIKALLLITSAIFISACSPYIVTANPNHSASKSDVKAEKIKNLFNEAHTTGVLVIQQGQ
TQQSYGNDLARASTEYVPASTFKMLNALIGLEHHKATTTEVFKWDGKKRLFPEWEK
DMTLGDAMKASAISVYQDLARRIGLELMSKEVKRVGYGNADIGTQVDNFWLVGPLK
ITPQQEAQFAYKLANKTLPFSQKVQDEVQSMLFIEEKNGNKIYAKSGWGWDVNPQV
GWLTGWWQPQGNIVAFSLNLEMKKGIPSSVRKEITYKSLEQLGIL SEQ ID No. 1246:
MAIRIFAILFSIFSLATFAHAQEGTLERSDWRKFFSEFQAKGTIVVADERQADRAMLV
FDPVRSKKRYSPASTFKIPHTLFALDAGAVRDEFQIFRWDGVNRGFAGHNQDQDLR
SAMRNSTVWVYELFAKEIGDDKARRYLKKIDYGNADPSTSNGDYWIEGSLAISAQE
QIAFLRKLYRNELPFRVEHQRLVKDLMIVEAGRNWILRAKTGWEGRMGWWVGWVE
WPTGSVFFALNIDTPNRMDDLFKREAIVRAILRSIEALPPNPAVNSDAAR SEQ ID No. 1247:
MKTIAAYLVLVFYASTALSESISENLAWNKEFSSESVHGVFVLCKSSSNSCTTNNAA
RASTAYIPASTFKIPNALIGLETGAIKDERQVFKWDGKPRAMKQWEKDLKLRGAIQV
SAVPVFQQIAREVGEIRMQKYLNLFSYGNANIGGGIDKFWLEGQLRISAFNQVKFLE
SLYLNNLPASKANQLIVKEAIVTEATPEYIVHSKTGYSGVGTESSPGVAWWVGWVE
KGTEVYFFAFNMDIDNESKLPSRKSISTKIMASEGIIIGG SEQ ID No. 1248:
MKTFAAYVITACLSSTALASSITENTFWNKEFSAEAVNGVFVLCKSSSKLACATNNLA
RASKEYLPASTFKIPNAIIGLETGVIKNEHQIFKWDGKPRAMKQWERDLSLRGAIQVS
AVPVFQQIAREVGEVRMQKYLKKFSYGNQNISGGIDKFWLEGQLRISAVNQVEFLE
SLFLNKLSASKENQLIVKEALVTEAPEYLVHSKTGFSGVGTESNPGVAWWVGWVEK
GAEVYFFAFNMDIDNENKLPLRKSIPTKIMASEGIIGG SEQ ID No. 1249:
MAIRIFAILFSTFVFGTFAHAQEGMRERSDWRKFFSEFQAKGTIVVADERQTDRVILV
FDQVRSEKRYSPASTFKIPHTLFALDAGAARDEFQVFRWDGIKRSFAAHNQDQDLR
SAMRNSTVWIYELFAKEIGEDKARRYLKQIDYGNADPSTSNGDYWIDGNLAIAAQEQ
IAFLRKLYHNELPFRVEHQRLVKDLMIVEAGRNWILRAKTGWEGRMGWWVGWVE
WPTGPVFFALNIDTPNRMDDLFKREAIVRAILRSIEALPPNPAVNSDAAR SEQ ID No. 1250:
MKTFAAYVIIACLSSTALAGSITENTSWNKEFSAEAVNGVFVLCKSSSKSCATNDLAR
ASKEYLPASTFKIPNAIIGLETGVIKNEHQVFKWDGKPRAMKQWERDLTLRGAIQVS
AVPVFQQIAREVGEVRMQKYLKKFSYGSQNISGGIDKFWLEDGQLRISAVNQVEFLES
LYLNKLSASKENQLIVKEALVTEAAPEYLVHSKTGFSGVGTESNPGVAWWVGWVEK
ETEVYFFAFNMDIDNESKLPLRKSIPTKIMESEGIIGG SEQ ID No. 1251:
MNKYFTCYVVASLFLSGCTVQHNLINETPSQIVQGHNQVIHQYFDEKNTSGVLVIQT
DKKINLYGNALSRANTEYVPASTFKMLNALIGLENQKTDINEIFKWKGEKRSFTAWE
KDMTLGEAMKLSAVPVYQELARRIGLDLMQKEVKRIGFGNAEIGQQVDNFWLVGPL
KVTPIQEVEFVSQLAHTQLPFSEKVQANVKNMLLLEESNGYKIFGKTGWAMDIKPQV
GWLTGWVEQPDGKIVAFALNMEMRSEMPASIRNELLMKSLKQLNII SEQ ID No. 1252:
MKKLSVLLWLTLFYCGTIWAQSTCFLVQENQTVLKHEGKDCNKRFAPESTFKIALSL
MGFDSGILKDTLNPEWPYKKEYELYLNVWKYPHNPRTWIRDSCVWYSQVLTQQLG

```
-continued
MTRFKNYVDAFHYGNQDISGDKGNNGLTHSWLSSSLAISPSEQIQFLQKIVNKKLS
VNPKAFTMTKDILYIQELAGGWKLYGKTGNGRQLTKDKSQKLSLQHGWFIGWIEKD
GRVITFTKHIADSKKHVTFASFRAKNETLNQLFYLINELEK SEQ ID No. 1253:
MNIKTLLLITSAIFISACSPYIVTANPNHSASKSDEKAEKIKNLFNEVHTTGVLVIQQGQ
TQQSYGNDLARASTEYVPASTFKMLNALIGLEHHKATTTEVFKWDGQKRLFPEWEK
DMTLGDAMKASAIPVYQDLARRIGLELMSKEVKRVGYGNADIGTQVDNFWLVGPLK
ITPQQEAQFAYKLANKTLPFSPKVQDEVQSMLFIEEKNGNKIYAKSGWGWDVDPQV
GWLTGWVVQPQGNIVAFSLNLEMKKGIPSSVRKEITYKSLEQLGIL SEQ ID No. 1254:
MKFRHALSSAFVLLGCIAASAHAKTICTAIADAGTGKLLVQDGDCGRRASPASTFKIA
ISLMGYDAGFLRNEHDPVLPYRDSYIAWGGEAWKQPTDPTRWLKYSVVWYSQQV
AHHLGAQRFAQYAKAFGYGNADVSGDPGQNNGLDRAWIGSSLQISPLEQLEFLGK
MLNRKLPVSPTAVDMTERIVESTTLADGTVVHGKTGVSYPLLADGTRDWARGSGW
FVGWIVRGNQTLVFARLTQDERKQPVSAGIRTREAFLRDLPRLLAAR SEQ ID No. 1255:
MKFRHALSSAFVLLGCIAASAHAKTICTAIADAGTGKLLVQDGDCGRRASPASTFKIA
ISLMGYDAGFLRNEHDPVLPYRDSYIAWGGEAWKQPTDPTRWLKYPVVWYSQQV
AHHLGAQRFAQYAKAFGYGNADVSGDPGQNNGLDRAWIGSSLQISPLEQLEFLGK
MLNRKLPVSPTAVDMTERIVESTTLADGTVVHGKTGVSYPLLADGTRDWARGSGW
FVGWIVRGKQTLVFARLTQDERKQPVSAGIRTREAFLRDLPRLLAAR SEQ ID No. 1256:
MRGKHTVILGAALSALFAGAAGAQMLECTLVADAASGQELYRKGACDKAFAPMSTF
KVPLAVMGYDAGILVDAHNPRWDYKPEFNGYKFQQKTTDPTIWEKDSIVWYSQQLT
RKMGQKRFAAYVAGFGYGNGDISGEPGKSNGLTHSWLGSSLKISPEGQVRFVRDL
LSAKLPASKDAQQMTVSILPHFAAGDWAVQGKTGTGSFIDARGAKAPLGWFIGWAT
HEERRVVFARMTAGGKKGEQPAGPAARDAFLKALPDLAKRF SEQ ID No. 1257:
MKFRHALSSAFVLLGCIAASAHAKTICTAIADAGTGKLLVQDGDCGRRASPASTFKIA
ISLMGYDAGFLRNEHDPVLPYRDSYIAWGGEAWKQPTDPTRWLKYSVVWYSQQV
AHHLGAQRFAQYAKAFGYGNADVSGDPGQNNGLDRAWIGSSLQISPLEQLEFLGK
MLDRKLPVSPTAVDMTERIVESTTLADGTVVHGKTGVSYPLLADGTRDWARGSGW
FVGWIVRGKQTLVFARLTQDERKQPVSAGIRTREAFLRDLPRLLAAR SEQ ID No. 1258:
MKFRHALSSAFVLLGCIAASAHAKTICTAIADAGTGKLLVQDGDCGRRASPASTFKIA
ISLMGYDAGFLRNEHDPVLPYRDSYIAWGGEAWKQPTDPTRWLKYSVVWYSQQV
AHHLGAQRFAQYAKAFGYGNADVSGDPGQNNGLDRAWIGSSLQISPLEQLEFLGK
MLNRKLPVSPTAVDMTERIVESTTLADGTVVHGKTGVSYPLLADGTRDWARGSGW
FVGWIVRGKQTLVFARLTQDERKQPVSAGIRTREAFLRDLPRLLAAR SEQ ID No. 1259:
MKTFAAYVIIACLSSTALAGSITENTSWNKEFSAEAVNGVFVLCKSSSKSCATNDLAR
ASKEYLPVSTFKIPSAIIGLETGVIKNEHQVFKWDGKPRAMKQWERDLTLRGAIQVS
AVPVFQQIAREVGEVRMQKYLKKFSYGNQNISGGIDKFWLEGQLRISAVNQVEFLE
SLYLNKLSASKENQLIVKEALVTEAAPEYLVHSKTGFSGVGTESNPGVAWWVGWVE
KETEVYFFAFNMDIDNESKLPRKSIPTKIMESEGIIGG SEQ ID No. 1260:
MNIKALLLITSAIFISACSPYIVTANPNHSASKSDEKAEKIKNLFNEAHTTGVLVIQQGQ
TQQSYGNDLARASTEYVPASTFKMLNALIGLEHHKATTTEVFKWDGKKRLFPEWEK
DMTLGDAMKASAIPVYQDLARRIGLELMSKEVKRVGYGNADIGTQVDNFWLVGPLK
ITPQQEAQFAYKLANKTLPFSQKVQDEVQSMLFIEEKNGNKIYAKSGWGWDVDPQV
GWLTGWVVQPQGNIVAFSLNLEMKKGIPSSVRKEITYKSLEQLGIL SEQ ID No. 1261:
MNIKALLLITSAIFISACSPYIVSANPNHSASKSDEKAEKIKNLFNEAHTTGVLVIQQGQ
TQQSYGNDLARASTEYVPASTFKMLNALIGLEHHKATTTEVFKWDGQKRLFPEWEK
NMTLGDAMKASAIPVYQDLARRIGLELMSNEVKRVGYGNADIGTQVDNFWLVGPLK
ITPQQEAQFAYKLANKTLPFSQKVQDEVQSMLFIEEKNGNKIYAKSGWGWDVNPQV
GWLTGWVVQPQGNIVAFSLNLEMKKGIPSSVRKEITYKSLEQLGIL SEQ ID No. 1262:
MKTFAAYVITACLSSTALASSITENTFWNKEFSAEAVNGVFVLCKSSSKSCATNNLA
RASKEYLPASTFKIPNAIIGLETGVIKNEHQVFKWDGKPRAMKQWERDLSLRGAIQV
SAVPVFQQIAREVGEVRMQKYLKKFSYGNQNISGGIDKFWLEGQLRISAVNQVEFL
ESLFLNKLSASKENQLIVKEALVTEAAPEYLVHSKTGFSGVGTESNPGVAWWVGWV
EKGTEVYFFAFNMDIDNENKLPRKSIPTKIMASEGIIGG SEQ ID No. 1263:
MKTIAAYLVLVFFAGTALSESISENLAWNKEFSSESVHGVFVLCKSSSNSCTTNNAT
RASTAYIPASTFKIPNALIGLETGAIKDARQVFKWDGKPRAMKQWEKDLTLRGAIQV
SAVPVFQQIARDIGKKRMQKYLNLFSYGNANIGGGIDKFWLEGQLRISAVNQVKFLE
SLYLNNLPASKANQLIVKEAIVTEATPEYIVHSKTGYSGVGTESNPGVAWWVGWVE
KGTEVYFFAFNMDIDNESKLPSRKSIPTKIMASEGIIGG
```

-continued

SEQ ID No. 1264:
MKKFILPIFSISILVSLSACSSIKTKSEDNFHISSQQHEKAIKSYFDEAQTQGVIIIKEGK
NLSTYGNALARANKEYVPASTFKMLIALIGLENHKATTNEIFKWDGKKRTYPMWEKD
MTLGEAMALSAVPVYQELARRTGLELMQKEVKRVNFGNTNIGTQVDNFWLVGPLKI
TPVQEVNFADDLAHNRLPFKLETQEEVKKMLLIKEVNGSKIYAKSGWGMGVTPQVG
WLTGWVEQANGKKIPFSLNLEMKEGMSGSIRNEITYKSLENLGII

SEQ ID No. 1265:
MNIKALLLITSAIFISACSPYIVTANPNHSASKSDDKAEKIKNLFNEAHTTGVLVIHQGQ
TQQSYGNDLARASTEYVPASTFKMLNALIGLEHHKATTTEVFKWNGQKRLFPEWEK
DMTLGDAMKASAIPVYQDLARRIGLELMSNEVKRVGYGNADIGTQVDNFWLVGPLK
ITPQQEAQFAYKLANKTLPFSQKVQDEVQSMLFIEEKNGNKIYAKSGWGWDVDPQV
GWLTGWVVQPQGNIVAFSLNLEMKKGIPSSVRKEITYKSLEQLGIL

SEQ ID No. 1266:
MNIKALLLITSAISISACSPYIVTANPNHSASKSDEKAEKIKNLFNEAHTTGVLVIQQGQ
TQQSYGNDLARASTEYVPASTFKMLNALIGLEHHKATTTEVFKWDGQKRLFPEWEK
DMTLGDAIKASAIPVYQDLARRIGLELMSKEVKRVGYGNADIGTQVDNFWLVGPLKI
TPQQEAQFAYKLANKTLPFSQKVQDEVQSMLFIEEKNGNKIYAKSGWGWDVDPQV said peptides being chosen, preferably, from the peptides of sequence SEQ ID No. 1267 to SEQ ID No. 1835 and SEQ ID No. 2160 to SEQ ID No. 2171 as defined hereafter:

| Peptide SEQ ID No. | Amino acid sequence | Position of the peptide in the OXA protein(s) | Clinical interest |
|---|---|---|---|
| SEQ ID No. 1267 | AAAYELAENLFEAGQADGWR | 183-202 for the proteins of SEQ No. 1191 | 2d |
| SEQ ID No. 1268 | AAEGFIPASTFK | 86-97 for the proteins of SEQ No. 1139 | 2df |
| SEQ ID No. 1269 | AALGR | 41-45 for the proteins of SEQ No. 1140 | 2df |
| SEQ ID No. 1270 | ADGQVVAFALNMQMK | 241-255 for the proteins of SEQ No. 1168, 1171, 1216 | 2df |
| SEQ ID No. 1271 | ADINEIFK | 95-102 for the proteins of SEQ No. 1124 | 2df |
| SEQ ID No. 1272 | ADWGK | 50-54 for the proteins of SEQ No. 1140 | 2df |
| SEQ ID No. 1273 | AEGAIVISDER | 40-50 for the proteins of SEQ No. 1127, 1130 | OXA |
| SEQ ID No. 1274 | AFALNLDIDK | 222-231 for the proteins of SEQ No. 1143 | 2d |
| SEQ ID No. 1275 | AFAPMSTFK | 49-57 for the proteins of SEQ No. 1256; 60-68 for the protein of sequence SEQ ID No. 1109 | OXA |
| SEQ ID No. 1276 | AFGYGNADVSGDPGQNNGLDR | 127-147 for the proteins of SEQ No. 1254, 1255, 1257, 1258 | 2d |
| SEQ ID No. 1277 | AFTMTK | 174-179 for the proteins of SEQ No. 1252 | 2de |
| SEQ ID No. 1278 | AGDDIALR | 256-263 for the proteins of SEQ No. 1168, 1171, 1216 | 2df |
| SEQ ID No. 1279 | AGHVYAFALNIDMPR | 233-247 for the proteins of SEQ No. 1137 | 2df |
| SEQ ID No. 1280 | AGLWR | 11-15 for the proteins of SEQ No. 1140 | 2df |
| SEQ ID No. 1281 | AHTEYVPASTFK | 73-84 for the proteins of SEQ No. 1205, 1224 | 2df |
| SEQ ID No. 1282 | AIIPWDGK | 112-119 for the proteins of SEQ No. 1140 | 2df |
| SEQ ID No. 1283 | AIIPWDGKPR | 112-121 for the proteins of SEQ No. 1140 | 2df |

-continued

| Peptide SEQ ID No. | Amino acid sequence | Position of the peptide in the OXA protein(s) | Clinical interest |
|---|---|---|---|
| SEQ ID No. 1284 | AISDITITR | 190-198 for the proteins of SEQ No. 1144 | 2d |
| SEQ ID No. 1285 | AISGK | 82-86 for the proteins of SEQ No. 1228 | 2df |
| SEQ ID No. 1286 | ALGQDR | 121-126 for the proteins of SEQ No. 1191 | 2d |
| SEQ ID No. 1287 | ALPDLAK | 256-262 for the proteins of SEQ No. 1256 | 2d |
| SEQ ID No. 1288 | ALQAK | 254-258 for the proteins of SEQ No. 1228 | 2df |
| SEQ ID No. 1289 | AMETFSPASTFK | 50-61 for the proteins of SEQ No. 1143 | 2d |
| SEQ ID No. 1290 | AMLFLQER | 196-203 for the proteins of SEQ No. 1227 | 2df |
| SEQ ID No. 1291 | AMLVFDPVR | 55-63 for the proteins of SEQ No. 1108, 1125, 1128, 1173, 1201, 1239, 1246; 44-52 for the protein of sequence SEQ ID No. 1120 | OXA |
| SEQ ID No. 1292 | AMTLLESGPGWELHGK | 189-204 for the proteins of SEQ No. 1138 | 2d |
| SEQ ID No. 1293 | ANLHITLHGK | 199-208 for the proteins of SEQ No. 1144 | 2d |
| SEQ ID No. 1294 | ANQLIVK | 183-189 for the proteins of SEQ No. 1247, 1263 | OXA |
| SEQ ID No. 1295 | ANTEYVPASTFK | 71-82 for the proteins of SEQ No. 1124, 1132, 1145, 1198, 1199, 1217, 1218, 1219, 1220, 1221, 1222, 1223, 1244, 1251; 66-77 for the protein of sequence SEQ ID No. 1227 | 2df |
| SEQ ID No. 1296 | ANVSR | 133-137 for the proteins of SEQ No 1138 | 2d |
| SEQ ID No. 1297 | APIGWFIGWATR | 224-235 for the proteins of SEQ No. 1109 | 2de |
| SEQ ID No. 1298 | APLGWFIGWATHEER | 213-227 for the proteins of SEQ No. 1256 | 2d |
| SEQ ID No. 1299 | AQDEVQSMLFIEEK | 196-209 for the proteins of SEQ No. 1161 | 2df |
| SEQ ID No. 1300 | AQGVIVLWNENK | 40-51 for the proteins of SEQ No. 1142 | 2df |
| SEQ ID No. 1301 | ASAIAVYQDLAR | 126-137 for the proteins of SEQ No. 1225 | 2df |
| SEQ ID No. 1302 | ASAILVYQDLAR | 126-137 for the proteins of SEQ No. 1175, 1184, 1215, 1230 | 2df |
| SEQ ID No. 1303 | ASAIPVYQDLAR | 126-137 for the proteins of SEQ No. 1146, 1147, 1148, 1149, 1150, 1151, 1152, 1153, 1154, 1156, 1157, 1160, 1161, 1162, 1163, 1164, 1165, 1166, 1167, 1169, 1170, 1174, 1176, 1177, 1178, 1181, 1182, 1183, 1185, 1186, 1192, 1194, 1195, 1197, 1202, 1203, 1204, 1206, 1211, 1212, 1213, 1214, 1226, 1233, 1236, 1237, 1238, 1240, 1241, 1253, 1260, 1261, 1265, 1266; 120-131 for the protein of sequence SEQ ID No. 1189; 120-131 for the protein of sequence SEQ ID No. 1190 | 2df |
| SEQ ID No. 1304 | ASAIPVYQDLPR | 126-137 for the proteins of SEQ No. 1155 | 2df |

-continued

| Peptide SEQ ID No. | Amino acid sequence | Position of the peptide in the OXA protein(s) | Clinical interest |
|---|---|---|---|
| SEQ ID No. 1305 | ASAIQVYQDLAR | 126-137 for the proteins of SEQ No. 1179, 1231 | 2df |
| SEQ ID No. 1306 | ASAISVYQDLAR | 126-137 for the proteins of SEQ No. 1158, 1245 | 2df |
| SEQ ID No. 1307 | ASALPVYQDLAR | 126-137 for the proteins of SEQ No. 1159, 1180 | 2df |
| SEQ ID No. 1308 | ASAMPVYQDLAR | 126-137 for the proteins of SEQ No, 1232 | 2df |
| SEQ ID No. 1309 | ASAVPVYQDLAR | 126-137 for the proteins of SEQ No. 1196, 1209, 1210 | 2df |
| SEQ ID No. 1310 | ASIEYVPASTFK | 72-83 for the proteins of SEQ No. 1157, 1161 | 2df |
| SEQ ID No. 1311 | ASNVPVYQELAR | 113-124 for the proteins of SEQ No. 1138 | 2d |
| SEQ ID No. 1312 | ASPASTFK | 49-56 for the proteins of SEQ No. 1254, 1255, 1257, 1258 | 2d |
| SEQ ID No. 1313 | ASTAYIPASTFK | 59-70 for the proteins of SEQ No. 1247, 1263 | OXA |
| SEQ ID No. 1314 | ASTEYVPASTFK | 72-83 for the proteins of SEQ No. 1146, 1147, 1148, 1149, 1150, 1151, 1152, 1153, 1154, 1155, 1156, 1158, 1159, 1160, 1162, 1163, 1164, 1165, 1166, 1167, 1169, 1170, 1174, 1175, 1176, 1177, 1178, 1179, 1180, 1181, 1182, 1183, 1184, 1185, 1186, 1192, 1194, 1195, 1196, 1197, 1202, 1203, 1204, 1206, 1209, 1210, 1211, 1212, 1213, 1214, 1215, 1225, 1226, 1230, 1231, 1232, 1233, 1236, 1237, 1238, 1240, 1241, 1245, 1253, 1260, 1261, 1265, 1266; 66-77 for the protein of sequence SEQ ID No. 1189; 66-77 for the protein of sequence SEQ ID No. 1190 | 2df |
| SEQ ID No. 1315 | ASTTEVFK | 96-103 for the proteins of SEQ No. 1202 | 2df |
| SEQ ID No. 1316 | ATSEIFK | 99-106 for the proteins of SEQ No. 1168, 1171, 1216 | 2df |
| SEQ ID No. 1317 | ATTNEIFK | 97-104 for the proteins of SEQ No. 1122, 1123, 1129, 1172, 1207, 1224, 1264; 90-97 for the protein of sequence SEQ ID No. 1227 | 2df |
| SEQ ID No. 1318 | ATTTAVFK | 96-103 for the proteins of SEQ No. 1154 | 2df |
| SEQ ID No. 1319 | ATTTEIFK | 97-104 for the proteins of SEQ No. 1205; 96-103 for the protein of sequence SEQ ID No. 1157; 96-103 for the protein of sequence SEQ ID No. 1161; 96-103 for the protein of sequence SEQ ID No. 1169 | 2df |
| SEQ ID No. 1320 | ATTTEVFK | 96-103 for the proteins of SEQ No. 1146, 1147, 1148, 1149, 1150, 1151, 1152, 1155, 1156, 1158, 1159, 1160, 1162, 1163, 1164, 1165, 1166, 1167, 1170, 1174, 1175, 1176, 1177, 1178, 1179, 1180, 1181, 1182, 1183, 1184, 1185, 1192, 1194, 1195, 1196, 1197, 1203, 1204, 1206, 1209, 1210, 1211, 1212, 1213, 1214, 1215, 1225, 1226, 1230, 1231, 1232, 1233, 1236, 1237, 1238, 1240, 1241, 1245, 1253, 1260, 1261, 1265, 1266; 90-97 for the protein of sequence SEQ ID No. 1189; 90-97 for the protein of sequence SEQ ID No. 1190 | 2df |

-continued

| Peptide SEQ ID No. | Amino acid sequence | Position of the peptide in the OXA protein(s) | Clinical interest |
|---|---|---|---|
| SEQ ID No. 1321 | AVSDITILEQTDNYTLHGK | 191-209 for the proteins of SEQ No. 1235 | OXA |
| SEQ ID No. 1322 | AVSDITILEQTYNYTLHGK | 191-209 for the proteins of SEQ No, 1187, 1188 | 2d |
| SEQ ID No. 1323 | AVVPHFEAGDWDVQGK | 195-210 for the proteins of SEQ No, 1109 | 2de |
| SEQ ID No. 1324 | AWEHDMSLR | 100-108 for the proteins of SEQ No. 1138 | 2d |
| SEQ ID No. 1325 | AWIGSSLQISPLEQLEFLGK | 148-167 for the proteins of SEQ No. 1254, 1255, 1257, 1258 | 2d |
| SEQ ID No. 1326 | CAAQMAPDSTFK | 63-74 for the proteins of SEQ No. 1134 | 2d |
| SEQ ID No. 1327 | CATQMAPDSTFK | 48-59 for the proteins of SEQ No. 1119; 63-74 for the protein of sequence SEQ ID No. 1118 | 2d |
| SEQ ID No. 1328 | CTIIADAITGNTLYETGECAR | 32-52 for the proteins of SEQ No. 1107 | 2d |
| SEQ ID No. 1329 | DAFLK | 251-255 for the proteins of SEQ No. 1256 | 2d |
| SEQ ID No. 1330 | DDFILHGK | 189-196 for the proteins of SEQ No. 1135 | 2d |
| SEQ ID No. 1331 | DDQEVLPYGGK | 92-102 for the proteins of SEQ No. 1137 | 2df |
| SEQ ID No. 1332 | DDVLK | 87-91 for the proteins of SEQ No. 1228 | 2df |
| SEQ ID No. 1333 | DEFHVFR | 90-96 for the proteins of SEQ No. 1113, 1121 | 2d |
| SEQ ID No. 1334 | DEFQIFR | 90-96 for the proteins of SEQ No. 1108, 1125, 1128, 1133, 1173, 1201, 1239, 1246; 79-85 for the protein of sequence SEQ ID No. 1120 | OXA |
| SEQ ID No. 1335 | DEFQVFR | 90-96 for the proteins of SEQ No. 1114, 1127, 1130, 1131, 1242, 1249 | 2d |
| SEQ ID No. 1336 | DELVR | 260-264 for the proteins of SEQ No. 1191 | 2d |
| SEQ ID No. 1337 | DETSR | 112-116 for the proteins of SEQ No. 1139 | 2df |
| SEQ ID No. 1338 | DFDYGNQDFSGDK | 141-153 for the proteins of SEQ No. 1118, 1134; 126-138 for the protein of sequence SEQ ID No. 1119 | 2d |
| SEQ ID No. 1339 | DFTLGEAMQASTVPVYQELAR | 120-140 for the proteins of SEQ No. 1168, 1171, 1216 | 2df |
| SEQ ID No. 1340 | DGNITSVAINIDMESEADAPK | 250-270 for the proteins of SEQ No. 1140 | 2df |
| SEQ ID No. 1341 | DHDLITAMK | 108-116 for the proteins of SEQ No. 1142, 1243 | 2df |
| SEQ ID No. 1342 | DIAAWNR | 101-107 for the proteins of SEQ No. 1142, 1243 | 2df |
| SEQ ID No. 1343 | DIGEDK | 131-136 for the proteins of SEQ No. 1131 | 2d |
| SEQ ID No. 1344 | DILYIQELAGGWK | 180-192 for the proteins of SEQ No. 1252 | 2de |

-continued

| Peptide SEQ ID No. | Amino acid sequence | Position of the peptide in the OXA protein(s) | Clinical interest |
|---|---|---|---|
| SEQ ID No. 1345 | DITILEK | 181-187 for the proteins of SEQ No. 1135 | 2d |
| SEQ ID No. 1346 | DLLSAK | 166-171 for the proteins of SEQ No. 1256 | 2d |
| SEQ ID No. 1347 | DLMITEAGR | 195-203 for the proteins of SEQ No. 1127, 1130, 1131 | 2d |
| SEQ ID No. 1348 | DLMIVEAGR | 195-203 for the proteins of SEQ No. 1108, 1114, 1125, 1128, 1133, 1173, 1201, 1239, 1246, 1249; 184-192 for the protein of sequence SEQ ID No. 1120 | OXA |
| SEQ ID No. 1349 | DLMIVEAK | 195-202 for the proteins of SEQ No. 1113, 1121 | 2d |
| SEQ ID No. 1350 | DLPLR | 243-247 for the proteins of SEQ No. 1228 | 2df |
| SEQ ID No. 1351 | DLSGNPGK | 131-138 for the proteins of SEQ No. 1105 | 2d |
| SEQ ID No. 1352 | DLSLR | 105-109 for the proteins of SEQ No. 1115, 1116, 1117, 1126, 1141, 1200, 1229, 1262; 106-110 for the protein of sequence SEQ ID No. 1248 | OXA |
| SEQ ID No. 1353 | DLTLR | 105-109 for the proteins of SEQ No. 1110, 1193, 1250, 1259, 1263; 96-100 for the protein of sequence SEQ ID No. 1106; 96-100 for the protein of sequence SEQ ID No. 1111; 96-100 for the protein of sequence SEQ ID No. 1112 | OXA |
| SEQ ID No. 1354 | DMTLGDAIK | 117-125 for the proteins of SEQ No. 1226, 1266 | 2df |
| SEQ ID No. 1355 | DMTLGDAMALSAVPVYQELAR | 118-138 for the proteins of SEQ No. 1205 | 2df |
| SEQ ID No. 1356 | DMTLGDAMK | 117-125 for the proteins of SEQ No. 1147, 1148, 1149, 1152, 1153, 1156, 1157, 1158, 1159, 1161, 1162, 1165, 1166, 1167, 1169, 1170, 1175, 1176, 1178, 1179, 1181, 1183, 1184, 1185, 1186, 1194, 1195, 1196, 1197, 1202, 1209, 1210, 1211, 1212, 1213, 1214, 1215, 1225, 1230, 1231, 1232, 1236, 1237, 1238, 1240, 1241, 1245, 1253, 1260, 1265 | 2df |
| SEQ ID No. 1357 | DMTLGEAMALSAVPVYQDLAR | 118-138 for the proteins of SEQ No. 1224 | 2df |
| SEQ ID No. 1358 | DMTLGEAMALSAVPVYQELAR | 118-138 for the proteins of SEQ No. 1122, 1123, 1129, 1172, 1207, 1264 | 2df |
| SEQ ID No. 1359 | DMTLGEAMK | 116-124 for the proteins of SEQ No. 1124, 1132, 1145, 1198, 1199, 1217, 1218, 1219, 1220, 1221, 1222, 1223, 1244, 1251 | 2df |
| SEQ ID No. 1360 | DMTLGQAMQASAVPVYQELAR | 111-131 for the proteins of SEQ No. 1227 | 2df |
| SEQ ID No. 1361 | DNNGK | 214-218 for the proteins of SEQ No. 1107 | 2d |
| SEQ ID No. 1362 | DQDLR | 110-114 for the proteins of SEQ No. 1108, 1114, 1125, 1127, 1128, 1130, 1131, 1133, 1173, 1201, 1239, 1242, 1246, 1249; 99-103 for the protein of sequence SEQ ID No. 1120 | 2d |
| SEQ ID No. 1363 | DQQIGWFVGWASK | 213-225 for the proteins of SEQ No. 1105 | 2d |
| SEQ ID No. 1364 | DQQIGWFVGWASKPGK | 213-228 for the proteins of SEQ No. 1105 | 2d |

-continued

| Peptide SEQ ID No. | Amino acid sequence | Position of the peptide in the OXA protein(s) | Clinical interest |
|---|---|---|---|
| SEQ ID No. 1365 | DQQVQVYGNDLNR | 53-65 for the proteins of SEQ No. 1227 | 2df |
| SEQ ID No. 1366 | DQSFR | 132-136 for the proteins of SEQ No. 1139 | 2df |
| SEQ ID No. 1367 | DQTLESAFK | 105-113 for the proteins of SEQ No. 1228 | 2df |
| SEQ ID No. 1368 | DSCVWYSQVLTQQLGMTR | 98-115 for the proteins of SEQ No. 1252 | 2de |
| SEQ ID No. 1369 | DSIVWYSQELTR | 113-124 for the proteins of SEQ No. 1109 | 2de |
| SEQ ID No. 1370 | DSIVWYSQQLTR | 102-113 for the proteins of SEQ No. 1256 | 2d |
| SEQ ID No. 1371 | DSNLR | 109-113 for the proteins of SEQ No. 1187, 1188, 1235; 96-100 for the protein of sequence SEQ ID No. 1135; 108-112 for the protein of sequence SEQ ID No. 1144 | 2d |
| SEQ ID No. 1372 | DSYIAWGGEAWK | 81-92 for the proteins of SEQ No. 1254, 1255, 1257, 1258 | 2d |
| SEQ ID No. 1373 | DTLNPEWPYK | 67-76 for the proteins of SEQ No. 1252 | 2de |
| SEQ ID No. 1374 | DVDEVFYK | 88-95 for the proteins of SEQ No. 1144, 1187, 1188, 1235 | 2d |
| SEQ ID No. 1375 | DVSGDPGK | 144-151 for the proteins of SEQ No, 1109 | 2de |
| SEQ ID No. 1376 | DWILR | 204-208 for the proteins of SEQ No. 1113, 1121 | 2d |
| SEQ ID No. 1377 | DWPAMAGAWR | 265-274 for the proteins of SEQ No. 1191 | 2d |
| SEQ ID No. 1378 | EAFLR | 256-260 for the proteins of SEQ No. 1254, 1255, 1257, 1258 | 2d |
| SEQ ID No. 1379 | EAIAR | 250-254 for the proteins of SEQ No. 1113, 1121, 1127, 1130, 1131, 1133, 1242 | 2d |
| SEQ ID No. 1380 | EAIVR | 250-254 for the proteins of SEQ No. 1108, 1114, 1125, 1128, 1173, 1201, 1239, 1246, 1249; 239-243 for the protein of sequence SEQ ID No. 1120 | OXA |
| SEQ ID No. 1381 | EAIVTEATPEYIVHSK | 190-205 for the proteins of SEQ No. 1247, 1263 | OXA |
| SEQ ID No. 1382 | EALVTEAAPEYLVHSK | 190-205 for the proteins of SEQ No. 1110, 1115, 1116, 1117, 1126, 1141, 1193, 1200, 1229, 1250, 1259, 1262; 181-196 for the protein of sequence SEQ ID No. 1106; 181-196 for the protein of sequence SEQ ID No. 1111; 181-196 for the protein of sequence SEQ ID No. 1112 | OXA |
| SEQ ID No. 1383 | EALVTEAPEYLVHSK | 191-205 for the proteins of SEQ No. 1248 | 2d |
| SEQ ID No. 1384 | EEIVR | 240-244 for the proteins of SEQ No. 1135 | 2d |
| SEQ ID No. 1385 | EEVLAALPAQLK | 251-262 for the proteins of SEQ No. 1105 | 2d |
| SEQ ID No. 1386 | EFNGSK | 209-214 for the proteins of SEQ No. 1205 | 2df |

-continued

| Peptide SEQ ID No. | Amino acid sequence | Position of the peptide in the OXA protein(s) | Clinical interest |
|---|---|---|---|
| SEQ ID No. 1387 | EFSAEAVNGVFVLCK | 31-45 for the proteins of SEQ No. 1110, 1115, 1116, 1117, 1126, 1141, 1193, 1200, 1229, 1248, 1250, 1259, 1262; 22-36 for the protein of sequence SEQ ID No. 1106; 22-36 for the protein of sequence SEQ ID No. 1111; 22-36 for the protein of sequence SEQ ID No. 1112 | OXA |
| SEQ ID No. 1388 | EFSSESVHGVFVLCK | 31-45 for the proteins of SEQ No. 1247, 1263 | OXA |
| SEQ ID No. 1389 | EGDMAK | 248-253 for the proteins of SEQ No. 1137 | 2df |
| SEQ ID No. 1390 | EGMSGSIR | 254-261 for the proteins of SEQ No. 1122, 1129, 1172, 1207, 1264 | 2df |
| SEQ ID No. 1391 | EGMTGSIR | 254-261 for the proteins of SEQ No. 1123 | 2df |
| SEQ ID No. 1392 | EGSCDK | 54-59 for the proteins of SEQ No. 1109 | 2de |
| SEQ ID No. 1393 | EIAVWNR | 125-131 for the proteins of SEQ No. 1139 | 2df |
| SEQ ID No. 1394 | EIAYK | 262-266 for the proteins of SEQ No. 1238 | 2df |
| SEQ ID No. 1395 | EIFER | 20-24 for the proteins of SEQ No. 1135 | 2d |
| SEQ ID No. 1396 | EIFYHYR | 79-85 for the proteins of SEQ No. 1143 | 2d |
| SEQ ID No. 1397 | EIGDDK | 131-136 for the proteins of SEQ No. 1108, 1125, 1128, 1173, 1201, 1239, 1246; 120-125 for the protein of sequence SEQ ID No. 1120 | OXA |
| SEQ ID No. 1398 | EIGDGK | 131-136 for the proteins of SEQ No. 1133 | 2d |
| SEQ ID No. 1399 | EIGEDK | 131-136 for the proteins of SEQ No. 1114, 1130, 1249 | 2d |
| SEQ ID No. 1400 | EIGEDNAR | 131-138 for the proteins of SEQ No. 1242 | OXA |
| SEQ ID No. 1401 | EIGENK | 131-136 for the proteins of SEQ No. 1113, 1121 | 2d |
| SEQ ID No. 1402 | EIGPK | 153-157 for the proteins of SEQ No. 1139 | 2df |
| SEQ ID No. 1403 | EIGSEIDK | 136-143 for the proteins of SEQ No. 1135 | 2d |
| SEQ ID No. 1404 | EITYK | 262-266 for the proteins of SEQ No. 1147, 1148, 1149, 1150, 1151, 1152, 1153, 1154, 1155, 1156, 1157, 1158, 1159, 1160, 1161, 1162, 1163, 1164, 1165, 1166, 1167, 1169, 1170, 1174, 1175, 1176, 1177, 1178, 1179, 1180, 1181, 1182, 1183, 1184, 1185, 1186, 1192, 1194, 1195, 1196, 1202, 1203, 1204, 1206, 1209, 1210, 1211, 1212, 1213, 1214, 1215, 1225, 1226, 1230, 1231, 1232, 1233, 1236, 1237, 1240, 1241, 1245, 1253, 1260, 1261, 1265, 1266; 263-267 for the protein of sequence SEQ ID No. 1122; 263-267 for the protein of sequence SEQ ID No. 1123; 263-267 for the protein of sequence SEQ ID No. 1129; 263-267 for the protein of sequence SEQ ID No. 1172; 256-260 for the protein of sequence SEQ ID No. 1189; 256-260 for the protein of sequence SEQ ID No. 1190; 263-267 for the | 2df |

-continued

| Peptide SEQ ID No. | Amino acid sequence | Position of the peptide in the OXA protein(s) | Clinical interest |
|---|---|---|---|
| | | protein of sequence SEQ ID No. 1205; 263-267 for the protein of sequence SEQ ID No. 1207; 263-267 for the protein of sequence SEQ ID No. 1224; 263-267 for the protein of sequence SEQ ID No. 1264 | |
| SEQ ID No. 1405 | EITYR | 262-266 for the proteins of SEQ No. 1146 | 2df |
| SEQ ID No. 1406 | EMIYLK | 181-186 for the proteins of SEQ No. 1143 | 2d |
| SEQ ID No. 1407 | EMLYVER | 205-211 for the proteins of SEQ No. 1168, 1171, 1216 | 2df |
| SEQ ID No. 1408 | EMTYK | 262-266 for the proteins of SEQ No. 1197 | 2df |
| SEQ ID No. 1409 | ENIEK | 138-142 for the proteins of SEQ No. 1187, 1188, 1235; 137-141 for the protein of sequence SEQ ID No. 1144 | 2d |
| SEQ ID No. 1410 | ENQLIVK | 183-189 for the proteins of SEQ No. 1110, 1115, 1116, 1117, 1126, 1141, 1193, 1200, 1229, 1250, 1259, 1262; 174-180 for the protein of sequence SEQ ID No. 1106; 174-180 for the protein of sequence SEQ ID No. 1111; 174-180 for the protein of sequence SEQ ID No. 1112; 184-190 for the protein of sequence SEQ ID No. 1248 | OXA |
| SEQ ID No. 1411 | EQAILLFR | 156-163 for the proteins of SEQ No. 1143 | 2d |
| SEQ ID No. 1412 | EQIQFLLR | 165-172 for the proteins of SEQ No. 1107 | 2d |
| SEQ ID No. 1413 | EQLAPDPQVQQQVK | 182-195 for the proteins of SEQ No. 1227 | 2df |
| SEQ ID No. 1414 | EQVDFVQR | 189-196 for the proteins of SEQ No. 1140 | 2df |
| SEQ ID No. 1415 | ETEVYFFAFNMDIDNESK | 229-246 for the proteins of SEQ No. 1110, 1193, 1250, 1259; 220-237 for the protein of sequence SEQ ID No. 1106; 220-237 for the protein of sequence SEQ ID No. 1111; 220-237 for the protein of sequence SEQ ID No. 1112 | OXA |
| SEQ ID No. 1416 | ETTTPR | 90-95 for the proteins of SEQ No. 1105 | 2d |
| SEQ ID No. 1417 | EVGEIR | 126-131 for the proteins of SEQ No. 1247 | 2d |
| SEQ ID No. 1418 | EVGEVR | 126-131 for the proteins of SEQ No. 1110, 1115, 1116, 1117, 1126, 1141, 1193, 1200, 1229, 1250, 1259, 1262; 117-122 for the protein of sequence SEQ ID No. 1106; 117-122 for the protein of sequence SEQ ID No. 1111; 117-122 for the protein of sequence SEQ ID No. 1112; 127-132 for the protein of sequence SEQ ID No. 1248 | OXA |
| SEQ ID No. 1419 | EVNGSK | 209-214 for the proteins of SEQ No. 1122, 1123, 1129, 1172, 1207, 1224, 1264 | 2df |
| SEQ ID No. 1420 | EWQENK | 24-29 for the proteins of SEQ No. 1136, 1208, 1234, 1243 | 2df |
| SEQ ID No. 1421 | EYELYLNVWK | 78-87 for the proteins of SEQ No. 1252 | 2de |
| SEQ ID No. 1422 | EYVPASTFK | 62-70 for the proteins of SEQ No. 1110, 1115, 1116, 1117, 1126, 1141, 1193, 1200, 1229, | OXA |

| Peptide SEQ ID No. | Amino acid sequence | Position of the peptide in the OXA protein(s) | Clinical interest |
|---|---|---|---|
| | | 1250, 1262; 53-61 for the protein of sequence SEQ ID No. 1106; 53-61 for the protein of sequence SEQ ID No. 1111; 53-61 for the protein of sequence SEQ ID No. 1112; 63-71 for the protein of sequence SEQ ID No. 1248 | |
| SEQ ID No. 1423 | EYLPVSTFK | 62-70 for the proteins of SEQ No. 1259 | 2de |
| SEQ ID No. 1424 | EYNTSGTFVFYDGK | 27-40 for the proteins of SEQ No. 1143 | 2d |
| SEQ ID No. 1425 | EYVPASTFK | 75-83 for the proteins of SEQ No. 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1169, 1170, 1174, 1175, 1176, 1177, 1178, 1179, 1180, 1181, 1182, 1183, 1184, 1185, 1186, 1192, 1194, 1195, 1196, 1197, 1202, 1203, 1204, 1206, 1209, 1210, 1211, 1212, 1213, 1214, 1215, 1225, 1226, 1230, 1231, 1232, 1233, 1236, 1237, 1238, 1240, 1241, 1245, 1253, 1260, 1261, 1265, 1266; 76-84 for the protein of sequence SEQ ID No. 1122; 76-84 for the protein of sequence SEQ ID No. 1123; 74-82 for the protein of sequence SEQ ID No. 1124; 76-84 for the protein of sequence SEQ ID No. 1129; 74-82 for the protein of sequence SEQ ID No. 1132; 74-82 for the protein of sequence SEQ ID No. 1145; 76-84 for the protein of sequence SEQ ID No. 1172; 69-77 for the protein of sequence SEQ ID No, 1189; 69-77 for the protein of sequence SEQ ID No. 1190; 74-82 for the protein of sequence SEQ ID No. 1198; 74-82 for the protein of sequence SEQ ID No. 1199; 76-84 for the protein of sequence SEQ ID No. 1205; 76-84 for the protein of sequence SEQ ID No. 1207; 74-82 for the protein of sequence SEQ ID No. 1217; 74-82 for the protein of sequence SEQ ID No. 1218; 74-82 for the protein of sequence SEQ ID No. 1219; 74-82 for the protein of sequence SEQ ID No. 1220; 74-82 for the protein of sequence SEQ ID No. 1221; 74-82 for the protein of sequence SEQ ID No. 1222; 74-82 for the protein of sequence SEQ ID No. 1223; 76-84 for the protein of sequence SEQ ID No. 1224; 69-77 for the protein of sequence SEQ ID No. 1227; 74-82 for the protein of sequence SEQ ID No. 1244; 74-82 for the protein of sequence SEQ ID No. 1251; 76-84 for the protein of sequence SEQ ID No. 1264 | 2df |
| SEQ ID No. 1426 | FAAYVAGFGYGNGDISGEPGK | 120-140 for the proteins of SEQ No. 1256 | 2d |
| SEQ ID No. 1427 | FAPESTFK | 45-52 for the proteins of SEQ No. 1252 | 2de |
| SEQ ID No. 1428 | FAQYAK | 121-126 for the proteins of SEQ No. 1254, 1255, 1257, 1258 | 2d |
| SEQ ID No. 1429 | FDYGNK | 138-143 for the proteins of SEQ No. 1109 | 2de |
| SEQ ID No. 1430 | FDYGNR | 146-151 for the proteins of SEQ No. 1137; 125-130 for the protein of sequence SEQ ID No. 1105 | 2d |
| SEQ ID No. 1431 | FEDLYK | 232-237 for the proteins of SEQ No. 1143 | 2d |
| SEQ ID No. 1432 | FEDTFHISNQK | 27-37 for the proteins of SEQ No. 1224 | 2df |

-continued

| Peptide SEQ ID No. | Amino acid sequence | Position of the peptide in the OXA protein(s) | Clinical interest |
|---|---|---|---|
| SEQ ID No. 1433 | FEDTFHTSNQQHEK | 27-40 for the proteins of SEQ No. 1205 | 2df |
| SEQ ID No. 1434 | FEYGNQDVSGDSGK | 133-146 for the proteins of SEQ No. 1107 | 2d |
| SEQ ID No. 1435 | FFSDFQAK | 34-41 for the proteins of SEQ No. 1133 | 2d |
| SEQ ID No. 1436 | FFSDLQAEGAIVIADER | 34-50 for the proteins of SEQ No. 1131, 1242 | 2d |
| SEQ ID No. 1437 | FFSDLR | 34-39 for the proteins of SEQ No. 1127, 1130 | OXA |
| SEQ ID No. 1438 | FFSEFQAK | 34-41 for the proteins of SEQ No. 1108, 1114, 1125, 1128, 1173, 1201, 1239, 1246, 1249; 23-30 for the protein of sequence SEQ ID No. 1120 | OXA |
| SEQ ID No. 1439 | FGLEGQLR | 153-160 for the proteins of SEQ No. 1117 | 2de |
| SEQ ID No. 1440 | FILPIFSISILVSLSACSSIK | 4-24 for the proteins of SEQ No. 1122, 1123, 1129, 1172, 1207, 1264 | 2df |
| SEQ ID No. 1441 | FLALLFSAVVLVSLGHAQDK | 5-24 for the proteins of SEQ No. 1121 | 2d |
| SEQ ID No. 1442 | FLALLFSAVVLVSLGHAQEK | 5-24 for the proteins of SEQ No. 1113 | 2d |
| SEQ ID No. 1443 | FLESLYLNNLPASK | 169-182 for the proteins of SEQ No. 1247, 1263 | OXA |
| SEQ ID No. 1444 | FLLEGQLR | 153-160 for the proteins of SEQ No. 1200 | 2de |
| SEQ ID No. 1445 | FQQYVDR | 118-124 for the proteins of SEQ No. 1105 | 2d |
| SEQ ID No. 1446 | FSDYVQR | 131-137 for the proteins of SEQ No. 1109 | 2de |
| SEQ ID No. 1447 | FSTASTFK | 63-70 for the proteins of SEQ No. 1228 | 2df |
| SEQ ID No. 1448 | FSWDGK | 117-122 for the proteins of SEQ No. 1139 | 2df |
| SEQ ID No. 1449 | FSYGNQNISGGIDK | 139-152 for the proteins of SEQ No. 1110, 1115, 1116, 1117, 1126, 1141, 1193, 1200, 1259, 1262; 130-143 for the protein of sequence SEQ ID No. 1106; 130-143 for the protein of sequence SEQ ID No. 1111; 130-143 for the protein of sequence SEQ ID No. 1112; 140-153 for the protein of sequence SEQ ID No. 1248 | OXA |
| SEQ ID No. 1450 | FSYGNQNISGGTDK | 139-152 for the proteins of SEQ No. 1229 | 2de |
| SEQ ID No. 1451 | FSYGSQNISGGIDK | 139-152 for the proteins of SEQ No. 1250 | 2de |
| SEQ ID No. 1452 | FTEYVK | 126-131 for the proteins of SEQ No. 1107 | 2d |
| SEQ ID No. 1453 | FVAHK | 173-177 for the proteins of SEQ No. 1107 | 2d |
| SEQ ID No. 1454 | FVPASTYK | 62-69 for the proteins of SEQ No. 1138 | 2d |

-continued

| Peptide SEQ ID No. | Amino acid sequence | Position of the peptide in the OXA protein(s) | Clinical interest |
|---|---|---|---|
| SEQ ID No. 1455 | FVYDLAQGQLPFK | 184-196 for the proteins of SEQ No. 1168, 1171, 1216 | 2df |
| SEQ ID No. 1456 | FVYDLAQGQLPFKPEVQQQVK | 184-204 for the proteins of SEQ No. 1168, 1171, 1216 | 2df |
| SEQ ID No. 1457 | FWLEDQLR | 153-160 for the proteins of SEQ No. 1116, 1193, 1229, 1250; 144-151 for the protein of sequence SEQ ID No. 1106; 144-151 for the protein of sequence SEQ ID No. 1111 | 2de |
| SEQ ID No. 1458 | FWLEGPLK | 144-151 for the proteins of SEQ No. 1135 | 2d |
| SEQ ID No. 1459 | FWLEGQLR | 153-160 for the proteins of SEQ No. 1110, 1115, 1126, 1141, 1247, 1259, 1262, 1263; 144-151 for the protein of sequence SEQ ID No. 1112; 154-161 for the protein of sequence SEQ ID No. 1248 | OXA |
| SEQ ID No. 1460 | FYPASSFK | 53-60 for the proteins of SEQ No. 1135 | 2d |
| SEQ ID No. 1461 | FYPASTFK | 66-73 for the proteins of SEQ No. 1144, 1187, 1188, 1235 | 2d |
| SEQ ID No. 1462 | GACDK | 44-48 for the proteins of SEQ No. 1256 | 2d |
| SEQ ID No. 1463 | GAEVYFFAFNMDIDNENK | 229-246 for the proteins of SEQ No. 1141, 1248 | 2d |
| SEQ ID No. 1464 | GAIQVSAVPVFQQIAR | 110-125 for the proteins of SEQ No. 1110, 1115, 1116, 1117, 1126, 1141, 1193, 1200, 1229, 1247, 1250, 1259, 1262, 1263; 101-116 for the protein of sequence SEQ ID No. 1106; 101-116 for the protein of sequence SEQ ID No. 1112; 111-126 for the protein of sequence SEQ ID No. 1248 | OXA |
| SEQ ID No. 1465 | GAIQVSAVPVFQQITR | 101-116 for the proteins of SEQ No. 1111 | 2de |
| SEQ ID No. 1466 | GDYWIDGNLEISAHEQISFLR | 156-176 for the proteins of SEQ No. 1127, 1130 | OXA |
| SEQ ID No. 1467 | GDYWIDGNLK | 156-165 for the proteins of SEQ No. 1131 | 2d |
| SEQ ID No. 1468 | GELPVSEDALEMTK | 181-194 for the proteins of SEQ No. 1109 | 2de |
| SEQ ID No. 1469 | GEQPAGPAAR | 241-250 for the proteins of SEQ No. 1256; 252-261 for the protein of sequence SEQ ID No. 1109 | OXA |
| SEQ ID No. 1470 | GFAGHNQDQDLR | 103-114 for the proteins of SEQ No. 1108, 1125, 1128, 1173, 1201, 1239, 1246; 92-103 for the protein of sequence SEQ ID No. 1120 | OXA |
| SEQ ID No. 1471 | GIPSSVR | 254-260 for the proteins of SEQ No. 1147, 1148, 1149, 1150, 1151, 1152, 1153, 1155, 1156, 1157, 1158, 1159, 1160, 1161, 1162, 1163, 1164, 1165, 1166, 1167, 1169, 1170, 1174, 1175, 1176, 1177, 1178, 1179, 1180, 1181, 1182, 1183, 1184, 1185, 1186, 1192, 1194, 1195, 1196, 1197, 1202, 1203, 1204, 1206, 1209, 1210, 1211, 1212, 1213, 1214, 1215, 1225, 1226, 1230, 1231, 1232, 1233, 1236, 1237, 1238, 1240, 1241, 1245, 1253, 1260, 1261, 1265, 1266; 248-254 for the protein of sequence SEQ ID No. 1189; 248-254 for the protein of sequence SEQ ID No. 1190 | 2df |

-continued

| Peptide SEQ ID No. | Amino acid sequence | Position of the peptide in the OXA protein(s) | Clinical interest |
|---|---|---|---|
| SEQ ID No. 1472 | GISSSVR | 254-260 for the proteins of SEQ No. 1146 | 2df |
| SEQ ID No. 1473 | GLNGTFVVYDLK | 26-37 for the proteins of SEQ No. 1135 | 2d |
| SEQ ID No. 1474 | GMEIWNSNHTPK | 101-112 for the proteins of SEQ No. 1118, 1134; 86-97 for the protein of sequence SEQ ID No. 1119 | 2d |
| SEQ ID No. 1475 | GNQTLVFAR | 230-238 for the proteins of SEQ No. 1254 | 2d |
| SEQ ID No. 1476 | GNYWIDGNLEISAHEQISFLR | 156-176 for the proteins of SEQ No. 1242 | OXA |
| SEQ ID No. 1477 | GPLEISAFEEAR | 164-175 for the proteins of SEQ No. 1137 | 2df |
| SEQ ID No. 1478 | GPLTITPIQEVK | 172-183 for the proteins of SEQ No. 1168, 1171, 1216 | 2df |
| SEQ ID No. 1479 | GSGWFVGWIVR | 219-229 for the proteins of SEQ No. 1254, 1255, 1257, 1258 | 2d |
| SEQ ID No. 1480 | GSLLLWDQK | 66-74 for the proteins of SEQ No. 1139 | 2df |
| SEQ ID No. 1481 | GTEVYFFAFNMDIDNENK | 229-246 for the proteins of SEQ No. 1115, 1116, 1117, 1126, 1200, 1229, 1262 | OXA |
| SEQ ID No. 1482 | GTEVYFFAFNMDIDNESK | 229-246 for the proteins of SEQ No. 1247, 1263 | OXA |
| SEQ ID No. 1483 | GTFVLYDVQR | 38-47 for the proteins of SEQ No. 1138 | 2d |
| SEQ ID No. 1484 | GTIVVADER | 42-50 for the proteins of SEQ No. 1108, 1114, 1125, 1128, 1133, 1173, 1201, 1239, 1246, 1249; 31-39 for the protein of sequence SEQ ID No. 1120 | OXA |
| SEQ ID No. 1485 | GTIVVLDAR | 63-71 for the proteins of SEQ No. 1140 | 2df |
| SEQ ID No. 1486 | GTIVVVDER | 42-50 for the proteins of SEQ No. 1113, 1121 | 2d |
| SEQ ID No. 1487 | GTLPFSAR | 200-207 for the proteins of SEQ No. 1140 | 2df |
| SEQ ID No. 1488 | GTPSSVR | 254-260 for the proteins of SEQ No. 1154 | 2df |
| SEQ ID No. 1489 | HALSSAFVLLGCIAASAHAK | 5-24 for the proteins of SEQ No. 1254, 1255, 1257, 1258 | 2d |
| SEQ ID No. 1490 | HIADSK | 234-239 for the proteins of SEQ No. 1252 | 2de |
| SEQ ID No. 1491 | HNGLTHAWLASSLK | 152-165 for the proteins of SEQ No. 1109 | 2de |
| SEQ ID No. 1492 | HNGLTQSWLMSSLTISPK | 147-164 for the proteins of SEQ No. 1107 | 2d |
| SEQ ID No. 1493 | HNGTDGAWIISSLR | 148-161 for the proteins of SEQ No. 1191 | 2d |
| SEQ ID No. 1494 | HTLSVFDQER | 54-63 for the proteins of SEQ No. 1131 | 2d |
| SEQ ID No. 1495 | HVTFASFR | 241-248 for the proteins of SEQ No. 1252 | 2de |

-continued

| Peptide SEQ ID No. | Amino acid sequence | Position of the peptide in the OXA protein(s) | Clinical interest |
|---|---|---|---|
| SEQ ID No. 1496 | IAISLMGYDAGFLR | 57-70 for the proteins of SEQ No. 1254, 1255, 1257, 1258 | 2d |
| SEQ ID No. 1497 | IALSLMAFDAEIIDQK | 75-90 for the proteins of SEQ No. 1118, 1134; 60-75 for the protein of sequence SEQ ID No. 1119 | 2d |
| SEQ ID No. 1498 | IALSLMGFDSGILK | 53-66 for the proteins of SEQ No. 1252 | 2de |
| SEQ ID No. 1499 | IANALIGLENHK | 87-98 for the proteins of SEQ No. 1168, 1171, 1216 | 2df |
| SEQ ID No. 1500 | IAWIVGFVYLK | 205-215 for the proteins of SEQ No. 1143 | 2d |
| SEQ ID No. 1501 | IDTFWLDNSLK | 141-151 for the proteins of SEQ No. 1143 | 2d |
| SEQ ID No. 1502 | IDYYNLDR | 41-48 for the proteins of SEQ No. 1135 | 2d |
| SEQ ID No. 1503 | IFNALIALDSGVIK | 62-75 for the proteins of SEQ No. 1143 | 2d |
| SEQ ID No. 1504 | IFNSLLALDSGALDNER | 95-111 for the proteins of SEQ No. 1140 | 2df |
| SEQ ID No. 1505 | IFNTLIGLENGIVK | 61-74 for the proteins of SEQ No. 1135 | 2d |
| SEQ ID No. 1506 | IGLDLMQK | 138-145 for the proteins of SEQ No. 1124, 1132, 1145, 1198, 1199, 1217, 1218, 1219, 1220, 1221, 1222, 1223, 1244, 1251 | 2df |
| SEQ ID No. 1507 | IGLEK | 131-135 for the proteins of SEQ No. 1235 | OXA |
| SEQ ID No. 1508 | IGLELMQQEVQR | 133-144 for the proteins of SEQ No. 1227 | 2df |
| SEQ ID No. 1509 | IGLELMSK | 139-146 for the proteins of SEQ No. 1147, 1148, 1149, 1151, 1153, 1156, 1157, 1158, 1159, 1160, 1161, 1162, 1166, 1167, 1169, 1170, 1175, 1177, 1178, 1179, 1180, 1181, 1182, 1183, 1184, 1185, 1186, 1194, 1195, 1196, 1197, 1209, 1210, 1211, 1212, 1213, 1214, 1215, 1225, 1226, 1230, 1231, 1232, 1236, 1237, 1238, 1240, 1241, 1245, 1253, 1260, 1266 | 2df |
| SEQ ID No. 1510 | IGLELMSNEVK | 139-149 for the proteins of SEQ No. 1146, 1150, 1152, 1154, 1155, 1163, 1164, 1165, 1174, 1176, 1192, 1202, 1203, 1204, 1206, 1233, 1261, 1265; 133-143 for the protein of sequence SEQ ID No. 1189; 133-143 for the protein of sequence SEQ ID No. 1190 | 2df |
| SEQ ID No. 1511 | IGLER | 126-130 for the proteins of SEQ No. 1138 | 2d |
| SEQ ID No. 1512 | IGLNK | 130-134 for the proteins of SEQ No. 1118, 1134; 115-119 for the protein of sequence SEQ ID No. 1119 | 2d |
| SEQ ID No. 1513 | IGLNLMQK | 140-147 for the proteins of SEQ No. 1224 | 2df |
| SEQ ID No. 1514 | IGPSLMQSELQR | 142-153 for the proteins of SEQ No. 1168, 1171, 1216 | 2df |
| SEQ ID No. 1515 | IGYGNMQIGTEVDQFWLK | 154-171 for the proteins of SEQ No. 1171, 1216 | 2df |

-continued

| Peptide SEQ ID No. | Amino acid sequence | Position of the peptide in the OXA protein(s) | Clinical interest |
|---|---|---|---|
| SEQ ID No. 1516 | IGYGNMQMGTEVDQFWLK | 154-171 for the proteins of SEQ No. 1168 | 2df |
| SEQ ID No. 1517 | IINHNLPVK | 167-175 for the proteins of SEQ No. 1119; 182-190 for the protein of sequence SEQ ID No. 1118 | 2d |
| SEQ ID No. 1518 | IINHNLPVR | 182-190 for the proteins of SEQ No. 1134 | 2d |
| SEQ ID No. 1519 | ILFQQGTQQACAER | 41-54 for the proteins of SEQ No. 1191 | 2d |
| SEQ ID No. 1520 | ILNNWFK | 20-26 for the proteins of SEQ No. 1143 | 2d |
| SEQ ID No. 1521 | ILNTLISLEEK | 71-81 for the proteins of SEQ No. 1228 | 2df |
| SEQ ID No. 1522 | ILSLVCLSISIGACAEHSMSR | 6-26 for the proteins of SEQ No. 1168, 1171, 1216 | 2df |
| SEQ ID No. 1523 | INESR | 219-223 for the proteins of SEQ No. 1107 | 2d |
| SEQ ID No. 1524 | INIVK | 255-259 for the proteins of SEQ No. 1187, 1188, 1235; 254-258 for the protein of sequence SEQ ID No. 1144 | 2d |
| SEQ ID No. 1525 | INLYGNALSR | 61-70 for the proteins of SEQ No. 1124, 1132, 1145, 1198, 1199, 1217, 1218, 1219, 1220, 1221, 1222, 1223, 1244, 1251 | 2df |
| SEQ ID No. 1526 | IPFSLNLEMK | 244-253 for the proteins of SEQ No. 1122, 1123, 1129, 1172, 1207, 1264 | 2df |
| SEQ ID No. 1527 | IPHTLFALDADAVR | 76-89 for the proteins of SEQ No. 1131 | 2d |
| SEQ ID No. 1528 | IPHTLFALDAGAAR | 76-89 for the proteins of SEQ No. 1114, 1249 | 2d |
| SEQ ID No. 1529 | IPHTLFALDAGAVR | 76-89 for the proteins of SEQ No. 1108, 1113, 1121, 1125, 1128, 1133, 1173, 1201, 1239, 1246; 65-78 for the protein of sequence SEQ ID No. 1120 | OXA |
| SEQ ID No. 1530 | IPLGK | 255-259 for the proteins of SEQ No. 1137 | 2df |
| SEQ ID No. 1531 | IPNAIIGLETGVIK | 71-84 for the proteins of SEQ No. 1110, 1116, 1117, 1126, 1141, 1200, 1229, 1250, 1262; 62-75 for the protein of sequence SEQ ID No. 1106; 62-75 for the protein of sequence SEQ ID No. 1111; 72-85 for the protein of sequence SEQ ID No. 1248 | OXA |
| SEQ ID No. 1532 | IPNALIGLETGAIK | 71-84 for the proteins of SEQ No. 1247, 1263 | OXA |
| SEQ ID No. 1533 | IPNSLIAFDTGAVR | 78-91 for the proteins of SEQ No. 1137 | 2df |
| SEQ ID No. 1534 | IPSAIIGLETGVIK | 71-84 for the proteins of SEQ No. 1115, 1193, 1259; 62-75 for the protein of sequence SEQ ID No. 1112 | 2de |
| SEQ ID No. 1535 | ISAFNQVK | 161-168 for the proteins of SEQ No. 1247 | 2d |
| SEQ ID No. 1536 | ISAHEQILFLR | 166-176 for the proteins of SEQ No. 1131 | 2d |

| Peptide SEQ ID No. | Amino acid sequence | Position of the peptide in the OXA protein(s) | Clinical interest |
|---|---|---|---|
| SEQ ID No. 1537 | ISAMEQTR | 160-167 for the proteins of SEQ No. 1138 | 2d |
| SEQ ID No. 1538 | ISAMEQVK | 165-172 for the proteins of SEQ No. 1187, 1235; 152-159 for the protein of sequence SEQ ID No. 1135; 164-171 for the protein of sequence SEQ ID No. 1144 | 2d |
| SEQ ID No. 1539 | ISATEQVAFLR | 164-174 for the proteins of SEQ No. 1142 | 2df |
| SEQ ID No. 1540 | ISATQQIAFLR | 164-174 for the proteins of SEQ No. 1243 | 2df |
| SEQ ID No. 1541 | ISAVNQVEFLESLFLNK | 161-177 for the proteins of SEQ No. 1115, 1116, 1117, 1126, 1141, 1200, 1229, 1262; 162-178 for the protein of sequence SEQ ID No. 1248 | OXA |
| SEQ ID No. 1542 | ISAVNQVEFLESLYLNK | 161-177 for the proteins of SEQ No. 1110, 1193, 1250, 1259; 152-168 for the protein of sequence SEQ ID No. 1106; 152-168 for the protein of sequence SEQ ID No. 1111; 152-168 for the protein of sequence SEQ ID No. 1112 | OXA |
| SEQ ID No. 1543 | ISAVNQVK | 161-168 for the proteins of SEQ No. 1263 | 2de |
| SEQ ID No. 1544 | ISPEEQIQFLR | 170-180 for the proteins of SEQ No. 1118, 1134; 155-165 for the protein of sequence SEQ ID No. 1119 | 2d |
| SEQ ID No. 1545 | ISPEEQVR | 166-173 for the proteins of SEQ No. 1109 | 2de |
| SEQ ID No. 1546 | ISPEGQVR | 155-162 for the proteins of SEQ No. 1256 | 2d |
| SEQ ID No. 1547 | ISPLEQLAFLR | 162-172 for the proteins of SEQ No. 1191 | 2d |
| SEQ ID No. 1548 | ITAFQQVDFLR | 188-198 for the proteins of SEQ No. 1139 | 2df |
| SEQ ID No. 1549 | ITLFLLFLNLVFGQDK | 4-19 for the proteins of SEQ No. 1143 | 2d |
| SEQ ID No. 1550 | ITPIQEVNFADDFANNR | 174-190 for the proteins of SEQ No. 1205 | 2df |
| SEQ ID No. 1551 | ITPIQEVNFADDLANNR | 174-190 for the proteins of SEQ No. 1224 | 2df |
| SEQ ID No. 1552 | ITPQQEAQFTYK | 173-184 for the proteins of SEQ No. 1146, 1147, 1148, 1149, 1150, 1151, 1152, 1153, 1154, 1155, 1156, 1157, 1158, 1159, 1160, 1161, 1162, 1164, 1165, 1166, 1167, 1169, 1170, 1174, 1175, 1176, 1177, 1178, 1179, 1180, 1181, 1182, 1183, 1184, 1185, 1186, 1192, 1194, 1195, 1196, 1197, 1202, 1203, 1204, 1206, 1209, 1210, 1211, 1212, 1213, 1214, 1215, 1225, 1226, 1230, 1231, 1232, 1233, 1236, 1237, 1238, 1240, 1241, 1245, 1253, 1260, 1261, 1265, 1266; 167-178 for the protein of sequence SEQ ID No. 1189; 167-178 for the protein of sequence SEQ ID No. 1190 | 2df |
| SEQ ID No. 1553 | ITPQQEAQFTYK | 173-184 for the proteins of SEQ No. 1163 | 2df |
| SEQ ID No. 1554 | ITPVQEVNFADDLAHNR | 174-190 for the proteins of SEQ No. 1122, 1123, 1129, 1172, 1207, 1264 | 2df |

-continued

| Peptide SEQ ID No. | Amino acid sequence | Position of the peptide in the OXA protein(s) | Clinical interest |
|---|---|---|---|
| SEQ ID No. 1555 | IVAFALK | 241-247 for the proteins of SEQ No. 1124, 1145 | 2df |
| SEQ ID No. 1556 | IVAFALNMEMR | 241-251 for the proteins of SEQ No. 1198, 1217, 1218, 1219, 1220, 1221, 1222, 1223, 1244, 1251; 242-252 for the protein of sequence SEQ ID No. 1132; 242-252 for the protein of sequence SEQ ID No. 1199 | 2df |
| SEQ ID No. 1557 | IVESTTLADGTVVHGK | 186-201 for the proteins of SEQ No. 1254, 1255, 1257, 1258 | 2d |
| SEQ ID No. 1558 | IYNSLIGLNEK | 74-84 for the proteins of SEQ No. 1144, 1187, 1188, 1235 | 2d |
| SEQ ID No. 1559 | KPDIGWWVGWIER | 237-249 for the proteins of SEQ No. 1140 | 2df |
| SEQ ID No. 1560 | LACATNNLAR | 50-59 for the proteins of SEQ No. 1248 | 2d |
| SEQ ID No. 1561 | LAQGELPFPAPVQSTVR | 172-188 for the proteins of SEQ No. 1138 | 2d |
| SEQ ID No. 1562 | LAQNELPYPIEIQK | 177-190 for the proteins of SEQ No. 1187, 1188, 1235 | 2d |
| SEQ ID No. 1563 | LAQNELQYPIEIQK | 176-189 for the proteins of SEQ No. 1144 | 2d |
| SEQ ID No. 1564 | LDFGNK | 143-148 for the proteins of SEQ No. 1187, 1188, 1235; 142-147 for the protein of sequence SEQ ID No. 1144 | 2d |
| SEQ ID No. 1565 | LDGSLNR | 206-212 for the proteins of SEQ No. 1105 | 2d |
| SEQ ID No. 1566 | LEIGK | 244-248 for the proteins of SEQ No. 1107 | 2d |
| SEQ ID No. 1567 | LEILQQALAELGLYPK | 255-270 for the proteins of SEQ No. 1227 | 2df |
| SEQ ID No. 1568 | LENQEQVK | 173-180 for the proteins of SEQ No. 1135 | 2d |
| SEQ ID No. 1569 | LETQEEVEK | 195-203 for the proteins of SEQ No. 1122 | 2df |
| SEQ ID No. 1570 | LETQEEVK | 195-202 for the proteins of SEQ No. 1123, 1129, 1172, 1205, 1207, 1224, 1264 | 2df |
| SEQ ID No. 1571 | LFAAEGVK | 55-62 for the proteins of SEQ No. 1140 | 2df |
| SEQ ID No. 1572 | LFESAGVK | 58-65 for the proteins of SEQ No. 1139 | 2df |
| SEQ ID No. 1573 | LFGAAGVK | 30-37 for the proteins of SEQ No. 1138 | 2d |
| SEQ ID No. 1574 | LFPEWEK | 110-116 for the proteins of SEQ No. 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1169, 1170, 1174, 1175, 1176, 1177, 1178, 1179, 1180, 1181, 1182, 1183, 1184, 1185, 1186, 1192, 1194, 1195, 1196, 1197, 1202, 1203, 1204, 1206, 1209, 1210, 1211, 1212, 1213, 1214, 1215, 1225, 1226, 1230, 1231, 1232, 1233, 1236, 1237, 1238, 1240, 1241, 1245, 1253, 1260, 1261, 1265, 1266; 104-110 | 2df |

-continued

| Peptide SEQ ID No. | Amino acid sequence | Position of the peptide in the OXA protein(s) | Clinical interest |
|---|---|---|---|
| | | for the protein of sequence SEQ ID No. 1189; 104-110 for the protein of sequence SEQ ID No. 1190 | |
| SEQ ID No. 1575 | LGESR | 126-130 for the proteins of SEQ No. 1109 | 2de |
| SEQ ID No. 1576 | LGVDR | 121-125 for the proteins of SEQ No. 1107 | |
| SEQ ID No. 1577 | LHVSER | 181-186 for the proteins of SEQ No. 1136, 1142, 1208, 1234, 1243 | 2df |
| SEQ ID No. 1578 | LHYGNAK | 131-137 for the proteins of SEQ No. 1143 | 2d |
| SEQ ID No. 1579 | LLNLLSQSK | 160-168 for the proteins of SEQ No. 1135 | 2d |
| SEQ ID No. 1580 | LLQDER | 243-248 for the proteins of SEQ No. 1191 | 2d |
| SEQ ID No. 1581 | LLVQDGDCGR | 38-47 for the proteins of SEQ No. 1254, 1255, 1257, 1258 | 2d |
| SEQ ID No. 1582 | LNEVGYGNR | 160-168 for the proteins of SEQ No. 1140 | 2df |
| SEQ ID No. 1583 | LNYGNADPSTK | 144-154 for the proteins of SEQ No. 1113, 1121 | 2d |
| SEQ ID No. 1584 | LNYGNK | 130-135 for the proteins of SEQ No. 1135 | 2d |
| SEQ ID No. 1585 | LPASK | 178-182 for the proteins of SEQ No. 1247, 1263; 172-176 for the protein of sequence SEQ ID No. 1256 | 2d |
| SEQ ID No. 1586 | LPHTLFALDADAVR | 76-89 for the proteins of SEQ No. 1127, 1130 | OXA |
| SEQ ID No. 1587 | LPHTLFALDAGAVR | 76-89 for the proteins of SEQ No. 1242 | OXA |
| SEQ ID No. 1588 | LPLAIMGFDSGILQSPK | 62-78 for the proteins of SEQ No. 1107 | 2d |
| SEQ ID No. 1589 | LPLAIMGYDADILLDATTPR | 69-88 for the proteins of SEQ No. 1109 | 2de |
| SEQ ID No. 1590 | LPSSLIALETGAVR | 98-111 for the proteins of SEQ NO. 1139 | 2df |
| SEQ ID No. 1591 | LPVSAQTLQYTANILK | 170-185 for the proteins of SEQ No. 1105 | 2d |
| SEQ ID No. 1592 | LPVSER | 205-210 for the proteins of SEQ No. 1139 | 2df |
| SEQ ID No. 1593 | LPVSPTAVDMTER | 173-185 for the proteins of SEQ No. 1254, 1255, 1257, 1258 | 2d |
| SEQ ID No. 1594 | LSASK | 178-182 for the proteins of SEQ No. 1110, 1115, 1116, 1117, 1126, 1141, 1193, 1200, 1229, 1250, 1259, 1262; 169-173 for the protein of sequence SEQ ID NO. 1106; 169-173 for the protein of sequence SEQ ID No. 1111; 169-173 for the protein of sequence SEQ ID No. 1112; 179-183 for the protein of sequence SEQ ID No. 1248 | OXA |
| SEQ ID No. 1595 | LSAVPIYQEVAR | 121-132 for the proteins of SEQ No. 1137 | 2df |

-continued

| Peptide SEQ ID No. | Amino acid sequence | Position of the peptide in the OXA protein(s) | Clinical interest |
|---|---|---|---|
| SEQ ID No. 1596 | LSAVPVYQELAR | 127-138 for the proteins of SEQ No. 1122, 1123, 1129, 1172, 1205, 1207, 1264; 125-136 for the protein of sequence SEQ ID No. 1124; 125-136 for the protein of sequence SEQ ID No. 1132; 125-136 for the protein of sequence SEQ ID No. 1145; 125-136 for the protein of sequence SEQ ID No. 1198; 125-136 for the protein of sequence SEQ ID No. 1199; 125-136 for the protein of sequence SEQ ID No. 1217; 125-136 for the protein of sequence SEQ ID No. 1218; 125-136 for the protein of sequence SEQ ID No. 1219; 125-136 for the protein of sequence SEQ ID No. 1220; 125-136 for the protein of sequence SEQ ID No. 1221; 125-136 for the protein of sequence SEQ ID No. 1222; 125-136 for the protein of sequence SEQ ID No. 1223; 125-136 for the protein of sequence SEQ ID No. 1244; 125-136 for the protein of sequence SEQ ID No. 1251 | 2df |
| SEQ ID No. 1597 | LSCTLVIDEASGDLEHR | 37-53 for the proteins of SEQ No. 1109 | 2de |
| SEQ ID No. 1598 | LSLQHGWFIGWIEK | 211-224 for the proteins of SEQ No. 1252 | 2de |
| SEQ ID No. 1599 | LSQNSLPFSQEAMNSVK | 164-180 for the proteins of SEQ No. 1143 | 2d |
| SEQ ID No. 1600 | LSVNPK | 168-173 for the proteins of SEQ No. 1252 | 2de |
| SEQ ID No. 1601 | LTQDER | 239-244 for the proteins of SEQ No. 1254, 1255, 1257, 1258 | 2d |
| SEQ ID No. 1602 | LTVGAR | 245-250 for the proteins of SEQ No. 1109 | 2de |
| SEQ ID No. 1603 | LYGFALNIDMPGGEADIGK | 228-246 for the proteins of SEQ No. 1138 | 2d |
| SEQ ID No. 1604 | LYHNELPFR | 178-186 for the proteins of SEQ No. 1114, 1249 | 2d |
| SEQ ID No. 1605 | LYHNK | 176-180 for the proteins of SEQ No. 1136, 1142, 1208, 1234, 1243 | 2df |
| SEQ ID No. 1606 | LYQNDLPFR | 178-186 for the proteins of SEQ No. 1133 | 2d |
| SEQ ID No. 1607 | MDDLFK | 243-248 for the proteins of SEQ No. 1108, 1114, 1125, 1128, 1133, 1173, 1201, 1239, 1246, 1249; 232-237 for the protein of sequence SEQ ID No. 1120 | OXA |
| SEQ ID No. 1608 | MEDLHK | 243-248 for the proteins of SEQ No. 1113, 1121 | 2d |
| SEQ ID No. 1609 | MLIALIGLENHK | 85-96 for the proteins of SEQ No. 1264 | 2df |
| SEQ ID No. 1610 | MLLIEQQGDAALYAK | 198-212 for the proteins of SEQ No. 1137 | 2df |
| SEQ ID No. 1611 | MLLIK | 204-208 for the proteins of SEQ No. 1122, 1123, 1129, 1172, 1205, 1207, 1224, 1264 | 2df |
| SEQ ID No. 1612 | MLNALIGLEHHK | 84-95 for the proteins of SEQ NO. 1146, 1147, 1148, 1149, 1150, 1151, 1152, 1153, 1154, 1155, 1156, 1157, 1158, 1159, 1160, 1161, 1162, 1163, 1164, 1166, 1167, 1169, 1170, 1174, 1175, 1176, 1177, 1178, 1179, 1180, 1181, 1182, 1183, 1184, 1185, 1186, 1192, 1194, 1195, 1196, 1197, 1202, 1203, 1204, | 2df |

| Peptide SEQ ID No. | Amino acid sequence | Position of the peptide in the OXA protein(s) | Clinical interest |
|---|---|---|---|
| | | 1206, 1209, 1210, 1211, 1212, 1213, 1214, 1215, 1225, 1226, 1230, 1231, 1232, 1233, 1236, 1237, 1238, 1240, 1245, 1253, 1260, 1261, 1265, 1266; 78-89 for the protein of sequence SEQ ID No. 1189; 78-89 for the protein of sequence SEQ ID No. 1190 | |
| SEQ ID No. 1613 | MLNALIGLENHK | 85-96 for the proteins of SEQ No. 1122, 1123, 1129, 1172, 1205, 1207, 1224 | 2d1 |
| SEQ ID No. 1614 | MLNALIGLENQK | 83-94 for the proteins of SEQ No. 1124, 1132, 1145, 1198, 1199, 1217, 1218, 1219, 1220, 1221, 1222, 1223, 1244, 1251 | 2df |
| SEQ ID No. 1615 | MLNALIGLEYHK | 84-95 for the proteins of SEQ No. 1241 | 2df |
| SEQ ID No. 1616 | MLNALIGLQHGK | 78-89 for the proteins of SEQ No. 1227 | 2df |
| SEQ ID No. 1617 | MLNALISLEHHK | 84-95 for the proteins of SEQ No. 1165 | 2df |
| SEQ ID No. 1618 | MQAYVDAFDYGNR | 139-151 for the proteins of SEQ No. 1137 | 2df |
| SEQ ID No. 1619 | MQEGLNK | 123-129 for the proteins of SEQ No. 1135 | 2d |
| SEQ ID No. 1620 | MSPASTYK | 87-94 for the proteins of SEQ No. 1140 | 2df |
| SEQ ID No. 1621 | MTAGGK | 234-239 for the proteins of SEQ No. 1256 | 2d |
| SEQ ID No. 1622 | MVSGK | 165-169 for the proteins of SEQ No. 1105 | 2d |
| SEQ ID No. 1623 | NEHDPVLPYR | 71-80 for the proteins of SEQ No. 1254, 1255, 1257, 1258 | 2d |
| SEQ ID No. 1624 | NEHQIFK | 86-92 for the proteins of SEQ No. 1248; 85-91 for the protein of sequence SEQ ID No. 1141 | 2d |
| SEQ ID No. 1625 | NEHQVFK | 85-91 for the proteins of SEQ NO. 1110, 1115, 1116, 1117, 1126, 1193, 1200, 1229, 1250, 1259, 1262; 76-82 for the protein of sequence SEQ ID No. 1106; 76-82 for the protein of sequence SEQ ID No. 1111; 76-82 for the protein of sequence SEQ ID No. 1112 | OXA |
| SEQ ID No. 1626 | NEITYK | 262-267 for the proteins of SEQ No. 1122, 1123, 1129, 1172, 1205, 1207, 1224, 1264 | 2df |
| SEQ ID No. 1627 | NELLMK | 260-265 for the proteins of SEQ No. 1124, 1145, 1198, 1217, 1218, 1220, 1221, 1222, 1223, 1244, 1251; 261-266 for the protein of sequence SEQ ID No. 1132; 261-266 for the protein of sequence SEQ ID No. 1199 | 2df |
| SEQ ID No. 1628 | NELMMK | 260-265 for the proteins of SEQ No. 1219 | 2df |
| SEQ ID No. 1629 | NELPFR | 181-186 for the proteins of SEQ No. 1108, 1113, 1114, 1121, 1125, 1128, 1173, 1201, 1239, 1246, 1249; 170-175 for the protein of sequence SEQ ID No. 1120 | OXA |
| SEQ ID No. 1630 | NFILIFIFVILISCK | 5-19 for the proteins of SEQ No. 1144, 1187, 1235 | 2d |
| SEQ ID No. 1631 | NFILIFIFVILTSCK | 5-19 for the proteins of SEQ No. 1188 | 2d |

-continued

| Peptide SEQ ID No. | Amino acid sequence | Position of the peptide in the OXA protein(s) | Clinical interest |
|---|---|---|---|
| SEQ ID No. 1632 | NISSYGNNLVR | 62-72 for the proteins of SEQ No. 1224 | 2df |
| SEQ ID No. 1633 | NISTYGNNLTR | 62-72 for the proteins of SEQ No. 1205 | 2df |
| SEQ ID No. 1634 | NLFNEVHTTGVLVIR | 43-57 for the proteins of SEQ No. 1170 | 2df |
| SEQ ID No. 1635 | NLSTYGNALAR | 62-72 for the proteins of SEQ No. 1122, 1123, 1129, 1172, 1207, 1264 | 2df |
| SEQ ID No. 1636 | NMENLELFGK | 187-196 for the proteins of SEQ No. 1143 | 2d |
| SEQ ID No. 1637 | NMLLLEENNGYK | 201-212 for the proteins of SEQ No. 1198 | 2df |
| SEQ ID No. 1638 | NMLLLEESNGYK | 201-212 for the proteins of SEQ No. 1124, 1132, 1145, 1199, 1217, 1218, 1219, 1220, 1221, 1223, 1244, 1251 | 2df |
| SEQ ID No. 1639 | NMLLLEK | 201-207 for the proteins of SEQ No. 1222 | 2df |
| SEQ ID No. 1640 | NMTLGDAMK | 117-125 for the proteins of SEQ No. 1146, 1150, 1151, 1154, 1155, 1160, 1163, 1164, 1174, 1177, 1180, 1182, 1192, 1203, 1204, 1206, 1233, 1261; 111-119 for the protein of sequence SEQ ID No. 1189; 111-119 for the protein of sequence SEQ ID No. 1190 | 2df |
| SEQ ID No. 1641 | NNGLTEAWLESSLK | 156-169 for the proteins of SEQ No. 1118, 1134; 141-154 for the protein of sequence SEQ ID No. 1119 | 2d |
| SEQ ID No. 1642 | NQLPFK | 181-186 for the proteins of SEQ No. 1131 | 2d |
| SEQ ID No. 1643 | NQLPFQVEHQR | 181-191 for the proteins of SEQ No. 1127, 1130, 1242 | OXA |
| SEQ ID No. 1644 | NSAIENTIDNMYLQDLENSTK | 191-211 for the proteins of SEQ No. 1134 | 2d |
| SEQ ID No. 1645 | NSAIENTIENMYLQDLDNSTK | 191-211 for the proteins of SEQ No. 1118 | 2d |
| SEQ ID No. 1646 | NSAIENTIENMYLQDLENSTK | 176-196 for the proteins of SEQ No. 1119 | 2d |
| SEQ ID No. 1647 | NSAVWVYELFAK | 119-130 for the proteins of SEQ No. 1127, 1130, 1242 | OXA |
| SEQ ID No. 1648 | NSQVPAYK | 118-125 for the proteins of SEQ No. 1187, 1188, 1235; 117-124 for the protein of sequence SEQ ID No. 1144 | 2d |
| SEQ ID No. 1649 | NSTVWIYELFAK | 119-130 for the proteins of SEQ No. 1114, 1249 | 2d |
| SEQ ID No. 1650 | NSTVWVYELFAK | 119-130 for the proteins of SEQ No. 1108, 1125, 1128, 1131, 1133, 1173, 1201, 1239, 1246; 108-119 for the protein of sequence SEQ ID No. 1120 | OXA |
| SEQ ID No. 1651 | NSTVWVYQLFAK | 119-130 for the proteins of SEQ No. 1113, 1121 | 2d |
| SEQ ID No. 1652 | NTSGALVIQTDK | 48-59 for the proteins of SEQ No. 1218 | 2df |

-continued

| Peptide SEQ ID No. | Amino acid sequence | Position of the peptide in the OXA protein(s) | Clinical interest |
|---|---|---|---|
| SEQ ID No. 1653 | NTSGVLVIQTDK | 48-59 for the proteins of SEQ NO. 1124, 1132, 1145, 1198, 1199, 1217, 1219, 1220, 1221, 1222, 1223, 1244, 1251 | 2d1 |
| SEQ ID No. 1654 | NVDEMFYYYDGSK | 75-87 for the proteins of SEQ No. 1135 | 2d |
| SEQ ID No. 1655 | NWILR | 204-208 for the proteins of SEQ No. 1108, 1114, 1125, 1127, 1128, 1130, 1133, 1173, 1201, 1239, 1242, 1246, 1249; 193-197 for the protein of sequence SEQ ID No. 1120 | OXA |
| SEQ ID No. 1656 | NWNAAMDLR | 125-133 for the proteins of SEQ No. 1140 | 2df |
| SEQ ID No. 1657 | NYVDAFHYGNQDISGDK | 118-134 for the proteins of SEQ No. 1252 | 2de |
| SEQ ID No. 1658 | QADHAILVFDQAR | 51-63 for the proteins of SEQ No. 1133 | 2d |
| SEQ ID No. 1659 | QAEHALLVFGQER | 51-63 for the proteins of SEQ No. 1127, 1130, 1242 | OXA |
| SEQ ID No. 1660 | QAITK | 251-255 for the proteins of SEQ No. 1136, 1142, 1208, 1243; 247-251 for the protein of sequence SEQ ID No. 1234 | 2df |
| SEQ ID No. 1661 | QAMLTEANSDYIIR | 193-206 for the proteins of SEQ No. 1142 | 2df |
| SEQ ID No. 1662 | QEVQFVSALAR | 171-181 for the proteins of SEQ No. 1227 | 2df |
| SEQ ID No. 1663 | QFASIK | 243-248 for the proteins of SEQ No. 1105 | 2d |
| SEQ ID No. 1664 | QGMPGSIR | 254-261 for the proteins of SEQ No. 1205 | 2df |
| SEQ ID No. 1665 | QGMSGSIR | 254-261 for the proteins of SEQ No. 1224 | 2df |
| SEQ ID No. 1666 | QGQTQQSYGNDLAR | 58-71 for the proteins of SEQ No. 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1169, 1170, 1174, 1175, 1176, 1177, 1178, 1179, 1180, 1181, 1182, 1183, 1184, 1185, 1186, 1194, 1195, 1196, 1197, 1202, 1203, 1204, 1206, 1209, 1210, 1211, 1212, 1213, 1214, 1215, 1225, 1226, 1230, 1231, 1232, 1233, 1236, 1237, 1238, 1240, 1241, 1245, 1253, 1260, 1261, 1265, 1266; 52-65 for the protein of sequence SEQ ID No. 1189; 52-65 for the protein of sequence SEQ ID No. 1190 | 2df |
| SEQ ID No. 1667 | QIDYGNADPSTIK | 143-155 for the proteins of SEQ No. 1127, 1130, 1242 | OXA |
| SEQ ID No. 1668 | QIDYGNVDPSTIK | 143-155 for the proteins of SEQ No. 1131 | 2d |
| SEQ ID No. 1669 | QIGQAR | 129-134 for the proteins of SEQ No. 1136, 1208, 1234, 1243 | 2df |
| SEQ ID No. 1670 | QIGQAR | 129-134 for the proteins of SEQ No. 1142 | 2df |
| SEQ ID No. 1671 | QIMLIEQTFAFTLR | 190-203 for the proteins of SEQ No. 1228 | 2df |
| SEQ ID No. 1672 | QLGSAIDQFWLR | 152-163 for the proteins of SEQ No. 1137 | 2df |

| Peptide SEQ ID No. | Amino acid sequence | Position of the peptide in the OXA protein(s) | Clinical interest |
|---|---|---|---|
| SEQ ID No. 1673 | QLHDNK | 199-204 for the proteins of SEQ No. 1139 | 2df |
| SEQ ID No. 1674 | QLIFVHTVVQK | 229-239 for the proteins of SEQ No. 1105 | 2d |
| SEQ ID No. 1675 | QLIFVHTVVQKPGK | 229-242 for the proteins of SEQ No. 1105 | 2d |
| SEQ ID No. 1676 | QLPVK | 178-182 for the proteins of SEQ No. 1191; 184-188 for the protein of sequence SEQ ID No. 1137 | OXA |
| SEQ ID No. 1677 | QLPVKPR | 184-190 for the proteins of SEQ No. 1137 | 2df |
| SEQ ID No. 1678 | QLSLDVLDK | 265-273 for the proteins of SEQ No. 1168, 1171, 1216 | 2df |
| SEQ ID No. 1679 | QLVYAR | 237-242 for the proteins of SEQ No. 1191 | 2d |
| SEQ ID No. 1680 | QMMLTEASTDYIIR | 217-230 for the proteins of SEQ No. 1139 | 2df |
| SEQ ID No. 1681 | QMSIVEATPDYVLHGK | 214-229 for the proteins of SEQ No. 1140 | 2df |
| SEQ ID No. 1682 | QPTDPAR | 99-105 for the proteins of SEQ No. 1191 | 2d |
| SEQ ID No. 1683 | QPTDPTR | 93-99 for the proteins of SEQ No. 1254, 1255, 1257, 1258 | 2d |
| SEQ ID No. 1684 | QPVSAGIR | 246-253 for the proteins of SEQ No. 1254, 1255, 1257, 1258 | 2d |
| SEQ ID No. 1685 | QQLVK | 275-279 for the proteins of SEQ No. 1139 | 2df |
| SEQ ID No. 1686 | QTLVFAR | 232-238 for the proteins of SEQ No. 1254, 1255, 1257, 1258 | 2d |
| SEQ ID No. 1687 | QVGAEK | 126-131 for the proteins of SEQ No. 1228 | 2df |
| SEQ ID No. 1688 | QVVFAR | 238-243 for the proteins of SEQ No. 1107 | 2d |
| SEQ ID No. 1689 | SADEVLPYGGK | 84-94 for the proteins of SEQ No. 1138 | 2d |
| SEQ ID No. 1690 | SADEVLPYGGKPQR | 84-97 for the proteins of SEQ No. 1138 | 2d |
| SEQ ID No. 1691 | SCATNDLAR | 50-58 for the proteins of SEQ No. 1110, 1193, 1250, 1259; 41-49 for the protein of sequence SEQ ID No. 1106; 41-49 for the protein of sequence SEQ ID No. 1111; 41-49 for the protein of sequence SEQ ID No. 1112 | OXA |
| SEQ ID No. 1692 | SCATNNLAR | 50-58 for the proteins of SEQ No. 1115, 1116, 1117, 1126, 1141, 1200, 1229, 1262 | OXA |
| SEQ ID No. 1693 | SDIPGGSK | 251-258 for the proteins of SEQ No. 1107 | 2d |
| SEQ ID No. 1694 | SDWGK | 29-33 for the proteins of SEQ No. 1133 | 2d |
| SEQ ID No. 1695 | SEDNFHISSQQHEK | 27-40 for the proteins of SEQ No. 1122, 1123, 1129, 1172, 1207, 1264 | 2df |

-continued

| Peptide SEQ ID No. | Amino acid sequence | Position of the peptide in the OXA protein(s) | Clinical interest |
|---|---|---|---|
| SEQ ID No. 1696 | SEMPASIR | 252-259 for the proteins of SEQ No. 1124, 1145, 1198, 1217, 1218, 1219, 1220, 1221, 1222, 1244, 1251; 253-260 for the protein of sequence SEQ ID No. 1132; 253-260 for the protein of sequence SEQ ID No. 1199 | 2df |
| SEQ ID No. 1697 | SEMPASTR | 252-259 for the proteins of SEQ No. 1223 | 2df |
| SEQ ID No. 1698 | SFAAHNQDQDLR | 103-114 for the proteins of SEQ No. 1114, 1249 | 2d |
| SEQ ID No. 1699 | SFAGHNK | 103-109 for the proteins of SEQ No. 1133 | 2d |
| SEQ ID No. 1700 | SFAGHNQDQDLR | 103-114 for the proteins of SEQ No. 1127, 1130, 1131, 1242 | 2d |
| SEQ ID No. 1701 | SFAGHNQDQNLR | 103-114 for the proteins of SEQ No. 1113, 1121 | 2d |
| SEQ ID No. 1702 | SFLESWAK | 100-107 for the proteins of SEQ No. 1144 | 2d |
| SEQ ID No. 1703 | SFTAWEK | 109-115 for the proteins of SEQ No. 1124, 1132, 1145, 1199, 1217, 1218, 1219, 1220, 1221, 1222, 1223, 1244, 1251; 104-110 for the protein of sequence SEQ ID No. 1227 | 2df |
| SEQ ID No. 1704 | SFTTWEK | 109-115 for the proteins of SEQ No. 1198 | 2df |
| SEQ ID No. 1705 | SGSGWLR | 207-213 for the proteins of SEQ No. 1107 | 2d |
| SEQ ID No. 1706 | SGWGMAVDPQVGWYVGFVEK | 221-240 for the proteins of SEQ No. 1168, 1171, 1216 | 2df |
| SEQ ID No. 1707 | SGWGMDVSPQVGWLTGWVEK | 219-238 for the proteins of SEQ No. 1224 | 2df |
| SEQ ID No. 1708 | SGWGMDVTPQVGWLTGWVEK | 219-238 for the proteins of SEQ No. 1205 | 2df |
| SEQ ID No. 1709 | SIHPASTFK | 69-77 for the proteins of SEQ No. 1137 | 2df |
| SEQ ID No. 1710 | SIPTK | 252-256 for the proteins of SEQ No. 1110, 1115, 1116, 1117, 1126, 1141, 1193, 1200, 1229, 1248, 1250, 1259, 1262, 1263; 243-247 for the protein of sequence SEQ ID No. 1106; 243-247 for the protein of sequence SEQ ID No. 1111; 243-247 for the protein of sequence SEQ ID No. 1112 | OXA |
| SEQ ID No. 1711 | SISTK | 252-256 for the proteins of SEQ No. 1247 | 2d |
| SEQ ID No. 1712 | SLGLSNNLSR | 76-85 for the proteins of SEQ No. 1139 | 2df |
| SEQ ID No. 1713 | SLSMSGK | 4-10 for the proteins of SEQ No. 1109 | 2de |
| SEQ ID No. 1714 | SMLFIEEK | 202-209 for the proteins of SEQ No. 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1169, 1174, 1175, 1176, 1177, 1178, 1179, 1180, 1182, 1183, 1184, 1185, 1186, 1192, 1194, 1195, 1196, 1197, 1202, 1203, 1204, 1209, 1210, 1211, 1212, 1213, 1214, 1215, 1225, 1226, 1230, 1231, 1232, 1233, 1236, 1237, 1238, 1240, 1241, 1245, 1253, 1260, | 2df |

-continued

| Peptide SEQ ID No. | Amino acid sequence | Position of the peptide in the OXA protein(s) | Clinical interest |
|---|---|---|---|
| | | 1261, 1265, 1266; 196-203 for the protein of sequence SEQ ID No. 1189; 196-203 for the protein of sequence SEQ ID No. 1190 | |
| SEQ ID No. 1715 | SNGEK | 239-243 for the proteins of SEQ No. 1205, 1224 | 2df |
| SEQ ID No. 1716 | SNGLTHSWLGSSLK | 141-154 for the proteins of SEQ No. 1256 | 2d |
| SEQ ID No. 1717 | SNGYK | 208-212 for the proteins of SEQ No. 1124, 1132, 1145, 1199, 1217, 1218, 1219, 1220, 1221, 1222, 1223, 1244, 1251 | 2df |
| SEQ ID No. 1718 | SPTWELK | 79-85 for the proteins of SEQ No. 1107 | 2d |
| SEQ ID No. 1719 | SPTWELKPEYNPSPR | 79-93 for the proteins of SEQ No. 1107 | 2d |
| SEQ ID No. 1720 | SQDIVR | 208-213 for the proteins of SEQ No. 1140 | 2df |
| SEQ ID No. 1721 | SQQKPTDPTIWLK | 100-112 for the proteins of SEQ No. 1109 | 2de |
| SEQ ID No. 1722 | SQVGWLTGWVEQPDGK | 225-240 for the proteins of SEQ No. 1244 | 2df |
| SEQ ID No. 1723 | SSSNSCTTNNAAR | 46-58 for the proteins of SEQ No. 1247 | 2d |
| SEQ ID No. 1724 | SSSNSCTTNNATR | 46-58 for the proteins of SEQ No. 1263 | 2de |
| SEQ ID No. 1725 | SVYGELR | 139-145 for the proteins of SEQ No. 1228 | 2df |
| SEQ ID No. 1726 | SWILR | 204-208 for the proteins of SEQ No. 1131 | 2d |
| SEQ ID No. 1727 | SYFDEAQTQGVIIIK | 44-58 for the proteins of SEQ No. 1122, 1123, 1129, 1172, 1205, 1207, 1224, 1264 | 2df |
| SEQ ID No. 1728 | SYLEK | 139-143 for the proteins of SEQ No. 1113, 1121 | 2d |
| SEQ ID No. 1729 | SYPMWEK | 111-117 for the proteins of SEQ No. 1205, 1224 | 2df |
| SEQ ID No. 1730 | TAYIPASTFK | 61-70 for the proteins of SEQ No. 1247, 1263; 77-86 for the protein of sequence SEQ ID No. 1168; 77-86 for the protein of sequence SEQ ID No. 1171; 77-86 for the protein of sequence SEQ ID No. 1216 | 2df |
| SEQ ID No. 1731 | TDDLFK | 243-248 for the proteins of SEQ No. 1127, 1130, 1131, 1242 | 2d |
| SEQ ID No. 1732 | TDINEIFK | 95-102 for the proteins of SEQ No. 1132, 1145, 1198, 1199, 1217, 1218, 1219, 1220, 1221, 1222, 1223, 1244, 1251 | 2df |
| SEQ ID No. 1733 | TFIHNDPR | 51-58 for the proteins of SEQ No. 1228 | 2df |
| SEQ ID No. 1734 | TGAGFTANR | 216-224 for the proteins of SEQ No. 1118, 1134; 201-209 for the protein of sequence SEQ ID No. 1119 | 2d |
| SEQ ID No. 1735 | TGFNDGQK | 197-204 for the proteins of SEQ No. 1143 | 2d |

-continued

| Peptide SEQ ID No. | Amino acid sequence | Position of the peptide in the OXA protein(s) | Clinical interest |
|---|---|---|---|
| SEQ ID No. 1736 | TGLADSK | 210-216 for the proteins of SEQ No. 1187, 1188; 209-215 for the protein of sequence SEQ ID No. 1144 | 2d |
| SEQ ID No. 1737 | TGLDLMQK | 140-147 for the proteins of SEQ No. 1205 | 2df |
| SEQ ID No. 1738 | TGLELMQK | 140-147 for the proteins of SEQ No. 1122, 1123, 1129, 1172, 1207, 1264 | 2df |
| SEQ ID No. 1739 | TGMGYPK | 198-204 for the proteins of SEQ No. 1105 | 2d |
| SEQ ID No. 1740 | TGNGR | 197-201 for the proteins of SEQ No. 1252 | 2de |
| SEQ ID No. 1741 | TGTGSFIDAR | 200-209 for the proteins of SEQ No. 1256 | 2d |
| SEQ ID No. 1742 | TGTGSLSDAK | 211-220 for the proteins of SEQ No. 1109 | 2de |
| SEQ ID No. 1743 | TGVATEYQPEIGWWAGWVER | 213-232 for the proteins of SEQ No. 1137 | 2df |
| SEQ ID No. 1744 | TGVSYPLLADGTR | 202-214 for the proteins of SEQ No. 1254, 1255, 1257, 1258 | 2d |
| SEQ ID No. 1745 | TGWAAMDIK | 217-225 for the proteins of SEQ No. 1132, 1199 | 2df |
| SEQ ID No. 1746 | TGWAMDIK | 217-224 for the proteins of SEQ No. 1124, 1145, 1198, 1218, 1219, 1220, 1221, 1222, 1223, 1244, 1251 | 2df |
| SEQ ID No. 1747 | TGWAMDVK | 217-224 for the proteins of SEQ No. 1217 | 2df |
| SEQ ID No. 1748 | TGWATR | 206-211 for the proteins of SEQ No. 1228 | 2df |
| SEQ ID No. 1749 | TGWCFDCTPELGWWVGWVK | 205-223 for the proteins of SEQ No. 1138 | 2d |
| SEQ ID No. 1750 | TGWEGR | 211-216 for the proteins of SEQ No. 1108, 1114, 1125, 1127, 1128, 1130, 1131, 1173, 1201, 1239, 1242, 1246, 1249; 200-205 for the protein of sequence SEQ ID No. 1120 | OXA |
| SEQ ID No. 1751 | TGWFVDK | 230-236 for the proteins of SEQ No. 1140 | 2df |
| SEQ ID No. 1752 | TGYDTK | 209-214 for the proteins of SEQ No. 1234 | 2df |
| SEQ ID No. 1753 | TGYGVR | 233-238 for the proteins of SEQ No. 1139 | 2df |
| SEQ ID No. 1754 | TGYSAR | 209-214 for the proteins of SEQ No. 1208 | 2df |
| SEQ ID No. 1755 | TGYSTR | 209-214 for the proteins of SEQ No. 1136, 1142, 1243 | 2df |
| SEQ ID No. 1756 | THESSNWGK | 25-33 for the proteins of SEQ No. 1113, 1121 | 2d |
| SEQ ID No. 1757 | TICTAIADAGTGK | 25-37 for the proteins of SEQ No. 1254, 1255, 1257, 1258 | 2d |
| SEQ ID No. 1758 | TIGGAPDAYWVDDSLQISAR | 169-188 for the proteins of SEQ No. 1140 | 2df |

| Peptide SEQ ID No. | Amino acid sequence | Position of the peptide in the OXA protein(s) | Clinical interest |
|---|---|---|---|
| SEQ ID No. 1759 | TLPFSASSYETLR | 177-189 for the proteins of SEQ No. 1228 | 2df |
| SEQ ID No. 1760 | TLPFSLK | 189-195 for the proteins of SEQ No. 1157, 1161, 1169 | 2df |
| SEQ ID No. 1761 | TLPFSPK | 189-195 for the proteins of SEQ No. 1147, 1153, 1170, 1181, 1186, 1197, 1203, 1225, 1240, 1241, 1253 | 2df |
| SEQ ID No. 1762 | TLPFSQEVQDEVQSILFIEEK | 189-209 for the proteins of SEQ No. 1206 | 2df |
| SEQ ID No. 1763 | TLPFSQEVQDEVQSMLFIEEK | 189-209 for the proteins of SEQ No. 1150, 1192 | 2df |
| SEQ ID No. 1764 | TLPFSQK | 189-195 for the proteins of SEQ No. 1146, 1148, 1149, 1151, 1152, 1154, 1155, 1156, 1158, 1159, 1160, 1162, 1163, 1164, 1165, 1166, 1167, 1174, 1175, 1176, 1177, 1178, 1179, 1180, 1182, 1183, 1184, 1185, 1194, 1195, 1196, 1202, 1204, 1209, 1210, 1211, 1212, 1213, 1214, 1215, 1226, 1230, 1231, 1232, 1233, 1236, 1238, 1245, 1260, 1261, 1265, 1266; 183-189 for the protein of sequence SEQ ID No. 1189; 183-189 for the protein of sequence SEQ ID No. 1190 | 2df |
| SEQ ID No. 1765 | TLPSSQK | 189-195 for the proteins of SEQ No. 1237 | 2df |
| SEQ ID No. 1766 | TLQNGWFEGFIISK | 225-238 for the proteins of SEQ No. 1118, 1134; 210-223 for the protein of sequence SEQ ID No. 1119 | 2d |
| SEQ ID No. 1767 | TMQEYLNK | 123-130 for the proteins of SEQ No. 1143 | 2d |
| SEQ ID No. 1768 | TNGNSTSVYNESR | 51-63 for the proteins of SEQ No. 1113, 1121 | 2d |
| SEQ ID No. 1769 | TQTYQAYDAAR | 72-82 for the proteins of SEQ No. 1140 | 2df |
| SEQ ID No. 1770 | TTDPTIWEK | 93-101 for the proteins of SEQ No. 1256 | 2d |
| SEQ ID No. 1771 | TTTTEVFK | 96-103 for the proteins of SEQ No. 1153, 1186 | 2df |
| SEQ ID No. 1772 | TWASNDFSR | 41-49 for the proteins of SEQ No. 1143 | 2d |
| SEQ ID No. 1773 | TWDMVQR | 191-197 for the proteins of SEQ No. 1137 | 2df |
| SEQ ID No. 1774 | TWMQFSVVWVSQEITQK | 113-129 for the proteins of SEQ No. 1118, 1134; 98-114 for the protein of sequence SEQ ID No. 1119 | 2d |
| SEQ ID No. 1775 | TYPMWEK | 111-117 for the proteins of SEQ No. 1122, 1123, 1129, 1172, 1207, 1264 | 2df |
| SEQ ID No. 1776 | TYVVDPAR | 58-65 for the proteins of SEQ No. 1137 | 2df |
| SEQ ID No. 1777 | VAFSLNIEMK | 244-253 for the proteins of SEQ No. 1205 | 2df |
| SEQ ID No. 1778 | VANSLIGLSTGAVR | 70-83 for the proteins of SEQ No. 1138 | 2d |
| SEQ ID No. 1779 | VEHQR | 187-191 for the proteins of SEQ No. 1108, 1113, 1114, 1121, 1125, 1127, 1128, 1130, | OXA |

-continued

| Peptide SEQ ID No. | Amino acid sequence | Position of the peptide in the OXA protein(s) | Clinical interest |
|---|---|---|---|
| | | 1131, 1133, 1173, 1201, 1239, 1242, 1246, 1249; 176-180 for the protein of sequence SEQ ID No. 1120 | |
| SEQ ID No. 1780 | VELGK | 248-252 for the proteins of SEQ No. 1138 | 2d |
| SEQ ID No. 1781 | VFDDAGVSGTFVLMDITADR | 38-57 for the proteins of SEQ No. 1137 | 2df |
| SEQ ID No. 1782 | VFLDSWAK | 88-95 for the proteins of SEQ No. 1135 | 2d |
| SEQ ID No. 1783 | VFLESWAK | 101-108 for the proteins of SEQ No. 1187, 1188, 1235 | 2d |
| SEQ ID No. 1784 | VELSSWAQDMNESSAIK | 89-105 for the proteins of SEQ No. 1143 | 2d |
| SEQ ID No. 1785 | VGFER | 134-138 for the proteins of SEQ No. 1137 | 2df |
| SEQ ID No. 1786 | VILVFDQVR | 55-63 for the proteins of SEQ No. 1114, 1249 | 2d |
| SEQ ID No. 1787 | VITFTK | 228-233 for the proteins of SEQ No. 1252 | 2de |
| SEQ ID No. 1788 | VMAAMVR | 158-164 for the proteins of SEQ No. 1139 | 2df |
| SEQ ID No. 1789 | VPLAVMGYDAGILVDAHNPR | 58-77 for the proteins of SEQ No. 1256 | 2d |
| SEQ ID No. 1790 | VQANVK | 195-200 for the proteins of SEQ No. 1124, 1132, 1145, 1198, 1199, 1217, 1218, 1219, 1220, 1221, 1222, 1223, 1244, 1251 | 2df |
| SEQ ID No. 1791 | VQDEVK | 196-201 for the proteins of SEQ No. 1202 | 2df |
| SEQ ID No. 1792 | VQDEVQSMLFIEEK | 196-209 for the proteins of SEQ No. 1146, 1147, 1148, 1149, 1150, 1151, 1153, 1154, 1155, 1156, 1157, 1158, 1159, 1160, 1162, 1163, 1164, 1165, 1166, 1167, 1169, 1174, 1175, 1176, 1177, 1178, 1179, 1180, 1182, 1183, 1184, 1185, 1186, 1192, 1194, 1195, 1196, 1197, 1203, 1204, 1209, 1210, 1211, 1212, 1213, 1215, 1225, 1226, 1230, 1231, 1232, 1233, 1236, 1237, 1238, 1240, 1241, 1245, 1253, 1260, 1261, 1265, 1266; 190-203 for the protein of sequence SEQ ID No. 1189; 190-203 for the protein of sequence SEQ ID No. 1190 | 2df |
| SEQ ID No. 1793 | VQDEVQSMLFIEEMNGNK | 196-213 for the proteins of SEQ No. 1170, 1181 | 2df |
| SEQ ID No. 1794 | VQDGVQSMLFIEEK | 196-209 for the proteins of SEQ No. 1214 | 2df |
| SEQ ID No. 1795 | VQDEVQSMLFIEEK | 196-209 for the proteins of SEQ No. 1152 | 2df |
| SEQ ID No. 1796 | VSCLPCYQVVSHK | 138-150 for the proteins of SEQ No. 1140 | 2df |
| SEQ ID No. 1797 | VSCVWCYQALAR | 114-125 for the proteins of SEQ No. 1228 | 2df |
| SEQ ID No. 1798 | VSDVCSEVTAEGWQEVR | 37-53 for the proteins of SEQ No. 1139 | 2df |
| SEQ ID No. 1799 | VSEVEGWQIHGK | 186-197 for the proteins of SEQ No. 1105 | 2d |

-continued

| Peptide SEQ ID No. | Amino acid sequence | Position of the peptide in the OXA protein(s) | Clinical interest |
|---|---|---|---|
| SEQ ID No. 1800 | VSFSLNIEMK | 244-253 for the proteins of SEQ No. 1224 | 2df |
| SEQ ID No. 1801 | VSPCSSFK | 54-61 for the proteins of SEQ No. 1107 | 2d |
| SEQ ID No. 1802 | VSQVPAYK | 105-112 for the proteins of SEQ No. 1135 | 2d |
| SEQ ID No. 1803 | VVFAR | 229-233 for the proteins of SEQ No. 1256; 239-243 for the protein of sequence SEQ ID No. 1107; 240-244 for the protein of sequence SEQ ID No. 1109 | OXA |
| SEQ ID No. 1804 | WDGAK | 97-101 for the proteins of SEQ No. 1113, 1121 | 2d |
| SEQ ID No. 1805 | WDGEK | 104-108 for the proteins of SEQ No. 1151, 1160, 1177, 1180, 1182 | 2df |
| SEQ ID No. 1806 | WDGHIYDFPDWNR | 92-104 for the proteins of SEQ No. 1228 | 2df |
| SEQ ID No. 1807 | WDGIK | 97-101 for the proteins of SEQ No. 1114, 1249 | 2d |
| SEQ ID No. 1808 | WDGKPR | 92-97 for the proteins of SEQ No. 1110, 1115, 1116, 1117, 1126, 1141, 1193, 1200, 1229, 1247, 1250, 1259, 1262, 1263; 83-88 for the protein of sequence SEQ ID No. 1106; 83-88 for the protein of sequence SEQ ID No. 1111; 83-88 for the protein of sequence SEQ ID No. 1112; 116-121 for the protein of sequence SEQ ID No. 1140; 107-112 for the protein of sequence SEQ ID No. 1168; 107-112 for the protein of sequence SEQ ID No. 1171; 107-112 for the protein of sequence SEQ ID No. 1216; 93-98 for the protein of sequence SEQ ID No. 1248 | OXA |
| SEQ ID No. 1809 | WDGQK | 104-108 for the proteins of SEQ No. 1146, 1147, 1150, 1153, 1154, 1155, 1157, 1161, 1163, 1164, 1165, 1169, 1170, 1181, 1186, 1192, 1197, 1203, 1204, 1206, 1225, 1226, 1240, 1241, 1253, 1261, 1266; 98-102 for the protein of sequence SEQ ID No. 1189; 98-102 for the protein of sequence SEQ ID No. 1190 | 2df |
| SEQ ID No. 1810 | WDGQTR | 95-100 for the proteins of SEQ No. 1136, 1142, 1208, 1234, 1243 | 2df |
| SEQ ID No. 1811 | WDGVK | 97-101 for the proteins of SEQ No. 1127, 1130, 1133, 1242 | 2d |
| SEQ ID No. 1812 | WDGVNR | 97-102 for the proteins of SEQ No. 1108, 1125, 1128, 1131, 1173, 1201, 1239, 1246; 86-91 for the protein of sequence SEQ ID No. 1120 | OXA |
| SEQ ID No. 1813 | WDYKPEFNGYK | 78-88 for the proteins of SEQ No. 1256; 89-99 for the protein of sequence SEQ ID No. 1109 | OXA |
| SEQ ID No. 1814 | WETYSVVWFSQQITEWLGMER | 97-117 for the proteins of SEQ No. 1105 | 2d |
| SEQ ID No. 1815 | WNGQK | 104-108 for the proteins of SEQ No. 1152, 1176, 1202, 1265 | 2df |
| SEQ ID No. 1816 | YAQAK | 155-159 for the proteins of SEQ No. 1140 | 2df |
| SEQ ID No. 1817 | YFSDFNAK | 34-41 for the proteins of SEQ No. 1113, 1121 | 2d |

-continued

| Peptide SEQ ID No. | Amino acid sequence | Position of the peptide in the OXA protein(s) | Clinical interest |
|---|---|---|---|
| SEQ ID No. 1818 | YGTHLDR | 68-74 for the proteins of SEQ No. 1168, 1171, 1216 | 2df |
| SEQ ID No. 1819 | YIIHNK | 54-59 for the proteins of SEQ No. 1144, 1187, 1188, 1235 | 2d |
| SEQ ID No. 1820 | YLDELVK | 245-251 for the proteins of SEQ No. 1143 | 2d |
| SEQ ID No. 1821 | YLMITEAGR | 195-203 for the proteins of SEQ No. 1242 | OXA |
| SEQ ID No. 1822 | YLNLESYGNANIGGGIDK | 135-152 for the proteins of SEQ No. 1247, 1263 | OXA |
| SEQ ID No. 1823 | YNGEK | 96-100 for the proteins of SEQ No. 1187, 1188, 1235 | 2d |
| SEQ ID No. 1824 | YPHNPR | 88-93 for the proteins of SEQ No. 1252 | 2de |
| SEQ ID No. 1825 | YPVVWYSQQVAHHLGAQR | 103-120 for the proteins of SEQ No. 1255 | 2d |
| SEQ ID No. 1826 | YSNVLAFK | 106-113 for the proteins of SEQ No. 1143 | 2d |
| SEQ ID No. 1827 | YSPASTFK | 68-75 for the proteins of SEQ No. 1108, 1113, 1114, 1121, 1125, 1127, 1128, 1130, 1131, 1133, 1173, 1201, 1239, 1242, 1246, 1249; 57-64 for the protein of sequence SEQ ID No. 1120 | OXA |
| SEQ ID No. 1828 | YSVVPVYQQLAR | 141-152 for the proteins of SEQ No. 1139 | 2df |
| SEQ ID No. 1829 | YSVVWYSQLTAK | 109-120 for the proteins of SEQ No. 1191 | 2d |
| SEQ ID No. 1830 | YSVVWYSQQVAHHLGAQR | 103-120 for the proteins of SEQ No. 1254, 1257, 1258 | 2d |
| SEQ ID No. 1831 | YTPASTFK | 55-62 for the proteins of SEQ No. 1191 | 2d |
| SEQ ID No. 1832 | YTSAFGYGNADVSGEPGK | 130-147 for the proteins of SEQ No. 1191 | 2d |
| SEQ ID No. 1833 | YVFVSALTGNLGSNLTSSIK | 228-247 for the proteins of SEQ No. 1119; 243-262 for the protein of sequence SEQ ID No. 1118 | 2d |
| SEQ ID No. 1834 | YVFVSALTGSLGSNLTSSIK | 243-262 for the proteins of SEQ No. 1134 | 2d |
| SEQ ID No. 1835 | YVGHDR | 50-55 for the proteins of SEQ No. 1138 | 2d |
| SEQ ID No. 2160 | ANQAFLPASTFK | 62-73 for the proteins of SEQ No. 1136, 1142, 1208, 1234, 1243 | 2df |
| SEQ ID No. 2161 | DEHQVFK | 88-94 for the proteins of SEQ No. 1136, 1142, 1208, 1234, 1243 | 2df |
| SEQ ID No. 2162 | DHNLITAMK | 108-116 for the proteins of SEQ No. 1136, 1208, 1234 | 2df |
| SEQ ID No. 2163 | DIATVVNR | 101-107 for the proteins of SEQ No. 1136, 1208, 1234 | 2df |
| SEQ ID No. 2164 | IPNSLIALDLGVVK | 74-87 for the proteins of SEQ No. 1136, 1142, 1208, 1234, 1243 | 2df |

-continued

| Peptide SEQ ID No. | Amino acid sequence | Position of the peptide in the OXA protein(s) | Clinical interest |
|---|---|---|---|
| SEQ ID No. 2165 | ISATEQISFLR | 164-174 for the proteins of SEQ No. 1136, 1208, 1234 | 2df |
| SEQ ID No. 2166 | QAMLTEANGDYIIR | 193-206 for the proteins of SEQ No. 1136, 1208, 1234, 1243 | 2df |
| SEQ ID No. 2167 | QQGFTNNLK | 52-60 for the proteins of SEQ No. 1136, 1142, 1208, 1234, 1243 | 2df |
| SEQ ID No. 2168 | SQGVVVLWNENK | 40-51 for the proteins of SEQ No. 1136, 1208, 1234, 1243 | 2df |
| SEQ ID No. 2169 | SWNAHFTEHK | 30-39 for the proteins of SEQ No. 1136, 1208, 1234, 1243 | 2df |
| SEQ ID No. 2170 | VLALSAVFLVASIIGMPAVAK | 3-23 for the proteins of SEQ No. 1136, 1208, 1234, 1243 | 2df |
| SEQ ID No. 2171 | YSVVPVYQEFAR | 117-128 for the proteins of SEQ No. 1136, 1142, 1208, 1234, 1243 | 2df |

In the clinical interest column, the entries 2d, 2de, 2df correspond to the functional subgroups of OXA beta-lactamases which the corresponding peptide makes it possible to detect. Therefore, the detection of a 2df peptide will indicate the presence of a carbapenemase beta-lactamase capable of hydrolysing carbapenems.

The entry 2de will indicate the presence of a beta-lactamase with an extended spectrum (ESBL) capable of hydrolysing penicillins, first-generation cephalosporins such as cephaloridine and cefalotin, and at least one antibiotic from the oxyimino-beta-lactam class such as cefotaxime, ceftazidime or monobactams such as aztreonam.

The entry OXA indicates a common peptide between at least two of the subgroups 2d, 2de and 2df. The corresponding peptide indicates the presence of an OXA beta-lactamase and the presence of a mechanism of resistance at least to penicillins and to first-generation cephalosporins.

The detection of a mechanism of resistance to ESBL (extended-spectrum beta-lactamase) cephalosporins, induced by the OXA protein, is characterised by the detection of at least one resistance-marking 2de peptide chosen from the sequences SEQ ID No, 1277, 1297, 1323, 1344, 1368, 1369, 1373, 1375, 1392, 1421, 1423, 1427, 1429, 1439, 1444, 1446, 1450, 1451, 1457, 1465, 1468, 1490, 1491, 1495, 1498, 1534, 1543, 1545, 1575, 1589, 1597, 1598, 1600, 1602, 1657, 1713, 1721, 1724, 1740, 1742, 1787, 1824, 1268, 1269, 1270, 1271, 1272, 1278, 1279, 1280, 1281, 1283, 1285, 1288, 1290, 1295, 1299, 1300, 1301, 1302, 1303, 1304, 1305, 1306, 1307, 1308, 1309, 1310, 1314, 1315, 1316, 1317, 1318, 1319, 1320, 1332, 1337, 1339, 1340, 1341, 1342, 1350, 1354, 1355, 1356, 1357, 1358, 1359, 1360, 1365, 1366, 1367, 1386, 1389, 1390, 1391, 1393, 1394, 1402, 1404, 1405, 1407, 1408, 1413, 1414, 1419, 1420, 1425, 1432, 1433, 1440, 1447, 1448, 1456, 1471, 1472, 1477, 1478, 1480, 1485, 1487, 1488, 1499, 1504, 1506, 1508, 1509, 1510, 1513, 1514, 1515, 1516, 1521, 1522, 1525, 1526, 1530, 1533, 1539, 1540, 1548, 1550, 1551, 1552, 1553, 1554, 1555, 1556, 1559, 1567, 1569, 1570, 1571, 1572, 1574, 1577, 1582, 1590, 1592, 1595, 1596, 1605, 1609, 1610, 1611, 1612, 1613, 1614, 1615, 1616, 1617, 1618, 1620, 1626, 1627, 1628, 1632, 1633, 1634, 1635, 1637, 1638, 1639, 1640, 1652, 1653, 1656, 1660, 1661, 1662, 1664, 1665, 1666, 1669, 1670, 1671, 1672, 1673, 1677, 1678, 1680, 1681, 1685, 1687, 1695, 1696, 1697, 1703, 1704, 1706, 1707, 1708, 1709, 1712, 1714, 1715, 1717, 1720, 1722, 1725, 1727, 1729, 1730, 1732, 1733, 1737, 1738, 1743, 1746, 1748, 1751, 1752, 1753, 1754, 1755, 1758, 1759, 1760, 1761, 1762, 1763, 1764, 1765, 1769, 1771, 1773, 1775, 1776, 1777, 1781, 1785, 1788, 1790, 1791, 1792, 1793, 1794, 1795, 1796, 1797, 1798, 1800, 1805, 1806, 1809, 1810, 1815, 1816, 1818, 1828, 2160, 2161, 2162, 2163, 2164, 2165, 2166, 2167, 2168, 2169, 2170, 2171.

The detection of a mechanism of resistance to carbapenems or to cephalosporins, induced by the expression of the GES protein, is characterised by the detection of at least one peptide belonging to the GES protein and to its different sequence variants SEQ ID No. 2114 to SEQ ID No. 2130.

SEQ ID No. 2114:
MRFIHALLLAGIAHSAYASEKLTFKTDLEKLEREKAAQIGVAIVDPQGEIVAGHRMAQ
RFAMCSTFKFPLAALVFERIDSGTERGDRKLSYGPDMIVEWSPATERFLASGHMTV
LEAAQAAVQLSDNGATNLLLREIGGPAAMTQYFRKIGDSVSRLDRKEPEMGDNTPG
DLRDTTTPIAMARTVAKVLYGGALTSTSTHTIERWLIGNQTGDATLRAGFPKDWVVG
EKTGTCANGGRNDIGFFKAQERDYAVAVYTTAPKLSAVERDELVASVGQVITQLILS
TDK

SEQ ID No. 2115:
MRFIHALLLAGIAHSAYASEKLTFKTDLEKLEREKAAQIGVAIVDPQGEIVAGHRMAQ
RFAMCSTFKFPLAALVFERIDSGTERGDRKLSYGPDMIVKWSPATERFLASGHMTV
LEAAQAAVQLSDNGATNLLLREIGGPAAMTQYFRKIGDSVSRLDRKEPEMGDNTPG
DLRDTTTPIAMARTVAKVLYGGALTSTSTHTIERWLIGNQTGDATLRAGFPKDWVVG

-continued

EKTGTCANGGRNDIGFFKAQERDYAVAVYTTAPKLSAVERDELVASVGQVITQLILS
TDK

SEQ ID No. 2116:
MRFIHALLLAGIAHSAYASEKLTFKTDLEKLEREKAAQIGVAIVDPQGEIVAGHRMAQ
RFAMCSTFKFPLAALVFERIDSGTERGDRKLSYGPDMIVEWSPATERFLASGHMTV
LEAAQLAVQLSDNGATNLLLREIGGPAAMTQYFRKIGDSVSRLDRKEPEMGDNTPG
DLRDTTTPIAMARTVAKVLYGGALTSTSTHTIERWLIGNQTGDATLRAGFPKDWVVG
EKTGTCANGGRNDIGFFKAQERDYAVAVYTTAPKLSAVERDELVASVGQVITQLILS
TDK

SEQ ID No. 2117:
MRFIHALLLAGIAHSAYASEKLTFKTDLEKLEREKAAQIGVAIVDPQGEIVAGHRMAQ
RFAMCSTFKFPLAALVFERIDSGTERGDRKLSYGPDMIVEWSPATERFLASGHMTV
LEAAQAAVQLSDNGATNLLLREIGGPAAMTQYFRKIGDSVSRLDRKEPEMNDNTPG
DLRDTTTPIAMARTVAKVLYGGALTSTSTHTIERWLIGNQTGDATLRAGFPKDWVVG
EKTGTCANGGRNDIGFFKAQERDYAVAVYTTAPKLSAVERDELVASVGQVITQLILS
TDK

SEQ ID No. 2118:
MRFIHALLLAGIAHSAYASEKLTFKTDLEKLEREKAAQIGVAIVDPQGEIVAGHRMAQ
RFAMCSTFKFPLAALVFERIDSGTERGDRKLSYGPDMIVEWSPATERFLASGHMTV
LEAAQAAVQLSDNGATNLLLREIGGPAAMTQYFRKIGDSVSRLDRKEPEMSDNTPG
DLRDTTTPIAMARTVAKVLYGGALTSTSTHTIERWLIGNQTGDATLRAGFPKDWVVG
EKTGTCANGGRNDIGFFKAQERDYAVAVYTTAPKLSAVERDELVASVGQVITQLILS
TDK

SEQ ID No. 2119:
MRFIHALLLAGIAHSAYASEKLTFKTDLEKLEREKAAQIGVAIVDPQGEIVAGHRMAQ
RFAMCSTFKFPLAALVFERIDSGTERGDRKLSYGPDMIVEWSPATERFLASGHMTV
LEAAQAAVQLSDNGATNLLLREIGGPAAMTQYFRKIGDSVSRLDRKEPEMSDNTPG
DLRDTTTPIAMARTVAKVLYGGALTSTSTHTIERWLIGNQTGDATLRAGFPKDWVVG
EKTGTCANGGRNDIGFFKAQERDYAVAVYTTAPKLSAVERDELVASVGQVITQLILS
TDK

SEQ ID No. 2120:
MRFIHALLLAGIAHSAYASEKLTFKTDLEKLEREKAAQIGVAIVDPQGEIVAGHRMAQ
RFAMCSTFKFPLAALVFERIDSGTERGDRKLSYGPDMIVEWSPATERFLASGHMTV
LEAAQAAVQLSDNGATNLLLREIGGPAAMTQYFRKIGDSVSRLDRKEPEMGDNTPG
DLRDTTTPIAMARTVAKVLYGGALTSTSTHTIERWLIGNQTGDATLRAGFPKDWVVG
EKTGTCANGSRNDIGFFKAQERDYAVAVYTTAPKLSAVERDELVASVGQVITQLILS
TDK

SEQ ID No. 2121:
MRFIHALLLAGIAHSAYASEKLTFKTDLEKLEREKAAQIGVAIVDPQGEIVAGHRMAQ
RFAMCSTFKFPLAALVFERIDSGTERGDRKLSYGPDMIVEWSPATERFLASGHMTV
LEAAQAAVQLSDNGATNLLLREIGGPAAMTQYFRKIGDSVSRLDRKEPEMGDNTPG
DLRDTTTPIAMARTVAKVLYGGALTSTSTHTIERWLIGNQTGDATLRAGFPKDWVVG
EKTGTCANGARNDIGFFKAQERDYAVAVYTTAPKLSAVERDELVASVGQVITQLILS
TDK

SEQ ID No. 2122:
MRFIHALLLAGTAHSAYASEKLTFKTDLEKLEREKAAQIGVAIVDPQGEIVAGHRTAQ
RFAMCSTFKFPLAALVFERIDSGTERGDRKLSYGPDMIVEWSPATERFLASGHMTV
LEAAQAAVQLCDNGATNLLLREIGGPAAMTQYFRKIGDSVSRLDRKEPEMGDNTPG
DLRDTTTPIAMARTVAKVLYGGALTSTSTHTIERWLIGNQTGDATLRAGFPKDWVVG
EKTGTCANGGRNDIGFFKAQERDYAVAVYTTAPKLSAVERDELVASVGQVITQLILS
TDK

SEQ ID No. 2123:
MRFIHALLLAGIAHSAYASEKLTFKTDLEKLEREKAAQIGVAIVDPQGEIVAGHRMAQ
RFAMCSTFKFPLAALVFERIDSGTERGDRKLSYGPDMIVKWSPATERFLASGHMTV
LEAAQAAVQLSDNGATNLLLREIGGPAAMTQYFRKIGDSVSRLDRKEPEMNDNTPG
DLRDTTTPIAMARTVAKVLYGGALTSTSTHTIERWLIGNQTGDATLRAGFPKDWVVG
EKTGTCANGGRNDIGFFKAQERDYAVAVYTTAPKLSAVERDELVASVGQVITQLILS
TDK

SEQ ID No. 2124:
MRFIHALLLAGIAHSAYASEKLTFKTDLEKLEREKAAQIGVAIVDPQGEIVAGHRMAQ
RFAMCSTFKFPLAALVFERIDSGTERGDRKLSYGPDMIVEWSPATERFLASGHMTV
LEAAQAVQLSDNGATNLLLREIGGPAAMTQYFRKIGDSVSRLDRKESEMSDNTPG
DLRDTTTPIAMARTVAKVLYGGALTSTSTHTIERWLIGNQTGDATLRAGFPKDWVVG
EKTGTCANGGRNDIGFFKAQERDYAVAVYTTAPKLSAVERDELVASVGQVITQLILS
TDK

SEQ ID No. 2125:
MRFIHALLLAGIAHSAYASEKLTFKTDLEKLEREKAAQIGVAIVDPQGEIVAGHRMAQ
RFAMCSTFKFPLAALVFERIDSGTERGDRKLSYGPDMIVEWSPATERFLASGHMTV
LEAAQAAVQLSDNGATNLLLREIGGPAAMTQYFRKIGDSVSRLDRKEPEMSDNTPG
DLRDTTTPIAMARTVAKVLYGGALTSTSTHTIERWLIGNQTGDATLRAGFPKDWVVG

-continued

```
EKTGTCANGARNDIGFFKAQERDYAVAVYTTAPKLSAVERDELVASVGQVITQLILS
TDK

SEQ ID No. 2126:
MRFIHALLLAGIAHSAYASEKLTFKTDLEKLEREKAAEIGVAIVDPQGEIVAGHRMAQ
RFAMCSTFKFPLAALVFERIDSGTERGDRKLSYGPDMIVEWSPATERFLASGHMTV
LEAAQAAVQLSDNGATNLLLREIGGPAAMTQYFRKIGDSVSRLDRKEPEMSDNTPG
DLRDTTTPIAMARTVAKVLYGGALTSTSTHTIERWLIGNQTGDATLRAGFPKDWVVG
EKTGTCANGGRNDIGFFKAQERDYAVAVYTTAPKLSAVERDELVASVGQVITQLILS
TDK

SEQ ID No. 2127:
MRFIHALLLAGIAHSAYASEKLTFKTDLEKLEREKAAQIGVAIVDPQGEIVAGHRMAQ
RFAMCSTFKFPLAALVFERIDSGTERGDRKLSYGPDMIVKWSPATERFLASCHMTV
LEAAQAAVQLSDNGATNLLLREIGGPAAMTQYFRKIGDSVSRLDRKEPEMGDNTPG
DLRDTTTPIAMARTVAKVLYGGALTSTSTHTIERWLIGNQTGDATLRAGFPKDWVVG
EKTGTCANGARNDIGFFKAQERDYAVAVYTTAPKLSAVERDELVASVGQVITQLILS
TDK

SEQ ID No. 2128:
MRFIHALLLAGIAHSAYASEKLTFKTDLEKLEREKAAQIGVAIVDPQGEIVAGHRTAQ
RFAMCSTFKFPLAALVFERIDSGTERGDRKLSYGPDMIVKWSPATERFLASGHMTV
LEAAQAAVQLSDNGATNLLLREIGGPAAMTQYFRKIGDSVSRLDRKEPEMGDNTPG
DLRDTTTPIAMARTVAKVLYGGALTSTSTHTIERWLIGNQTGDATLRAGFPKDWVVG
EKTGTCANGGRNDIGFFKAQERDYAVAVYTTAPKLSAVERDELVASVGQVITQLILS
TDK

SEQ ID No. 2129:
MRFIHALLLAGIAHSAYASEKLTFKTDLEKLEREKAAQIGVAIVDPQGEIVAGHRTAQ
RFAMCSTFKFPLAALVFERIDSGTERGDRKLSYGPDMIVKWSPATERFLASGHMTV
LEAAQAAVQLSDNGATNLLLREIGGPAAMTQYFRKIGDSVSRLDRKEPEMSDNTPG
DLRDTTTPIAMARTVAKVLYGGALTSTSTHTIERWLIGNOTGDATLRAGFPKDWVVG
EKTGTCANGGRNDIGFFKAQERDYAVAVYTTAPKLSAVERDELVASVGQVITQLILS
TDK

SEQ ID No. 2130:
MRFIHALLLAGIAHSAYASEKLTFKTDLEKLEREKAAQIGVAIVDPQGEIVAGHRMAQ
RFAMCSTFKFPLAALVFERIDSGTERGDRKLSYGPDMIVEWSPATERFLASGHMTV
LEAAQAAVQLSDNGATNLLLREIGGPAAMTQYFRKIGDSVSRLDRKEPEMGDNTPG
DLRDTTTPIAMARTVAKVLYGGALTSTSTHTIERWLIGNQTGDATLRAGFPKDWVVG
EKTGACANGARNDIGFFKAQERDYAVAVYTTAPKLSAVERDELVASVGQVITQLILS
TDK
``` said peptides being chosen, preferably, from the peptides of sequence SEQ ID No, 2131 to SEQ ID No. 2159 as defined hereafter:

| Peptide SEQ ID No. | Amino acid sequence | Position of the peptide in the GES protein(s) | Clinical interest |
|---|---|---|---|
| SEQ ID No. 2131 | AAEIGVAIVDPQGEIVAGHR | 36-55 for the proteins of SEQ No. 2126 | carba |
| SEQ ID No. 2132 | AAQIGVAIVDPQGEIVAGHR | 36-55 for the proteins of SEQ No. 2114, 2115, 2116, 2117, 2118, 2119, 2120, 2121, 2122, 2123, 2124, 2125, 2127, 2128, 2129, 2130 | ESBL |
| SEQ ID No. 2133 | AGFPK | 218-222 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2134 | DTTTPIAMAR | 174-183 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2135 | DWVVGEK | 223-229 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2136 | DYAVAVYTTAPK | 250-261 for the proteins of SEQ No. 2114, 2115, 2116, 2117, 2118, 2119, 2120, 2121, 2122, 2123, 2124, 2125, 2126, 2127, 2128, 2129, 2130 | ESBL |

-continued

| Peptide SEQ ID No. | Amino acid sequence | Position of the peptide in the GES protein(s) | Clinical interest |
|---|---|---|---|
| SEQ ID No. 2137 | EIGGPAAMTQYFR | 136-148 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2138 | EPEMGDNTPGDLR | 161-173 for the proteins of SEQ No. 2114, 2115, 2116, 2120, 2121, 2122, 2127, 2128, 2130 | ESBL |
| SEQ ID No. 2139 | EPEMNDNTPGDLR | 161-173 for the proteins of SEQ No. 2117, 2123 | carba |
| SEQ ID No. 2140 | EPEMSDNTPGDLR | 161-173 for the proteins of SEQ No. 2118, 2119, 2125, 2126, 2129 | carba |
| SEQ ID No. 2141 | ESEMSDNTPGDLR | 161-173 for the proteins of SEQ No. 2124 | carba |
| SEQ ID No. 2142 | FAMCSTFK | 60-67 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2143 | FIHALLLAGIAHSAYASEK | 3-21 for the proteins of SEQ No. 2114, 2115, 2116, 2117, 2118, 2119, 2120, 2121, 2123, 2124, 2125, 2126, 2127, 2128, 2129, 2130 | ESBL |
| SEQ ID No. 2144 | FIHALLLAGTAHSAYASEK | 3-21 for the proteins of SEQ No. 2122 | carba |
| SEQ ID No. 2145 | FPLAALVFER | 68-77 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2146 | IDSGTER | 78-84 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2147 | IGDSVSR | 150-156 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2148 | LSAVER | 262-267 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2149 | LSYGPDMIVEWSPATER | 89-105 for the proteins of SEQ No. 2114, 2116, 2117, 2118, 2120, 2121, 2122, 2124, 2125, 2126, 2130 | ESBL |
| SEQ ID No. 2150 | LSYGPDMIVK | 89-98 for the proteins of SEQ No. 2115, 2119, 2123, 2127, 2128, 2129 | carba |
| SEQ ID No. 2151 | NDIGFFK | 239-245 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2152 | TDLEK | 26-30 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2153 | TGACANGAR | 230-238 for the proteins of SEQ No. 2130 | carba |
| SEQ ID No. 2154 | TGTCANGAR | 230-238 for the proteins of SEQ No. 2121, 2125, 2127 | carba |
| SEQ ID No. 2155 | TGTCANGGR | 230-238 for the proteins of SEQ No. 2114, 2115, 2116, 2117, 2118, 2119, 2122, 2123, 2124, 2126, 2128, 2129 | ESBL |
| SEQ ID No. 2156 | TGTCANGSR | 230-238 for the proteins of SEQ No. 2120 | carba |

-continued

| Peptide SEQ ID No. | Amino acid sequence | Position of the peptide in the GES protein(s) | Clinical interest |
|---|---|---|---|
| SEQ ID No. 2157 | VLYGGALTSTSTHTIER | 188-204 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2158 | WLIGNQTGDATLR | 205-217 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2159 | WSPATER | 99-105 for the proteins of SEQ No. 2114, 2115, 2116, 2117, 2118, 2119, 2120, 2121, 2122, 2123, 2124, 2125, 2126, 2127, 2128, 2129, 2130 | carba |

In the clinical interest column, the ESBL and carba entries correspond to the GES beta-lactamase activities which the corresponding peptide makes it possible to detect. Therefore, the detection of a carba peptide will indicate the presence of a carbapenemase beta-lactamase capable of hydrolysing carbapenems, penicillins, first-generation cephalosporins such as cephaloridine and cefalotin, and at least one antibiotic from the oxyimino-beta-lactam class such as cefotaxime, ceftazidime or the monobactames such as aztreonam.

If no peptide referred to as carba is detected, the detection of a peptide referred to as ESBL will indicate the presence of a beta-lactamase with an extended spectrum (ESBL) capable of hydrolysing penicillins, first-generation cephalosporins such as cephaloridine and cefalotin, and at least one antibiotic from the oxyimino-beta-lactam class such as cefotaxime, ceftazidime or monobactams such as aztreonam.

The detection of a mechanism of resistance to cephalosporinases with an extended spectrum (ESBL) induced by the GES protein is thus characterised by the detection of at least one resistance-marking ESBL peptide chosen from the sequences SEQ ID No. 2131 to SEQ ID No. 2159.

Certain peptide sequences can be common to several resistance mechanisms. Therefore, the following sequences are identical:
SEQ ID No. 834 and SEQ ID No. 978
SEQ ID No. 833 and SEQ ID No. 977
SEQ ID No. 832 and SEQ ID No. 976
SEQ ID No. 831 and SEQ ID No. 975
SEQ ID No. 826 and SEQ ID No. 974
SEQ ID No. 825 and SEQ ID No. 973
SEQ ID No. 824 and SEQ ID No. 972
SEQ ID No. 823 and SEQ ID No. 971
SEQ ID No. 822 and SEQ ID No. 970
SEQ ID No. 817 and SEQ ID No. 969
SEQ ID No. 813 and SEQ ID No. 967
SEQ ID No. 802 and SEQ ID No. 964
SEQ ID No. 798 and SEQ ID No. 963
SEQ ID No. 666 and SEQ ID No. 895
SEQ ID No, 350 and SEQ ID No. 1035
SEQ ID No. 349 and SEQ ID No. 1031
SEQ ID No. 347 and SEQ ID No. 1030
SEQ ID No, 346 and SEQ ID No. 1029
SEQ ID No. 345 and SEQ ID No. 1028
SEQ ID No. 343 and SEQ ID No. 1037 and SEQ ID No. 725
SEQ ID No. 342 and SEQ ID No. 1026
SEQ ID No. 341 and SEQ ID No. 1025
SEQ ID No. 340 and SEQ ID No. 1024
SEQ ID No. 339 and SEQ ID No. 1023
SEQ ID No. 338 and SEQ ID No. 1020
SEQ ID No. 337 and SEQ ID No. 1036 and SEQ ID No. 719
SEQ ID No. 337 and SEQ ID No. 1036
SEQ ID No. 336 and SEQ ID No. 841 and SEQ ID No. 981
SEQ ID No. 323 and SEQ ID No. 840 and SEQ ID No. 980
SEQ ID No. 315 and SEQ ID No. 839 and SEQ ID No. 948 and SEQ ID No. 979
SEQ ID No. 240 and SEQ ID No. 679
SEQ ID No. 184 and SEQ ID No. 626
SEQ ID No. 182 and SEQ ID No. 625
SEQ ID No. 1034 and SEQ ID No. 1999
SEQ ID No. 1032 and SEQ ID No. 1988
SEQ ID No. 1027 and SEQ ID No. 1970
SEQ ID No. 1022 and SEQ ID No. 1952
SEQ ID No. 1021 and SEQ ID No. 1937
SEQ ID No. 1019 and SEQ ID No. 1933
SEQ ID No. 809 and SEQ ID No. 966
SEQ ID No. 1033 and SEQ ID No. 1989

In all cases, the sequences above indicate the expression of a mechanism of resistance to cephalosporins.

The method of the invention and its advantages will become apparent from the rest of the present description which presents several non-limiting examples of implementation of said method.

EXAMPLE 1

Identification of Microorganisms from a Sample by Biochemical Profile

1. Culturing of the Sample on a Culture Medium

The optimum culture media and the optimum culture conditions are different according to the species of microorganism. By default, the sample is seeded on different media:
sheep blood Columbia agar (bioMérieux ref. 43041) for 18 to 24 h at 35° C., in an aerobic or anaerobic atmosphere;
TSA agar (bioMerieux ref. 43011) for 18 to 24 h at 37° C.

2. Identification of the Microorganisms

The identification is performed as follows:
1. Selection of isolated colonies
2. While maintaining the aseptic conditions, transfer of 3.0 mL of aqueous sterile saline solution (0.45-0.50% NaCl, pH 4.5 to 7.0) into a transparent plastic (polystyrene) test tube
3. With the aid of a stirrer or a sterile swab, transfer of a sufficient number of identical colonies into the saline solution tube prepared in step 2, and adjustment of the bacterial suspension between 0.50 and 0.63 McFarland with a calibrated DENSICHEK from VITEK®
4. Positioning of the bacterial suspension tube and of a VITEK® identification card on a VITEK® cartridge
5. Loading of the cartridge into the VITEK® instrument
6. The filling, sealing, incubation and reading operations are automatic
7. Acquisition of a biochemical profile
8. Identification with the VITEK® system performed by comparing to the biochemical profiles of known strains

EXAMPLE 2

Preparation of a Primary Urine Sample by Microorganism Enrichment

The following protocol is performed in 16 steps (steps 5 to 12 are optional and could be omitted if the enriched sample is subsequently treated according to examples 4 and onwards):
1. Centrifuging of 5 mL of contaminated urine, at 2000 g for 30 seconds
2. Recovery of the supernatant
3. Centrifuging at 15000 g for 5 minutes
4. Elimination of the supernatant
5. Washing of the pellet with 3 mL of distilled water by resuspension
6. Centrifuging at 15000 g for 5 minutes
7. Elimination of the supernatant
8. Place the pellet in the presence of solvent (8 acetone volumes for 1 methanol volume) for 1/10 dilution
9. Leave for 1 hour at −20° C.
10. Centrifuging at 15000 g for 5 minutes
11. Elimination of the supernatant
12. Place the pellet in the presence of solvent (8 acetone volumes for 1 methanol volume) for 1/10 dilution
13. Leave for 1 hour at −20° C.
14. Centrifuging at 15000 g for 5 minutes
15. Elimination of the supernatant
16. The pellet constitutes the microorganism-enriched sample

EXAMPLE 3

Identification of Microorganisms from a Sample by MALDI-TOF

The identification is performed as follows:
1. Transfer, with the aid of a 1 µl oese, of a portion of microorganism colony obtained according to example 1, or of an enriched sample according to example 2, and uniform deposition on a plate for MALDI-TOF mass spectrometry
2. Covering the deposit with 1 µl of matrix. The matrix used is a saturated solution of HCCA (alpha-cyano-4-hydroxycinnamic acid) in organic solvent (50% acetonitrile and 2.5% trifluoroacetic acid)
3. Drying at ambient temperature
4. Introducing the plate into the mass spectrometer
5. Acquiring a mass spectrum
6. Comparing the obtained spectrum with the spectra contained in a knowledge base
7. Identification of the microorganism by comparing the obtained peaks with those in the knowledge base

EXAMPLE 4

Identification of Microorganisms from a Sample by ESI-TOF

The identification is performed as follows:
1. Sampling of a microorganism colony, obtained according to example 1, or of an enriched sample according to example 2, and suspension in 100 µl of demineralised water.
2. Centrifuging at 3000 g for 5 minutes.
3. Elimination of the supernatant.
4. Resuspension in 100 µl of demineralised water.
5. Centrifuging at 3000 g for 5 minutes.
6. Elimination of the supernatant.
7. Resuspension in 100 µl of an acetonitrile, demineralised water and formic acid mixture (50/50/0.1%).
8. Filtration with a filter with a porosity of 0.45 µm.
9. Injection into a mass spectrometer in single MS mode.
10. Acquisition of a mass spectrum.
11. Comparing the obtained spectrum with the spectra contained in a knowledge base.
12. Identification of the microorganism by referring to reference spectra.

EXAMPLE 5

Obtaining Digested Proteins from Microorganisms

The following protocol is conventionally performed in 17 steps:
1. Sampling of a microorganism colony, obtained according to example 1, or of an enriched sample according to example 2, and suspension in 10 to 100 µl of a 6M guanidine hydrochloride solution, 50 mM Tris-HCl, pH=8.0.
2. Addition of dithiothreitol (DTT) to achieve an end concentration of 5 mM.
3. Reduction for 20 minutes at 95° C. in a water bath.
4. Cooling the tubes to ambient temperature
5. Addition of iodoacetamide to obtain an end concentration of 12.5 mM.
6. Alkylation for 40 minutes at ambient temperature and in the dark.
7. Dilution by a factor of 6 with a 50 mM $NH_4HCO_3$ solution, pH=8.0 to obtain an end guanidine hydrochloride concentration of 1M.
8. Addition of 1 µg of trypsin.
9. Digestion at 37° C. for between 6 hours and one night.
10. Addition of formic acid down to a pH below 4 to stop the reaction.
11. The sample volume is made up to 1 mL with water/0.5% (v/v) formic acid
12. Balancing of the Waters Oasis HLB columns with 1 ml of methanol and then 1 ml of $H_2O$/0.1% (v/v) formic acid
13. Deposition of the sample which runs off by gravity
14. Washing with 1 ml of $H_2O$/0.1% (v/v) formic acid 15. Elution with 1 ml of a mixture of 80% methanol and 20% water/0.1% (v/v) formic acid
16. The eluate is evaporated with a SpeedVac@ SPD2010 evaporator (Thermo Electron Corporation, Waltham, Mass., United States of America) over 2 hours, in order to obtain a volume of around 100 μl.
17. The eluate is then taken up in a water/0.5% (v/v) formic acid solution in a quantity sufficient for (QSF) 250 μl

EXAMPLE 6

Identification of a Resistance to TEM Beta-Lactams

Samples Sam10 to Sam61 are identified according to one of the methods described in examples 1, 3 or 4. The identification of the species is set out in TABLE 1.

TABLE 1

| Names | Species |
|---|---|
| Sam10 | P. mirabilis |
| Sam11 | E. coli |
| Sam12 | E. aerogenes |
| Sam13 | E. coli |
| Sam14 | E. coli |
| Sam15 | E. coli |
| Sam16 | S. marcescens |
| Sam17 | E. coli |
| Sam18 | E. coli |
| Sam19 | P. mirabilis |
| Sam20 | C. freundii |
| Sam21 | E. coli |
| Sam22 | P. mirabilis |
| Sam23 | E. coli |
| Sam24 | K. pneumoniae |
| Sam25 | E. coli |
| Sam26 | K. oxytoca |
| Sam27 | P. mirabilis |
| Sam28 | E. coli |
| Sam29 | P. mirabilis |
| Sam30 | P. rettgeri |
| Sam31 | P. stuartii |
| Sam32 | S. Derby |
| Sam33 | E. coli |
| Sam34 | E. coli |
| Sam35 | E. coli |
| Sam36 | E. coli |
| Sam37 | E. coli |
| Sam38 | E. coli |
| Sam39 | E. coli |
| Sam40 | E. coli |
| Sam41 | E. coli |
| Sam42 | E. coli |
| Sam43 | E. coli |
| Sam44 | E. coli |
| Sam45 | K. pneumoniae |
| Sam46 | E. coli |
| Sam47 | K. pneumoniae |
| Sam48 | P. mirabilis |

TABLE 1-continued

| Names | Species |
|---|---|
| Sam49 | P. mirabilis |
| Sam50 | P. mirabilis |
| Sam51 | P. mirabilis |
| Sam52 | P. mirabilis |
| Sam53 | K. pneumoniae |
| Sam54 | P. mirabilis |
| Sam55 | E. coli |
| Sam56 | E. coli |
| Sam57 | P. mirabilis |
| Sam58 | E. aerogenes |
| Sam59 | E. aerogenes |
| Sam60 | E. coli |
| Sam61 | E. coli |

Samples Sam10 to Sam61 correspond to a species able to comprise a TEM resistance mechanism (Enterobacteriaceae . . . ). The following method is then performed to search for such a mechanism.

Each sample is treated according to example 5, then a volume of 50 μl of digested proteins is injected and analysed according to the following conditions:
Dionex Ultimate 3000 chromatographic channel from the Dionex Corporation (Sunnyvale, United States of America).
Waters BEH130 C18 Column, 2.1 mm inner diameter, 100 mm length, 3.5 μm particle size (Waters, Saint-Quentin En Yvelines, France).
Solvent A: $N_2O$+0.1% formic acid.
Solvent B: ACN+0.1% formic acid.
HPLC gradient defined in Table 2 hereafter:

TABLE 2

| Time (min) | Flow (μl) | Solvent A (%) | Solvent B (%) |
|---|---|---|---|
| 0 | 300 | 98 | 2 |
| 3 | 300 | 98 | 2 |
| 34 | 300 | 54.6 | 45.4 |
| 35 | 300 | 0 | 100 |
| 55 | 300 | 0 | 100 |
| 55.1 | 300 | 98 | 2 |
| 74 | 300 | 98 | 2 |

The eluate coming from the chromatographic column is directly injected into the ionising source of the QTRAP® 5500 mass spectrometer from Applied Biosystems (Foster City, United States of America).
The peptides coming from the digestion of the microorganism proteins are analysed by the mass spectrometer in MRM mode. Only the peptides indicated in TABLE 3 are detected. To this end, the fragment(s) of the peptides indicated in TABLE 3 is/are detected. The charge state of the precursor, and the possible existence of an oxidised methionine, are also indicated in TABLE 3.

TABLE 3

| Transition number | Peptide | Methionine oxidation | Fragment ion | Charge state of the precursor | Clinical interest |
|---|---|---|---|---|---|
| 1 | DAENQLGAR | no | y4 monocharged | 2 | TEM |
| 2 | DAENQLGAR | no | y6 monocharged | 2 | TEM |
| 3 | DAENQLGAR | no | y7 monocharged | 2 | TEM |
| 4 | ELTAFLHNIGDHVTR | no | y4 monocharged | 2 | TEM |
| 5 | ELTAFLHNIGDHVTR | no | y8 monocharged | 2 | TEM |

TABLE 3-continued

| Transition number | Peptide | Methionine oxidation | Fragment ion | Charge state of the precursor | Clinical interest |
|---|---|---|---|---|---|
| 6 | ELTAFLHNIGDHVTR | no | y9 monocharged | 2 | TEM |
| 7 | ELTAFLHNMGDNVTR | no | y7 monocharged | 2 | 2b |
| 8 | ELTAFLHNMGDNVTR | no | y8 monocharged | 2 | 2b |
| 9 | ELTAFLHNMGDNVTR | no | y9 monocharged | 2 | 2b |
| 10 | FPMISTFK | yes | y5 monocharged | 2 | 2br |
| 11 | FPMISTFK | yes | y6 monocharged | 2 | 2br |
| 12 | FPMISTFK | yes | y7 monocharged | 2 | 2br |
| 13 | FPMISTFK | no | y5 monocharged | 2 | 2br |
| 14 | FPMISTFK | no | y6 monocharged | 2 | 2br |
| 15 | FPMISTFK | no | y7 monocharged | 2 | 2br |
| 16 | GEPELNEAIPNDER | no | y12 dicharged | 2 | 2be |
| 17 | GEPELNEAIPNDER | no | y5 monocharged | 2 | 2be |
| 18 | GEPELNEAIPNDER | no | y7 monocharged | 2 | 2be |
| 19 | GSLGIIAALGPDGKPSR | no | y10 monocharged | 2 | 2br |
| 20 | GSLGIIAALGPDGKPSR | no | y8 monocharged | 2 | 2br |
| 21 | GSLGIIAALGPDGKPSR | no | y9 monocharged | 2 | 2br |
| 22 | IHYSQNDLVEYSPVTEK | no | y6 monocharged | 3 | TEM |
| 23 | IHYSQNDLVEYSPVTEK | no | y7 monocharged | 3 | TEM |
| 24 | IHYSQNDLVEYSPVTEK | no | y8 monocharged | 3 | TEM |
| 25 | ILESFRPEER | no | b6 monocharged | 2 | TEM |
| 26 | ILESFRPEER | no | b8 monocharged | 2 | TEM |
| 27 | ILESFRPEER | no | y7 dicharged | 2 | TEM |
| 28 | IWIYTTGGQATMDER | yes | y7 monocharged | 2 | 2be |
| 29 | IWIYTTGGQATMDER | yes | y8 monocharged | 2 | 2be |
| 30 | IWIYTTGGQATMDER | yes | y9 monocharged | 2 | 2be |
| 31 | IWIYTTGGQATMDER | no | y6 monocharged | 2 | 2be |
| 32 | IWIYTTGGQATMDER | no | y8 monocharged | 2 | 2be |
| 33 | IWIYTTGGQATMDER | no | y9 monocharged | 2 | 2be |
| 34 | LDSWEPELNEAIPNDER | no | y5 monocharged | 3 | 2be |
| 35 | LDSWEPELNEAIPNDER | no | y6 monocharged | 3 | 2be |
| 36 | LDSWEPELNEAIPNDER | no | y7 monocharged | 3 | 2be |
| 37 | QIAEICASLIK | no | y6 monocharged | 2 | TEM |
| 38 | QIAEICASLIK | no | y7 monocharged | 2 | TEM |
| 39 | QIAEICASLIK | no | y8 monocharged | 2 | TEM |
| 40 | SGANER | no | y3 monocharged | 2 | TEM |
| 41 | SGANER | no | y4 monocharged | 2 | TEM |
| 42 | SGANER | no | y5 monocharged | 2 | TEM |
| 43 | SGGSER | no | y3 monocharged | 2 | 2be |

TABLE 3-continued

| Transition number | Peptide | Methionine oxidation | Fragment ion | Charge state of the precursor | Clinical interest |
|---|---|---|---|---|---|
| 44 | SGGSER | no | y4 monocharged | 2 | 2be |
| 45 | SGGSER | no | y5 monocharged | 2 | 2be |
| 46 | VDAGQEQLDR | no | y7 monocharged | 2 | TEM |
| 47 | VDAGQEQLDR | no | y8 monocharged | 2 | TEM |
| 48 | VDAGQEQLDR | no | y9 monocharged | 2 | TEM |
| 49 | VKPAEDK | no | y4 monocharged | 2 | 2be |
| 50 | VKPAEDK | no | y5 monocharged | 2 | 2be |
| 51 | VKPAEDK | no | y6 monocharged | 2 | 2be |
| 52 | WEPELNEAIPIDER | no | y12 dicharged | 2 | 2be |
| 53 | WEPELNEAIPIDER | no | y5 monocharged | 2 | 2be |
| 54 | WEPELNEAIPIDER | no | y7 monocharged | 2 | 2be |
| 55 | DTTMPAAMATK | yes | y7 monocharged | 2 | TEM |
| 56 | DTTMPAAMATK | yes | y8 monocharged | 2 | TEM |
| 57 | DTTMPAAMATK | yes | y9 monocharged | 2 | TEM |
| 58 | DTTMPAAMATK | no | y7 monocharged | 2 | TEM |
| 59 | DTTMPAAMATK | no | y8 monocharged | 2 | TEM |
| 60 | DTTMPAAMATK | no | y9 monocharged | 2 | TEM |
| 61 | ELTAFLHNMGDHVTR | no | y13 dicharged | 2 | TEM |
| 62 | ELTAFLHNMGDHVTR | no | y4 monocharged | 2 | TEM |
| 63 | ELTAFLHNMGDHVTR | no | y8 monocharged | 2 | TEM |
| 64 | EPELNEAIPNDER | no | y5 monocharged | 2 | TEM |
| 65 | EPELNEAIPNDER | no | y7 monocharged | 2 | TEM |
| 66 | EPELNEAIPNDER | no | y8 monocharged | 2 | TEM |
| 67 | FPMMSTFK | yes | y6 monocharged | 2 | TEM |
| 68 | FPMMSTFK | yes | y7 monocharged | 2 | TEM |
| 69 | FPMMSTFK | yes | y7 dicharged | 2 | TEM |
| 70 | FPMMSTFK | no | y6 monocharged | 2 | TEM |
| 71 | FPMMSTFK | no | y7 monocharged | 2 | TEM |
| 72 | FPMMSTFK | no | y7 dicharged | 2 | TEM |
| 73 | GIIAALGPDGKPSR | no | y7 monocharged | 2 | TEM |
| 74 | GIIAALGPDGKPSR | no | y8 monocharged | 2 | TEM |
| 75 | GIIAALGPDGKPSR | no | y9 monocharged | 2 | TEM |
| 76 | IDAGQEQLGR | no | y7 monocharged | 2 | TEM |
| 77 | IDAGQEQLGR | no | y8 monocharged | 2 | TEM |
| 78 | IDAGQEQLGR | no | y9 monocharged | 2 | TEM |
| 79 | IHYSQNDLVK | no | y7 monocharged | 2 | 2be |
| 80 | IHYSQNDLVK | no | y8 monocharged | 2 | 2be |
| 81 | IHYSQNDLVK | no | y9 dicharged | 2 | 2be |
| 82 | IHYSQSDWEYSPVTEK | no | y16 dicharged | 2 | TEM |

TABLE 3-continued

| Transition number | Peptide | Methionine oxidation | Fragment ion | Charge state of the precursor | Clinical interest |
|---|---|---|---|---|---|
| 83 | IHYSQSDWEYSPVTEK | no | y5 monocharged | 2 | TEM |
| 84 | IHYSQSDWEYSPVTEK | no | y6 monocharged | 2 | TEM |
| 85 | IWIYMTGGQATMDER | no | y6 monocharged | 2 | 2be |
| 86 | IWIYMTGGQATMDER | no | y8 monocharged | 2 | 2be |
| 87 | IWIYMTGGQATMDER | no | y9 monocharged | 2 | 2be |
| 88 | LDCWEPELNEAIPNDER | no | y5 monocharged | 3 | 2be |
| 89 | LDCWEPELNEAIPNDER | no | y6 monocharged | 3 | 2be |
| 90 | LDCWEPELNEAIPNDER | no | y7 monocharged | 3 | 2be |
| 91 | MSIQHFR | yes | y4 monocharged | 2 | TEM |
| 92 | MSIQHFR | yes | y5 monocharged | 2 | TEM |
| 93 | MSIQHFR | yes | y6 monocharged | 2 | TEM |
| 94 | MSIQHFR | no | y4 monocharged | 2 | TEM |
| 95 | MSIQHFR | no | y5 monocharged | 2 | TEM |
| 96 | MSIQHFR | no | y6 monocharged | 2 | TEM |
| 97 | QQLIDWMEADK | no | y5 monocharged | 2 | TEM |
| 98 | QQLIDWMEADK | no | y6 monocharged | 2 | TEM |
| 99 | QQLIDWMEADK | no | y7 monocharged | 2 | TEM |
| 100 | SGASER | no | y3 monocharged | 2 | 2be |
| 101 | SGASER | no | y4 monocharged | 2 | 2be |
| 102 | SGASER | no | y5 monocharged | 2 | 2be |
| 103 | VALIPFLAAFCLPVFAHPETLVK | no | y11 dicharged | 3 | 2ber |
| 104 | VALIPFLAAFCLPVFAHPETLVK | no | y6 monocharged | 3 | 2ber |
| 105 | VALIPFLAAFCLPVFAHPETLVK | no | y8 monocharged | 3 | 2ber |
| 106 | VGYIELDLNSGK | no | y7 monocharged | 2 | TEM |
| 107 | VGYIELDLNSGK | no | y8 monocharged | 2 | TEM |
| 108 | VGYIELDLNSGK | no | y9 monocharged | 2 | TEM |
| 109 | VLLCGAELSR | no | y6 monocharged | 2 | TEM |
| 110 | VLLCGAELSR | no | y7 monocharged | 2 | TEM |
| 111 | VLLCGAELSR | no | y8 monocharged | 2 | TEM |
| 112 | DAEDQLGAR | no | y5 monocharged | 2 | TEM |
| 113 | DAEDQLGAR | no | y6 monocharged | 2 | TEM |
| 114 | DAEDQLGAR | no | y7 monocharged | 2 | TEM |
| 115 | ETTTPAAMATTLR | yes | y7 monocharged | 2 | 2be |
| 116 | ETTTPAAMATTLR | yes | y9 monocharged | 2 | 2be |
| 117 | ETTTPAAMATTLR | yes | y9 dicharged | 2 | 2be |
| 118 | ETTTPAAMATTLR | no | y7 monocharged | 2 | 2be |
| 119 | ETTTPAAMATTLR | no | y9 monocharged | 2 | 2be |
| 120 | ETTTPAAMATTLR | no | y9 dicharged | 2 | 2be |

TABLE 3-continued

| Transition number | Peptide | Methionine oxidation | Fragment ion | Charge state of the precursor | Clinical interest |
|---|---|---|---|---|---|
| 121 | FPMVSTFK | yes | y6 monocharged | 2 | TEM |
| 122 | FPMVSTFK | yes | y7 monocharged | 2 | TEM |
| 123 | FPMVSTFK | yes | y7 dicharged | 2 | TEM |
| 124 | FPMVSTFK | no | y6 monocharged | 2 | TEM |
| 125 | FPMVSTFK | no | y7 monocharged | 2 | TEM |
| 126 | FPMVSTFK | no | y7 dicharged | 2 | TEM |
| 127 | GSGGIIAALGPDGKPSR | no | y7 monocharged | 2 | 2br |
| 128 | GSGGIIAALGPDGKPSR | no | y8 monocharged | 2 | 2br |
| 129 | GSGGIIAALGPDGKPSR | no | y9 monocharged | 2 | 2br |
| 130 | HLTDGMTVR | yes | y5 monocharged | 2 | TEM |
| 131 | HLTDGMTVR | yes | y7 monocharged | 2 | TEM |
| 132 | HLTDGMTVR | yes | y8 monocharged | 2 | TEM |
| 133 | HLTDGMTVR | no | y4 monocharged | 2 | TEM |
| 134 | HLTDGMTVR | no | y7 monocharged | 2 | TEM |
| 135 | HLTDGMTVR | no | y8 monocharged | 2 | TEM |
| 136 | IVIIYTTGSQATMDER | no | y4 monocharged | 2 | 2br |
| 137 | IVIIYTTGSQATMDER | no | y2 monocharged | 2 | 2br |
| 138 | IVIIYTTGSQATMDER | no | y9 monocharged | 2 | 2br |
| 139 | IWIYTTGSQATMDEQNR | yes | y5 monocharged | 3 | 2br |
| 140 | IWIYTTGSQATMDEQNR | yes | y6 monocharged | 3 | 2br |
| 141 | IWIYTTGSQATMDEQNR | yes | y7 monocharged | 3 | 2br |
| 142 | IWIYTTGSQATMDEQNR | no | y5 monocharged | 3 | 2br |
| 143 | IWIYTTGSQATMDEQNR | no | y6 monocharged | 3 | 2br |
| 144 | IVVIYTTGSQATMDEQNR | no | y7 monocharged | 3 | 2br |
| 145 | LDHWEPELNEAVPNDER | no | y5 monocharged | 3 | 2be |
| 146 | LDHWEPELNEAVPNDER | no | y6 monocharged | 3 | 2be |
| 147 | LDHWEPELNEAVPNDER | no | y7 monocharged | 3 | 2be |
| 148 | LLTGELLTLASQQQLIDWMEADK | yes | b8 monocharged | 3 | TEM |
| 149 | LLTGELLTLASQQQLIDWMEADK | yes | y6 monocharged | 3 | TEM |
| 150 | LLTGELLTLASQQQLIDWMEADK | yes | y7 monocharged | 3 | TEM |
| 151 | LLTGELLTLASQQQLIDWMEADK | no | b4 monocharged | 3 | TEM |
| 152 | LLTGELLTLASQQQLIDWMEADK | no | y6 monocharged | 3 | TEM |
| 153 | LLTGELLTLASQQQLIDWMEADK | no | y7 monocharged | 3 | TEM |
| 154 | QIAEIGASLIK | no | y7 monocharged | 2 | TEM |
| 155 | QIAEIGASLIK | no | y8 monocharged | 2 | TEM |
| 156 | QIAEIGASLIK | no | y9 monocharged | 2 | TEM |
| 157 | QTAEIGASLIK | no | y7 monocharged | 2 | 2be |
| 158 | QTAEIGASLIK | no | y8 monocharged | 2 | 2be |
| 159 | QTAEIGASLIK | no | y9 monocharged | 2 | 2be |

TABLE 3-continued

| Transition number | Peptide | Methionine oxidation | Fragment ion | Charge state of the precursor | Clinical interest |
|---|---|---|---|---|---|
| 160 | SGADER | no | y3 monocharged | 2 | TEM |
| 161 | SGADER | no | y4 monocharged | 2 | TEM |
| 162 | SGADER | no | y5 monocharged | 2 | TEM |
| 163 | SGASK | no | y2 monocharged | 2 | 2be |
| 164 | SGASK | no | y3 monocharged | 2 | 2be |
| 165 | SGASK | no | y4 monocharged | 2 | 2be |
| 166 | VAGPLLR | no | y4 monocharged | 2 | TEM |
| 167 | VAGPLLR | no | y5 monocharged | 2 | TEM |
| 168 | VAGPLLR | no | y6 monocharged | 2 | TEM |
| 169 | VGYIEMDLNSGK | yes | y10 dicharged | 2 | 2be |
| 170 | VGYIEMDLNSGK | yes | y7 monocharged | 2 | 2be |
| 171 | VGYIEMDLNSGK | yes | y8 monocharged | 2 | 2be |
| 172 | VGYIEMDLNSGK | no | y7 monocharged | 2 | 2be |
| 173 | VGYIEMDLNSGK | no | y8 monocharged | 2 | 2be |
| 174 | VGYIEMDLNSGK | no | y9 monocharged | 2 | 2be |
| 175 | WEPELNEAIPNDER | no | y12 dicharged | 2 | TEM |
| 176 | WEPELNEAIPNDER | no | y5 monocharged | 2 | TEM |
| 177 | WEPELNEAIPNDER | no | y7 monocharged | 2 | TEM |
| 178 | ELTAFLHNMGEHVTR | no | y7 monocharged | 2 | 2b |
| 179 | ELTAFLHNMGEHVTR | no | y8 monocharged | 2 | 2b |
| 180 | ELTAFLHNMGEHVTR | no | y9 monocharged | 2 | 2b |
| 181 | FPMLSTFK | yes | y6 monocharged | 2 | TEM |
| 182 | FPMLSTFK | yes | y7 monocharged | 2 | TEM |
| 183 | FPMLSTFK | yes | y7 dicharged | 2 | TEM |
| 184 | FPMLSTFK | no | y6 monocharged | 2 | TEM |
| 185 | FPMLSTFK | no | y7 monocharged | 2 | TEM |
| 186 | FPMLSTFK | no | y7 dicharged | 2 | TEM |
| 187 | GSCGIIAALGPDGKPSR | no | y7 monocharged | 2 | 2br |
| 188 | GSCGIIAALGPDGKPSR | no | y8 monocharged | 2 | 2br |
| 189 | GSCGIIAALGPDGKPSR | no | y9 monocharged | 2 | 2br |
| 190 | GSSGIIAALGPDGKPSR | no | y7 monocharged | 2 | TEM |
| 191 | GSSGIIAALGPDGKPSR | no | y8 monocharged | 2 | TEM |
| 192 | GSSGIIAALGPDGKPSR | no | y9 monocharged | 2 | TEM |
| 193 | ILESFRPEK | no | y5 monocharged | 2 | TEM |
| 194 | ILESFRPEK | no | y6 monocharged | 2 | TEM |
| 195 | ILESFRPEK | no | y7 monocharged | 2 | TEM |
| 196 | IVVIYTTGSQATMDELNR | yes | y5 monocharged | 3 | 2br |
| 197 | IVVIYTTGSQATMDELNR | yes | y6 monocharged | 3 | 2br |

TABLE 3-continued

| Transition number | Peptide | Methionine oxidation | Fragment ion | Charge state of the precursor | Clinical interest |
|---|---|---|---|---|---|
| 198 | IVVIYTTGSQATMDELNR | yes | y7 monocharged | 3 | 2br |
| 199 | IVVIYTTGSQATMDELNR | no | y5 monocharged | 3 | 2br |
| 200 | IVVIYTTGSQATMDELNR | no | y6 monocharged | 3 | 2br |
| 201 | IVVIYTTGSQATMDELNR | no | y7 monocharged | 3 | 2br |
| 202 | IVVIYTTGSQATMDER | no | y6 monocharged | 2 | TEM |
| 203 | IVVIYTTGSQATMDER | no | y8 monocharged | 2 | TEM |
| 204 | IVVIYTTGSQATMDER | no | y9 monocharged | 2 | TEM |
| 205 | LHCWEPELNEAIPNDER | no | y5 monocharged | 3 | 2be |
| 206 | LHCWEPELNEAIPNDER | no | y6 monocharged | 3 | 2be |
| 207 | LHCWEPELNEAIPNDER | no | y7 monocharged | 3 | 2be |
| 208 | LLTGELLTLASR | no | y6 monocharged | 2 | TEM |
| 209 | LLTGELLTLASR | no | y7 monocharged | 2 | TEM |
| 210 | LLTGELLTLASR | no | y9 monocharged | 2 | TEM |
| 211 | QQLIDWMADK | yes | y6 monocharged | 2 | 2ber |
| 212 | QQLIDWMADK | yes | y7 monocharged | 2 | 2ber |
| 213 | QQLIDWMADK | yes | y8 monocharged | 2 | 2ber |
| 214 | QQLIDWMADK | no | y6 monocharged | 2 | 2ber |
| 215 | QQLIDWMADK | no | y7 monocharged | 2 | 2ber |
| 216 | QQLIDWMADK | no | y8 monocharged | 2 | 2ber |
| 217 | SALPAGWFIADK | no | y7 monocharged | 2 | TEM |
| 218 | SALPAGWFIADK | no | y9 monocharged | 2 | TEM |
| 219 | SALPAGWFIADK | no | y9 dicharged | 2 | TEM |
| 220 | SGAGVR | no | y3 monocharged | 2 | 2be |
| 221 | SGAGVR | no | y4 monocharged | 2 | 2be |
| 222 | SGAGVR | no | y5 monocharged | 2 | 2be |
| 223 | SGTGER | no | y3 monocharged | 2 | 2be |
| 224 | SGTGER | no | y4 monocharged | 2 | 2be |
| 225 | SGTGER | no | y5 monocharged | 2 | 2be |
| 226 | VALIPFFAAFCIPVFAHPETLVK | no | y11 dicharged | 3 | 2br |
| 227 | VALIPFFAAFCIPVFAHPETLVK | no | y6 monocharged | 3 | 2br |
| 228 | VALIPFFAAFCIPVFAHPETLVK | no | y7 monocharged | 3 | 2br |
| 229 | VLLCGAVLSR | no | y6 monocharged | 2 | TEM |
| 230 | VLLCGAVLSR | no | y7 monocharged | 2 | TEM |
| 231 | VLLCGAVLSR | no | y8 monocharged | 2 | TEM |
| 232 | YSPVTEK | no | y4 monocharged | 2 | 2be |
| 233 | YSPVTEK | no | y5 monocharged | 2 | 2be |
| 234 | YSPVTEK | no | y6 monocharged | 2 | 2be |
| 235 | CEPELNEAIPNDER | no | y12 dicharged | 2 | 2br |
| 236 | CEPELNEAIPNDER | no | y5 monocharged | 2 | 2br |

TABLE 3-continued

| Transition number | Peptide | Methionine oxidation | Fragment ion | Charge state of the precursor | Clinical interest |
|---|---|---|---|---|---|
| 237 | CEPELNEAIPNDER | no | y8 monocharged | 2 | 2br |
| 238 | DAEDQVGAR | no | y5 monocharged | 2 | 2be |
| 239 | DAEDQVGAR | no | y6 monocharged | 2 | 2be |
| 240 | DAEDQVGAR | no | y7 monocharged | 2 | 2be |
| 241 | DTTMPVAMATTLR | no | y7 monocharged | 2 | TEM |
| 242 | DTTMPVAMATTLR | no | y9 monocharged | 2 | TEM |
| 243 | DTTMPVAMATTLR | no | y9 dicharged | 2 | TEM |
| 244 | ELTAFLR | no | y4 monocharged | 2 | 2be |
| 245 | ELTAFLR | no | y5 monocharged | 2 | 2be |
| 246 | ELTAFLR | no | y6 monocharged | 2 | 2be |
| 247 | GSTGIIAALGPDGKPSR | no | y10 monocharged | 2 | TEM |
| 248 | GSTGIIAALGPDGKPSR | no | y7 monocharged | 2 | TEM |
| 249 | GSTGIIAALGPDGKPSR | no | y9 monocharged | 2 | TEM |
| 250 | HLTGGMTVR | yes | y5 monocharged | 2 | 2b |
| 251 | HLTGGMTVR | yes | y6 monocharged | 2 | 2b |
| 252 | HLTGGMTVR | yes | y7 monocharged | 2 | 2b |
| 253 | HLTGGMTVR | no | y5 monocharged | 2 | 2b |
| 254 | HLTGGMTVR | no | y6 monocharged | 2 | 2b |
| 255 | HLTGGMTVR | no | y7 monocharged | 2 | 2b |
| 256 | IVVIYMTGSQATMDELNR | yes | y6 monocharged | 3 | 2ber |
| 257 | IVVIYMTGSQATMDELNR | yes | y7 monocharged | 3 | 2ber |
| 258 | IVVIYMTGSQATMDELNR | yes | y8 monocharged | 3 | 2ber |
| 259 | IVVIYMTGSQATMDELNR | no | y5 monocharged | 3 | 2ber |
| 260 | IVVIYMTGSQATMDELNR | no | y6 monocharged | 3 | 2ber |
| 261 | IVVIYMTGSQATMDELNR | no | y7 monocharged | 3 | 2ber |
| 262 | LDHWEPELNEAIPNDER | no | y5 monocharged | 3 | 2be |
| 263 | LDHWEPELNEAIPNDER | no | y6 monocharged | 3 | 2be |
| 264 | LDHWEPELNEAIPNDER | no | y7 monocharged | 3 | 2be |
| 265 | LLTSELLTLASR | no | y10 monocharged | 2 | TEM |
| 266 | LLTSELLTLASR | no | y7 monocharged | 2 | TEM |
| 267 | LLTSELLTLASR | no | y9 monocharged | 2 | TEM |
| 268 | QIAEIGGSLIK | no | y7 monocharged | 2 | 2ber |
| 269 | QIAEIGGSLIK | no | y8 monocharged | 2 | 2ber |
| 270 | QIAEIGGSLIK | no | y9 monocharged | 2 | 2ber |
| 271 | QQLIDWMEVDK | yes | y6 monocharged | 2 | TEM |
| 272 | QQLIDWMEVDK | yes | y7 monocharged | 2 | TEM |
| 273 | QQLIDWMEVDK | yes | y8 monocharged | 2 | TEM |
| 274 | QQLIDWMEVDK | no | y5 monocharged | 2 | TEM |

TABLE 3-continued

| Transition number | Peptide | Methionine oxidation | Fragment ion | Charge state of the precursor | Clinical interest |
|---|---|---|---|---|---|
| 275 | QQLIDWMEVDK | no | y6 monocharged | 2 | TEM |
| 276 | QQLIDWMEVDK | no | y7 monocharged | 2 | TEM |
| 277 | SVLPAGWFIADK | no | y10 dicharged | 2 | 2be |
| 278 | SVLPAGWFIADK | no | y9 monocharged | 2 | 2be |
| 279 | SVLPAGWFIADK | no | y9 dicharged | 2 | 2be |
| 280 | VAGPLMR | yes | y4 monocharged | 2 | 2br |
| 281 | VAGPLMR | yes | y5 monocharged | 2 | 2br |
| 282 | VAGPLMR | yes | y6 monocharged | 2 | 2br |
| 283 | VAGPLMR | no | y4 monocharged | 2 | 2br |
| 284 | VAGPLMR | no | y5 monocharged | 2 | 2br |
| 285 | VAGPLMR | no | y6 monocharged | 2 | 2br |
| 286 | VALIPFFAAFCLPVFAHPDTLVK | no | y11 dicharged | 3 | TEM |
| 287 | VALIPFFAAFCLPVFAHPDTLVK | no | y17 dicharged | 3 | TEM |
| 288 | VALIPFFAAFCLPVFAHPDTLVK | no | y6 monocharged | 3 | TEM |
| 289 | VALIPFFAAFCLPVFAHPK | no | y15 dicharged | 3 | TEM |
| 290 | VALIPFFAAFCLPVFAHPK | no | y7 monocharged | 3 | TEM |
| 291 | VALIPFFAAFCLPVFAHPK | no | y9 dicharged | 3 | TEM |
| 292 | VEDAEDQLGAR | no | y7 monocharged | 2 | 2b |
| 293 | VEDAEDQLGAR | no | y8 monocharged | 2 | 2b |
| 294 | VEDAEDQLGAR | no | y9 monocharged | 2 | 2b |
| 295 | DAEDQLGSTSGYIELDLNSGK | no | y7 monocharged | 3 | 2ber |
| 296 | DAEDQLGSTSGYIELDLNSGK | no | y8 monocharged | 3 | 2ber |
| 297 | DAEDQLGSTSGYIELDLNSGK | no | y9 monocharged | 3 | 2ber |
| 298 | DTTMPAAMATTLR | no | y7 monocharged | 2 | TEM |
| 299 | DTTMPAAMATTLR | no | y8 monocharged | 2 | TEM |
| 300 | DTTMPAAMATTLR | no | y9 monocharged | 2 | TEM |
| 301 | DTTTPAAMATTLR | yes | y7 monocharged | 2 | TEM |
| 302 | DTTTPAAMATTLR | yes | y8 monocharged | 2 | TEM |
| 303 | DTTTPAAMATTLR | yes | y9 dicharged | 2 | TEM |
| 304 | DTTTPAAMATTLR | no | y7 monocharged | 2 | TEM |
| 305 | DTTTPAAMATTLR | no | y9 monocharged | 2 | TEM |
| 306 | DTTTPAAMATTLR | no | y9 dicharged | 2 | TEM |
| 307 | GSHGIIAALGPDGKPSR | no | b6 monocharged | 2 | 2br |
| 308 | GSHGIIAALGPDGKPSR | no | y15 dicharged | 2 | 2br |
| 309 | GSHGIIAALGPDGKPSR | no | y8 monocharged | 2 | 2br |
| 310 | HLPDGMTVR | no | y5 monocharged | 2 | TEM |
| 311 | HLPDGMTVR | no | y7 monocharged | 2 | TEM |
| 312 | HLPDGMTVR | no | y8 monocharged | 2 | TEM |
| 313 | IHYSQSDLVEYSPVTEK | no | y16 dicharged | 2 | 2be |

TABLE 3-continued

| Transition number | Peptide | Methionine oxidation | Fragment ion | Charge state of the precursor | Clinical interest |
|---|---|---|---|---|---|
| 314 | IHYSQSDLVEYSPVTEK | no | y7 monocharged | 2 | 2be |
| 315 | IHYSQSDLVEYSPVTEK | no | y8 monocharged | 2 | 2be |
| 316 | IVVIYMTGSQATMDER | no | y6 monocharged | 2 | TEM |
| 317 | IVVIYMTGSQATMDER | no | y8 monocharged | 2 | TEM |
| 318 | IVVIYMTGSQATMDER | no | y9 monocharged | 2 | TEM |
| 319 | LLTDELLTLASR | no | y5 monocharged | 2 | 2be |
| 320 | LLTDELLTLASR | no | y6 monocharged | 2 | 2be |
| 321 | LLTDELLTLASR | no | y7 monocharged | 2 | 2be |
| 322 | NMGDHVTR | yes | y4 monocharged | 2 | 2be |
| 323 | NMGDHVTR | yes | y5 monocharged | 2 | 2be |
| 324 | NMGDHVTR | yes | y6 monocharged | 2 | 2be |
| 325 | NMGDHVTR | no | y4 monocharged | 2 | 2be |
| 326 | NMGDHVTR | no | y5 monocharged | 2 | 2be |
| 327 | NMGDHVTR | no | y6 monocharged | 2 | 2be |
| 328 | QIVEIGASLIK | no | y7 monocharged | 2 | 2be |
| 329 | QIVEIGASLIK | no | y8 monocharged | 2 | 2be |
| 330 | QIVEIGASLIK | no | y9 monocharged | 2 | 2be |
| 331 | SGAGER | no | y3 monocharged | 2 | TEM |
| 332 | SGAGER | no | y4 monocharged | 2 | TEM |
| 333 | SGAGER | no | y5 monocharged | 2 | TEM |
| 334 | VAEPLLR | no | y4 monocharged | 2 | 2b |
| 335 | VAEPLLR | no | y5 monocharged | 2 | 2b |
| 336 | VAEPLLR | no | y6 monocharged | 2 | 2b |
| 337 | VALIPFFAAFCFPVFAHPETLVK | no | b11 monocharged | 3 | TEM |
| 338 | VALIPFFAAFCFPVFAHPETLVK | no | y11 dicharged | 3 | TEM |
| 339 | VALIPFFAAFCFPVFAHPETLVK | no | y6 monocharged | 3 | TEM |
| 340 | VALIPFFAAFCLPVFAHPETLVK | no | b7 monocharged | 3 | TEM |
| 341 | VALIPFFAAFCLPVFAHPETLVK | no | y11 dicharged | 3 | TEM |
| 342 | VALIPFFAAFCLPVFAHPETLVK | no | y6 monocharged | 3 | TEM |
| 343 | VDAGQEQLGR | no | y5 monocharged | 2 | TEM |
| 344 | VDAGQEQLGR | no | y7 monocharged | 2 | TEM |
| 345 | VDAGQEQLGR | no | y8 monocharged | 2 | TEM |
| 346 | VGYIELDPNSGK | no | y5 monocharged | 2 | 2be |
| 347 | VGYIELDPNSGK | no | y7 monocharged | 2 | 2be |
| 348 | VGYIELDPNSGK | no | y8 monocharged | 2 | 2be |

The transitions mentioned in TABLE 3 are detected by using the parameters set out in TABLE 4. The precursor peptide retention time and the transitions, i.e. the (m/z) 1 ratio in Q1 and (m/z)2 ratio in Q3, as well as the collision energy used to fragment the precursor ion, are indicated in TABLE 4. The threshold above which the transition is considered to be detected is also indicated in TABLE 4.

TABLE 4

| Transition number | Retention time (minutes) | (m/z) filtered in Q1 | (m/z) filtered in Q3 | Collision energy (eV) | Positivity threshold |
| --- | --- | --- | --- | --- | --- |
| 1 | 9.9 | 487.24 | 416.26 | 26 | 2500 |
| 2 | 9.9 | 487.24 | 658.36 | 26 | 2500 |
| 3 | 9.9 | 487.24 | 787.41 | 26 | 2500 |
| 4 | 19.3 | 861.95 | 512.29 | 43 | 2500 |
| 5 | 19.3 | 861.95 | 911.47 | 43 | 2500 |
| 6 | 19.3 | 861.95 | 1048.53 | 43 | 2500 |
| 7 | 19.3 | 859.42 | 792.37 | 43 | 2500 |
| 8 | 19.3 | 859.42 | 906.41 | 43 | 2500 |
| 9 | 19.3 | 859.42 | 1043.47 | 43 | 2500 |
| 10 | 18.1 | 493.751 | 595.34 | 27 | 2500 |
| 11 | 18.1 | 493.751 | 742.38 | 27 | 2500 |
| 12 | 18.1 | 493.751 | 839.43 | 27 | 2500 |
| 13 | 19.8 | 485.757 | 595.34 | 26 | 2500 |
| 14 | 19.8 | 485.757 | 726.39 | 26 | 2500 |
| 15 | 19.8 | 485.757 | 823.44 | 26 | 2500 |
| 16 | 15 | 791.87 | 698.84 | 40 | 2500 |
| 17 | 15 | 791.87 | 630.28 | 40 | 2500 |
| 18 | 15 | 791.87 | 814.41 | 40 | 2500 |
| 19 | 19.1 | 804.96 | 997.54 | 40 | 5000 |
| 20 | 19.1 | 804.96 | 813.42 | 40 | 5000 |
| 21 | 19.1 | 804.96 | 926.51 | 40 | 5000 |
| 22 | 16.6 | 674.67 | 660.36 | 38 | 2500 |
| 23 | 16.6 | 674.67 | 823.42 | 38 | 2500 |
| 24 | 16.6 | 674.67 | 952.46 | 38 | 2500 |
| 25 | 14.6 | 638.34 | 746.42 | 33 | 2500 |
| 26 | 14.6 | 638.34 | 972.51 | 33 | 2500 |
| 27 | 14.6 | 638.34 | 460.73 | 33 | 2500 |
| 28 | 15.9 | 885.44 | 866.37 | 44 | 2500 |
| 29 | 15.9 | 885.44 | 923.39 | 44 | 2500 |
| 30 | 15.9 | 885.44 | 980.41 | 44 | 2500 |
| 31 | 17 | 877.44 | 722.31 | 44 | 2500 |
| 32 | 17 | 877.44 | 907.39 | 44 | 2500 |
| 33 | 17 | 877.44 | 964.42 | 44 | 2500 |
| 34 | 19.5 | 676.32 | 630.28 | 38 | 2500 |
| 35 | 19.5 | 676.32 | 743.37 | 38 | 2500 |
| 36 | 19.5 | 676.32 | 814.41 | 38 | 2500 |
| 37 | 18.6 | 623.35 | 691.38 | 32 | 2500 |
| 38 | 18.6 | 623.35 | 804.46 | 32 | 2500 |
| 39 | 18.6 | 623.35 | 933.51 | 32 | 2500 |
| 40 | 1.3 | 317.15 | 418.2 | 19 | 6000 |
| 41 | 1.3 | 317.15 | 489.24 | 19 | 6000 |
| 42 | 1.3 | 317.15 | 546.26 | 19 | 6000 |
| 43 | 1 | 296.64 | 391.19 | 18 | 2500 |
| 44 | 1 | 296.64 | 448.22 | 18 | 2500 |
| 45 | 1 | 296.64 | 505.24 | 18 | 2500 |
| 46 | 10.5 | 565.78 | 845.41 | 30 | 2500 |
| 47 | 10.6 | 565.78 | 916.45 | 30 | 2500 |
| 48 | 10.6 | 565.78 | 1031.48 | 30 | 2500 |
| 49 | 4.1 | 393.72 | 462.22 | 22 | 2500 |
| 50 | 4.1 | 393.72 | 559.27 | 22 | 2500 |
| 51 | 4.1 | 393.72 | 687.37 | 22 | 2500 |
| 52 | 20.1 | 855.92 | 698.36 | 43 | 2500 |
| 53 | 20.1 | 855.92 | 629.33 | 43 | 2500 |
| 54 | 20.1 | 855.92 | 813.44 | 43 | 2500 |
| 55 | 17 | 585.26 | 705.36 | 31 | 4000 |
| 56 | 17 | 585.26 | 852.4 | 31 | 4000 |
| 57 | 16.9 | 585.26 | 953.44 | 31 | 4000 |
| 58 | 13.2 | 569.27 | 689.37 | 30 | 2500 |
| 59 | 13.2 | 569.27 | 820.41 | 30 | 2500 |
| 60 | 13.2 | 569.27 | 921.45 | 30 | 2500 |
| 61 | 18.3 | 870.93 | 749.86 | 43 | 2500 |
| 62 | 18.3 | 870.93 | 512.29 | 43 | 2500 |
| 63 | 18.3 | 870.93 | 929.43 | 43 | 2500 |
| 64 | 14.9 | 763.36 | 630.28 | 39 | 2500 |
| 65 | 14.9 | 763.36 | 814.41 | 39 | 2500 |
| 66 | 14.9 | 763.36 | 943.45 | 39 | 2500 |
| 67 | 14.9 | 510.73 | 776.33 | 27 | 2500 |
| 68 | 14.9 | 510.73 | 873.38 | 27 | 2500 |

TABLE 4-continued

| Transition number | Retention time (minutes) | (m/z) filtered in Q1 | (m/z) filtered in Q3 | Collision energy (eV) | Positivity threshold |
|---|---|---|---|---|---|
| 69 | 14.9 | 510.73 | 437.2 | 27 | 2500 |
| 70 | 18.9 | 494.74 | 744.34 | 27 | 2500 |
| 71 | 18.9 | 494.74 | 841.39 | 27 | 2500 |
| 72 | 18.9 | 494.74 | 421.2 | 27 | 2500 |
| 73 | 15.5 | 676.39 | 756.4 | 35 | 2500 |
| 74 | 15.5 | 676.39 | 813.42 | 35 | 2500 |
| 75 | 15.5 | 676.39 | 926.51 | 35 | 2500 |
| 76 | 11.5 | 543.78 | 787.41 | 29 | 2500 |
| 77 | 11.5 | 543.78 | 858.44 | 29 | 2500 |
| 78 | 11.5 | 543.78 | 973.47 | 29 | 2500 |
| 79 | 12.5 | 608.82 | 803.43 | 32 | 2500 |
| 80 | 12.5 | 608.82 | 966.49 | 32 | 2500 |
| 81 | 12.5 | 608.82 | 552.28 | 32 | 2500 |
| 82 | 15.5 | 990.98 | 934.44 | 49 | 2500 |
| 83 | 15.5 | 990.98 | 573.32 | 49 | 2500 |
| 84 | 15.5 | 990.98 | 660.36 | 49 | 2500 |
| 85 | 19 | 892.44 | 722.31 | 44 | 2500 |
| 86 | 19 | 892.44 | 907.39 | 44 | 2500 |
| 87 | 19 | 892.44 | 964.42 | 44 | 2500 |
| 88 | 19.4 | 700.65 | 630.28 | 39 | 2500 |
| 89 | 19.4 | 700.65 | 743.37 | 39 | 2500 |
| 90 | 19.4 | 700.65 | 814.41 | 39 | 2500 |
| 91 | 10.4 | 467.73 | 587.3 | 26 | 2500 |
| 92 | 10.4 | 467.73 | 700.39 | 26 | 2500 |
| 93 | 10.4 | 467.73 | 787.42 | 26 | 2500 |
| 94 | 12.8 | 459.73 | 587.3 | 25 | 2500 |
| 95 | 12.8 | 459.73 | 700.39 | 25 | 2500 |
| 96 | 12.8 | 459.73 | 787.42 | 25 | 2500 |
| 97 | 20.1 | 688.83 | 593.26 | 35 | 2500 |
| 98 | 20.1 | 688.83 | 779.34 | 35 | 2500 |
| 99 | 20.1 | 688.83 | 894.37 | 35 | 2500 |
| 100 | 1.4 | 303.646 | 391.19 | 18 | 13000 |
| 101 | 1.4 | 303.646 | 462.23 | 18 | 13000 |
| 102 | 1.4 | 303.646 | 519.25 | 18 | 13000 |
| 103 | 31.6 | 851.81 | 619.35 | 47 | 2500 |
| 104 | 31.6 | 851.81 | 686.41 | 47 | 2500 |
| 105 | 31.6 | 851.81 | 894.5 | 47 | 2500 |
| 106 | 18.8 | 654.35 | 746.4 | 34 | 2500 |
| 107 | 18.8 | 654.35 | 875.45 | 34 | 2500 |
| 108 | 18.8 | 654.35 | 988.53 | 34 | 2500 |
| 109 | 16.3 | 559.31 | 632.34 | 30 | 2500 |
| 110 | 16.3 | 559.31 | 792.37 | 30 | 2500 |
| 111 | 16.3 | 559.31 | 905.45 | 30 | 2500 |
| 112 | 10.5 | 487.73 | 544.32 | 26 | 2500 |
| 113 | 10.5 | 487.73 | 659.35 | 26 | 2500 |
| 114 | 10.5 | 487.73 | 788.39 | 26 | 2500 |
| 115 | 12.6 | 690.35 | 779.41 | 35 | 2500 |
| 116 | 12.6 | 690.35 | 947.5 | 35 | 2500 |
| 117 | 12.6 | 690.35 | 474.26 | 35 | 2500 |
| 118 | 15.9 | 682.35 | 763.41 | 35 | 2500 |
| 119 | 15.9 | 682.35 | 931.5 | 35 | 2500 |
| 120 | 15.9 | 682.35 | 466.26 | 35 | 2500 |
| 121 | 19.8 | 486.75 | 728.36 | 26 | 2500 |
| 122 | 19.8 | 486.75 | 825.42 | 26 | 2500 |
| 123 | 19.8 | 486.75 | 413.21 | 26 | 2500 |
| 124 | 18.4 | 478.75 | 712.37 | 26 | 2500 |
| 125 | 18.4 | 478.75 | 809.42 | 26 | 2500 |
| 126 | 18.4 | 478.75 | 405.21 | 26 | 2500 |
| 127 | 16.3 | 776.93 | 756.4 | 39 | 2500 |
| 128 | 16.3 | 776.93 | 813.42 | 39 | 2500 |
| 129 | 16.3 | 776.93 | 926.51 | 39 | 2500 |
| 130 | 12.2 | 523.26 | 579.3 | 28 | 2500 |
| 131 | 12.2 | 523.26 | 795.37 | 28 | 2500 |
| 132 | 12.2 | 523.26 | 908.45 | 28 | 2500 |
| 133 | 12 | 515.26 | 506.28 | 28 | 2500 |
| 134 | 12 | 515.26 | 779.37 | 28 | 2500 |
| 135 | 12 | 515.26 | 892.46 | 28 | 2500 |
| 136 | 18 | 899.46 | 439.33 | 36 | 2500 |
| 137 | 18 | 899.46 | 304.16 | 57 | 2500 |
| 138 | 18 | 899.46 | 994.43 | 36 | 2500 |
| 139 | 15.6 | 681.33 | 661.29 | 38 | 2500 |
| 140 | 15.6 | 681.33 | 808.33 | 38 | 2500 |
| 141 | 15.6 | 681.33 | 909.37 | 38 | 2500 |
| 142 | 16.6 | 676 | 661.29 | 38 | 3100 |
| 143 | 16.6 | 676 | 792.33 | 38 | 3100 |
| 144 | 16.6 | 676 | 893.38 | 38 | 3100 |
| 145 | 17.2 | 688.32 | 630.28 | 38 | 2500 |

TABLE 4-continued

| Transition number | Retention time (minutes) | (m/z) filtered in Q1 | (m/z) filtered in Q3 | Collision energy (eV) | Positivity threshold |
|---|---|---|---|---|---|
| 146 | 17.2 | 688.32 | 729.35 | 38 | 2500 |
| 147 | 17.2 | 688.32 | 800.39 | 38 | 2500 |
| 148 | 27 | 878.12 | 841.5 | 48 | 2500 |
| 149 | 27 | 878.12 | 795.34 | 48 | 2500 |
| 150 | 27 | 878.12 | 910.37 | 48 | 2500 |
| 151 | 27.9 | 872.79 | 462.22 | 48 | 2500 |
| 152 | 27.9 | 872.79 | 779.34 | 48 | 2500 |
| 153 | 27.9 | 872.79 | 894.37 | 48 | 2500 |
| 154 | 18.8 | 571.84 | 701.46 | 30 | 2500 |
| 155 | 18.8 | 571.84 | 830.5 | 30 | 2500 |
| 156 | 18.8 | 571.84 | 901.54 | 30 | 2500 |
| 157 | 16.6 | 565.82 | 701.46 | 30 | 2500 |
| 158 | 16.6 | 565.82 | 830.5 | 30 | 2500 |
| 159 | 16.6 | 565.82 | 901.54 | 30 | 2500 |
| 160 | 1.5 | 317.64 | 419.19 | 19 | 9000 |
| 161 | 1.5 | 317.64 | 490.23 | 19 | 9000 |
| 162 | 1.5 | 317.64 | 547.25 | 19 | 9000 |
| 163 | 0.9 | 225.12 | 234.14 | 18 | 2500 |
| 164 | 0.9 | 225.12 | 305.18 | 13 | 2500 |
| 165 | 0.9 | 225.12 | 362.2 | 13 | 2500 |
| 166 | 14.1 | 363.24 | 498.34 | 21 | 2500 |
| 167 | 14.1 | 363.24 | 555.36 | 21 | 2500 |
| 168 | 14.1 | 363.24 | 626.4 | 21 | 2500 |
| 169 | 14.7 | 671.32 | 593.28 | 35 | 4500 |
| 170 | 14.7 | 671.32 | 780.36 | 35 | 4500 |
| 171 | 14.7 | 671.32 | 909.4 | 35 | 4500 |
| 172 | 17.5 | 663.32 | 764.36 | 34 | 2500 |
| 173 | 17.5 | 663.32 | 893.4 | 34 | 2500 |
| 174 | 17.5 | 663.32 | 1006.49 | 34 | 2500 |
| 175 | 18 | 856.4 | 698.84 | 43 | 2500 |
| 176 | 18 | 856.4 | 630.28 | 43 | 2500 |
| 177 | 18 | 856.4 | 814.41 | 43 | 2500 |
| 178 | 18.6 | 877.94 | 829.4 | 44 | 2500 |
| 179 | 18.6 | 877.94 | 943.44 | 44 | 2500 |
| 180 | 18.6 | 877.94 | 1080.5 | 44 | 2500 |
| 181 | 18.1 | 493.75 | 742.38 | 27 | 2500 |
| 182 | 18.1 | 493.75 | 839.43 | 27 | 2500 |
| 183 | 18.1 | 493.75 | 420.22 | 27 | 2500 |
| 184 | 19.8 | 485.76 | 726.39 | 26 | 2500 |
| 185 | 19.8 | 485.76 | 823.44 | 26 | 2500 |
| 186 | 19.8 | 485.76 | 412.22 | 26 | 2500 |
| 187 | 16.5 | 828.43 | 756.4 | 41 | 2500 |
| 188 | 16.5 | 828.43 | 813.42 | 41 | 2500 |
| 189 | 16.5 | 828.43 | 926.51 | 41 | 2500 |
| 190 | 16.1 | 791.93 | 756.4 | 40 | 2500 |
| 191 | 16.1 | 791.93 | 813.42 | 40 | 2500 |
| 192 | 16.1 | 791.93 | 926.51 | 40 | 2500 |
| 193 | 15.7 | 559.81 | 676.38 | 30 | 2500 |
| 194 | 14.1 | 559.81 | 763.41 | 30 | 2500 |
| 195 | 14.1 | 559.81 | 892.45 | 30 | 2500 |
| 196 | 16.6 | 676.34 | 646.31 | 38 | 2500 |
| 197 | 16.6 | 676.34 | 793.96 | 38 | 2500 |
| 198 | 16.6 | 676.34 | 894.4 | 38 | 2500 |
| 199 | 18.9 | 671.01 | 646.31 | 38 | 4000 |
| 200 | 18.9 | 671.01 | 777.96 | 38 | 4000 |
| 201 | 18.9 | 671.01 | 878.4 | 38 | 4000 |
| 202 | 16.9 | 892.45 | 722.31 | 44 | 2500 |
| 203 | 16.9 | 892.45 | 937.4 | 44 | 2500 |
| 204 | 16.9 | 892.45 | 994.43 | 44 | 2500 |
| 205 | 17.9 | 707.99 | 630.28 | 39 | 6000 |
| 206 | 17.9 | 707.99 | 743.37 | 39 | 6000 |
| 207 | 17.9 | 707.99 | 814.41 | 39 | 6000 |
| 208 | 22.5 | 643.89 | 660.4 | 33 | 2500 |
| 209 | 22.5 | 643.89 | 773.49 | 33 | 2500 |
| 210 | 22.5 | 643.89 | 959.55 | 33 | 2500 |
| 211 | 17.5 | 632.31 | 781.32 | 33 | 3000 |
| 212 | 17.5 | 632.31 | 894.4 | 33 | 3000 |
| 213 | 17.5 | 632.31 | 1007.49 | 33 | 3000 |
| 214 | 19.8 | 624.31 | 765.32 | 32 | 2500 |
| 215 | 19.8 | 624.31 | 878.41 | 32 | 2500 |
| 216 | 19.8 | 624.31 | 991.49 | 32 | 2500 |
| 217 | 21.4 | 638.34 | 836.43 | 33 | 2500 |
| 218 | 21.4 | 838.34 | 1004.52 | 33 | 2500 |
| 219 | 21.5 | 638.34 | 502.76 | 33 | 2500 |
| 220 | 3.2 | 273.65 | 331.21 | 17 | 2500 |
| 221 | 3.2 | 273.65 | 402.25 | 17 | 2500 |
| 222 | 3.2 | 273.65 | 459.27 | 17 | 2500 |

TABLE 4-continued

| Transition number | Retention time (minutes) | (m/z) filtered in Q1 | (m/z) filtered in Q3 | Collision energy (eV) | Positivity threshold |
|---|---|---|---|---|---|
| 223 | 1.3 | 303.65 | 361.18 | 18 | 21000 |
| 224 | 1.3 | 303.65 | 462.23 | 18 | 21000 |
| 225 | 1.3 | 303.65 | 519.25 | 18 | 21000 |
| 226 | 31.3 | 863.138 | 619.35 | 47 | 2500 |
| 227 | 31.3 | 863.138 | 686.41 | 47 | 2500 |
| 228 | 31.3 | 863.138 | 823.47 | 47 | 2500 |
| 229 | 17.7 | 544.32 | 602.36 | 29 | 2500 |
| 230 | 17.7 | 544.32 | 762.39 | 29 | 2500 |
| 231 | 17.7 | 544.32 | 875.48 | 29 | 2500 |
| 232 | 9.8 | 412.21 | 476.27 | 23 | 2500 |
| 233 | 9.8 | 412.21 | 573.32 | 23 | 2500 |
| 234 | 9.8 | 412.21 | 660.36 | 23 | 2500 |
| 235 | 15.2 | 843.38 | 698.84 | 42 | 2500 |
| 236 | 15.2 | 843.38 | 630.28 | 42 | 2500 |
| 237 | 15.2 | 843.38 | 943.45 | 42 | 2500 |
| 238 | 8.7 | 480.72 | 530.3 | 26 | 2500 |
| 239 | 8.7 | 480.72 | 645.33 | 26 | 2500 |
| 240 | 8.7 | 480.72 | 774.37 | 26 | 2500 |
| 241 | 18.8 | 704.35 | 763.41 | 36 | 2500 |
| 242 | 18.8 | 704.35 | 959.53 | 36 | 2500 |
| 243 | 18.8 | 704.35 | 480.27 | 36 | 2500 |
| 244 | 18.3 | 425.25 | 506.31 | 24 | 2500 |
| 245 | 18.3 | 425.25 | 607.36 | 24 | 2500 |
| 246 | 18.3 | 425.25 | 720.44 | 24 | 2500 |
| 247 | 16.4 | 798.94 | 997.54 | 40 | 2500 |
| 248 | 16.3 | 798.94 | 756.4 | 40 | 2500 |
| 249 | 16.3 | 798.94 | 926.51 | 40 | 2500 |
| 250 | 8.3 | 494.26 | 850.45 | 27 | 2500 |
| 251 | 8.3 | 494.26 | 636.31 | 27 | 2500 |
| 252 | 8.3 | 494.26 | 737.36 | 27 | 2500 |
| 253 | 10.9 | 486.26 | 834.45 | 26 | 2500 |
| 254 | 10.9 | 486.26 | 620.32 | 26 | 2500 |
| 255 | 10.9 | 486.26 | 721.37 | 26 | 2500 |
| 256 | 19.3 | 691.67 | 793.36 | 39 | 2500 |
| 257 | 19.3 | 691.67 | 894.4 | 39 | 2500 |
| 258 | 19.3 | 691.67 | 965.44 | 39 | 2500 |
| 259 | 20.6 | 681.01 | 646.31 | 38 | 2500 |
| 260 | 20.6 | 681.01 | 777.36 | 38 | 2500 |
| 261 | 20.6 | 681.01 | 878.4 | 38 | 2500 |
| 262 | 18 | 692.99 | 630.28 | 39 | 2500 |
| 263 | 18 | 692.99 | 743.37 | 39 | 2500 |
| 264 | 18 | 692.99 | 814.41 | 39 | 2500 |
| 265 | 23 | 658.89 | 1090.61 | 34 | 2500 |
| 266 | 23 | 658.89 | 773.49 | 34 | 2500 |
| 267 | 23 | 658.89 | 989.56 | 34 | 2500 |
| 268 | 17.9 | 564.83 | 687.44 | 30 | 2500 |
| 269 | 17.9 | 564.83 | 816.48 | 30 | 2500 |
| 270 | 17.9 | 564.83 | 887.52 | 30 | 2500 |
| 271 | 18.9 | 710.84 | 823.37 | 36 | 2500 |
| 272 | 18.9 | 710.84 | 938.39 | 36 | 2500 |
| 273 | 18.9 | 710.84 | 1051.48 | 36 | 2500 |
| 274 | 20.9 | 702.84 | 621.29 | 36 | 2500 |
| 275 | 20.9 | 702.84 | 807.37 | 36 | 2500 |
| 276 | 20.9 | 702.84 | 922.4 | 36 | 2500 |
| 277 | 22.6 | 652.36 | 559.31 | 34 | 2500 |
| 278 | 22.6 | 652.36 | 1004.52 | 34 | 2500 |
| 279 | 22.6 | 652.36 | 502.76 | 34 | 2500 |
| 280 | 11.1 | 380.21 | 532.29 | 22 | 2500 |
| 281 | 11.1 | 380.21 | 589.31 | 22 | 2500 |
| 282 | 11.1 | 380.21 | 660.35 | 22 | 2500 |
| 283 | 13.1 | 372.22 | 516.3 | 21 | 2500 |
| 284 | 13.1 | 372.22 | 573.32 | 21 | 2500 |
| 285 | 13.1 | 372.22 | 644.35 | 21 | 2500 |
| 286 | 31.3 | 858.47 | 612.34 | 47 | 2500 |
| 287 | 31.3 | 858.47 | 967.1 | 47 | 2500 |
| 288 | 31.3 | 858.47 | 672.39 | 47 | 2500 |
| 289 | 30.5 | 715.73 | 874.95 | 40 | 2500 |
| 290 | 30.5 | 715.73 | 795.45 | 40 | 2500 |
| 291 | 30.6 | 715.73 | 534.79 | 40 | 2500 |
| 292 | 11.7 | 601.79 | 788.39 | 31 | 2500 |
| 293 | 11.7 | 601.79 | 859.43 | 31 | 2500 |
| 294 | 11.7 | 601.79 | 974.45 | 31 | 2500 |
| 295 | 20 | 738.01 | 746.4 | 41 | 2500 |
| 296 | 20 | 738.01 | 875.45 | 41 | 2500 |
| 297 | 20 | 738.01 | 988.53 | 41 | 2500 |
| 298 | 17.6 | 690.34 | 763.61 | 35 | 2500 |
| 299 | 17.6 | 690.34 | 834.45 | 35 | 2500 |

TABLE 4-continued

| Transition number | Retention time (minutes) | (m/z) filtered in Q1 | (m/z) filtered in Q3 | Collision energy (eV) | Positivity threshold |
|---|---|---|---|---|---|
| 300 | 17.6 | 690.34 | 931.5 | 35 | 2500 |
| 301 | 19.5 | 683.34 | 779.41 | 35 | 6000 |
| 302 | 19.5 | 683.34 | 850.45 | 35 | 6000 |
| 303 | 19.5 | 683.34 | 474.25 | 35 | 6000 |
| 304 | 16.1 | 675.34 | 763.41 | 35 | 2500 |
| 305 | 16.1 | 675.34 | 931.5 | 35 | 2500 |
| 306 | 16.1 | 675.34 | 466.25 | 35 | 2500 |
| 307 | 14.4 | 816.94 | 565.31 | 41 | 2500 |
| 308 | 14.4 | 816.94 | 744.92 | 41 | 2500 |
| 309 | 14.4 | 816.94 | 813.42 | 41 | 2500 |
| 310 | 13 | 513.26 | 563.3 | 28 | 2500 |
| 311 | 13 | 513.26 | 775.38 | 28 | 2500 |
| 312 | 13 | 513.26 | 888.46 | 28 | 2500 |
| 313 | 16.6 | 997.99 | 941.45 | 49 | 2500 |
| 314 | 16.6 | 997.99 | 573.32 | 49 | 2500 |
| 315 | 16.6 | 997.99 | 952.46 | 49 | 2500 |
| 316 | 18.9 | 907.44 | 722.32 | 45 | 2500 |
| 317 | 18.9 | 907.44 | 937.4 | 45 | 2500 |
| 318 | 18.9 | 907.44 | 994.43 | 45 | 2500 |
| 319 | 23.7 | 672.89 | 547.32 | 35 | 2500 |
| 320 | 23.7 | 672.89 | 660.4 | 35 | 2500 |
| 321 | 23.7 | 672.89 | 773.49 | 35 | 2500 |
| 322 | 17.1 | 473.21 | 528.29 | 26 | 2500 |
| 323 | 17.9 | 473.21 | 627.32 | 26 | 2500 |
| 324 | 17.8 | 473.21 | 684.34 | 26 | 2500 |
| 325 | 8.4 | 465.22 | 512.29 | 25 | 9000 |
| 326 | 8.4 | 465.22 | 627.32 | 25 | 9000 |
| 327 | 8.4 | 465.22 | 684.34 | 25 | 9000 |
| 328 | 19.8 | 585.86 | 701.46 | 31 | 2500 |
| 329 | 19.8 | 585.86 | 830.5 | 31 | 2500 |
| 330 | 19.8 | 585.86 | 929.57 | 31 | 2500 |
| 331 | 1.3 | 288.64 | 361.18 | 18 | 8000 |
| 332 | 1.3 | 288.64 | 432.22 | 18 | 8000 |
| 333 | 1.3 | 288.64 | 489.24 | 18 | 8000 |
| 334 | 14.5 | 399.25 | 498.34 | 23 | 6000 |
| 335 | 14.5 | 399.25 | 627.38 | 23 | 6000 |
| 336 | 14.5 | 399.25 | 698.42 | 23 | 6000 |
| 337 | 31.3 | 874.47 | 823.47 | 48 | 2500 |
| 338 | 31.3 | 874.47 | 619.41 | 48 | 2500 |
| 339 | 31.3 | 874.47 | 686.41 | 48 | 2500 |
| 340 | 31.3 | 863.14 | 823.47 | 47 | 2500 |
| 341 | 31.3 | 863.14 | 619.34 | 47 | 2500 |
| 342 | 31.3 | 863.14 | 686.41 | 47 | 2500 |
| 343 | 10.6 | 536.77 | 602.38 | 29 | 2500 |
| 344 | 10.6 | 536.77 | 787.41 | 29 | 2500 |
| 345 | 10.6 | 536.77 | 858.44 | 29 | 2500 |
| 346 | 16.5 | 646.33 | 502.26 | 33 | 7000 |
| 347 | 16.5 | 646.33 | 730.37 | 33 | 7000 |
| 348 | 16.5 | 646.33 | 859.42 | 33 | 7000 |

The other machine parameters used are as follows:
Scan type: MRM
MRM planned; yes
Polarity: Positive
Ionising source: Turbo V™ (Applied BioSystems)
Q1 setting: Filtering with unit resolution
Q3 setting: Filtering with unit resolution
Inter-scan pause: 5.00 msec
Scanning speed: 10 Da/s
Curtain gas: 50.00 psi
Cone voltage: 5500.00 V
Source temperature: 500.00° C.
Nebulising gas: 50.00 psi
Heating gas: 40.00 psi
Collision gas which induces dissociation: 9.00 psi
Dynamic filling: activated
Declustering potential (DP): 80.00 V
Entry potential before Q0 (EP): 10.00 V
Collision cell exit potential (CXP): 35 V
Total cycle time: 1.2 sec
Detection window: 90 sec The areas obtained for each of the transitions and for each of the microorganisms studied were measured. When the areas of the 3 transitions of the same peptide are greater than or equal to the positivity threshold described in TABLE 4, the detection of the peptide is considered to be positive and is labelled "1" in TABLE 5. When at least one transition comprises an area less than the positivity threshold described in TABLE 4, the corresponding peptide is considered non-detected and is labelled 0 in TABLE 5.

TABLE 5

| Transition number | Sam10 | Sam11 | Sam12 | Sam13 | Sam14 | Sam15 | Sam16 | Sam17 | Sam18 | Sam19 | Sam20 | Sam21 | Sam22 |
|---|---|---|---|---|---|---|---|---|---|---|---|---|---|
| 1-3 | 0 | 0 | 0 | 0 | 0 | 0 | 0 | 0 | 0 | 0 | 0 | 0 | 0 |
| 4-6 | 0 | 0 | 0 | 0 | 0 | 0 | 0 | 0 | 0 | 0 | 0 | 0 | 0 |
| 7-9 | 0 | 0 | 0 | 0 | 0 | 0 | 0 | 0 | 0 | 0 | 0 | 0 | 0 |
| 10-12 | 0 | 0 | 0 | 0 | 0 | 0 | 0 | 0 | 0 | 0 | 0 | 0 | 0 |
| 13-15 | 0 | 0 | 0 | 0 | 0 | 0 | 0 | 0 | 0 | 0 | 0 | 0 | 0 |
| 16-18 | 0 | 0 | 0 | 0 | 0 | 0 | 0 | 0 | 0 | 0 | 0 | 0 | 0 |
| 19-21 | 0 | 0 | 0 | 0 | 0 | 0 | 0 | 0 | 0 | 0 | 0 | 0 | 0 |
| 22-24 | 0 | 1 | 0 | 0 | 1 | 0 | 0 | 0 | 0 | 0 | 0 | 1 | 0 |
| 25-27 | 0 | 1 | 0 | 1 | 1 | 0 | 0 | 1 | 1 | 1 | 0 | 1 | 0 |
| 28-30 | 0 | 0 | 0 | 0 | 0 | 0 | 0 | 0 | 0 | 0 | 0 | 0 | 0 |
| 31-33 | 0 | 0 | 0 | 0 | 0 | 0 | 0 | 0 | 0 | 0 | 0 | 0 | 0 |
| 34-36 | 0 | 0 | 0 | 0 | 1 | 0 | 1 | 1 | 1 | 1 | 0 | 1 | 0 |
| 37-39 | 0 | 0 | 0 | 0 | 0 | 0 | 0 | 0 | 0 | 0 | 0 | 0 | 0 |
| 40-42 | 0 | 0 | 0 | 0 | 0 | 0 | 0 | 0 | 0 | 0 | 0 | 0 | 0 |
| 43-45 | 0 | 0 | 0 | 0 | 0 | 0 | 0 | 0 | 0 | 0 | 0 | 0 | 0 |
| 46-48 | 0 | 0 | 0 | 0 | 0 | 0 | 0 | 0 | 0 | 0 | 0 | 0 | 0 |
| 49-51 | 0 | 0 | 0 | 0 | 0 | 0 | 0 | 0 | 0 | 0 | 0 | 0 | 0 |
| 52-54 | 0 | 0 | 0 | 0 | 0 | 0 | 0 | 0 | 0 | 0 | 0 | 0 | 0 |
| 55-57 | 0 | 0 | 0 | 0 | 0 | 0 | 0 | 0 | 0 | 0 | 0 | 0 | 0 |
| 58-60 | 0 | 0 | 0 | 0 | 0 | 0 | 0 | 0 | 0 | 0 | 0 | 0 | 0 |
| 61-63 | 0 | 0 | 0 | 0 | 0 | 0 | 0 | 0 | 0 | 0 | 0 | 0 | 0 |
| 64-66 | 0 | 0 | 0 | 0 | 0 | 0 | 0 | 0 | 0 | 0 | 0 | 0 | 0 |
| 67-69 | 0 | 0 | 0 | 0 | 0 | 0 | 0 | 0 | 0 | 0 | 0 | 0 | 0 |
| 70-72 | 0 | 0 | 0 | 0 | 0 | 0 | 0 | 0 | 0 | 0 | 0 | 0 | 0 |
| 73-75 | 0 | 1 | 1 | 1 | 1 | 1 | 1 | 1 | 1 | 1 | 1 | 1 | 0 |
| 76-78 | 0 | 0 | 0 | 0 | 0 | 0 | 0 | 0 | 0 | 0 | 0 | 0 | 0 |
| 79-81 | 0 | 0 | 0 | 1 | 0 | 0 | 0 | 0 | 1 | 0 | 0 | 0 | 0 |
| 82-84 | 0 | 0 | 0 | 0 | 0 | 0 | 0 | 0 | 0 | 0 | 0 | 0 | 0 |
| 85-87 | 0 | 0 | 0 | 0 | 0 | 0 | 0 | 0 | 0 | 0 | 0 | 0 | 0 |
| 88-90 | 0 | 0 | 0 | 0 | 0 | 0 | 0 | 0 | 0 | 0 | 0 | 0 | 0 |
| 91-93 | 0 | 0 | 0 | 0 | 0 | 0 | 0 | 0 | 0 | 0 | 0 | 0 | 0 |
| 94-96 | 0 | 0 | 0 | 0 | 0 | 0 | 0 | 0 | 0 | 0 | 0 | 0 | 0 |
| 97-99 | 0 | 1 | 1 | 1 | 1 | 1 | 1 | 1 | 1 | 1 | 0 | 1 | 0 |
| 100-102 | 0 | 0 | 0 | 0 | 0 | 0 | 0 | 0 | 0 | 0 | 0 | 0 | 0 |
| 103-105 | 0 | 0 | 0 | 0 | 0 | 0 | 0 | 0 | 0 | 0 | 0 | 0 | 0 |
| 106-108 | 0 | 1 | 1 | 1 | 1 | 1 | 1 | 1 | 1 | 1 | 1 | 1 | 1 |
| 109-111 | 0 | 0 | 0 | 0 | 0 | 0 | 0 | 0 | 0 | 0 | 0 | 0 | 0 |
| 112-114 | 0 | 0 | 0 | 1 | 1 | 0 | 0 | 0 | 1 | 1 | 0 | 0 | 0 |
| 115-117 | 0 | 0 | 0 | 0 | 0 | 0 | 0 | 0 | 0 | 0 | 0 | 0 | 0 |
| 118-120 | 0 | 0 | 0 | 0 | 0 | 0 | 0 | 0 | 0 | 0 | 0 | 0 | 0 |
| 121-123 | 0 | 0 | 0 | 0 | 0 | 0 | 0 | 0 | 0 | 0 | 0 | 0 | 0 |
| 124-126 | 0 | 0 | 0 | 0 | 0 | 0 | 0 | 0 | 0 | 0 | 0 | 0 | 0 |
| 127-129 | 0 | 0 | 0 | 0 | 0 | 0 | 0 | 0 | 0 | 0 | 0 | 0 | 0 |
| 130-132 | 0 | 0 | 0 | 0 | 0 | 0 | 0 | 0 | 0 | 0 | 0 | 0 | 0 |
| 133-135 | 0 | 1 | 0 | 1 | 1 | 0 | 1 | 1 | 1 | 0 | 0 | 1 | 0 |
| 136-138 | 0 | 0 | 0 | 0 | 0 | 0 | 0 | 0 | 0 | 0 | 0 | 0 | 0 |
| 139-141 | 0 | 0 | 0 | 0 | 0 | 0 | 0 | 0 | 0 | 0 | 0 | 0 | 0 |
| 142-144 | 0 | 0 | 0 | 0 | 0 | 0 | 0 | 0 | 0 | 0 | 0 | 0 | 0 |
| 145-147 | 0 | 0 | 0 | 0 | 0 | 0 | 0 | 0 | 0 | 0 | 0 | 0 | 0 |
| 148-150 | 0 | 0 | 0 | 0 | 0 | 0 | 0 | 0 | 0 | 0 | 0 | 0 | 0 |
| 151-153 | 0 | 0 | 0 | 0 | 0 | 0 | 0 | 0 | 0 | 0 | 0 | 0 | 0 |
| 154-156 | 0 | 1 | 1 | 1 | 1 | 1 | 1 | 1 | 1 | 1 | 0 | 1 | 0 |
| 157-159 | 0 | 0 | 0 | 0 | 0 | 0 | 0 | 0 | 0 | 0 | 0 | 0 | 0 |
| 160-162 | 0 | 0 | 0 | 0 | 0 | 0 | 0 | 0 | 0 | 0 | 0 | 0 | 0 |
| 163-165 | 0 | 0 | 0 | 0 | 0 | 0 | 0 | 0 | 0 | 0 | 0 | 0 | 0 |
| 166-168 | 0 | 1 | 1 | 1 | 1 | 1 | 1 | 1 | 1 | 1 | 1 | 1 | 1 |
| 169-171 | 0 | 0 | 0 | 0 | 0 | 0 | 0 | 0 | 0 | 0 | 0 | 0 | 0 |
| 172-174 | 0 | 0 | 0 | 0 | 0 | 0 | 0 | 0 | 0 | 0 | 0 | 0 | 0 |
| 175-177 | 0 | 1 | 0 | 0 | 0 | 0 | 0 | 0 | 0 | 0 | 0 | 0 | 0 |
| 178-180 | 0 | 0 | 0 | 0 | 0 | 0 | 0 | 0 | 0 | 0 | 0 | 0 | 0 |
| 181-183 | 0 | 0 | 0 | 0 | 0 | 0 | 0 | 0 | 0 | 0 | 0 | 0 | 0 |
| 184-186 | 0 | 0 | 0 | 0 | 0 | 0 | 0 | 0 | 0 | 0 | 0 | 0 | 0 |
| 187-189 | 0 | 0 | 0 | 0 | 0 | 0 | 0 | 0 | 0 | 0 | 0 | 0 | 0 |
| 190-192 | 0 | 0 | 0 | 0 | 0 | 0 | 0 | 0 | 0 | 0 | 0 | 0 | 0 |
| 193-195 | 0 | 0 | 0 | 0 | 0 | 0 | 0 | 0 | 0 | 0 | 0 | 0 | 0 |
| 196-198 | 0 | 0 | 0 | 0 | 0 | 0 | 0 | 0 | 0 | 0 | 0 | 0 | 0 |
| 199-201 | 0 | 0 | 0 | 0 | 0 | 0 | 0 | 0 | 0 | 0 | 0 | 0 | 0 |
| 202-204 | 0 | 0 | 0 | 0 | 0 | 0 | 0 | 0 | 0 | 0 | 0 | 0 | 0 |
| 205-207 | 0 | 0 | 0 | 0 | 0 | 0 | 0 | 0 | 0 | 0 | 0 | 0 | 0 |
| 208-210 | 0 | 0 | 1 | 1 | 1 | 1 | 0 | 1 | 1 | 0 | 1 | 1 | 0 |
| 211-213 | 0 | 0 | 0 | 0 | 0 | 0 | 0 | 0 | 0 | 0 | 0 | 0 | 0 |
| 214-216 | 0 | 0 | 0 | 0 | 0 | 0 | 0 | 0 | 0 | 0 | 0 | 0 | 0 |
| 217-219 | 0 | 0 | 0 | 0 | 0 | 0 | 0 | 0 | 0 | 0 | 0 | 0 | 0 |
| 220-222 | 0 | 0 | 0 | 0 | 0 | 0 | 0 | 0 | 0 | 0 | 0 | 0 | 0 |
| 223-225 | 0 | 0 | 0 | 0 | 0 | 0 | 0 | 0 | 0 | 0 | 0 | 0 | 0 |
| 226-228 | 0 | 0 | 0 | 0 | 0 | 0 | 0 | 0 | 0 | 0 | 0 | 0 | 0 |
| 229-231 | 0 | 0 | 0 | 0 | 0 | 0 | 0 | 0 | 0 | 0 | 0 | 0 | 0 |

TABLE 5-continued

| | | | | | | | | | | | | | |
|---|---|---|---|---|---|---|---|---|---|---|---|---|---|
| 232-234 | 0 | 0 | 1 | 1 | 0 | 1 | 0 | 1 | 1 | 0 | 1 | 0 | 0 |
| 235-237 | 0 | 0 | 0 | 0 | 0 | 0 | 0 | 0 | 0 | 0 | 0 | 0 | 0 |
| 238-240 | 0 | 0 | 0 | 0 | 0 | 0 | 0 | 0 | 0 | 0 | 0 | 0 | 0 |
| 241-243 | 0 | 0 | 0 | 0 | 0 | 0 | 0 | 0 | 0 | 0 | 0 | 0 | 0 |
| 244-246 | 0 | 0 | 0 | 0 | 0 | 0 | 0 | 0 | 0 | 0 | 0 | 0 | 0 |
| 247-249 | 0 | 0 | 0 | 0 | 0 | 0 | 0 | 0 | 0 | 0 | 0 | 0 | 0 |
| 250-252 | 0 | 0 | 0 | 0 | 0 | 0 | 0 | 0 | 0 | 0 | 0 | 0 | 0 |
| 253-255 | 0 | 0 | 0 | 0 | 0 | 0 | 0 | 0 | 0 | 0 | 0 | 0 | 0 |
| 256-258 | 0 | 0 | 0 | 0 | 0 | 0 | 0 | 0 | 0 | 0 | 0 | 0 | 0 |
| 259-261 | 0 | 0 | 0 | 0 | 0 | 0 | 0 | 0 | 0 | 0 | 0 | 0 | 0 |
| 262-264 | 0 | 0 | 0 | 0 | 0 | 1 | 0 | 0 | 0 | 0 | 0 | 0 | 0 |
| 265-267 | 0 | 0 | 0 | 0 | 0 | 0 | 0 | 0 | 0 | 0 | 0 | 0 | 0 |
| 268-270 | 0 | 0 | 0 | 0 | 0 | 0 | 0 | 0 | 0 | 0 | 0 | 0 | 0 |
| 271-273 | 0 | 0 | 0 | 0 | 0 | 0 | 0 | 0 | 0 | 0 | 0 | 0 | 0 |
| 274-276 | 0 | 0 | 0 | 0 | 0 | 0 | 0 | 0 | 0 | 0 | 0 | 0 | 0 |
| 277-279 | 0 | 0 | 0 | 0 | 0 | 0 | 0 | 0 | 0 | 0 | 0 | 0 | 0 |
| 280-282 | 0 | 0 | 0 | 0 | 0 | 0 | 0 | 0 | 0 | 0 | 0 | 0 | 0 |
| 283-285 | 0 | 0 | 0 | 0 | 0 | 0 | 0 | 0 | 0 | 0 | 0 | 0 | 0 |
| 286-288 | 0 | 0 | 0 | 0 | 0 | 0 | 0 | 0 | 0 | 0 | 0 | 0 | 0 |
| 289-291 | 0 | 0 | 0 | 0 | 0 | 0 | 0 | 0 | 0 | 0 | 0 | 0 | 0 |
| 292-294 | 0 | 0 | 0 | 0 | 0 | 0 | 0 | 0 | 0 | 0 | 0 | 0 | 0 |
| 295-297 | 0 | 0 | 0 | 0 | 0 | 0 | 0 | 0 | 0 | 0 | 0 | 0 | 0 |
| 298-300 | 0 | 1 | 0 | 1 | 1 | 0 | 1 | 1 | 1 | 0 | 0 | 1 | 0 |
| 301-303 | 0 | 0 | 0 | 0 | 0 | 0 | 0 | 0 | 0 | 0 | 0 | 0 | 0 |
| 304-306 | 0 | 0 | 0 | 0 | 0 | 0 | 0 | 0 | 0 | 0 | 0 | 0 | 0 |
| 307-309 | 0 | 0 | 0 | 0 | 0 | 0 | 0 | 0 | 0 | 0 | 0 | 0 | 0 |
| 310-312 | 0 | 0 | 0 | 0 | 0 | 0 | 0 | 0 | 0 | 0 | 0 | 0 | 0 |
| 313-315 | 0 | 0 | 0 | 0 | 0 | 0 | 0 | 0 | 0 | 0 | 0 | 0 | 0 |
| 316-318 | 0 | 0 | 0 | 0 | 0 | 0 | 0 | 0 | 0 | 0 | 0 | 0 | 0 |
| 319-321 | 0 | 0 | 0 | 0 | 0 | 0 | 0 | 0 | 0 | 0 | 0 | 0 | 0 |
| 322-324 | 0 | 0 | 0 | 0 | 0 | 0 | 0 | 0 | 0 | 0 | 0 | 0 | 0 |
| 325-327 | 0 | 0 | 0 | 0 | 0 | 0 | 0 | 0 | 0 | 0 | 0 | 0 | 0 |
| 328-330 | 0 | 0 | 0 | 0 | 0 | 0 | 0 | 0 | 0 | 0 | 0 | 0 | 0 |
| 331-333 | 0 | 0 | 0 | 0 | 0 | 0 | 0 | 0 | 0 | 0 | 0 | 0 | 0 |
| 334-336 | 0 | 0 | 0 | 0 | 0 | 0 | 0 | 0 | 0 | 0 | 0 | 0 | 0 |
| 337-339 | 0 | 0 | 0 | 0 | 0 | 0 | 0 | 0 | 0 | 0 | 0 | 0 | 0 |
| 340-342 | 0 | 0 | 0 | 0 | 0 | 0 | 0 | 0 | 0 | 0 | 0 | 0 | 0 |
| 343-345 | 0 | 1 | 1 | 1 | 1 | 1 | 1 | 1 | 1 | 1 | 0 | 1 | 0 |
| 346-348 | 0 | 0 | 0 | 0 | 0 | 0 | 0 | 0 | 0 | 0 | 0 | 0 | 0 |
| TEM peptides | 0 | 11 | 8 | 13 | 13 | 9 | 9 | 12 | 14 | 9 | 5 | 12 | 2 |
| 2b peptides | 0 | 0 | 0 | 0 | 0 | 0 | 0 | 0 | 0 | 0 | 0 | 0 | 0 |
| 2br peptides | 0 | 0 | 0 | 0 | 0 | 0 | 0 | 0 | 0 | 0 | 0 | 0 | 0 |
| 2be peptides | 0 | 0 | 1 | 2 | 1 | 2 | 1 | 2 | 3 | 1 | 1 | 1 | 0 |
| 2ber peptides | 0 | 0 | 0 | 0 | 0 | 0 | 0 | 0 | 0 | 0 | 0 | 0 | 0 |

| Transition number | Sam23 | Sam24 | Sam25 | Sam26 | Sam27 | Sam28 | Sam29 | Sam30 | Sam31 | Sam32 | Sam33 | Sam34 | Sam35 |
|---|---|---|---|---|---|---|---|---|---|---|---|---|---|
| 1-3 | 0 | 0 | 0 | 0 | 0 | 0 | 0 | 0 | 0 | 0 | 0 | 0 | 0 |
| 4-6 | 0 | 0 | 0 | 0 | 0 | 0 | 0 | 0 | 0 | 0 | 0 | 0 | 0 |
| 7-9 | 0 | 0 | 0 | 0 | 0 | 0 | 0 | 0 | 0 | 0 | 0 | 0 | 0 |
| 10-12 | 0 | 0 | 0 | 0 | 0 | 0 | 0 | 0 | 0 | 0 | 0 | 0 | 0 |
| 13-15 | 0 | 0 | 0 | 0 | 0 | 0 | 0 | 0 | 0 | 0 | 0 | 0 | 0 |
| 16-18 | 0 | 0 | 0 | 0 | 0 | 0 | 0 | 0 | 0 | 0 | 0 | 0 | 0 |
| 19-21 | 0 | 0 | 0 | 0 | 0 | 0 | 0 | 0 | 0 | 0 | 0 | 0 | 0 |
| 22-24 | 0 | 0 | 0 | 0 | 0 | 0 | 0 | 0 | 0 | 0 | 0 | 1 | 1 |
| 25-27 | 1 | 1 | 0 | 1 | 1 | 0 | 0 | 0 | 0 | 0 | 0 | 1 | 1 |
| 28-30 | 0 | 0 | 0 | 0 | 0 | 0 | 0 | 0 | 0 | 0 | 0 | 0 | 0 |
| 31-33 | 0 | 0 | 0 | 0 | 0 | 0 | 0 | 0 | 0 | 0 | 0 | 0 | 0 |
| 34-36 | 1 | 0 | 0 | 0 | 0 | 0 | 0 | 0 | 0 | 1 | 0 | 0 | 0 |
| 37-39 | 0 | 0 | 0 | 0 | 0 | 0 | 0 | 0 | 0 | 0 | 0 | 0 | 0 |
| 40-42 | 0 | 0 | 0 | 0 | 0 | 0 | 0 | 0 | 0 | 0 | 0 | 0 | 0 |
| 43-45 | 0 | 0 | 0 | 0 | 0 | 0 | 0 | 0 | 0 | 0 | 0 | 0 | 0 |
| 46-48 | 0 | 0 | 0 | 0 | 0 | 0 | 0 | 0 | 0 | 0 | 0 | 0 | 0 |
| 49-51 | 0 | 0 | 0 | 0 | 0 | 0 | 0 | 0 | 0 | 0 | 0 | 0 | 0 |
| 52-54 | 0 | 0 | 0 | 0 | 0 | 0 | 0 | 0 | 0 | 0 | 0 | 0 | 0 |
| 55-57 | 0 | 0 | 0 | 0 | 0 | 0 | 0 | 0 | 0 | 0 | 0 | 0 | 0 |
| 58-60 | 0 | 0 | 0 | 0 | 0 | 0 | 0 | 0 | 0 | 0 | 0 | 0 | 0 |
| 61-63 | 0 | 0 | 0 | 0 | 0 | 0 | 0 | 0 | 0 | 0 | 0 | 0 | 0 |
| 64-66 | 0 | 0 | 0 | 0 | 0 | 0 | 0 | 0 | 0 | 0 | 0 | 0 | 0 |
| 67-69 | 0 | 0 | 0 | 0 | 0 | 0 | 0 | 0 | 0 | 0 | 0 | 0 | 0 |
| 70-72 | 0 | 0 | 0 | 0 | 0 | 0 | 0 | 0 | 0 | 0 | 0 | 0 | 0 |
| 73-75 | 1 | 1 | 1 | 1 | 1 | 0 | 1 | 1 | 1 | 1 | 1 | 0 | 0 |
| 76-78 | 0 | 0 | 0 | 0 | 0 | 0 | 0 | 0 | 0 | 0 | 0 | 0 | 0 |
| 79-81 | 0 | 1 | 0 | 1 | 1 | 0 | 0 | 0 | 0 | 1 | 0 | 0 | 0 |

TABLE 5-continued

| | | | | | | | | | | | | | |
|---|---|---|---|---|---|---|---|---|---|---|---|---|---|
| 82-84 | 0 | 0 | 0 | 0 | 0 | 0 | 0 | 0 | 0 | 0 | 0 | 0 | 0 |
| 85-87 | 0 | 0 | 0 | 0 | 0 | 0 | 0 | 0 | 0 | 0 | 0 | 0 | 0 |
| 88-90 | 0 | 0 | 0 | 0 | 0 | 0 | 0 | 0 | 0 | 0 | 0 | 0 | 0 |
| 91-93 | 0 | 0 | 0 | 0 | 0 | 0 | 0 | 0 | 0 | 0 | 0 | 0 | 0 |
| 94-96 | 0 | 0 | 0 | 0 | 0 | 0 | 0 | 0 | 0 | 0 | 0 | 0 | 0 |
| 97-99 | 1 | 1 | 0 | 1 | 1 | 0 | 0 | 1 | 0 | 0 | 0 | 1 | 1 |
| 100-102 | 0 | 0 | 0 | 0 | 0 | 0 | 0 | 0 | 0 | 0 | 0 | 0 | 0 |
| 103-105 | 0 | 0 | 0 | 0 | 0 | 0 | 0 | 0 | 0 | 0 | 0 | 0 | 0 |
| 106-108 | 1 | 1 | 1 | 1 | 1 | 0 | 1 | 1 | 1 | 1 | 1 | 1 | 1 |
| 109-111 | 0 | 0 | 0 | 0 | 0 | 0 | 0 | 0 | 0 | 0 | 0 | 0 | 0 |
| 112-114 | 1 | 1 | 0 | 1 | 0 | 0 | 0 | 0 | 0 | 0 | 0 | 1 | 1 |
| 115-117 | 0 | 0 | 0 | 0 | 0 | 0 | 0 | 0 | 0 | 0 | 0 | 0 | 0 |
| 118-120 | 0 | 0 | 0 | 0 | 0 | 0 | 0 | 0 | 0 | 0 | 0 | 0 | 0 |
| 121-123 | 0 | 0 | 0 | 0 | 0 | 0 | 0 | 0 | 0 | 0 | 0 | 0 | 0 |
| 124-126 | 0 | 0 | 0 | 0 | 0 | 0 | 0 | 0 | 0 | 0 | 0 | 0 | 0 |
| 127-129 | 0 | 0 | 0 | 0 | 0 | 0 | 0 | 0 | 0 | 0 | 0 | 0 | 0 |
| 130-132 | 0 | 0 | 0 | 0 | 0 | 0 | 0 | 0 | 0 | 0 | 0 | 0 | 0 |
| 133-135 | 1 | 1 | 0 | 1 | 1 | 0 | 0 | 0 | 0 | 1 | 1 | 1 | 1 |
| 136-138 | 0 | 0 | 0 | 0 | 0 | 0 | 0 | 0 | 0 | 0 | 0 | 0 | 0 |
| 139-141 | 0 | 0 | 0 | 0 | 0 | 0 | 0 | 0 | 0 | 0 | 0 | 0 | 0 |
| 142-144 | 0 | 0 | 0 | 0 | 0 | 0 | 0 | 0 | 0 | 0 | 0 | 0 | 0 |
| 145-147 | 0 | 0 | 0 | 0 | 0 | 0 | 0 | 0 | 0 | 0 | 0 | 0 | 0 |
| 148-150 | 0 | 0 | 0 | 0 | 0 | 0 | 0 | 0 | 0 | 0 | 0 | 0 | 0 |
| 151-153 | 0 | 0 | 0 | 0 | 0 | 0 | 0 | 0 | 0 | 0 | 0 | 0 | 0 |
| 154-156 | 1 | 1 | 0 | 1 | 1 | 0 | 1 | 0 | 0 | 0 | 0 | 1 | 1 |
| 157-159 | 0 | 0 | 0 | 0 | 0 | 0 | 0 | 0 | 0 | 0 | 0 | 0 | 0 |
| 160-162 | 0 | 0 | 0 | 0 | 0 | 0 | 0 | 0 | 0 | 0 | 0 | 0 | 0 |
| 163-165 | 0 | 0 | 0 | 0 | 0 | 0 | 0 | 0 | 0 | 0 | 0 | 0 | 0 |
| 166-168 | 1 | 1 | 1 | 1 | 1 | 1 | 1 | 1 | 1 | 1 | 1 | 1 | 1 |
| 169-171 | 0 | 0 | 0 | 0 | 0 | 0 | 0 | 0 | 0 | 0 | 0 | 0 | 0 |
| 172-174 | 0 | 0 | 0 | 0 | 0 | 0 | 0 | 0 | 0 | 0 | 0 | 0 | 0 |
| 175-177 | 0 | 1 | 0 | 1 | 1 | 0 | 0 | 0 | 0 | 0 | 0 | 1 | 1 |
| 178-180 | 0 | 0 | 0 | 0 | 0 | 0 | 0 | 0 | 0 | 0 | 0 | 0 | 0 |
| 181-183 | 0 | 0 | 0 | 0 | 0 | 0 | 0 | 0 | 0 | 0 | 0 | 0 | 0 |
| 184-186 | 0 | 0 | 0 | 0 | 0 | 0 | 0 | 0 | 0 | 0 | 0 | 0 | 0 |
| 187-189 | 0 | 0 | 0 | 0 | 0 | 0 | 0 | 0 | 0 | 0 | 0 | 0 | 1 |
| 190-192 | 0 | 0 | 0 | 0 | 0 | 0 | 0 | 0 | 0 | 0 | 0 | 1 | 0 |
| 193-195 | 0 | 0 | 0 | 0 | 0 | 0 | 0 | 0 | 0 | 0 | 0 | 0 | 0 |
| 196-198 | 0 | 0 | 0 | 0 | 0 | 0 | 0 | 0 | 0 | 0 | 0 | 0 | 0 |
| 199-201 | 0 | 0 | 0 | 0 | 0 | 0 | 0 | 0 | 0 | 0 | 0 | 0 | 0 |
| 202-204 | 0 | 0 | 0 | 0 | 0 | 0 | 0 | 0 | 0 | 0 | 0 | 0 | 0 |
| 205-207 | 0 | 0 | 0 | 0 | 0 | 0 | 0 | 0 | 0 | 0 | 0 | 0 | 0 |
| 208-210 | 1 | 1 | 1 | 1 | 0 | 1 | 0 | 0 | 0 | 1 | 1 | 1 | 1 |
| 211-213 | 0 | 0 | 0 | 0 | 0 | 0 | 0 | 0 | 0 | 0 | 0 | 0 | 0 |
| 214-216 | 0 | 0 | 0 | 0 | 0 | 0 | 0 | 0 | 0 | 0 | 0 | 0 | 0 |
| 217-219 | 0 | 0 | 0 | 0 | 0 | 0 | 0 | 0 | 0 | 0 | 0 | 0 | 0 |
| 220-222 | 0 | 0 | 0 | 0 | 0 | 0 | 0 | 0 | 0 | 0 | 0 | 0 | 0 |
| 223-225 | 0 | 0 | 0 | 0 | 0 | 0 | 0 | 0 | 0 | 0 | 0 | 0 | 0 |
| 226-228 | 0 | 0 | 0 | 0 | 0 | 0 | 0 | 0 | 0 | 0 | 0 | 0 | 0 |
| 229-231 | 0 | 0 | 0 | 0 | 0 | 0 | 0 | 0 | 0 | 0 | 0 | 0 | 0 |
| 232-234 | 0 | 1 | 1 | 1 | 1 | 0 | 1 | 0 | 0 | 1 | 0 | 0 | 0 |
| 235-237 | 0 | 0 | 0 | 0 | 0 | 0 | 0 | 0 | 0 | 0 | 0 | 0 | 0 |
| 238-240 | 0 | 0 | 0 | 0 | 0 | 0 | 0 | 0 | 0 | 0 | 0 | 0 | 0 |
| 241-243 | 0 | 0 | 0 | 0 | 0 | 0 | 0 | 0 | 0 | 0 | 0 | 0 | 0 |
| 244-246 | 0 | 0 | 0 | 0 | 0 | 0 | 0 | 0 | 0 | 0 | 0 | 0 | 0 |
| 247-249 | 0 | 0 | 0 | 0 | 0 | 0 | 0 | 0 | 0 | 0 | 0 | 0 | 0 |
| 250-252 | 0 | 0 | 0 | 0 | 0 | 0 | 0 | 0 | 0 | 0 | 0 | 0 | 0 |
| 253-255 | 0 | 0 | 0 | 0 | 0 | 0 | 0 | 0 | 0 | 0 | 0 | 0 | 0 |
| 256-258 | 0 | 0 | 0 | 0 | 0 | 0 | 0 | 0 | 0 | 0 | 0 | 0 | 0 |
| 259-261 | 0 | 0 | 0 | 0 | 0 | 0 | 0 | 0 | 0 | 0 | 0 | 0 | 0 |
| 262-264 | 0 | 0 | 0 | 0 | 0 | 0 | 0 | 0 | 0 | 0 | 1 | 0 | 0 |
| 265-267 | 0 | 0 | 0 | 0 | 0 | 0 | 0 | 0 | 0 | 0 | 0 | 0 | 0 |
| 268-270 | 0 | 0 | 0 | 0 | 0 | 0 | 0 | 0 | 0 | 0 | 0 | 0 | 0 |
| 271-273 | 0 | 0 | 0 | 0 | 0 | 0 | 0 | 0 | 0 | 0 | 0 | 0 | 0 |
| 274-276 | 0 | 0 | 0 | 0 | 0 | 0 | 0 | 0 | 0 | 0 | 0 | 0 | 0 |
| 277-279 | 0 | 0 | 0 | 0 | 0 | 0 | 0 | 0 | 0 | 0 | 0 | 0 | 0 |
| 280-282 | 0 | 0 | 0 | 0 | 0 | 0 | 0 | 0 | 0 | 0 | 0 | 0 | 0 |
| 283-285 | 0 | 0 | 0 | 0 | 0 | 0 | 0 | 0 | 0 | 0 | 0 | 0 | 0 |
| 286-288 | 0 | 0 | 0 | 0 | 0 | 0 | 0 | 0 | 0 | 0 | 0 | 0 | 0 |
| 289-291 | 0 | 0 | 0 | 0 | 0 | 0 | 0 | 0 | 0 | 0 | 0 | 0 | 0 |
| 292-294 | 0 | 0 | 0 | 0 | 0 | 0 | 0 | 0 | 0 | 0 | 0 | 0 | 0 |
| 295-297 | 0 | 0 | 0 | 0 | 0 | 0 | 0 | 0 | 0 | 0 | 0 | 0 | 0 |
| 298-300 | 1 | 1 | 0 | 0 | 0 | 0 | 0 | 1 | 0 | 0 | 0 | 0 | 0 |
| 301-303 | 0 | 0 | 0 | 0 | 0 | 0 | 0 | 0 | 0 | 0 | 0 | 0 | 0 |
| 304-306 | 0 | 0 | 0 | 0 | 0 | 0 | 0 | 0 | 0 | 0 | 0 | 0 | 0 |
| 307-309 | 0 | 0 | 0 | 0 | 0 | 0 | 0 | 0 | 0 | 0 | 0 | 0 | 0 |
| 310-312 | 0 | 0 | 0 | 0 | 0 | 0 | 0 | 0 | 0 | 0 | 0 | 0 | 0 |
| 313-315 | 0 | 0 | 0 | 0 | 0 | 0 | 0 | 0 | 0 | 0 | 0 | 0 | 0 |
| 316-318 | 0 | 0 | 0 | 0 | 0 | 0 | 0 | 0 | 0 | 0 | 0 | 0 | 0 |
| 319-321 | 0 | 0 | 0 | 0 | 0 | 0 | 0 | 0 | 0 | 0 | 0 | 0 | 0 |

TABLE 5-continued

| | | | | | | | | | | | | | |
|---|---|---|---|---|---|---|---|---|---|---|---|---|---|
| 322-324 | 0 | 0 | 0 | 0 | 0 | 0 | 0 | 0 | 0 | 0 | 0 | 0 | 0 |
| 325-327 | 0 | 0 | 0 | 0 | 0 | 0 | 0 | 0 | 0 | 0 | 0 | 0 | 0 |
| 328-330 | 0 | 0 | 0 | 0 | 0 | 0 | 0 | 0 | 0 | 0 | 0 | 0 | 0 |
| 331-333 | 0 | 0 | 0 | 0 | 0 | 0 | 0 | 0 | 0 | 0 | 0 | 0 | 0 |
| 334-336 | 0 | 0 | 0 | 0 | 0 | 0 | 0 | 0 | 0 | 0 | 0 | 0 | 0 |
| 337-339 | 0 | 0 | 0 | 0 | 0 | 0 | 0 | 0 | 0 | 0 | 0 | 0 | 0 |
| 340-342 | 0 | 0 | 0 | 0 | 0 | 0 | 0 | 0 | 0 | 0 | 0 | 0 | 0 |
| 343-345 | 1 | 1 | 1 | 1 | 1 | 0 | 1 | 1 | 0 | 1 | 1 | 1 | 1 |
| 346-348 | 0 | 0 | 0 | 0 | 0 | 0 | 0 | 0 | 0 | 0 | 0 | 0 | 0 |
| TEM peptides | 12 | 14 | 6 | 13 | 11 | 2 | 6 | 6 | 3 | 9 | 7 | 12 | 12 |
| 2b peptides | 0 | 0 | 0 | 0 | 0 | 0 | 0 | 0 | 0 | 0 | 0 | 0 | 0 |
| 2br peptides | 0 | 0 | 0 | 0 | 0 | 0 | 0 | 0 | 0 | 0 | 0 | 0 | 1 |
| 2be peptides | 1 | 2 | 1 | 2 | 2 | 0 | 1 | 0 | 0 | 3 | 1 | 0 | 0 |
| 2ber peptides | 0 | 0 | 0 | 0 | 0 | 0 | 0 | 0 | 0 | 0 | 0 | 0 | 0 |

| Transition number | Sam36 | Sam37 | Sam38 | Sam39 | Sam40 | Sam41 | Sam42 | Sam43 | Sam44 | Sam45 | Sam46 | Sam47 | Sam48 |
|---|---|---|---|---|---|---|---|---|---|---|---|---|---|
| 1-3 | 0 | 0 | 0 | 0 | 0 | 0 | 0 | 0 | 0 | 0 | 0 | 0 | 0 |
| 4-6 | 0 | 0 | 0 | 0 | 0 | 0 | 0 | 0 | 0 | 0 | 0 | 0 | 0 |
| 7-9 | 0 | 0 | 0 | 0 | 0 | 0 | 0 | 0 | 0 | 0 | 0 | 0 | 0 |
| 10-12 | 0 | 0 | 0 | 0 | 0 | 0 | 0 | 0 | 0 | 0 | 0 | 0 | 0 |
| 13-15 | 0 | 0 | 0 | 0 | 0 | 0 | 0 | 0 | 0 | 0 | 0 | 0 | 0 |
| 16-18 | 0 | 0 | 0 | 0 | 0 | 0 | 0 | 0 | 0 | 0 | 0 | 0 | 0 |
| 19-21 | 0 | 0 | 0 | 0 | 0 | 0 | 0 | 0 | 0 | 0 | 0 | 0 | 0 |
| 22-24 | 0 | 0 | 1 | 1 | 0 | 1 | 0 | 0 | 0 | 0 | 0 | 0 | 0 |
| 25-27 | 1 | 0 | 1 | 1 | 1 | 1 | 1 | 0 | 0 | 0 | 1 | 0 | 0 |
| 28-30 | 0 | 0 | 0 | 0 | 0 | 0 | 0 | 0 | 0 | 0 | 0 | 0 | 0 |
| 31-33 | 0 | 0 | 0 | 0 | 0 | 0 | 0 | 0 | 0 | 0 | 0 | 0 | 0 |
| 34-36 | 0 | 0 | 0 | 0 | 0 | 0 | 0 | 0 | 0 | 0 | 0 | 0 | 0 |
| 37-39 | 0 | 0 | 0 | 0 | 0 | 0 | 0 | 0 | 0 | 0 | 0 | 0 | 0 |
| 40-42 | 0 | 0 | 0 | 0 | 0 | 0 | 0 | 0 | 0 | 0 | 0 | 0 | 0 |
| 43-45 | 0 | 0 | 0 | 0 | 0 | 0 | 0 | 0 | 0 | 0 | 0 | 0 | 0 |
| 46-48 | 0 | 0 | 0 | 0 | 0 | 0 | 0 | 0 | 0 | 0 | 0 | 0 | 0 |
| 49-51 | 0 | 0 | 0 | 0 | 0 | 0 | 0 | 0 | 0 | 0 | 0 | 0 | 0 |
| 52-54 | 0 | 0 | 0 | 0 | 0 | 0 | 0 | 0 | 0 | 0 | 0 | 0 | 0 |
| 55-57 | 0 | 0 | 0 | 0 | 0 | 0 | 0 | 0 | 0 | 0 | 0 | 0 | 0 |
| 58-60 | 0 | 0 | 0 | 0 | 0 | 0 | 0 | 0 | 0 | 0 | 0 | 0 | 0 |
| 61-63 | 0 | 0 | 0 | 0 | 0 | 0 | 0 | 0 | 0 | 0 | 0 | 0 | 0 |
| 64-66 | 0 | 0 | 0 | 0 | 0 | 0 | 1 | 0 | 0 | 0 | 0 | 0 | 0 |
| 67-69 | 0 | 0 | 0 | 0 | 0 | 0 | 0 | 0 | 0 | 0 | 0 | 0 | 0 |
| 70-72 | 0 | 0 | 0 | 0 | 0 | 0 | 0 | 0 | 0 | 0 | 0 | 0 | 0 |
| 73-75 | 1 | 1 | 1 | 1 | 1 | 1 | 1 | 1 | 1 | 1 | 1 | 1 | 1 |
| 76-78 | 0 | 0 | 0 | 0 | 0 | 0 | 0 | 0 | 0 | 0 | 0 | 0 | 0 |
| 79-81 | 0 | 0 | 0 | 0 | 0 | 0 | 0 | 0 | 0 | 0 | 0 | 1 | 0 | 0 |
| 82-84 | 0 | 0 | 0 | 0 | 0 | 0 | 0 | 0 | 0 | 0 | 0 | 0 | 0 |
| 85-87 | 0 | 0 | 0 | 0 | 0 | 0 | 0 | 0 | 0 | 0 | 0 | 0 | 0 |
| 88-90 | 0 | 0 | 0 | 0 | 0 | 0 | 0 | 0 | 0 | 0 | 0 | 0 | 0 |
| 91-93 | 0 | 0 | 0 | 0 | 0 | 0 | 0 | 0 | 0 | 0 | 0 | 0 | 0 |
| 94-96 | 0 | 0 | 0 | 0 | 0 | 0 | 0 | 0 | 0 | 0 | 0 | 0 | 0 |
| 97-99 | 1 | 0 | 1 | 1 | 1 | 1 | 1 | 0 | 0 | 0 | 1 | 0 | 0 |
| 100-102 | 0 | 0 | 0 | 0 | 0 | 0 | 0 | 0 | 0 | 0 | 0 | 0 | 0 |
| 103-105 | 0 | 0 | 0 | 0 | 0 | 0 | 0 | 0 | 0 | 0 | 0 | 0 | 0 |
| 106-108 | 1 | 1 | 1 | 1 | 1 | 1 | 1 | 1 | 1 | 1 | 1 | 1 | 1 |
| 109-111 | 0 | 0 | 0 | 0 | 0 | 0 | 0 | 0 | 0 | 0 | 0 | 0 | 0 |
| 112-114 | 1 | 0 | 1 | 1 | 1 | 1 | 1 | 0 | 0 | 0 | 1 | 0 | 0 |
| 115-117 | 0 | 0 | 0 | 0 | 0 | 0 | 0 | 0 | 0 | 0 | 0 | 0 | 0 |
| 118-120 | 0 | 0 | 0 | 0 | 0 | 0 | 0 | 0 | 0 | 0 | 0 | 0 | 0 |
| 121-123 | 0 | 0 | 0 | 0 | 0 | 0 | 0 | 0 | 0 | 0 | 0 | 0 | 0 |
| 124-126 | 0 | 0 | 0 | 0 | 0 | 0 | 0 | 0 | 0 | 0 | 0 | 0 | 0 |
| 127-129 | 0 | 0 | 0 | 0 | 0 | 0 | 0 | 0 | 0 | 0 | 0 | 0 | 0 |
| 130-132 | 0 | 0 | 0 | 0 | 0 | 0 | 0 | 0 | 0 | 0 | 0 | 0 | 0 |
| 133-135 | 1 | 1 | 1 | 1 | 1 | 1 | 1 | 1 | 1 | 0 | 1 | 0 | 0 |
| 136-138 | 0 | 0 | 0 | 0 | 0 | 0 | 0 | 0 | 0 | 0 | 0 | 0 | 0 |
| 139-141 | 0 | 0 | 0 | 0 | 0 | 0 | 0 | 0 | 0 | 0 | 0 | 0 | 0 |
| 142-144 | 0 | 0 | 0 | 0 | 0 | 0 | 0 | 0 | 0 | 0 | 0 | 0 | 0 |
| 145-147 | 0 | 0 | 0 | 0 | 0 | 0 | 0 | 0 | 0 | 0 | 0 | 0 | 0 |
| 148-150 | 0 | 0 | 0 | 0 | 0 | 0 | 0 | 0 | 0 | 0 | 0 | 0 | 0 |
| 151-153 | 0 | 0 | 0 | 0 | 0 | 0 | 0 | 0 | 0 | 0 | 0 | 0 | 0 |
| 154-156 | 1 | 0 | 1 | 1 | 1 | 1 | 1 | 0 | 0 | 0 | 1 | 0 | 0 |
| 157-159 | 0 | 0 | 0 | 0 | 0 | 0 | 0 | 0 | 0 | 0 | 0 | 0 | 0 |
| 160-162 | 0 | 0 | 0 | 0 | 0 | 0 | 0 | 0 | 0 | 0 | 0 | 0 | 0 |
| 163-165 | 0 | 0 | 0 | 0 | 0 | 0 | 0 | 0 | 0 | 0 | 0 | 0 | 0 |
| 166-168 | 1 | 1 | 1 | 1 | 1 | 1 | 1 | 1 | 1 | 1 | 1 | 1 | 0 |
| 169-171 | 0 | 0 | 0 | 0 | 0 | 0 | 0 | 0 | 0 | 0 | 0 | 0 | 0 |

TABLE 5-continued

| | | | | | | | | | | | | | |
|---|---|---|---|---|---|---|---|---|---|---|---|---|---|
| 172-174 | 0 | 0 | 0 | 0 | 0 | 0 | 0 | 0 | 0 | 0 | 0 | 0 | 0 |
| 175-177 | 1 | 0 | 1 | 1 | 1 | 1 | 0 | 0 | 0 | 1 | 1 | 0 | 0 |
| 178-180 | 0 | 0 | 0 | 0 | 0 | 0 | 0 | 0 | 0 | 0 | 0 | 0 | 0 |
| 181-183 | 0 | 0 | 0 | 0 | 0 | 0 | 0 | 0 | 0 | 0 | 0 | 0 | 0 |
| 184-186 | 0 | 0 | 0 | 0 | 0 | 0 | 0 | 0 | 0 | 0 | 0 | 0 | 0 |
| 187-189 | 0 | 0 | 0 | 0 | 0 | 0 | 0 | 0 | 0 | 0 | 0 | 0 | 0 |
| 190-192 | 0 | 0 | 0 | 0 | 0 | 0 | 0 | 0 | 0 | 0 | 0 | 0 | 0 |
| 193-195 | 0 | 0 | 0 | 0 | 0 | 0 | 0 | 0 | 0 | 0 | 0 | 0 | 0 |
| 196-198 | 0 | 0 | 0 | 0 | 0 | 0 | 0 | 0 | 0 | 0 | 0 | 0 | 0 |
| 199-201 | 0 | 0 | 0 | 0 | 0 | 0 | 0 | 0 | 0 | 0 | 0 | 0 | 0 |
| 202-204 | 0 | 0 | 0 | 0 | 0 | 0 | 0 | 0 | 0 | 0 | 0 | 0 | 0 |
| 205-207 | 0 | 0 | 0 | 0 | 0 | 0 | 0 | 0 | 0 | 0 | 0 | 0 | 0 |
| 208-210 | 1 | 1 | 1 | 1 | 1 | 1 | 1 | 1 | 1 | 1 | 1 | 1 | 0 |
| 211-213 | 0 | 0 | 0 | 0 | 0 | 0 | 0 | 0 | 0 | 0 | 0 | 0 | 0 |
| 214-216 | 0 | 0 | 0 | 0 | 0 | 0 | 0 | 0 | 0 | 0 | 0 | 0 | 0 |
| 217-219 | 0 | 0 | 0 | 0 | 0 | 0 | 0 | 0 | 0 | 0 | 0 | 0 | 0 |
| 220-222 | 0 | 0 | 0 | 0 | 0 | 0 | 0 | 0 | 0 | 0 | 0 | 0 | 0 |
| 223-225 | 0 | 0 | 0 | 0 | 0 | 0 | 0 | 0 | 0 | 0 | 0 | 0 | 0 |
| 226-228 | 0 | 0 | 0 | 0 | 0 | 0 | 0 | 0 | 0 | 0 | 0 | 0 | 0 |
| 229-231 | 0 | 0 | 0 | 0 | 0 | 0 | 0 | 0 | 0 | 0 | 0 | 0 | 0 |
| 232-234 | 0 | 0 | 0 | 0 | 0 | 0 | 0 | 0 | 1 | 0 | 1 | 0 | 0 |
| 235-237 | 0 | 0 | 0 | 0 | 0 | 0 | 0 | 0 | 0 | 0 | 0 | 0 | 0 |
| 238-240 | 0 | 0 | 0 | 0 | 0 | 0 | 0 | 0 | 0 | 0 | 0 | 0 | 0 |
| 241-243 | 0 | 0 | 0 | 0 | 0 | 0 | 0 | 0 | 0 | 0 | 0 | 0 | 0 |
| 244-246 | 0 | 0 | 0 | 0 | 0 | 0 | 0 | 0 | 0 | 0 | 0 | 0 | 0 |
| 247-249 | 0 | 0 | 0 | 0 | 0 | 0 | 0 | 0 | 0 | 0 | 0 | 0 | 0 |
| 250-252 | 0 | 0 | 0 | 0 | 0 | 0 | 0 | 0 | 0 | 0 | 0 | 0 | 0 |
| 253-255 | 0 | 0 | 0 | 0 | 0 | 0 | 0 | 0 | 0 | 0 | 0 | 0 | 0 |
| 256-258 | 0 | 0 | 0 | 0 | 0 | 0 | 0 | 0 | 0 | 0 | 0 | 0 | 0 |
| 259-261 | 0 | 0 | 0 | 0 | 0 | 0 | 0 | 0 | 0 | 0 | 0 | 0 | 0 |
| 262-264 | 0 | 0 | 0 | 0 | 0 | 0 | 0 | 0 | 0 | 0 | 0 | 0 | 0 |
| 265-267 | 0 | 0 | 0 | 0 | 0 | 0 | 0 | 0 | 0 | 0 | 0 | 0 | 0 |
| 268-270 | 0 | 0 | 0 | 0 | 0 | 0 | 0 | 0 | 0 | 0 | 0 | 0 | 0 |
| 271-273 | 0 | 0 | 0 | 0 | 0 | 0 | 0 | 0 | 0 | 0 | 0 | 0 | 0 |
| 274-276 | 0 | 0 | 0 | 0 | 0 | 0 | 0 | 0 | 0 | 0 | 0 | 0 | 0 |
| 277-279 | 0 | 0 | 0 | 0 | 0 | 0 | 0 | 0 | 0 | 0 | 0 | 0 | 0 |
| 280-282 | 0 | 0 | 0 | 0 | 0 | 0 | 0 | 0 | 0 | 0 | 0 | 0 | 0 |
| 283-285 | 0 | 0 | 0 | 0 | 0 | 0 | 0 | 0 | 0 | 0 | 0 | 0 | 0 |
| 286-288 | 0 | 0 | 0 | 0 | 0 | 0 | 0 | 0 | 0 | 0 | 0 | 0 | 0 |
| 289-291 | 0 | 0 | 0 | 0 | 0 | 0 | 0 | 0 | 0 | 0 | 0 | 0 | 0 |
| 292-294 | 0 | 0 | 0 | 0 | 0 | 0 | 0 | 0 | 0 | 0 | 0 | 0 | 0 |
| 295-297 | 0 | 0 | 0 | 0 | 0 | 0 | 0 | 0 | 0 | 0 | 0 | 0 | 0 |
| 298-300 | 1 | 0 | 1 | 1 | 0 | 1 | 1 | 0 | 0 | 0 | 0 | 0 | 0 |
| 301-303 | 0 | 0 | 0 | 0 | 0 | 0 | 0 | 0 | 0 | 0 | 0 | 0 | 0 |
| 304-306 | 0 | 0 | 0 | 0 | 0 | 0 | 0 | 0 | 0 | 0 | 1 | 0 | 0 |
| 307-309 | 0 | 0 | 0 | 0 | 0 | 0 | 0 | 0 | 0 | 0 | 0 | 0 | 0 |
| 310-312 | 0 | 0 | 0 | 0 | 0 | 0 | 0 | 0 | 0 | 0 | 0 | 0 | 0 |
| 313-315 | 0 | 0 | 0 | 0 | 0 | 0 | 0 | 0 | 0 | 0 | 0 | 0 | 0 |
| 316-318 | 0 | 0 | 0 | 0 | 0 | 0 | 0 | 0 | 0 | 0 | 0 | 0 | 0 |
| 319-321 | 0 | 0 | 0 | 0 | 0 | 0 | 0 | 0 | 0 | 0 | 0 | 0 | 0 |
| 322-324 | 0 | 0 | 0 | 0 | 0 | 0 | 0 | 0 | 0 | 0 | 0 | 0 | 0 |
| 325-327 | 0 | 0 | 0 | 0 | 0 | 0 | 0 | 0 | 0 | 0 | 0 | 0 | 0 |
| 328-330 | 0 | 0 | 0 | 0 | 0 | 0 | 0 | 0 | 0 | 0 | 0 | 0 | 0 |
| 331-333 | 0 | 0 | 0 | 0 | 0 | 0 | 0 | 0 | 0 | 0 | 0 | 0 | 0 |
| 334-336 | 0 | 0 | 0 | 0 | 0 | 0 | 0 | 0 | 0 | 0 | 0 | 0 | 0 |
| 337-339 | 0 | 0 | 0 | 0 | 0 | 0 | 0 | 0 | 0 | 0 | 0 | 0 | 0 |
| 340-342 | 0 | 0 | 0 | 0 | 0 | 0 | 0 | 0 | 0 | 0 | 0 | 0 | 0 |
| 343-345 | 1 | 1 | 1 | 1 | 1 | 1 | 1 | 1 | 1 | 1 | 1 | 1 | 0 |
| 346-348 | 0 | 0 | 0 | 0 | 0 | 0 | 0 | 0 | 0 | 0 | 0 | 0 | 0 |
| TEM peptides | 12 | 6 | 13 | 13 | 11 | 13 | 12 | 6 | 7 | 6 | 14 | 5 | 2 |
| 2b peptides | 0 | 0 | 0 | 0 | 0 | 0 | 0 | 0 | 0 | 0 | 0 | 0 | 0 |
| 2br peptides | 0 | 0 | 0 | 0 | 0 | 0 | 0 | 0 | 0 | 0 | 0 | 0 | 0 |
| 2be peptides | 0 | 0 | 0 | 0 | 0 | 0 | 0 | 0 | 1 | 0 | 2 | 0 | 0 |
| 2ber peptides | 0 | 0 | 0 | 0 | 0 | 0 | 0 | 0 | 0 | 0 | 0 | 0 | 0 |

| Transition number | Sam49 | Sam50 | Sam51 | Sam52 | Sam53 | Sam54 | Sam55 | Sam56 | Sam57 | Sam58 | Sam59 | Sam60 | Sam61 |
|---|---|---|---|---|---|---|---|---|---|---|---|---|---|
| 1-3 | 0 | 0 | 0 | 0 | 0 | 0 | 0 | 0 | 0 | 0 | 0 | 0 | 0 |
| 4-6 | 0 | 0 | 0 | 0 | 0 | 0 | 0 | 0 | 0 | 0 | 0 | 0 | 0 |
| 7-9 | 0 | 0 | 0 | 0 | 0 | 0 | 0 | 0 | 0 | 0 | 0 | 0 | 0 |
| 10-12 | 0 | 0 | 0 | 0 | 0 | 0 | 0 | 0 | 0 | 0 | 0 | 0 | 0 |
| 13-15 | 0 | 0 | 0 | 0 | 0 | 0 | 0 | 0 | 0 | 0 | 0 | 0 | 0 |
| 16-18 | 0 | 0 | 0 | 0 | 0 | 0 | 0 | 0 | 0 | 0 | 0 | 0 | 0 |
| 19-21 | 0 | 0 | 0 | 0 | 0 | 0 | 0 | 0 | 0 | 0 | 0 | 0 | 0 |

TABLE 5-continued

| | | | | | | | | | | | | | |
|---|---|---|---|---|---|---|---|---|---|---|---|---|---|
| 22-24 | 0 | 0 | 0 | 0 | 1 | 0 | 0 | 1 | 0 | 0 | 0 | 0 | 0 |
| 25-27 | 0 | 1 | 1 | 1 | 1 | 0 | 1 | 1 | 1 | 1 | 1 | 1 | 1 |
| 28-30 | 0 | 0 | 0 | 0 | 0 | 0 | 0 | 0 | 0 | 0 | 0 | 0 | 0 |
| 31-33 | 0 | 0 | 0 | 0 | 0 | 0 | 0 | 0 | 0 | 0 | 0 | 0 | 0 |
| 34-36 | 0 | 0 | 0 | 0 | 0 | 0 | 0 | 0 | 0 | 1 | 1 | 0 | 1 |
| 37-39 | 0 | 0 | 0 | 0 | 0 | 0 | 0 | 0 | 0 | 0 | 0 | 0 | 0 |
| 40-42 | 0 | 0 | 0 | 0 | 0 | 0 | 0 | 0 | 0 | 0 | 0 | 0 | 0 |
| 43-45 | 0 | 0 | 0 | 0 | 0 | 0 | 0 | 0 | 0 | 0 | 0 | 0 | 0 |
| 46-48 | 0 | 0 | 0 | 0 | 0 | 0 | 0 | 0 | 0 | 0 | 0 | 0 | 0 |
| 49-51 | 0 | 0 | 0 | 0 | 0 | 0 | 0 | 0 | 0 | 0 | 0 | 0 | 0 |
| 52-54 | 0 | 0 | 0 | 0 | 0 | 0 | 0 | 0 | 0 | 0 | 0 | 0 | 0 |
| 55-57 | 0 | 0 | 0 | 0 | 0 | 0 | 0 | 0 | 0 | 0 | 0 | 0 | 0 |
| 58-60 | 0 | 0 | 0 | 0 | 0 | 0 | 0 | 0 | 0 | 0 | 0 | 0 | 0 |
| 61-63 | 0 | 0 | 0 | 0 | 0 | 0 | 0 | 0 | 0 | 0 | 0 | 0 | 0 |
| 64-66 | 0 | 0 | 0 | 0 | 0 | 0 | 0 | 0 | 0 | 0 | 0 | 0 | 0 |
| 67-69 | 0 | 0 | 0 | 0 | 0 | 0 | 0 | 0 | 0 | 0 | 0 | 0 | 0 |
| 70-72 | 0 | 0 | 0 | 0 | 0 | 0 | 0 | 0 | 0 | 0 | 0 | 0 | 0 |
| 73-75 | 0 | 0 | 0 | 1 | 1 | 0 | 1 | 1 | 1 | 1 | 0 | 1 | 1 |
| 76-78 | 0 | 0 | 0 | 0 | 0 | 0 | 0 | 0 | 0 | 0 | 0 | 0 | 0 |
| 79-81 | 0 | 0 | 0 | 1 | 0 | 0 | 1 | 0 | 1 | 0 | 1 | 0 | 1 |
| 82-84 | 0 | 0 | 0 | 0 | 0 | 0 | 0 | 0 | 0 | 0 | 0 | 0 | 0 |
| 85-87 | 0 | 0 | 0 | 0 | 0 | 0 | 0 | 0 | 0 | 0 | 0 | 0 | 0 |
| 88-90 | 0 | 0 | 0 | 0 | 0 | 0 | 0 | 0 | 0 | 0 | 0 | 0 | 0 |
| 91-93 | 0 | 0 | 0 | 0 | 0 | 0 | 0 | 0 | 0 | 0 | 0 | 0 | 0 |
| 94-96 | 0 | 0 | 0 | 0 | 0 | 0 | 0 | 0 | 0 | 0 | 0 | 0 | 0 |
| 97-99 | 0 | 1 | 0 | 0 | 1 | 0 | 0 | 1 | 1 | 1 | 1 | 0 | 0 |
| 100-102 | 0 | 0 | 0 | 0 | 0 | 0 | 0 | 0 | 0 | 0 | 0 | 0 | 0 |
| 103-105 | 0 | 0 | 0 | 0 | 0 | 0 | 0 | 0 | 0 | 0 | 0 | 0 | 0 |
| 106-108 | 1 | 1 | 1 | 1 | 1 | 0 | 1 | 1 | 1 | 1 | 1 | 1 | 1 |
| 109-111 | 0 | 0 | 0 | 0 | 0 | 0 | 0 | 0 | 0 | 0 | 0 | 0 | 0 |
| 112-114 | 0 | 1 | 1 | 1 | 1 | 0 | 1 | 1 | 0 | 0 | 0 | 0 | 0 |
| 115-117 | 0 | 0 | 0 | 0 | 0 | 0 | 0 | 0 | 0 | 0 | 0 | 0 | 0 |
| 118-120 | 0 | 0 | 0 | 0 | 0 | 0 | 0 | 0 | 0 | 0 | 0 | 0 | 0 |
| 121-123 | 0 | 0 | 0 | 0 | 0 | 0 | 0 | 0 | 0 | 0 | 0 | 0 | 0 |
| 124-126 | 0 | 0 | 0 | 0 | 0 | 0 | 0 | 0 | 0 | 0 | 0 | 0 | 0 |
| 127-129 | 0 | 0 | 0 | 0 | 0 | 0 | 0 | 0 | 0 | 0 | 0 | 0 | 0 |
| 130-132 | 0 | 0 | 0 | 0 | 0 | 0 | 0 | 0 | 0 | 0 | 0 | 0 | 0 |
| 133-135 | 0 | 1 | 0 | 1 | 1 | 0 | 1 | 1 | 1 | 1 | 1 | 1 | 0 |
| 136-138 | 0 | 0 | 0 | 0 | 0 | 0 | 0 | 0 | 0 | 0 | 0 | 0 | 0 |
| 139-141 | 0 | 0 | 0 | 0 | 0 | 0 | 0 | 0 | 0 | 0 | 0 | 0 | 0 |
| 142-144 | 0 | 0 | 0 | 0 | 0 | 0 | 0 | 0 | 0 | 0 | 0 | 0 | 0 |
| 145-147 | 0 | 0 | 0 | 0 | 0 | 0 | 0 | 0 | 0 | 0 | 0 | 0 | 0 |
| 148-150 | 0 | 0 | 0 | 0 | 0 | 0 | 0 | 0 | 0 | 0 | 0 | 0 | 0 |
| 151-153 | 0 | 0 | 0 | 0 | 0 | 0 | 0 | 0 | 0 | 0 | 0 | 0 | 0 |
| 154-156 | 0 | 1 | 0 | 1 | 1 | 0 | 0 | 1 | 1 | 1 | 1 | 1 | 0 |
| 157-159 | 0 | 0 | 0 | 0 | 0 | 0 | 0 | 0 | 0 | 0 | 0 | 0 | 0 |
| 160-162 | 0 | 0 | 0 | 0 | 0 | 0 | 0 | 0 | 0 | 0 | 0 | 0 | 0 |
| 163-165 | 0 | 0 | 0 | 0 | 0 | 0 | 0 | 0 | 0 | 0 | 0 | 0 | 0 |
| 166-168 | 1 | 1 | 1 | 1 | 1 | 0 | 1 | 1 | 1 | 1 | 1 | 1 | 1 |
| 169-171 | 0 | 0 | 0 | 0 | 0 | 0 | 0 | 0 | 0 | 0 | 0 | 0 | 0 |
| 172-174 | 0 | 0 | 0 | 0 | 0 | 0 | 0 | 0 | 0 | 0 | 0 | 0 | 0 |
| 175-177 | 1 | 1 | 1 | 1 | 1 | 0 | 1 | 1 | 1 | 0 | 0 | 1 | 0 |
| 178-180 | 0 | 0 | 0 | 0 | 0 | 0 | 0 | 0 | 0 | 0 | 0 | 0 | 0 |
| 181-183 | 0 | 0 | 0 | 0 | 0 | 0 | 0 | 0 | 0 | 0 | 0 | 0 | 0 |
| 184-186 | 0 | 0 | 0 | 0 | 0 | 0 | 0 | 0 | 0 | 0 | 0 | 0 | 0 |
| 187-189 | 1 | 1 | 0 | 0 | 0 | 0 | 0 | 0 | 0 | 0 | 0 | 0 | 0 |
| 190-192 | 0 | 0 | 1 | 0 | 0 | 0 | 0 | 0 | 0 | 0 | 1 | 0 | 0 |
| 193-195 | 0 | 0 | 0 | 0 | 0 | 0 | 0 | 0 | 0 | 0 | 0 | 0 | 0 |
| 196-198 | 0 | 0 | 0 | 0 | 0 | 0 | 0 | 0 | 0 | 0 | 0 | 0 | 0 |
| 199-201 | 0 | 0 | 0 | 0 | 0 | 0 | 0 | 0 | 0 | 0 | 0 | 0 | 0 |
| 202-204 | 0 | 0 | 0 | 0 | 0 | 0 | 0 | 0 | 0 | 0 | 0 | 0 | 0 |
| 205-207 | 0 | 0 | 0 | 0 | 0 | 0 | 0 | 0 | 0 | 0 | 0 | 0 | 0 |
| 208-210 | 0 | 0 | 0 | 0 | 1 | 0 | 1 | 1 | 0 | 1 | 1 | 1 | 1 |
| 211-213 | 0 | 0 | 0 | 0 | 0 | 0 | 0 | 0 | 0 | 0 | 0 | 0 | 0 |
| 214-216 | 0 | 0 | 0 | 0 | 0 | 0 | 0 | 0 | 0 | 0 | 0 | 0 | 0 |
| 217-219 | 0 | 0 | 0 | 0 | 0 | 0 | 0 | 0 | 0 | 0 | 0 | 0 | 0 |
| 220-222 | 0 | 0 | 0 | 0 | 0 | 0 | 0 | 0 | 0 | 0 | 0 | 0 | 0 |
| 223-225 | 0 | 0 | 0 | 0 | 0 | 0 | 0 | 0 | 0 | 0 | 0 | 0 | 0 |
| 226-228 | 0 | 0 | 0 | 0 | 0 | 0 | 0 | 0 | 0 | 0 | 0 | 0 | 0 |
| 229-231 | 0 | 0 | 0 | 0 | 0 | 0 | 0 | 0 | 0 | 0 | 0 | 0 | 0 |
| 232-234 | 0 | 0 | 0 | 1 | 0 | 0 | 1 | 0 | 1 | 0 | 1 | 0 | 1 |
| 235-237 | 0 | 0 | 0 | 0 | 0 | 0 | 0 | 0 | 0 | 0 | 0 | 0 | 0 |
| 238-240 | 0 | 0 | 0 | 0 | 0 | 0 | 0 | 0 | 0 | 0 | 0 | 0 | 0 |
| 241-243 | 0 | 0 | 0 | 0 | 0 | 0 | 0 | 0 | 0 | 0 | 0 | 0 | 0 |
| 244-246 | 0 | 0 | 0 | 0 | 0 | 0 | 0 | 0 | 0 | 0 | 0 | 0 | 0 |
| 247-249 | 0 | 0 | 0 | 0 | 0 | 0 | 0 | 0 | 0 | 0 | 0 | 0 | 0 |
| 250-252 | 0 | 0 | 0 | 0 | 0 | 0 | 0 | 0 | 0 | 0 | 0 | 0 | 0 |
| 253-255 | 0 | 0 | 0 | 0 | 0 | 0 | 0 | 0 | 0 | 0 | 0 | 0 | 0 |
| 256-258 | 0 | 0 | 0 | 0 | 0 | 0 | 0 | 0 | 0 | 0 | 0 | 0 | 0 |
| 259-261 | 0 | 0 | 0 | 0 | 0 | 0 | 0 | 0 | 0 | 0 | 0 | 0 | 0 |

TABLE 5-continued

| | | | | | | | | | | | | | |
|---|---|---|---|---|---|---|---|---|---|---|---|---|---|
| 262-264 | 0 | 0 | 0 | 0 | 0 | 0 | 0 | 0 | 0 | 0 | 0 | 0 | 0 |
| 265-267 | 0 | 0 | 0 | 0 | 0 | 0 | 0 | 0 | 0 | 0 | 0 | 0 | 0 |
| 268-270 | 0 | 0 | 0 | 0 | 0 | 0 | 0 | 0 | 0 | 0 | 0 | 0 | 0 |
| 271-273 | 0 | 0 | 0 | 0 | 0 | 0 | 0 | 0 | 0 | 0 | 0 | 0 | 0 |
| 274-276 | 0 | 0 | 0 | 0 | 0 | 0 | 0 | 0 | 0 | 0 | 0 | 0 | 0 |
| 277-279 | 0 | 0 | 0 | 0 | 0 | 0 | 0 | 0 | 0 | 0 | 0 | 0 | 0 |
| 280-282 | 0 | 0 | 0 | 0 | 0 | 0 | 0 | 0 | 0 | 0 | 0 | 0 | 0 |
| 283-285 | 0 | 0 | 0 | 0 | 0 | 0 | 0 | 0 | 0 | 0 | 0 | 0 | 0 |
| 286-288 | 0 | 0 | 0 | 0 | 0 | 0 | 0 | 0 | 0 | 0 | 0 | 0 | 0 |
| 289-291 | 0 | 0 | 0 | 0 | 0 | 0 | 0 | 0 | 0 | 0 | 0 | 0 | 0 |
| 292-294 | 0 | 0 | 0 | 0 | 0 | 0 | 0 | 0 | 0 | 0 | 0 | 0 | 0 |
| 295-297 | 0 | 0 | 0 | 0 | 0 | 0 | 0 | 0 | 0 | 0 | 0 | 0 | 0 |
| 298-300 | 0 | 0 | 0 | 0 | 0 | 0 | 1 | 1 | 0 | 0 | 1 | 0 | 0 |
| 301-303 | 0 | 0 | 0 | 0 | 0 | 0 | 0 | 0 | 0 | 0 | 0 | 0 | 0 |
| 304-306 | 0 | 0 | 0 | 1 | 1 | 0 | 0 | 0 | 1 | 0 | 0 | 0 | 0 |
| 307-309 | 0 | 0 | 0 | 0 | 0 | 0 | 0 | 0 | 0 | 0 | 0 | 0 | 0 |
| 310-312 | 0 | 0 | 0 | 0 | 0 | 0 | 0 | 0 | 0 | 0 | 0 | 0 | 0 |
| 313-315 | 0 | 0 | 0 | 0 | 0 | 0 | 0 | 0 | 0 | 0 | 0 | 0 | 0 |
| 316-318 | 0 | 0 | 0 | 0 | 0 | 0 | 0 | 0 | 0 | 0 | 0 | 0 | 0 |
| 319-321 | 0 | 0 | 0 | 0 | 0 | 0 | 0 | 0 | 0 | 0 | 0 | 0 | 0 |
| 322-324 | 0 | 0 | 0 | 0 | 0 | 0 | 0 | 0 | 0 | 0 | 0 | 0 | 0 |
| 325-327 | 0 | 0 | 0 | 0 | 0 | 0 | 0 | 0 | 0 | 0 | 0 | 0 | 0 |
| 328-330 | 0 | 0 | 0 | 0 | 0 | 0 | 0 | 0 | 0 | 0 | 0 | 0 | 0 |
| 331-333 | 0 | 0 | 0 | 0 | 0 | 0 | 0 | 0 | 0 | 0 | 0 | 0 | 0 |
| 334-336 | 0 | 0 | 0 | 0 | 0 | 0 | 0 | 0 | 0 | 0 | 0 | 0 | 0 |
| 337-339 | 0 | 0 | 0 | 0 | 0 | 0 | 0 | 0 | 0 | 0 | 0 | 0 | 0 |
| 340-342 | 0 | 0 | 0 | 0 | 0 | 0 | 0 | 0 | 0 | 0 | 0 | 0 | 0 |
| 343-345 | 1 | 1 | 1 | 1 | 1 | 1 | 1 | 1 | 1 | 1 | 1 | 1 | 1 |
| 346-348 | 0 | 0 | 0 | 0 | 0 | 0 | 0 | 0 | 0 | 0 | 0 | 0 | 0 |
| TEM peptides | 5 | 10 | 7 | 12 | 13 | 1 | 12 | 13 | 12 | 10 | 13 | 9 | 9 |
| 2b peptides | 0 | 0 | 0 | 0 | 0 | 0 | 0 | 0 | 0 | 0 | 0 | 0 | 0 |
| 2br peptides | 1 | 1 | 0 | 0 | 0 | 0 | 0 | 0 | 0 | 0 | 0 | 0 | 0 |
| 2be peptides | 0 | 0 | 0 | 2 | 0 | 0 | 2 | 0 | 2 | 1 | 3 | 2 | 3 |
| 2ber peptides | 0 | 0 | 0 | 0 | 0 | 0 | 0 | 0 | 0 | 0 | 0 | 0 | 0 |

Sample Sam10 does not present any peptide which is characteristic of TEMs. The bacteria present in sample Sam10 may be sensitive to cephalosporins and to penicillins.

Samples Sam11 to Sam61 comprise at least one peptide which is characteristic of TEMs. The bacteria present in samples Sam11 to Sam61 therefore express a beta-lactamase which confers on them a resistance to penicillins.

No peptide specific to phenotype 2b is observed, and no sample tested is identified as being resistant solely to penicillins.

Samples Sam35, Sam49 and Sam50 comprise at least one peptide specific to phenotype 2br. Samples Sam35, Sam49 and Sam50 are therefore resistant to penicillins associated with an inhibitor of the clavulanic acid and tazobactam type.

No peptide specific to phenotype 2ber is observed, and no sample tested is identified as belonging only to this phenotype.

Samples Sam12 to Sam21, Sam23 to Sam27, Sam29, Sam32, Sam33, Sam44, Sam46, Sam52, Sam55 and Sam57 to Sam61 comprise at least one peptide specific to the phenotype 2be or to the phenotype 2ber. Samples Sam12 to Sam21, Sam23 to Sam27, Sam29, Sam32, Sam33, Sam44, Sam46, Sam52, Sam55, and Sam57 to Sam61 are therefore resistant to penicillins, to cephalosporins and to monobactams.

EXAMPLE 7

Identification of a Resistance to CMY Beta-Lactams

The samples corresponding to a species able to comprise a CMY resistance mechanism can be detected by employing the following method.

Each sample is treated according to example 5, then analysed according to example 6 by detecting the peptides from TABLE 6 instead of the peptides from TABLE 3.

TABLE 6

| Transition number | Peptide | Fragment ion | Charge state of the precursor | Retention time | (m/z) filtered in Q1 | (m/z) filtered in Q3 | Collision energy |
|---|---|---|---|---|---|---|---|
| 1 | LSDPVTK | y6 | 2 | 10 | 380.22 | 646.34 | 22 |
| 2 | LSDPVTK | y5 | 2 | 10 | 380.22 | 559.31 | 22 |
| 3 | LSDPVTK | y4 | 2 | 10 | 380.22 | 444.28 | 22 |
| 4 | ADSIINGSDSK | y9 | 2 | 10.2 | 553.77 | 920.47 | 29 |

TABLE 6-continued

| Transition number | Peptide | Fragment ion | Charge state of the precursor | Retention time | (m/z) filtered in Q1 | (m/z) filtered in Q3 | Collision energy |
|---|---|---|---|---|---|---|---|
| 5 | ADSIINGSDSK | y8 | 2 | 10.2 | 553.77 | 833.44 | 29 |
| 6 | ADSIINGSDSK | y7 | 2 | 10.2 | 553.77 | 720.35 | 29 |
| 7 | ASWVHK | y5 | 2 | 11.6 | 364.2 | 656.35 | 21 |
| 8 | ASWVHK | y4 | 2 | 11.6 | 364.2 | 569.32 | 21 |
| 9 | ASWVHK | y3 | 2 | 11.6 | 364.2 | 383.24 | 21 |
| 10 | SYPNPVR | y6 | 2 | 11.6 | 416.72 | 745.4 | 23 |
| 11 | SYPNPVR | y5 | 2 | 11.6 | 416.72 | 582.34 | 23 |
| 12 | SYPNPVR | y4 | 2 | 11.6 | 416.72 | 485.28 | 23 |
| 13 | VEAAWR | y5 | 2 | 12.3 | 366.2 | 632.32 | 21 |
| 14 | VEAAWR | y4 | 2 | 12.3 | 366.2 | 503.27 | 21 |
| 15 | VEAAWR | y3 | 2 | 12.3 | 366.2 | 432.24 | 21 |
| 16 | QWQGIR | y5 | 2 | 13.8 | 394.21 | 659.36 | 22 |
| 17 | QWQGIR | y4 | 2 | 13.8 | 394.21 | 473.28 | 22 |
| 18 | QWQGIR | y3 | 2 | 13.8 | 394.21 | 345.22 | 22 |
| 19 | VLQPLK | y5 | 2 | 14 | 349.23 | 598.39 | 20 |
| 20 | VLQPLK | y4 | 2 | 14 | 349.23 | 485.31 | 20 |
| 21 | VLQPLK | y3 | 2 | 14 | 349.23 | 357.25 | 20 |
| 22 | SSVIDMAR | y7 | 2 | 14.2 | 439.72 | 791.41 | 24 |
| 23 | SSVIDMAR | y6 | 2 | 14.2 | 439.72 | 704.38 | 24 |
| 24 | SSVIDMAR | y5 | 2 | 14.2 | 439.72 | 605.31 | 24 |
| 25 | WVQANMDASHVQEK | y9 | 2 | 14.4 | 821.89 | 1044.48 | 41 |
| 26 | WVQANMDASHVQEK | y8 | 2 | 14.4 | 821.89 | 913.44 | 41 |
| 27 | WVQANMDASHVQEK | y7 | 2 | 14.4 | 821.89 | 798.41 | 41 |
| 28 | TLQQGIALAQSR | y9 | 2 | 15.2 | 643.36 | 943.53 | 33 |
| 29 | TLQQGIALAQSR | y8 | 2 | 15.2 | 643.36 | 815.47 | 33 |
| 30 | TLQQGIALAQSR | y7 | 2 | 15.2 | 643.36 | 758.45 | 33 |
| 31 | TEQQIADIVNR | y9 | 2 | 15.6 | 643.84 | 1056.58 | 33 |
| 32 | TEQQIADIVNR | y8 | 2 | 15.6 | 643.84 | 928.52 | 33 |
| 33 | TEQQIADIVNR | y7 | 2 | 15.6 | 643.84 | 800.46 | 33 |
| 34 | LAHTWITVPQNEQK | y9 | 2 | 16 | 832.94 | 1056.57 | 42 |
| 35 | LAHTWITVPQNEQK | y8 | 2 | 16 | 832.94 | 943.48 | 42 |
| 36 | LAHTWITVPQNEQK | y7 | 2 | 16 | 832.94 | 842.44 | 42 |
| 37 | DYAWGYR | y6 | 2 | 16.4 | 465.71 | 815.38 | 25 |
| 38 | DYAWGYR | y5 | 2 | 16.4 | 465.71 | 652.32 | 25 |
| 39 | DYAWGYR | y4 | 2 | 16.4 | 465.71 | 581.28 | 25 |
| 40 | YWPELTGK | y7 | 2 | 17.4 | 497.26 | 830.44 | 27 |
| 41 | YWPELTGK | y6 | 2 | 17.4 | 497.26 | 644.36 | 27 |
| 42 | YWPELTGK | y5 | 2 | 17.4 | 497.26 | 547.31 | 27 |

TABLE 6-continued

| Transition number | Peptide | Fragment ion | Charge state of the precursor | Retention time | (m/z) filtered in Q1 | (m/z) filtered in Q3 | Collision energy |
|---|---|---|---|---|---|---|---|
| 43 | TFNGVLGGDAIAR | y9 | 2 | 17.6 | 645.84 | 871.5 | 33 |
| 44 | TFNGVLGGDAIAR | y8 | 2 | 17.6 | 645.84 | 772.43 | 33 |
| 45 | TFNGVLGGDAIAR | y7 | 2 | 17.6 | 645.84 | 659.35 | 33 |
| 46 | NLGIVMLANK | y9 | 2 | 19.1 | 536.81 | 958.58 | 29 |
| 47 | NLGIVMLANK | y8 | 2 | 19.1 | 536.81 | 845.49 | 29 |
| 48 | NLGIVMLANK | y7 | 2 | 19.1 | 536.81 | 788.47 | 29 |
| 49 | TGSTGGFGSYVAFVPEK | y9 | 2 | 19.5 | 852.42 | 1039.55 | 43 |
| 50 | TGSTGGFGSYVAFVPEK | y8 | 2 | 19.5 | 852.42 | 952.51 | 43 |
| 51 | TGSTGGFGSYVAFVPEK | y7 | 2 | 19.5 | 852.42 | 789.45 | 43 |
| 52 | ADIANNHPVTQQTLFELGSVSK | y9 | 3 | 20 | 790.41 | 979.55 | 44 |
| 53 | ADIANNHPVTQQTLFELGSVSK | y8 | 3 | 20 | 790.41 | 866.46 | 44 |
| 54 | ADIANNHPVTQQTLFELGSVSK | y7 | 3 | 20 | 790.41 | 719.39 | 44 |
| 55 | VALAALPAVEVNPPAPAVK | y9 | 2 | 20.4 | 914.04 | 892.53 | 45 |
| 56 | VALAALPAVEVNPPAPAVK | y8 | 2 | 20.4 | 914.04 | 793.46 | 45 |
| 57 | VALAALPAVEVNPPAPAVK | y7 | 2 | 20.4 | 914.04 | 679.41 | 45 |
| 58 | LLHLATYTAGGLPLQIPDDVR | y9 | 3 | 22.4 | 755.09 | 1052.57 | 42 |
| 59 | LLHLATYTAGGLPLQIPDDVR | y8 | 3 | 22.4 | 755.09 | 955.52 | 42 |
| 60 | LLHLATYTAGGLPLQIPDDVR | y7 | 3 | 22.4 | 755.09 | 842.44 | 42 |
| 61 | TITPLMQEQAIPGMAVAVIYQGK | y9 | 3 | 22.5 | 820.44 | 948.55 | 45 |
| 62 | TITPLMQEQAIPGMAVAVIYQGK | y8 | 3 | 22.5 | 820.44 | 877.51 | 45 |
| 63 | TITPLMQEQAIPGMAVAVIYQGK | y7 | 3 | 22.5 | 820.44 | 778.45 | 45 |
| 64 | AALLHFYQNWQPQWTPGAK | y9 | 3 | 23.2 | 752.72 | 1012.52 | 42 |
| 65 | AALLHFYQNWQPQWTPGAK | y8 | 3 | 23.2 | 752.72 | 884.46 | 42 |
| 66 | AALLHFYQNWQPQWTPGAK | y7 | 3 | 23.2 | 752.72 | 787.41 | 42 |
| 67 | LYANSSIGLFGALAVK | y9 | 2 | 25.1 | 812.46 | 875.53 | 41 |
| 68 | LYANSSIGLFGALAVK | y8 | 2 | 25.1 | 812.46 | 818.51 | 41 |
| 69 | LYANSSIGLFGALAVK | y7 | 2 | 25.1 | 812.46 | 705.43 | 41 |
| 70 | SLCCALLLTASFSTFAAAK | y9 | 3 | 25.4 | 678.01 | 929.47 | 38 |
| 71 | SLCCALLLTASFSTFAAAK | y8 | 3 | 25.4 | 678.01 | 842.44 | 38 |
| 72 | SLCCALLLTASFSTFAAAK | y7 | 3 | 25.4 | 678.01 | 695.37 | 38 |
| 73 | IGDMYQGLGWEMLNWPLK | y9 | 3 | 28.5 | 717.68 | 1216.62 | 40 |
| 74 | IGDMYQGLGWEMLNWPLK | y8 | 3 | 28.5 | 717.68 | 1030.54 | 40 |
| 75 | IGDMYQGLGWEMLNWPLK | y7 | 3 | 28.5 | 717.68 | 901.5 | 40 |
| 76 | AHYFNYGVANR | y7 | 2 | 15.5 | 656.32 | 793.4 | 34 |
| 77 | AHYFNYGVANR | y8 | 2 | 15.5 | 656.32 | 940.46 | 34 |
| 78 | AHYFNYGVANR | y9 | 2 | 15.5 | 656.32 | 1103.53 | 34 |
| 79 | ANIGGVDDK | y5 | 2 | 9.6 | 444.72 | 533.26 | 25 |
| 80 | ANIGGVDDK | y6 | 2 | 9.6 | 444.72 | 590.28 | 25 |

TABLE 6-continued

| Transition number | Peptide | Fragment ion | Charge state of the precursor | Retention time | (m/z) filtered in Q1 | (m/z) filtered in Q3 | Collision energy |
|---|---|---|---|---|---|---|---|
| 81 | ANIGGVDDK | y7 | 2 | 9.6 | 444.72 | 703.36 | 25 |
| 82 | ESGSQVLFNK | y6 | 2 | 15.1 | 554.79 | 748.44 | 29 |
| 83 | ESGSQVLFNK | y7 | 2 | 15.1 | 554.79 | 835.47 | 29 |
| 84 | ESGSQVLFNK | y8 | 2 | 15.1 | 554.79 | 892.49 | 29 |
| 85 | GAMQLDDK | y5 | 2 | 11.5 | 439.21 | 618.31 | 24 |
| 86 | GAMQLDDK | y6 | 2 | 11.5 | 439.21 | 749.35 | 24 |
| 87 | GAMQLDDK | y7 | 2 | 11.5 | 439.21 | 820.39 | 24 |
| 88 | GIGIVMLANR | y6 | 2 | 18.7 | 522.31 | 703.39 | 28 |
| 89 | GIGIVMLANR | y7 | 2 | 18.7 | 522.31 | 816.48 | 28 |
| 90 | GIGIVMLANR | y8 | 2 | 18.7 | 522.31 | 873.5 | 28 |
| 91 | HAPWLK | y4 | 2 | 15 | 376.22 | 543.33 | 22 |
| 92 | HAPWLK | y5 | 2 | 15 | 376.22 | 614.37 | 22 |
| 93 | HAPWLK | b5 | 2 | 15 | 376.22 | 605.32 | 22 |
| 94 | IPGMAVAVLK | y6 | 2 | 18.1 | 499.81 | 600.41 | 27 |
| 95 | IPGMAVAVLK | y7 | 2 | 18.1 | 499.81 | 731.45 | 27 |
| 96 | IPGMAVAVLK | y8 | 2 | 18.1 | 499.81 | 788.47 | 27 |
| 97 | PVVDASIQPLLK | y7 | 2 | 19.3 | 640.38 | 798.51 | 33 |
| 98 | PVVDASIQPLLK | y8 | 2 | 19.3 | 640.38 | 869.55 | 33 |
| 99 | PVVDASIQPLLK | y9 | 2 | 19.3 | 640.38 | 984.57 | 33 |
| 100 | QAMASYAYGYSK | y7 | 2 | 15.5 | 670.3 | 851.39 | 34 |
| 101 | QAMASYAYGYSK | y8 | 2 | 15.5 | 670.3 | 938.43 | 34 |
| 102 | QAMASYAYGYSK | y9 | 2 | 15.5 | 670.3 | 1009.46 | 34 |
| 103 | QWAPVYSPGSHR | y8 | 2 | 14.8 | 692.84 | 902.45 | 35 |
| 104 | QWAPVYSPGSHR | y9 | 2 | 14.8 | 692.84 | 999.5 | 35 |
| 105 | QWAPVYSPGSHR | y10 | 2 | 14.8 | 692.84 | 1070.54 | 35 |
| 106 | QYSNPSIGLFGHLAASSLK | y11 | 2 | 22 | 995.52 | 1143.65 | 49 |
| 107 | QYSNPSIGLFGHLAASSLK | y12 | 2 | 22 | 995.52 | 1200.67 | 49 |
| 108 | QYSNPSIGLFGHLAASSLK | y11 | 2 | 22 | 664.02 | 1143.65 | 37 |
| 109 | TGSTNGFGAYVAFVPAR | y9 | 2 | 19.4 | 857.93 | 993.55 | 43 |
| 110 | TGSTNGFGAYVAFVPAR | y10 | 2 | 19.4 | 857.93 | 1050.57 | 43 |
| 111 | TGSTNGFGAYVAFVPAR | y11 | 2 | 19.4 | 857.93 | 1197.64 | 43 |
| 112 | TLTATLGAYAVVK | y8 | 2 | 18.3 | 654.38 | 820.49 | 34 |
| 113 | TLTATLGAYAVVK | y9 | 2 | 18.3 | 654.38 | 921.54 | 34 |
| 114 | TLTATLGAYAVVK | y10 | 2 | 18.3 | 654.38 | 992.58 | 34 |
| 115 | VNPGMLADEAYGIK | y8 | 2 | 18.8 | 739.37 | 866.43 | 38 |
| 116 | VNPGMLADEAYGIK | y9 | 2 | 18.8 | 739.37 | 979.51 | 38 |
| 117 | VNPGMLADEAYGIK | y10 | 2 | 18.8 | 739.37 | 1110.55 | 38 |
| 118 | PSGMSYEEAMTR | y10 | 2 | 15.5 | 679.79 | 1174.49 | 35 |

TABLE 6-continued

| Transition number | Peptide | Fragment ion | Charge state of the precursor | Retention time | (m/z) filtered in Q1 | (m/z) filtered in Q3 | Collision energy |
|---|---|---|---|---|---|---|---|
| 119 | PSGMSYEEAMTR | y9 | 2 | 15.5 | 679.79 | 1117.47 | 35 |
| 120 | PSGMSYEEAMTR | y8 | 2 | 15.5 | 679.79 | 986.42 | 35 |
| 121 | PYYFTWGK | y7 | 2 | 20.3 | 531.26 | 964.46 | 29 |
| 122 | PYYFTWGK | y6 | 2 | 20.3 | 531.26 | 801.39 | 29 |
| 123 | PYYFTWGK | y5 | 2 | 20.3 | 531.26 | 638.33 | 29 |

The areas obtained for each of the transitions and for each of the microorganisms studied were measured. When the areas of the 3 transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 8

Identification of a Resistance to CTX-M Beta-Lactams

The samples corresponding to a species able to comprise a CTX-M resistance mechanism can be detected by employing the following method.

Each sample is treated according to example 5, then analysed according to example 6 by detecting the peptides from TABLE 7 instead of the peptides from TABLE 3.

TABLE 7

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 1 | AGLPK | 2 | y4 | 9.5 | 243.16 | 414.27 | 16 |
| 2 | AGLPK | 2 | y3 | 9.5 | 243.16 | 357.25 | 16 |
| 3 | AGLPK | 2 | y2 | 9.5 | 243.16 | 244.17 | 16 |
| 4 | AGLPTSWTVGDK | 2 | y9 | 16.6 | 616.32 | 990.49 | 32 |
| 5 | AGLPTSWTVGDK | 2 | y8 | 16.6 | 616.32 | 893.44 | 32 |
| 6 | AGLPTSWTVGDK | 2 | y7 | 16.6 | 616.32 | 792.39 | 32 |
| 7 | AIGDETFR | 2 | y7 | 14 | 454.73 | 837.41 | 25 |
| 8 | AIGDETFR | 2 | y6 | 14 | 454.73 | 724.33 | 25 |
| 9 | AIGDETFR | 2 | y5 | 14 | 454.73 | 667.3 | 25 |
| 10 | ALAETQR | 2 | y6 | 7.4 | 394.72 | 717.39 | 22 |
| 11 | ALAETQR | 2 | y5 | 7.4 | 394.72 | 604.3 | 22 |
| 12 | ALAETQR | 2 | y4 | 7.4 | 394.72 | 533.27 | 22 |
| 13 | ALGDSQR | 2 | y6 | 7 | 373.69 | 675.34 | 21 |
| 14 | ALGDSQR | 2 | y5 | 7 | 373.69 | 562.26 | 21 |
| 15 | ALGDSQR | 2 | y4 | 7 | 373.69 | 505.24 | 21 |
| 16 | AMAQTLR | 2 | y6 | 12.1 | 395.72 | 719.39 | 22 |
| 17 | AMAQTLR | 2 | y5 | 12.1 | 395.72 | 588.35 | 22 |

TABLE 7-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 18 | AMAQTLR | 2 | y4 | 12.1 | 395.72 | 517.31 | 22 |
| 19 | APLILVTYFTQPQPK | 2 | y9 | 22.4 | 858.49 | 1109.6 | 43 |
| 20 | APLILVTYFTQPQPK | 2 | y8 | 22.4 | 858.49 | 1008.5 | 43 |
| 21 | APLILVTYFTQPQPK | 2 | y7 | 22.4 | 858.49 | 845.45 | 43 |
| 22 | APLVLVTYFTQPQQNAESR | 3 | y9 | 21.4 | 721.38 | 1057.5 | 40 |
| 23 | APLVLVTYFTQPQQNAESR | 3 | y8 | 21.4 | 721.38 | 929.44 | 40 |
| 24 | APLVLVTYFTQPQQNAESR | 3 | y7 | 21.4 | 721.38 | 832.39 | 40 |
| 25 | AQLVTWLK | 2 | y7 | 21 | 479.79 | 887.53 | 26 |
| 26 | AQLVTWLK | 2 | y6 | 21 | 479.79 | 759.48 | 26 |
| 27 | AQLVTWLK | 2 | y5 | 21 | 479.79 | 646.39 | 26 |
| 28 | AQLVTWMK | 2 | y7 | 19 | 488.77 | 905.49 | 27 |
| 29 | AQLVTWMK | 2 | y6 | 19 | 488.77 | 777.43 | 27 |
| 30 | AQLVTWMK | 2 | y5 | 19 | 488.77 | 664.35 | 27 |
| 31 | DILAAAAK | 2 | y7 | 12.1 | 386.73 | 657.43 | 22 |
| 32 | DILAAAAK | 2 | y6 | 12.1 | 386.73 | 544.35 | 22 |
| 33 | DILAAAAK | 2 | y5 | 12.1 | 386.73 | 431.26 | 22 |
| 34 | DTTSPR | 2 | y5 | 4.6 | 338.67 | 561.3 | 20 |
| 35 | DTTSPR | 2 | y4 | 4.6 | 338.67 | 460.25 | 20 |
| 36 | DTTSPR | 2 | y3 | 4.6 | 338.67 | 359.2 | 20 |
| 37 | DTTTPLAMAQTLK | 2 | y9 | 17 | 695.87 | 972.55 | 36 |
| 38 | DTTTPLAMAQTLK | 2 | y8 | 17 | 695.87 | 875.5 | 36 |
| 39 | DTTTPLAMAQTLK | 2 | y7 | 17 | 695.87 | 762.42 | 36 |
| 40 | DTTTPR | 2 | y5 | 4.8 | 345.67 | 575.31 | 20 |
| 41 | DTTTPR | 2 | y4 | 4.8 | 345.67 | 474.27 | 20 |
| 42 | DTTTPR | 2 | y3 | 4.8 | 345.67 | 373.22 | 20 |
| 43 | DVLAAAAK | 2 | y7 | 10.5 | 379.72 | 643.41 | 22 |
| 44 | DVLAAAAK | 2 | y6 | 10.5 | 379.72 | 544.35 | 22 |
| 45 | DVLAAAAK | 2 | y5 | 10.5 | 379.72 | 431.26 | 22 |
| 46 | DVLASAAK | 2 | y7 | 10.8 | 387.72 | 659.41 | 22 |
| 47 | DVLASAAK | 2 | y6 | 10.8 | 387.72 | 560.34 | 22 |
| 48 | DVLASAAK | 2 | y5 | 10.8 | 387.72 | 447.26 | 22 |
| 49 | DVLASAAR | 2 | y7 | 11.4 | 401.72 | 687.41 | 23 |
| 50 | DVLASAAR | 2 | y6 | 11.4 | 401.72 | 588.35 | 23 |
| 51 | DVLASAAR | 2 | y5 | 11.4 | 401.72 | 475.26 | 23 |
| 52 | FAMCSTSK | 2 | y7 | 11.1 | 466.2 | 784.33 | 26 |
| 53 | FAMCSTSK | 2 | y6 | 11.1 | 466.2 | 713.3 | 26 |
| 54 | FAMCSTSK | 2 | y5 | 11.1 | 466.2 | 582.26 | 26 |

TABLE 7-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 55 | FPMCSTSK | 2 | y7 | 12.1 | 479.21 | 810.35 | 26 |
| 56 | FPMCSTSK | 2 | y6 | 12.1 | 479.21 | 713.3 | 26 |
| 57 | FPMCSTSK | 2 | y5 | 12.1 | 479.21 | 582.26 | 26 |
| 58 | GNTTGAASIQAGLPASWVVGDK | 3 | y9 | 19.5 | 700.7 | 958.5 | 39 |
| 59 | GNTTGAASIQAGLPASWVVGDK | 3 | y8 | 19.5 | 700.7 | 861.45 | 39 |
| 60 | GNTTGAASIQAGLPASWVVGDK | 3 | y7 | 19.5 | 700.7 | 790.41 | 39 |
| 61 | GNTTGAASIQAGLPTSWVVGDK | 3 | y9 | 19.3 | 710.7 | 988.51 | 40 |
| 62 | GNTTGAASIQAGLPTSWVVGDK | 3 | y8 | 19.3 | 710.7 | 891.46 | 40 |
| 63 | GNTTGAASIQAGLPTSWVVGDK | 3 | y7 | 19.3 | 710.7 | 790.41 | 40 |
| 64 | GNTTGAASIR | 2 | y9 | 9 | 474.25 | 890.47 | 26 |
| 65 | GNTTGAASIR | 2 | y8 | 9 | 474.25 | 776.43 | 26 |
| 66 | GNTTGAASIR | 2 | y7 | 9 | 474.25 | 675.38 | 26 |
| 67 | GNTTGSASIR | 2 | y9 | 8.5 | 482.25 | 906.46 | 26 |
| 68 | GNTTGSASIR | 2 | y8 | 8.5 | 482.25 | 792.42 | 26 |
| 69 | GNTTGSASIR | 2 | y7 | 8.5 | 482.25 | 691.37 | 26 |
| 70 | HLLNQR | 2 | y5 | 10.2 | 390.73 | 643.39 | 22 |
| 71 | HLLNQR | 2 | y4 | 10.2 | 390.73 | 530.3 | 22 |
| 72 | HLLNQR | 2 | y3 | 10.2 | 390.73 | 417.22 | 22 |
| 73 | LAALEK | 2 | y5 | 11 | 322.7 | 531.31 | 19 |
| 74 | LAALEK | 2 | y4 | 11 | 322.7 | 460.28 | 19 |
| 75 | LAALEK | 2 | y3 | 11 | 322.7 | 389.24 | 19 |
| 76 | LAELER | 2 | y5 | 12.1 | 365.71 | 617.33 | 21 |
| 77 | LAELER | 2 | y4 | 12.1 | 365.71 | 546.29 | 21 |
| 78 | LAELER | 2 | y3 | 12.1 | 365.71 | 417.25 | 21 |
| 79 | LGVALIDTADNTQVLYR | 2 | y9 | 21.4 | 931.5 | 1079.6 | 46 |
| 80 | LGVALIDTADNTQVLYR | 2 | y8 | 21.4 | 931.5 | 1008.5 | 46 |
| 81 | LGVALIDTADNTQVLYR | 2 | y7 | 21.4 | 931.5 | 893.48 | 46 |
| 82 | LGVALINTADNSQILYR | 2 | y9 | 21.1 | 931.01 | 1079.6 | 46 |
| 83 | LGVALINTADNSQILYR | 2 | y8 | 21.1 | 931.01 | 1008.5 | 46 |
| 84 | LGVALINTADNSQILYR | 2 | y7 | 21.1 | 931.01 | 893.48 | 46 |
| 85 | LIAHLGGPDK | 2 | y9 | 12.7 | 510.8 | 907.5 | 27 |
| 86 | LIAHLGGPDK | 2 | y8 | 12.7 | 510.8 | 794.42 | 27 |
| 87 | LIAHLGGPDK | 2 | y7 | 12.7 | 510.8 | 723.38 | 27 |
| 88 | LIAHVGGPASVTAFAR | 2 | y9 | 17.5 | 783.94 | 919.5 | 39 |
| 89 | LIAHVGGPASVTAFAR | 2 | y8 | 17.5 | 783.94 | 822.45 | 39 |
| 90 | LIAHVGGPASVTAFAR | 2 | y7 | 17.5 | 783.94 | 751.41 | 39 |
| 91 | LIAQLGGPGGVTAFAR | 2 | y9 | 19.3 | 764.44 | 875.47 | 39 |
| 92 | LIAQLGGPGGVTAFAR | 2 | y8 | 19.3 | 764.44 | 778.42 | 39 |

TABLE 7-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 93 | LIAQLGGPGGVTAFAR | 2 | y7 | 19.3 | 764.44 | 721.4 | 39 |
| 94 | NLTLGK | 2 | y5 | 12.2 | 323.2 | 531.35 | 19 |
| 95 | NLTLGK | 2 | y4 | 12.2 | 323.2 | 418.27 | 19 |
| 96 | NLTLGK | 2 | y3 | 12.2 | 323.2 | 317.22 | 19 |
| 97 | QLGDETFR | 2 | y7 | 14.4 | 483.24 | 837.41 | 26 |
| 98 | QLGDETFR | 2 | y6 | 14.4 | 483.24 | 724.33 | 26 |
| 99 | QLGDETFR | 2 | y5 | 14.4 | 483.24 | 667.3 | 26 |
| 100 | QLLNQPVEIK | 2 | y9 | 16.2 | 591.35 | 1053.6 | 31 |
| 101 | QLLNQPVEIK | 2 | y8 | 16.2 | 591.35 | 940.55 | 31 |
| 102 | QLLNQPVEIK | 2 | y7 | 16.2 | 591.35 | 827.46 | 31 |
| 103 | QLTLGHALGETQR | 2 | y9 | 14.9 | 712.39 | 968.49 | 36 |
| 104 | QLTLGHALGETQR | 2 | y8 | 14.9 | 712.39 | 911.47 | 36 |
| 105 | QLTLGHALGETQR | 2 | y7 | 14.9 | 712.39 | 774.41 | 36 |
| 106 | QSESDK | 2 | y5 | 1.7 | 347.16 | 565.25 | 20 |
| 107 | QSESDK | 2 | y4 | 1.7 | 347.16 | 478.21 | 20 |
| 108 | QSESDK | 2 | y3 | 1.7 | 347.16 | 349.17 | 20 |
| 109 | QSETQK | 2 | y5 | 3.7 | 360.68 | 592.29 | 21 |
| 110 | QSETQK | 2 | y4 | 3.7 | 360.68 | 505.26 | 21 |
| 111 | QSETQK | 2 | y3 | 3.7 | 360.68 | 376.22 | 21 |
| 112 | QSGGR | 2 | y4 | 5.5 | 252.63 | 376.19 | 16 |
| 113 | QSGGR | 2 | y3 | 5.5 | 252.63 | 289.16 | 16 |
| 114 | QSGGR | 2 | b4 | 5.5 | 252.63 | 330.14 | 16 |
| 115 | SDLVNYNPIAEK | 2 | y9 | 17.1 | 681.85 | 1047.6 | 35 |
| 116 | SDLVNYNPIAEK | 2 | y8 | 17.1 | 681.85 | 948.48 | 35 |
| 117 | SDLVNYNPIAEK | 2 | y7 | 17.1 | 681.85 | 834.44 | 35 |
| 118 | SESEPNLLNQR | 2 | y9 | 13.3 | 643.82 | 1070.6 | 33 |
| 119 | SESEPNLLNQR | 2 | y8 | 13.3 | 643.82 | 983.53 | 33 |
| 120 | SESEPNLLNQR | 2 | y7 | 13.3 | 643.82 | 854.48 | 33 |
| 121 | SLGDETFR | 2 | y7 | 14.6 | 462.72 | 837.41 | 25 |
| 122 | SLGDETFR | 2 | y6 | 14.6 | 462.72 | 724.33 | 25 |
| 123 | SLGDETFR | 2 | y5 | 14.6 | 462.72 | 667.3 | 25 |
| 124 | SSGGR | 2 | y4 | 5.9 | 232.12 | 376.19 | 15 |
| 125 | SSGGR | 2 | y3 | 5.9 | 232.12 | 289.16 | 15 |
| 126 | SWVVGDK | 2 | y6 | 14.2 | 395.71 | 703.38 | 22 |
| 127 | SWVVGDK | 2 | y5 | 14.2 | 395.71 | 517.3 | 22 |
| 128 | SVVVGDK | 2 | y4 | 14.2 | 395.71 | 418.23 | 22 |
| 129 | TEPTLNTAIPGDPR | 2 | y9 | 15.6 | 741.38 | 940.48 | 38 |

TABLE 7-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 130 | TEPTLNTAIPGDPR | 2 | y8 | 15.6 | 741.38 | 826.44 | 38 |
| 131 | TEPTLNTAIPGDPR | 2 | y7 | 15.6 | 741.38 | 725.39 | 38 |
| 132 | TGSGDYGTTNDIAVIWPK | 2 | y8 | 19.9 | 947.96 | 941.55 | 47 |
| 133 | TGSGDYGTTNDIAVIWPK | 2 | y7 | 19.9 | 947.96 | 826.52 | 47 |
| 134 | TGSGDYGTTNDIAVIWPK | 2 | y6 | 19.9 | 947.96 | 713.43 | 47 |
| 135 | TGSGDYGTTNDIAVIWPQGR | 3 | y9 | 19.7 | 703.34 | 1039.6 | 39 |
| 136 | TGSGDYGTTNDIAVIWPQGR | 3 | y8 | 19.7 | 703.34 | 926.52 | 39 |
| 137 | TGSGDYGTTNDIAVIWPQGR | 3 | y7 | 19.7 | 703.34 | 855.48 | 39 |
| 138 | TGSGGYGTTNDIAVIWPK | 2 | y9 | 19.5 | 918.96 | 1055.6 | 45 |
| 139 | TGSGGYGTTNDIAVIWPK | 2 | y8 | 19.5 | 918.96 | 941.55 | 45 |
| 140 | TGSGGYGTTNDIAVIWPK | 2 | y7 | 19.5 | 918.96 | 826.52 | 45 |
| 141 | VMAAAAVLK | 2 | y8 | 15.3 | 437.26 | 774.45 | 24 |
| 142 | VMAAAAVLK | 2 | y7 | 15.3 | 437.26 | 643.41 | 24 |
| 143 | VMAAAAVLK | 2 | y6 | 15.3 | 437.26 | 572.38 | 24 |
| 144 | VMAVAAVLK | 2 | y8 | 16.3 | 451.28 | 802.49 | 25 |
| 145 | VMAVAAVLK | 2 | y7 | 16.3 | 451.28 | 671.45 | 25 |
| 146 | VMAVAAVLK | 2 | y6 | 16.3 | 451.28 | 600.41 | 25 |
| 147 | VTAFAR | 2 | y5 | 11.6 | 332.69 | 565.31 | 20 |
| 148 | VTAFAR | 2 | y4 | 11.6 | 332.69 | 464.26 | 20 |
| 149 | VTAFAR | 2 | y3 | 11.6 | 332.69 | 393.22 | 20 |

The areas obtained for each of the transitions and for each of the microorganisms studied were measured. When the areas of the 3 transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 9

Identification of a Resistance to SHV Beta-Lactams

The samples corresponding to a species able to comprise an SHV resistance mechanism can be detected by employing the following method.

Each sample is treated according to example 5, then analysed according to example 6 by detecting the peptides from TABLE 8 instead of the peptides from TABLE 3.

TABLE 8

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 1 | AGAGER | 2 | y5 | 5 | 280.64 | 489.24 | 17 |
| 2 | AGAGER | 2 | y4 | 5 | 280.64 | 432.22 | 17 |

TABLE 8-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 3 | AGAGER | 2 | y3 | 5 | 280.64 | 361.18 | 17 |
| 4 | ATTTPASMAATLR | 2 | y9 | 15.1 | 646.34 | 917.49 | 33 |
| 5 | ATTTPASMAATLR | 2 | y8 | 15.1 | 646.34 | 820.43 | 33 |
| 6 | ATTTPASMAATLR | 2 | y7 | 15.1 | 646.34 | 749.4 | 33 |
| 7 | CIISLLATLPLAVHASPQPLEQIK | 3 | y9 | 27.3 | 871.5 | 1039.6 | 48 |
| 8 | CIISLLATLPLAVHASPQPLEQIK | 3 | y8 | 27.3 | 871.5 | 952.55 | 48 |
| 9 | CIISLLATLPLAVHASPQPLEQIK | 3 | y7 | 27.3 | 871.5 | 855.49 | 48 |
| 10 | DMPASMAER | 2 | y8 | 12 | 504.22 | 892.4 | 27 |
| 11 | DMPASMAER | 2 | y7 | 12 | 504.22 | 761.36 | 27 |
| 12 | DMPASMAER | 2 | y6 | 12 | 504.22 | 664.31 | 27 |
| 13 | DSPASMAER | 2 | y8 | 8.8 | 482.21 | 848.39 | 26 |
| 14 | DSPASMAER | 2 | y7 | 8.8 | 482.21 | 761.36 | 26 |
| 15 | DSPASMAER | 2 | y6 | 8.8 | 482.21 | 664.31 | 26 |
| 16 | DTLASMAER | 2 | y8 | 13.3 | 497.24 | 878.44 | 27 |
| 17 | DTLASMAER | 2 | y7 | 13.3 | 497.24 | 777.39 | 27 |
| 18 | DTLASMAER | 2 | y6 | 13.3 | 497.24 | 664.31 | 27 |
| 19 | DTPASMAER | 2 | y8 | 9.2 | 489.22 | 862.41 | 27 |
| 20 | DTPASMAER | 2 | y7 | 9.2 | 489.22 | 761.36 | 27 |
| 21 | DTPASMAER | 2 | y6 | 9.2 | 489.22 | 664.31 | 27 |
| 22 | DTPASMAK | 2 | y7 | 8.5 | 410.7 | 705.36 | 23 |
| 23 | DTPASMAK | 2 | y6 | 8.5 | 410.7 | 604.31 | 23 |
| 24 | DTPASMAK | 2 | y5 | 8.5 | 410.7 | 507.26 | 23 |
| 25 | DTTTPASMAATLR | 2 | y9 | 15.2 | 668.33 | 917.49 | 34 |
| 26 | DTTTPASMAATLR | 2 | y8 | 15.2 | 668.33 | 820.43 | 34 |
| 27 | DTTTPASMAATLR | 2 | y7 | 15.2 | 668.33 | 749.4 | 34 |
| 28 | DTTTPASMAGTLR | 2 | y9 | 15.1 | 661.32 | 903.47 | 34 |
| 29 | DTTTPASMAGTLR | 2 | y8 | 15.1 | 661.32 | 806.42 | 34 |
| 30 | DTTTPASMAGTLR | 2 | y7 | 15.1 | 661.32 | 735.38 | 34 |
| 31 | DTTTPASMTATLR | 2 | y9 | 14.9 | 683.34 | 947.5 | 35 |
| 32 | DTTTPASMTATLR | 2 | y8 | 14.9 | 683.34 | 850.45 | 35 |
| 33 | DTTTPASMTATLR | 2 | y7 | 14.9 | 683.34 | 779.41 | 35 |
| 34 | FPMISTFK | 2 | y7 | 19.7 | 485.76 | 823.44 | 26 |
| 35 | FPMISTFK | 2 | y6 | 19.7 | 485.76 | 726.39 | 26 |
| 36 | FPMISTFK | 2 | y5 | 19.7 | 485.76 | 595.34 | 26 |
| 38 | FPMMSTFK | 2 | y6 | 19.3 | 494.74 | 744.34 | 27 |
| 39 | FPMMSTFK | 2 | y5 | 19.3 | 494.74 | 613.3 | 27 |
| 40 | GIVALLGGNIK | 2 | y9 | 18.4 | 527.83 | 884.56 | 28 |
| 41 | GIVALLGGNIK | 2 | y8 | 18.4 | 527.83 | 785.49 | 28 |

TABLE 8-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 42 | GIVALLGGNIK | 2 | y7 | 18.4 | 527.83 | 714.45 | 28 |
| 43 | GIVALLGPDNK | 2 | y8 | 16.9 | 548.82 | 827.46 | 29 |
| 44 | GIVALLGPDNK | 2 | y7 | 16.9 | 548.82 | 756.43 | 29 |
| 45 | GIVALLGPDNK | 2 | y6 | 16.9 | 548.82 | 643.34 | 29 |
| 46 | GIVALLGPNHK | 2 | y9 | 16.3 | 559.84 | 948.56 | 30 |
| 47 | GIVALLGPNHK | 2 | y8 | 16.3 | 559.84 | 849.49 | 30 |
| 48 | GIVALLGPNHK | 2 | y7 | 16.3 | 559.84 | 778.46 | 30 |
| 49 | GIVALLGPNNK | 2 | y9 | 16.5 | 548.33 | 925.55 | 29 |
| 50 | GIVALLGPNNK | 2 | y8 | 16.5 | 548.33 | 826.48 | 29 |
| 51 | GIVALLGPNNK | 2 | y7 | 16.5 | 548.33 | 755.44 | 29 |
| 52 | GIVALLGPNNNAER | 2 | y9 | 16.4 | 719.39 | 984.49 | 37 |
| 53 | GIVALLGPNNNAER | 2 | y8 | 16.4 | 719.39 | 871.4 | 37 |
| 54 | GIVALLGPNNNAER | 2 | y7 | 16.4 | 719.39 | 814.38 | 37 |
| 55 | GIVALR | 2 | y5 | 14.2 | 314.71 | 571.39 | 19 |
| 56 | GIVALR | 2 | y4 | 14.2 | 314.71 | 458.31 | 19 |
| 57 | GIVALR | 2 | y3 | 14.2 | 314.71 | 359.24 | 19 |
| 58 | GPNNK | 2 | y4 | 5.3 | 265.14 | 472.25 | 17 |
| 59 | GPNNK | 2 | y3 | 5.3 | 265.14 | 375.2 | 17 |
| 60 | GPNNK | 2 | b4 | 5.3 | 265.14 | 383.17 | 17 |
| 61 | GTTTPASMAATLR | 2 | y9 | 15.3 | 639.33 | 917.49 | 33 |
| 62 | GTTTPASMAATLR | 2 | y8 | 15.3 | 639.33 | 820.43 | 33 |
| 63 | GTTTPASMAATLR | 2 | y7 | 15.3 | 639.33 | 749.4 | 33 |
| 64 | HLADGMTVGELCAAAITMSDNSAAK | 3 | y9 | 20 | 845.39 | 924.41 | 46 |
| 65 | HLADGMTVGELCAAAITMSDNSAAK | 3 | y8 | 20 | 845.39 | 823.36 | 46 |
| 66 | HLADGMTVGELCAAAITMSDNSAAK | 3 | y7 | 20 | 845.39 | 692.32 | 46 |
| 67 | HLLQWMVDDR | 2 | y9 | 21.2 | 656.83 | 1175.6 | 34 |
| 68 | HLLQWMVDDR | 2 | y8 | 21.2 | 656.83 | 1062.5 | 34 |
| 69 | HLLQWMVDDR | 2 | y7 | 21.2 | 656.83 | 949.42 | 34 |
| 70 | IHYLQQDLVDYSPVSEK | 3 | y9 | 19.9 | 678.68 | 1023.5 | 38 |
| 71 | IHYLQQDLVDYSPVSEK | 3 | y8 | 19.9 | 678.68 | 924.43 | 38 |
| 72 | IHYLQQDLVDYSPVSEK | 3 | y7 | 19.9 | 678.68 | 809.4 | 38 |
| 73 | IVVIYLR | 2 | y6 | 19.1 | 438.29 | 762.49 | 24 |
| 74 | IVVIYLR | 2 | y5 | 19.1 | 438.29 | 663.42 | 24 |
| 75 | IVVIYLR | 2 | y4 | 19.1 | 438.29 | 564.35 | 24 |
| 76 | LCIISLLAALPLAVHASPQPLEQIK | 3 | y9 | 29.8 | 899.19 | 1039.6 | 49 |
| 77 | LCIISLLAALPLAVHASPQPLEQIK | 3 | y8 | 29.8 | 899.19 | 952.55 | 49 |
| 78 | LCIISLLAALPLAVHASPQPLEQIK | 3 | y7 | 29.8 | 899.19 | 855.49 | 49 |
| 79 | LCIISLLATLPLAVHASPQPLDQIK | 3 | y9 | 29.5 | 904.52 | 1025.6 | 49 |

TABLE 8-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 80 | LCIISLLATLPLAVHASPQPLDQIK | 3 | y8 | 29.5 | 904.52 | 938.53 | 49 |
| 81 | LCIISLLATLPLAVHASPQPLDQIK | 3 | y7 | 29.5 | 904.52 | 841.48 | 49 |
| 82 | LCIISLLATLPLAVHASPQPLEQIK | 3 | y9 | 29.6 | 909.19 | 1039.6 | 49 |
| 83 | LCIISLLATLPLAVHASPQPLEQIK | 3 | y8 | 29.6 | 909.19 | 952.55 | 49 |
| 84 | LCIISLLATLPLAVHASPQPLEQIK | 3 | y7 | 29.6 | 909.19 | 855.49 | 49 |
| 85 | LCIISLLATLPLAVHSSPQPLEQIK | 3 | y9 | 29.3 | 914.53 | 1039.6 | 50 |
| 86 | LCIISLLATLPLAVHSSPQPLEQIK | 3 | y8 | 29.3 | 914.53 | 952.55 | 50 |
| 87 | LCIISLLATLPLAVHSSPQPLEQIK | 3 | y7 | 29.3 | 914.53 | 855.49 | 50 |
| 88 | LCIISLLATLPLAVHTSPQPLEQIK | 3 | y9 | 29.5 | 919.2 | 1039.6 | 50 |
| 89 | LCIISLLATLPLAVHTSPQPLEQIK | 3 | y8 | 29.5 | 919.2 | 952.55 | 50 |
| 90 | LCIISLLATLPLAVHTSPQPLEQIK | 3 | y7 | 29.5 | 919.2 | 855.49 | 50 |
| 91 | LCIISLLATLPLTVHASPQPLEQIK | 3 | y9 | 29.3 | 919.2 | 1039.6 | 50 |
| 92 | LCIISLLATLPLTVHASPQPLEQIK | 3 | y8 | 29.3 | 919.2 | 952.55 | 50 |
| 93 | LCIISLLATLPLTVHASPQPLEQIK | 3 | y7 | 29.3 | 919.2 | 855.49 | 50 |
| 94 | LCIISLLATLPLVVHASPQPLEQIK | 3 | y9 | 30.3 | 918.54 | 1039.6 | 50 |
| 95 | LCIISLLATLPLVVHASPQPLEQIK | 3 | y8 | 30.3 | 918.54 | 952.55 | 50 |
| 96 | LCIISLLATLPLVVHASPQPLEQIK | 3 | y7 | 30.3 | 918.54 | 855.49 | 50 |
| 97 | LCIISLLATLSLAVHASPQPLEQIK | 3 | y9 | 29.5 | 905.85 | 1039.6 | 49 |
| 98 | LCIISLLATLSLAVHASPQPLEQIK | 3 | y8 | 29.5 | 905.85 | 952.55 | 49 |
| 99 | LCIISLLATLSLAVHASPQPLEQIK | 3 | y7 | 29.5 | 905.85 | 855.49 | 49 |
| 100 | LCIISLLATMPLAVHASPQPLEQIK | 3 | y9 | 27.4 | 915.18 | 1039.6 | 50 |
| 101 | LCIISLLATMPLAVHASPQPLEQIK | 3 | y8 | 27.4 | 915.18 | 952.55 | 50 |
| 102 | LCIISLLATMPLAVHASPQPLEQIK | 3 | y7 | 27.4 | 915.18 | 855.49 | 50 |
| 103 | LCIISLLAVLPLAVHASPQPLEQIK | 3 | y9 | 30.5 | 908.53 | 1039.6 | 49 |
| 104 | LCIISLLAVLPLAVHASPQPLEQIK | 3 | y8 | 30.5 | 908.53 | 952.55 | 49 |
| 105 | LCIISLLAVLPLAVHASPQPLEQIK | 3 | y7 | 30.5 | 908.53 | 855.49 | 49 |
| 106 | LLISQR | 2 | y5 | 12.9 | 365.23 | 616.38 | 21 |
| 107 | LLISQR | 2 | y4 | 12.9 | 365.23 | 503.29 | 21 |
| 108 | LLISQR | 2 | y3 | 12.9 | 365.23 | 390.21 | 21 |
| 109 | LLLATVGGPAGLTAFLR | 2 | y9 | 24 | 835.5 | 945.55 | 42 |
| 110 | LLLATVGGPAGLTAFLR | 2 | y8 | 24 | 835.5 | 848.5 | 42 |
| 111 | LLLATVGGPAGLTAFLR | 2 | y7 | 24 | 835.5 | 777.46 | 42 |
| 112 | LLNSQR | 2 | y5 | 9.4 | 365.71 | 617.34 | 21 |
| 113 | LLNSQR | 2 | y4 | 9.4 | 365.71 | 504.25 | 21 |
| 114 | LLNSQR | 2 | y3 | 9.4 | 365.71 | 390.21 | 21 |
| 115 | LLTNQR | 2 | y5 | 9.8 | 372.72 | 631.35 | 21 |
| 116 | LLTNQR | 2 | y4 | 9.8 | 372.72 | 518.27 | 21 |
| 117 | LLTNQR | 2 | y3 | 9.8 | 372.72 | 417.22 | 21 |

TABLE 8-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 118 | LLTSQR | 2 | y5 | 9.8 | 359.22 | 604.34 | 21 |
| 119 | LLTSQR | 2 | y4 | 9.8 | 359.22 | 491.26 | 21 |
| 120 | LLTSQR | 2 | y3 | 9.8 | 359.22 | 390.21 | 21 |
| 121 | LNIISLLATLPLAVHASPQPLEQIK | 3 | y9 | 29.6 | 893.87 | 1039.6 | 49 |
| 122 | LNIISLLATLPLAVHASPQPLEQIK | 3 | y8 | 29.6 | 893.87 | 952.55 | 49 |
| 123 | LNIISLLATLPLAVHASPQPLEQIK | 3 | y7 | 29.6 | 893.87 | 855.49 | 49 |
| 124 | LSASSQR | 2 | y6 | 6.2 | 374.7 | 635.31 | 21 |
| 125 | LSASSQR | 2 | y5 | 6.2 | 374.7 | 548.28 | 21 |
| 126 | LSASSQR | 2 | y4 | 6.2 | 374.7 | 477.24 | 21 |
| 127 | LSESQLSGR | 2 | y8 | 10.5 | 488.76 | 863.42 | 27 |
| 128 | LSESQLSGR | 2 | y7 | 10.5 | 488.76 | 776.39 | 27 |
| 129 | LSESQLSGR | 2 | y6 | 10.5 | 488.76 | 647.35 | 27 |
| 130 | LSESQLSGSVGMIEMDLASGR | 3 | y9 | 21.1 | 723.02 | 991.49 | 40 |
| 131 | LSESQLSGSVGMIEMDLASGR | 3 | y8 | 21.1 | 723.02 | 878.4 | 40 |
| 132 | LSESQLSGSVGMIEMDLASGR | 3 | y7 | 21.1 | 723.02 | 749.36 | 40 |
| 133 | MVVIYLR | 2 | y6 | 18.9 | 447.27 | 762.49 | 25 |
| 134 | MVVIYLR | 2 | y5 | 18.9 | 447.27 | 663.42 | 25 |
| 135 | MVVIYLR | 2 | y4 | 18.9 | 447.27 | 564.35 | 25 |
| 136 | NEALPGDAR | 2 | y8 | 10.6 | 471.74 | 828.42 | 26 |
| 137 | NEALPGDAR | 2 | y7 | 10.6 | 471.74 | 699.38 | 26 |
| 138 | NEALPGDAR | 2 | y6 | 10.6 | 471.74 | 628.34 | 26 |
| 139 | NQHIAGIGAALIEHWQR | 2 | y9 | 21.2 | 957.51 | 1123.6 | 47 |
| 140 | NQHIAGIGAALIEHWQR | 2 | y8 | 21.2 | 957.51 | 1052.6 | 47 |
| 141 | NQHIAGIGAALIEHWQR | 2 | y7 | 21.2 | 957.51 | 981.53 | 47 |
| 142 | NQQIAGIGAALIEHWQR | 2 | y9 | 22.1 | 953.01 | 1123.6 | 47 |
| 143 | NQQIAGIGAALIEHWQR | 2 | y8 | 22.1 | 953.01 | 1052.6 | 47 |
| 144 | NQQIAGIGAALIEHWQR | 2 | y7 | 22.1 | 953.01 | 981.53 | 47 |
| 145 | NQQIAGLGAALIEHWQR | 2 | y9 | 22.3 | 953.01 | 1123.6 | 47 |
| 146 | NQQIAGLGAALIEHWQR | 2 | y8 | 22.3 | 953.01 | 1052.6 | 47 |
| 147 | NQQIAGLGAALIEHWQR | 2 | y7 | 22.3 | 953.01 | 981.53 | 47 |
| 148 | NTTTPASMAATLR | 2 | y9 | 15.3 | 667.84 | 917.49 | 34 |
| 149 | NTTTPASMAATLR | 2 | y8 | 15.3 | 667.84 | 820.43 | 34 |
| 150 | NTTTPASMAATLR | 2 | y7 | 15.3 | 667.84 | 749.4 | 34 |
| 151 | NVLTSQR | 2 | y6 | 9.6 | 409.23 | 703.41 | 23 |
| 152 | NVLTSQR | 2 | y5 | 9.6 | 409.23 | 604.34 | 23 |
| 153 | NVLTSQR | 2 | y4 | 9.6 | 409.23 | 491.26 | 23 |
| 154 | QIDDNVTR | 2 | y7 | 9.4 | 480.74 | 832.42 | 26 |
| 155 | QIDDNVTR | 2 | y6 | 9.4 | 480.74 | 719.33 | 26 |

TABLE 8-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 156 | QIDDNVTR | 2 | y5 | 9.4 | 480.74 | 604.3 | 26 |
| 157 | QIGDK | 2 | y4 | 5.8 | 280.66 | 432.25 | 17 |
| 158 | QIGDK | 2 | y3 | 5.8 | 280.66 | 319.16 | 17 |
| 159 | QIGDK | 2 | b4 | 5.8 | 280.66 | 414.2 | 17 |
| 160 | QIGDNVTR | 2 | y7 | 9.5 | 451.74 | 774.41 | 25 |
| 161 | QIGDNVTR | 2 | y6 | 9.5 | 451.74 | 661.33 | 25 |
| 162 | QIGDNVTR | 2 | y5 | 9.5 | 451.74 | 604.3 | 25 |
| 163 | QIGENVTR | 2 | y7 | 9.5 | 458.75 | 788.43 | 25 |
| 164 | QIGENVTR | 2 | y6 | 9.5 | 458.75 | 675.34 | 25 |
| 165 | QIGENVTR | 2 | y5 | 9.5 | 458.75 | 618.32 | 25 |
| 166 | QLLQWMVDAR | 2 | y9 | 21.5 | 630.33 | 1131.6 | 33 |
| 167 | QLLQWMVDAR | 2 | y8 | 21.5 | 630.33 | 1018.5 | 33 |
| 168 | QLLQWMVDAR | 2 | y7 | 21.5 | 630.33 | 905.43 | 33 |
| 169 | QLLQWMVDDGVAGPLIR | 2 | y9 | 25 | 956.01 | 897.52 | 47 |
| 170 | QLLQWMVDDGVAGPLIR | 2 | y8 | 25 | 956.01 | 782.49 | 47 |
| 171 | QLLQWMVDDGVAGPLIR | 2 | y7 | 25 | 956.01 | 725.47 | 47 |
| 172 | QLLQWMVDDR | 2 | y9 | 21.7 | 652.33 | 1175.6 | 34 |
| 173 | QLLQWMVDDR | 2 | y8 | 21.7 | 652.33 | 1062.5 | 34 |
| 174 | QLLQWMVDDR | 2 | y7 | 21.7 | 652.33 | 949.42 | 34 |
| 175 | QLLQWMVDGR | 2 | y8 | 21.3 | 623.32 | 1004.5 | 32 |
| 176 | QLLQWMVDGR | 2 | y7 | 21.3 | 623.32 | 891.41 | 32 |
| 177 | QLLQWMVDGR | 2 | y6 | 21.3 | 623.32 | 763.36 | 32 |
| 178 | QLLQWMVEDR | 2 | y9 | 21.9 | 659.33 | 1189.6 | 34 |
| 179 | QLLQWMVEDR | 2 | y8 | 21.9 | 659.33 | 1076.5 | 34 |
| 180 | QLLQWMVEDR | 2 | y7 | 21.9 | 659.33 | 963.44 | 34 |
| 181 | QQDLVDYSPVSEK | 2 | y9 | 15.6 | 754.37 | 1023.5 | 38 |
| 182 | QQDLVDYSPVSEK | 2 | y8 | 15.6 | 754.37 | 924.43 | 38 |
| 183 | QQDLVDYSPVSEK | 2 | y7 | 15.6 | 754.37 | 809.4 | 38 |
| 184 | QQHLVDYSPVSEK | 2 | y9 | 13.9 | 765.38 | 1023.5 | 39 |
| 185 | QQHLVDYSPVSEK | 2 | y8 | 13.9 | 765.38 | 924.43 | 39 |
| 186 | QQHLVDYSPVSEK | 2 | y7 | 13.9 | 765.38 | 809.4 | 39 |
| 187 | QSESQLSGR | 2 | y8 | 7.6 | 496.24 | 863.42 | 27 |
| 188 | QSESQLSGR | 2 | y7 | 7.6 | 496.24 | 776.39 | 27 |
| 189 | QSESQLSGR | 2 | y6 | 7.6 | 496.24 | 647.35 | 27 |

TABLE 8-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 190 | QSESQLSGSVGMIEMDLASGR | 3 | y9 | 19.7 | 728.01 | 991.49 | 40 |
| 191 | QSESQLSGSVGMIEMDLASGR | 3 | y8 | 19.7 | 728.01 | 878.4 | 40 |
| 192 | QSESQLSGSVGMIEMDLASGR | 3 | y7 | 19.7 | 728.01 | 749.36 | 40 |
| 193 | SQLQLLQWMVDDR | 2 | y9 | 26.3 | 816.41 | 1175.6 | 41 |
| 194 | SQLQLLQWMVDDR | 2 | y8 | 26.3 | 816.41 | 1062.5 | 41 |
| 195 | SQLQLLQWMVDDR | 2 | y7 | 26.3 | 816.41 | 949.42 | 41 |
| 196 | SVLPAGWFIADK | 2 | y9 | 22.9 | 652.36 | 1004.5 | 34 |
| 197 | SVLPAGWFIADK | 2 | y8 | 22.9 | 652.36 | 907.47 | 34 |
| 198 | SVLPAGWFIADK | 2 | y7 | 22.9 | 652.36 | 836.43 | 34 |
| 199 | SVLPAGWFIADR | 2 | y9 | 23 | 666.36 | 1032.5 | 34 |
| 200 | SVLPAGWFIADR | 2 | y8 | 23 | 666.36 | 935.47 | 34 |
| 201 | SVLPAGWFIADR | 2 | y7 | 23 | 666.36 | 864.44 | 34 |
| 202 | SVLSAGWFIADK | 2 | y9 | 22.7 | 647.35 | 994.5 | 33 |
| 203 | SVLSAGWFIADK | 2 | y8 | 22.7 | 647.35 | 907.47 | 33 |
| 204 | SVLSAGWFIADK | 2 | y7 | 22.7 | 647.35 | 836.43 | 33 |
| 205 | TGAAER | 2 | y5 | 4.8 | 302.66 | 503.26 | 18 |
| 206 | TGAAER | 2 | y4 | 4.8 | 302.66 | 446.24 | 18 |
| 207 | TGAAER | 2 | y3 | 4.8 | 302.66 | 375.2 | 18 |
| 208 | TGAAK | 2 | y4 | 6 | 224.13 | 346.21 | 15 |
| 209 | TGAAK | 2 | y3 | 6 | 224.13 | 289.19 | 15 |
| 210 | TGAAK | 2 | b4 | 6 | 224.13 | 301.15 | 15 |
| 211 | TGAGER | 2 | y5 | 4.9 | 295.65 | 489.24 | 18 |
| 212 | TGAGER | 2 | y4 | 4.9 | 295.65 | 432.22 | 18 |
| 213 | TGAGER | 2 | y3 | 4.9 | 295.65 | 361.18 | 18 |
| 214 | TGAGK | 2 | y4 | 6.1 | 217.12 | 332.19 | 15 |
| 215 | TGAGK | 2 | y3 | 6.1 | 217.12 | 275.17 | 15 |
| 216 | TGAGK | 2 | b4 | 6.1 | 217.12 | 287.13 | 15 |
| 217 | TGASER | 2 | y5 | 4.5 | 310.65 | 519.25 | 19 |
| 218 | TGASER | 2 | y4 | 4.5 | 310.65 | 462.23 | 19 |
| 219 | TGASER | 2 | y3 | 4.5 | 310.65 | 391.19 | 19 |
| 220 | TGASK | 2 | y4 | 5.8 | 232.13 | 362.2 | 15 |
| 221 | TGASK | 2 | y3 | 5.8 | 232.13 | 305.18 | 15 |
| 222 | TGASK | 2 | b4 | 5.8 | 232.13 | 317.15 | 15 |
| 223 | TGASR | 2 | y4 | 5.8 | 246.13 | 390.21 | 16 |

TABLE 8-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 224 | TGASR | 2 | y3 | 5.8 | 246.13 | 333.19 | 16 |
| 225 | TGASR | 2 | y2 | 5.8 | 246.13 | 262.15 | 16 |
| 226 | TLTAWCADER | 2 | y9 | 15.9 | 611.78 | 1121.5 | 32 |
| 227 | TLTAWCADER | 2 | y8 | 15.9 | 611.78 | 1008.4 | 32 |
| 228 | TLTAWCADER | 2 | y7 | 15.9 | 611.78 | 907.37 | 32 |
| 229 | TLTAWHADER | 2 | y9 | 14.4 | 600.29 | 1098.5 | 31 |
| 230 | TLTAWHADER | 2 | y8 | 14.4 | 600.29 | 985.45 | 31 |
| 231 | TLTAWHADER | 2 | y7 | 14.4 | 600.29 | 884.4 | 31 |
| 232 | TLTAWR | 2 | y5 | 15 | 374.21 | 646.37 | 21 |
| 233 | TLTAWR | 2 | y4 | 15 | 374.21 | 533.28 | 21 |
| 234 | TLTAWR | 2 | y3 | 15 | 374.21 | 432.24 | 21 |
| 235 | TVGGPAGLTAFLR | 2 | y9 | 19.7 | 630.36 | 945.55 | 33 |
| 236 | TVGGPAGLTAFLR | 2 | y8 | 19.7 | 630.36 | 848.5 | 33 |
| 237 | TVGGPAGLTAFLR | 2 | y7 | 19.7 | 630.36 | 777.46 | 33 |
| 238 | TVVIYLR | 2 | y6 | 17.4 | 432.27 | 762.49 | 24 |
| 239 | TVVIYLR | 2 | y5 | 17.4 | 432.27 | 663.42 | 24 |
| 240 | TVVIYLR | 2 | y4 | 17.4 | 432.27 | 564.35 | 24 |
| 241 | VAGPLIR | 2 | y6 | 14.1 | 363.24 | 626.4 | 21 |
| 242 | VAGPLIR | 2 | y5 | 14.1 | 363.24 | 555.36 | 21 |
| 243 | VAGPLIR | 2 | y4 | 14.1 | 363.24 | 498.34 | 21 |
| 244 | VALCGAVLAR | 2 | y9 | 17.2 | 515.3 | 930.52 | 28 |
| 245 | VALCGAVLAR | 2 | y8 | 17.2 | 515.3 | 859.48 | 28 |
| 246 | VALCGAVLAR | 2 | y7 | 17.2 | 515.3 | 746.4 | 28 |
| 247 | VDAGDEQLER | 2 | y9 | 10.9 | 566.27 | 1032.5 | 30 |
| 248 | VDAGDEQLER | 2 | y8 | 10.9 | 566.27 | 917.43 | 30 |
| 249 | VDAGDEQLER | 2 | y7 | 10.9 | 566.27 | 846.4 | 30 |
| 250 | VDAGDK | 2 | y5 | 4.1 | 302.65 | 505.23 | 18 |
| 251 | VDAGDK | 2 | y4 | 4.1 | 302.65 | 390.2 | 18 |
| 252 | VDAGDK | 2 | y3 | 4.1 | 302.65 | 319.16 | 18 |
| 253 | VGMIEMDLASGR | 2 | y9 | 18.7 | 639.81 | 991.49 | 33 |
| 254 | VGMIEMDLASGR | 2 | y8 | 18.7 | 639.81 | 878.4 | 33 |
| 255 | VGMIEMDLASGR | 2 | y7 | 18.7 | 639.81 | 749.36 | 33 |
| 256 | VGMIEMDLASR | 2 | y9 | 18.7 | 611.3 | 1065.5 | 32 |
| 257 | VGMIEMDLASR | 2 | y8 | 18.7 | 611.3 | 934.47 | 32 |

TABLE 8-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 258 | VGMIEMDLASR | 2 | y7 | 18.7 | 611.3 | 821.38 | 32 |
| 259 | VGMIEMDLASSR | 2 | y9 | 18.4 | 654.82 | 1021.5 | 34 |
| 260 | VGMIEMDLASSR | 2 | y8 | 18.4 | 654.82 | 908.41 | 34 |
| 261 | VGMIEMDLASSR | 2 | y7 | 18.4 | 654.82 | 779.37 | 34 |
| 262 | VLLCGAVLAR | 2 | y9 | 19.3 | 536.32 | 972.57 | 29 |
| 263 | VLLCGAVLAR | 2 | y8 | 19.3 | 536.32 | 859.48 | 29 |
| 264 | VLLCGAVLAR | 2 | y7 | 19.3 | 536.32 | 746.4 | 29 |
| 265 | VVLCGAMLAR | 2 | y8 | 18.1 | 545.3 | 891.45 | 29 |
| 266 | VVLCGAMLAR | 2 | y7 | 18.1 | 545.3 | 778.37 | 29 |
| 267 | VVLCGAMLAR | 2 | y6 | 18.1 | 545.3 | 618.34 | 29 |
| 268 | VVLCGAVLAR | 2 | y9 | 18 | 529.31 | 958.55 | 28 |
| 269 | VVLCGAVLAR | 2 | y8 | 18 | 529.31 | 859.48 | 28 |
| 270 | VVLCGAVLAR | 2 | y7 | 18 | 529.31 | 746.4 | 28 |
| 271 | VVLCGTVLAR | 2 | y9 | 16.6 | 544.32 | 988.56 | 29 |
| 272 | VVLCGTVLAR | 2 | y8 | 16.6 | 544.32 | 889.49 | 29 |
| 273 | VVLCGTVLAR | 2 | y7 | 16.6 | 544.32 | 776.41 | 29 |
| 274 | WETDR | 2 | y4 | 9.8 | 353.66 | 520.24 | 21 |
| 275 | WETDR | 2 | y3 | 9.8 | 353.66 | 391.19 | 21 |
| 276 | WETDR | 2 | b4 | 9.8 | 353.66 | 532.2 | 21 |
| 277 | WETELNEAFPGDAR | 2 | y9 | 19 | 817.88 | 976.45 | 41 |
| 278 | WETELNEAFPGDAR | 2 | y8 | 19 | 817.88 | 862.41 | 41 |
| 279 | WETELNEAFPGDAR | 2 | y7 | 19 | 817.88 | 733.36 | 41 |
| 280 | WETELNEALPADAR | 2 | y9 | 18.9 | 807.89 | 956.48 | 41 |
| 281 | WETELNEALPADAR | 2 | y8 | 18.9 | 807.89 | 842.44 | 41 |
| 282 | WETELNEALPADAR | 2 | y7 | 18.9 | 807.89 | 713.39 | 41 |
| 283 | WETELNEALPGDAR | 2 | y9 | 18.5 | 800.88 | 942.46 | 40 |
| 284 | WETELNEALPGDAR | 2 | y8 | 18.5 | 800.88 | 828.42 | 40 |
| 285 | WETELNEALPGDAR | 2 | y7 | 18.5 | 800.88 | 699.38 | 40 |
| 286 | WETELNEALSGDAR | 2 | y9 | 18 | 795.87 | 932.44 | 40 |
| 287 | WETELNEALSGDAR | 2 | y8 | 18 | 795.87 | 818.4 | 40 |
| 288 | WETELNEALSGDAR | 2 | y7 | 18 | 795.87 | 689.36 | 40 |
| 289 | WETELNEVLPGDAR | 2 | y9 | 19.4 | 814.9 | 970.5 | 41 |
| 290 | WETELNEVLPGDAR | 2 | y8 | 19.4 | 814.9 | 856.45 | 41 |
| 291 | WETELNEVLPGDAR | 2 | y7 | 19.4 | 814.9 | 727.41 | 41 |
| 292 | WETER | 2 | y4 | 10.4 | 360.67 | 534.25 | 21 |

TABLE 8-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 293 | WETER | 2 | y3 | 10.4 | 360.67 | 405.21 | 21 |
| 294 | WETER | 2 | b4 | 10.4 | 360.67 | 546.22 | 21 |

The areas obtained for each of the transitions and for each of the microorganisms studied were measured. When the areas of the 3 transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 10

Identification of a Resistance to FOX Beta-Lactams

The samples corresponding to a species able to comprise a FOX resistance mechanism can be detected by employing the following method.

Each sample is treated according to example 5, then analysed according to example 6 by detecting the peptides from TABLE 9 instead of the peptides from TABLE 3.

TABLE 9

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 1 | AHYFNYGVANR | 2 | y9 | 15.5 | 656.32 | 1103.53 | 34 |
| 2 | AHYFNYGVANR | 2 | y8 | 15.5 | 656.32 | 940.46 | 34 |
| 3 | AHYFNYGVANR | 2 | y7 | 15.5 | 656.32 | 793.4 | 34 |
| 4 | AMGEQR | 2 | y5 | 5.3 | 346.16 | 620.28 | 20 |
| 5 | AMGEQR | 2 | y4 | 5.3 | 346.16 | 489.24 | 20 |
| 6 | AMGEQR | 2 | y3 | 5.3 | 346.16 | 432.22 | 20 |
| 7 | ESGQR | 2 | y4 | 4.3 | 288.64 | 447.23 | 18 |
| 8 | ESGQR | 2 | y3 | 4.3 | 288.64 | 360.2 | 18 |
| 9 | ESGQR | 2 | b4 | 4.3 | 288.64 | 402.16 | 18 |
| 10 | FAVPK | 2 | y4 | 11.3 | 281.17 | 414.27 | 17 |
| 11 | FAVPK | 2 | y3 | 11.3 | 281.17 | 343.23 | 17 |
| 12 | FAVPK | 2 | b4 | 11.3 | 281.17 | 415.23 | 17 |
| 13 | GGFELDDK | 2 | y7 | 14.5 | 440.71 | 823.38 | 24 |
| 14 | GGFELDDK | 2 | y6 | 14.5 | 440.71 | 766.36 | 24 |
| 15 | GGFELDDK | 2 | y5 | 14.5 | 440.71 | 619.29 | 24 |
| 16 | GIAIVMLANR | 2 | y9 | 19.3 | 529.31 | 1000.6 | 28 |

TABLE 9-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 17 | GIAIVMLANR | 2 | y8 | 19.3 | 529.31 | 887.51 | 28 |
| 18 | GIAIVMLANR | 2 | y7 | 19.3 | 529.31 | 816.48 | 28 |
| 19 | IPGMAVAVLK | 2 | y9 | 18.1 | 499.81 | 885.52 | 27 |
| 20 | IPGMAVAVLK | 2 | y8 | 18.1 | 499.81 | 788.47 | 27 |
| 21 | IPGMAVAVLK | 2 | y7 | 18.1 | 499.81 | 731.45 | 27 |
| 22 | NYPIEAR | 2 | y6 | 12.2 | 431.72 | 748.4 | 24 |
| 23 | NYPIEAR | 2 | y5 | 12.2 | 431.72 | 585.34 | 24 |
| 24 | NYPIEAR | 2 | y4 | 12.2 | 431.72 | 488.28 | 24 |
| 25 | SWSPVYPAGTHR | 2 | y9 | 15.5 | 679.34 | 997.52 | 35 |
| 26 | SWSPVYPAGTHR | 2 | y8 | 15.5 | 679.34 | 900.47 | 35 |
| 27 | SWSPVYPAGTHR | 2 | y7 | 15.5 | 679.34 | 801.4 | 35 |
| 28 | TGSADLLK | 2 | y7 | 14 | 402.73 | 703.4 | 23 |
| 29 | TGSADLLK | 2 | y6 | 14 | 402.73 | 646.38 | 23 |
| 30 | TGSADLLK | 2 | y5 | 14 | 402.73 | 559.34 | 23 |
| 31 | TGSTGGFGAYVAFVPAR | 2 | y9 | 19.5 | 829.42 | 993.55 | 41 |
| 32 | TGSTGGFGAYVAFVPAR | 2 | y8 | 19.5 | 829.42 | 922.51 | 41 |
| 33 | TGSTGGFGAYVAFVPAR | 2 | y7 | 19.5 | 829.42 | 759.45 | 41 |
| 34 | TLTATLGAYAAVK | 2 | y9 | 17.2 | 640.37 | 893.51 | 33 |
| 35 | TLTATLGAYAAVK | 2 | y8 | 17.2 | 640.37 | 792.46 | 33 |
| 36 | TLTATLGAYAAVK | 2 | y7 | 17.2 | 640.37 | 679.38 | 33 |
| 37 | VSEQTLFEIGSVSK | 2 | y9 | 19.6 | 762.4 | 979.55 | 39 |
| 38 | VSEQTLFEIGSVSK | 2 | y8 | 19.6 | 762.4 | 866.46 | 39 |
| 39 | VSEQTLFEIGSVSK | 2 | y7 | 19.6 | 762.4 | 719.39 | 39 |
| 40 | VSQHAPWLK | 2 | y8 | 15.3 | 533.3 | 966.52 | 28 |
| 41 | VSQHAPWLK | 2 | y7 | 15.3 | 533.3 | 879.48 | 28 |
| 42 | VSQHAPWLK | 2 | y6 | 15.3 | 533.3 | 751.42 | 28 |
| 43 | VTPGVLAAEAYGIK | 2 | y9 | 18.4 | 694.89 | 935.52 | 36 |

TABLE 9-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 44 | VTPGVLAAEAYGIK | 2 | y8 | 18.4 | 694.89 | 822.44 | 36 |
| 45 | VTPGVLAAEAYGIK | 2 | y7 | 18.4 | 694.89 | 751.4 | 36 |

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 11

Identification of a Resistance to TEM or CTX-M Beta-Lactams

The samples corresponding to a species able to comprise a TEM or CTX-M resistance mechanism can be detected by employing the following method.

Each sample is treated according to example 5, then analysed according to example 6 by detecting the peptides from TABLE 10 instead of the peptides from TABLE 3.

TABLE 10

| Transition number | Protein | Peptide | First-generation fragment ion | Charge state of the precursor | Clinical interest |
|---|---|---|---|---|---|
| 1 | CTX-M | AMAQTLR | y4 monocharged | 2 | 2be |
| 2 | CTX-M | AMAQTLR | y5 monocharged | 2 | 2be |
| 3 | CTX-M | AMAQTLR | y6 monocharged | 2 | 2be |
| 4 | CTX-M | AQLVTWLK | y5 monocharged | 2 | 2be |
| 5 | CTX-M | AQLVTWLK | y6 monocharged | 2 | 2be |
| 6 | CTX-M | AQLVTWLK | y7 monocharged | 2 | 2be |
| 7 | CTX-M | FAMCSTSK | y5 monocharged | 2 | 2be |
| 8 | CTX-M | FAMCSTSK | y6 monocharged | 2 | 2be |
| 9 | CTX-M | FAMCSTSK | y7 monocharged | 2 | 2be |
| 10 | CTX-M | LAALEK | y3 monocharged | 2 | 2be |
| 11 | CTX-M | LAALEK | y4 monocharged | 2 | 2be |
| 12 | CTX-M | LAALEK | y5 monocharged | 2 | 2be |
| 13 | CTX-M | LGVALINTADNSQILYR | y7 monocharged | 2 | 2be |
| 14 | CTX-M | LGVALINTADNSQILYR | y8 monocharged | 2 | 2be |
| 15 | CTX-M | LGVALINTADNSQILYR | y9 monocharged | 2 | 2be |
| 16 | CTX-M | NLTLGK | y3 monocharged | 2 | 2be |
| 17 | CTX-M | NLTLGK | y4 monocharged | 2 | 2be |
| 18 | CTX-M | NLTLGK | y5 monocharged | 2 | 2be |
| 19 | CTX-M | QSETQK | y3 monocharged | 2 | 2be |

TABLE 10-continued

| Transition number | Protein | Peptide | First-generation fragment ion | Charge state of the precursor | Clinical interest |
|---|---|---|---|---|---|
| 20 | CTX-M | QSETQK | y4 monocharged | 2 | 2be |
| 21 | CTX-M | QSETQK | y5 monocharged | 2 | 2be |
| 22 | CTX-M | SDLVNYNPIAEK | y7 monocharged | 2 | 2be |
| 23 | CTX-M | SDLVNYNPIAEK | y8 monocharged | 2 | 2be |
| 24 | CTX-M | SDLVNYNPIAEK | y9 monocharged | 2 | 2be |
| 25 | CTX-M | TEPTLNTAIPGDPR | y7 monocharged | 2 | 2be |
| 26 | CTX-M | TEPTLNTAIPGDPR | y8 monocharged | 2 | 2be |
| 27 | CTX-M | TEPTLNTAIPGDPR | y9 monocharged | 2 | 2be |
| 28 | CTX-M | VMAAAAVLK | y6 monocharged | 2 | 2be |
| 29 | CTX-M | VMAAAAVLK | y7 monocharged | 2 | 2be |
| 30 | CTX-M | VMAAAAVLK | y8 monocharged | 2 | 2be |
| 31 | TEM | DAEDQLGAR | y5 monocharged | 2 | TEM |
| 32 | TEM | DAEDQLGAR | y6 monocharged | 2 | TEM |
| 33 | TEM | DAEDQLGAR | y7 monocharged | 2 | TEM |
| 34 | TEM | DTTMPAAMATTLR | y7 monocharged | 2 | TEM |
| 35 | TEM | DTTMPAAMATTLR | y8 monocharged | 2 | TEM |
| 36 | TEM | DTTMPAAMATTLR | y9 monocharged | 2 | TEM |
| 37 | TEM | DTTTPAAMATTLR | y7 monocharged | 2 | TEM |
| 38 | TEM | DTTTPAAMATTLR | y9 dicharged | 2 | TEM |
| 39 | TEM | DTTTPAAMATTLR | y9 monocharged | 2 | TEM |
| 40 | TEM | EPELNEAIPNDER | y5 monocharged | 2 | TEM |
| 41 | TEM | EPELNEAIPNDER | y7 monocharged | 2 | TEM |
| 42 | TEM | EPELNEAIPNDER | y8 monocharged | 2 | TEM |
| 43 | TEM | GIIAALGPDGKPSR | y7 monocharged | 2 | TEM |
| 44 | TEM | GIIAALGPDGKPSR | y8 monocharged | 2 | TEM |
| 45 | TEM | GIIAALGPDGKPSR | y9 monocharged | 2 | TEM |
| 46 | TEM | GSCGIIAALGPDGKPSR | y7 monocharged | 2 | 2br |
| 47 | TEM | GSCGIIAALGPDGKPSR | y8 monocharged | 2 | 2br |
| 48 | TEM | GSCGIIAALGPDGKPSR | y9 monocharged | 2 | 2br |
| 49 | TEM | GSSGIIAALGPDGKPSR | y7 monocharged | 2 | TEM |
| 50 | TEM | GSSGIIAALGPDGKPSR | y8 monocharged | 2 | TEM |
| 51 | TEM | GSSGIIAALGPDGKPSR | y9 monocharged | 2 | TEM |
| 52 | TEM | HLTDGMTVR | y4 monocharged | 2 | TEM |
| 53 | TEM | HLTDGMTVR | y7 monocharged | 2 | TEM |
| 54 | TEM | HLTDGMTVR | y8 monocharged | 2 | TEM |
| 55 | TEM | IHYSQNDLVEYSPVTEK | y6 monocharged | 3 | TEM |
| 56 | TEM | IHYSQNDLVEYSPVTEK | y7 monocharged | 3 | TEM |
| 57 | TEM | IHYSQNDLVEYSPVTEK | y8 monocharged | 3 | TEM |

TABLE 10-continued

| Transition number | Protein | Peptide | First-generation fragment ion | Charge state of the precursor | Clinical interest |
|---|---|---|---|---|---|
| 58 | TEM | IHYSQNDLVK | y7 monocharged | 2 | 2be |
| 59 | TEM | IHYSQNDLVK | y8 monocharged | 2 | 2be |
| 60 | TEM | IHYSQNDLVK | y9 dicharged | 2 | 2be |
| 61 | TEM | ILESFRPEER | b6 monocharged | 2 | TEM |
| 62 | TEM | ILESFRPEER | b8 monocharged | 2 | TEM |
| 63 | TEM | ILESFRPEER | y7 dicharged | 2 | TEM |
| 64 | TEM | LDHWEPELNEAIPNDER | y5 monocharged | 3 | 2be |
| 65 | TEM | LDHWEPELNEAIPNDER | y6 monocharged | 3 | 2be |
| 66 | TEM | LDHWEPELNEAIPNDER | y7 monocharged | 3 | 2be |
| 67 | TEM | LDSWEPELNEAIPNDER | y5 monocharged | 3 | 2be |
| 68 | TEM | LDSWEPELNEAIPNDER | y6 monocharged | 3 | 2be |
| 69 | TEM | LDSWEPELNEAIPNDER | y7 monocharged | 3 | 2be |
| 70 | TEM | LLTGELLTLASR | y6 monocharged | 2 | TEM |
| 71 | TEM | LLTGELLTLASR | y7 monocharged | 2 | TEM |
| 72 | TEM | LLTGELLTLASR | y9 monocharged | 2 | TEM |
| 73 | TEM | QIAEIGASLIK | y7 monocharged | 2 | TEM |
| 74 | TEM | QIAEIGASLIK | y8 monocharged | 2 | TEM |
| 75 | TEM | QIAEIGASLIK | y9 monocharged | 2 | TEM |
| 76 | TEM | QQLIDWMEADK | y5 monocharged | 2 | TEM |
| 77 | TEM | QQLIDWMEADK | y6 monocharged | 2 | TEM |
| 78 | TEM | QQLIDWMEADK | y7 monocharged | 2 | TEM |
| 79 | TEM | VAGPLLR | y4 monocharged | 2 | TEM |
| 80 | TEM | VAGPLLR | y5 monocharged | 2 | TEM |
| 81 | TEM | VAGPLLR | y6 monocharged | 2 | TEM |
| 82 | TEM | VDAGQEQLGR | y5 monocharged | 2 | TEM |
| 83 | TEM | VDAGQEQLGR | y7 monocharged | 2 | TEM |
| 84 | TEM | VDAGQEQLGR | y8 monocharged | 2 | TEM |
| 85 | TEM | VGYIELDLNSGK | y7 monocharged | 2 | TEM |
| 86 | TEM | VGYIELDLNSGK | y8 monocharged | 2 | TEM |
| 87 | TEM | VGYIELDLNSGK | y9 monocharged | 2 | TEM |
| 88 | TEM | WEPELNEAIPNDER | y12 dicharged | 2 | TEM |
| 89 | TEM | WEPELNEAIPNDER | y5 monocharged | 2 | TEM |
| 90 | TEM | WEPELNEAIPNDER | y7 monocharged | 2 | TEM |
| 91 | TEM | YSPVTEK | y4 monocharged | 2 | 2be |
| 92 | TEM | YSPVTEK | y5 monocharged | 2 | 2be |
| 93 | TEM | YSPVTEK | y6 monocharged | 2 | 2be |

In the clinical interest column, the entries TEM, 2b, 2br, 2be and 2ber correspond to the same meanings as in TABLE 4.

The transitions mentioned in TABLE 10 are detected by using the parameters set out in TABLE 11.

TABLE 11

| Transition number | Retention time (minutes) | (m/z) filtered in Q1 | (m/z) filtered in Q3 | Collision energy (eV) | Positivity threshold |
|---|---|---|---|---|---|
| 1 | 12.1 | 395.72 | 517.31 | 22 | 2500 |
| 2 | 12.1 | 395.72 | 588.35 | 22 | 2500 |
| 3 | 12.1 | 395.72 | 719.39 | 22 | 2500 |
| 4 | 21 | 479.79 | 646.39 | 26 | 2500 |
| 5 | 21 | 479.79 | 759.48 | 26 | 2500 |
| 6 | 21 | 479.79 | 887.53 | 26 | 2500 |
| 7 | 11.1 | 466.2 | 582.26 | 26 | 2500 |
| 8 | 11.1 | 466.2 | 713.3 | 26 | 2500 |
| 9 | 11.1 | 466.2 | 784.33 | 26 | 2500 |
| 10 | 11 | 322.7 | 389.24 | 19 | 2500 |
| 11 | 11 | 322.7 | 460.28 | 19 | 2500 |
| 12 | 11 | 322.7 | 531.31 | 19 | 2500 |
| 13 | 21.1 | 931.01 | 893.48 | 46 | 2500 |
| 14 | 21.1 | 931.01 | 1008.51 | 46 | 2500 |
| 15 | 21.1 | 931.01 | 1079.55 | 46 | 2500 |
| 16 | 12.2 | 323.2 | 317.22 | 19 | 2500 |
| 17 | 12.2 | 323.2 | 418.27 | 19 | 2500 |
| 18 | 12.2 | 323.2 | 531.35 | 19 | 2500 |
| 19 | 3.7 | 360.68 | 376.22 | 21 | 2500 |
| 20 | 3.7 | 360.68 | 505.26 | 21 | 2500 |
| 21 | 3.7 | 360.68 | 592.29 | 21 | 2500 |
| 22 | 17.1 | 681.85 | 834.44 | 35 | 2500 |
| 23 | 17.1 | 681.85 | 948.48 | 35 | 2500 |
| 24 | 17.1 | 681.85 | 1047.55 | 35 | 2500 |
| 25 | 15.6 | 741.38 | 725.39 | 38 | 2500 |
| 26 | 15.6 | 741.38 | 826.44 | 38 | 2500 |
| 27 | 15.6 | 741.38 | 940.48 | 38 | 2500 |
| 28 | 15.3 | 437.26 | 572.38 | 24 | 2500 |
| 29 | 15.3 | 437.26 | 643.41 | 24 | 2500 |
| 30 | 15.3 | 437.26 | 774.45 | 24 | 2500 |
| 31 | 10.5 | 487.73 | 544.32 | 26 | 2500 |
| 32 | 10.5 | 487.73 | 659.35 | 26 | 2500 |
| 33 | 10.5 | 487.73 | 788.39 | 26 | 2500 |
| 34 | 17.6 | 690.34 | 763.61 | 35 | 2500 |
| 35 | 17.6 | 690.34 | 834.45 | 35 | 2500 |
| 36 | 17.6 | 690.34 | 931.5 | 35 | 2500 |
| 37 | 16.1 | 675.34 | 763.41 | 35 | 2500 |
| 38 | 16.1 | 675.34 | 466.25 | 35 | 2500 |
| 39 | 16.1 | 675.34 | 931.5 | 35 | 2500 |
| 40 | 14.9 | 763.36 | 630.28 | 39 | 2500 |
| 41 | 14.9 | 763.36 | 814.41 | 39 | 2500 |
| 42 | 14.9 | 763.36 | 943.45 | 39 | 2500 |
| 43 | 15.5 | 676.39 | 756.4 | 35 | 2500 |
| 44 | 15.5 | 676.39 | 813.42 | 35 | 2500 |
| 45 | 15.5 | 676.39 | 926.51 | 35 | 2500 |
| 46 | 16.5 | 828.43 | 756.4 | 41 | 2500 |
| 47 | 16.5 | 828.43 | 813.42 | 41 | 2500 |
| 48 | 16.5 | 828.43 | 926.51 | 41 | 2500 |
| 49 | 16.1 | 791.93 | 756.4 | 40 | 2500 |
| 50 | 16.1 | 791.93 | 813.42 | 40 | 2500 |
| 51 | 16.1 | 791.93 | 926.51 | 40 | 2500 |
| 52 | 12 | 515.26 | 506.28 | 28 | 2500 |
| 53 | 12 | 515.26 | 779.37 | 28 | 2500 |
| 54 | 12 | 515.26 | 892.46 | 28 | 2500 |
| 55 | 16.6 | 674.67 | 660.36 | 38 | 2500 |
| 56 | 16.6 | 674.67 | 823.42 | 38 | 2500 |
| 57 | 16.6 | 674.67 | 952.46 | 38 | 2500 |
| 58 | 12.5 | 608.82 | 803.43 | 32 | 2500 |
| 59 | 12.5 | 608.82 | 966.49 | 32 | 2500 |
| 60 | 12.5 | 608.82 | 552.28 | 32 | 2500 |
| 61 | 14.6 | 638.34 | 746.42 | 33 | 2500 |
| 62 | 14.6 | 638.34 | 972.51 | 33 | 2500 |
| 63 | 14.6 | 638.34 | 460.73 | 33 | 2500 |
| 64 | 18 | 692.99 | 630.28 | 39 | 2500 |
| 65 | 18 | 692.99 | 743.37 | 39 | 2500 |
| 66 | 18 | 692.99 | 814.41 | 39 | 2500 |
| 67 | 19.5 | 676.32 | 630.28 | 38 | 2500 |
| 68 | 19.5 | 676.32 | 743.37 | 38 | 2500 |
| 69 | 19.5 | 676.32 | 814.41 | 38 | 2500 |
| 70 | 22.5 | 643.89 | 660.4 | 33 | 2500 |
| 71 | 22.5 | 643.89 | 773.49 | 33 | 2500 |
| 72 | 22.5 | 643.89 | 959.55 | 33 | 2500 |
| 73 | 18.8 | 571.84 | 701.46 | 30 | 2500 |
| 74 | 18.8 | 571.84 | 830.5 | 30 | 2500 |
| 75 | 18.8 | 571.84 | 901.54 | 30 | 2500 |
| 76 | 20.1 | 688.83 | 593.26 | 35 | 2500 |
| 77 | 20.1 | 688.83 | 779.34 | 35 | 2500 |
| 78 | 20.1 | 688.83 | 894.37 | 35 | 2500 |
| 79 | 14.1 | 363.24 | 498.34 | 21 | 2500 |
| 80 | 14.1 | 363.24 | 555.36 | 21 | 2500 |
| 81 | 14.1 | 363.24 | 626.4 | 21 | 2500 |
| 82 | 10.6 | 536.77 | 602.38 | 29 | 2500 |
| 83 | 10.6 | 536.77 | 787.41 | 29 | 2500 |
| 84 | 10.6 | 536.77 | 858.44 | 29 | 2500 |
| 85 | 18.8 | 654.35 | 746.4 | 34 | 2500 |
| 86 | 18.8 | 654.35 | 875.45 | 34 | 2500 |
| 87 | 18.8 | 654.35 | 988.53 | 34 | 2500 |
| 88 | 18 | 856.4 | 698.84 | 43 | 2500 |
| 89 | 18 | 856.4 | 630.28 | 43 | 2500 |
| 90 | 18 | 856.4 | 814.41 | 43 | 2500 |
| 91 | 9.8 | 412.21 | 476.27 | 23 | 2500 |
| 92 | 9.8 | 412.21 | 573.32 | 23 | 2500 |
| 93 | 9.8 | 412.21 | 660.36 | 23 | 2500 |

When the areas of at least two transitions of the same peptide are greater than or equal to the positivity threshold described in TABLE 11, the detection of the peptide is considered to be positive. When more than two transitions of the same peptide comprise an area less than the positivity threshold described in TABLE 11, the corresponding peptide is considered non-detected.

A sample contains bacteria which express the TEM protein, when at least one peptide corresponding to the TEM resistance mechanism is detected. These bacteria are resistant to penicillins.

A sample contains bacteria which express the TEM protein, phenotype 2b, when at least one peptide corresponding to the TEM resistance mechanism clinical interest 2b is detected. These bacteria are only resistant to penicillins.

A sample contains bacteria which express the TEM protein, phenotype 2br, when at least one peptide corresponding to the TEM resistance mechanism clinical interest 2br is detected. These bacteria are resistant to penicillins associated with an inhibitor of the clavulanic acid and tazobactam type.

A sample contains bacteria which express the CTX-M protein or the TEM protein, phenotype 2be, when at least one peptide corresponding to the CTX-M or TEM resistance mechanism clinical interest 2be is detected. These bacteria are resistant to penicillins, to cephalosporins and to monobactams.

A sample contains bacteria which express the TEM protein, phenotype 2ber, when at least one peptide corresponding to the TEM resistance mechanism clinical interest 2ber, is detected. These bacteria are resistant to penicillins, to cephalosporins and to monobactams, and are insensitive to inhibition by clavulanic acid, sulfobactam or tazobactam.

EXAMPLE 12

Identification of a Resistance to PER Beta-Lactams

Samples Sam74 to Sam78 are identified according to one of the methods described in examples 1, 3 or 4. The identification of the species is set out in TABLE 12.

TABLE 12

| Names | Species |
|---|---|
| Ech74 | A. baumannii |
| Ech75 | A. baumannii |
| Ech76 | P. aeruginosa |
| Ech77 | P. aeruginosa |
| Ech78 | P. aeruginosa |

Samples Sam74 to Sam78 correspond to a species able to comprise a PER resistance mechanism. Each sample is treated according to example 5, then analysed according to example 6 by detecting the peptides from TABLE 13 instead of the peptides from TABLE 3.

TABLE 13

| Transition number | Peptide | Retention time (minutes) | (m/z) filtered in Q1 | (m/z) filtered in Q3 | Collision energy (eV) | positivity threshold |
|---|---|---|---|---|---|---|
| 1 | AAAQLLR | 12.91 | 371.73 | 401.29 | 16.9 | 2000 |
| 2 | AAAQLLR | 12.89 | 371.73 | 529.35 | 16.9 | 2000 |
| 3 | AAAQLLR | 12.91 | 371.73 | 600.38 | 16.9 | 2000 |
| 4 | AAAQVLQK | 10.24 | 414.75 | 487.32 | 19.4 | 2000 |
| 5 | AAAQVLQK | 10.24 | 414.75 | 615.38 | 19.4 | 2000 |
| 6 | AAAQVLQK | 10.18 | 414.75 | 686.42 | 19.4 | 2000 |
| 7 | AAVLQNTWSPMMK | 19.35 | 738.87 | 506.25 | 37.9 | 2000 |
| 8 | AAVLQNTWSPMMK | 19.35 | 738.87 | 593.28 | 37.9 | 2000 |
| 9 | AAVLQNTWSPMMK | 19.35 | 738.87 | 994.45 | 37.9 | 2000 |
| 10 | EQIESIVIGK | 17.24 | 558.32 | 317.22 | 27.6 | 2000 |
| 11 | EQIESIVIGK | 17.26 | 558.32 | 616.40 | 27.6 | 2000 |
| 12 | EQIESIVIGK | 17.24 | 558.32 | 745.45 | 27.6 | 2000 |
| 13 | EQIETIVTGK | 15.48 | 559.31 | 305.18 | 27.6 | 2000 |
| 14 | EQIETIVTGK | 15.48 | 559.31 | 618.38 | 27.6 | 2000 |
| 15 | EQIETIVTGK | 15.48 | 559.31 | 747.43 | 27.6 | 2000 |
| 16 | ETEVVANEAQMHADDQVQYK | 14.17 | 769.02 | 838.87 | 30.9 | 5000 |
| 17 | ETEVVANEAQMHADDQVQYK | 14.17 | 769.02 | 874.39 | 30.9 | 5000 |
| 18 | ETEVVANEAQMHADDQVQYK | 14.17 | 769.02 | 923.92 | 30.9 | 5000 |
| 19 | FPMQSVFK | 19.09 | 492.26 | 418.72 | 23.8 | 2000 |
| 20 | FPMQSVFK | 19.09 | 492.26 | 739.38 | 23.8 | 2000 |
| 21 | FPMQSVFK | 19.07 | 492.26 | 836.43 | 23.8 | 2000 |
| 22 | GAAEILK | 12.66 | 351.21 | 322.70 | 15.8 | 2000 |
| 23 | GAAEILK | 12.65 | 351.21 | 502.32 | 15.8 | 2000 |
| 24 | GAAEILK | 12.65 | 351.21 | 573.36 | 15.8 | 2000 |
| 25 | GLLPAGTIVAHK | 16.8 | 588.86 | 447.26 | 29.3 | 2000 |
| 26 | GLLPAGTIVAHK | 16.8 | 588.86 | 503.81 | 29.3 | 2000 |
| 27 | GLLPAGTIVAHK | 16.82 | 588.86 | 893.52 | 29.3 | 2000 |
| 28 | GLLPAGTVVAHK | 15.73 | 581.85 | 440.26 | 28.9 | 2000 |
| 29 | GLLPAGTVVAHK | 15.73 | 581.85 | 496.80 | 28.9 | 2000 |

TABLE 13-continued

| Transition number | Peptide | Retention time (minutes) | (m/z) filtered in Q1 | (m/z) filtered in Q3 | Collision energy (eV) | positivity threshold |
|---|---|---|---|---|---|---|
| 30 | GLLPAGTVVAHK | 15.75 | 581.85 | 879.51 | 28.9 | 2000 |
| 31 | GQIESIVIGK | 16.8 | 522.31 | 616.40 | 25.5 | 5000 |
| 32 | GQIESIVIGK | 16.8 | 522.31 | 745.45 | 25.5 | 5000 |
| 33 | GQIESIVIGK | 16.8 | 522.31 | 858.53 | 25.5 | 5000 |
| 34 | LDLNK | 10.5 | 301.68 | 342.20 | 12.9 | 2000 |
| 35 | LDLNK | 10.5 | 301.68 | 374.24 | 12.9 | 2000 |
| 36 | LDLNK | 10.52 | 301.68 | 489.27 | 12.9 | 2000 |
| 37 | LDLNQSVTVNR | 15.11 | 629.84 | 338.19 | 31.6 | 2000 |
| 38 | LDLNQSVTVNR | 15.11 | 629.84 | 489.28 | 31.6 | 2000 |
| 39 | LDLNQSVTVNR | 15.11 | 629.84 | 675.38 | 31.6 | 2000 |
| 40 | LDLNQTVIVNR | 17.29 | 642.87 | 501.31 | 32.4 | 2000 |
| 41 | LDLNQTVIVNR | 17.29 | 642.87 | 600.38 | 32.4 | 2000 |
| 42 | LDLNQTVIVNR | 17.28 | 642.87 | 701.43 | 32.4 | 2000 |
| 43 | LHLAMLVLHQVDQGK | 19.84 | 567.99 | 568.83 | 24.7 | 2000 |
| 44 | LHLAMLVLHQVDQGK | 19.84 | 567.99 | 669.86 | 24.7 | 2000 |
| 45 | LHLAMLVLHQVDQGK | 19.84 | 567.99 | 726.41 | 24.7 | 2000 |
| 46 | MHLAMLVLHQVDQGK | 19.35 | 573.97 | 332.19 | 24.9 | 2000 |
| 47 | MHLAMLVLHQVDQGK | 19.35 | 573.97 | 669.86 | 24.9 | 2000 |
| 48 | MHLAMLVLHQVDQGK | 19.35 | 573.97 | 726.41 | 24.9 | 2000 |
| 49 | NWTSMK | 12.59 | 383.68 | 365.19 | 17.6 | 2000 |
| 50 | NWTSMK | 12.59 | 383.68 | 466.23 | 17.6 | 2000 |
| 51 | NWTSMK | 12.61 | 383.68 | 652.31 | 17.6 | 2000 |
| 52 | QLSETSQALLWK | 18.84 | 702.38 | 1162.61 | 35.8 | 2000 |
| 53 | QLSETSQALLWK | 18.84 | 702.38 | 446.28 | 35.8 | 2000 |
| 54 | QLSETSQALLWK | 18.84 | 702.38 | 845.49 | 35.8 | 2000 |
| 55 | TGTSGIK | 3.31 | 332.19 | 404.25 | 14.7 | 2000 |
| 56 | TGTSGIK | 3.29 | 332.19 | 505.30 | 14.7 | 2000 |
| 57 | TGTSGIK | 3.23 | 332.19 | 562.32 | 14.7 | 2000 |
| 58 | TGTSGVR | 1.56 | 339.18 | 418.24 | 15.1 | 2000 |
| 59 | TGTSGVR | 1.56 | 339.18 | 519.29 | 15.1 | 2000 |
| 60 | TGTSGVR | 1.56 | 339.18 | 576.31 | 15.1 | 2000 |
| 61 | TNEAIIAQVAQAAYQFELK | 26.27 | 703.37 | 1168.60 | 28.9 | 2000 |
| 62 | TNEAIIAQVAQAAYQFELK | 26.21 | 703.37 | 827.43 | 28.9 | 2000 |
| 63 | TNEAIIAQVAQAAYQFELK | 26.25 | 703.37 | 898.47 | 28.9 | 2000 |
| 64 | TNEAIIAQVAQTAYQFELK | 25.39 | 713.38 | 1198.61 | 29.2 | 2000 |
| 65 | TNEAIIAQVAQTAYQFELK | 25.37 | 713.38 | 827.43 | 29.2 | 2000 |
| 66 | TNEAIIAQVAQTAYQFELK | 25.37 | 713.38 | 898.47 | 29.2 | 2000 |
| 67 | TQLSETSQALLWK | 19.41 | 502.27 | 559.36 | 38.7 | 2000 |

TABLE 13-continued

| Transition number | Peptide | Retention time (minutes) | (m/z) filtered in Q1 | (m/z) filtered in Q3 | Collision energy (eV) | positivity threshold |
|---|---|---|---|---|---|---|
| 68 | TQLSETSQALLWK | 19.41 | 502.27 | 630.40 | 22.7 | 2000 |
| 69 | TQLSETSQALLWK | 19.43 | 752.90 | 1162.61 | 22.7 | 2000 |
| 70 | TVAVNR | 7.08 | 330.20 | 388.23 | 14.6 | 2000 |
| 71 | TVAVNR | 7.08 | 330.20 | 459.27 | 14.6 | 2000 |
| 72 | TVAVNR | 7.05 | 330.20 | 558.34 | 14.6 | 2000 |
| 73 | VLQNTWAPIMK | 19.32 | 650.86 | 488.29 | 32.8 | 2000 |
| 74 | VLQNTWAPIMK | 19.3 | 650.86 | 559.33 | 32.8 | 2000 |
| 75 | VLQNTWAPIMK | 19.3 | 650.86 | 745.41 | 32.8 | 2000 |
| 76 | WMVETTTGPER | 15.5 | 653.81 | 761.38 | 33 | 2000 |
| 77 | WMVETTTGPER | 15.48 | 653.81 | 890.42 | 33 | 2000 |
| 78 | WMVETTTGPER | 15.48 | 653.81 | 989.49 | 33 | 2000 |
| 79 | WMVETTTGPQR | 15.19 | 653.32 | 457.25 | 33 | 2000 |
| 80 | WMVETTTGPQR | 15.19 | 653.32 | 889.44 | 33 | 2000 |
| 81 | WMVETTTGPQR | 15.23 | 653.32 | 988.51 | 33 | 2000 |

The other machine parameters used are as follows:
Scan type: MRM
MRM planned: yes
Polarity: Positive
Ionising source: Turbo V™ (Applied BioSystems)
Q1 setting: Filtering with unit resolution
Q3 setting: Filtering with unit resolution
Inter-scan pause: 5.00 msec
Scanning speed: 10 Da/s
Curtain gas: 50.00 psi
Cone voltage: 5500.00 V
Source temperature: 500.00° C.
Nebulising gas: 40.00 psi
Heating gas: 40.00 psi
Collision gas which induces dissociation: 9.00 psi
Dynamic filling: activated
Declustering potential (DP): 100.00 V
Entry potential before Q0 (EP): 10.00 V
Collision cell exit potential (CXP): 15 V
Total cycle time: 1 sec
Detection window: 240 sec The areas obtained for each of the transitions and for each of the microorganisms studied were measured. When the areas of the transitions are greater than or equal to the positivity threshold described in TABLE 13, the detection of the transition is considered to be positive and is labelled "1" in TABLE 14. When a transition has an area less than the positivity threshold described in TABLE 13, the transition is considered non-detected and is labelled "0" in TABLE 14.

For a given peptide, when at least 3 transitions are labelled "1", the peptide is considered as being detected.

TABLE 14

| Transition number | Sam74 | Sam75 | Sam76 | Sam77 | Sam78 |
|---|---|---|---|---|---|
| 1 | 0 | 0 | 0 | 0 | 0 |
| 2 | 0 | 0 | 0 | 0 | 0 |
| 3 | 0 | 0 | 0 | 0 | 0 |
| 4 | 0 | 0 | 0 | 0 | 0 |
| 5 | 0 | 0 | 0 | 0 | 0 |
| 6 | 0 | 0 | 0 | 0 | 0 |
| 7 | 0 | 1 | 0 | 1 | 0 |
| 8 | 0 | 0 | 0 | 0 | 1 |
| 9 | 1 | 1 | 1 | 1 | 1 |
| 10 | 1 | 1 | 1 | 1 | 1 |
| 11 | 1 | 1 | 1 | 1 | 1 |
| 12 | 1 | 1 | 1 | 1 | 1 |
| 13 | 0 | 0 | 0 | 0 | 0 |
| 14 | 0 | 0 | 0 | 0 | 0 |
| 15 | 0 | 0 | 0 | 0 | 0 |
| 16 | 0 | 0 | 0 | 0 | 0 |
| 17 | 1 | 1 | 0 | 0 | 0 |
| 18 | 0 | 0 | 0 | 0 | 0 |
| 19 | 1 | 1 | 0 | 0 | 0 |
| 20 | 1 | 1 | 0 | 0 | 0 |
| 21 | 1 | 1 | 0 | 0 | 0 |
| 22 | 1 | 1 | 1 | 1 | 1 |
| 23 | 1 | 1 | 1 | 1 | 1 |
| 24 | 1 | 1 | 1 | 1 | 1 |
| 25 | 0 | 0 | 0 | 0 | 0 |
| 26 | 0 | 0 | 0 | 0 | 0 |
| 27 | 0 | 0 | 0 | 0 | 0 |
| 28 | 1 | 1 | 1 | 1 | 1 |
| 29 | 1 | 1 | 1 | 1 | 1 |
| 30 | 1 | 1 | 1 | 1 | 1 |
| 31 | 0 | 0 | 0 | 0 | 0 |
| 32 | 0 | 0 | 0 | 0 | 0 |
| 33 | 1 | 1 | 0 | 0 | 0 |
| 34 | 0 | 0 | 0 | 0 | 0 |
| 35 | 0 | 0 | 0 | 0 | 0 |
| 36 | 0 | 0 | 0 | 0 | 0 |
| 37 | 0 | 0 | 1 | 1 | 1 |
| 38 | 0 | 0 | 0 | 0 | 0 |
| 39 | 0 | 0 | 0 | 0 | 0 |
| 40 | 1 | 1 | 1 | 1 | 1 |
| 41 | 1 | 1 | 1 | 1 | 1 |

TABLE 14-continued

| Transition number | Sam74 | Sam75 | Sam76 | Sam77 | Sam78 |
|---|---|---|---|---|---|
| 42 | 1 | 1 | 1 | 1 | 1 |
| 43 | 0 | 0 | 0 | 0 | 0 |
| 44 | 0 | 0 | 0 | 0 | 0 |
| 45 | 0 | 0 | 0 | 0 | 0 |
| 46 | 0 | 0 | 0 | 0 | 0 |
| 47 | 0 | 0 | 0 | 0 | 0 |
| 48 | 0 | 0 | 0 | 0 | 0 |
| 49 | 0 | 0 | 0 | 0 | 0 |
| 50 | 0 | 0 | 0 | 0 | 0 |
| 51 | 0 | 0 | 0 | 0 | 0 |
| 52 | 0 | 0 | 0 | 0 | 0 |
| 53 | 0 | 0 | 0 | 0 | 0 |
| 54 | 0 | 0 | 0 | 0 | 0 |
| 55 | 1 | 1 | 0 | 1 | 1 |
| 56 | 1 | 1 | 0 | 0 | 0 |
| 57 | 1 | 1 | 0 | 0 | 0 |
| 58 | 0 | 0 | 0 | 0 | 0 |
| 59 | 0 | 0 | 0 | 0 | 0 |
| 60 | 0 | 0 | 0 | 0 | 0 |
| 61 | 0 | 0 | 0 | 0 | 0 |
| 62 | 0 | 0 | 0 | 0 | 0 |
| 63 | 0 | 0 | 0 | 0 | 0 |
| 64 | 0 | 0 | 0 | 0 | 0 |
| 65 | 0 | 0 | 0 | 0 | 0 |
| 66 | 0 | 0 | 0 | 0 | 0 |
| 67 | 1 | 1 | 1 | 1 | 1 |
| 68 | 1 | 1 | 1 | 1 | 1 |
| 69 | 1 | 1 | 1 | 1 | 0 |
| 70 | 0 | 0 | 0 | 0 | 0 |
| 71 | 0 | 0 | 0 | 0 | 0 |
| 72 | 0 | 0 | 0 | 0 | 0 |
| 73 | 1 | 1 | 1 | 1 | 1 |
| 74 | 1 | 1 | 1 | 1 | 1 |
| 75 | 1 | 1 | 1 | 1 | 1 |
| 76 | 1 | 1 | 1 | 1 | 1 |
| 77 | 1 | 1 | 1 | 1 | 1 |
| 78 | 1 | 1 | 1 | 1 | 1 |
| 79 | 0 | 0 | 0 | 0 | 0 |
| 80 | 0 | 0 | 0 | 0 | 0 |
| 81 | 0 | 0 | 0 | 0 | 0 |

Samples Sam74 to Sam78 comprise at least one peptide which is characteristic of PERs. The bacteria present in samples Sam74 to Sam78 therefore express a beta-lactamase which confers on them a resistance to penicillins, cephalosporins and monobactams.

EXAMPLE 13

Identification of a Resistance to VEB Beta-Lactams

Samples Sam79 to Sam82 are identified according to one of the methods described in examples 1, 3 or 4. The identification of the species is set out in TABLE 15.

TABLE 15

| Names | Species |
|---|---|
| Sam79 | *A. baumannii* |
| Sam80 | *A. baumannii* |
| Sam81 | *A. baumannii* |
| Sam82 | *E. coli* |

Samples Sam79 to Sam82 correspond to a species able to comprise a VEB resistance mechanism. Each sample is treated according to example 5, then analysed according to example 6 by detecting the peptides from TABLE 16 instead of the peptides from TABLE 3.

TABLE 16

| Transition number | Peptide | Retention time (minutes) | (m/z) filtered in Q1 | (m/z) filtered in Q3 | Collision energy (eV) | Positivity threshold |
|---|---|---|---|---|---|---|
| 1 | ANEEQMHK | 1.44 | 493.72 | 458.20 | 23.9 | 2000 |
| 2 | ANEEQMHK | 1.44 | 493.72 | 672.31 | 23.9 | 2000 |
| 3 | ANEEQMHK | 1.44 | 493.72 | 801.36 | 23.9 | 2000 |
| 4 | DWNTQYQNWATPTAMNK | 19.05 | 1034.96 | 661.33 | 54.7 | 2000 |
| 5 | DWNTQYQNWATPTAMNK | 19 | 690.31 | 661.33 | 28.5 | 2000 |
| 6 | DWNTQYQNWATPTAMNK | 19.02 | 690.31 | 762.38 | 28.5 | 2000 |
| 7 | ETSEINEK | 6.84 | 475.23 | 390.20 | 22.8 | 2000 |
| 8 | ETSEINEK | 6.84 | 475.23 | 503.28 | 22.8 | 2000 |
| 9 | ETSEINEK | 6.83 | 475.23 | 719.36 | 22.8 | 2000 |
| 10 | ETTTGSNR | 1.38 | 433.20 | 433.22 | 20.4 | 1500 |
| 11 | ETTTGSNR | 1.38 | 433.20 | 534.26 | 20.4 | 1500 |
| 12 | ETTTGSNR | 1.38 | 433.20 | 635.31 | 20.4 | 1500 |
| 13 | FLNANHFTDISIK | 18.72 | 507.27 | 573.30 | 22.8 | 2000 |
| 14 | FLNANHFTDISIK | 18.72 | 507.27 | 630.32 | 22.8 | 2000 |
| 15 | FLNANHFTDISIK | 18.74 | 507.27 | 686.87 | 22.8 | 2000 |
| 16 | FPIALAVLSEIDK | 27.01 | 708.41 | 634.88 | 36.1 | 2000 |

TABLE 16-continued

| Transition number | Peptide | Retention time (minutes) | (m/z) filtered in Q1 | (m/z) filtered in Q3 | Collision energy (eV) | Positivity threshold |
|---|---|---|---|---|---|---|
| 17 | FPIALAVLSEIDK | 27.04 | 708.41 | 704.38 | 36.1 | 2000 |
| 18 | FPIALAVLSEIDK | 27.01 | 708.41 | 874.49 | 36.1 | 2000 |
| 19 | GNLSFEQK | 12.65 | 461.74 | 551.28 | 22.1 | 2000 |
| 20 | GNLSFEQK | 12.65 | 461.74 | 638.31 | 22.1 | 2000 |
| 21 | GNLSFEQK | 12.65 | 461.74 | 751.40 | 22.1 | 2000 |
| 22 | GQLPK | 7.19 | 271.67 | 243.16 | 11.2 | 2000 |
| 23 | GQLPK | 7.19 | 271.67 | 357.25 | 11.2 | 2000 |
| 24 | GQLPK | 7.19 | 271.67 | 485.31 | 11.2 | 2000 |
| 25 | IEITPQDLLPK | 21.67 | 633.87 | 405.74 | 31.9 | 2000 |
| 26 | IEITPQDLLPK | 21.67 | 633.87 | 810.47 | 31.9 | 2000 |
| 27 | IEITPQDLLPK | 21.63 | 633.87 | 911.52 | 31.9 | 2000 |
| 28 | IENVLK | 12.89 | 358.22 | 359.27 | 16.2 | 2000 |
| 29 | IENVLK | 12.91 | 358.22 | 473.31 | 16.2 | 2000 |
| 30 | IENVLK | 12.89 | 358.22 | 602.35 | 16.2 | 2000 |
| 31 | IGVAIFNSNEK | 18.09 | 596.32 | 738.34 | 29.7 | 2000 |
| 32 | IGVAIFNSNEK | 18.09 | 596.32 | 851.43 | 29.7 | 2000 |
| 33 | IGVAIFNSNEK | 18.09 | 596.32 | 922.46 | 29.7 | 2000 |
| 34 | IISDIAK | 12.6 | 380.23 | 331.23 | 17.4 | 2000 |
| 35 | IISDIAK | 12.58 | 380.23 | 533.29 | 17.4 | 2000 |
| 36 | IISDIAK | 12.56 | 380.23 | 646.38 | 17.4 | 2000 |
| 37 | INNDFHFPMQSVMK | 20.04 | 569.94 | 740.84 | 24.8 | 2000 |
| 38 | INNDFHFPMQSVMK | 20.04 | 569.94 | 797.86 | 24.8 | 2000 |
| 39 | INNDFHFPMQSVMK | 20.05 | 569.94 | 820.41 | 24.8 | 2000 |
| 40 | LIGGTDSVQK | 11.48 | 509.28 | 734.37 | 24.8 | 2000 |
| 41 | LIGGTDSVQK | 11.46 | 509.28 | 791.39 | 24.8 | 2000 |
| 42 | LIGGTDSVQK | 11.46 | 509.28 | 904.47 | 24.8 | 2000 |
| 43 | LLIDTYNNK | 15.7 | 547.30 | 639.31 | 26.9 | 2000 |
| 44 | LLIDTYNNK | 15.7 | 547.30 | 754.34 | 26.9 | 2000 |
| 45 | LLIDTYNNK | 15.7 | 547.30 | 867.42 | 26.9 | 2000 |
| 46 | MWSPIK | 16.91 | 381.20 | 357.25 | 17.5 | 2000 |
| 47 | MWSPIK | 16.91 | 381.20 | 444.28 | 17.5 | 2000 |
| 48 | MWSPIK | 16.87 | 381.20 | 630.36 | 17.5 | 2000 |
| 49 | NQLLSK | 10.59 | 351.71 | 347.23 | 15.8 | 2000 |
| 50 | NQLLSK | 10.59 | 351.71 | 460.31 | 15.8 | 2000 |
| 51 | NQLLSK | 10.59 | 351.71 | 588.37 | 15.8 | 2000 |
| 52 | NTIVAHK | 23.75 | 391.73 | 454.28 | 18.1 | 2000 |
| 53 | NTIVAHK | 23.73 | 391.73 | 567.36 | 18.1 | 2000 |
| 54 | NTIVAHK | 23.75 | 391.73 | 668.41 | 18.1 | 2000 |

TABLE 16-continued

| Transition number | Peptide | Retention time (minutes) | (m/z) filtered in Q1 | (m/z) filtered in Q3 | Collision energy (eV) | Positivity threshold |
|---|---|---|---|---|---|---|
| 55 | SYDFIWK | 19.92 | 479.74 | 446.28 | 23.1 | 2000 |
| 56 | SYDFIWK | 19.9 | 479.74 | 593.35 | 23.1 | 2000 |
| 57 | SYDFIWK | 19.9 | 479.74 | 708.37 | 23.1 | 2000 |
| 58 | TWSPIK | 14.95 | 366.21 | 357.25 | 16.6 | 2000 |
| 59 | TWSPIK | 14.93 | 366.21 | 444.28 | 16.6 | 2000 |
| 60 | TWSPIK | 14.95 | 366.21 | 630.36 | 16.6 | 2000 |

The other machine parameters used are as follows:
Scan type: MRM
MRM planned: yes
Polarity: Positive
ionising source: Turbo V™ (Applied BioSystems)
Q1 setting: Filtering with unit resolution
Q3 setting: Filtering with unit resolution
Inter-scan pause: 5.00 msec
Scanning speed: 10 Da/s
Curtain gas: 50.00 psi
Cone voltage: 5500.00 V
Source temperature: 500.00° C.
Nebulising gas: 40.00 psi
Heating gas: 40.00 psi
Collision gas which induces dissociation: 9.00 psi
Dynamic filling: activated
Declustering potential (DP): 100.00 V
Entry potential before Q0 (EP): 10.00 V
Collision cell exit potential (CXP): 15 V
Total cycle time: 1.2 sec
Detection window: 240 sec The areas obtained for each of the transitions and for each of the microorganisms studied were measured. When the areas of the transitions are greater than or equal to the positivity threshold described in TABLE 16, the detection of the transition is considered to be positive and is labelled "1" in TABLE 17. When a transition has an area less than the positivity threshold described in TABLE 16, the transition is considered non-detected and is labelled "0" in TABLE 17.

For a given peptide, when at least 3 transitions are labelled "1", the peptide is considered as being detected.

TABLE 17

| Transition number | Sam79 | Sam80 | Sam81 | Sam82 |
|---|---|---|---|---|
| 1 | 0 | 0 | 0 | 0 |
| 2 | 0 | 0 | 0 | 0 |
| 3 | 0 | 0 | 0 | 0 |
| 4 | 0 | 0 | 0 | 0 |
| 5 | 0 | 0 | 0 | 0 |
| 6 | 0 | 0 | 0 | 0 |
| 7 | 0 | 0 | 0 | 0 |
| 8 | 0 | 0 | 0 | 0 |
| 9 | 0 | 0 | 0 | 0 |
| 10 | 1 | 1 | 1 | 1 |
| 11 | 1 | 1 | 1 | 1 |
| 12 | 1 | 1 | 1 | 0 |
| 13 | 0 | 1 | 1 | 0 |
| 14 | 0 | 1 | 1 | 0 |
| 15 | 0 | 1 | 1 | 0 |
| 16 | 0 | 0 | 0 | 0 |
| 17 | 0 | 0 | 0 | 0 |
| 18 | 0 | 0 | 0 | 0 |
| 19 | 0 | 0 | 0 | 0 |
| 20 | 0 | 0 | 0 | 0 |
| 21 | 0 | 0 | 0 | 0 |
| 22 | 0 | 0 | 0 | 0 |
| 23 | 0 | 0 | 0 | 0 |
| 24 | 0 | 0 | 0 | 0 |
| 25 | 1 | 1 | 1 | 1 |
| 26 | 1 | 1 | 1 | 1 |
| 27 | 1 | 1 | 1 | 1 |
| 28 | 0 | 0 | 0 | 0 |
| 29 | 0 | 0 | 0 | 0 |
| 30 | 0 | 0 | 0 | 0 |
| 31 | 0 | 0 | 0 | 0 |
| 32 | 0 | 0 | 0 | 0 |
| 33 | 0 | 0 | 0 | 0 |
| 34 | 0 | 0 | 0 | 0 |
| 35 | 0 | 0 | 0 | 0 |
| 36 | 0 | 0 | 0 | 0 |
| 37 | 0 | 0 | 0 | 0 |
| 38 | 0 | 0 | 0 | 0 |
| 39 | 0 | 0 | 0 | 0 |
| 40 | 1 | 1 | 1 | 0 |
| 41 | 0 | 1 | 0 | 0 |
| 42 | 1 | 0 | 1 | 0 |
| 43 | 0 | 0 | 0 | 0 |
| 44 | 0 | 0 | 0 | 0 |
| 45 | 0 | 0 | 0 | 0 |
| 46 | 0 | 0 | 0 | 0 |
| 47 | 0 | 0 | 0 | 0 |
| 48 | 0 | 0 | 0 | 0 |
| 49 | 0 | 0 | 0 | 0 |
| 50 | 0 | 0 | 0 | 0 |
| 51 | 0 | 0 | 0 | 0 |
| 52 | 0 | 0 | 0 | 0 |
| 53 | 0 | 0 | 0 | 0 |
| 54 | 0 | 0 | 0 | 0 |
| 55 | 1 | 1 | 1 | 0 |
| 56 | 1 | 1 | 1 | 0 |
| 57 | 1 | 1 | 1 | 0 |
| 58 | 0 | 0 | 0 | 0 |
| 59 | 0 | 0 | 0 | 0 |
| 60 | 0 | 0 | 0 | 0 |

Samples Sam79 to Sam82 comprise at least one peptide which is characteristic of VEBs. The bacteria present in samples Sam79 to Sam82 therefore express a beta-lactamase which confers on them a resistance to penicillins, cephalosporins and monobactams.

EXAMPLE 14

Identification of a Resistance to MOX Beta-Lactams

Sample Sam83 is identified according to one of the methods described in examples 1, 3 or 4. The identification of the species is set out in TABLE 18.

TABLE 18

| Names | Species |
| --- | --- |
| Sam83 | E. coli |

Sample Sam83 corresponds to a species able to comprise a MOX resistance mechanism. Each sample is treated according to example 5, then analysed according to example 6 by detecting the peptides from TABLE 19 instead of the peptides from TABLE 3.

TABLE 19

| Transition number | Peptide | Retention time (minutes) | (m/z) filtered in Q1 | (m/z) filtered in Q3 | Collision energy (eV) | Positivity threshold |
| --- | --- | --- | --- | --- | --- | --- |
| 1 | AHYFNYGVADR | 14.36 | 656.807 | 621.289 | 33.2 | 2000 |
| 2 | AHYFNYGVADR | 14.36 | 656.807 | 941.448 | 33.2 | 2000 |
| 3 | AHYFNYGVADR | 14.34 | 656.807 | 1104.511 | 33.2 | 2000 |
| 4 | ANISGVDDK | 9.88 | 459.73 | 533.257 | 21.9 | 2000 |
| 5 | ANISGVDDK | 9.86 | 459.73 | 620.289 | 21.9 | 2000 |
| 6 | ANISGVDDK | 9.86 | 459.73 | 733.373 | 21.9 | 2000 |
| 7 | ANISGVHDK | 7.75 | 470.746 | 555.289 | 22.6 | 2000 |
| 8 | ANISGVHDK | 7.67 | 470.746 | 642.321 | 22.6 | 2000 |
| 9 | ANISGVHDK | 7.69 | 470.746 | 755.405 | 22.6 | 2000 |
| 10 | ASLFAPWLK | 23.52 | 516.797 | 543.329 | 25.2 | 2000 |
| 11 | ASLFAPWLK | 23.56 | 516.797 | 614.366 | 25.2 | 2000 |
| 12 | ASLFAPWLK | 23.56 | 516.797 | 761.434 | 25.2 | 2000 |
| 13 | EDKPFR | 8.09 | 396.206 | 419.24 | 18.3 | 2000 |
| 14 | EDKPFR | 8.07 | 396.206 | 547.335 | 18.3 | 2000 |
| 15 | EDKPFR | 8.09 | 396.206 | 662.362 | 18.3 | 2000 |
| 16 | ESGNLMLFNK | 18.39 | 576.79 | 408.224 | 28.6 | 2000 |
| 17 | ESGNLMLFNK | 18.39 | 576.79 | 521.308 | 28.6 | 2000 |
| 18 | ESGNLMLFNK | 18.39 | 576.79 | 652.349 | 28.6 | 2000 |
| 19 | ESGSQMLFNK | 15.08 | 570.771 | 408.224 | 28.3 | 2000 |
| 20 | ESGSQMLFNK | 15.14 | 570.771 | 521.308 | 28.3 | 2000 |
| 21 | ESGSQMLFNK | 15.12 | 570.771 | 652.349 | 28.3 | 2000 |
| 22 | GHPVLFNK | 12.74 | 456.259 | 408.224 | 21.7 | 2000 |
| 23 | GHPVLFNK | 12.78 | 456.259 | 521.308 | 21.7 | 2000 |
| 24 | GHPVLFNK | 12.78 | 456.259 | 717.429 | 21.7 | 2000 |
| 25 | GIGVVMLANR | 18.19 | 515.297 | 604.324 | 25.1 | 2000 |
| 26 | GIGVVMLANR | 18.17 | 515.297 | 703.392 | 25.1 | 2000 |
| 27 | GIGVVMLANR | 18.17 | 515.297 | 859.482 | 25.1 | 2000 |
| 28 | MQAYYR | 11.12 | 416.195 | 501.246 | 19.5 | 2000 |
| 29 | MQAYYR | 11.14 | 416.195 | 572.283 | 19.5 | 2000 |

TABLE 19-continued

| Transition number | Peptide | Retention time (minutes) | (m/z) filtered in Q1 | (m/z) filtered in Q3 | Collision energy (eV) | Positivity threshold |
|---|---|---|---|---|---|---|
| 30 | MQAYYR | 11.12 | 416.195 | 700.341 | 19.5 | 2000 |
| 31 | NSPIEAR | 9.4 | 393.709 | 375.199 | 18.2 | 2000 |
| 32 | NSPIEAR | 9.4 | 393.709 | 488.283 | 18.2 | 2000 |
| 33 | NSPIEAR | 9.4 | 393.709 | 585.335 | 18.2 | 2000 |
| 34 | NSPIEGTLK | 13.36 | 479.764 | 379.226 | 23.1 | 2000 |
| 35 | NSPIEGTLK | 13.36 | 479.764 | 547.309 | 23.1 | 2000 |
| 36 | NSPIEGTLK | 13.34 | 479.764 | 757.445 | 23.1 | 2000 |
| 37 | NYPNEGTLK | 11.6 | 518.259 | 379.706 | 25.3 | 2000 |
| 38 | NYPNEGTLK | 11.62 | 518.259 | 661.352 | 25.3 | 2000 |
| 39 | NYPNEGTLK | 11.58 | 518.259 | 758.404 | 25.3 | 2000 |
| 40 | QPFDR | 9.48 | 331.666 | 437.214 | 14.6 | 2000 |
| 41 | QPFDR | 9.5 | 331.666 | 488.214 | 14.6 | 2000 |
| 42 | QPFDR | 9.48 | 331.666 | 534.267 | 14.6 | 2000 |
| 43 | QWTPAYSPGSHR | 13.34 | 693.831 | 486.238 | 35.3 | 2000 |
| 44 | QWTPAYSPGSHR | 13.34 | 693.831 | 640.316 | 35.3 | 2000 |
| 45 | QWTPAYSPGSHR | 13.34 | 693.831 | 971.469 | 35.3 | 2000 |
| 46 | QWTPAYSR | 13.46 | 504.749 | 496.251 | 24.5 | 2000 |
| 47 | QWTPAYSR | 13.48 | 504.749 | 593.304 | 24.5 | 2000 |
| 48 | QWTPAYSR | 13.46 | 504.749 | 694.352 | 24.5 | 2000 |
| 49 | QYANPSIGLFGYLAASSMK | 25.46 | 673.34 | 594.292 | 28 | 2000 |
| 50 | QYANPSIGLFGYLAASSMK | 25.5 | 673.34 | 594.31 | 28 | 2000 |
| 51 | QYANPSIGLFGYLAASSMK | 25.5 | 673.34 | 927.46 | 28 | 2000 |
| 52 | QYSNPSIGLFGHLAASSMK | 21.21 | 670.003 | 609.819 | 27.9 | 2000 |
| 53 | QYSNPSIGLFGHLAASSMK | 21.17 | 670.003 | 758.403 | 27.9 | 2000 |
| 54 | QYSNPSIGLFGHLAASSMK | 21.21 | 670.003 | 858.941 | 27.9 | 2000 |
| 55 | TGSSNGFGAYVAFVPAR | 20.79 | 850.923 | 343.209 | 100 | 2000 |
| 56 | TGSSNGFGAYVAFVPAR | 20.78 | 850.923 | 380.229 | 100 | 2000 |
| 57 | TGSSNGFGAYVAFVPAR | 20.78 | 850.923 | 442.277 | 100 | 2000 |
| 58 | TGSTNGFGAYVAFVPAK | 20.45 | 843.928 | 315.203 | 100 | 2000 |
| 59 | TGSTNGFGAYVAFVPAK | 20.46 | 843.928 | 366.226 | 100 | 2000 |
| 60 | TGSTNGFGAYVAFVPAK | 20.46 | 843.928 | 414.271 | 100 | 2000 |
| 61 | TGSTSGFGAYVAFVPAK | 20.64 | 553.951 | 632.377 | 24.3 | 2000 |
| 62 | TGSTSGFGAYVAFVPAK | 20.66 | 830.422 | 315.203 | 43.1 | 2000 |
| 63 | TGSTSGFGAYVAFVPAK | 20.66 | 830.422 | 414.271 | 43.1 | 2000 |
| 64 | TLTATLGAYAVVQGSFELDDK | 18.71 | 733.711 | 569.275 | 29.8 | 2000 |
| 65 | TLTATLGAYAVVQGSFELDDK | 18.71 | 733.711 | 654.328 | 29.8 | 2000 |
| 66 | TLTATLGAYAVVQGSFELDDK | 18.71 | 733.711 | 1137.542 | 29.8 | 2000 |
| 67 | VSPGMLADEAYGIK | 18.63 | 725.866 | 632.816 | 37.1 | 2000 |

TABLE 19-continued

| Transition number | Peptide | Retention time (minutes) | (m/z) filtered in Q1 | (m/z) filtered in Q3 | Collision energy (eV) | Positivity threshold |
|---|---|---|---|---|---|---|
| 68 | VSPGMLADEAYGIK | 18.63 | 725.866 | 866.425 | 37.1 | 2000 |
| 69 | VSPGMLADEAYGIK | 18.65 | 725.866 | 1167.571 | 37.1 | 2000 |
| 70 | VTPAMLAEEPYGIK | 19.05 | 506.934 | 577.334 | 22.8 | 2000 |
| 71 | VTPAMLAEEPYGIK | 19.05 | 759.897 | 659.839 | 39 | 2000 |
| 72 | VTPAMLAEEPYGIK | 19.07 | 759.897 | 906.457 | 39 | 2000 |
| 73 | YAYPVSEQTLLAGNSAK | 18.09 | 604.644 | 547.283 | 25.8 | 2000 |
| 74 | YAYPVSEQTLLAGNSAK | 18.07 | 604.644 | 660.368 | 25.8 | 2000 |
| 75 | YAYPVSEQTLLAGNSAK | 18.09 | 906.462 | 707.88 | 47.4 | 2000 |

The other machine parameters used are as follows:
Scan type: MRM
MRM planned: yes
Polarity: Positive
Ionising source: Turbo V™ (Applied BioSystems)
Q1 setting: Filtering with unit resolution
Q3 setting: Filtering with unit resolution
Inter-scan pause: 5.00 msec
Scanning speed: 10 Da/s
Curtain gas: 40.00 psi
Cone voltage: 5500.00 V
Source temperature: 500.00° C.
Nebulising gas: 40.00 psi
Heating gas: 40.00 psi
Collision gas which induces dissociation: 9.00 psi
Dynamic filling: activated
Declustering potential (DP): 100.00 V
Entry potential before Q0 (EP): 10.00 V
Collision cell exit potential (CXP): 15 V
Total cycle time: 1 sec
Detection window: 240 sec The areas obtained for each of the transitions and for each of the microorganisms studied were measured. When the areas of the transitions are greater than or equal to the positivity threshold described in TABLE 19, the detection of the transition is considered to be positive and is labelled "1" in TABLE 20. When a transition has an area less than the positivity threshold described in TABLE 19, the transition is considered non-detected and is labelled "0" in TABLE 20.

For a given peptide, when at least 3 transitions are labelled "1", the peptide is considered as being detected.

TABLE 20

| Transition number | Sam83 |
|---|---|
| 1 | 0 |
| 2 | 0 |
| 3 | 0 |
| 4 | 0 |
| 5 | 0 |
| 6 | 0 |
| 7 | 1 |
| 8 | 1 |
| 9 | 1 |
| 10 | 0 |
| 11 | 0 |
| 12 | 0 |

TABLE 20-continued

| Transition number | Sam83 |
|---|---|
| 13 | 0 |
| 14 | 0 |
| 15 | 0 |
| 16 | 0 |
| 17 | 0 |
| 18 | 0 |
| 19 | 0 |
| 20 | 0 |
| 21 | 0 |
| 22 | 0 |
| 23 | 0 |
| 24 | 0 |
| 25 | 0 |
| 26 | 0 |
| 27 | 0 |
| 28 | 0 |
| 29 | 0 |
| 30 | 0 |
| 31 | 0 |
| 32 | 0 |
| 33 | 0 |
| 34 | 0 |
| 35 | 0 |
| 36 | 0 |
| 37 | 0 |
| 38 | 0 |
| 39 | 0 |
| 40 | 0 |
| 41 | 0 |
| 42 | 0 |
| 43 | 1 |
| 44 | 1 |
| 45 | 1 |
| 46 | 0 |
| 47 | 0 |
| 48 | 0 |
| 49 | 0 |
| 50 | 0 |
| 51 | 0 |
| 52 | 0 |
| 53 | 0 |
| 54 | 0 |
| 55 | 0 |
| 56 | 0 |
| 57 | 0 |
| 58 | 0 |
| 59 | 0 |
| 60 | 0 |
| 61 | 0 |
| 62 | 0 |
| 63 | 0 |

TABLE 20-continued

| Transition number | Sam83 |
|---|---|
| 64 | 0 |
| 65 | 0 |
| 66 | 0 |
| 67 | 1 |
| 68 | 1 |
| 69 | 1 |
| 70 | 0 |
| 71 | 0 |
| 72 | 0 |
| 73 | 0 |
| 74 | 0 |
| 75 | 0 |

Sample Sam83 comprises at least one peptide which is characteristic of MOXs. The bacteria present in sample Sam83 therefore express a beta-lactamase which confers on them a resistance to penicillins and to cephalosporins, with the exception of fourth-generation cephalosporins.

EXAMPLE 15

Identification of a Resistance to ACC Beta-Lactams

The samples corresponding to a species able to comprise an ACC resistance mechanism can be detected by employing the following method.

Each sample is treated according to example 5, then analysed according to example 6 by detecting the peptides from TABLE 21 instead of the peptides from TABLE 3.

TABLE 21

| Transition number | Peptide | Retention time (minutes) | (m/z) filtered in Q1 | (m/z) filtered in Q3 | Collision energy (eV) |
|---|---|---|---|---|---|
| 1 | ALTDTHIGYFK | 15.83 | 422.56 | 457.24 | 25 |
| 2 | ALTDTHIGYFK | 15.83 | 422.56 | 514.27 | 25 |
| 3 | ALTDTHIGYFK | 15.83 | 422.56 | 627.35 | 25 |
| 4 | AWKPADPAGTHR | 10.49 | 436.23 | 470.25 | 26 |
| 5 | AWKPADPAGTHR | 10.49 | 436.23 | 638.34 | 26 |
| 6 | AWKPADPAGTHR | 10.49 | 436.23 | 669.34 | 26 |
| 7 | DEPVHGNMEILGNEAYGIK | 18.07 | 696 | 851.43 | 39 |
| 8 | DEPVHGNMEILGNEAYGIK | 18.07 | 696 | 1009.4 | 39 |
| 9 | DEPVHGNMEILGNEAYGIK | 18.07 | 696 | 1122.49 | 39 |
| 10 | DTVDGLIQPLMQK | 20.72 | 729.39 | 857.49 | 37 |
| 11 | DTVDGLIQPLMQK | 20.72 | 729.39 | 970.58 | 37 |
| 12 | DTVDGLIQPLMQK | 20.72 | 729.39 | 1027.6 | 37 |
| 13 | DTVDSLIQPLMQK | 21.62 | 744.39 | 857.49 | 38 |
| 14 | DTVDSLIQPLMQK | 21.62 | 744.39 | 1057.61 | 38 |
| 15 | DTVDSLIQPLMQK | 21.62 | 744.39 | 1172.63 | 38 |
| 16 | IQHALTATHTGYFK | 12.76 | 397.71 | 514.27 | 23 |
| 17 | IQHALTATHTGYFK | 12.76 | 397.71 | 615.31 | 23 |
| 18 | IQHALTATHTGYFK | 12.76 | 397.71 | 752.37 | 23 |
| 19 | LDGNSTLQK | 9.44 | 488.26 | 576.34 | 26 |
| 20 | LDGNSTLQK | 9.44 | 488.26 | 747.4 | 26 |
| 21 | LDGNSTLQK | 9.44 | 488.26 | 862.43 | 26 |
| 22 | LSLDK | 10.73 | 288.17 | 375.22 | 18 |
| 23 | LSLDK | 10.73 | 288.17 | 429.23 | 18 |
| 24 | LSLDK | 10.73 | 288.17 | 462.26 | 18 |
| 25 | LSLEQSVSHYVPELR | 20.3 | 586.31 | 776.43 | 33 |
| 26 | LSLEQSVSHYVPELR | 20.3 | 586.31 | 913.49 | 33 |
| 27 | LSLEQSVSHYVPELR | 20.3 | 586.31 | 1000.52 | 33 |
| 28 | NEPIHVNMEVLGNEAYGIR | 19.55 | 719.02 | 879.43 | 40 |

TABLE 21-continued

| Transition number | Peptide | Retention time (minutes) | (m/z) filtered in Q1 | (m/z) filtered in Q3 | Collision energy (eV) |
|---|---|---|---|---|---|
| 29 | NEPIHVNMEVLGNEAYGIR | 19.55 | 719.02 | 992.52 | 40 |
| 30 | NEPIHVNMEVLGNEAYGIR | 19.55 | 719.02 | 1163.55 | 40 |
| 31 | NNIPGMSVAVTIR | 18.3 | 457.92 | 559.36 | 27 |
| 32 | NNIPGMSVAVTIR | 18.3 | 686.37 | 933.52 | 35 |
| 33 | NNIPGMSVAVTIR | 18.3 | 686.37 | 1030.57 | 35 |
| 34 | NTDQLMAYLK | 18.78 | 598.8 | 625.34 | 31 |
| 35 | NTDQLMAYLK | 18.78 | 598.8 | 738.42 | 31 |
| 36 | NTDQLMAYLK | 18.78 | 598.8 | 981.51 | 31 |
| 37 | NTTQLMTYLK | 17.75 | 606.82 | 768.43 | 32 |
| 38 | NTTQLMTYLK | 17.75 | 606.82 | 896.49 | 32 |
| 39 | NTTQLMTYLK | 17.75 | 606.82 | 997.54 | 32 |
| 40 | NYIYNYGLASK | 15.9 | 653.33 | 752.39 | 34 |
| 41 | NYIYNYGLASK | 15.9 | 653.33 | 915.46 | 34 |
| 42 | NYIYNYGLASK | 15.9 | 653.33 | 1028.54 | 34 |
| 43 | SISHYVPELR | 15 | 400.88 | 514.3 | 24 |
| 44 | SISHYVPELR | 15 | 400.88 | 613.37 | 24 |
| 45 | SISHYVPELR | 15 | 400.88 | 776.43 | 24 |
| 46 | TFAAILASYAQASGK | 21.64 | 749.9 | 811.39 | 38 |
| 47 | TFAAILASYAQASGK | 21.64 | 749.9 | 882.43 | 38 |
| 48 | TFAAILASYAQASGK | 21.64 | 749.9 | 995.52 | 38 |
| 49 | TLLPK | 12.05 | 286.19 | 357.25 | 18 |
| 50 | TLLPK | 12.05 | 286.19 | 425.28 | 18 |
| 51 | TLLPK | 12.05 | 286.19 | 470.33 | 18 |
| 52 | TNASDLIR | 12.95 | 445.24 | 516.31 | 25 |
| 53 | TNASDLIR | 12.95 | 445.24 | 603.35 | 25 |
| 54 | TNASDLIR | 12.95 | 445.24 | 674.38 | 25 |
| 55 | VTVAYK | 10.34 | 340.7 | 381.21 | 20 |
| 56 | VTVAYK | 10.34 | 340.7 | 480.28 | 20 |
| 57 | VTVAYK | 10.34 | 340.7 | 581.33 | 20 |

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 16

Identification of a Resistance to ACT Beta-Lactams

The samples corresponding to a species able to comprise an ACT resistance mechanism can be detected by employing the following method.

Each sample is treated according to example 5, then analysed according to example 6 by detecting the peptides from TABLE 22 instead of the peptides from TABLE 3.

TABLE 22

| Transition number | Peptide | Retention time (minutes) | (m/z) filtered in Q1 | (m/z) filtered in Q3 | Collision energy (eV) |
|---|---|---|---|---|---|
| 1 | AEEAHYAWGYR | 14.21 | 676.81 | 815.38 | 34.8 |
| 2 | AEEAHYAWGYR | 14.21 | 676.81 | 952.44 | 34.8 |
| 3 | AEEAHYAWGYR | 14.21 | 676.81 | 1152.52 | 34.8 |
| 4 | AIHVSPGMLDAEAYGVK | 18.71 | 586.64 | 666.35 | 33.3 |
| 5 | AIHVSPGMLDAEAYGVK | 18.71 | 586.64 | 737.38 | 33.3 |
| 6 | AIHVSPGMLDAEAYGVK | 18.74 | 586.64 | 852.41 | 33.3 |
| 7 | AVHVSPGMLDAEAYGVK | 17.93 | 581.96 | 666.35 | 33.1 |
| 8 | AVHVSPGMLDAEAYGVK | 17.93 | 581.96 | 737.38 | 33.1 |
| 9 | AVHVSPGMLDAEAYGVK | 17.93 | 581.96 | 852.41 | 33.1 |
| 10 | DMANWVMVNMKPDSLQDSSLK | 22.23 | 803.71 | 896.45 | 44.2 |
| 11 | DMANWVMVNMKPDSLQDSSLK | 22.21 | 803.71 | 989.49 | 44.2 |
| 12 | DMANWVMVNMKPDSLQDSSLK | 22.23 | 803.71 | 1082.03 | 44.2 |
| 13 | DNASLLR | 12.76 | 394.72 | 401.29 | 22.4 |
| 14 | DNASLLR | 12.76 | 394.72 | 488.32 | 22.4 |
| 15 | DNASLLR | 12.76 | 394.72 | 559.36 | 22.4 |
| 16 | EGITLAQSR | 13.23 | 487.77 | 574.33 | 26.5 |
| 17 | EGITLAQSR | 13.25 | 487.77 | 675.38 | 26.5 |
| 18 | EGITLAQSR | 13.23 | 487.77 | 788.46 | 26.5 |
| 19 | EVNPPAPPVNASWVHK | 16.59 | 581.31 | 700.38 | 33.1 |
| 20 | EVNPPAPPVNASWVHK | 16.61 | 581.31 | 757.4 | 33.1 |
| 21 | EVNPPAPPVNASWVHK | 16.61 | 581.31 | 1134.61 | 33.1 |
| 22 | FYQNWQPQWKPGTTR | 17.43 | 968.98 | 531.29 | 47.6 |
| 23 | FYQNWQPQWKPGTTR | 17.43 | 968.98 | 1070.57 | 47.6 |
| 24 | FYQNWQPQWKPGTTR | 17.43 | 968.98 | 1198.63 | 47.6 |
| 25 | GEISLDDPVTR | 16.1 | 601.31 | 702.34 | 31.5 |
| 26 | GEISLDDPVTR | 16.1 | 601.31 | 815.43 | 31.5 |
| 27 | GEISLDDPVTR | 16.12 | 601.31 | 902.46 | 31.5 |
| 28 | GEISLGDPVTK | 15.7 | 558.3 | 559.31 | 29.6 |
| 29 | GEISLGDPVTK | 15.68 | 558.3 | 616.33 | 29.6 |
| 30 | GEISLGDPVTK | 15.68 | 558.3 | 816.45 | 29.6 |
| 31 | GLTLAQSR | 12.67 | 423.25 | 461.25 | 23.6 |
| 32 | GLTLAQSR | 12.68 | 423.25 | 574.33 | 23.6 |
| 33 | GLTLAQSR | 12.65 | 423.25 | 675.38 | 23.6 |
| 34 | LDHTWINVPK | 16.79 | 611.83 | 497.78 | 31.9 |

TABLE 22-continued

| Transition number | Peptide | Retention time (minutes) | (m/z) filtered in Q1 | (m/z) filtered in Q3 | Collision energy (eV) |
|---|---|---|---|---|---|
| 35 | LDHTWINVPK | 16.79 | 611.83 | 756.44 | 31.9 |
| 36 | LDHTWINVPK | 16.79 | 611.83 | 857.49 | 31.9 |
| 37 | MLDLATYTAGGLPLQVPDEVK | 23.87 | 744.39 | 512.79 | 41.2 |
| 38 | MLDLATYTAGGLPLQVPDEVK | 23.89 | 744.39 | 587.3 | 41.2 |
| 39 | MLDLATYTAGGLPLQVPDEVK | 23.89 | 1116.09 | 587.3 | 54.1 |
| 40 | QGIALAQSR | 12.72 | 472.27 | 574.33 | 25.8 |
| 41 | QGIALAQSR | 12.7 | 472.27 | 645.37 | 25.8 |
| 42 | QGIALAQSR | 12.72 | 472.27 | 758.45 | 25.8 |
| 43 | QGISLAQSR | 12.83 | 480.27 | 661.36 | 26.1 |
| 44 | QGISLAQSR | 12.83 | 480.27 | 774.45 | 26.1 |
| 45 | QGISLAQSR | 12.83 | 480.27 | 831.47 | 26.1 |
| 46 | QIGIVMLANK | 18.95 | 543.82 | 576.32 | 28.9 |
| 47 | QIGIVMLANK | 18.95 | 543.82 | 675.39 | 28.9 |
| 48 | QIGIVMLANK | 18.95 | 543.82 | 845.49 | 28.9 |
| 49 | QIGIVMLANTSYPNPAR | 21.86 | 615.66 | 554.31 | 34.8 |
| 50 | QIGIVMLANTSYPNPAR | 21.86 | 615.66 | 717.37 | 34.8 |
| 51 | QIGIVMLANTSYPNPAR | 21.86 | 922.99 | 554.31 | 45.6 |
| 52 | QLAEVVANTVTPLMK | 21.94 | 807.45 | 488.29 | 40.5 |
| 53 | QLAEVVANTVTPLMK | 21.94 | 807.45 | 974.53 | 40.5 |
| 54 | QLAEVVANTVTPLMK | 21.94 | 807.45 | 1073.6 | 40.5 |
| 55 | QLAEVVER | 13.05 | 472.26 | 502.3 | 25.8 |
| 56 | QLAEVVER | 13.03 | 472.26 | 631.34 | 25.8 |
| 57 | QLAEVVER | 13.03 | 472.26 | 702.38 | 25.8 |
| 58 | QLGIVMLANK | 19.27 | 543.82 | 576.32 | 28.9 |
| 59 | QLGIVMLANK | 19.27 | 543.82 | 675.39 | 28.9 |
| 60 | QLGIVMLANK | 19.27 | 543.82 | 845.49 | 28.9 |
| 61 | SYPNPAR | 9.83 | 402.7 | 343.21 | 22.7 |
| 62 | SYPNPAR | 9.83 | 402.7 | 457.25 | 22.7 |
| 63 | SYPNPAR | 9.83 | 402.7 | 554.31 | 22.7 |
| 64 | TFTGVLGGDAIAR | 18.42 | 639.35 | 659.35 | 33.1 |
| 65 | TFTGVLGGDAIAR | 18.39 | 639.35 | 772.43 | 33.1 |
| 66 | TFTGVLGGDAIAR | 18.42 | 639.35 | 1029.57 | 33.1 |
| 67 | TGSTGGFGSYVAFIPEK | 21.14 | 573.29 | 373.21 | 32.7 |
| 68 | TGSTGGFGSYVAFIPEK | 21.14 | 573.29 | 633.36 | 32.7 |

TABLE 22-continued

| Transition number | Peptide | Retention time (minutes) | (m/z) filtered in Q1 | (m/z) filtered in Q3 | Collision energy (eV) |
|---|---|---|---|---|---|
| 69 | TGSTGGFGSYVAFIPEK | 21.14 | 573.29 | 704.4 | 32.7 |
| 70 | TVTPLMK | 13.65 | 395.23 | 488.29 | 22.4 |
| 71 | TVTPLMK | 13.65 | 395.23 | 589.34 | 22.4 |
| 72 | TVTPLMK | 13.62 | 395.23 | 688.41 | 22.4 |
| 73 | TVVEGSDNK | 4.64 | 474.74 | 520.24 | 25.9 |
| 74 | TVVEGSDNK | 4.64 | 474.74 | 649.28 | 25.9 |
| 75 | TVVEGSDNK | 4.64 | 474.74 | 748.35 | 25.9 |
| 76 | VALAPLPAR | 15.96 | 454.29 | 553.35 | 25 |
| 77 | VALAPLPAR | 15.99 | 454.29 | 624.38 | 25 |
| 78 | VALAPLPAR | 15.96 | 454.29 | 737.47 | 25 |
| 79 | VALAPLPVAEVNPPAPPVK | 21.12 | 627.04 | 705.43 | 35.4 |
| 80 | VALAPLPVAEVNPPAPPVK | 21.14 | 627.04 | 762.94 | 35.4 |
| 81 | VALAPLPVAEVNPPAPPVK | 21.14 | 627.04 | 819.47 | 35.4 |
| 82 | VEAAYR | 8.39 | 354.69 | 409.22 | 20.6 |
| 83 | VEAAYR | 8.39 | 354.69 | 480.26 | 20.6 |
| 84 | VEAAYR | 8.39 | 354.69 | 609.3 | 20.6 |
| 85 | VFKPLK | 11.66 | 366.24 | 357.25 | 21.1 |
| 86 | VFKPLK | 11.66 | 366.24 | 485.35 | 21.1 |
| 87 | VFKPLK | 11.66 | 366.24 | 632.41 | 21.1 |
| 88 | VGAMYQGLGWEMLNWPVDAK | 26.23 | 755.7 | 529.3 | 41.8 |
| 89 | VGAMYQGLGWEMLNWPVDAK | 26.23 | 755.7 | 829.42 | 41.8 |
| 90 | VGAMYQGLGWEMLNWPVDAK | 26.26 | 755.7 | 1073.55 | 41.8 |
| 91 | VLKPLK | 10.38 | 349.25 | 357.25 | 20.4 |
| 92 | VLKPLK | 10.36 | 349.25 | 485.35 | 20.4 |
| 93 | VLKPLK | 10.36 | 349.25 | 598.43 | 20.4 |
| 94 | VSPGMLDAQAYGMK | 17.62 | 734.35 | 641.3 | 37.3 |
| 95 | VSPGMLDAQAYGMK | 17.62 | 734.35 | 883.4 | 37.3 |
| 96 | VSPGMLDAQAYGMK | 17.62 | 734.35 | 996.48 | 37.3 |
| 97 | VSPGMLDAQAYGVK | 17.36 | 718.37 | 625.32 | 36.6 |
| 98 | VSPGMLDAQAYGVK | 17.36 | 718.37 | 851.43 | 36.6 |
| 99 | VSPGMLDAQAYGVK | 17.36 | 718.37 | 964.51 | 36.6 |
| 100 | YWPQLTGK | 17.33 | 496.76 | 322.19 | 26.9 |

TABLE 22-continued

| Transition number | Peptide | Retention time (minutes) | (m/z) filtered in Q1 | (m/z) filtered in Q3 | Collision energy (eV) |
|---|---|---|---|---|---|
| 101 | YWPQLTGK | 17.33 | 496.76 | 643.38 | 26.9 |
| 102 | YWPQLTGK | 17.31 | 496.76 | 829.46 | 26.9 |

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 17

Identification of a Resistance to CMY Beta-Lactams

The samples corresponding to a species able to comprise a CMY resistance mechanism can be detected by employing the following method.

Each sample is treated according to example 5, then analysed according to example 6 by detecting the peptides from TABLE 23 instead of the peptides from TABLE 3.

TABLE 23

| Transition number | Peptide | Retention time (minutes) | (m/z) filtered in Q1 | (m/z) filtered in Q3 | Collision energy (eV) |
|---|---|---|---|---|---|
| 1 | AALLR | 10.85 | 272.18 | 288.2 | 17 |
| 2 | AALLR | 10.85 | 272.18 | 401.29 | 17 |
| 3 | AALLR | 10.85 | 272.18 | 472.32 | 17 |
| 4 | ADSIINGSDNK | 10.62 | 567.28 | 747.36 | 30 |
| 5 | ADSIINGSDNK | 10.62 | 567.28 | 860.45 | 30 |
| 6 | ADSIINGSDNK | 10.62 | 567.28 | 947.48 | 30 |
| 7 | AELLR | 11.13 | 301.19 | 401.29 | 18 |
| 8 | AELLR | 11.13 | 301.19 | 427.26 | 18 |
| 9 | AELLR | 11.13 | 301.19 | 530.33 | 18 |
| 10 | ALQQAISLTHK | 13.79 | 605.35 | 698.42 | 32 |
| 11 | ALQQAISLTHK | 13.79 | 605.35 | 769.46 | 32 |
| 12 | ALQQAISLTHK | 13.79 | 605.35 | 897.52 | 32 |
| 13 | AVHVSPGQLDAEAYGVK | 15.59 | 580.97 | 737.38 | 33 |
| 14 | AVHVSPGQLDAEAYGVK | 15.59 | 580.97 | 776.4 | 33 |
| 15 | AVHVSPGQLDAEAYGVK | 15.59 | 580.97 | 852.41 | 33 |
| 16 | DYAC[CAM]GYR | 9.86 | 452.68 | 555.23 | 25 |
| 17 | DYAC[CAM]GYR | 9.86 | 452.68 | 626.27 | 25 |
| 18 | DYAC[CAM]GYR | 9.86 | 452.68 | 789.33 | 25 |
| 19 | DYALGYR | 13.44 | 429.21 | 508.29 | 24 |

TABLE 23-continued

| Transition number | Peptide | Retention time (minutes) | (m/z) filtered in Q1 | (m/z) filtered in Q3 | Collision energy (eV) |
|---|---|---|---|---|---|
| 20 | DYALGYR | 13.44 | 429.21 | 579.32 | 24 |
| 21 | DYALGYR | 13.44 | 429.21 | 742.39 | 24 |
| 22 | EGKPVHASPGQLDAEAYGVK | 13.47 | 685.02 | 737.38 | 38 |
| 23 | EGKPVHASPGQLDAEAYGVK | 13.47 | 685.02 | 852.41 | 38 |
| 24 | EGKPVHASPGQLDAEAYGVK | 13.47 | 685.02 | 965.49 | 38 |
| 25 | EGKPVHGSPGQLDAEAYGVK | 13.08 | 510.51 | 537.3 | 29 |
| 26 | EGKPVHGSPGQLDAEAYGVK | 13.08 | 510.51 | 666.35 | 29 |
| 27 | EGKPVHGSPGQLDAEAYGVK | 13.08 | 510.51 | 737.38 | 29 |
| 28 | EGKPVHVSPEQLDAEAYGVK | 15.07 | 539.03 | 737.38 | 30 |
| 29 | EGKPVHVSPEQLDAEAYGVK | 15.07 | 539.03 | 852.41 | 30 |
| 30 | EGKPVHVSPEQLDAEAYGVK | 15.07 | 718.37 | 852.41 | 40 |
| 31 | EGKPVHVSPGQFDAEAYGVK | 15.01 | 529.52 | 537.3 | 29 |
| 32 | EGKPVHVSPGQFDAEAYGVK | 15.01 | 529.52 | 632.33 | 29 |
| 33 | EGKPVHVSPGQFDAEAYGVK | 15.01 | 705.69 | 999.48 | 39 |
| 34 | EGKPVHVSPGQLDAEAYC[CAM]VK | 14.63 | 546.77 | 569.28 | 30 |
| 35 | EGKPVHVSPGQLDAEAYC[CAM]VK | 14.63 | 546.77 | 640.31 | 30 |
| 36 | EGKPVHVSPGQLDAEAYC[CAM]VK | 14.63 | 546.77 | 769.35 | 30 |
| 37 | EGKPVHVSPGQLDAEAYGVK | 14.65 | 521.02 | 537.3 | 29 |
| 38 | EGKPVHVSPGQLDAEAYGVK | 14.65 | 521.02 | 737.38 | 29 |
| 39 | EGKPVHVSPGQLDAEAYGVK | 14.65 | 521.02 | 852.41 | 29 |
| 40 | EGKPVHVSPGQLDAGAYGVK | 14.19 | 503.02 | 594.32 | 28 |
| 41 | EGKPVHVSPGQLDAGAYGVK | 14.19 | 503.02 | 665.36 | 28 |
| 42 | EGKPVHVSPGQLDAGAYGVK | 14.19 | 503.02 | 780.39 | 28 |
| 43 | EGKPVHVSPGQLNAEAYGVK | 14.25 | 520.78 | 537.3 | 29 |
| 44 | EGKPVHVSPGQLNAEAYGVK | 14.25 | 520.78 | 737.38 | 29 |
| 45 | EGKPVHVSPGQLNAEAYGVK | 14.25 | 520.78 | 834.45 | 29 |
| 46 | EGKPVHVTPGQLDAEAYGVK | 14.72 | 524.53 | 848.46 | 29 |
| 47 | EGKPVHVTPGQLDAEAYGVK | 14.72 | 699.03 | 852.41 | 39 |
| 48 | EGKPVHVTPGQLDAEAYGVK | 14.72 | 699.03 | 1247.63 | 39 |
| 49 | EGKPVYVSPGQLDAEAYGVK | 16.73 | 703.03 | 852.41 | 39 |
| 50 | EGKPVYVSPGQLDAEAYGVK | 16.73 | 703.03 | 860.45 | 39 |
| 51 | EGKPVYVSPGQLDAEAYGVK | 16.73 | 703.03 | 1247.63 | 39 |
| 52 | ESGASVSEQTLFDIGSVSK | 20.37 | 970.98 | 976.42 | 48 |
| 53 | ESGASVSEQTLFDIGSVSK | 20.37 | 970.98 | 1066.58 | 48 |
| 54 | ESGASVSEQTLFDIGSVSK | 20.37 | 970.98 | 1194.64 | 48 |
| 55 | FSDPVTK | 11.61 | 397.21 | 559.31 | 22 |
| 56 | FSDPVTK | 11.61 | 397.21 | 646.34 | 22 |
| 57 | FSDPVTK | 11.61 | 397.21 | 647.3 | 22 |

TABLE 23-continued

| Transition number | Peptide | Retention time (minutes) | (m/z) filtered in Q1 | (m/z) filtered in Q3 | Collision energy (eV) |
|---|---|---|---|---|---|
| 58 | FYQNWQPQWAPGAK | 18.61 | 860.92 | 867.38 | 43 |
| 59 | FYQNWQPQWAPGAK | 18.61 | 860.92 | 982.51 | 43 |
| 60 | FYQNWQPQWAPGAK | 18.61 | 860.92 | 1168.59 | 43 |
| 61 | FYQNWQPQWTPGAK | 18.53 | 875.92 | 884.46 | 44 |
| 62 | FYQNWQPQWTPGAK | 18.53 | 875.92 | 1012.52 | 44 |
| 63 | FYQNWQPQWTPGAK | 18.53 | 875.92 | 1198.6 | 44 |
| 64 | HAPWLK | 11.85 | 376.22 | 543.33 | 22 |
| 65 | HAPWLK | 11.85 | 376.22 | 605.32 | 22 |
| 66 | HAPWLK | 11.85 | 376.22 | 614.37 | 22 |
| 67 | IPDDVR | 9.9 | 357.69 | 504.24 | 21 |
| 68 | IPDDVR | 9.9 | 357.69 | 540.27 | 21 |
| 69 | IPDDVR | 9.9 | 357.69 | 601.29 | 21 |
| 70 | LAHTWIK | 12.56 | 434.76 | 547.32 | 24 |
| 71 | LAHTWIK | 12.56 | 434.76 | 684.38 | 24 |
| 72 | LAHTWIK | 12.56 | 434.76 | 755.42 | 24 |
| 73 | LAHTWITVPENEQK | 15.87 | 555.96 | 609.31 | 32 |
| 74 | LAHTWITVPENEQK | 15.87 | 555.96 | 744.35 | 32 |
| 75 | LAHTWITVPENEQK | 15.87 | 555.96 | 823.45 | 32 |
| 76 | LAHTWITVPQSEQK | 15.75 | 546.63 | 1029.56 | 31 |
| 77 | LAHTWITVPQSEQK | 15.75 | 819.44 | 1029.56 | 41 |
| 78 | LAHTWITVPQSEQK | 15.75 | 819.44 | 1215.64 | 41 |
| 79 | LDAEAYGVK | 12.86 | 483.25 | 537.3 | 26 |
| 80 | LDAEAYGVK | 12.86 | 483.25 | 737.38 | 26 |
| 81 | LDAEAYGVK | 12.86 | 483.25 | 852.41 | 26 |
| 82 | LLHLATYTAGGLPLK | 19.26 | 523.31 | 584.38 | 30 |
| 83 | LLHLATYTAGGLPLK | 19.26 | 523.31 | 655.41 | 30 |
| 84 | LLHLATYTAGGLPLK | 19.26 | 523.31 | 756.46 | 30 |
| 85 | LLHLATYTAGGLPLQFPDDVR | 22.76 | 575.06 | 601.29 | 32 |
| 86 | LLHLATYTAGGLPLQFPDDVR | 22.76 | 766.41 | 1086.56 | 42 |
| 87 | LLHLATYTAGGLPLQFPDDVR | 22.76 | 766.41 | 1098.59 | 42 |
| 88 | NYAWGYR | 14.18 | 465.22 | 581.28 | 25 |
| 89 | NYAWGYR | 14.18 | 465.22 | 652.32 | 25 |
| 90 | NYAWGYR | 14.18 | 465.22 | 815.38 | 25 |
| 91 | NYPIPAR | 12.32 | 415.73 | 456.29 | 23 |
| 92 | NYPIPAR | 12.32 | 415.73 | 553.35 | 23 |
| 93 | NYPIPAR | 12.32 | 415.73 | 716.41 | 23 |
| 94 | NYPNEAR | 6.92 | 432.2 | 489.21 | 24 |
| 95 | NYPNEAR | 6.92 | 432.2 | 586.29 | 24 |

TABLE 23-continued

| Transition number | Peptide | Retention time (minutes) | (m/z) filtered in Q1 | (m/z) filtered in Q3 | Collision energy (eV) |
|---|---|---|---|---|---|
| 96 | NYPNEAR | 6.92 | 432.2 | 749.36 | 24 |
| 97 | SLC[CAM]C[CAM]ALLLTAPLSTFAAAK | 26.05 | 670.02 | 905.51 | 38 |
| 98 | SLC[CAM]C[CAM]ALLLTAPLSTFAAAK | 26.05 | 1004.53 | 1077.59 | 49 |
| 99 | SLC[CAM]C[CAM]ALLLTAPLSTFAAAK | 26.05 | 1004.53 | 1190.68 | 49 |
| 100 | SNVTDMAR | 10.56 | 447.21 | 492.22 | 25 |
| 101 | SNVTDMAR | 10.56 | 447.21 | 593.27 | 25 |
| 102 | SNVTDMAR | 10.56 | 447.21 | 692.34 | 25 |
| 103 | TALLHFYQNWQPQWAPGAK | 21.7 | 752.72 | 854.45 | 42 |
| 104 | TALLHFYQNWQPQWAPGAK | 21.7 | 752.72 | 974.51 | 42 |
| 105 | TALLHFYQNWQPQWAPGAK | 21.7 | 752.72 | 1088.55 | 42 |
| 106 | TDSIINGSDSK | 10.86 | 568.78 | 720.35 | 30 |
| 107 | TDSIINGSDSK | 10.86 | 568.78 | 833.44 | 30 |
| 108 | TDSIINGSDSK | 10.86 | 568.78 | 920.47 | 30 |
| 109 | TFIGVLGGDAIAR | 20.29 | 645.36 | 659.35 | 33 |
| 110 | TFIGVLGGDAIAR | 20.29 | 645.36 | 772.43 | 33 |
| 111 | TFIGVLGGDAIAR | 20.29 | 645.36 | 928.52 | 33 |
| 112 | TFNGVLGGDC[CAM]IAR | 16.85 | 690.34 | 748.34 | 35 |
| 113 | TFNGVLGGDC[CAM]IAR | 16.85 | 690.34 | 861.42 | 35 |
| 114 | TFNGVLGGDC[CAM]IAR | 16.85 | 690.34 | 1131.56 | 35 |
| 115 | TFNGVLGGEAIAR | 17.2 | 435.57 | 673.36 | 26 |
| 116 | TFNGVLGGEAIAR | 17.2 | 652.85 | 673.36 | 34 |
| 117 | TFNGVLGGEAIAR | 17.2 | 652.85 | 786.45 | 34 |
| 118 | TGSTVGFGSYVAFVPEK | 20.65 | 873.44 | 1039.55 | 43 |
| 119 | TGSTVGFGSYVAFVPEK | 20.65 | 873.44 | 1096.57 | 43 |
| 120 | TGSTVGFGSYVAFVPEK | 20.65 | 873.44 | 1243.64 | 43 |
| 121 | TGYTGGFGSYVAFVPEK | 20.58 | 890.43 | 1039.55 | 44 |
| 122 | TGYTGGFGSYVAFVPEK | 20.58 | 890.43 | 1096.57 | 44 |
| 123 | TGYTGGFGSYVAFVPEK | 20.58 | 890.43 | 1243.64 | 44 |
| 124 | TLQQGIELAQSR | 15.04 | 448.58 | 461.25 | 26 |
| 125 | TLQQGIELAQSR | 15.04 | 672.37 | 703.37 | 35 |
| 126 | TLQQGIELAQSR | 15.04 | 672.37 | 873.48 | 35 |
| 127 | TSSADLLAFVK | 20.76 | 576.32 | 805.48 | 30 |
| 128 | TSSADLLAFVK | 20.76 | 576.32 | 876.52 | 30 |
| 129 | TSSADLLAFVK | 20.76 | 576.32 | 963.55 | 30 |
| 130 | TSSADLLR | 12.72 | 431.73 | 587.35 | 24 |
| 131 | TSSADLLR | 12.72 | 431.73 | 674.38 | 24 |
| 132 | TSSADLLR | 12.72 | 431.73 | 761.42 | 24 |
| 133 | TYYFTWGK | 18.46 | 533.26 | 801.39 | 28 |

TABLE 23-continued

| Transition number | Peptide | Retention time (minutes) | (m/z) filtered in Q1 | (m/z) filtered in Q3 | Collision energy (eV) |
|---|---|---|---|---|---|
| 134 | TYYFTWGK | 18.46 | 533.26 | 919.4 | 28 |
| 135 | TYYFTWGK | 18.46 | 533.26 | 964.46 | 28 |
| 136 | VAALPAVEVNPPAPAVK | 18.04 | 821.98 | 964.55 | 41 |
| 137 | VAALPAVEVNPPAPAVK | 18.04 | 821.98 | 1021.57 | 41 |
| 138 | VAALPAVEVNPPAPAVK | 18.04 | 821.98 | 1120.64 | 41 |
| 139 | VAFAALPAVEVNPPAPAVK | 21.03 | 621.02 | 679.41 | 35 |
| 140 | VAFAALPAVEVNPPAPAVK | 21.03 | 621.02 | 793.46 | 35 |
| 141 | VAFAALPAVEVNPPAPAVK | 21.03 | 931.03 | 1021.57 | 46 |
| 142 | VALAAIPAVEVNPPAPAVK | 20.17 | 457.52 | 679.41 | 26 |
| 143 | VALAAIPAVEVNPPAPAVK | 20.17 | 609.7 | 679.41 | 34 |
| 144 | VALAAIPAVEVNPPAPAVK | 20.17 | 609.7 | 793.46 | 34 |
| 145 | VALAALHTVEVNPPAPAVK | 18 | 475.03 | 582.36 | 27 |
| 146 | VALAALHTVEVNPPAPAVK | 18 | 475.03 | 679.41 | 27 |
| 147 | VALAALHTVEVNPPAPAVK | 18 | 633.03 | 679.41 | 36 |
| 148 | VALAALPAVEINPPAPAVK | 21.5 | 614.37 | 679.41 | 35 |
| 149 | VALAALPAVEINPPAPAVK | 21.5 | 614.37 | 793.46 | 35 |
| 150 | VALAALPAVEINPPAPAVK | 21.5 | 614.37 | 935.56 | 35 |
| 151 | VALAALPTVEVNPPAPAVK | 20.41 | 619.7 | 679.41 | 35 |
| 152 | VALAALPTVEVNPPAPAVK | 20.41 | 619.7 | 793.46 | 35 |
| 153 | VALAALPTVEVNPPAPAVK | 20.41 | 619.7 | 1021.57 | 35 |
| 154 | VAPAVEVNPPAPAVK | 15.16 | 729.92 | 793.46 | 37 |
| 155 | VAPAVEVNPPAPAVK | 15.16 | 729.92 | 892.53 | 37 |
| 156 | VAPAVEVNPPAPAVK | 15.16 | 729.92 | 1021.57 | 37 |
| 157 | VEAYWR | 13.37 | 412.21 | 524.26 | 23 |
| 158 | VEAYWR | 13.37 | 412.21 | 595.3 | 23 |
| 159 | VEAYWR | 13.37 | 412.21 | 724.34 | 23 |
| 160 | VILEANPTAAPR | 14.25 | 417.91 | 612.35 | 25 |
| 161 | VILEANPTAAPR | 14.25 | 626.36 | 797.43 | 33 |
| 162 | VILEANPTAAPR | 14.25 | 626.36 | 1039.55 | 33 |
| 163 | VSLEANPTAAPR | 13.15 | 613.33 | 726.39 | 32 |
| 164 | VSLEANPTAAPR | 13.15 | 613.33 | 797.43 | 32 |
| 165 | VSLEANPTAAPR | 13.15 | 613.33 | 926.47 | 32 |
| 166 | WIQVNMDASR | 16.68 | 610.3 | 693.3 | 32 |
| 167 | WIQVNMDASR | 16.68 | 610.3 | 792.37 | 32 |
| 168 | WIQVNMDASR | 16.68 | 610.3 | 920.43 | 32 |
| 169 | WVQANMDASR | 12.82 | 589.27 | 764.34 | 31 |
| 170 | WVQANMDASR | 12.82 | 589.27 | 892.39 | 31 |
| 171 | WVQANMDASR | 12.82 | 589.27 | 991.46 | 31 |

TABLE 23-continued

| Transition number | Peptide | Retention time (minutes) | (m/z) filtered in Q1 | (m/z) filtered in Q3 | Collision energy (eV) |
|---|---|---|---|---|---|
| 172 | WVQVNMDASR | 15.27 | 603.29 | 792.37 | 32 |
| 173 | WVQVNMDASR | 15.27 | 603.29 | 920.43 | 32 |
| 174 | WVQVNMDASR | 15.27 | 603.29 | 1019.49 | 32 |
| 175 | YWSELTGK | 14.9 | 492.25 | 547.31 | 27 |
| 176 | YWSELTGK | 14.9 | 492.25 | 634.34 | 27 |
| 177 | YWSELTGK | 14.9 | 492.25 | 820.42 | 27 |

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 18

Identification of a Resistance to CTX-M Beta-Lactams

The samples corresponding to a species able to comprise a CTX-M resistance mechanism can be detected by employing the following method.

Each sample is treated according to example 5, then analysed according to example 6 by detecting the peptides from TABLE 24 instead of the peptides from TABLE 3.

TABLE 24

| Transition number | Peptide | Retention time (minutes) | (m/z) filtered in Q1 | (m/z) filtered in Q3 | Collision energy (eV) |
|---|---|---|---|---|---|
| 1 | AGADVASLR | 11.83 | 430.24 | 446.27 | 24 |
| 2 | AGADVASLR | 11.83 | 430.24 | 485.24 | 24 |
| 3 | AGADVASLR | 11.83 | 430.24 | 660.37 | 24 |
| 4 | AGLPASWVVGDK | 18.32 | 600.32 | 790.41 | 31 |
| 5 | AGLPASWVVGDK | 18.32 | 600.32 | 861.45 | 31 |
| 6 | AGLPASWVVGDK | 18.32 | 600.32 | 958.5 | 31 |
| 7 | AGLPTSWTAGDK | 15.73 | 602.3 | 764.36 | 32 |
| 8 | AGLPTSWTAGDK | 15.73 | 602.3 | 865.41 | 32 |
| 9 | AGLPTSWTAGDK | 15.73 | 602.3 | 962.46 | 32 |
| 10 | AGLPTSWTVGDR | 17.31 | 630.32 | 820.39 | 33 |
| 11 | AGLPTSWTVGDR | 17.31 | 630.32 | 921.44 | 33 |
| 12 | AGLPTSWTVGDR | 17.31 | 630.32 | 1018.5 | 33 |
| 13 | AGLPTSWVVGDK | 18.62 | 615.33 | 790.41 | 32 |
| 14 | AGLPTSWVVGDK | 18.62 | 615.33 | 891.46 | 32 |
| 15 | AGLPTSWVVGDK | 18.62 | 615.33 | 988.51 | 32 |

TABLE 24-continued

| Transition number | Peptide | Retention time (minutes) | (m/z) filtered in Q1 | (m/z) filtered in Q3 | Collision energy (eV) |
|---|---|---|---|---|---|
| 16 | AIGDDTFR | 12.79 | 447.72 | 653.29 | 25 |
| 17 | AIGDDTFR | 12.79 | 447.72 | 710.31 | 25 |
| 18 | AIGDDTFR | 12.79 | 447.72 | 823.39 | 25 |
| 19 | AMAVAAVLK | 16.36 | 437.26 | 501.34 | 24 |
| 20 | AMAVAAVLK | 16.36 | 437.26 | 600.41 | 24 |
| 21 | AMAVAAVLK | 16.36 | 437.26 | 671.45 | 24 |
| 22 | APLILVTYFTQPEQK | 23.95 | 583.33 | 730.37 | 33 |
| 23 | APLILVTYFTQPEQK | 23.95 | 874.49 | 1040.5 | 43 |
| 24 | APLILVTYFTQPEQK | 23.95 | 874.49 | 1141.55 | 43 |
| 25 | APLVLVTYFTQPEPK | 23.37 | 568.32 | 699.37 | 32 |
| 26 | APLVLVTYFTQPEPK | 23.37 | 568.32 | 846.44 | 32 |
| 27 | APLVLVTYFTQPEPK | 23.37 | 851.97 | 1110.55 | 42 |
| 28 | APLVLVTYFTQPQQNAENR | 22.93 | 730.38 | 956.45 | 41 |
| 29 | APLVLVTYFTQPQQNAENR | 22.93 | 1095.07 | 1185.56 | 53 |
| 30 | APLVLVTYFTQPQQNAENR | 22.93 | 1095.07 | 1233.69 | 53 |
| 31 | APLVLVTYFTQPQQNAER | 23.02 | 692.37 | 745.36 | 39 |
| 32 | APLVLVTYFTQPQQNAER | 23.02 | 692.37 | 842.41 | 39 |
| 33 | APLVLVTYFTQPQQNAER | 23.02 | 692.37 | 857.51 | 39 |
| 34 | APLVLVTYFTQSEPK | 23.53 | 564.98 | 689.35 | 32 |
| 35 | APLVLVTYFTQSEPK | 23.53 | 846.96 | 1100.53 | 42 |
| 36 | APLVLVTYFTQSEPK | 23.53 | 846.96 | 1199.59 | 42 |
| 37 | AQLVAWLK | 19.52 | 464.78 | 517.31 | 25 |
| 38 | AQLVAWLK | 19.52 | 464.78 | 616.38 | 25 |
| 39 | AQLVAWLK | 19.52 | 464.78 | 729.47 | 25 |
| 40 | AQLVMWLK | 20.53 | 494.79 | 577.32 | 27 |
| 41 | AQLVMWLK | 20.53 | 494.79 | 676.39 | 27 |
| 42 | AQLVMWLK | 20.53 | 494.79 | 789.47 | 27 |
| 43 | ASDLVNYNPIAEK | 16.72 | 717.37 | 834.44 | 37 |
| 44 | ASDLVNYNPIAEK | 16.72 | 717.37 | 948.48 | 37 |
| 45 | ASDLVNYNPIAEK | 16.72 | 717.37 | 1047.55 | 37 |
| 46 | DFLAAAAK | 14.5 | 403.72 | 431.26 | 23 |
| 47 | DFLAAAAK | 14.5 | 403.72 | 518.26 | 23 |
| 48 | DFLAAAAK | 14.5 | 403.72 | 544.35 | 23 |
| 49 | DILASAAK | 12.62 | 394.73 | 447.26 | 22 |
| 50 | DILASAAK | 12.62 | 394.73 | 560.34 | 22 |
| 51 | DILASAAK | 12.62 | 394.73 | 571.31 | 22 |
| 52 | DNTQVLYR | 12.19 | 504.76 | 550.33 | 27 |
| 53 | DNTQVLYR | 12.19 | 504.76 | 678.39 | 27 |

TABLE 24-continued

| Transition number | Peptide | Retention time (minutes) | (m/z) filtered in Q1 | (m/z) filtered in Q3 | Collision energy (eV) |
|---|---|---|---|---|---|
| 54 | DNTQVLYR | 12.19 | 504.76 | 779.44 | 27 |
| 55 | DTTTPLAMAQALR | 19.92 | 694.86 | 760.41 | 36 |
| 56 | DTTTPLAMAQALR | 19.92 | 694.86 | 873.5 | 36 |
| 57 | DTTTPLAMAQALR | 19.92 | 694.86 | 970.55 | 36 |
| 58 | DTTTPLAMAQSLR | 19.22 | 702.86 | 776.41 | 36 |
| 59 | DTTTPLAMAQSLR | 19.22 | 702.86 | 889.49 | 36 |
| 60 | DTTTPLAMAQSLR | 19.22 | 702.86 | 986.55 | 36 |
| 61 | DTTTPLAMAQTLR | 18.99 | 709.87 | 719.39 | 36 |
| 62 | DTTTPLAMAQTLR | 18.99 | 709.87 | 790.42 | 36 |
| 63 | DTTTPLAMAQTLR | 18.99 | 709.87 | 1000.56 | 36 |
| 64 | DVLAAAAR | 12.11 | 393.73 | 459.27 | 22 |
| 65 | DVLAAAAR | 12.11 | 393.73 | 572.35 | 22 |
| 66 | DVLAAAAR | 12.11 | 393.73 | 671.42 | 22 |
| 67 | EIGDETFR | 12.99 | 483.73 | 552.28 | 26 |
| 68 | EIGDETFR | 12.99 | 483.73 | 667.3 | 26 |
| 69 | EIGDETFR | 12.99 | 483.73 | 724.33 | 26 |
| 70 | EQLVTWLK | 19.13 | 508.79 | 547.32 | 27 |
| 71 | EQLVTWLK | 19.13 | 508.79 | 646.39 | 27 |
| 72 | EQLVTWLK | 19.13 | 508.79 | 759.48 | 27 |
| 73 | GNTTGSASIQAGLPK | 13.81 | 701.37 | 813.48 | 36 |
| 74 | GNTTGSASIQAGLPK | 13.81 | 701.37 | 1028.57 | 36 |
| 75 | GNTTGSASIQAGLPK | 13.81 | 701.37 | 1129.62 | 36 |
| 76 | HDVLASAAK | 9.32 | 456.25 | 659.41 | 25 |
| 77 | HDVLASAAK | 9.32 | 456.25 | 765.39 | 25 |
| 78 | HDVLASAAK | 9.32 | 456.25 | 774.44 | 25 |
| 79 | HDVLASAAR | 9.88 | 470.25 | 588.35 | 26 |
| 80 | HDVLASAAR | 9.88 | 470.25 | 687.41 | 26 |
| 81 | HDVLASAAR | 9.88 | 470.25 | 802.44 | 26 |
| 82 | HLTLGSALGETQR | 15.07 | 691.87 | 918.46 | 35 |
| 83 | HLTLGSALGETQR | 15.07 | 691.87 | 1031.55 | 35 |
| 84 | HLTLGSALGETQR | 15.07 | 691.87 | 1132.6 | 35 |
| 85 | LAELEQQSGGR | 11.17 | 594.3 | 761.35 | 31 |
| 86 | LAELEQQSGGR | 11.17 | 594.3 | 874.44 | 31 |
| 87 | LAELEQQSGGR | 11.17 | 594.3 | 1003.48 | 31 |
| 88 | LAGLER | 11.22 | 329.7 | 474.27 | 20 |
| 89 | LAGLER | 11.22 | 329.7 | 484.28 | 20 |
| 90 | LAGLER | 11.22 | 329.7 | 545.3 | 20 |
| 91 | LDGTEPTLNTAIPGDPR | 16.6 | 589.64 | 1053.57 | 33 |

TABLE 24-continued

| Transition number | Peptide | Retention time (minutes) | (m/z) filtered in Q1 | (m/z) filtered in Q3 | Collision energy (eV) |
|---|---|---|---|---|---|
| 92 | LDGTEPTLNTAIPGDPR | 16.6 | 883.95 | 1053.57 | 44 |
| 93 | LDGTEPTLNTAIPGDPR | 16.6 | 883.95 | 1154.62 | 44 |
| 94 | LGVALIDTADNAQTLYR | 20.27 | 917.49 | 980.48 | 45 |
| 95 | LGVALIDTADNAQTLYR | 20.27 | 917.49 | 1051.52 | 45 |
| 96 | LGVALIDTADNAQTLYR | 20.27 | 917.49 | 1152.56 | 45 |
| 97 | LGVALIDTADNTHVLYR | 19.46 | 624.34 | 801.42 | 35 |
| 98 | LGVALIDTADNTHVLYR | 19.46 | 624.34 | 902.48 | 35 |
| 99 | LGVALIDTADNTHVLYR | 19.46 | 624.34 | 1189.6 | 35 |
| 100 | LGVALIDTK | 16.93 | 465.29 | 589.36 | 25 |
| 101 | LGVALIDTK | 16.93 | 465.29 | 660.39 | 25 |
| 102 | LGVALIDTK | 16.93 | 465.29 | 816.48 | 25 |
| 103 | LGVALINTADNSR | 16.92 | 672.37 | 777.35 | 35 |
| 104 | LGVALINTADNSR | 16.92 | 672.37 | 890.43 | 35 |
| 105 | LGVALINTADNSR | 16.92 | 672.37 | 1003.52 | 35 |
| 106 | LGVALINTADNTQTLYR | 19.63 | 621.67 | 1081.53 | 35 |
| 107 | LGVALINTADNTQTLYR | 19.63 | 932 | 1081.53 | 46 |
| 108 | LGVALINTADNTQTLYR | 19.63 | 932 | 1182.57 | 46 |
| 109 | LGVPLIDTADNTQVLYR | 21.54 | 944.51 | 1008.51 | 47 |
| 110 | LGVPLIDTADNTQVLYR | 21.54 | 944.51 | 1079.55 | 47 |
| 111 | LGVPLIDTADNTQVLYR | 21.54 | 944.51 | 1180.6 | 47 |
| 112 | LIAHLGGPGK | 12.27 | 321.53 | 358.21 | 20 |
| 113 | LIAHLGGPGK | 12.27 | 321.53 | 415.23 | 20 |
| 114 | LIAHLGGPGK | 12.27 | 321.53 | 528.31 | 20 |
| 115 | LIAQLGGQGGVTAFAR | 18.73 | 779.94 | 963.5 | 39 |
| 116 | LIAQLGGQGGVTAFAR | 18.73 | 779.94 | 1020.52 | 39 |
| 117 | LIAQLGGQGGVTAFAR | 18.73 | 779.94 | 1133.61 | 39 |
| 118 | LISHVGGPASVTAFAR | 16.27 | 528.29 | 565.31 | 30 |
| 119 | LISHVGGPASVTAFAR | 16.27 | 528.29 | 664.38 | 30 |
| 120 | LISHVGGPASVTAFAR | 16.27 | 791.94 | 1033.54 | 40 |
| 121 | LLLNQR | 12.81 | 378.74 | 417.22 | 22 |
| 122 | LLLNQR | 12.81 | 378.74 | 530.3 | 22 |
| 123 | LLLNQR | 12.81 | 378.74 | 643.39 | 22 |
| 124 | NLTLGNALGDTQR | 16.67 | 686.86 | 931.46 | 35 |
| 125 | NLTLGNALGDTQR | 16.67 | 686.86 | 1044.54 | 35 |
| 126 | NLTLGNALGDTQR | 16.67 | 686.86 | 1145.59 | 35 |
| 127 | NLTLGSALGETQR | 17.15 | 453.91 | 590.29 | 27 |
| 128 | NLTLGSALGETQR | 17.15 | 680.36 | 918.46 | 35 |
| 129 | NLTLGSALGETQR | 17.15 | 680.36 | 1031.55 | 35 |

TABLE 24-continued

| Transition number | Peptide | Retention time (minutes) | (m/z) filtered in Q1 | (m/z) filtered in Q3 | Collision energy (eV) |
|---|---|---|---|---|---|
| 130 | QLGDDTFR | 13.1 | 476.23 | 653.29 | 26 |
| 131 | QLGDDTFR | 13.1 | 476.23 | 710.31 | 26 |
| 132 | QLGDDTFR | 13.1 | 476.23 | 823.39 | 26 |
| 133 | SDLVNYSPIAEK | 16.24 | 668.34 | 807.42 | 34 |
| 134 | SDLVNYSPIAEK | 16.24 | 668.34 | 921.47 | 34 |
| 135 | SDLVNYSPIAEK | 16.24 | 668.34 | 1020.54 | 34 |
| 136 | SESEPSLLNQR | 13.8 | 630.31 | 730.42 | 33 |
| 137 | SESEPSLLNQR | 13.8 | 630.31 | 827.47 | 33 |
| 138 | SESEPSLLNQR | 13.8 | 630.31 | 1043.55 | 33 |
| 139 | SLGDESFR | 12.8 | 455.72 | 653.29 | 25 |
| 140 | SLGDESFR | 12.8 | 455.72 | 710.31 | 25 |
| 141 | SLGDESFR | 12.8 | 455.72 | 823.39 | 25 |
| 142 | SSDLINYNPIAEK | 17.68 | 732.37 | 834.44 | 37 |
| 143 | SSDLINYNPIAEK | 17.68 | 732.37 | 948.48 | 37 |
| 144 | SSDLINYNPIAEK | 17.68 | 732.37 | 1061.56 | 37 |
| 145 | SSDLINYNPITEK | 17.72 | 747.38 | 864.45 | 38 |
| 146 | SSDLINYNPITEK | 17.72 | 747.38 | 978.49 | 38 |
| 147 | SSDLINYNPITEK | 17.72 | 747.38 | 1091.57 | 38 |
| 148 | SWGVGDK | 11.6 | 374.68 | 475.25 | 21 |
| 149 | SWGVGDK | 11.6 | 374.68 | 602.26 | 21 |
| 150 | SWGVGDK | 11.6 | 374.68 | 661.33 | 21 |
| 151 | TELTLNTAIPGDPR | 17.63 | 749.4 | 826.44 | 38 |
| 152 | TELTLNTAIPGDPR | 17.63 | 749.4 | 940.48 | 38 |
| 153 | TELTLNTAIPGDPR | 17.63 | 749.4 | 957.53 | 38 |
| 154 | TEPTLNSAIPGDPR | 15.33 | 734.38 | 812.43 | 37 |
| 155 | TEPTLNSAIPGDPR | 15.33 | 734.38 | 926.47 | 37 |
| 156 | TEPTLNSAIPGDPR | 15.33 | 734.38 | 1237.65 | 37 |
| 157 | TEQTLNTAIPGDPR | 14.47 | 756.89 | 940.48 | 38 |
| 158 | TEQTLNTAIPGDPR | 14.47 | 756.89 | 972.5 | 38 |
| 159 | TEQTLNTAIPGDPR | 14.47 | 756.89 | 1154.62 | 38 |
| 160 | TESTLNTAIPGDPR | 14.52 | 736.37 | 940.48 | 37 |
| 161 | TESTLNTAIPGDPR | 14.52 | 736.37 | 1053.57 | 37 |
| 162 | TESTLNTAIPGDPR | 14.52 | 736.37 | 1154.62 | 37 |
| 163 | TETTLNTAIPGDPR | 14.88 | 743.38 | 826.44 | 38 |
| 164 | TETTLNTAIPGDPR | 14.88 | 743.38 | 940.48 | 38 |
| 165 | TETTLNTAIPGDPR | 14.88 | 743.38 | 945.49 | 38 |
| 166 | TGSC[CAM]DYGTTNDIAVIWPK | 20.38 | 999.47 | 1055.59 | 49 |
| 167 | TGSC[CAM]DYGTTNDIAVIWPK | 20.38 | 999.47 | 1156.64 | 49 |

TABLE 24-continued

| Transition number | Peptide | Retention time (minutes) | (m/z) filtered in Q1 | (m/z) filtered in Q3 | Collision energy (eV) |
|---|---|---|---|---|---|
| 168 | TGSC[CAM]DYGTTNDIAVIWPK | 20.38 | 999.47 | 1172.42 | 49 |
| 169 | TGSC[CAM]GYGTTNDIAVIWPK | 20.21 | 970.46 | 1055.59 | 48 |
| 170 | TGSC[CAM]GYGTTNDIAVIWPK | 20.21 | 970.46 | 1114.41 | 48 |
| 171 | TGSC[CAM]GYGTTNDIAVIWPK | 20.21 | 970.46 | 1156.64 | 48 |
| 172 | TGSGDYGTTNDIAVIWPEGR | 20.27 | 1055 | 1069.41 | 51 |
| 173 | TGSGDYGTTNDIAVIWPEGR | 20.27 | 1055 | 1155.62 | 51 |
| 174 | TGSGDYGTTNDIAVIWPEGR | 20.27 | 1055 | 1182.49 | 51 |
| 175 | TGSGGYGTTNDIAVIWPEGR | 20.16 | 684.33 | 757.4 | 38 |
| 176 | TGSGGYGTTNDIAVIWPEGR | 20.16 | 684.33 | 927.5 | 38 |
| 177 | TGSGGYGTTNDIAVIWPEGR | 20.16 | 684.33 | 1011.4 | 38 |
| 178 | TGSGGYGTTNDIAVIWPQGR | 19.81 | 684 | 756.42 | 38 |
| 179 | TGSGGYGTTNDIAVIWPQGR | 19.81 | 684 | 926.52 | 38 |
| 180 | TGSGGYGTTNDIAVIWPQGR | 19.81 | 684 | 1011.4 | 38 |
| 181 | TIGDDTFR | 12.86 | 462.72 | 538.26 | 25 |
| 182 | TIGDDTFR | 12.86 | 462.72 | 653.29 | 25 |
| 183 | TIGDDTFR | 12.86 | 462.72 | 710.31 | 25 |
| 184 | TQLVTWLK | 19.07 | 494.79 | 646.39 | 27 |
| 185 | TQLVTWLK | 19.07 | 494.79 | 759.48 | 27 |
| 186 | TQLVTWLK | 19.07 | 494.79 | 887.53 | 27 |
| 187 | VEIKPSDLINYNPIAEK | 20.21 | 648.35 | 769.41 | 36 |
| 188 | VEIKPSDLINYNPIAEK | 20.21 | 648.35 | 882.49 | 36 |
| 189 | VEIKPSDLINYNPIAEK | 20.21 | 648.35 | 948.48 | 36 |
| 190 | VEIKPSDLVNYNPIAEK | 19.33 | 643.68 | 769.41 | 36 |
| 191 | VEIKPSDLVNYNPIAEK | 19.33 | 643.68 | 882.49 | 36 |
| 192 | VEIKPSDLVNYNPIAEK | 19.33 | 643.68 | 948.48 | 36 |
| 193 | VIGDDTFR | 13.3 | 461.73 | 538.26 | 25 |
| 194 | VIGDDTFR | 13.3 | 461.73 | 710.31 | 25 |
| 195 | VIGDDTFR | 13.3 | 461.73 | 823.39 | 25 |
| 196 | VMAAAALLK | 17.06 | 444.27 | 586.39 | 25 |
| 197 | VMAAAALLK | 17.06 | 444.27 | 657.43 | 25 |
| 198 | VMAAAALLK | 17.06 | 444.27 | 788.47 | 25 |
| 199 | VMAAAVLEQSETQK | 16.62 | 788.41 | 962.48 | 40 |
| 200 | VMAAAVLEQSETQK | 16.62 | 788.41 | 1061.55 | 40 |
| 201 | VMAAAVLEQSETQK | 16.62 | 788.41 | 1132.58 | 40 |
| 202 | WAKPSGAVGDVAQR | 12.73 | 481.26 | 628.34 | 28 |

TABLE 24-continued

| Transition number | Peptide | Retention time (minutes) | (m/z) filtered in Q1 | (m/z) filtered in Q3 | Collision energy (eV) |
|---|---|---|---|---|---|
| 203 | WAKPSGAVGDVAQR | 12.73 | 481.26 | 645.33 | 28 |
| 204 | WAKPSGAVGDVAQR | 12.73 | 481.26 | 698.36 | 28 |

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 19

Identification of a Resistance to DHA Beta-Lactams

The samples corresponding to a species able to comprise a DHA resistance mechanism can be detected by employing the following method.

Each sample is treated according to example 5, then analysed according to example 6 by detecting the peptides from TABLE 25 instead of the peptides from TABLE 3.

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 20

Identification of a Resistance to FOX Beta-Lactams

The samples corresponding to a species able to comprise a FOX resistance mechanism can be detected by employing the following method.

Each sample is treated according to example 5, then analysed according to example 6 by detecting the peptides from TABLE 26 instead of the peptides from TABLE 3.

TABLE 25

| Transition number | Peptide | Retention time (minutes) | (m/z) filtered in Q1 | (m/z) filtered in Q3 | Collision energy (eV) |
|---|---|---|---|---|---|
| 1 | ADLLHFYQQWQPSR | 20.9 | 596.97 | 673.34 | 34 |
| 2 | ADLLHFYQQWQPSR | 20.9 | 596.97 | 988.49 | 34 |
| 3 | ADLLHFYQQWQPSR | 20.9 | 596.97 | 1116.55 | 34 |
| 4 | AELLHFYQQWQPSR | 19.23 | 601.64 | 673.34 | 34 |
| 5 | AELLHFYQQWQPSR | 19.23 | 601.64 | 801.4 | 34 |
| 6 | AELLHFYQQWQPSR | 19.23 | 601.64 | 1130.56 | 34 |
| 7 | EMMLNDPAEK | 13.78 | 589.26 | 786.4 | 31 |
| 8 | EMMLNDPAEK | 13.78 | 589.26 | 917.44 | 31 |
| 9 | EMMLNDPAEK | 13.78 | 589.26 | 1048.48 | 31 |
| 10 | GKPYYFNYGFADVQAK | 18.12 | 623.31 | 631.34 | 35 |
| 11 | GKPYYFNYGFADVQAK | 18.12 | 623.31 | 778.41 | 35 |
| 12 | GKPYYFNYGFADVQAK | 18.12 | 623.31 | 835.43 | 35 |
| 13 | TAAINQGLGWEMYDWPQQK | 21.57 | 746.02 | 964.45 | 41 |
| 14 | TAAINQGLGWEMYDWPQQK | 21.57 | 746.02 | 1095.49 | 41 |
| 15 | TAAINQGLGWEMYDWPQQK | 21.57 | 1118.53 | 1224.54 | 54 |
| 16 | WAEMNIEPSR | 15.85 | 616.79 | 715.37 | 32 |
| 17 | WAEMNIEPSR | 15.85 | 616.79 | 975.46 | 32 |
| 18 | WAEMNIEPSR | 15.85 | 616.79 | 1046.49 | 32 |

TABLE 26

| Transition number | Peptide | Retention time (minutes) | (m/z) filtered in Q1 | (m/z) filtered in Q3 | Collision energy (eV) |
|---|---|---|---|---|---|
| 1 | ATPGVLAAEAYGIK | 17.72 | 680.88 | 751.4 | 35 |
| 2 | ATPGVLAAEAYGIK | 17.72 | 680.88 | 822.44 | 35 |
| 3 | ATPGVLAAEAYGIK | 17.72 | 680.88 | 935.52 | 35 |
| 4 | FAEANMGYQGDAAVK | 14.08 | 786.36 | 908.45 | 40 |
| 5 | FAEANMGYQGDAAVK | 14.08 | 786.36 | 1039.49 | 40 |
| 6 | FAEANMGYQGDAAVK | 14.08 | 786.36 | 1224.57 | 40 |
| 7 | FAEANMGYQGDALVK | 16.35 | 538.59 | 602.35 | 31 |
| 8 | FAEANMGYQGDALVK | 16.35 | 538.59 | 730.41 | 31 |
| 9 | FAEANMGYQGDALVK | 16.35 | 807.38 | 950.49 | 41 |
| 10 | GEAPLTAAVDGIIQPMLK | 25.85 | 912.5 | 1014.57 | 45 |
| 11 | GEAPLTAAVDGIIQPMLK | 25.85 | 912.5 | 1113.63 | 45 |
| 12 | GEAPLTAAVDGIIQPMLK | 25.85 | 912.5 | 1184.67 | 45 |
| 13 | HWSPVYPAGTHR | 12.55 | 469.9 | 541.28 | 27 |
| 14 | HWSPVYPAGTHR | 12.55 | 469.9 | 607.3 | 27 |
| 15 | HWSPVYPAGTHR | 12.55 | 469.9 | 638.34 | 27 |
| 16 | IPGIAVAVLK | 19.45 | 490.83 | 600.41 | 27 |
| 17 | IPGIAVAVLK | 19.45 | 490.83 | 770.51 | 27 |
| 18 | IPGIAVAVLK | 19.45 | 490.83 | 867.57 | 27 |
| 19 | LMSQTLLPK | 16.18 | 515.8 | 699.44 | 28 |
| 20 | LMSQTLLPK | 16.18 | 515.8 | 786.47 | 28 |
| 21 | LMSQTLLPK | 16.18 | 515.8 | 917.51 | 28 |
| 22 | MQTYYR | 10.72 | 431.2 | 602.29 | 24 |
| 23 | MQTYYR | 10.72 | 431.2 | 687.28 | 24 |
| 24 | MQTYYR | 10.72 | 431.2 | 730.35 | 24 |
| 25 | VSHHAPWLK | 11.49 | 537.8 | 614.37 | 29 |
| 26 | VSHHAPWLK | 11.49 | 537.8 | 751.42 | 29 |
| 27 | VSHHAPWLK | 11.49 | 537.8 | 888.48 | 29 |
| 28 | VTPGMLAAEAYGIK | 19 | 710.88 | 822.44 | 36 |

TABLE 26-continued

| Transition number | Peptide | Retention time (minutes) | (m/z) filtered in Q1 | (m/z) filtered in Q3 | Collision energy (eV) |
|---|---|---|---|---|---|
| 29 | VTPGMLAAEAYGIK | 19 | 710.88 | 1123.58 | 36 |
| 30 | VTPGMLAAEAYGIK | 19 | 710.88 | 1220.63 | 36 |

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 21

Identification of a Resistance to MIR Beta-Lactams

The samples corresponding to a species able to comprise an MIR resistance mechanism can be detected by employing the following method.

Each sample is treated according to example 5, then analysed according to example 6 by detecting the peptides from TABLE 27 instead of the peptides from TABLE 3.

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 22

Identification of a Resistance to SHV Beta-Lactams

The samples corresponding to a species able to comprise an SHV resistance mechanism can be detected by employing the following method.

Each sample is treated according to example 5, then analysed according to example 6 by detecting the peptides from TABLE 28 instead of the peptides from TABLE 3.

TABLE 27

| Transition number | Peptide | Retention time (minutes) | (m/z) filtered in Q1 | (m/z) filtered in Q3 | Collision energy (eV) |
|---|---|---|---|---|---|
| 1 | AEEAHFAWGYR | 16.38 | 446.21 | 568.77 | 20.9 |
| 2 | AEEAHFAWGYR | 16.36 | 446.21 | 633.29 | 20.9 |
| 3 | AEEAHFAWGYR | 16.36 | 446.21 | 652.32 | 20.9 |
| 4 | DMASWLIANMKPDSLHAPSLK | 24.18 | 775.73 | 811.44 | 31.1 |
| 5 | DMASWLIANMKPDSLHAPSLK | 24.18 | 775.73 | 867.98 | 31.1 |
| 6 | DMASWLIANMKPDSLHAPSLK | 24.18 | 775.73 | 1004.54 | 31.1 |
| 7 | DMASWLIANMKPDSLQAPSLK | 25.04 | 772.73 | 528.29 | 31 |
| 8 | DMASWLIANMKPDSLQAPSLK | 25.04 | 772.73 | 806.94 | 31 |
| 9 | DMASWLIANMKPDSLQAPSLK | 25.04 | 772.73 | 863.48 | 31 |
| 10 | DMASWVIANMKPDSLQAPSLK | 24 | 768.06 | 806.94 | 30.9 |
| 11 | DMASWVIANMKPDSLQAPSLK | 24 | 768.06 | 856.47 | 30.9 |
| 12 | DMASWVIANMKPDSLQAPSLK | 24 | 768.06 | 949.51 | 30.9 |
| 13 | GEIALGDPVAK | 15.79 | 535.3 | 586.32 | 26.2 |
| 14 | GEIALGDPVAK | 15.77 | 535.3 | 699.4 | 26.2 |
| 15 | GEIALGDPVAK | 15.77 | 535.3 | 770.44 | 26.2 |
| 16 | TVVGGSDNK | 3.35 | 438.73 | 520.24 | 20.7 |
| 17 | TVVGGSDNK | 3.35 | 438.73 | 577.26 | 20.7 |
| 18 | TVVGGSDNK | 3.35 | 438.73 | 676.33 | 20.7 |

TABLE 28

| Transition number | Peptide | Retention time (minutes) | (m/z) filtered in Q1 | (m/z) filtered in Q3 | Collision energy (eV) |
|---|---|---|---|---|---|
| 1 | EIGDNVTR | 10.07 | 452.23 | 489.28 | 25 |
| 2 | EIGDNVTR | 10.07 | 452.23 | 529.23 | 25 |
| 3 | EIGDNVTR | 10.07 | 452.23 | 661.33 | 25 |
| 4 | GIVALLGPHNK | 16.52 | 373.56 | 398.21 | 23 |
| 5 | GIVALLGPHNK | 16.52 | 373.56 | 552.29 | 23 |
| 6 | GIVALLGPHNK | 16.52 | 373.56 | 665.37 | 23 |
| 7 | HLADGMTVGELR | 14.93 | 433.56 | 474.27 | 26 |
| 8 | HLADGMTVGELR | 14.93 | 433.56 | 494.24 | 26 |
| 9 | HLADGMTVGELR | 14.93 | 433.56 | 573.34 | 26 |
| 10 | IHYSQQDLVDYSPVSEK | 16.22 | 669.99 | 872.39 | 37 |
| 11 | IHYSQQDLVDYSPVSEK | 16.22 | 669.99 | 924.43 | 37 |
| 12 | IHYSQQDLVDYSPVSEK | 16.22 | 669.99 | 985.47 | 37 |

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 23

Identification of a Resistance to CARB Beta-Lactams

The samples corresponding to a species able to comprise a CARB resistance mechanism can be detected by employing the following method.

Each sample is treated according to example 5, then analysed according to example 6 by detecting the peptides from TABLE 29 instead of the peptides from TABLE 3.

TABLE 29

| Transition number | Peptide | Retention time (minutes) | (m/z) filtered in Q1 | (m/z) filtered in Q3 | Collision energy (eV) |
|---|---|---|---|---|---|
| 1 | ADLVTYSPVIEK | 17.48 | 667.86 | 672.39 | 34.4 |
| 2 | ADLVTYSPVIEK | 17.48 | 667.86 | 835.46 | 34.4 |
| 3 | ADLVTYSPVIEK | 17.48 | 667.86 | 936.5 | 34.4 |
| 4 | ADLVTYSPVLEK | 18.01 | 667.86 | 672.39 | 34.4 |
| 5 | ADLVTYSPVLEK | 18.01 | 667.86 | 835.46 | 34.4 |
| 6 | ADLVTYSPVLEK | 18.01 | 667.86 | 936.5 | 34.4 |
| 7 | AIASTLNK | 10.86 | 409.24 | 475.29 | 23 |
| 8 | AIASTLNK | 10.86 | 409.24 | 562.32 | 23 |
| 9 | AIASTLNK | 10.86 | 409.24 | 633.36 | 23 |

TABLE 29-continued

| Transition number | Peptide | Retention time (minutes) | (m/z) filtered in Q1 | (m/z) filtered in Q3 | Collision energy (eV) |
|---|---|---|---|---|---|
| 10 | AIASTLNQLLFGSTLSEASQK | 25.39 | 727.06 | 362.2 | 40.4 |
| 11 | AIASTLNQLLFGSTLSEASQK | 25.39 | 727.06 | 649.32 | 40.4 |
| 12 | AIASTLNQLLFGSTLSEASQK | 25.39 | 727.06 | 998.02 | 40.4 |
| 13 | AIEVSLSAR | 15.46 | 473.27 | 533.3 | 25.8 |
| 14 | AIEVSLSAR | 15.46 | 473.27 | 632.37 | 25.8 |
| 15 | AIEVSLSAR | 15.46 | 473.27 | 761.42 | 25.8 |
| 16 | DTTTPIAMVTTLEK | 21.41 | 507.6 | 591.34 | 29.4 |
| 17 | DTTTPIAMVTTLEK | 21.41 | 507.6 | 690.4 | 29.4 |
| 18 | DTTTPIAMVTTLEK | 21.41 | 507.6 | 892.48 | 29.4 |
| 19 | DTTTPK | 1.54 | 331.67 | 345.21 | 19.6 |
| 20 | DTTTPK | 1.54 | 331.67 | 446.26 | 19.6 |
| 21 | DTTTPK | 1.54 | 331.67 | 547.31 | 19.6 |
| 22 | FLFGSALSEMNK | 21.32 | 672.34 | 879.42 | 34.6 |
| 23 | FLFGSALSEMNK | 21.32 | 672.34 | 936.45 | 34.6 |
| 24 | FLFGSALSEMNK | 21.32 | 672.34 | 1083.51 | 34.6 |
| 25 | FPLSSTFK | 17.51 | 463.75 | 390.22 | 25.4 |
| 26 | FPLSSTFK | 17.51 | 463.75 | 682.38 | 25.4 |
| 27 | FPLSSTFK | 17.51 | 463.75 | 779.43 | 25.4 |
| 28 | FPLTSTFK | 17.85 | 470.76 | 397.23 | 25.7 |
| 29 | FPLTSTFK | 17.85 | 470.76 | 696.39 | 25.7 |
| 30 | FPLTSTFK | 17.85 | 470.76 | 793.45 | 25.7 |
| 31 | FQQVEQDAK | 10.02 | 546.77 | 590.28 | 29.1 |
| 32 | FQQVEQDAK | 10.02 | 546.77 | 689.35 | 29.1 |
| 33 | FQQVEQDAK | 10.02 | 546.77 | 817.41 | 29.1 |
| 34 | FQQVEQDVK | 11.76 | 560.79 | 618.31 | 29.7 |
| 35 | FQQVEQDVK | 11.76 | 560.79 | 717.38 | 29.7 |
| 36 | FQQVEQDVK | 11.76 | 560.79 | 845.44 | 29.7 |
| 37 | FQSVEQEIK | 14.17 | 554.29 | 745.41 | 29.4 |
| 38 | FQSVEQEIK | 14.17 | 554.29 | 832.44 | 29.4 |
| 39 | FQSVEQEIK | 14.17 | 554.29 | 960.5 | 29.4 |
| 40 | FSESNLVTYSPVTEK | 17.84 | 567.62 | 462.74 | 32.4 |
| 41 | FSESNLVTYSPVTEK | 17.84 | 567.62 | 777.39 | 32.4 |
| 42 | FSESNLVTYSPVTEK | 17.85 | 567.62 | 924.47 | 32.4 |
| 43 | GIESSLSAR | 12.88 | 460.25 | 533.3 | 25.3 |
| 44 | GIESSLSAR | 12.88 | 460.25 | 620.34 | 25.3 |
| 45 | GIESSLSAR | 12.88 | 460.25 | 749.38 | 25.3 |
| 46 | GNEVGDALFR | 17.15 | 539.27 | 678.36 | 28.7 |
| 47 | GNEVGDALFR | 17.15 | 539.27 | 777.43 | 28.7 |

TABLE 29-continued

| Transition number | Peptide | Retention time (minutes) | (m/z) filtered in Q1 | (m/z) filtered in Q3 | Collision energy (eV) |
|---|---|---|---|---|---|
| 48 | GNEVGDALFR | 17.15 | 539.27 | 906.47 | 28.7 |
| 49 | GVPSDWIVADR | 18.32 | 607.81 | 529.77 | 31.7 |
| 50 | GVPSDWIVADR | 18.32 | 607.81 | 759.42 | 31.7 |
| 51 | GVPSDWIVADR | 18.32 | 607.81 | 1058.53 | 31.7 |
| 52 | GVTDFLR | 17.69 | 404.22 | 326.18 | 22.8 |
| 53 | GVTDFLR | 17.69 | 404.22 | 550.3 | 22.8 |
| 54 | GVTDFLR | 17.69 | 404.22 | 651.35 | 22.8 |
| 55 | IEPDLNEGK | 12.13 | 507.76 | 386.7 | 27.3 |
| 56 | IEPDLNEGK | 12.13 | 507.76 | 772.38 | 27.3 |
| 57 | IEPDLNEGK | 12.13 | 507.76 | 901.43 | 27.3 |
| 58 | IEPELNEGK | 12.2 | 514.77 | 393.7 | 27.6 |
| 59 | IEPELNEGK | 12.2 | 514.77 | 786.4 | 27.6 |
| 60 | IEPELNEGK | 12.2 | 514.77 | 915.44 | 27.6 |
| 61 | IGEQIAK | 10.58 | 379.72 | 459.29 | 21.7 |
| 62 | IGEQIAK | 10.58 | 379.72 | 588.34 | 21.7 |
| 63 | IGEQIAK | 10.58 | 379.72 | 645.36 | 21.7 |
| 64 | IGLAVHDLETGK | 16.05 | 626.85 | 799.39 | 32.6 |
| 65 | IGLAVHDLETGK | 16.05 | 626.85 | 898.46 | 32.6 |
| 66 | IGLAVHDLETGK | 16.05 | 626.85 | 969.5 | 32.6 |
| 67 | KPIVAALYITETDASFEER | 21.09 | 718.38 | 667.31 | 39.9 |
| 68 | KPIVAALYITETDASFEER | 21.09 | 718.38 | 787.37 | 39.9 |
| 69 | KPIVAALYITETDASFEER | 21.09 | 718.38 | 853.37 | 39.9 |
| 70 | LESWMVNNQVTGNLLR | 22.01 | 625.32 | 564.81 | 32.5 |
| 71 | LESWMVNNQVTGNLLR | 22.01 | 625.32 | 673.4 | 32.5 |
| 72 | LESWMVNNQVTGNLLR | 22.01 | 625.32 | 772.47 | 32.5 |
| 73 | LEYWMVNNQVTGNLLR | 22.96 | 650.67 | 564.81 | 33.6 |
| 74 | LEYWMVNNQVTGNLLR | 22.96 | 650.67 | 673.4 | 33.6 |
| 75 | LEYWMVNNQVTGNLLR | 22.96 | 650.67 | 772.47 | 33.6 |
| 76 | LLFGSALSEMNQK | 21.03 | 719.37 | 389.21 | 36.7 |
| 77 | LLFGSALSEMNQK | 21.03 | 719.37 | 736.33 | 36.7 |
| 78 | LLFGSALSEMNQK | 21.03 | 719.37 | 1211.57 | 36.7 |
| 79 | LLIDETLSIK | 20.7 | 572.85 | 805.43 | 30.2 |
| 80 | LLIDETLSIK | 20.7 | 572.85 | 918.51 | 30.2 |
| 81 | LLIDETLSIK | 20.7 | 572.85 | 1031.6 | 30.2 |
| 82 | LLYDAEHGK | 11.75 | 523.27 | 656.3 | 28 |
| 83 | LLYDAEHGK | 11.75 | 523.27 | 819.36 | 28 |
| 84 | LLYDAEHGK | 11.75 | 523.27 | 932.45 | 28 |
| 85 | LLYDAEQGEINPK | 15.72 | 745.38 | 358.21 | 37.8 |

TABLE 29-continued

| Transition number | Peptide | Retention time (minutes) | (m/z) filtered in Q1 | (m/z) filtered in Q3 | Collision energy (eV) |
|---|---|---|---|---|---|
| 86 | LLYDAEQGEINPK | 15.72 | 745.38 | 632.3 | 37.8 |
| 87 | LLYDAEQGEINPK | 15.72 | 745.38 | 785.42 | 37.8 |
| 88 | LLYDAEQGK | 13.05 | 518.77 | 647.3 | 27.8 |
| 89 | LLYDAEQGK | 13.05 | 518.77 | 810.36 | 27.8 |
| 90 | LLYDAEQGK | 13.05 | 518.77 | 923.45 | 27.8 |
| 91 | MCDNQNYGVTYMK | 14.67 | 541.89 | 641.33 | 31.1 |
| 92 | MCDNQNYGVTYMK | 14.67 | 541.89 | 698.35 | 31.1 |
| 93 | MCDNQNYGVTYMK | 14.67 | 541.89 | 861.42 | 31.1 |
| 94 | NAVIAK | 7.68 | 308.2 | 331.23 | 18.6 |
| 95 | NAVIAK | 7.68 | 308.2 | 430.3 | 18.6 |
| 96 | NAVIAK | 7.68 | 308.2 | 501.34 | 18.6 |
| 97 | NDAIVK | 8.38 | 330.19 | 359.27 | 19.5 |
| 98 | NDAIVK | 8.38 | 330.19 | 430.3 | 19.5 |
| 99 | NDAIVK | 8.38 | 330.19 | 545.33 | 19.5 |
| 100 | QQLESWLK | 17.65 | 516.28 | 533.31 | 27.7 |
| 101 | QQLESWLK | 17.65 | 516.28 | 662.35 | 27.7 |
| 102 | QQLESWLK | 17.65 | 516.28 | 775.44 | 27.7 |
| 103 | QVEQDVK | 6.63 | 423.22 | 361.21 | 23.6 |
| 104 | QVEQDVK | 6.63 | 423.22 | 489.27 | 23.6 |
| 105 | QVEQDVK | 6.63 | 423.22 | 618.31 | 23.6 |
| 106 | SGAGGFGAR | 9.32 | 390.19 | 507.27 | 22.2 |
| 107 | SGAGGFGAR | 9.32 | 390.19 | 564.29 | 22.2 |
| 108 | SGAGGFGAR | 9.32 | 390.19 | 635.33 | 22.2 |
| 109 | SIGDDTTR | 7.76 | 432.71 | 492.24 | 24 |
| 110 | SIGDDTTR | 7.76 | 432.71 | 607.27 | 24 |
| 111 | SIGDDTTR | 7.76 | 432.71 | 664.29 | 24 |
| 112 | SITAIVWSEEK | 18.92 | 631.84 | 405.2 | 32.8 |
| 113 | SITAIVWSEEK | 18.92 | 631.84 | 777.38 | 32.8 |
| 114 | SITAIVWSEEK | 18.92 | 631.84 | 1062.55 | 32.8 |
| 115 | SITDFLR | 19.34 | 426.24 | 435.27 | 23.8 |
| 116 | SITDFLR | 19.34 | 426.24 | 550.3 | 23.8 |
| 117 | SITDFLR | 19.34 | 426.24 | 651.35 | 23.8 |
| 118 | STIEIK | 11.83 | 345.71 | 389.24 | 20.2 |
| 119 | STIEIK | 11.83 | 345.71 | 502.32 | 20.2 |
| 120 | STIEIK | 11.83 | 345.71 | 603.37 | 20.2 |
| 121 | SVLPAGWNIADR | 19.61 | 649.85 | 500.25 | 33.6 |
| 122 | SVLPAGWNIADR | 19.61 | 649.85 | 556.8 | 33.6 |
| 123 | SVLPAGWNIADR | 19.61 | 649.85 | 999.5 | 33.6 |

TABLE 29-continued

| Transition number | Peptide | Retention time (minutes) | (m/z) filtered in Q1 | (m/z) filtered in Q3 | Collision energy (eV) |
| --- | --- | --- | --- | --- | --- |
| 124 | SVLPEGWNIADR | 19.62 | 678.85 | 529.26 | 34.9 |
| 125 | SVLPEGWNIADR | 19.62 | 678.85 | 585.8 | 34.9 |
| 126 | SVLPEGWNIADR | 19.62 | 678.85 | 1057.51 | 34.9 |
| 127 | SVLPVK | 13.24 | 321.71 | 343.23 | 19.2 |
| 128 | SVLPVK | 13.24 | 321.71 | 456.32 | 19.2 |
| 129 | SVLPVK | 13.24 | 321.71 | 555.39 | 19.2 |
| 130 | SVLPVTWSIADR | 21.34 | 672.37 | 522.78 | 34.6 |
| 131 | SVLPVTWSIADR | 21.34 | 672.37 | 1044.55 | 34.6 |
| 132 | SVLPVTWSIADR | 21.34 | 672.37 | 1157.63 | 34.6 |
| 133 | TGAGGYGSR | 3.77 | 413.2 | 596.28 | 23.2 |
| 134 | TGAGGYGSR | 3.77 | 413.2 | 667.32 | 23.2 |
| 135 | TGAGGYGSR | 3.77 | 413.2 | 724.34 | 23.2 |
| 136 | TIACAK | 3.86 | 332.18 | 378.18 | 19.6 |
| 137 | TIACAK | 3.86 | 332.18 | 449.22 | 19.6 |
| 138 | TIACAK | 3.86 | 332.18 | 562.3 | 19.6 |
| 139 | TILMENSR | 13.19 | 482.25 | 505.24 | 26.2 |
| 140 | TILMENSR | 13.19 | 482.25 | 636.28 | 26.2 |
| 141 | TILMENSR | 13.19 | 482.25 | 749.36 | 26.2 |
| 142 | TLACANVLQR | 14.83 | 573.31 | 466.24 | 30.2 |
| 143 | TLACANVLQR | 14.83 | 573.31 | 860.44 | 30.2 |
| 144 | TLACANVLQR | 14.83 | 573.31 | 931.48 | 30.2 |
| 145 | TVLMENSR | 11.76 | 475.24 | 505.24 | 25.9 |
| 146 | TVLMENSR | 11.76 | 475.24 | 636.28 | 25.9 |
| 147 | TVLMENSR | 11.76 | 475.24 | 749.36 | 25.9 |
| 148 | VEPELNEGK | 11.18 | 507.76 | 393.7 | 27.3 |
| 149 | VEPELNEGK | 11.18 | 507.76 | 447.22 | 27.3 |
| 150 | VEPELNEGK | 11.18 | 507.76 | 560.3 | 27.3 |
| 151 | VNLNSTVEIK | 15.48 | 558.82 | 790.43 | 29.6 |
| 152 | VNLNSTVEIK | 15.48 | 558.82 | 903.52 | 29.6 |
| 153 | VNLNSTVEIK | 15.48 | 558.82 | 1017.56 | 29.6 |
| 154 | VNLNSTVEVK | 14.23 | 551.81 | 776.42 | 29.3 |
| 155 | VNLNSTVEVK | 14.23 | 551.81 | 889.5 | 29.3 |
| 156 | VNLNSTVEVK | 14.23 | 551.81 | 1003.54 | 29.3 |
| 157 | VNPNSTVEIK | 12.41 | 550.8 | 444.25 | 29.2 |
| 158 | VNPNSTVEIK | 12.41 | 550.8 | 887.48 | 29.2 |
| 159 | VNPNSTVEIK | 12.41 | 550.8 | 1001.53 | 29.2 |
| 160 | VNSNSTVEIK | 11.24 | 545.79 | 790.43 | 29 |
| 161 | VNSNSTVEIK | 11.24 | 545.79 | 877.46 | 29 |

TABLE 29-continued

| Transition number | Peptide | Retention time (minutes) | (m/z) filtered in Q1 | (m/z) filtered in Q3 | Collision energy (eV) |
|---|---|---|---|---|---|
| 162 | VNSNSTVEIK | 11.24 | 545.79 | 991.51 | 29 |
| 163 | WETELNEAVPGDK | 16.5 | 744.35 | 358.19 | 37.8 |
| 164 | WETELNEAVPGDK | 16.5 | 744.35 | 415.21 | 37.8 |
| 165 | WETELNEAVPGDK | 16.5 | 744.35 | 471.75 | 37.8 |
| 166 | WSIADR | 14.14 | 374.19 | 361.18 | 21.5 |
| 167 | WSIADR | 14.14 | 374.19 | 474.27 | 21.5 |
| 168 | WSIADR | 14.14 | 374.19 | 561.3 | 21.5 |

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 24

Identification of a Resistance to OXA Beta-Lactams

The samples corresponding to a species able to comprise an OXA resistance mechanism can be detected by employing the following method.

Each sample is treated according to example 5, then analysed according to example 6 by detecting the peptides from TABLE 30 instead of the peptides from TABLE 3.

TABLE 30

| Transition number | Peptide | Retention time (minutes) | (m/z) filtered in Q1 | (m/z) filtered in Q3 | Collision energy (eV) |
|---|---|---|---|---|---|
| 1 | AAAYELAENLFEAGQADGWR | 24.48 | 728.01 | 1249.6 | 40 |
| 2 | AAAYELAENLFEAGQADGWR | 24.48 | 1091.51 | 1193.58 | 53 |
| 3 | AAAYELAENLFEAGQADGWR | 24.48 | 1091.51 | 1249.6 | 53 |
| 4 | AAEGFIPASTFK | 17.74 | 619.82 | 763.43 | 32 |
| 5 | AAEGFIPASTFK | 17.74 | 619.82 | 910.5 | 32 |
| 6 | AAEGFIPASTFK | 17.74 | 619.82 | 967.52 | 32 |
| 7 | ADGQVVAFALNMQMK | 21.27 | 811.91 | 982.48 | 41 |
| 8 | ADGQVVAFALNMQMK | 21.29 | 811.91 | 1053.52 | 41 |
| 9 | ADGQVVAFALNMQMK | 21.27 | 811.91 | 1152.59 | 41 |
| 10 | ADINEIFK | 17.3 | 475.25 | 650.35 | 26 |
| 11 | ADINEIFK | 17.3 | 475.25 | 763.43 | 26 |
| 12 | ADINEIFK | 17.3 | 475.25 | 878.46 | 26 |
| 13 | ADWGK | 6.9 | 288.64 | 390.21 | 18 |
| 14 | ADWGK | 6.91 | 288.64 | 430.17 | 18 |
| 15 | ADWGK | 6.89 | 288.64 | 505.24 | 18 |

TABLE 30-continued

| Transition number | Peptide | Retention time (minutes) | (m/z) filtered in Q1 | (m/z) filtered in Q3 | Collision energy (eV) |
|---|---|---|---|---|---|
| 16 | AEGAIVISDER | 13.52 | 387.2 | 419.19 | 23 |
| 17 | AEGAIVISDER | 13.53 | 387.2 | 506.22 | 23 |
| 18 | AEGAIVISDER | 13.52 | 387.2 | 619.3 | 23 |
| 19 | AFALNLDIDK | 20.16 | 560.31 | 717.38 | 30 |
| 20 | AFALNLDIDK | 20.16 | 560.31 | 830.46 | 30 |
| 21 | AFALNLDIDK | 20.16 | 560.31 | 901.5 | 30 |
| 22 | AFAPMSTFK | 16.96 | 500.25 | 710.35 | 27 |
| 23 | AFAPMSTFK | 16.96 | 500.25 | 781.39 | 27 |
| 24 | AFAPMSTFK | 16.96 | 500.25 | 928.46 | 27 |
| 25 | AFGYGNADVSGDPGQNNGLDR | 15.12 | 708.65 | 873.42 | 39 |
| 26 | AFGYGNADVSGDPGQNNGLDR | 15.12 | 708.65 | 970.47 | 39 |
| 27 | AFGYGNADVSGDPGQNNGLDR | 15.12 | 708.65 | 1154.47 | 39 |
| 28 | AFTMTK | 11.32 | 349.68 | 480.25 | 20 |
| 29 | AFTMTK | 11.33 | 349.68 | 552.25 | 20 |
| 30 | AFTMTK | 11.33 | 349.68 | 627.32 | 20 |
| 31 | AGDDIALR | 12.23 | 415.72 | 587.35 | 23 |
| 32 | AGDDIALR | 12.23 | 415.72 | 702.38 | 23 |
| 33 | AGDDIALR | 12.23 | 415.72 | 759.4 | 23 |
| 34 | AGHVYAFALNIDMPR | 20.63 | 558.95 | 631.32 | 32 |
| 35 | AGHVYAFALNIDMPR | 20.63 | 558.95 | 745.37 | 32 |
| 36 | AGHVYAFALNIDMPR | 20.63 | 558.95 | 817.4 | 32 |
| 37 | AGLWR | 13.44 | 301.67 | 361.2 | 18 |
| 38 | AGLWR | 13.44 | 301.67 | 474.28 | 18 |
| 39 | AGLWR | 13.44 | 301.67 | 531.3 | 18 |
| 40 | AHTEYVPASTFK | 13.18 | 450.89 | 553.3 | 27 |
| 41 | AHTEYVPASTFK | 13.18 | 450.89 | 602.26 | 27 |
| 42 | AHTEYVPASTFK | 13.18 | 450.89 | 650.35 | 27 |
| 43 | AIIPWDGKPR | 15.84 | 384.89 | 428.23 | 23 |
| 44 | AIIPWDGKPR | 15.84 | 384.89 | 457.29 | 23 |
| 45 | AIIPWDGKPR | 15.84 | 384.89 | 572.32 | 23 |
| 46 | AISDITITR | 14.8 | 495.28 | 603.38 | 27 |
| 47 | AISDITITR | 14.8 | 495.28 | 718.41 | 27 |
| 48 | AISDITITR | 14.8 | 495.28 | 805.44 | 27 |
| 49 | ALGQDR | 11.25 | 330.18 | 475.23 | 20 |
| 50 | ALGQDR | 11.25 | 330.18 | 485.24 | 20 |
| 51 | ALGQDR | 11.25 | 330.18 | 588.31 | 20 |
| 52 | ALQAK | 1.86 | 265.67 | 346.21 | 17 |
| 53 | ALQAK | 1.87 | 265.67 | 384.22 | 17 |

TABLE 30-continued

| Transition number | Peptide | Retention time (minutes) | (m/z) filtered in Q1 | (m/z) filtered in Q3 | Collision energy (eV) |
|---|---|---|---|---|---|
| 54 | ALQAK | 1.87 | 265.67 | 459.29 | 17 |
| 55 | AMETFSPASTFK | 17.06 | 658.81 | 737.38 | 34 |
| 56 | AMETFSPASTFK | 17.05 | 658.81 | 985.5 | 34 |
| 57 | AMETFSPASTFK | 17.06 | 658.81 | 1114.54 | 34 |
| 58 | AMLFLQER | 18.48 | 504.27 | 545.3 | 27 |
| 59 | AMLFLQER | 18.48 | 504.27 | 692.37 | 27 |
| 60 | AMLFLQER | 18.48 | 504.27 | 805.46 | 27 |
| 61 | AMLVFDPVR | 19.87 | 524.29 | 732.4 | 28 |
| 62 | AMLVFDPVR | 19.87 | 524.29 | 845.49 | 28 |
| 63 | AMLVFDPVR | 19.87 | 524.29 | 976.53 | 28 |
| 64 | AMTLLESGPGWELHGK | 19.32 | 575.96 | 923.47 | 33 |
| 65 | AMTLLESGPGWELHGK | 19.32 | 575.96 | 980.49 | 33 |
| 66 | AMTLLESGPGWELHGK | 19.32 | 575.96 | 1067.53 | 33 |
| 67 | ANLHITLHGK | 12.18 | 368.55 | 403.24 | 22 |
| 68 | ANLHITLHGK | 12.18 | 368.55 | 555.32 | 22 |
| 69 | ANLHITLHGK | 12.18 | 368.55 | 668.41 | 22 |
| 70 | ANQLIVK | 11.87 | 393.25 | 600.41 | 22 |
| 71 | ANQLIVK | 11.86 | 393.25 | 639.38 | 22 |
| 72 | ANQLIVK | 11.86 | 393.25 | 714.45 | 22 |
| 73 | ANTEYVPASTFK | 14.54 | 664.33 | 912.48 | 34 |
| 74 | ANTEYVPASTFK | 14.54 | 664.33 | 1041.53 | 34 |
| 75 | ANTEYVPASTFK | 14.54 | 664.33 | 1142.57 | 34 |
| 76 | ANVSR | 9.57 | 273.65 | 361.22 | 17 |
| 77 | ANVSR | 9.57 | 273.65 | 372.19 | 17 |
| 78 | ANVSR | 9.57 | 273.65 | 475.26 | 17 |
| 79 | APIGWFIGWATR | 25.58 | 687.87 | 850.46 | 35 |
| 80 | APIGWFIGWATR | 25.58 | 687.87 | 1093.56 | 35 |
| 81 | APIGWFIGWATR | 25.58 | 687.87 | 1206.64 | 35 |
| 82 | APLGWFIGWATHEER | 24.69 | 590.63 | 742.35 | 34 |
| 83 | APLGWFIGWATHEER | 24.69 | 590.63 | 985.45 | 34 |
| 84 | APLGWFIGWATHEER | 24.69 | 590.63 | 1098.53 | 34 |
| 85 | AQDEVQSMLFIEEK | 20.15 | 833.9 | 996.51 | 42 |
| 86 | AQDEVQSMLFIEEK | 20.14 | 833.9 | 1124.57 | 42 |
| 87 | AQDEVQSMLFIEEK | 20.15 | 833.9 | 1223.63 | 42 |
| 88 | AQGVIVLWNENK | 18.95 | 685.87 | 902.47 | 35 |
| 89 | AQGVIVLWNENK | 18.95 | 685.87 | 1015.56 | 35 |
| 90 | AQGVIVLWNENK | 18.95 | 685.87 | 1171.65 | 35 |
| 91 | ASAIAVYQDLAR | 18.05 | 639.35 | 765.39 | 33 |

TABLE 30-continued

| Transition number | Peptide | Retention time (minutes) | (m/z) filtered in Q1 | (m/z) filtered in Q3 | Collision energy (eV) |
|---|---|---|---|---|---|
| 92 | ASAIAVYQDLAR | 18.05 | 639.35 | 864.46 | 33 |
| 93 | ASAIAVYQDLAR | 18.05 | 639.35 | 935.49 | 33 |
| 94 | ASAILVYQDLAR | 19.08 | 660.37 | 765.39 | 34 |
| 95 | ASAILVYQDLAR | 19.08 | 660.37 | 864.46 | 34 |
| 96 | ASAILVYQDLAR | 19.08 | 660.37 | 977.54 | 34 |
| 97 | ASAIPVYQDLAR | 17.45 | 652.35 | 765.39 | 34 |
| 98 | ASAIPVYQDLAR | 17.45 | 652.35 | 864.46 | 34 |
| 99 | ASAIPVYQDLAR | 17.45 | 652.35 | 961.51 | 34 |
| 100 | ASAIPVYQDLPR | 17.59 | 665.36 | 791.4 | 34 |
| 101 | ASAIPVYQDLPR | 17.59 | 665.36 | 890.47 | 34 |
| 102 | ASAIPVYQDLPR | 17.6 | 665.36 | 987.53 | 34 |
| 103 | ASAIQVYQDLAR | 18.37 | 667.86 | 765.39 | 34 |
| 104 | ASAIQVYQDLAR | 18.37 | 667.86 | 864.46 | 34 |
| 105 | ASAIQVYQDLAR | 18.37 | 667.86 | 992.52 | 34 |
| 106 | ASAISVYQDLAR | 17.93 | 647.34 | 765.39 | 33 |
| 107 | ASAISVYQDLAR | 17.93 | 647.34 | 864.46 | 33 |
| 108 | ASAISVYQDLAR | 17.93 | 647.34 | 951.49 | 33 |
| 109 | ASALPVYQDLAR | 17.77 | 652.35 | 864.46 | 34 |
| 110 | ASALPVYQDLAR | 17.77 | 652.35 | 961.51 | 34 |
| 111 | ASALPVYQDLAR | 17.77 | 652.35 | 1074.59 | 34 |
| 112 | ASAMPVYQDLAR | 16.64 | 661.33 | 765.39 | 34 |
| 113 | ASAMPVYQDLAR | 16.64 | 661.33 | 864.46 | 34 |
| 114 | ASAMPVYQDLAR | 16.64 | 661.33 | 961.51 | 34 |
| 115 | ASAVPVYQDLAR | 16.29 | 645.35 | 765.39 | 33 |
| 116 | ASAVPVYQDLAR | 16.29 | 645.35 | 864.46 | 33 |
| 117 | ASAVPVYQDLAR | 16.29 | 645.35 | 961.51 | 33 |
| 118 | ASIEYVPASTFK | 16.7 | 656.84 | 749.42 | 34 |
| 119 | ASIEYVPASTFK | 16.7 | 656.84 | 912.48 | 34 |
| 120 | ASIEYVPASTFK | 16.7 | 656.84 | 1041.53 | 34 |
| 121 | ASNVPVYQELAR | 18.48 | 673.86 | 779.4 | 35 |
| 122 | ASNVPVYQELAR | 18.48 | 673.86 | 878.47 | 35 |
| 123 | ASNVPVYQELAR | 18.48 | 673.86 | 975.53 | 35 |
| 124 | ASPASTFK | 10.29 | 404.71 | 553.3 | 23 |
| 125 | ASPASTFK | 10.29 | 404.71 | 650.35 | 23 |
| 126 | ASPASTFK | 10.28 | 404.71 | 737.38 | 23 |
| 127 | ASTAYIPASTFK | 15.69 | 628.83 | 763.43 | 33 |
| 128 | ASTAYIPASTFK | 15.69 | 628.83 | 926.5 | 33 |
| 129 | ASTAYIPASTFK | 15.69 | 628.83 | 997.54 | 33 |

TABLE 30-continued

| Transition number | Peptide | Retention time (minutes) | (m/z) filtered in Q1 | (m/z) filtered in Q3 | Collision energy (eV) |
|---|---|---|---|---|---|
| 130 | ASTEYVPASTFK | 14.59 | 650.82 | 749.42 | 34 |
| 131 | ASTEYVPASTFK | 14.59 | 650.82 | 912.48 | 34 |
| 132 | ASTEYVPASTFK | 14.6 | 650.82 | 1041.53 | 34 |
| 133 | ASTTEVFK | 11.78 | 441.73 | 623.34 | 24 |
| 134 | ASTTEVFK | 11.78 | 441.73 | 724.39 | 24 |
| 135 | ASTTEVFK | 11.78 | 441.73 | 811.42 | 24 |
| 136 | ATSTEIFK | 13.15 | 448.74 | 637.36 | 25 |
| 137 | ATSTEIFK | 13.15 | 448.74 | 724.39 | 25 |
| 138 | ATSTEIFK | 13.15 | 448.74 | 825.44 | 25 |
| 139 | ATTNEIFK | 13.21 | 462.25 | 650.35 | 25 |
| 140 | ATTNEIFK | 13.21 | 462.25 | 751.4 | 25 |
| 141 | ATTNEIFK | 13.21 | 462.25 | 852.45 | 25 |
| 142 | ATTTAVFK | 11.9 | 419.74 | 464.29 | 23 |
| 143 | ATTTAVFK | 11.9 | 419.74 | 565.33 | 23 |
| 144 | ATTTAVFK | 11.9 | 419.74 | 666.38 | 23 |
| 145 | ATTTEIFK | 13.64 | 455.75 | 637.36 | 25 |
| 146 | ATTTEIFK | 13.65 | 455.75 | 738.4 | 25 |
| 147 | ATTTEIFK | 13.65 | 455.75 | 839.45 | 25 |
| 148 | ATTTEVFK | 11.98 | 448.74 | 623.34 | 25 |
| 149 | ATTTEVFK | 11.98 | 448.74 | 724.39 | 25 |
| 150 | ATTTEVFK | 11.98 | 448.74 | 825.44 | 25 |
| 151 | AVSDITILEQTDNYTLHGK | 19.19 | 706.7 | 974.49 | 39 |
| 152 | AVSDITILEQTDNYTLHGK | 19.19 | 706.7 | 1048.51 | 39 |
| 153 | AVSDITILEQTDNYTLHGK | 19.18 | 706.7 | 1176.56 | 39 |
| 154 | AVSDITILEQTYNYTLHGK | 22.29 | 722.71 | 995.49 | 40 |
| 155 | AVSDITILEQTYNYTLHGK | 22.29 | 722.71 | 998.5 | 40 |
| 156 | AVSDITILEQTYNYTLHGK | 22.28 | 722.71 | 1224.6 | 40 |
| 157 | AVVPHFEAGDWDVQGK | 17.81 | 585.62 | 743.34 | 33 |
| 158 | AVVPHFEAGDWDVQGK | 17.81 | 585.62 | 792.88 | 33 |
| 159 | AVVPHFEAGDWDVQGK | 17.81 | 585.62 | 904.42 | 33 |
| 160 | AWEHDMSLR | 13.99 | 572.76 | 758.36 | 30 |
| 161 | AWEHDMSLR | 13.99 | 572.76 | 887.4 | 30 |
| 162 | AWEHDMSLR | 13.99 | 572.76 | 1073.48 | 30 |
| 163 | AWIGSSLQISPLEQLEFLGK | 26.98 | 739.4 | 963.51 | 41 |
| 164 | AWIGSSLQISPLEQLEFLGK | 26.99 | 739.4 | 1173.65 | 41 |
| 165 | AWIGSSLQISPLEQLEFLGK | 26.98 | 1108.6 | 1173.65 | 54 |
| 166 | DAFLK | 12.42 | 297.17 | 407.27 | 18 |
| 167 | DAFLK | 12.43 | 297.17 | 447.22 | 18 |

TABLE 30-continued

| Transition number | Peptide | Retention time (minutes) | (m/z) filtered in Q1 | (m/z) filtered in Q3 | Collision energy (eV) |
|---|---|---|---|---|---|
| 168 | DAFLK | 12.42 | 297.17 | 478.3 | 18 |
| 169 | DDFILHGK | 13.99 | 472.75 | 714.43 | 26 |
| 170 | DDFILHGK | 13.99 | 472.75 | 798.38 | 26 |
| 171 | DDFILHGK | 13.99 | 472.75 | 829.46 | 26 |
| 172 | DDVLK | 8.62 | 295.16 | 359.27 | 18 |
| 173 | DDVLK | 8.63 | 295.16 | 443.21 | 18 |
| 174 | DDVLK | 8.62 | 295.16 | 474.29 | 18 |
| 175 | DEFHVFR | 15.39 | 475.23 | 705.38 | 26 |
| 176 | DEFHVFR | 15.39 | 475.23 | 775.34 | 26 |
| 177 | DEFHVFR | 15.39 | 475.23 | 834.43 | 26 |
| 178 | DEFQIFR | 19.02 | 477.74 | 520.2 | 26 |
| 179 | DEFQIFR | 19.02 | 477.74 | 563.33 | 26 |
| 180 | DEFQIFR | 19.02 | 477.74 | 710.4 | 26 |
| 181 | DEFQVFR | 17.29 | 470.73 | 549.31 | 26 |
| 182 | DEFQVFR | 17.28 | 470.73 | 619.27 | 26 |
| 183 | DEFQVFR | 17.29 | 470.73 | 696.38 | 26 |
| 184 | DELVR | 9.33 | 316.17 | 387.27 | 19 |
| 185 | DELVR | 9.35 | 316.17 | 457.23 | 19 |
| 186 | DELVR | 9.33 | 316.17 | 516.31 | 19 |
| 187 | DFDYGNQDFSGDK | 14.72 | 754.3 | 967.41 | 38 |
| 188 | DFDYGNQDFSGDK | 14.72 | 754.3 | 1130.47 | 38 |
| 189 | DFDYGNQDFSGDK | 14.72 | 754.3 | 1245.5 | 38 |
| 190 | DFTLGEAMQASTVPVYQELAR | 24.19 | 776.05 | 975.53 | 43 |
| 191 | DFTLGEAMQASTVPVYQELAR | 24.19 | 776.05 | 1074.59 | 43 |
| 192 | DFTLGEAMQASTVPVYQELAR | 24.19 | 1163.57 | 1175.64 | 56 |
| 193 | DHDLITAMK | 14.23 | 522.26 | 563.32 | 28 |
| 194 | DHDLITAMK | 14.23 | 522.26 | 695.34 | 28 |
| 195 | DHDLITAMK | 14.23 | 522.26 | 791.43 | 28 |
| 196 | DIAAWNR | 13.63 | 423.22 | 546.28 | 24 |
| 197 | DIAAWNR | 13.63 | 423.22 | 617.32 | 24 |
| 198 | DIAAWNR | 13.62 | 423.22 | 730.4 | 24 |
| 199 | DILYIQELAGGWK | 24.49 | 753.4 | 888.46 | 38 |
| 200 | DILYIQELAGGWK | 24.48 | 753.4 | 1001.54 | 38 |
| 201 | DILYIQELAGGWK | 24.49 | 753.4 | 1164.6 | 38 |
| 202 | DITILEK | 15.9 | 416.24 | 603.37 | 23 |
| 203 | DITILEK | 15.91 | 416.24 | 685.38 | 23 |
| 204 | DITILEK | 15.91 | 416.24 | 716.46 | 23 |
| 205 | DLLSAK | 12.45 | 323.69 | 429.23 | 19 |

TABLE 30-continued

| Transition number | Peptide | Retention time (minutes) | (m/z) filtered in Q1 | (m/z) filtered in Q3 | Collision energy (eV) |
|---|---|---|---|---|---|
| 206 | DLLSAK | 12.44 | 323.69 | 500.27 | 19 |
| 207 | DLLSAK | 12.45 | 323.69 | 531.35 | 19 |
| 208 | DLMITEAGR | 15.07 | 503.26 | 533.27 | 27 |
| 209 | DLMITEAGR | 15.07 | 503.26 | 646.35 | 27 |
| 210 | DLMITEAGR | 15.07 | 503.26 | 777.39 | 27 |
| 211 | DLMIVEAGR | 16.68 | 502.27 | 531.29 | 27 |
| 212 | DLMIVEAGR | 16.68 | 502.27 | 644.37 | 27 |
| 213 | DLMIVEAGR | 16.68 | 502.27 | 775.41 | 27 |
| 214 | DLMIVEAK | 16.23 | 459.75 | 473.24 | 25 |
| 215 | DLMIVEAK | 16.23 | 459.75 | 559.34 | 25 |
| 216 | DLMIVEAK | 16.23 | 459.75 | 690.39 | 25 |
| 217 | DLSGNPGK | 6.69 | 394.2 | 472.25 | 22 |
| 218 | DLSGNPGK | 6.69 | 394.2 | 559.28 | 22 |
| 219 | DLSGNPGK | 6.7 | 394.2 | 672.37 | 22 |
| 220 | DLSLR | 12.37 | 302.18 | 375.24 | 18 |
| 221 | DLSLR | 12.35 | 302.18 | 429.23 | 18 |
| 222 | DLSLR | 12.36 | 302.18 | 488.32 | 18 |
| 223 | DLTLR | 12.48 | 309.18 | 389.25 | 19 |
| 224 | DLTLR | 12.47 | 309.18 | 443.25 | 19 |
| 225 | DLTLR | 12.47 | 309.18 | 502.33 | 19 |
| 226 | DMTLGDAIK | 15.97 | 482.24 | 503.28 | 26 |
| 227 | DMTLGDAIK | 15.97 | 482.24 | 616.37 | 26 |
| 228 | DMTLGDAIK | 15.97 | 482.24 | 717.41 | 26 |
| 229 | DMTLGDAMALSAVPVYQELAR | 25.76 | 751.04 | 975.53 | 42 |
| 230 | DMTLGDAMALSAVPVYQELAR | 25.76 | 1126.06 | 1145.63 | 55 |
| 231 | DMTLGDAMALSAVPVYQELAR | 25.75 | 1126.06 | 1232.66 | 55 |
| 232 | DMTLGDAMK | 14.46 | 491.22 | 634.32 | 27 |
| 233 | DMTLGDAMK | 14.46 | 491.22 | 735.37 | 27 |
| 234 | DMTLGDAMK | 14.46 | 491.22 | 866.41 | 27 |
| 235 | DMTLGEAMALSAVPVYQDLAR | 25.92 | 751.04 | 961.51 | 42 |
| 236 | DMTLGEAMALSAVPVYQDLAR | 25.92 | 1126.06 | 1131.62 | 55 |
| 237 | DMTLGEAMALSAVPVYQDLAR | 25.92 | 1126.06 | 1218.65 | 55 |
| 238 | DMTLGEAMALSAVPVYQELAR | 26.48 | 755.71 | 779.4 | 42 |
| 239 | DMTLGEAMALSAVPVYQELAR | 26.48 | 755.71 | 975.53 | 42 |
| 240 | DMTLGEAMALSAVPVYQELAR | 26.47 | 1133.07 | 1232.66 | 55 |
| 241 | DMTLGEAMK | 15.09 | 498.23 | 535.25 | 27 |
| 242 | DMTLGEAMK | 15.09 | 498.23 | 648.34 | 27 |
| 243 | DMTLGEAMK | 15.09 | 498.23 | 749.39 | 27 |

TABLE 30-continued

| Transition number | Peptide | Retention time (minutes) | (m/z) filtered in Q1 | (m/z) filtered in Q3 | Collision energy (eV) |
|---|---|---|---|---|---|
| 244 | DMTLGQAMQASAVPVYQELAR | 23.29 | 760.38 | 779.4 | 42 |
| 245 | DMTLGQAMQASAVPVYQELAR | 23.29 | 760.38 | 975.53 | 42 |
| 246 | DMTLGQAMQASAVPVYQELAR | 23.29 | 760.38 | 976.42 | 42 |
| 247 | DQDLR | 2.54 | 323.66 | 403.23 | 19 |
| 248 | DQDLR | 2.55 | 323.66 | 472.2 | 19 |
| 249 | DQDLR | 2.55 | 323.66 | 531.29 | 19 |
| 250 | DQQIGWFVGWASKPGK | 21.64 | 601.98 | 830.45 | 34 |
| 251 | DQQIGWFVGWASKPGK | 21.64 | 902.46 | 929.52 | 45 |
| 252 | DQQIGWFVGWASKPGK | 21.64 | 902.46 | 1076.59 | 45 |
| 253 | DQQVQVYGNDLNR | 13.59 | 774.87 | 851.4 | 39 |
| 254 | DQQVQVYGNDLNR | 13.58 | 774.87 | 950.47 | 39 |
| 255 | DQQVQVYGNDLNR | 13.59 | 774.87 | 1078.53 | 39 |
| 256 | DQTLESAFK | 15.21 | 519.76 | 581.29 | 28 |
| 257 | DQTLESAFK | 15.21 | 519.76 | 694.38 | 28 |
| 258 | DQTLESAFK | 15.21 | 519.76 | 795.42 | 28 |
| 259 | DSIVWYSQELTR | 19.61 | 748.87 | 896.45 | 38 |
| 260 | DSIVWYSQELTR | 19.61 | 748.87 | 1082.53 | 38 |
| 261 | DSIVWYSQELTR | 19.61 | 748.87 | 1181.59 | 38 |
| 262 | DSIVWYSQQLTR | 19.1 | 748.38 | 895.46 | 38 |
| 263 | DSIVWYSQQLTR | 19.11 | 748.38 | 1081.54 | 38 |
| 264 | DSIVWYSQQLTR | 19.1 | 748.38 | 1180.61 | 38 |
| 265 | DSNLR | 1.77 | 302.66 | 402.25 | 18 |
| 266 | DSNLR | 1.77 | 302.66 | 430.19 | 18 |
| 267 | DSNLR | 1.77 | 302.66 | 489.28 | 18 |
| 268 | DSYIAWGGEAWK | 19.67 | 691.82 | 833.39 | 35 |
| 269 | DSYIAWGGEAWK | 19.67 | 691.82 | 904.43 | 35 |
| 270 | DSYIAWGGEAWK | 19.66 | 691.82 | 1017.52 | 35 |
| 271 | DTLNPEWPYK | 17.3 | 631.81 | 819.4 | 33 |
| 272 | DTLNPEWPYK | 17.3 | 631.81 | 933.45 | 33 |
| 273 | DTLNPEWPYK | 17.3 | 631.81 | 1046.53 | 33 |
| 274 | DVDEVFYK | 15.62 | 507.74 | 685.36 | 27 |
| 275 | DVDEVFYK | 15.62 | 507.74 | 800.38 | 27 |
| 276 | DVDEVFYK | 15.62 | 507.74 | 899.45 | 27 |
| 277 | DWILR | 17.44 | 351.7 | 415.2 | 20 |
| 278 | DWILR | 17.44 | 351.7 | 528.28 | 20 |
| 279 | DWILR | 17.44 | 351.7 | 587.37 | 20 |
| 280 | EAFLR | 12.51 | 318.18 | 435.27 | 19 |
| 281 | EAFLR | 12.51 | 318.18 | 461.24 | 19 |

TABLE 30-continued

| Transition number | Peptide | Retention time (minutes) | (m/z) filtered in Q1 | (m/z) filtered in Q3 | Collision energy (eV) |
|---|---|---|---|---|---|
| 282 | EAFLR | 12.51 | 318.18 | 506.31 | 19 |
| 283 | EAIVR | 7.84 | 294.18 | 387.27 | 18 |
| 284 | EAIVR | 7.84 | 294.18 | 413.24 | 18 |
| 285 | EAIVR | 7.84 | 294.18 | 458.31 | 18 |
| 286 | EAIVTEATPEYIVHSK | 16.43 | 596.31 | 746.42 | 34 |
| 287 | EAIVTEATPEYIVHSK | 16.43 | 596.31 | 972.51 | 34 |
| 288 | EAIVTEATPEYIVHSK | 16.42 | 596.31 | 1073.56 | 34 |
| 289 | EALVTEAAPEYLVHSK | 17.3 | 586.31 | 875.46 | 33 |
| 290 | EALVTEAAPEYLVHSK | 17.3 | 586.31 | 972.51 | 33 |
| 291 | EALVTEAAPEYLVHSK | 17.3 | 586.31 | 1114.59 | 33 |
| 292 | EALVTEAPEYLVHSK | 17.58 | 562.63 | 637.32 | 32 |
| 293 | EALVTEAPEYLVHSK | 17.58 | 562.63 | 972.51 | 32 |
| 294 | EALVTEAPEYLVHSK | 17.58 | 562.63 | 1043.55 | 32 |
| 295 | EEIVR | 8.41 | 323.18 | 387.27 | 19 |
| 296 | EEIVR | 8.4 | 323.18 | 471.24 | 19 |
| 297 | EEIVR | 8.4 | 323.18 | 516.31 | 19 |
| 298 | EEVLAALPAQLK | 19.48 | 641.37 | 740.47 | 33 |
| 299 | EEVLAALPAQLK | 19.47 | 641.37 | 811.5 | 33 |
| 300 | EEVLAALPAQLK | 19.47 | 641.37 | 924.59 | 33 |
| 301 | EFSAEAVNGVFVLC[CAM]K | 21.1 | 835.42 | 936.5 | 42 |
| 302 | EFSAEAVNGVFVLC[CAM]K | 21.1 | 835.42 | 1106.6 | 42 |
| 303 | EFSAEAVNGVFVLC[CAM]K | 21.1 | 835.42 | 1235.65 | 42 |
| 304 | EFSSESVHGVFVLC[CAM]K | 18.26 | 575.62 | 666.36 | 33 |
| 305 | EFSSESVHGVFVLC[CAM]K | 18226 | 575.62 | 822.45 | 33 |
| 306 | EFSSESVHGVFVLC[CAM]K | 18.26 | 575.62 | 959.51 | 33 |
| 307 | EGMSGSIR | 9.88 | 418.7 | 432.26 | 23 |
| 308 | EGMSGSIR | 9.88 | 418.7 | 519.29 | 23 |
| 309 | EGMSGSIR | 9.88 | 418.7 | 707.35 | 23 |
| 310 | EGMTGSIR | 10.63 | 425.71 | 432.26 | 24 |
| 311 | EGMTGSIR | 10.63 | 425.71 | 533.3 | 24 |
| 312 | EGMTGSIR | 10.63 | 425.71 | 664.34 | 24 |
| 313 | EIAVWNR | 14.78 | 444.24 | 475.24 | 25 |
| 314 | EIAVWNR | 14.77 | 444.24 | 574.31 | 25 |
| 315 | EIAVWNR | 14.77 | 444.24 | 645.35 | 25 |
| 316 | EIAYK | 8.46 | 312.17 | 381.21 | 19 |
| 317 | EIAYK | 8.46 | 312.17 | 477.23 | 19 |
| 318 | EIAYK | 8.46 | 312.17 | 494.3 | 19 |
| 319 | EIFER | 11.7 | 347.18 | 451.23 | 20 |

TABLE 30-continued

| Transition number | Peptide | Retention time (minutes) | (m/z) filtered in Q1 | (m/z) filtered in Q3 | Collision energy (eV) |
|---|---|---|---|---|---|
| 320 | EIFER | 11.7 | 347.18 | 519.24 | 20 |
| 321 | EIFER | 11.7 | 347.18 | 564.31 | 20 |
| 322 | EIFYHYR | 13.31 | 514.25 | 785.37 | 28 |
| 323 | EIFYHYR | 13.31 | 514.25 | 853.39 | 28 |
| 324 | EIFYHYR | 13.32 | 514.25 | 898.46 | 28 |
| 325 | EIGDDK | 1.99 | 338.66 | 434.19 | 20 |
| 326 | EIGDDK | 1.99 | 338.66 | 530.21 | 20 |
| 327 | EIGDDK | 1.99 | 338.66 | 547.27 | 20 |
| 328 | EIGDGK | 1.76 | 309.66 | 376.18 | 19 |
| 329 | EIGDGK | 1.75 | 309.66 | 472.2 | 19 |
| 330 | EIGDGK | 1.75 | 309.66 | 489.27 | 19 |
| 331 | EIGEDK | 2.32 | 345.67 | 448.2 | 20 |
| 332 | EIGEDK | 2.33 | 345.67 | 544.22 | 20 |
| 333 | EIGEDK | 2.33 | 345.67 | 561.29 | 20 |
| 334 | EIGEDNAR | 10.05 | 452.21 | 604.27 | 25 |
| 335 | EIGEDNAR | 10.05 | 452.21 | 661.29 | 25 |
| 336 | EIGEDNAR | 10.06 | 452.21 | 774.37 | 25 |
| 337 | EIGENK | 1.86 | 345.18 | 447.22 | 20 |
| 338 | EIGENK | 1.86 | 345.18 | 543.24 | 20 |
| 339 | EIGENK | 1.86 | 345.18 | 560.3 | 20 |
| 340 | EIGSEIDK | 11.04 | 445.73 | 591.3 | 25 |
| 341 | EIGSEIDK | 11.04 | 445.73 | 648.32 | 25 |
| 342 | EIGSEIDK | 11.04 | 445.73 | 761.4 | 25 |
| 343 | EMIYLK | 15.11 | 398.72 | 536.34 | 23 |
| 344 | EMIYLK | 15.11 | 398.72 | 650.32 | 23 |
| 345 | EMIYLK | 15.11 | 398.72 | 667.38 | 23 |
| 346 | EMLYVER | 14.12 | 470.23 | 566.29 | 26 |
| 347 | EMLYVER | 14.12 | 470.23 | 679.38 | 26 |
| 348 | EMLYVER | 14.12 | 470.23 | 810.42 | 26 |
| 349 | ENIEK | 11.07 | 316.67 | 389.24 | 19 |
| 350 | ENIEK | 11.07 | 316.67 | 486.22 | 19 |
| 351 | ENIEK | 11.07 | 316.67 | 503.28 | 19 |
| 352 | ENQLIVK | 12.15 | 422.25 | 472.35 | 24 |
| 353 | ENQLIVK | 12.15 | 422.25 | 600.41 | 24 |
| 354 | ENQLIVK | 12.15 | 422.25 | 714.45 | 24 |
| 355 | EQAILLFR | 19.88 | 495.29 | 548.36 | 27 |
| 356 | EQAILLFR | 19.88 | 495.29 | 661.44 | 27 |
| 357 | EQAILLFR | 19.88 | 495.29 | 732.48 | 27 |

TABLE 30-continued

| Transition number | Peptide | Retention time (minutes) | (m/z) filtered in Q1 | (m/z) filtered in Q3 | Collision energy (eV) |
|---|---|---|---|---|---|
| 358 | EQIQFLLR | 19.45 | 523.8 | 548.36 | 28 |
| 359 | EQIQFLLR | 19.45 | 523.8 | 676.41 | 28 |
| 360 | EQIQFLLR | 19.45 | 523.8 | 789.5 | 28 |
| 361 | EQLAFDPQVQQQVK | 16.43 | 829.43 | 954.54 | 41 |
| 362 | EQLAFDPQVQQQVK | 16.42 | 829.43 | 1069.56 | 41 |
| 363 | EQLAFDPQVQQQVK | 16.42 | 829.43 | 1216.63 | 41 |
| 364 | EQVDFVQR | 13.09 | 510.76 | 549.31 | 27 |
| 365 | EQVDFVQR | 13.09 | 510.76 | 664.34 | 27 |
| 366 | EQVDFVQR | 13.09 | 510.76 | 763.41 | 27 |
| 367 | EVGEIR | 9.35 | 351.69 | 474.27 | 20 |
| 368 | EVGEIR | 9.35 | 351.69 | 528.27 | 20 |
| 369 | EVGEIR | 9.35 | 351.69 | 573.34 | 20 |
| 370 | EVGEVR | 6.91 | 344.68 | 460.25 | 20 |
| 371 | EVGEVR | 6.91 | 344.68 | 514.25 | 20 |
| 372 | EVGEVR | 6.91 | 344.68 | 559.32 | 20 |
| 373 | EYLPASTFK | 15.41 | 528.27 | 553.3 | 28 |
| 374 | EYLPASTFK | 15.41 | 528.27 | 650.35 | 28 |
| 375 | EYLPASTFK | 15.41 | 528.27 | 763.43 | 28 |
| 376 | EYLPVSTFK | 17.16 | 542.29 | 581.33 | 29 |
| 377 | EYLPVSTFK | 17.16 | 542.29 | 678.38 | 29 |
| 378 | EYLPVSTFK | 17.16 | 542.29 | 791.47 | 29 |
| 379 | EYNTSGTFVFYDGK | 18.2 | 814.37 | 1033.5 | 41 |
| 380 | EYNTSGTFVFYDGK | 18.2 | 814.37 | 1120.53 | 41 |
| 381 | EYNTSGTFVFYDGK | 18.2 | 814.37 | 1221.58 | 41 |
| 382 | EYVPASTFK | 13.89 | 521.27 | 553.3 | 28 |
| 383 | EYVPASTFK | 13.89 | 521.27 | 650.35 | 28 |
| 384 | EYVPASTFK | 13.89 | 521.27 | 749.42 | 28 |
| 385 | FAPESTFK | 13.67 | 463.73 | 482.26 | 25 |
| 386 | FAPESTFK | 13.67 | 463.73 | 611.3 | 25 |
| 387 | FAPESTFK | 13.67 | 463.73 | 708.36 | 25 |
| 388 | FAQYAK | 9.39 | 364.19 | 509.27 | 21 |
| 389 | FAQYAK | 9.39 | 364.19 | 580.31 | 21 |
| 390 | FAQYAK | 9.39 | 364.19 | 581.27 | 21 |
| 391 | FDYGNR | 10.1 | 386.17 | 509.25 | 22 |
| 392 | FDYGNR | 10.1 | 386.17 | 597.23 | 22 |
| 393 | FDYGNR | 10.09 | 386.17 | 624.27 | 22 |
| 394 | FEDLYK | 13.52 | 407.7 | 423.26 | 23 |
| 395 | FEDLYK | 13.52 | 407.7 | 538.29 | 23 |

TABLE 30-continued

| Transition number | Peptide | Retention time (minutes) | (m/z) filtered in Q1 | (m/z) filtered in Q3 | Collision energy (eV) |
|---|---|---|---|---|---|
| 396 | FEDLYK | 13.52 | 407.7 | 667.33 | 23 |
| 397 | FEDTFHISNQK | 14.33 | 455.89 | 476.25 | 27 |
| 398 | FEDTFHISNQK | 14.33 | 455.89 | 589.33 | 27 |
| 399 | FEDTFHISNQK | 14.33 | 455.89 | 726.39 | 27 |
| 400 | FEDTFHTSNQQHEK | 10.66 | 583.26 | 870.41 | 33 |
| 401 | FEDTFHTSNQQHEK | 10.66 | 583.26 | 971.45 | 33 |
| 402 | FEDTFHTSNQQHEK | 10.66 | 583.26 | 1108.51 | 33 |
| 403 | FEYGNQDVSGDSGK | 11.95 | 751.82 | 764.34 | 38 |
| 404 | FEYGNQDVSGDSGK | 11.95 | 751.82 | 1063.47 | 38 |
| 405 | FEYGNQDVSGDSGK | 11.95 | 751.82 | 1226.53 | 38 |
| 406 | FFSDFQAK | 16 | 495.24 | 608.3 | 27 |
| 407 | FFSDFQAK | 16 | 495.24 | 695.34 | 27 |
| 408 | FFSDFQAK | 16 | 495.24 | 842.4 | 27 |
| 409 | FFSDLQAEGAIVIADER | 20.44 | 627.65 | 1143.6 | 35 |
| 410 | FFSDLQAEGAIVIADER | 20.43 | 940.97 | 1143.6 | 46 |
| 411 | FFSDLQAEGAIVIADER | 20.44 | 940.97 | 1179.57 | 46 |
| 412 | FFSDLR | 15.38 | 392.7 | 490.26 | 22 |
| 413 | FFSDLR | 15.38 | 392.7 | 610.29 | 22 |
| 414 | FFSDLR | 15.38 | 392.7 | 637.33 | 22 |
| 415 | FFSEFQAK | 16.13 | 502.25 | 622.32 | 27 |
| 416 | FFSEFQAK | 16.13 | 502.25 | 709.35 | 27 |
| 417 | FFSEFQAK | 16.13 | 502.25 | 856.42 | 27 |
| 418 | FGLEGQLR | 15.8 | 460.25 | 473.28 | 25 |
| 419 | FGLEGQLR | 15.8 | 460.25 | 602.33 | 25 |
| 420 | FGLEGQLR | 15.8 | 460.25 | 772.43 | 25 |
| 421 | FLESLYLNNLPASK | 20.75 | 804.94 | 856.49 | 40 |
| 422 | FLESLYLNNLPASK | 20.75 | 804.94 | 1019.55 | 40 |
| 423 | FLESLYLNNLPASK | 20.75 | 804.94 | 1219.67 | 40 |
| 424 | FLLEGQLR | 18.06 | 488.28 | 602.33 | 26 |
| 425 | FLLEGQLR | 18.06 | 488.28 | 715.41 | 26 |
| 426 | FLLEGQLR | 18.06 | 488.28 | 828.49 | 26 |
| 427 | FQQYVDR | 11.19 | 478.24 | 552.28 | 26 |
| 428 | FQQYVDR | 11.19 | 478.24 | 680.34 | 26 |
| 429 | FQQYVDR | 11.19 | 478.24 | 808.39 | 26 |
| 430 | FSDYVQR | 11.83 | 457.72 | 565.31 | 25 |
| 431 | FSDYVQR | 11.83 | 457.72 | 680.34 | 25 |
| 432 | FSDYVQR | 11.83 | 457.72 | 767.37 | 25 |
| 433 | FSTASTFK | 12.71 | 444.73 | 553.3 | 25 |

TABLE 30-continued

| Transition number | Peptide | Retention time (minutes) | (m/z) filtered in Q1 | (m/z) filtered in Q3 | Collision energy (eV) |
|---|---|---|---|---|---|
| 434 | FSTASTFK | 12.7 | 444.73 | 654.35 | 25 |
| 435 | FSTASTFK | 12.7 | 444.73 | 741.38 | 25 |
| 436 | FSWDGK | 14.32 | 370.17 | 505.24 | 21 |
| 437 | FSWDGK | 14.32 | 370.17 | 592.27 | 21 |
| 438 | FSWDGK | 14.32 | 370.17 | 593.24 | 21 |
| 439 | FSYGNQNISGGIDK | 14.61 | 750.36 | 803.43 | 38 |
| 440 | FSYGNQNISGGIDK | 14.61 | 750.36 | 1045.53 | 38 |
| 441 | FSYGNQNISGGIDK | 14.61 | 750.36 | 1102.55 | 38 |
| 442 | FSYGNQNISGGTDK | 12.74 | 744.34 | 791.39 | 38 |
| 443 | FSYGNQNISGGTDK | 12.74 | 744.34 | 1033.49 | 38 |
| 444 | FSYGNQNISGGTDK | 12.74 | 744.34 | 1090.51 | 38 |
| 445 | FSYGSQNISGGIDK | 14.74 | 736.85 | 803.43 | 37 |
| 446 | FSYGSQNISGGIDK | 14.74 | 736.85 | 1075.54 | 37 |
| 447 | FSYGSQNISGGIDK | 14.75 | 736.85 | 1238.6 | 37 |
| 448 | FTEYVK | 11.81 | 393.71 | 538.29 | 22 |
| 449 | FTEYVK | 11.81 | 393.71 | 639.33 | 22 |
| 450 | FTEYVK | 11.81 | 393.71 | 640.3 | 22 |
| 451 | FVPASTYK | 11.76 | 456.74 | 498.26 | 25 |
| 452 | FVPASTYK | 11.76 | 456.74 | 569.29 | 25 |
| 453 | FVPASTYK | 11.77 | 456.74 | 666.35 | 25 |
| 454 | FVYDLAQGQLPFKPEVQQQVK | 20.48 | 821.44 | 955.52 | 45 |
| 455 | FVYDLAQGQLPFKPEVQQQVK | 20.48 | 821.44 | 1108.59 | 45 |
| 456 | FVYDLAQGQLPFKPEVQQQVK | 20.49 | 821.44 | 1109.07 | 45 |
| 457 | FWLEDQLR | 20.39 | 553.79 | 660.33 | 29 |
| 458 | FWLEDQLR | 20.39 | 553.79 | 773.42 | 29 |
| 459 | FWLEDQLR | 20.38 | 553.79 | 959.49 | 29 |
| 460 | FWLEGPLK | 20.63 | 495.28 | 543.31 | 27 |
| 461 | FWLEGPLK | 20.63 | 495.28 | 656.4 | 27 |
| 462 | FWLEGPLK | 20.63 | 495.28 | 842.48 | 27 |
| 463 | FWLEGQLR | 19.49 | 524.78 | 602.33 | 28 |
| 464 | FWLEGQLR | 19.49 | 524.78 | 715.41 | 28 |
| 465 | FWLEGQLR | 19.48 | 524.78 | 901.49 | 28 |
| 466 | FYPASSFK | 14.74 | 473.74 | 636.34 | 26 |
| 467 | FYPASSFK | 14.74 | 473.74 | 799.4 | 26 |
| 468 | FYPASSFK | 14.74 | 473.74 | 800.36 | 26 |
| 469 | FYPASTFK | 14.98 | 480.74 | 553.3 | 26 |
| 470 | FYPASTFK | 14.99 | 480.74 | 650.35 | 26 |
| 471 | FYPASTFK | 14.98 | 480.74 | 813.41 | 26 |

TABLE 30-continued

| Transition number | Peptide | Retention time (minutes) | (m/z) filtered in Q1 | (m/z) filtered in Q3 | Collision energy (eV) |
|---|---|---|---|---|---|
| 472 | GAIQVSAVPVFQQIAR | 21.6 | 842.48 | 958.55 | 42 |
| 473 | GAIQVSAVPVFQQIAR | 21.6 | 842.48 | 1057.62 | 42 |
| 474 | GAIQVSAVPVFQQIAR | 21.59 | 842.48 | 1128.65 | 42 |
| 475 | GAIQVSAVPVFQQITR | 21.52 | 857.49 | 988.56 | 43 |
| 476 | GAIQVSAVPVFQQITR | 21.51 | 857.49 | 1087.63 | 43 |
| 477 | GAIQVSAVPVFQQITR | 21.52 | 857.49 | 1158.66 | 43 |
| 478 | GELPVSEDALEMTK | 18.1 | 759.87 | 936.43 | 38 |
| 479 | GELPVSEDALEMTK | 18.11 | 759.87 | 1023.47 | 38 |
| 480 | GELPVSEDALEMTK | 18.11 | 759.87 | 1122.53 | 38 |
| 481 | GISSSVR | 8.65 | 353.2 | 448.25 | 21 |
| 482 | GISSSVR | 8.65 | 353.2 | 535.28 | 21 |
| 483 | GISSSVR | 8.67 | 353.2 | 648.37 | 21 |
| 484 | GNQTLVFAR | 14.83 | 503.28 | 605.38 | 27 |
| 485 | GNQTLVFAR | 14.83 | 503.28 | 706.42 | 27 |
| 486 | GNQTLVFAR | 14.83 | 503.28 | 834.48 | 27 |
| 487 | GPLEISAFEEAR | 18.95 | 659.84 | 809.38 | 34 |
| 488 | GPLEISAFEEAR | 18.94 | 659.84 | 922.46 | 34 |
| 489 | GPLEISAFEEAR | 18.94 | 659.84 | 1051.51 | 34 |
| 490 | GPLTITPIQEVK | 18.14 | 648.38 | 814.47 | 34 |
| 491 | GPLTITPIQEVK | 18.15 | 648.38 | 927.55 | 34 |
| 492 | GPLTITPIQEVK | 18.14 | 648.38 | 1028.6 | 34 |
| 493 | GSLLLWDQK | 19.61 | 530.3 | 576.28 | 28 |
| 494 | GSLLLWDQK | 19.61 | 530.3 | 689.36 | 28 |
| 495 | GSLLLWDQK | 19.61 | 530.3 | 802.45 | 28 |
| 496 | GTFVLYDVQR | 17.93 | 599.32 | 680.34 | 31 |
| 497 | GTFVLYDVQR | 17.93 | 599.32 | 793.42 | 31 |
| 498 | GTFVLYDVQR | 17.93 | 599.32 | 892.49 | 31 |
| 499 | GTIVVADER | 11.82 | 480.26 | 490.23 | 26 |
| 500 | GTIVVADER | 11.82 | 480.26 | 589.29 | 26 |
| 501 | GTIVVADER | 11.82 | 480.26 | 688.36 | 26 |
| 502 | GTIVVLDAR | 15.77 | 472.28 | 573.34 | 26 |
| 503 | GTIVVLDAR | 15.77 | 472.28 | 672.4 | 26 |
| 504 | GTIVVLDAR | 15.77 | 472.28 | 785.49 | 26 |
| 505 | GTIVVVDER | 13.6 | 494.28 | 518.26 | 27 |
| 506 | GTIVVVDER | 13.6 | 494.28 | 617.33 | 27 |
| 507 | GTIVVVDER | 13.6 | 494.28 | 716.39 | 27 |
| 508 | GTLPFSAR | 14.96 | 424.73 | 577.31 | 24 |
| 509 | GTLPFSAR | 14.96 | 424.73 | 690.39 | 24 |

TABLE 30-continued

| Transition number | Peptide | Retention time (minutes) | (m/z) filtered in Q1 | (m/z) filtered in Q3 | Collision energy (eV) |
|---|---|---|---|---|---|
| 510 | GTLPFSAR | 14.97 | 424.73 | 791.44 | 24 |
| 511 | HIADSK | 11.91 | 335.68 | 420.21 | 20 |
| 512 | HIADSK | 11.9 | 335.68 | 524.25 | 20 |
| 513 | HIADSK | 11.91 | 335.68 | 533.29 | 20 |
| 514 | HNGTDGAWIISSLR | 19.36 | 509.6 | 575.35 | 29 |
| 515 | HNGTDGAWIISSLR | 19.35 | 509.6 | 653.26 | 29 |
| 516 | HNGTDGAWIISSLR | 19.36 | 509.6 | 688.44 | 29 |
| 517 | HTLSVFDQER | 14.25 | 411.21 | 432.22 | 25 |
| 518 | HTLSVFDQER | 14.25 | 411.21 | 547.25 | 25 |
| 519 | HTLSVFDQER | 14.25 | 411.21 | 694.32 | 25 |
| 520 | HVTFASFR | 14.36 | 322.17 | 338.18 | 20 |
| 521 | HVTFASFR | 14.36 | 322.17 | 409.22 | 20 |
| 522 | HVTFASFR | 14.36 | 322.17 | 485.25 | 20 |
| 523 | IAISLMGYDAGFLR | 23.93 | 763.91 | 898.44 | 39 |
| 524 | IAISLMGYDAGFLR | 23.93 | 763.91 | 1029.48 | 39 |
| 525 | IAISLMGYDAGFLR | 23.94 | 763.91 | 1229.6 | 39 |
| 526 | IALSLMGFDSGILK | 24.91 | 732.91 | 836.45 | 37 |
| 527 | IALSLMGFDSGILK | 24.91 | 732.91 | 967.49 | 37 |
| 528 | IALSLMGFDSGILK | 24.91 | 732.91 | 1167.61 | 37 |
| 529 | IANALIGLENHK | 15.95 | 431.58 | 697.36 | 26 |
| 530 | IANALIGLENHK | 15.95 | 646.87 | 697.36 | 33 |
| 531 | IANALIGLENHK | 15.95 | 646.87 | 810.45 | 33 |
| 532 | IDTFWLDNSLK | 21.79 | 676.35 | 689.38 | 35 |
| 533 | IDTFWLDNSLK | 21.79 | 676.35 | 875.46 | 35 |
| 534 | IDTFWLDNSLK | 21.79 | 676.35 | 1123.58 | 35 |
| 535 | IDYYNLDR | 14.85 | 536.26 | 680.34 | 29 |
| 536 | IDYYNLDR | 14.85 | 536.26 | 843.4 | 29 |
| 537 | IDYYNLDR | 14.85 | 536.26 | 958.43 | 29 |
| 538 | IFNALIALDSGVIK | 24.74 | 737.44 | 802.47 | 37 |
| 539 | IFNALIALDSGVIK | 24.74 | 737.44 | 915.55 | 37 |
| 540 | IFNALIALDSGVIK | 24.74 | 737.44 | 1028.64 | 37 |
| 541 | IFNSLLALDSGALDNER | 22.76 | 924.48 | 976.43 | 46 |
| 542 | IFNSLLALDSGALDNER | 22.77 | 924.48 | 1089.52 | 46 |
| 543 | IFNSLLALDSGALDNER | 22.76 | 924.48 | 1160.55 | 46 |
| 544 | IFNTLIGLENGIVK | 23.29 | 765.95 | 829.48 | 39 |
| 545 | IFNTLIGLENGIVK | 23.3 | 765.95 | 942.56 | 39 |
| 546 | IFNTLIGLENGIVK | 23.3 | 765.95 | 1055.65 | 39 |
| 547 | IGLDLMQK | 17.7 | 459.26 | 634.32 | 25 |

TABLE 30-continued

| Transition number | Peptide | Retention time (minutes) | (m/z) filtered in Q1 | (m/z) filtered in Q3 | Collision energy (eV) |
|---|---|---|---|---|---|
| 548 | IGLDLMQK | 17.7 | 459.26 | 747.41 | 25 |
| 549 | IGLDLMQK | 17.7 | 459.26 | 804.43 | 25 |
| 550 | IGLEK | 8.54 | 280.18 | 389.24 | 17 |
| 551 | IGLEK | 8.55 | 280.18 | 413.24 | 17 |
| 552 | IGLEK | 8.54 | 280.18 | 446.26 | 17 |
| 553 | IGLELMQQEVQR | 18.73 | 722.38 | 787.41 | 37 |
| 554 | IGLELMQQEVQR | 18.73 | 722.38 | 918.45 | 37 |
| 555 | IGLELMQQEVQR | 18.73 | 722.38 | 1031.53 | 37 |
| 556 | IGLELMSK | 17.52 | 445.75 | 478.27 | 25 |
| 557 | IGLELMSK | 17.52 | 445.75 | 720.4 | 25 |
| 558 | IGLELMSK | 17.52 | 445.75 | 777.42 | 25 |
| 559 | IGLELMSNEVK | 18.73 | 616.83 | 707.34 | 32 |
| 560 | IGLELMSNEVK | 18.73 | 616.83 | 820.42 | 32 |
| 561 | IGLELMSNEVK | 18.73 | 616.83 | 949.47 | 32 |
| 562 | IGLER | 10.96 | 294.18 | 304.16 | 18 |
| 563 | IGLER | 10.96 | 294.18 | 417.25 | 18 |
| 564 | IGLER | 10.96 | 294.18 | 474.27 | 18 |
| 565 | IGLNK | 9.59 | 272.68 | 374.24 | 17 |
| 566 | IGLNK | 9.59 | 272.68 | 398.24 | 17 |
| 567 | IGLNK | 9.59 | 272.68 | 431.26 | 17 |
| 568 | IGLNLMQK | 17.1 | 458.77 | 633.34 | 25 |
| 569 | IGLNLMQK | 17.09 | 458.77 | 746.42 | 25 |
| 570 | IGLNLMQK | 17.11 | 458.77 | 803.44 | 25 |
| 571 | IGPSLMQSELQR | 17.02 | 679.86 | 760.39 | 35 |
| 572 | IGPSLMQSELQR | 17.02 | 679.86 | 891.44 | 35 |
| 573 | IGPSLMQSELQR | 17.02 | 679.86 | 1188.6 | 35 |
| 574 | IGYGNMQIGTEVDQFWLK | 24.31 | 700.35 | 935.5 | 39 |
| 575 | IGYGNMQIGTEVDQFWLK | 24.32 | 1050.02 | 1164.54 | 51 |
| 576 | IGYGNMQIGTEVDQFWLK | 24.3 | 1050.02 | 1222.61 | 51 |
| 577 | IINHNLPVK | 11.88 | 349.88 | 456.32 | 21 |
| 578 | IINHNLPVK | 11.88 | 349.88 | 570.36 | 21 |
| 579 | IINHNLPVK | 11.88 | 349.88 | 592.32 | 21 |
| 580 | IINHNLPVR | 12.04 | 359.22 | 598.37 | 22 |
| 581 | IINHNLPVR | 12.04 | 538.32 | 598.37 | 29 |
| 582 | IINHNLPVR | 12.04 | 538.32 | 849.47 | 29 |
| 583 | ILFQQGTQQAC[CAM]AER | 14.51 | 550.61 | 606.27 | 32 |
| 584 | ILFQQGTQQAC[CAM]AER | 14.51 | 825.41 | 1020.45 | 41 |
| 585 | ILFQQGTQQAC[CAM]AER | 14.51 | 825.41 | 1148.51 | 41 |

TABLE 30-continued

| Transition number | Peptide | Retention time (minutes) | (m/z) filtered in Q1 | (m/z) filtered in Q3 | Collision energy (eV) |
|---|---|---|---|---|---|
| 586 | ILNNWFK | 18.98 | 467.76 | 594.3 | 26 |
| 587 | ILNNWFK | 18.98 | 467.76 | 708.35 | 26 |
| 588 | ILNNWFK | 18.97 | 467.76 | 821.43 | 26 |
| 589 | ILNTLISLEEK | 19.98 | 636.87 | 718.4 | 33 |
| 590 | ILNTLISLEEK | 19.98 | 636.87 | 1046.57 | 33 |
| 591 | ILNTLISLEEK | 19.98 | 636.87 | 1159.66 | 33 |
| 592 | INIVK | 11.43 | 293.7 | 359.27 | 18 |
| 593 | INIVK | 11.43 | 293.7 | 440.29 | 18 |
| 594 | INIVK | 11.43 | 293.7 | 473.31 | 18 |
| 595 | INLYGNALSR | 16.05 | 560.81 | 617.34 | 30 |
| 596 | INLYGNALSR | 16.05 | 560.81 | 780.4 | 30 |
| 597 | INLYGNALSR | 16.05 | 560.81 | 893.48 | 30 |
| 598 | IPFSLNLEMK | 21.68 | 596.33 | 834.44 | 31 |
| 599 | IPFSLNLEMK | 21.67 | 596.33 | 981.51 | 31 |
| 600 | IPFSLNLEMK | 21.67 | 596.33 | 1078.56 | 31 |
| 601 | IPHTLFALDADAVR | 20 | 513.62 | 531.29 | 30 |
| 602 | IPHTLFALDADAVR | 20 | 513.62 | 646.32 | 30 |
| 603 | IPHTLFALDADAVR | 20 | 769.92 | 1191.64 | 39 |
| 604 | IPHTLFALDAGAAR | 18.58 | 726.9 | 744.4 | 37 |
| 605 | IPHTLFALDAGAAR | 18.58 | 726.9 | 891.47 | 37 |
| 606 | IPHTLFALDAGAAR | 18.58 | 726.9 | 1004.55 | 37 |
| 607 | IPHTLFALDAGAVR | 19.72 | 494.28 | 588.31 | 29 |
| 608 | IPHTLFALDAGAVR | 19.71 | 494.28 | 780.44 | 29 |
| 609 | IPHTLFALDAGAVR | 19.72 | 740.92 | 1133.63 | 38 |
| 610 | IPNAIIGLETGVIK | 21.75 | 719.44 | 816.48 | 37 |
| 611 | IPNAIIGLETGVIK | 21.75 | 719.44 | 929.57 | 37 |
| 612 | IPNAIIGLETGVIK | 21.75 | 719.44 | 1227.73 | 37 |
| 613 | IPNALIGLETGAIK | 20.96 | 705.42 | 788.45 | 36 |
| 614 | IPNALIGLETGAIK | 20.96 | 705.42 | 901.54 | 36 |
| 615 | IPNALIGLETGAIK | 20.96 | 705.42 | 1014.62 | 36 |
| 616 | IPNSLIAFDTGAVR | 20.24 | 737.41 | 765.39 | 37 |
| 617 | IPNSLIAFDTGAVR | 20.24 | 737.41 | 836.43 | 37 |
| 618 | IPNSLIAFDTGAVR | 20.24 | 737.41 | 949.51 | 37 |
| 619 | IPSAIIGLETGVIK | 21.66 | 705.93 | 816.48 | 36 |
| 620 | IPSAIIGLETGVIK | 21.67 | 705.93 | 929.57 | 36 |
| 621 | IPSAIIGLETGVIK | 21.66 | 705.93 | 1200.72 | 36 |
| 622 | ISAFNQVK | 13.02 | 453.76 | 488.28 | 25 |
| 623 | ISAFNQVK | 13.02 | 453.76 | 706.39 | 25 |

TABLE 30-continued

| Transition number | Peptide | Retention time (minutes) | (m/z) filtered in Q1 | (m/z) filtered in Q3 | Collision energy (eV) |
|---|---|---|---|---|---|
| 624 | ISAFNQVK | 13.02 | 453.76 | 793.42 | 25 |
| 625 | ISAHEQILFLR | 18.28 | 442.92 | 548.36 | 26 |
| 626 | ISAHEQILFLR | 18.28 | 442.92 | 789.5 | 26 |
| 627 | ISAHEQILFLR | 18.28 | 663.88 | 918.54 | 34 |
| 628 | ISAMEQTR | 9.84 | 468.23 | 664.31 | 26 |
| 629 | ISAMEQTR | 9.84 | 468.23 | 735.35 | 26 |
| 630 | ISAMEQTR | 9.84 | 468.23 | 822.38 | 26 |
| 631 | ISAMEQVK | 11.65 | 453.24 | 634.32 | 25 |
| 632 | ISAMEQVK | 11.65 | 453.24 | 705.36 | 25 |
| 633 | ISAMEQVK | 11.65 | 453.24 | 792.39 | 25 |
| 634 | ISATEQVAFLR | 17.7 | 412.23 | 435.27 | 25 |
| 635 | ISATEQVAFLR | 17.71 | 412.23 | 506.31 | 25 |
| 636 | ISATEQVAFLR | 17.7 | 412.23 | 605.38 | 25 |
| 637 | ISATQQIAFLR | 18.58 | 624.36 | 747.45 | 32 |
| 638 | ISATQQIAFLR | 18.58 | 624.36 | 1047.59 | 32 |
| 639 | ISATQQIAFLR | 18.58 | 624.36 | 1134.63 | 32 |
| 640 | ISAVNQVEFLESLFLNK | 28.77 | 976.03 | 988.51 | 48 |
| 641 | ISAVNQVEFLESLFLNK | 28.77 | 976.03 | 1110.62 | 48 |
| 642 | ISAVNQVEFLESLFLNK | 28.77 | 976.03 | 1239.66 | 48 |
| 643 | ISAVNQVK | 10.32 | 429.76 | 488.28 | 24 |
| 644 | ISAVNQVK | 10.32 | 429.76 | 658.39 | 24 |
| 645 | ISAVNQVK | 10.32 | 429.76 | 745.42 | 24 |
| 646 | ISPEEQIQFLR | 18.87 | 680.37 | 933.52 | 35 |
| 647 | ISPEEQIQFLR | 18.87 | 680.37 | 1062.56 | 35 |
| 648 | ISPEEQIQFLR | 18.87 | 680.37 | 1159.61 | 35 |
| 649 | ISPEEQVR | 10.49 | 479.25 | 531.29 | 26 |
| 650 | ISPEEQVR | 10.49 | 479.25 | 660.33 | 26 |
| 651 | ISPEEQVR | 10.49 | 479.25 | 757.38 | 26 |
| 652 | ISPEGQVR | 9.86 | 443.24 | 459.27 | 25 |
| 653 | ISPEGQVR | 9.86 | 443.24 | 588.31 | 25 |
| 654 | ISPEGQVR | 9.86 | 443.24 | 685.36 | 25 |
| 655 | ISPLEQLAFLR | 24.02 | 643.88 | 876.49 | 33 |
| 656 | ISPLEQLAFLR | 24.01 | 643.88 | 989.58 | 33 |
| 657 | ISPLEQLAFLR | 24.02 | 643.88 | 1086.63 | 33 |
| 658 | ITAFQQVDFLR | 21.11 | 669.36 | 777.43 | 34 |
| 659 | ITAFQQVDFLR | 21.12 | 669.36 | 905.48 | 34 |
| 660 | ITAFQQVDFLR | 21.12 | 669.36 | 1123.59 | 34 |
| 661 | ITPIQEVNFADDFANNR | 21.25 | 655.32 | 736.34 | 37 |

TABLE 30-continued

| Transition number | Peptide | Retention time (minutes) | (m/z) filtered in Q1 | (m/z) filtered in Q3 | Collision energy (eV) |
|---|---|---|---|---|---|
| 662 | ITPIQEVNFADDFANNR | 21.25 | 655.32 | 851.36 | 37 |
| 663 | ITPIQEVNFADDFANNR | 21.25 | 655.32 | 922.4 | 37 |
| 664 | ITPIQEVNFADDLANNR | 20.95 | 643.99 | 817.38 | 36 |
| 665 | ITPIQEVNFADDLANNR | 20.95 | 965.49 | 1149.53 | 47 |
| 666 | ITPIQEVNFADDLANNR | 20.96 | 965.49 | 1248.6 | 47 |
| 667 | ITPQQEAQFAYK | 14.52 | 712.36 | 856.42 | 36 |
| 668 | ITPQQEAQFAYK | 14.52 | 712.36 | 984.48 | 36 |
| 669 | ITPQQEAQFAYK | 14.52 | 712.36 | 1209.59 | 36 |
| 670 | ITPQQEAQFTYK | 14.33 | 485.25 | 558.29 | 28 |
| 671 | ITPQQEAQFTYK | 14.33 | 727.37 | 1014.49 | 37 |
| 672 | ITPQQEAQFTYK | 14.33 | 727.37 | 1239.6 | 37 |
| 673 | ITPVQEVNFADDLAHNR | 18.98 | 646.99 | 840.4 | 36 |
| 674 | ITPVQEVNFADDLAHNR | 18.98 | 646.99 | 862.92 | 36 |
| 675 | ITPVQEVNFADDLAHNR | 18.98 | 646.99 | 911.43 | 36 |
| 676 | IVAFALK | 17.21 | 381.25 | 478.3 | 22 |
| 677 | IVAFALK | 17.22 | 381.25 | 549.34 | 22 |
| 678 | IVAFALK | 17.21 | 381.25 | 648.41 | 22 |
| 679 | IVAFALNMEMR | 17.95 | 647.84 | 864.41 | 34 |
| 680 | IVAFALNMEMR | 17.95 | 647.84 | 1011.48 | 34 |
| 681 | IVAFALNMEMR | 17.97 | 647.84 | 1082.51 | 34 |
| 682 | IVESTTLADGTVVHGK | 13.69 | 542.96 | 697.4 | 31 |
| 683 | IVESTTLADGTVVHGK | 13.69 | 542.96 | 812.43 | 31 |
| 684 | IVESTTLADGTVVHGK | 13.68 | 542.96 | 883.46 | 31 |
| 685 | IYNSLIGLNEK | 17.37 | 632.35 | 673.39 | 33 |
| 686 | IYNSLIGLNEK | 17.37 | 632.35 | 786.47 | 33 |
| 687 | IYNSLIGLNEK | 17.37 | 632.35 | 987.55 | 33 |
| 688 | KPDIGWWVGWIER | 24.47 | 547.96 | 660.35 | 31 |
| 689 | KPDIGWWVGWIER | 24.47 | 547.96 | 883.45 | 31 |
| 690 | KPDIGWWVGWIER | 24.46 | 821.43 | 1188.59 | 41 |
| 691 | LAC[CAM]ATNNLAR | 11.22 | 552.28 | 688.37 | 29 |
| 692 | LAC[CAM]ATNNLAR | 11.22 | 552.28 | 759.41 | 29 |
| 693 | LAC[CAM]ATNNLAR | 11.22 | 552.28 | 919.44 | 29 |
| 694 | LAQGELPFPAPVQSTVR | 19.84 | 905.5 | 954.54 | 45 |
| 695 | LAQGELPFPAPVQSTVR | 19.84 | 905.5 | 1101.61 | 45 |
| 696 | LAQGELPFPAPVQSTVR | 19.84 | 905.5 | 1198.66 | 45 |
| 697 | LAQNELPYPIEIQK | 19.09 | 828.45 | 929.47 | 41 |
| 698 | LAQNELPYPIEIQK | 19.09 | 828.45 | 987.55 | 41 |
| 699 | LAQNELPYPIEIQK | 19.08 | 828.45 | 1100.64 | 41 |

TABLE 30-continued

| Transition number | Peptide | Retention time (minutes) | (m/z) filtered in Q1 | (m/z) filtered in Q3 | Collision energy (eV) |
|---|---|---|---|---|---|
| 700 | LAQNELQYPIEIQK | 17.98 | 843.96 | 890.5 | 42 |
| 701 | LAQNELQYPIEIQK | 17.98 | 843.96 | 1018.56 | 42 |
| 702 | LAQNELQYPIEIQK | 17.98 | 843.96 | 1131.64 | 42 |
| 703 | LDFGNK | 11.75 | 347.18 | 465.25 | 20 |
| 704 | LDFGNK | 11.74 | 347.18 | 547.25 | 20 |
| 705 | LDFGNK | 11.75 | 347.18 | 580.27 | 20 |
| 706 | LDGSLNR | 9.48 | 387.71 | 402.25 | 22 |
| 707 | LDGSLNR | 9.48 | 387.71 | 546.3 | 22 |
| 708 | LDGSLNR | 9.48 | 387.71 | 661.33 | 22 |
| 709 | LEILQQALAELGLYPK | 29.81 | 900.02 | 1003.58 | 45 |
| 710 | LEILQQALAELGLYPK | 29.81 | 900.02 | 1074.62 | 45 |
| 711 | LEILQQALAELGLYPK | 29.81 | 900.02 | 1202.68 | 45 |
| 712 | LENQEQVK | 7.6 | 494.26 | 631.34 | 27 |
| 713 | LENQEQVK | 7.59 | 494.26 | 745.38 | 27 |
| 714 | LENQEQVK | 7.59 | 494.26 | 874.43 | 27 |
| 715 | LETQEEVEK | 9.88 | 552.77 | 633.31 | 29 |
| 716 | LETQEEVEK | 9.88 | 552.77 | 862.42 | 29 |
| 717 | LETQEEVEK | 9.88 | 552.77 | 991.46 | 29 |
| 718 | LETQEEVK | 9.5 | 488.25 | 504.27 | 26 |
| 719 | LETQEEVK | 9.49 | 488.25 | 733.37 | 26 |
| 720 | LETQEEVK | 9.49 | 488.25 | 862.42 | 26 |
| 721 | LFAAEGVK | 13.53 | 417.74 | 503.28 | 23 |
| 722 | LFAAEGVK | 13.53 | 417.74 | 574.32 | 23 |
| 723 | LFAAEGVK | 13.53 | 417.74 | 721.39 | 23 |
| 724 | LFESAGVK | 12.99 | 425.74 | 461.27 | 24 |
| 725 | LFESAGVK | 12.99 | 425.74 | 590.31 | 24 |
| 726 | LFESAGVK | 12.99 | 425.74 | 737.38 | 24 |
| 727 | LFGAAGVK | 13.94 | 381.73 | 445.28 | 22 |
| 728 | LFGAAGVK | 13.94 | 381.73 | 502.3 | 22 |
| 729 | LFGAAGVK | 13.94 | 381.73 | 649.37 | 22 |
| 730 | LGVDR | 8.51 | 280.16 | 290.15 | 17 |
| 731 | LGVDR | 8.51 | 280.16 | 389.21 | 17 |
| 732 | LGVDR | 8.5 | 280.16 | 446.24 | 17 |
| 733 | LLNLLSQSK | 17.97 | 508.31 | 562.32 | 27 |
| 734 | LLNLLSQSK | 17.97 | 508.31 | 789.45 | 27 |
| 735 | LLNLLSQSK | 17.97 | 508.31 | 902.53 | 27 |
| 736 | LLQDER | 9.34 | 387.21 | 547.25 | 22 |
| 737 | LLQDER | 9.31 | 387.21 | 599.3 | 22 |

TABLE 30-continued

| Transition number | Peptide | Retention time (minutes) | (m/z) filtered in Q1 | (m/z) filtered in Q3 | Collision energy (eV) |
|---|---|---|---|---|---|
| 738 | LLQDER | 9.34 | 387.21 | 660.33 | 22 |
| 739 | LLVQDGDC[CAM]GR | 11.92 | 566.77 | 679.25 | 30 |
| 740 | LLVQDGDC[CAM]GR | 11.92 | 566.77 | 807.3 | 30 |
| 741 | LLVQDGDC[CAM]GR | 11.92 | 566.77 | 906.37 | 30 |
| 742 | LNEVGYGNR | 10.74 | 511.26 | 566.27 | 27 |
| 743 | LNEVGYGNR | 10.74 | 511.26 | 665.34 | 27 |
| 744 | LNEVGYGNR | 10.73 | 511.26 | 794.38 | 27 |
| 745 | LNYGNADPSTK | 10.76 | 590.29 | 732.35 | 31 |
| 746 | LNYGNADPSTK | 10.76 | 590.29 | 789.37 | 31 |
| 747 | LNYGNADPSTK | 10.76 | 590.29 | 952.44 | 31 |
| 748 | LNYGNK | 7.21 | 354.69 | 481.24 | 21 |
| 749 | LNYGNK | 7.24 | 354.69 | 562.26 | 21 |
| 750 | LNYGNK | 7.22 | 354.69 | 595.28 | 21 |
| 751 | LPASK | 1.93 | 258.16 | 305.18 | 16 |
| 752 | LPASK | 1.93 | 258.16 | 369.21 | 16 |
| 753 | LPASK | 1.93 | 258.16 | 402.23 | 16 |
| 754 | LPHTLFALDADAVR | 19.98 | 769.92 | 977.51 | 39 |
| 755 | LPHTLFALDADAVR | 19.98 | 769.92 | 1090.59 | 39 |
| 756 | LPHTLFALDADAVR | 19.98 | 769.92 | 1191.64 | 39 |
| 757 | LPHTLFALDAGAVR | 19.7 | 740.92 | 919.5 | 38 |
| 758 | LPHTLFALDAGAVR | 19.67 | 740.92 | 1032.58 | 38 |
| 759 | LPHTLFALDAGAVR | 19.7 | 740.92 | 1133.63 | 38 |
| 760 | LPLAIMGFDSGILQSPK | 25.08 | 893.99 | 944.5 | 44 |
| 761 | LPLAIMGFDSGILQSPK | 25.08 | 893.99 | 1091.57 | 44 |
| 762 | LPLAIMGFDSGILQSPK | 25.08 | 893.99 | 1148.59 | 44 |
| 763 | LPLAIMGYDADILLDATTPR | 27.86 | 720.39 | 773.42 | 40 |
| 764 | LPLAIMGYDADILLDATTPR | 27.87 | 720.39 | 886.5 | 40 |
| 765 | LPLAIMGYDADILLDATTPR | 27.87 | 720.39 | 1160.57 | 40 |
| 766 | LPSSLIALETGAVR | 20.6 | 713.92 | 816.46 | 36 |
| 767 | LPSSLIALETGAVR | 20.6 | 713.92 | 929.54 | 36 |
| 768 | LPSSLIALETGAVR | 20.6 | 713.92 | 1216.69 | 36 |
| 769 | LPVSAQTLQYTANILK | 21.84 | 880.5 | 950.53 | 44 |
| 770 | LPVSAQTLQYTANILK | 21.84 | 880.5 | 1063.61 | 44 |
| 771 | LPVSAQTLQYTANILK | 21.85 | 880.5 | 1164.66 | 44 |
| 772 | LPVSER | 9.57 | 350.7 | 490.26 | 20 |
| 773 | LPVSER | 9.57 | 350.7 | 526.29 | 20 |
| 774 | LPVSER | 9.57 | 350.7 | 587.31 | 20 |
| 775 | LPVSPTAVDMTER | 16.21 | 708.36 | 1019.48 | 36 |

TABLE 30-continued

| Transition number | Peptide | Retention time (minutes) | (m/z) filtered in Q1 | (m/z) filtered in Q3 | Collision energy (eV) |
|---|---|---|---|---|---|
| 776 | LPVSPTAVDMTER | 16.21 | 708.36 | 1106.51 | 36 |
| 777 | LPVSPTAVDMTER | 16.21 | 708.36 | 1205.58 | 36 |
| 778 | LSASK | 10.72 | 253.15 | 305.18 | 16 |
| 779 | LSASK | 10.71 | 253.15 | 359.19 | 16 |
| 780 | LSASK | 10.71 | 253.15 | 392.21 | 16 |
| 781 | LSAVPIYQEVAR | 17.96 | 673.38 | 765.39 | 35 |
| 782 | LSAVPIYQEVAR | 17.96 | 673.38 | 975.53 | 35 |
| 783 | LSAVPIYQEVAR | 17.95 | 673.38 | 1074.59 | 35 |
| 784 | LSAVPVYQELAR | 18.45 | 449.25 | 616.34 | 26 |
| 785 | LSAVPVYQELAR | 18.44 | 673.38 | 779.4 | 35 |
| 786 | LSAVPVYQELAR | 18.44 | 673.38 | 975.53 | 35 |
| 787 | LSC[CAM]TLVIDEASGDLLHR | 20.38 | 633.66 | 797.43 | 36 |
| 788 | LSC[CAM]TLVIDEASGDLLHR | 20.38 | 633.66 | 868.46 | 36 |
| 789 | LSC[CAM]TLVIDEASGDLLHR | 20.38 | 633.66 | 1112.53 | 36 |
| 790 | LSLQHGWFIGWIEK | 23.95 | 571.98 | 632.34 | 33 |
| 791 | LSLQHGWFIGWIEK | 23.95 | 571.98 | 892.49 | 33 |
| 792 | LSLQHGWFIGWIEK | 23.95 | 571.98 | 969.49 | 33 |
| 793 | LSQNSLPFSQEAMNSVK | 18.64 | 627.31 | 1140.54 | 35 |
| 794 | LSQNSLPFSQEAMNSVK | 18.63 | 940.46 | 1140.54 | 46 |
| 795 | LSQNSLPFSQEAMNSVK | 18.64 | 940.46 | 1237.59 | 46 |
| 796 | LSVNPK | 9.8 | 329.2 | 457.28 | 19 |
| 797 | LSVNPK | 9.79 | 329.2 | 511.29 | 19 |
| 798 | LSVNPK | 9.8 | 329.2 | 544.31 | 19 |
| 799 | LTVGAR | 9.51 | 308.69 | 402.25 | 19 |
| 800 | LTVGAR | 9.51 | 308.69 | 442.27 | 19 |
| 801 | LTVGAR | 9.51 | 308.69 | 503.29 | 19 |
| 802 | LYGFALNIDMPGGEADIGK | 23.35 | 661 | 843.42 | 37 |
| 803 | LYGFALNIDMPGGEADIGK | 23.35 | 990.99 | 1089.49 | 49 |
| 804 | LYGFALNIDMPGGEADIGK | 23.35 | 990.99 | 1202.57 | 49 |
| 805 | LYHNELPFR | 15.29 | 396.88 | 414.21 | 24 |
| 806 | LYHNELPFR | 15.29 | 396.88 | 419.24 | 24 |
| 807 | LYHNELPFR | 15.29 | 396.88 | 657.3 | 24 |
| 808 | LYHNK | 8.54 | 337.68 | 414.21 | 20 |
| 809 | LYHNK | 8.53 | 337.68 | 528.26 | 20 |
| 810 | LYHNK | 8.53 | 337.68 | 561.28 | 20 |
| 811 | LYQNDLPFR | 17.2 | 583.3 | 761.39 | 31 |
| 812 | LYQNDLPFR | 17.2 | 583.3 | 889.45 | 31 |
| 813 | LYQNDLPFR | 17.2 | 583.3 | 1052.52 | 31 |

TABLE 30-continued

| Transition number | Peptide | Retention time (minutes) | (m/z) filtered in Q1 | (m/z) filtered in Q3 | Collision energy (eV) |
|---|---|---|---|---|---|
| 814 | MDDLFK | 15.5 | 384.68 | 522.29 | 22 |
| 815 | MDDLFK | 15.5 | 384.68 | 622.25 | 22 |
| 816 | MDDLFK | 15.5 | 384.68 | 637.32 | 22 |
| 817 | MEDLHK | 6.66 | 386.69 | 512.28 | 22 |
| 818 | MEDLHK | 6.65 | 386.69 | 626.26 | 22 |
| 819 | MEDLHK | 6.66 | 386.69 | 641.33 | 22 |
| 820 | MLIALIGLENHK | 21.33 | 451.26 | 527.26 | 27 |
| 821 | MLIALIGLENHK | 21.33 | 451.26 | 697.36 | 27 |
| 822 | MLIALIGLENHK | 21.33 | 451.26 | 810.45 | 27 |
| 823 | MLLIK | 15.81 | 309.21 | 373.28 | 19 |
| 824 | MLLIK | 15.81 | 309.21 | 471.3 | 19 |
| 825 | MLLIK | 15.81 | 309.21 | 486.36 | 19 |
| 826 | MLNALIGLEHHK | 16.89 | 459.26 | 550.27 | 27 |
| 827 | MLNALIGLEHHK | 16.89 | 459.26 | 720.38 | 27 |
| 828 | MLNALIGLEHHK | 16.89 | 459.26 | 833.46 | 27 |
| 829 | MLNALIGLENHK | 18.39 | 451.58 | 697.36 | 27 |
| 830 | MLNALIGLENHK | 18.38 | 676.87 | 697.36 | 35 |
| 831 | MLNALIGLENHK | 18.39 | 676.87 | 810.45 | 35 |
| 832 | MLNALIGLENQK | 19.71 | 672.37 | 688.36 | 35 |
| 833 | MLNALIGLENQK | 19.71 | 672.37 | 801.45 | 35 |
| 834 | MLNALIGLENQK | 19.71 | 672.37 | 914.53 | 35 |
| 835 | MLNALIGLEYHK | 19.6 | 701.38 | 746.38 | 36 |
| 836 | MLNALIGLEYHK | 19.6 | 701.38 | 859.47 | 36 |
| 837 | MLNALIGLEYHK | 19.6 | 701.38 | 1157.63 | 36 |
| 838 | MLNALIGLQHGK | 17.5 | 432.25 | 582.34 | 26 |
| 839 | MLNALIGLQHGK | 17.5 | 432.25 | 639.36 | 26 |
| 840 | MLNALIGLQHGK | 17.5 | 432.25 | 752.44 | 26 |
| 841 | MLNALISLEHHK | 17.2 | 352.2 | 359.17 | 21 |
| 842 | MLNALISLEHHK | 17.21 | 469.26 | 750.39 | 27 |
| 843 | MLNALISLEHHK | 17.2 | 469.26 | 863.47 | 27 |
| 844 | MQAYVDAFDYGNR | 17.56 | 775.34 | 957.41 | 39 |
| 845 | MQAYVDAFDYGNR | 17.56 | 775.34 | 1056.47 | 39 |
| 846 | MQAYVDAFDYGNR | 17.56 | 775.34 | 1219.54 | 39 |
| 847 | MQEGLNK | 8.68 | 410.21 | 560.3 | 23 |
| 848 | MQEGLNK | 8.66 | 410.21 | 673.3 | 23 |
| 849 | MQEGLNK | 8.68 | 410.21 | 688.36 | 23 |
| 850 | MSPASTYK | 9.49 | 442.71 | 569.29 | 24 |
| 851 | MSPASTYK | 9.49 | 442.71 | 666.35 | 24 |

TABLE 30-continued

| Transition number | Peptide | Retention time (minutes) | (m/z) filtered in Q1 | (m/z) filtered in Q3 | Collision energy (eV) |
|---|---|---|---|---|---|
| 852 | MSPASTYK | 9.49 | 442.71 | 753.38 | 24 |
| 853 | NEHDPVLPYR | 13.09 | 413.88 | 435.24 | 25 |
| 854 | NEHDPVLPYR | 13.09 | 620.31 | 744.44 | 32 |
| 855 | NEHDPVLPYR | 13.09 | 620.31 | 859.47 | 32 |
| 856 | NEHQIFK | 9.91 | 458.24 | 509.21 | 25 |
| 857 | NEHQIFK | 9.91 | 458.24 | 622.29 | 25 |
| 858 | NEHQIFK | 9.91 | 458.24 | 672.38 | 25 |
| 859 | NEHQVFK | 7.74 | 451.23 | 658.37 | 25 |
| 860 | NEHQVFK | 7.74 | 451.23 | 755.35 | 25 |
| 861 | NEHQVFK | 7.74 | 451.23 | 787.41 | 25 |
| 862 | NEITYK | 9.35 | 384.2 | 524.31 | 22 |
| 863 | NEITYK | 9.35 | 384.2 | 621.29 | 22 |
| 864 | NEITYK | 9.35 | 384.2 | 653.35 | 22 |
| 865 | NELLMK | 13.08 | 374.21 | 504.32 | 21 |
| 866 | NELLMK | 13.09 | 374.21 | 601.3 | 21 |
| 867 | NELLMK | 13.09 | 374.21 | 633.36 | 21 |
| 868 | NELPFR | 14.39 | 388.21 | 419.24 | 22 |
| 869 | NELPFR | 14.39 | 388.21 | 532.32 | 22 |
| 870 | NELPFR | 14.4 | 388.21 | 661.37 | 22 |
| 871 | NISSYGNNLVR | 14.36 | 618.82 | 835.44 | 32 |
| 872 | NISSYGNNLVR | 14.36 | 618.82 | 922.47 | 32 |
| 873 | NISSYGNNLVR | 14.36 | 618.82 | 1009.51 | 32 |
| 874 | NISTYGNNLTR | 13.1 | 626.82 | 674.36 | 33 |
| 875 | NISTYGNNLTR | 13.09 | 626.82 | 837.42 | 33 |
| 876 | NISTYGNNLTR | 13.1 | 626.82 | 1025.5 | 33 |
| 877 | NLFNEVHTTGVLVIR | 20.69 | 571.32 | 757.49 | 33 |
| 878 | NLFNEVHTTGVLVIR | 20.7 | 571.32 | 858.54 | 33 |
| 879 | NLFNEVHTTGVLVIR | 20.7 | 571.32 | 995.6 | 33 |
| 880 | NLSTYGNALAR | 14.34 | 590.31 | 764.4 | 31 |
| 881 | NLSTYGNALAR | 14.35 | 590.31 | 865.45 | 31 |
| 882 | NLSTYGNALAR | 14.35 | 590.31 | 952.48 | 31 |
| 883 | NMENLELFGK | 19.08 | 597.79 | 820.46 | 31 |
| 884 | NMENLELFGK | 19.08 | 597.79 | 949.5 | 31 |
| 885 | NMENLELFGK | 19.08 | 597.79 | 1080.54 | 31 |
| 886 | NMLLLEENNGYK | 16.71 | 719.36 | 853.37 | 37 |
| 887 | NMLLLEENNGYK | 16.69 | 719.36 | 966.45 | 37 |
| 888 | NMLLLEENNGYK | 16.68 | 719.36 | 1079.54 | 37 |
| 889 | NMLLLEESNGYK | 18.12 | 705.85 | 939.44 | 36 |

TABLE 30-continued

| Transition number | Peptide | Retention time (minutes) | (m/z) filtered in Q1 | (m/z) filtered in Q3 | Collision energy (eV) |
|---|---|---|---|---|---|
| 890 | NMLLLEESNGYK | 18.13 | 705.85 | 1052.53 | 36 |
| 891 | NMLLLEESNGYK | 18.11 | 705.85 | 1165.61 | 36 |
| 892 | NMLLLEK | 16.99 | 430.75 | 502.32 | 24 |
| 893 | NMLLLEK | 16.98 | 430.75 | 615.41 | 24 |
| 894 | NMLLLEK | 16.98 | 430.75 | 746.45 | 24 |
| 895 | NMTLGDAMK | 14.42 | 490.73 | 521.24 | 27 |
| 896 | NMTLGDAMK | 14.42 | 490.73 | 634.32 | 27 |
| 897 | NMTLGDAMK | 14.42 | 490.73 | 735.37 | 27 |
| 898 | NNGLTEAWLESSLK | 20.61 | 781.4 | 862.47 | 39 |
| 899 | NNGLTEAWLESSLK | 20.6 | 781.4 | 933.5 | 39 |
| 900 | NNGLTEAWLESSLK | 20.62 | 781.4 | 1163.59 | 39 |
| 901 | NQLPFK | 13.49 | 373.71 | 391.23 | 21 |
| 902 | NQLPFK | 13.49 | 373.71 | 504.32 | 21 |
| 903 | NQLPFK | 13.49 | 373.71 | 632.38 | 21 |
| 904 | NQLPFQVEHQR | 14.33 | 698.36 | 796.41 | 36 |
| 905 | NQLPFQVEHQR | 14.33 | 698.36 | 1040.53 | 36 |
| 906 | NQLPFQVEHQR | 14.33 | 698.36 | 1153.61 | 36 |
| 907 | NSAIENTIDNMYLQDLENSTK | 22.77 | 805.04 | 934.45 | 44 |
| 908 | NSAIENTIDNMYLQDLENSTK | 22.77 | 805.04 | 1047.53 | 44 |
| 909 | NSAIENTIDNMYLQDLENSTK | 22.77 | 805.04 | 1210.6 | 44 |
| 910 | NSAIENTIENMYLQDLDNSTK | 23.13 | 805.04 | 920.43 | 44 |
| 911 | NSAIENTIENMYLQDLDNSTK | 23.13 | 805.04 | 1033.52 | 44 |
| 912 | NSAIENTIENMYLQDLDNSTK | 23.14 | 805.04 | 1196.58 | 44 |
| 913 | NSAIENTIENMYLQDLENSTK | 23.7 | 809.72 | 934.45 | 44 |
| 914 | NSAIENTIENMYLQDLENSTK | 23.7 | 809.72 | 1047.53 | 44 |
| 915 | NSAIENTIENMYLQDLENSTK | 23.7 | 809.72 | 1217.55 | 44 |
| 916 | NSAVWVYELFAK | 24.66 | 713.87 | 869.48 | 36 |
| 917 | NSAVWVYELFAK | 24.66 | 713.87 | 1055.56 | 36 |
| 918 | NSAVWVYELFAK | 24.65 | 713.87 | 1154.62 | 36 |
| 919 | NSQVPAYK | 9.78 | 453.74 | 478.27 | 25 |
| 920 | NSQVPAYK | 9.78 | 453.74 | 577.33 | 25 |
| 921 | NSQVPAYK | 9.78 | 453.74 | 705.39 | 25 |
| 922 | NSTVWIYELFAK | 25.64 | 735.88 | 883.49 | 37 |
| 923 | NSTVWIYELFAK | 25.64 | 735.88 | 1069.57 | 37 |
| 924 | NSTVWIYELFAK | 25.64 | 735.88 | 1168.64 | 37 |
| 925 | NSTVWVYELFAK | 24.42 | 728.88 | 770.41 | 37 |
| 926 | NSTVWVYELFAK | 24.43 | 728.88 | 869.48 | 37 |
| 927 | NSTVWVYELFAK | 24.42 | 728.88 | 1055.56 | 37 |

TABLE 30-continued

| Transition number | Peptide | Retention time (minutes) | (m/z) filtered in Q1 | (m/z) filtered in Q3 | Collision energy (eV) |
| --- | --- | --- | --- | --- | --- |
| 928 | NSTVWVYQLFAK | 23.9 | 728.39 | 769.42 | 37 |
| 929 | NSTVWVYQLFAK | 23.91 | 728.39 | 1054.57 | 37 |
| 930 | NSTVWVYQLFAK | 23.91 | 728.39 | 1153.64 | 37 |
| 931 | NTSGALVIQTDK | 13.34 | 623.84 | 816.48 | 32 |
| 932 | NTSGALVIQTDK | 13.34 | 623.84 | 944.54 | 32 |
| 933 | NTSGALVIQTDK | 13.34 | 623.84 | 1031.57 | 32 |
| 934 | NTSGVLVIQTDK | 14.9 | 637.85 | 816.48 | 33 |
| 935 | NTSGVLVIQTDK | 14.9 | 637.85 | 972.57 | 33 |
| 936 | NTSGVLVIQTDK | 14.91 | 637.85 | 1059.6 | 33 |
| 937 | NVDEMFYYYDGSK | 18.86 | 815.84 | 895.38 | 41 |
| 938 | NVDEMFYYYDGSK | 18.86 | 815.84 | 1042.45 | 41 |
| 939 | NVDEMFYYYDGSK | 18.85 | 815.84 | 1173.49 | 41 |
| 940 | NWILR | 16.3 | 351.21 | 414.21 | 20 |
| 941 | NWILR | 16.29 | 351.21 | 527.3 | 20 |
| 942 | NWILR | 16.3 | 351.21 | 587.37 | 20 |
| 943 | NWNAAMDLR | 16.54 | 545.76 | 605.31 | 29 |
| 944 | NWNAAMDLR | 16.55 | 545.76 | 676.34 | 29 |
| 945 | NWNAAMDLR | 16.54 | 545.76 | 790.39 | 29 |
| 946 | NYVDAFHYGNQDISGDK | 15.76 | 648.29 | 933.43 | 36 |
| 947 | NYVDAFHYGNQDISGDK | 15.77 | 648.29 | 1096.49 | 36 |
| 948 | NYVDAFHYGNQDISGDK | 15.76 | 971.93 | 1233.55 | 48 |
| 949 | QADHAILVFDQAR | 16.58 | 495.26 | 523.23 | 29 |
| 950 | QADHAILVFDQAR | 16.61 | 495.26 | 636.31 | 29 |
| 951 | QADHAILVFDQAR | 16.58 | 495.26 | 635.38 | 29 |
| 952 | QAEHALLVFGQER | 16.86 | 499.93 | 636.31 | 29 |
| 953 | QAEHALLVFGQER | 16.85 | 499.93 | 735.38 | 29 |
| 954 | QAEHALLVFGQER | 16.87 | 499.93 | 763.41 | 29 |
| 955 | QAITK | 11 | 280.67 | 361.24 | 17 |
| 956 | QAITK | 11 | 280.67 | 414.23 | 17 |
| 957 | QAITK | 11.01 | 280.67 | 432.28 | 17 |
| 958 | QAMLTEANSDYIIR | 18.26 | 812.9 | 951.49 | 41 |
| 959 | QAMLTEANSDYIIR | 18.25 | 812.9 | 1080.53 | 41 |
| 960 | QAMLTEANSDYIIR | 18.26 | 812.9 | 1181.58 | 41 |
| 961 | QEVQFVSALAR | 17.69 | 624.34 | 763.45 | 32 |
| 962 | QEVQFVSALAR | 17.68 | 624.34 | 891.5 | 32 |
| 963 | QEVQFVSALAR | 17.68 | 624.34 | 990.57 | 32 |
| 964 | QFASIK | 11.66 | 347.2 | 434.2 | 20 |
| 965 | QFASIK | 11.66 | 347.2 | 547.29 | 20 |

TABLE 30-continued

| Transition number | Peptide | Retention time (minutes) | (m/z) filtered in Q1 | (m/z) filtered in Q3 | Collision energy (eV) |
|---|---|---|---|---|---|
| 966 | QFASIK | 11.68 | 347.2 | 565.33 | 20 |
| 967 | QGMPGSIR | 11.4 | 423.22 | 529.31 | 24 |
| 968 | QGMPGSIR | 11.43 | 423.22 | 660.35 | 24 |
| 969 | QGMPGSIR | 11.4 | 423.22 | 717.37 | 24 |
| 970 | QGMSGSIR | 9.44 | 418.21 | 519.29 | 23 |
| 971 | QGMSGSIR | 9.45 | 418.21 | 650.33 | 23 |
| 972 | QGMSGSIR | 9.44 | 418.21 | 707.35 | 23 |
| 973 | QGQTQQSYGNDLAR | 11.16 | 783.37 | 895.43 | 39 |
| 974 | QGQTQQSYGNDLAR | 11.17 | 783.37 | 1023.49 | 39 |
| 975 | QGQTQQSYGNDLAR | 11.16 | 783.37 | 1151.54 | 39 |
| 976 | QIDYGNADPSTIK | 13.41 | 711.35 | 845.44 | 36 |
| 977 | QIDYGNADPSTIK | 13.42 | 711.35 | 902.46 | 36 |
| 978 | QIDYGNADPSTIK | 13.42 | 711.35 | 1065.52 | 36 |
| 979 | QIDYGNVDPSTIK | 15.08 | 725.36 | 873.47 | 37 |
| 980 | QIDYGNVDPSTIK | 15.07 | 725.36 | 930.49 | 37 |
| 981 | QIDYGNVDPSTIK | 15.07 | 725.36 | 1093.55 | 37 |
| 982 | QIGQAR | 2.3 | 336.69 | 431.24 | 20 |
| 983 | QIGQAR | 2.33 | 336.69 | 498.27 | 20 |
| 984 | QIGQAR | 2.32 | 336.69 | 544.32 | 20 |
| 985 | QIMLIEQTPAFTLR | 24.42 | 830.96 | 933.52 | 42 |
| 986 | QIMLIEQTPAFTLR | 24.42 | 830.96 | 1062.56 | 42 |
| 987 | QIMLIEQTPAFTLR | 24.42 | 830.96 | 1175.64 | 42 |
| 988 | QLGSAIDQFWLR | 22.67 | 717.38 | 864.44 | 37 |
| 989 | QLGSAIDQFWLR | 22.68 | 717.38 | 977.52 | 37 |
| 990 | QLGSAIDQFWLR | 22.67 | 717.38 | 1192.61 | 37 |
| 991 | QLPVK | 9.57 | 292.69 | 343.23 | 18 |
| 992 | QLPVK | 9.58 | 292.69 | 438.27 | 18 |
| 993 | QLPVK | 9.57 | 292.69 | 456.32 | 18 |
| 994 | QLSLDVLDK | 18.63 | 515.79 | 589.32 | 28 |
| 995 | QLSLDVLDK | 18.62 | 515.79 | 789.44 | 28 |
| 996 | QLSLDVLDK | 18.63 | 515.79 | 902.52 | 28 |
| 997 | QLVYAR | 11.04 | 375.22 | 508.29 | 22 |
| 998 | QLVYAR | 11.04 | 375.22 | 575.32 | 22 |
| 999 | QLVYAR | 11.04 | 375.22 | 621.37 | 22 |
| 1000 | QMMLTEASTDYIIR | 19.82 | 836.41 | 867.46 | 42 |
| 1001 | QMMLTEASTDYIIR | 19.82 | 836.41 | 1067.54 | 42 |
| 1002 | QMMLTEASTDYIIR | 19.82 | 836.41 | 1168.58 | 42 |
| 1003 | QMSIVEATPDYVLHGK | 18.77 | 894.45 | 1029.54 | 44 |

TABLE 30-continued

| Transition number | Peptide | Retention time (minutes) | (m/z) filtered in Q1 | (m/z) filtered in Q3 | Collision energy (eV) |
|---|---|---|---|---|---|
| 1004 | QMSIVEATPDYVLHGK | 18.77 | 894.45 | 1100.57 | 44 |
| 1005 | QMSIVEATPDYVLHGK | 18.77 | 894.45 | 1229.62 | 44 |
| 1006 | QTLVFAR | 14.65 | 417.75 | 492.29 | 23 |
| 1007 | QTLVFAR | 14.65 | 417.75 | 605.38 | 23 |
| 1008 | QTLVFAR | 14.65 | 417.75 | 706.42 | 23 |
| 1009 | QVVFAR | 12.06 | 360.21 | 492.29 | 21 |
| 1010 | QVVFAR | 12.04 | 360.21 | 545.31 | 21 |
| 1011 | QVVFAR | 12.06 | 360.21 | 591.36 | 21 |
| 1012 | SADEVLPYGGKPQR | 12.96 | 506.26 | 642.37 | 29 |
| 1013 | SADEVLPYGGKPQR | 12.96 | 506.26 | 805.43 | 29 |
| 1014 | SADEVLPYGGKPQR | 12.96 | 506.26 | 902.48 | 29 |
| 1015 | SC[CAM]ATNDLAR | 9.37 | 504.23 | 689.36 | 27 |
| 1016 | SC[CAM]ATNDLAR | 9.37 | 504.23 | 760.39 | 27 |
| 1017 | SC[CAM]ATNDLAR | 9.37 | 504.23 | 920.43 | 27 |
| 1018 | SC[CAM]ATNNLAR | 8.66 | 503.74 | 688.37 | 27 |
| 1019 | SC[CAM]ATNNLAR | 8.66 | 503.74 | 759.41 | 27 |
| 1020 | SC[CAM]ATNNLAR | 8.67 | 503.74 | 919.44 | 27 |
| 1021 | SDIPGGSK | 7.63 | 380.7 | 558.32 | 22 |
| 1022 | SDIPGGSK | 7.63 | 380.7 | 614.28 | 22 |
| 1023 | SDIPGGSK | 7.63 | 380.7 | 673.35 | 22 |
| 1024 | SDWGK | 5.75 | 296.64 | 390.21 | 18 |
| 1025 | SDWGK | 5.75 | 296.64 | 446.17 | 18 |
| 1026 | SDWGK | 5.75 | 296.64 | 505.24 | 18 |
| 1027 | SEDNFHISSQQHEK | 10.36 | 422.19 | 541.27 | 24 |
| 1028 | SEDNFHISSQQHEK | 10.36 | 422.19 | 730.28 | 24 |
| 1029 | SEDNFHISSQQHEK | 10.36 | 422.19 | 756.36 | 24 |
| 1030 | SEMPASIR | 12.02 | 445.72 | 674.37 | 25 |
| 1031 | SEMPASIR | 12.02 | 445.72 | 716.33 | 25 |
| 1032 | SEMPASIR | 12.02 | 445.72 | 803.41 | 25 |
| 1033 | SEMPASTR | 8.2 | 439.71 | 662.33 | 24 |
| 1034 | SEMPASTR | 8.19 | 439.71 | 704.29 | 24 |
| 1035 | SEMPASTR | 8.19 | 439.71 | 791.37 | 24 |
| 1036 | SFAAHNQDQDLR | 10.35 | 467.89 | 531.29 | 27 |
| 1037 | SFAAHNQDQDLR | 10.35 | 467.89 | 871.37 | 27 |
| 1038 | SFAAHNQDQDLR | 10.35 | 467.89 | 888.42 | 27 |
| 1039 | SFAGHNK | 9.4 | 380.69 | 455.24 | 22 |
| 1040 | SFAGHNK | 9.4 | 380.69 | 526.27 | 22 |
| 1041 | SFAGHNK | 9.38 | 380.69 | 673.34 | 22 |

TABLE 30-continued

| Transition number | Peptide | Retention time (minutes) | (m/z) filtered in Q1 | (m/z) filtered in Q3 | Collision energy (eV) |
|---|---|---|---|---|---|
| 1042 | SFAGHNQDQDLR | 10.18 | 694.32 | 888.42 | 36 |
| 1043 | SFAGHNQDQDLR | 10.18 | 694.32 | 1025.48 | 36 |
| 1044 | SFAGHNQDQDLR | 10.18 | 694.32 | 1082.5 | 36 |
| 1045 | SFAGHNQDQNLR | 9.8 | 462.89 | 530.3 | 27 |
| 1046 | SFAGHNQDQNLR | 9.8 | 462.89 | 773.39 | 27 |
| 1047 | SFAGHNQDQNLR | 9.8 | 462.89 | 887.43 | 27 |
| 1048 | SFLESWAK | 18.27 | 484.25 | 491.26 | 26 |
| 1049 | SFLESWAK | 18.27 | 484.25 | 620.3 | 26 |
| 1050 | SFLESWAK | 18.27 | 484.25 | 733.39 | 26 |
| 1051 | SFTAWEK | 14.44 | 434.71 | 462.23 | 24 |
| 1052 | SFTAWEK | 14.44 | 434.71 | 533.27 | 24 |
| 1053 | SFTAWEK | 14.44 | 434.71 | 634.32 | 24 |
| 1054 | SFTTWEK | 14.1 | 449.72 | 462.23 | 25 |
| 1055 | SFTTWEK | 14.1 | 449.72 | 563.28 | 25 |
| 1056 | SFTTWEK | 14.1 | 449.72 | 664.33 | 25 |
| 1057 | SGSGWLR | 13.25 | 381.7 | 531.3 | 22 |
| 1058 | SGSGWLR | 13.25 | 381.7 | 618.34 | 22 |
| 1059 | SGSGWLR | 13.25 | 381.7 | 675.36 | 22 |
| 1060 | SGWGMAVDPQVGWYVGFVEK | 24.65 | 738.02 | 841.45 | 41 |
| 1061 | SGWGMAVDPQVGWYVGFVEK | 24.65 | 738.02 | 1029.45 | 41 |
| 1062 | SGWGMAVDPQVGWYVGFVEK | 24.68 | 1106.53 | 1128.51 | 54 |
| 1063 | SGWGMDVSPQVGWLTGWVEK | 26.32 | 1110.03 | 1144.51 | 54 |
| 1064 | SGWGMDVSPQVGWLTGWVEK | 26.32 | 1110.03 | 1174.63 | 54 |
| 1065 | SGWGMDVSPQVGWLTGWVEK | 26.32 | 1110.03 | 1201.53 | 54 |
| 1066 | SGWGMDVTPQVGWLTGWVEK | 26.61 | 745.03 | 832.46 | 41 |
| 1067 | SGWGMDVTPQVGWLTGWVEK | 26.61 | 745.03 | 1018.54 | 41 |
| 1068 | SGWGMDVTPQVGWLTGWVEK | 26.61 | 745.03 | 1075.56 | 41 |
| 1069 | SIHPASTFK | 10.74 | 494.27 | 650.35 | 27 |
| 1070 | SIHPASTFK | 10.73 | 494.27 | 787.41 | 27 |
| 1071 | SIHPASTFK | 10.73 | 494.27 | 900.49 | 27 |
| 1072 | SISTK | 10.41 | 268.16 | 335.19 | 17 |
| 1073 | SISTK | 10.42 | 268.16 | 389.2 | 17 |
| 1074 | SISTK | 10.42 | 268.16 | 448.28 | 17 |
| 1075 | SLGLSNNLSR | 14.23 | 530.79 | 690.35 | 28 |
| 1076 | SLGLSNNLSR | 14.23 | 530.79 | 803.44 | 28 |
| 1077 | SLGLSNNLSR | 14.23 | 530.79 | 860.46 | 28 |
| 1078 | SLSMSGK | 9.31 | 355.18 | 509.24 | 21 |
| 1079 | SLSMSGK | 9.32 | 355.18 | 563.25 | 21 |

TABLE 30-continued

| Transition number | Peptide | Retention time (minutes) | (m/z) filtered in Q1 | (m/z) filtered in Q3 | Collision energy (eV) |
|---|---|---|---|---|---|
| 1080 | SLSMSGK | 9.32 | 355.18 | 622.32 | 21 |
| 1081 | SMLFIEEK | 17.82 | 498.76 | 518.28 | 27 |
| 1082 | SMLFIEEK | 17.82 | 498.76 | 665.35 | 27 |
| 1083 | SMLFIEEK | 17.82 | 498.76 | 778.43 | 27 |
| 1084 | SNGLTHSWLGSSLK | 16.78 | 743.89 | 877.48 | 38 |
| 1085 | SNGLTHSWLGSSLK | 16.78 | 743.89 | 1014.54 | 38 |
| 1086 | SNGLTHSWLGSSLK | 16.78 | 743.89 | 1115.58 | 38 |
| 1087 | SPTWELKPEYNPSPR | 16.02 | 600.97 | 733.36 | 34 |
| 1088 | SPTWELKPEYNPSPR | 16.02 | 600.97 | 808.91 | 34 |
| 1089 | SPTWELKPEYNPSPR | 16.02 | 600.97 | 959.46 | 34 |
| 1090 | SQDIVR | 8.4 | 359.2 | 502.3 | 21 |
| 1091 | SQDIVR | 8.38 | 359.2 | 543.28 | 21 |
| 1092 | SQDIVR | 8.4 | 359.2 | 630.36 | 21 |
| 1093 | SQQKPTDPTIWLK | 16.6 | 514.62 | 660.41 | 30 |
| 1094 | SQQKPTDPTIWLK | 16.6 | 514.62 | 757.46 | 30 |
| 1095 | SQQKPTDPTIWLK | 16.6 | 514.62 | 785.38 | 30 |
| 1096 | SQVGWLTGWVEQPDGK | 22.27 | 893.94 | 1015.5 | 44 |
| 1097 | SQVGWLTGWVEQPDGK | 22.28 | 893.94 | 1116.53 | 44 |
| 1098 | SQVGWLTGWVEQPDGK | 22.28 | 893.94 | 1229.62 | 44 |
| 1099 | SSSNSC[CAM]TTNNAAR | 16.84 | 685.29 | 907.41 | 35 |
| 1100 | SSSNSC[CAM]TTNNAAR | 16.85 | 685.29 | 994.44 | 35 |
| 1101 | SSSNSC[CAM]TTNNAAR | 16.84 | 685.29 | 1108.48 | 35 |
| 1102 | SVYGELR | 12.65 | 412.22 | 417.25 | 23 |
| 1103 | SVYGELR | 12.65 | 412.22 | 474.27 | 23 |
| 1104 | SVYGELR | 12.65 | 412.22 | 637.33 | 23 |
| 1105 | SWILR | 16.33 | 337.7 | 401.29 | 20 |
| 1106 | SWILR | 16.32 | 337.7 | 500.29 | 20 |
| 1107 | SWILR | 16.33 | 337.7 | 587.37 | 20 |
| 1108 | SYLEK | 9.09 | 320.17 | 389.24 | 19 |
| 1109 | SYLEK | 9.09 | 320.17 | 493.23 | 19 |
| 1110 | SYLEK | 9.1 | 320.17 | 552.3 | 19 |
| 1111 | TAYIPASTFK | 15.43 | 549.8 | 650.35 | 29 |
| 1112 | TAYIPASTFK | 15.43 | 549.8 | 763.43 | 29 |
| 1113 | TAYIPASTFK | 15.43 | 549.8 | 926.5 | 29 |
| 1114 | TDDLFK | 13.48 | 369.69 | 407.27 | 21 |
| 1115 | TDDLFK | 13.48 | 369.69 | 522.29 | 21 |
| 1116 | TDDLFK | 13.48 | 369.69 | 637.32 | 21 |
| 1117 | TDINEIFK | 17.44 | 490.26 | 650.35 | 27 |

TABLE 30-continued

| Transition number | Peptide | Retention time (minutes) | (m/z) filtered in Q1 | (m/z) filtered in Q3 | Collision energy (eV) |
|---|---|---|---|---|---|
| 1118 | TDINEIFK | 17.44 | 490.26 | 763.43 | 27 |
| 1119 | TDINEIFK | 17.44 | 490.26 | 878.46 | 27 |
| 1120 | TFIHNDPR | 18.92 | 500.25 | 751.38 | 27 |
| 1121 | TFIHNDPR | 18.92 | 500.25 | 825.39 | 27 |
| 1122 | TFIHNDPR | 18.92 | 500.25 | 898.45 | 27 |
| 1123 | TGAGFTANR | 9.64 | 447.72 | 461.25 | 25 |
| 1124 | TGAGFTANR | 9.64 | 447.72 | 665.34 | 25 |
| 1125 | TGAGFTANR | 9.64 | 447.72 | 793.4 | 25 |
| 1126 | TGFNDGQK | 7.5 | 433.7 | 561.26 | 24 |
| 1127 | TGFNDGQK | 7.5 | 433.7 | 708.33 | 24 |
| 1128 | TGFNDGQK | 7.5 | 433.7 | 765.35 | 24 |
| 1129 | TGLADSK | 9.7 | 346.18 | 533.29 | 20 |
| 1130 | TGLADSK | 9.67 | 346.18 | 545.26 | 20 |
| 1131 | TGLADSK | 9.7 | 346.18 | 590.31 | 20 |
| 1132 | TGLDLMQK | 15.32 | 453.24 | 634.32 | 25 |
| 1133 | TGLDLMQK | 15.32 | 453.24 | 747.41 | 25 |
| 1134 | TGLDLMQK | 15.32 | 453.24 | 804.43 | 25 |
| 1135 | TGLELMQK | 15.03 | 460.25 | 648.34 | 25 |
| 1136 | TGLELMQK | 15.03 | 460.25 | 761.42 | 25 |
| 1137 | TGLELMQK | 15.03 | 460.25 | 818.44 | 25 |
| 1138 | TGMGYPK | 10.28 | 377.18 | 464.25 | 22 |
| 1139 | TGMGYPK | 10.28 | 377.18 | 595.29 | 22 |
| 1140 | TGMGYPK | 10.28 | 377.18 | 652.31 | 22 |
| 1141 | TGNGR | 0.8 | 252.63 | 330.14 | 16 |
| 1142 | TGNGR | 0.8 | 252.63 | 346.18 | 16 |
| 1143 | TGNGR | 0.81 | 252.63 | 403.2 | 16 |
| 1144 | TGTGSFIDAR | 13.35 | 512.76 | 708.37 | 28 |
| 1145 | TGTGSFIDAR | 13.35 | 512.76 | 765.39 | 28 |
| 1146 | TGTGSFIDAR | 13.35 | 512.76 | 866.44 | 28 |
| 1147 | TGTGSLSDAK | 8.32 | 468.74 | 620.32 | 26 |
| 1148 | TGTGSLSDAK | 8.32 | 468.74 | 677.35 | 26 |
| 1149 | TGTGSLSDAK | 8.32 | 468.74 | 778.39 | 26 |
| 1150 | TGVATEYQPEIGWWAGWVER | 25.49 | 779.04 | 903.45 | 43 |
| 1151 | TGVATEYQPEIGWWAGWVER | 25.5 | 779.04 | 1146.55 | 43 |
| 1152 | TGVATEYQPEIGWWAGWVER | 25.52 | 1168.06 | 1189.57 | 56 |
| 1153 | TGVSYPLLADGTR | 17.4 | 675.36 | 842.47 | 35 |
| 1154 | TGVSYPLLADGTR | 17.41 | 675.36 | 1005.54 | 35 |
| 1155 | TGVSYPLLADGTR | 17.4 | 675.36 | 1092.57 | 35 |

TABLE 30-continued

| Transition number | Peptide | Retention time (minutes) | (m/z) filtered in Q1 | (m/z) filtered in Q3 | Collision energy (eV) |
| --- | --- | --- | --- | --- | --- |
| 1156 | TGWAMDIK | 16.71 | 461.23 | 577.3 | 25 |
| 1157 | TGWAMDIK | 16.71 | 461.23 | 763.38 | 25 |
| 1158 | TGWAMDIK | 16.72 | 461.23 | 820.4 | 25 |
| 1159 | TGWATR | 9.71 | 346.18 | 517.24 | 20 |
| 1160 | TGWATR | 9.69 | 346.18 | 533.28 | 20 |
| 1161 | TGWATR | 9.69 | 346.18 | 590.3 | 20 |
| 1162 | TGWC[CAM]FDC[CAM]TPELGWWVGWVK | 28.39 | 795.36 | 960.51 | 44 |
| 1163 | TGWC[CAM]FDC[CAM]TPELGWWVGWVK | 28.39 | 795.36 | 1017.53 | 44 |
| 1164 | TGWC[CAM]FDC[CAM]TPELGWWVGWVK | 28.38 | 795.36 | 1028.36 | 44 |
| 1165 | TGWEGR | 9.1 | 353.17 | 531.22 | 21 |
| 1166 | TGWEGR | 9.09 | 353.17 | 547.26 | 21 |
| 1167 | TGWEGR | 9.09 | 353.17 | 604.28 | 21 |
| 1168 | TGWFVDK | 16.08 | 426.72 | 694.36 | 24 |
| 1169 | TGWFVDK | 16.1 | 426.72 | 706.32 | 24 |
| 1170 | TGWFVDK | 16.08 | 426.72 | 751.38 | 24 |
| 1171 | TGYDTK | 2.09 | 342.66 | 526.25 | 20 |
| 1172 | TGYDTK | 2.09 | 342.66 | 538.21 | 20 |
| 1173 | TGYDTK | 2.08 | 342.66 | 583.27 | 20 |
| 1174 | TGYGVR | 8.09 | 326.67 | 478.23 | 19 |
| 1175 | TGYGVR | 8.1 | 326.67 | 494.27 | 19 |
| 1176 | TGYGVR | 8.1 | 326.67 | 551.29 | 19 |
| 1177 | TGYSAR | 2.24 | 327.66 | 480.21 | 19 |
| 1178 | TGYSAR | 2.24 | 327.66 | 496.25 | 19 |
| 1179 | TGYSAR | 2.24 | 327.66 | 553.27 | 19 |
| 1180 | TGYSTR | 2.08 | 342.67 | 510.22 | 20 |
| 1181 | TGYSTR | 2.08 | 342.67 | 526.26 | 20 |
| 1182 | TGYSTR | 2.08 | 342.67 | 583.28 | 20 |
| 1183 | THESSNWGK | 5.36 | 523.24 | 678.32 | 28 |
| 1184 | THESSNWGK | 5.37 | 523.24 | 807.36 | 28 |
| 1185 | THESSNWGK | 5.37 | 523.24 | 944.42 | 28 |
| 1186 | TIC[CAM]TAIADAGTGK | 14.35 | 639.82 | 732.39 | 33 |
| 1187 | TIC[CAM]TAIADAGTGK | 14.35 | 639.82 | 904.47 | 33 |
| 1188 | TIC[CAM]TAIADAGTGK | 14.35 | 639.82 | 1064.5 | 33 |
| 1189 | TIGGAPDAYWVDDSLQISAR | 21.22 | 712.35 | 1004.5 | 40 |
| 1190 | TIGGAPDAYWVDDSLQISAR | 21.22 | 712.35 | 1103.57 | 40 |
| 1191 | TIGGAPDAYWVDDSLQISAR | 21.21 | 1068.02 | 1103.57 | 52 |
| 1192 | TLPFSASSYETLR | 18.73 | 736.37 | 855.42 | 37 |
| 1193 | TLPFSASSYETLR | 18.73 | 736.37 | 1013.49 | 37 |

TABLE 30-continued

| Transition number | Peptide | Retention time (minutes) | (m/z) filtered in Q1 | (m/z) filtered in Q3 | Collision energy (eV) |
|---|---|---|---|---|---|
| 1194 | TLPFSASSYETLR | 18.73 | 736.37 | 1160.56 | 37 |
| 1195 | TLPFSPK | 15 | 395.23 | 478.27 | 22 |
| 1196 | TLPFSPK | 15 | 395.23 | 575.32 | 22 |
| 1197 | TLPFSPK | 15 | 395.23 | 688.4 | 22 |
| 1198 | TLPFSQEVQDEVQSILFIEEK | 28.55 | 827.09 | 891.52 | 45 |
| 1199 | TLPFSQEVQDEVQSILFIEEK | 28.56 | 827.09 | 978.55 | 45 |
| 1200 | TLPFSQEVQDEVQSILFIEEK | 28.56 | 827.09 | 1106.61 | 45 |
| 1201 | TLPFSQEVQDEVQSMLFIEEK | 27.7 | 833.08 | 996.51 | 46 |
| 1202 | TLPFSQEVQDEVQSMLFIEEK | 27.69 | 833.08 | 1124.57 | 46 |
| 1203 | TLPFSQEVQDEVQSMLFIEEK | 27.7 | 833.08 | 1223.63 | 46 |
| 1204 | TLQNGWFEGFIISK | 24.12 | 820.43 | 940.51 | 41 |
| 1205 | TLQNGWFEGFIISK | 24.11 | 820.43 | 1126.59 | 41 |
| 1206 | TLQNGWFEGFIISK | 24.11 | 820.43 | 1183.61 | 41 |
| 1207 | TMQEYLNK | 12.6 | 513.75 | 666.35 | 28 |
| 1208 | TMQEYLNK | 12.6 | 513.75 | 794.4 | 28 |
| 1209 | TMQEYLNK | 12.6 | 513.75 | 925.44 | 28 |
| 1210 | TQTYQAYDAAR | 11.2 | 644.3 | 666.32 | 33 |
| 1211 | TQTYQAYDAAR | 11.2 | 644.3 | 957.44 | 33 |
| 1212 | TQTYQAYDAAR | 11.2 | 644.3 | 1058.49 | 33 |
| 1213 | TTDPTIWEK | 14.39 | 545.77 | 676.37 | 29 |
| 1214 | TTDPTIWEK | 14.39 | 545.77 | 773.42 | 29 |
| 1215 | TTDPTIWEK | 14.39 | 545.77 | 888.45 | 29 |
| 1216 | TTTTEVFK | 12.06 | 463.75 | 522.29 | 25 |
| 1217 | TTTTEVFK | 12.06 | 463.75 | 623.34 | 25 |
| 1218 | TTTTEVFK | 12.06 | 463.75 | 724.39 | 25 |
| 1219 | TWASNDFSR | 13.73 | 542.25 | 638.29 | 29 |
| 1220 | TWASNDFSR | 13.73 | 542.25 | 725.32 | 29 |
| 1221 | TWASNDFSR | 13.73 | 542.25 | 796.36 | 29 |
| 1222 | TWDMVQR | 14.28 | 468.22 | 648.31 | 26 |
| 1223 | TWDMVQR | 14.28 | 468.22 | 761.33 | 26 |
| 1224 | TWDMVQR | 14.28 | 468.22 | 834.39 | 26 |
| 1225 | TYVVDPAR | 12.15 | 460.75 | 557.3 | 25 |
| 1226 | TYVVDPAR | 12.14 | 460.75 | 656.37 | 25 |
| 1227 | TYVVDPAR | 12.15 | 460.75 | 819.44 | 25 |
| 1228 | VAFSLNIEMK | 20.65 | 576.31 | 747.41 | 30 |
| 1229 | VAFSLNIEMK | 20.65 | 576.31 | 834.44 | 30 |
| 1230 | VAFSLNIEMK | 20.65 | 576.31 | 981.51 | 30 |
| 1231 | VANSLIGLSTGAVR | 17.97 | 679.39 | 760.43 | 35 |

TABLE 30-continued

| Transition number | Peptide | Retention time (minutes) | (m/z) filtered in Q1 | (m/z) filtered in Q3 | Collision energy (eV) |
|---|---|---|---|---|---|
| 1232 | VANSLIGLSTGAVR | 17.97 | 679.39 | 873.52 | 35 |
| 1233 | VANSLIGLSTGAVR | 17.97 | 679.39 | 986.6 | 35 |
| 1234 | VELGK | 7.74 | 273.17 | 342.2 | 17 |
| 1235 | VELGK | 7.75 | 273.17 | 399.22 | 17 |
| 1236 | VELGK | 7.74 | 273.17 | 446.26 | 17 |
| 1237 | VFLDSWAK | 18.2 | 483.26 | 606.29 | 26 |
| 1238 | VFLDSWAK | 18.2 | 483.26 | 719.37 | 26 |
| 1239 | VFLDSWAK | 18.2 | 483.26 | 866.44 | 26 |
| 1240 | VFLESWAK | 18.11 | 490.27 | 620.3 | 27 |
| 1241 | VFLESWAK | 18.11 | 490.27 | 733.39 | 27 |
| 1242 | VFLESWAK | 18.11 | 490.27 | 880.46 | 27 |
| 1243 | VFLSSWAQDMNLSSAIK | 23.66 | 948.98 | 978.49 | 47 |
| 1244 | VFLSSWAQDMNLSSAIK | 23.66 | 948.98 | 1106.55 | 47 |
| 1245 | VFLSSWAQDMNLSSAIK | 23.66 | 948.98 | 1177.59 | 47 |
| 1246 | VGFER | 10.32 | 304.16 | 433.21 | 18 |
| 1247 | VGFER | 10.32 | 304.16 | 451.23 | 18 |
| 1248 | VGFER | 10.32 | 304.16 | 508.25 | 18 |
| 1249 | VILVFDQVR | 19.69 | 544.83 | 664.34 | 29 |
| 1250 | VILVFDQVR | 19.69 | 544.83 | 763.41 | 29 |
| 1251 | VILVFDQVR | 19.69 | 544.83 | 876.49 | 29 |
| 1252 | VMAAMVR | 12.3 | 389.21 | 476.26 | 22 |
| 1253 | VMAAMVR | 12.3 | 389.21 | 547.3 | 22 |
| 1254 | VMAAMVR | 12.3 | 389.21 | 678.34 | 22 |
| 1255 | VPLAVMGYDAGILVDAHNPR | 21.61 | 703.37 | 709.34 | 39 |
| 1256 | VPLAVMGYDAGILVDAHNPR | 21.61 | 703.37 | 808.41 | 39 |
| 1257 | VPLAVMGYDAGILVDAHNPR | 21.61 | 703.37 | 921.49 | 39 |
| 1258 | VQDEVQSMLFIEEK | 20.48 | 847.92 | 996.51 | 42 |
| 1259 | VQDEVQSMLFIEEK | 20.48 | 847.92 | 1124.57 | 42 |
| 1260 | VQDEVQSMLFIEEK | 20.47 | 847.92 | 1223.63 | 42 |
| 1261 | VQDGVQSMLFIEEK | 20.26 | 811.91 | 996.51 | 41 |
| 1262 | VQDGVQSMLFIEEK | 20.27 | 811.91 | 1124.57 | 41 |
| 1263 | VQDGVQSMLFIEEK | 20.25 | 811.91 | 1223.63 | 41 |
| 1264 | VSC[CAM]LPC[CAM]YQVVSHK | 14.32 | 526.26 | 569.34 | 30 |
| 1265 | VSC[CAM]LPC[CAM]YQVVSHK | 14.32 | 526.26 | 860.46 | 30 |
| 1266 | VSC[CAM]LPC[CAM]YQVVSHK | 14.31 | 526.26 | 1020.49 | 30 |
| 1267 | VSC[CAM]VWC[CAM]YQALAR | 18.41 | 756.86 | 881.43 | 38 |
| 1268 | VSC[CAM]VWC[CAM]YQALAR | 18.41 | 756.86 | 1067.51 | 38 |
| 1269 | VSC[CAM]VWC[CAM]YQALAR | 18.41 | 756.86 | 1166.58 | 38 |

TABLE 30-continued

| Transition number | Peptide | Retention time (minutes) | (m/z) filtered in Q1 | (m/z) filtered in Q3 | Collision energy (eV) |
|---|---|---|---|---|---|
| 1270 | VSDVC[CAM]SEVTAEGWQEVR | 17.33 | 650.97 | 774.39 | 37 |
| 1271 | VSDVC[CAM]SEVTAEGWQEVR | 17.34 | 975.95 | 1075.52 | 48 |
| 1272 | VSDVC[CAM]SEVTAEGWQEVR | 17.34 | 975.95 | 1174.59 | 48 |
| 1273 | VSEVEGWQIHGK | 13.92 | 456.9 | 582.34 | 27 |
| 1274 | VSEVEGWQIHGK | 13.92 | 456.9 | 768.42 | 27 |
| 1275 | VSEVEGWQIHGK | 13.92 | 456.9 | 825.44 | 27 |
| 1276 | VSFSLNIEMK | 20.65 | 584.31 | 834.44 | 31 |
| 1277 | VSFSLNIEMK | 20.64 | 584.31 | 981.51 | 31 |
| 1278 | VSFSLNIEMK | 20.65 | 584.31 | 1068.54 | 31 |
| 1279 | VSPC[CAM]SSFK | 11.04 | 456.22 | 468.25 | 25 |
| 1280 | VSPC[CAM]SSFK | 11.04 | 456.22 | 628.28 | 25 |
| 1281 | VSPC[CAM]SSFK | 11.04 | 456.22 | 725.33 | 25 |
| 1282 | VSQVPAYK | 10.68 | 446.25 | 478.27 | 25 |
| 1283 | VSQVPAYK | 10.68 | 446.25 | 577.33 | 25 |
| 1284 | VSQVPAYK | 10.68 | 446.25 | 705.39 | 25 |
| 1285 | VVFAR | 11.17 | 296.18 | 393.22 | 18 |
| 1286 | VVFAR | 11.17 | 296.18 | 417.25 | 18 |
| 1287 | VVFAR | 11.17 | 296.18 | 492.29 | 18 |
| 1288 | WDGAK | 4.9 | 288.64 | 302.11 | 18 |
| 1289 | WDGAK | 4.9 | 288.64 | 390.2 | 18 |
| 1290 | WDGAK | 4.9 | 288.64 | 430.17 | 18 |
| 1291 | WDGHIYDFPDWNR | 20.52 | 574.25 | 590.27 | 33 |
| 1292 | WDGHIYDFPDWNR | 20.52 | 574.25 | 687.32 | 33 |
| 1293 | WDGHIYDFPDWNR | 20.52 | 574.25 | 887.37 | 33 |
| 1294 | WDGIK | 12.03 | 309.67 | 359.13 | 19 |
| 1295 | WDGIK | 12.03 | 309.67 | 432.25 | 19 |
| 1296 | WDGIK | 12.03 | 309.67 | 472.22 | 19 |
| 1297 | WDGKPR | 6.36 | 379.7 | 457.29 | 22 |
| 1298 | WDGKPR | 6.35 | 379.7 | 572.32 | 22 |
| 1299 | WDGKPR | 6.36 | 379.7 | 584.28 | 22 |
| 1300 | WDGQTR | 7.41 | 381.68 | 461.25 | 22 |
| 1301 | WDGQTR | 7.41 | 381.68 | 576.27 | 22 |
| 1302 | WDGQTR | 7.41 | 381.68 | 588.24 | 22 |
| 1303 | WDGVK | 10.1 | 302.66 | 359.13 | 18 |
| 1304 | WDGVK | 10.1 | 302.66 | 418.23 | 18 |
| 1305 | WDGVK | 10.1 | 302.66 | 458.2 | 18 |
| 1306 | WDGVNR | 10.39 | 373.68 | 445.25 | 21 |
| 1307 | WDGVNR | 10.39 | 373.68 | 560.28 | 21 |

TABLE 30-continued

| Transition number | Peptide | Retention time (minutes) | (m/z) filtered in Q1 | (m/z) filtered in Q3 | Collision energy (eV) |
|---|---|---|---|---|---|
| 1308 | WDGVNR | 10.42 | 373.68 | 572.25 | 21 |
| 1309 | YAQAK | 12.58 | 290.66 | 363.17 | 18 |
| 1310 | YAQAK | 12.58 | 290.66 | 417.25 | 18 |
| 1311 | YAQAK | 12.58 | 290.66 | 434.2 | 18 |
| 1312 | YFSDFNAK | 14.21 | 496.23 | 681.32 | 27 |
| 1313 | YFSDFNAK | 14.21 | 496.23 | 828.39 | 27 |
| 1314 | YFSDFNAK | 14.21 | 496.23 | 828.39 | 27 |
| 1315 | YGTHLDR | 8.51 | 431.21 | 641.34 | 24 |
| 1316 | YGTHLDR | 8.52 | 431.21 | 687.31 | 24 |
| 1317 | YGTHLDR | 8.51 | 431.21 | 698.36 | 24 |
| 1318 | YLDELVK | 15.52 | 440.24 | 488.31 | 24 |
| 1319 | YLDELVK | 15.53 | 440.24 | 603.33 | 24 |
| 1320 | YLDELVK | 15.52 | 440.24 | 716.42 | 24 |
| 1321 | YLMITEAGR | 15.86 | 527.27 | 533.27 | 28 |
| 1322 | YLMITEAGR | 15.86 | 527.27 | 646.35 | 28 |
| 1323 | YLMITEAGR | 15.86 | 527.27 | 777.39 | 28 |
| 1324 | YLNLFSYGNANIGGGIDK | 22.16 | 639.32 | 773.42 | 36 |
| 1325 | YLNLFSYGNANIGGGIDK | 22.16 | 958.48 | 1015.52 | 47 |
| 1326 | YLNLFSYGNANIGGGIDK | 22.16 | 958.48 | 1178.58 | 47 |
| 1327 | YPVVWYSQQVAHHLGAQR | 18.11 | 535.53 | 544.32 | 30 |
| 1328 | YPVVWYSQQVAHHLGAQR | 18.11 | 535.53 | 681.38 | 30 |
| 1329 | YPVVWYSQQVAHHLGAQR | 18.11 | 535.53 | 889.48 | 30 |
| 1330 | YSNVLAFK | 16.44 | 471.26 | 478.3 | 26 |
| 1331 | YSNVLAFK | 16.44 | 471.26 | 691.41 | 26 |
| 1332 | YSNVLAFK | 16.44 | 471.26 | 778.45 | 26 |
| 1333 | YSPASTFK | 12.22 | 450.73 | 553.3 | 25 |
| 1334 | YSPASTFK | 12.22 | 450.73 | 650.35 | 25 |
| 1335 | YSPASTFK | 12.22 | 450.73 | 737.38 | 25 |
| 1336 | YSVVPVYQQLAR | 18.42 | 711.89 | 778.42 | 36 |
| 1337 | YSVVPVYQQLAR | 18.42 | 711.89 | 974.54 | 36 |
| 1338 | YSVVPVYQQLAR | 18.43 | 711.89 | 1073.61 | 36 |
| 1339 | YSVVWYSQLTAK | 19.75 | 722.88 | 810.44 | 37 |
| 1340 | YSVVWYSQLTAK | 19.76 | 722.88 | 996.51 | 37 |
| 1341 | YSVVWYSQLTAK | 19.76 | 722.88 | 1095.58 | 37 |
| 1342 | YSVVWYSQQVAHHLGAQR | 18.61 | 533.02 | 544.32 | 30 |
| 1343 | YSVVWYSQQVAHHLGAQR | 18.61 | 533.02 | 681.38 | 30 |
| 1344 | YSVVWYSQQVAHHLGAQR | 18.61 | 533.02 | 889.48 | 30 |
| 1345 | YTPASTFK | 11.95 | 305.49 | 553.3 | 19 |

TABLE 30-continued

| Transition number | Peptide | Retention time (minutes) | (m/z) filtered in Q1 | (m/z) filtered in Q3 | Collision energy (eV) |
|---|---|---|---|---|---|
| 1346 | YTPASTFK | 11.98 | 457.73 | 553.3 | 25 |
| 1347 | YTPASTFK | 11.98 | 457.73 | 650.35 | 25 |
| 1348 | YTSAFGYGNADVSGEPGK | 15.03 | 607.28 | 673.35 | 34 |
| 1349 | YTSAFGYGNADVSGEPGK | 15.02 | 607.28 | 788.38 | 34 |
| 1350 | YTSAFGYGNADVSGEPGK | 15.02 | 910.41 | 1030.48 | 45 |
| 1351 | YVFVSALTGNLGSNLTSSIK | 23.66 | 691.04 | 906.49 | 39 |
| 1352 | YVFVSALTGNLGSNLTSSIK | 23.66 | 1036.06 | 1165.63 | 51 |
| 1353 | YVFVSALTGNLGSNLTSSIK | 23.67 | 1036.06 | 1190.64 | 51 |
| 1354 | YVFVSALTGSLGSNLTSSIK | 24.04 | 682.04 | 906.49 | 38 |
| 1355 | YVFVSALTGSLGSNLTSSIK | 24.04 | 1022.55 | 1106.61 | 50 |
| 1356 | YVFVSALTGSLGSNLTSSIK | 24.04 | 1022.55 | 1163.63 | 50 |

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 25

Identification of a Resistance to ACC Beta-Lactams

Samples Sam96 to Sam101 are identified according to one of the methods described in examples 1, 3 or 4. The identification of the species is set out in TABLE 31.

TABLE 31

| Names | Species |
|---|---|
| Sam96 | K. oxytoca |
| Sam97 | S. livingstone |
| Sam98 | Salmonella spp |
| Sam99 | S. enterica ssp enterica |
| Sam100 | K. pneumoniae |
| Sam101 | H. alvei |

Samples Sam96 to Sam101 correspond to a species able to comprise an ACC resistance mechanism. Each sample is treated according to example 5, then analysed according to example 6 by detecting the peptides from TABLE 32 instead of the peptides from TABLE 3.

TABLE 32

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 1 | ANIDESK | 2 | y4 monocharged | 2.45 | 388.69 | 478.21 | 17.9 | 2500 |
| 2 | ANIDESK | 2 | y5 monocharged | 2.37 | 388.69 | 591.3 | 17.9 | 2500 |
| 3 | ANIDESK | 2 | y6 monocharged | 2.41 | 388.69 | 705.34 | 17.9 | 2500 |
| 4 | AWKPADAAGTHR | 3 | y9 dicharged | 10.61 | 427.56 | 448.22 | 20.3 | 2500 |
| 5 | AWKPADAAGTHR | 3 | y4 monocharged | 10.61 | 427.56 | 470.25 | 20.3 | 2500 |
| 6 | AWKPADAAGTHR | 3 | y10 dicharged | 10.61 | 427.56 | 512.27 | 20.3 | 2500 |
| 7 | DEPVHVNMEILGNEAYGIK | 3 | y9 dicharged | 20.81 | 710.02 | 482.76 | 29.1 | 2500 |
| 8 | DEPVHVNMEILGNEAYGIK | 3 | y8 monocharged | 20.81 | 710.02 | 851.43 | 29.1 | 2500 |
| 9 | DEPVHVNMEILGNEAYGIK | 3 | y9 monocharged | 20.81 | 710.02 | 964.51 | 29.1 | 2500 |
| 10 | DTVDDLIQPLMQK | 3 | y5 monocharged | 22.36 | 505.93 | 616.35 | 22.8 | 2500 |
| 11 | DTVDDLIQPLMQK | 2 | y5 monocharged | 22.36 | 758.39 | 616.35 | 39 | 2500 |
| 12 | DTVDDLIQPLMQK | 2 | y10 monocharged | 22.36 | 758.39 | 1200.63 | 39 | 2500 |

TABLE 32-continued

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 13 | ILSSLEGNK | 2 | y6 monocharged | 13.47 | 480.77 | 647.34 | 23.1 | 2500 |
| 14 | ILSSLEGNK | 2 | y7 monocharged | 13.47 | 480.77 | 734.37 | 23.1 | 2500 |
| 15 | ILSSLEGNK | 2 | y8 monocharged | 13.47 | 480.77 | 847.45 | 23.1 | 2500 |
| 16 | LSLDQSVSHYVPELR | 3 | y12 dicharged | 20.27 | 581.64 | 715.36 | 25.1 | 2500 |
| 17 | LSLDQSVSHYVPELR | 3 | y13 dicharged | 20.27 | 581.64 | 771.9 | 25.1 | 2500 |
| 18 | LSLDQSVSHYVPELR | 3 | y14 dicharged | 20.27 | 581.64 | 815.42 | 25.1 | 2500 |
| 19 | MGIVMLANK | 2 | y5 monocharged | 18.15 | 488.77 | 576.32 | 23.6 | 2500 |
| 20 | MGIVMLANK | 2 | y6 monocharged | 18.15 | 488.77 | 675.39 | 23.6 | 2500 |
| 21 | MGIVMLANK | 2 | y8 monocharged | 18.13 | 488.77 | 845.49 | 23.6 | 2500 |
| 22 | MQQALTATHTGYFK | 3 | y9 dicharged | 15.01 | 532.93 | 513.26 | 23.6 | 2500 |
| 23 | MQQALTATHTGYFK | 3 | y11 dicharged | 15.01 | 532.93 | 605.32 | 23.6 | 2500 |
| 24 | MQQALTATHTGYFK | 3 | y12 dicharged | 15.01 | 532.93 | 669.35 | 23.6 | 2500 |
| 25 | NNIPGMSVAVTVNGK | 2 | y5 monocharged | 17.45 | 750.9 | 518.29 | 38.5 | 2500 |
| 26 | NNIPGMSVAVTVNGK | 2 | y12 dicharged | 17.43 | 750.9 | 580.31 | 38.5 | 2500 |
| 27 | NNIPGMSVAVTVNGK | 2 | y12 monocharged | 17.43 | 750.9 | 1159.61 | 38.5 | 2500 |
| 28 | NTTQLMAYLK | 2 | y5 monocharged | 19.34 | 591.81 | 625.34 | 29.5 | 2500 |
| 29 | NTTQLMAYLK | 2 | y6 monocharged | 19.34 | 591.81 | 738.42 | 29.5 | 2500 |
| 30 | NTTQLMAYLK | 2 | y8 monocharged | 19.36 | 591.81 | 967.53 | 29.5 | 2500 |
| 31 | NYIYNYGLAAK | 2 | y7 monocharged | 16.98 | 645.33 | 736.4 | 32.5 | 2500 |
| 32 | NYIYNYGLAAK | 2 | y8 monocharged | 16.98 | 645.33 | 899.46 | 32.5 | 2500 |
| 33 | NYIYNYGLAAK | 2 | y9 monocharged | 16.98 | 645.33 | 1012.55 | 32.5 | 2500 |
| 34 | NYSIDQR | 2 | y3 monocharged | 10.93 | 448.22 | 418.2 | 21.3 | 2500 |
| 35 | NYSIDQR | 2 | y4 monocharged | 10.91 | 448.22 | 531.29 | 21.3 | 2500 |
| 36 | NYSIDQR | 2 | y5 monocharged | 10.91 | 448.22 | 618.32 | 21.3 | 2500 |
| 37 | QPQQPVTENTLFEVGSLSK | 3 | y5 monocharged | 20.77 | 701.36 | 491.28 | 28.8 | 2500 |
| 38 | QPQQPVTENTLFEVGSLSK | 3 | y7 monocharged | 20.77 | 701.36 | 719.39 | 28.8 | 2500 |
| 39 | QPQQPVTENTLFEVGSLSK | 3 | y8 monocharged | 20.79 | 701.36 | 866.46 | 28.8 | 2500 |
| 40 | SLGVSYEDAIEK | 2 | y6 monocharged | 16.42 | 655.83 | 704.35 | 33.1 | 2500 |
| 41 | SLGVSYEDAIEK | 2 | y8 monocharged | 16.42 | 655.83 | 954.44 | 33.1 | 2500 |
| 42 | SLGVSYEDAIEK | 2 | y10 monocharged | 16.42 | 655.83 | 1110.53 | 33.1 | 2500 |
| 43 | SVATPIVPPLPPQENVWINK | 3 | y10 dicharged | 22.31 | 733.74 | 612.82 | 29.8 | 2500 |
| 44 | SVATPIVPPLPPQENVWINK | 3 | y13 dicharged | 22.29 | 733.74 | 766.42 | 29.8 | 2500 |
| 45 | SVATPIVPPLPPQENVWINK | 3 | y10 monocharged | 22.35 | 733.74 | 1224.64 | 29.8 | 2500 |
| 46 | TFAATLASYAQVSGK | 3 | y6 monocharged | 19.93 | 505.6 | 589.33 | 22.8 | 2500 |
| 47 | TFAATLASYAQVSGK | 2 | y8 monocharged | 19.93 | 757.9 | 839.43 | 38.9 | 2500 |
| 48 | TFAATLASYAQVSGK | 2 | y9 monocharged | 19.93 | 757.9 | 910.46 | 38.9 | 2500 |
| 49 | TGSTNGFGAYIAFVPAK | 3 | y3 monocharged | 21.68 | 567.63 | 315.2 | 24.7 | 2500 |

TABLE 32-continued

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 50 | TGSTNGFGAYIAFVPAK | 3 | y6 monocharged | 21.68 | 567.63 | 632.38 | 24.7 | 2500 |
| 51 | TGSTNGFGAYIAFVPAK | 2 | y3 monocharged | 21.68 | 850.94 | 315.2 | 44.2 | 2500 |
| 52 | TLLPQLGMHHSYLK | 3 | y11 dicharged | 17.99 | 546.63 | 655.84 | 24 | 2500 |
| 53 | TLLPQLGMHHSYLK | 3 | y12 dicharged | 17.95 | 546.63 | 712.38 | 24 | 2500 |
| 54 | TLLPQLGMHHSYLK | 2 | y11 dicharged | 17.97 | 819.45 | 655.84 | 42.4 | 2500 |
| 55 | TTSSDLLR | 2 | y4 monocharged | 13 | 446.74 | 516.31 | 21.2 | 2500 |
| 56 | TTSSDLLR | 2 | y5 monocharged | 13 | 446.74 | 603.35 | 21.2 | 2500 |
| 57 | TTSSDLLR | 2 | y6 monocharged | 13 | 446.74 | 690.38 | 21.2 | 2500 |
| 58 | VPADQMENYAWGYNK | 3 | y4 monocharged | 17.53 | 595.94 | 481.24 | 25.6 | 2500 |
| 59 | VPADQMENYAWGYNK | 3 | y5 monocharged | 17.53 | 595.94 | 667.32 | 25.6 | 2500 |
| 60 | VPADQMENYAWGYNK | 3 | y6 monocharged | 17.53 | 595.94 | 738.36 | 25.6 | 2500 |
| 61 | VYSNIGTGLLGMIAAK | 3 | y6 monocharged | 24.59 | 536.63 | 590.33 | 23.7 | 2500 |
| 62 | VYSNIGTGLLGMIAAK | 3 | y7 monocharged | 24.59 | 536.63 | 703.42 | 23.7 | 2500 |
| 63 | VYSNIGTGLLGMIAAK | 2 | y11 monocharged | 24.59 | 804.45 | 1031.59 | 41.6 | 2500 |
| 64 | YVQANMGQLK | 2 | y4 monocharged | 13.88 | 576.3 | 445.28 | 28.6 | 2500 |
| 65 | YVQANMGQLK | 2 | y7 monocharged | 13.88 | 576.3 | 761.4 | 28.6 | 2500 |
| 66 | YVQANMGQLK | 2 | y8 monocharged | 13.88 | 576.3 | 889.46 | 28.6 | 2500 |

The other machine parameters used are as follows:
Scan type: MRM
MRM planned: no
Polarity: Positive
Ionising source: Turbo V™ (Applied BioSystems)
Q1 setting: Filtering with unit resolution
Q3 setting: Filtering with unit resolution
Inter-scan pause: 5.00 msec
Scanning speed: 10 Da/s
Curtain gas: 50.00 psi
Cone voltage: 5500.00 V
Source temperature: 500.00° C.
Nebulising gas: 50.00 psi
Heating gas: 50.00 psi
Collision gas which induces dissociation: 9.00 psi
Dynamic filling: activated
Declustering potential (DP): 100.00 V
Entry potential before Q0 (EP): 6.00 V
Collision cell exit potential (CXP): 15 V
Total cycle time: 1.32 sec The areas obtained for each of the transitions and for each of the microorganisms studied were measured. When the areas of the transitions are greater than or equal to the positivity threshold described in TABLE 32, the detection of the transition is considered to be positive and is labelled "1" in TABLE 33. When a transition has an area less than the positivity threshold described in TABLE 32, the transition is considered non-detected and is labelled "0" in TABLE 33.

For a given peptide, when at least 3 transitions are labelled "1", the peptide is considered as being detected.

TABLE 33

| Transition number | Sam96 | Sam97 | Sam98 | Sam99 | Sam100 | Sam101 |
|---|---|---|---|---|---|---|
| 1 | 0 | 1 | 1 | 1 | 1 | 0 |
| 2 | 0 | 1 | 1 | 1 | 1 | 0 |
| 3 | 0 | 1 | 1 | 1 | 1 | 0 |
| 4 | 1 | 1 | 1 | 1 | 1 | 1 |
| 5 | 1 | 1 | 1 | 1 | 1 | 1 |
| 6 | 1 | 1 | 1 | 1 | 1 | 1 |
| 7 | 1 | 1 | 1 | 1 | 1 | 0 |
| 8 | 1 | 1 | 1 | 1 | 1 | 0 |
| 9 | 1 | 1 | 1 | 1 | 1 | 0 |
| 10 | 1 | 1 | 1 | 1 | 1 | 0 |
| 11 | 1 | 1 | 1 | 1 | 1 | 0 |
| 12 | 1 | 1 | 1 | 1 | 1 | 0 |
| 13 | 1 | 1 | 1 | 1 | 1 | 0 |
| 14 | 1 | 1 | 1 | 1 | 1 | 0 |
| 15 | 1 | 1 | 1 | 1 | 1 | 0 |
| 16 | 1 | 1 | 1 | 1 | 1 | 1 |
| 17 | 1 | 1 | 1 | 1 | 1 | 1 |
| 18 | 1 | 1 | 1 | 1 | 1 | 1 |
| 19 | 1 | 1 | 1 | 1 | 1 | 0 |
| 20 | 1 | 1 | 1 | 1 | 1 | 0 |
| 21 | 1 | 1 | 1 | 1 | 1 | 0 |
| 22 | 1 | 1 | 1 | 1 | 1 | 1 |
| 23 | 1 | 1 | 1 | 1 | 1 | 1 |
| 24 | 1 | 1 | 1 | 1 | 1 | 1 |
| 25 | 1 | 1 | 1 | 1 | 1 | 1 |
| 26 | 1 | 1 | 1 | 1 | 1 | 1 |
| 27 | 1 | 1 | 1 | 1 | 1 | 1 |
| 28 | 1 | 1 | 1 | 1 | 1 | 0 |
| 29 | 1 | 1 | 1 | 1 | 1 | 0 |
| 30 | 1 | 1 | 1 | 1 | 1 | 0 |
| 31 | 1 | 1 | 1 | 1 | 1 | 0 |
| 32 | 1 | 1 | 1 | 1 | 1 | 0 |
| 33 | 1 | 1 | 1 | 1 | 1 | 0 |

TABLE 33-continued

| Transition number | Sam96 | Sam97 | Sam98 | Sam99 | Sam100 | Sam101 |
|---|---|---|---|---|---|---|
| 34 | 1 | 1 | 1 | 1 | 1 | 0 |
| 35 | 1 | 1 | 1 | 1 | 1 | 0 |
| 36 | 1 | 1 | 1 | 1 | 1 | 0 |
| 37 | 1 | 1 | 1 | 1 | 1 | 0 |
| 38 | 1 | 1 | 1 | 1 | 1 | 0 |
| 39 | 1 | 1 | 1 | 1 | 1 | 0 |
| 40 | 1 | 1 | 1 | 1 | 1 | 1 |
| 41 | 1 | 1 | 1 | 1 | 1 | 1 |
| 42 | 1 | 1 | 1 | 1 | 1 | 1 |
| 43 | 1 | 1 | 1 | 1 | 1 | 1 |
| 44 | 1 | 1 | 1 | 1 | 1 | 1 |
| 45 | 1 | 1 | 1 | 1 | 1 | 1 |
| 46 | 1 | 1 | 1 | 1 | 1 | 0 |
| 47 | 1 | 1 | 1 | 1 | 1 | 0 |
| 48 | 1 | 1 | 1 | 1 | 1 | 0 |
| 49 | 1 | 1 | 1 | 1 | 1 | 1 |
| 50 | 1 | 1 | 1 | 1 | 1 | 1 |
| 51 | 1 | 1 | 1 | 1 | 1 | 1 |
| 52 | 1 | 1 | 1 | 1 | 1 | 0 |
| 53 | 1 | 1 | 1 | 1 | 1 | 0 |
| 54 | 1 | 1 | 1 | 1 | 1 | 0 |
| 55 | 1 | 1 | 1 | 1 | 1 | 1 |
| 56 | 1 | 1 | 1 | 1 | 1 | 1 |
| 57 | 1 | 1 | 1 | 1 | 1 | 1 |
| 58 | 1 | 0 | 0 | 0 | 1 | 0 |
| 59 | 1 | 0 | 0 | 0 | 1 | 0 |
| 60 | 1 | 0 | 0 | 0 | 1 | 0 |
| 61 | 1 | 1 | 1 | 1 | 1 | 1 |
| 62 | 1 | 1 | 1 | 1 | 1 | 1 |
| 63 | 1 | 1 | 1 | 1 | 1 | 1 |
| 64 | 1 | 1 | 1 | 1 | 1 | 1 |
| 65 | 1 | 1 | 1 | 1 | 1 | 1 |
| 66 | 1 | 1 | 1 | 1 | 1 | 1 |

Samples Sam96 to Sam101 comprise at least one peptide which is characteristic of the ACC proteins. The bacteria present in samples Sam96 to Sam101 therefore express a beta-lactamase which confers on them a resistance to penicillins and to cephalosporins, with the exception of fourth-generation cephalosporins.

EXAMPLE 26

Identification of a Resistance to CMY Beta-Lactams

Samples Sam102 to Sam108 are identified according to one of the methods described in examples 1, 3 or 4. The identification of the species is set out in TABLE 34.

TABLE 34

| Names | Species |
|---|---|
| Sam102 | *P. mirabilis* |
| Sam103 | *S. senftenberg* |
| Sam104 | *P. mirabilis* |
| Sam105 | *K. oxytoca* |
| Sam106 | *E. coli* |
| Sam107 | *S. enterica* ssp *enterica* |
| Sam108 | *P. mirabilis* |

Samples Sam102 to Sam108 correspond to a species able to comprise a CMY resistance mechanism. Each sample is treated according to example 5, then analysed according to example 6 by detecting the peptides from TABLE 35 instead of the peptides from TABLE 3.

TABLE 35

| Transition number | Peptide | Retention time (minutes) | (m/z) filtered in Q1 | (m/z) filtered in Q3 | Collision energy (eV) | Positivity threshold |
|---|---|---|---|---|---|---|
| 1 | AALLHFYQNWQPQWTPGAK | 22.2 | 752.72 | 372.22 | 30.4 | 2500 |
| 2 | AALLHFYQNWQPQWTPGAK | 22.1 | 752.72 | 442.74 | 30.4 | 2500 |
| 3 | AALLHFYQNWQPQWTPGAK | 22.2 | 752.72 | 884.46 | 30.4 | 2500 |
| 4 | ADIANNHPVTQQTLFELGSVSK | 19.9 | 790.41 | 427.27 | 31.6 | 2500 |
| 5 | ADIANNHPVTQQTLFELGSVSK | 19.9 | 790.41 | 719.39 | 31.6 | 2500 |
| 6 | ADIANNHPVTQQTLFELGSVSK | 19.9 | 790.41 | 866.46 | 31.6 | 2500 |
| 7 | ADSIINGSDSK | 11.3 | 553.77 | 493.23 | 27.3 | 2500 |
| 8 | ADSIINGSDSK | 11.3 | 553.77 | 607.27 | 27.3 | 2500 |
| 9 | ADSIINGSDSK | 11.3 | 553.77 | 720.35 | 27.3 | 2500 |
| 10 | ANIGGVDDK | 10 | 444.73 | 533.26 | 21.1 | 2500 |
| 11 | ANIGGVDDK | 10 | 444.73 | 590.28 | 21.1 | 2500 |
| 12 | ANIGGVDDK | 10.1 | 444.73 | 703.36 | 21.1 | 2500 |
| 13 | ASWVHK | 9.3 | 364.2 | 383.24 | 16.5 | 2500 |
| 14 | ASWVHK | 9.3 | 364.2 | 569.32 | 16.5 | 2500 |
| 15 | ASWVHK | 9.3 | 364.2 | 656.35 | 16.5 | 2500 |
| 16 | DYAWGYR | 15.6 | 465.71 | 395.2 | 22.3 | 2500 |
| 17 | DYAWGYR | 15.6 | 465.71 | 581.28 | 22.3 | 2500 |

TABLE 35-continued

| Transition number | Peptide | Retention time (minutes) | (m/z) filtered in Q1 | (m/z) filtered in Q3 | Collision energy (eV) | Positivity threshold |
|---|---|---|---|---|---|---|
| 18 | DYAWGYR | 15.6 | 465.71 | 652.32 | 22.3 | 2500 |
| 19 | ESGSQVLFNK | 14.5 | 554.79 | 408.22 | 27.4 | 2500 |
| 20 | ESGSQVLFNK | 14.5 | 554.79 | 521.31 | 27.4 | 2500 |
| 21 | ESGSQVLFNK | 14.5 | 554.79 | 620.38 | 27.4 | 2500 |
| 22 | GAMQLDDK | 11.4 | 439.21 | 490.25 | 20.8 | 2500 |
| 23 | GAMQLDDK | 11.4 | 439.21 | 618.31 | 20.8 | 2500 |
| 24 | GAMQLDDK | 11.4 | 439.21 | 749.35 | 20.8 | 2500 |
| 25 | GIGIVMLANR | 19.9 | 522.31 | 604.32 | 25.5 | 2500 |
| 26 | GIGIVMLANR | 19.9 | 522.31 | 703.39 | 25.5 | 2500 |
| 27 | GIGIVMLANR | 19.9 | 522.31 | 873.5 | 25.5 | 2500 |
| 28 | IGDMYQGLGWEMLNWPLK | 27.9 | 717.69 | 357.25 | 29.3 | 2500 |
| 29 | IGDMYQGLGWEMLNWPLK | 27.9 | 717.69 | 657.37 | 29.3 | 2500 |
| 30 | IGDMYQGLGWEMLNWPLK | 27.9 | 717.69 | 901.5 | 29.3 | 2500 |
| 31 | IPGMAVAVLK | 19.3 | 499.81 | 600.41 | 24.2 | 2500 |
| 32 | IPGMAVAVLK | 19.3 | 499.81 | 788.47 | 24.2 | 2500 |
| 33 | IPGMAVAVLK | 19.3 | 499.81 | 885.52 | 24.2 | 2500 |
| 34 | LAHTWITVPQNEQK | 16.5 | 832.94 | 743.37 | 43.2 | 2500 |
| 35 | LAHTWITVPQNEQK | 16.5 | 832.94 | 943.48 | 43.2 | 2500 |
| 36 | LAHTWITVPQNEQK | 16.5 | 832.94 | 1242.65 | 43.2 | 2500 |
| 37 | LLHLATYTAGGLPLQIPDDVR | 22.8 | 755.09 | 526.79 | 30.5 | 2500 |
| 38 | LLHLATYTAGGLPLQIPDDVR | 23 | 755.09 | 601.29 | 30.5 | 2500 |
| 39 | LLHLATYTAGGLPLQIPDDVR | 23 | 755.09 | 1052.57 | 30.5 | 2500 |
| 40 | LSDPVTK | 11.1 | 380.22 | 444.28 | 17.4 | 2500 |
| 41 | LSDPVTK | 11.1 | 380.22 | 559.31 | 17.4 | 2500 |
| 42 | LSDPVTK | 11.1 | 380.22 | 646.34 | 17.4 | 2500 |
| 43 | NLGIVMLANK | 19.6 | 536.81 | 576.32 | 26.3 | 2500 |
| 44 | NLGIVMLANK | 19.6 | 536.81 | 675.39 | 26.3 | 2500 |
| 45 | NLGIVMLANK | 19.6 | 536.81 | 845.49 | 26.3 | 2500 |
| 46 | QAMASYAYGYSK | 14.1 | 670.3 | 454.23 | 33.9 | 2500 |
| 47 | QAMASYAYGYSK | 14.2 | 670.3 | 617.29 | 33.9 | 2500 |
| 48 | QAMASYAYGYSK | 14.1 | 670.3 | 688.33 | 33.9 | 2500 |
| 49 | QWAPVYSPGSHR | 14.7 | 692.84 | 553.28 | 35.2 | 2500 |
| 50 | QWAPVYSPGSHR | 14.8 | 692.84 | 640.32 | 35.2 | 2500 |
| 51 | QWAPVYSPGSHR | 14.8 | 692.84 | 999.5 | 35.2 | 2500 |
| 52 | QWQGIR | 13.1 | 394.21 | 345.22 | 18.2 | 2500 |
| 53 | QWQGIR | 13.1 | 394.21 | 473.28 | 18.2 | 2500 |
| 54 | QWQGIR | 13.1 | 394.21 | 659.36 | 18.2 | 2500 |
| 55 | SSVIDMAR | 14.3 | 439.72 | 492.22 | 20.8 | 2500 |

TABLE 35-continued

| Transition number | Peptide | Retention time (minutes) | (m/z) filtered in Q1 | (m/z) filtered in Q3 | Collision energy (eV) | Positivity threshold |
|---|---|---|---|---|---|---|
| 56 | SSVIDMAR | 14.3 | 439.72 | 605.31 | 20.8 | 2500 |
| 57 | SSVIDMAR | 14.3 | 439.72 | 704.38 | 20.8 | 2500 |
| 58 | SYPNPVR | 11.6 | 416.72 | 371.24 | 19.5 | 2500 |
| 59 | SYPNPVR | 11.6 | 416.72 | 485.28 | 19.5 | 2500 |
| 60 | SYPNPVR | 11.6 | 416.72 | 582.34 | 19.5 | 2500 |
| 61 | TEQQIADIVNR | 15.8 | 643.84 | 616.34 | 32.4 | 2500 |
| 62 | TEQQIADIVNR | 15.8 | 643.84 | 687.38 | 32.4 | 2500 |
| 63 | TEQQIADIVNR | 15.8 | 643.84 | 800.46 | 32.4 | 2500 |
| 64 | TFNGVLGGDAIAR | 17.9 | 645.84 | 602.33 | 32.5 | 2500 |
| 65 | TFNGVLGGDAIAR | 17.9 | 645.84 | 659.35 | 32.5 | 2500 |
| 66 | TFNGVLGGDAIAR | 17.9 | 645.84 | 772.43 | 32.5 | 2500 |
| 67 | TITPLMQEQAIPGMAVAVIYQGK | 24.9 | 820.44 | 617.34 | 32.5 | 2500 |
| 68 | TITPLMQEQAIPGMAVAVIYQGK | 25 | 820.44 | 778.45 | 32.5 | 2500 |
| 69 | TITPLMQEQAIPGMAVAVIYQGK | 24.9 | 820.44 | 1233.67 | 32.5 | 2500 |
| 70 | TLQQGIALAQSR | 15.5 | 643.37 | 574.33 | 32.4 | 2500 |
| 71 | TLQQGIALAQSR | 15.5 | 643.37 | 645.37 | 32.4 | 2500 |
| 72 | TLQQGIALAQSR | 15.5 | 643.37 | 815.47 | 32.4 | 2500 |
| 73 | TLTATLGAYAVVK | 19.7 | 654.38 | 707.41 | 33 | 2500 |
| 74 | TLTATLGAYAVVK | 19.7 | 654.38 | 820.49 | 33 | 2500 |
| 75 | TLTATLGAYAVVK | 19.7 | 654.38 | 921.54 | 33 | 2500 |
| 76 | VALAALPAVEVNPPAPAVK | 21.1 | 609.7 | 644.87 | 26 | 2500 |
| 77 | VALAALPAVEVNPPAPAVK | 21 | 609.7 | 679.41 | 26 | 2500 |
| 78 | VALAALPAVEVNPPAPAVK | 21 | 609.7 | 793.46 | 26 | 2500 |
| 79 | VEAAWR | 12 | 366.2 | 432.24 | 16.6 | 2500 |
| 80 | VEAAWR | 12 | 366.2 | 503.27 | 16.6 | 2500 |
| 81 | VEAAWR | 12 | 366.2 | 632.32 | 16.6 | 2500 |
| 82 | VLQPLK | 13.1 | 349.23 | 357.25 | 15.6 | 2500 |
| 83 | VLQPLK | 13.1 | 349.23 | 485.31 | 15.6 | 2500 |
| 84 | VLQPLK | 13 | 349.23 | 598.39 | 15.6 | 2500 |
| 85 | VNPGMLADEAYGIK | 18.8 | 739.37 | 632.82 | 37.9 | 2500 |
| 86 | VNPGMLADEAYGIK | 18.9 | 739.37 | 795.39 | 37.9 | 2500 |
| 87 | VNPGMLADEAYGIK | 18.9 | 739.37 | 866.43 | 37.9 | 2500 |
| 88 | WVQANMDASHVQEK | 13.4 | 548.26 | 615.28 | 24.1 | 2500 |
| 89 | WVQANMDASHVQEK | 13.4 | 548.26 | 679.31 | 24.1 | 2500 |
| 90 | WVQANMDASHVQEK | 13.4 | 548.26 | 728.85 | 24.1 | 2500 |
| 91 | YWPELTGK | 17.8 | 497.26 | 305.18 | 24.1 | 2500 |
| 92 | YWPELTGK | 17.8 | 497.26 | 418.27 | 24.1 | 2500 |
| 93 | YWPELTGK | 17.8 | 497.26 | 644.36 | 24.1 | 2500 |

The other machine parameters used are as follows:
Scan type: MRM
MRM planned: yes
Polarity: Positive
Ionising source: Turbo V™ (Applied BioSystems)
Q1 setting: Filtering with unit resolution
Q3 setting: Filtering with unit resolution
Inter-scan pause: 5.00 msec
Scanning speed: 10 Da/s
Curtain gas: 50.00 psi
Cone voltage: 5500.00 V
Source temperature: 500.00° C.
Nebulising gas: 50.00 psi
Heating gas: 50.00 psi
Collision gas which induces dissociation: 9.00 psi
Dynamic filling: activated
Declustering potential (DP): 100.00 V
Entry potential before Q0 (EP): 6.00 V
Collision cell exit potential (CXP): 15 V
Total cycle time: 0.04 sec
Detection window: 120 sec The areas obtained for each of the transitions and for each of the microorganisms studied were measured. When the areas of the transitions are greater than or equal to the positivity threshold described in TABLE 35, the detection of the transition is considered to be positive and is labelled "1" in TABLE 36. When a transition has an area less than the positivity threshold described in TABLE 35, the transition is considered non-detected and is labelled "0" in TABLE 36.

For a given peptide, when at least 3 transitions are labelled "1", the peptide is considered as being detected.

TABLE 36

| Transition number | Sam102 | Sam103 | Sam104 | Sam105 | Sam106 | Sam107 | Sam108 |
|---|---|---|---|---|---|---|---|
| 1 | 0 | 0 | 0 | 1 | 0 | 0 | 1 |
| 2 | 0 | 0 | 0 | 1 | 0 | 0 | 1 |
| 3 | 0 | 0 | 0 | 1 | 0 | 0 | 1 |
| 4 | 0 | 0 | 0 | 0 | 1 | 0 | 0 |
| 5 | 0 | 0 | 0 | 0 | 1 | 0 | 0 |
| 6 | 0 | 0 | 0 | 0 | 1 | 0 | 0 |
| 7 | 1 | 1 | 1 | 1 | 1 | 1 | 1 |
| 8 | 1 | 1 | 1 | 1 | 1 | 1 | 1 |
| 9 | 1 | 1 | 1 | 1 | 1 | 1 | 1 |
| 10 | 0 | 0 | 0 | 0 | 0 | 0 | 0 |
| 11 | 0 | 0 | 0 | 0 | 0 | 0 | 0 |
| 12 | 0 | 0 | 0 | 0 | 0 | 0 | 0 |
| 13 | 1 | 1 | 1 | 1 | 1 | 1 | 1 |
| 14 | 1 | 1 | 1 | 1 | 1 | 1 | 1 |
| 15 | 1 | 1 | 1 | 1 | 1 | 1 | 1 |
| 16 | 0 | 1 | 0 | 1 | 1 | 1 | 0 |
| 17 | 0 | 1 | 0 | 1 | 1 | 1 | 0 |
| 18 | 0 | 1 | 0 | 1 | 1 | 1 | 0 |
| 19 | 0 | 0 | 0 | 1 | 0 | 0 | 0 |
| 20 | 0 | 0 | 0 | 1 | 0 | 0 | 0 |
| 21 | 0 | 0 | 0 | 1 | 0 | 0 | 0 |
| 22 | 0 | 0 | 0 | 0 | 0 | 0 | 1 |
| 23 | 0 | 0 | 0 | 0 | 0 | 0 | 1 |
| 24 | 0 | 0 | 0 | 0 | 0 | 0 | 1 |
| 25 | 0 | 0 | 0 | 0 | 0 | 0 | 0 |
| 26 | 0 | 0 | 0 | 0 | 0 | 0 | 0 |
| 27 | 0 | 0 | 0 | 0 | 0 | 0 | 0 |
| 28 | 0 | 0 | 0 | 1 | 0 | 0 | 0 |
| 29 | 0 | 0 | 0 | 1 | 0 | 0 | 0 |
| 30 | 0 | 0 | 0 | 1 | 0 | 0 | 0 |
| 31 | 0 | 0 | 0 | 0 | 0 | 0 | 0 |
| 32 | 0 | 0 | 0 | 0 | 0 | 0 | 0 |
| 33 | 0 | 0 | 0 | 0 | 0 | 0 | 0 |
| 34 | 1 | 1 | 1 | 1 | 1 | 1 | 1 |
| 35 | 1 | 1 | 1 | 1 | 1 | 1 | 1 |
| 36 | 1 | 1 | 1 | 1 | 1 | 1 | 1 |
| 37 | 0 | 0 | 0 | 0 | 0 | 0 | 0 |
| 38 | 0 | 0 | 0 | 0 | 0 | 0 | 0 |
| 39 | 0 | 0 | 0 | 0 | 0 | 0 | 0 |
| 40 | 1 | 1 | 1 | 1 | 0 | 1 | 1 |
| 41 | 1 | 1 | 1 | 1 | 0 | 1 | 1 |
| 42 | 1 | 1 | 1 | 1 | 0 | 1 | 1 |
| 43 | 1 | 1 | 1 | 1 | 1 | 1 | 1 |
| 44 | 1 | 1 | 1 | 1 | 1 | 1 | 1 |
| 45 | 1 | 1 | 1 | 1 | 1 | 1 | 1 |
| 46 | 0 | 0 | 0 | 0 | 0 | 0 | 0 |
| 47 | 0 | 0 | 0 | 0 | 0 | 0 | 0 |
| 48 | 0 | 0 | 0 | 0 | 0 | 0 | 0 |
| 49 | 0 | 0 | 0 | 0 | 0 | 0 | 0 |
| 50 | 0 | 0 | 0 | 0 | 0 | 0 | 0 |
| 51 | 0 | 0 | 0 | 0 | 0 | 0 | 0 |
| 52 | 1 | 1 | 1 | 1 | 1 | 1 | 1 |
| 53 | 1 | 1 | 1 | 1 | 1 | 1 | 1 |
| 54 | 1 | 1 | 1 | 1 | 1 | 1 | 1 |
| 55 | 1 | 1 | 1 | 1 | 1 | 1 | 1 |
| 56 | 1 | 1 | 1 | 1 | 1 | 1 | 1 |

TABLE 36-continued

| Transition number | Sam102 | Sam103 | Sam104 | Sam105 | Sam106 | Sam107 | Sam108 |
|---|---|---|---|---|---|---|---|
| 57 | 1 | 1 | 1 | 1 | 1 | 1 | 1 |
| 58 | 0 | 1 | 1 | 1 | 1 | 0 | 1 |
| 59 | 0 | 1 | 1 | 1 | 1 | 0 | 1 |
| 60 | 0 | 1 | 1 | 1 | 1 | 0 | 1 |
| 61 | 1 | 1 | 1 | 1 | 1 | 1 | 1 |
| 62 | 1 | 1 | 1 | 1 | 1 | 1 | 1 |
| 63 | 1 | 1 | 1 | 1 | 1 | 1 | 1 |
| 64 | 1 | 1 | 1 | 1 | 1 | 1 | 1 |
| 65 | 1 | 1 | 1 | 1 | 1 | 1 | 1 |
| 66 | 1 | 1 | 1 | 1 | 1 | 1 | 1 |
| 67 | 1 | 0 | 0 | 0 | 0 | 1 | 0 |
| 68 | 1 | 0 | 0 | 0 | 0 | 1 | 0 |
| 69 | 1 | 0 | 0 | 0 | 0 | 1 | 0 |
| 70 | 1 | 1 | 1 | 1 | 1 | 1 | 1 |
| 71 | 1 | 1 | 1 | 1 | 1 | 1 | 1 |
| 72 | 1 | 1 | 1 | 1 | 1 | 1 | 1 |
| 73 | 0 | 0 | 0 | 0 | 0 | 0 | 0 |
| 74 | 0 | 0 | 0 | 0 | 0 | 0 | 0 |
| 75 | 0 | 0 | 0 | 0 | 0 | 0 | 0 |
| 76 | 1 | 1 | 1 | 1 | 1 | 1 | 1 |
| 77 | 1 | 1 | 1 | 1 | 1 | 1 | 1 |
| 78 | 1 | 1 | 1 | 1 | 1 | 1 | 1 |
| 79 | 1 | 1 | 1 | 1 | 1 | 1 | 1 |
| 80 | 1 | 1 | 1 | 1 | 1 | 1 | 1 |
| 81 | 1 | 1 | 1 | 1 | 1 | 1 | 1 |
| 82 | 1 | 1 | 1 | 1 | 1 | 1 | 1 |
| 83 | 1 | 1 | 1 | 1 | 1 | 1 | 1 |
| 84 | 1 | 1 | 1 | 1 | 1 | 1 | 1 |
| 85 | 0 | 0 | 1 | 0 | 1 | 1 | 1 |
| 86 | 0 | 0 | 1 | 0 | 1 | 1 | 1 |
| 87 | 0 | 0 | 1 | 0 | 1 | 1 | 1 |
| 88 | 1 | 1 | 1 | 1 | 1 | 1 | 1 |
| 89 | 1 | 1 | 1 | 1 | 1 | 1 | 1 |
| 90 | 1 | 1 | 1 | 1 | 1 | 1 | 1 |
| 91 | 1 | 1 | 1 | 1 | 0 | 1 | 1 |
| 92 | 1 | 1 | 1 | 1 | 0 | 1 | 1 |
| 93 | 1 | 1 | 1 | 1 | 0 | 1 | 1 |

Samples Sam102 to Sam108 comprise at least one peptide which is characteristic of the CMY proteins. The bacteria present in samples Sam102 to Sam108 therefore express a beta-lactamase which confers on them a resistance to penicillins and to cephalosporins, with the exception of fourth-generation cephalosporins.

EXAMPLE 27

Identification of a Resistance to CTX-M Beta-Lactams

Samples Sam109 to Sam118 are identified according to one of the methods described in examples 1, 3 or 4. The identification of the species is set out in TABLE 37.

TABLE 37

| Names | Species |
|---|---|
| Sam109 | *E. aerogenes* |
| Sam110 | *E. coli* |
| Sam111 | *E. coli* |
| Sam112 | *E. coli* |
| Sam113 | *E. coli* |
| Sam114 | *K. pneumoniae* |
| Sam115 | *K. pneumoniae* |
| Sam116 | *P. mirabilis* |
| Sam117 | *Salmonella* spp |
| Sam118 | *Salmonella* spp |

Samples Sam109 to Sam118 correspond to a species able to comprise a CTX-M resistance mechanism. Each sample is treated according to example 5, then analysed according to example 6 by detecting the peptides from TABLE 38 instead of the peptides from TABLE 3.

TABLE 38

| Transition number | Peptide | Charge state of the precursor | Charge state of the fragment ion | Fragment | Retention time (minutes) | (m/z) filtered in Q1 | (m/z) filtered in Q3 | Collision energy (eV) | Positivity threshold |
|---|---|---|---|---|---|---|---|---|---|
| 1 | AGLPK | 2 | 1 | y4 | 8.4 | 243.16 | 414.27 | 9.6 | 3000 |
| 2 | AGLPK | 2 | 1 | y3 | 8.4 | 243.16 | 357.25 | 9.6 | 3000 |
| 3 | AGLPK | 2 | 2 | y3 | 8.4 | 243.16 | 179.13 | 9.6 | 3000 |
| 4 | AGLPTSWTVGDK | 2 | 1 | y9 | 18 | 616.32 | 990.49 | 30.9 | 2000 |
| 5 | AGLPTSWTVGDK | 2 | 1 | y7 | 18 | 616.32 | 792.39 | 30.9 | 2000 |
| 6 | AGLPTSWTVGDK | 2 | 2 | y9 | 17.9 | 616.32 | 495.75 | 30.9 | 2000 |
| 7 | AIGDETFR | 2 | 1 | y6 | 13.5 | 454.73 | 724.33 | 21.7 | 2000 |
| 8 | AIGDETFR | 2 | 1 | y5 | 13.5 | 454.73 | 667.31 | 21.7 | 2000 |
| 9 | AIGDETFR | 2 | 1 | y4 | 13.5 | 454.73 | 552.28 | 21.7 | 2000 |
| 10 | ALAETQR | 2 | 1 | y5 | 7.5 | 394.72 | 604.31 | 18.2 | 2000 |
| 11 | ALAETQR | 2 | 1 | y4 | 7.5 | 394.72 | 533.27 | 18.2 | 2000 |
| 12 | ALAETQR | 2 | 2 | y6 | 7.5 | 394.72 | 359.2 | 18.2 | 2000 |
| 13 | ALGDSQR | 2 | 1 | y5 | 3.5 | 373.69 | 562.26 | 17 | 2000 |
| 14 | ALGDSQR | 2 | 1 | y3 | 3.6 | 373.69 | 390.21 | 17 | 2000 |
| 15 | ALGDSQR | 2 | 2 | y6 | 3.5 | 373.69 | 338.18 | 17 | 2000 |
| 16 | AMAQTLR | 2 | 1 | y5 | 10.7 | 395.72 | 588.35 | 18.3 | 2000 |
| 17 | AMAQTLR | 2 | 1 | y4 | 10.7 | 395.72 | 517.31 | 18.3 | 2000 |
| 18 | AMAQTLR | 2 | 1 | y3 | 10.7 | 395.72 | 389.25 | 18.3 | 2000 |
| 19 | APLILVTYFTQPQPK | 2 | 1 | y10 | 24.6 | 858.49 | 1208.63 | 44.7 | 2000 |
| 20 | APLILVTYFTQPQPK | 3 | 1 | y6 | 24.6 | 572.66 | 695.38 | 24.8 | 2000 |
| 21 | APLILVTYFTQPQPK | 3 | 1 | y4 | 24.6 | 572.66 | 469.28 | 24.8 | 2000 |
| 22 | APLVLVTYFTQPQQNAESR | 3 | 1 | y8 | 23.6 | 721.38 | 929.44 | 29.4 | 2000 |
| 23 | APLVLVTYFTQPQQNAESR | 3 | 1 | y6 | 23.6 | 721.38 | 704.33 | 29.4 | 2000 |
| 24 | APLVLVTYFTQPQQNAESR | 3 | 2 | y8 | 23.6 | 721.38 | 465.23 | 29.4 | 2000 |
| 25 | AQLVTWLK | 2 | 1 | y6 | 20 | 479.79 | 759.48 | 23.1 | 2000 |
| 26 | AQLVTWLK | 2 | 1 | y5 | 20 | 479.79 | 646.39 | 23.1 | 2000 |
| 27 | AQLVTWLK | 2 | 1 | y4 | 20 | 479.79 | 547.32 | 23.1 | 2000 |
| 28 | AQLVTWMK | 2 | 1 | y6 | 18.5 | 488.77 | 777.43 | 23.6 | 2000 |
| 29 | AQLVTWMK | 2 | 1 | y5 | 18.6 | 488.77 | 664.35 | 23.6 | 2000 |
| 30 | AQLVTWMK | 2 | 1 | y4 | 18.5 | 488.77 | 565.28 | 23.6 | 2000 |
| 31 | DILAAAAK | 2 | 1 | y6 | 14.1 | 386.73 | 544.35 | 17.8 | 2000 |
| 32 | DILAAAAK | 2 | 1 | y5 | 14.1 | 386.73 | 431.26 | 17.8 | 2000 |
| 33 | DILAAAAK | 2 | 1 | y4 | 14.1 | 386.73 | 360.22 | 17.8 | 2000 |
| 34 | DTTSPR | 2 | 1 | y5 | 1 | 338.67 | 561.3 | 15 | 2000 |
| 35 | DTTSPR | 2 | 1 | y4 | 1 | 338.67 | 460.25 | 15 | 2000 |
| 36 | DTTSPR | 2 | 1 | y3 | 1 | 338.67 | 359.2 | 15 | 2000 |
| 37 | DTTTPLAMAQTLK | 2 | 1 | y9 | 19.4 | 695.87 | 972.56 | 35.4 | 2000 |
| 38 | DTTTPLAMAQTLK | 2 | 1 | y7 | 19.4 | 695.87 | 762.42 | 35.4 | 2000 |

TABLE 38-continued

| Transition number | Peptide | Charge state of the precursor | Charge state of the fragment | Fragment ion | Retention time (minutes) | (m/z) filtered in Q1 | (m/z) filtered in Q3 | Collision energy (eV) | Positivity threshold |
|---|---|---|---|---|---|---|---|---|---|
| 39 | DTTTPLAMAQTLK | 2 | 2 | y9 | 19.4 | 695.87 | 486.78 | 35.4 | 2000 |
| 40 | DTTTPR | 2 | 1 | y5 | 1 | 345.67 | 575.32 | 15.4 | 2000 |
| 41 | DTTTPR | 2 | 1 | y4 | 1 | 345.67 | 474.27 | 15.4 | 2000 |
| 42 | DTTTPR | 2 | 1 | y3 | 1 | 345.67 | 373.22 | 15.4 | 2000 |
| 43 | DVLAAAAK | 2 | 1 | y6 | 12.2 | 379.72 | 544.35 | 17.4 | 2000 |
| 44 | DVLAAAAK | 2 | 1 | y5 | 12.2 | 379.72 | 431.26 | 17.4 | 2000 |
| 45 | DVLAAAAK | 2 | 1 | y4 | 12.2 | 379.72 | 360.22 | 17.4 | 2000 |
| 46 | DVLASAAK | 2 | 1 | y6 | 11.4 | 387.72 | 560.34 | 17.8 | 2000 |
| 47 | DVLASAAK | 2 | 1 | y5 | 11.4 | 387.72 | 447.26 | 17.8 | 2000 |
| 48 | DVLASAAK | 2 | 1 | y4 | 11.4 | 387.72 | 376.22 | 17.8 | 2000 |
| 49 | DVLASAAR | 2 | 1 | y6 | 11.9 | 401.73 | 588.35 | 18.6 | 2000 |
| 50 | DVLASAAR | 2 | 1 | y5 | 11.9 | 401.73 | 475.26 | 18.6 | 2000 |
| 51 | DVLASAAR | 2 | 1 | y4 | 11.9 | 401.73 | 404.23 | 18.6 | 2000 |
| 52 | FAMCSTSK | 2 | 1 | y7 | 11.6 | 466.2 | 784.33 | 22.3 | 2000 |
| 53 | FAMCSTSK | 2 | 1 | y6 | 11.6 | 466.2 | 713.3 | 22.3 | 2000 |
| 54 | FAMCSTSK | 2 | 1 | y6 | 11.6 | 466.2 | 582.26 | 22.3 | 2000 |
| 55 | FPMCSTSK | 2 | 1 | y7 | 12.3 | 479.21 | 810.35 | 23.1 | 2000 |
| 56 | FPMCSTSK | 2 | 1 | y6 | 12.3 | 479.21 | 713.3 | 23.1 | 2000 |
| 57 | FPMCSTSK | 2 | 2 | y7 | 12.3 | 479.21 | 405.68 | 23.1 | 2000 |
| 58 | GNTTGAASIQAGLPASWVVGDK | 3 | 1 | y9 | 21.1 | 700.7 | 958.5 | 29.1 | 2000 |
| 59 | GNTTGAASIQAGLPASWVVGDK | 3 | 1 | y7 | 21.1 | 700.7 | 790.41 | 29.1 | 2000 |
| 60 | GNTTGAASIQAGLPASWVVGDK | 3 | 2 | y9 | 21.2 | 700.7 | 479.75 | 29.1 | 2000 |
| 61 | GNTTGAASIQAGLPTSWVVGDK | 3 | 1 | y9 | 21.3 | 710.7 | 988.51 | 29.1 | 8500 |
| 62 | GNTTGAASIQAGLPTSWVVGDK | 3 | 2 | y9 | 21.3 | 710.7 | 494.76 | 29.1 | 8500 |
| 63 | GNTTGAASIQAGLPTSWVVGDK | 3 | 1 | y3 | 21.3 | 710.7 | 319.16 | 29.1 | 8500 |
| 64 | GNTTGAASIR | 2 | 1 | y7 | 9.3 | 474.25 | 675.38 | 22.8 | 2000 |
| 65 | GNTTGAASIR | 2 | 1 | y6 | 9.3 | 474.25 | 574.33 | 22.8 | 2000 |
| 66 | GNTTGAASIR | 2 | 1 | y4 | 9.3 | 474.25 | 446.27 | 22.8 | 2000 |
| 67 | GNTTGSASIR | 2 | 1 | y8 | 8 | 482.25 | 792.42 | 23.2 | 2000 |
| 68 | GNTTGSASIR | 2 | 1 | y7 | 8 | 482.25 | 691.37 | 23.2 | 2000 |
| 69 | GNTTGSASIR | 2 | 1 | y6 | 8 | 482.25 | 590.33 | 23.2 | 2000 |
| 70 | HLLNQR | 2 | 1 | y5 | 8.1 | 390.73 | 643.39 | 18 | 2000 |
| 71 | HLLNQR | 2 | 1 | y4 | 8.1 | 390.73 | 530.31 | 18 | 2000 |
| 72 | HLLNQR | 2 | 1 | y3 | 8.1 | 390.73 | 417.22 | 18 | 2000 |
| 73 | LAALEK | 2 | 1 | y5 | 11.3 | 322.7 | 531.31 | 14.1 | 2000 |
| 74 | LAALEK | 2 | 1 | y4 | 11.3 | 322.7 | 460.28 | 14.1 | 2000 |
| 75 | LAALEK | 2 | 1 | y3 | 11.3 | 322.7 | 389.24 | 14.1 | 2000 |

TABLE 38-continued

| Transition number | Peptide | Charge state of the precursor | Charge state of the fragment | Fragment ion | Retention time (minutes) | (m/z) filtered in Q1 | (m/z) filtered in Q3 | Collision energy (eV) | Positivity threshold |
|---|---|---|---|---|---|---|---|---|---|
| 76 | LAELER | 2 | 1 | y5 | 11.7 | 365.71 | 617.33 | 16.6 | 2000 |
| 77 | LAELER | 2 | 1 | y4 | 11.7 | 365.71 | 546.29 | 16.6 | 2000 |
| 78 | LAELER | 2 | 1 | y3 | 11.7 | 365.71 | 417.25 | 16.6 | 2000 |
| 79 | LGVALIDTADNTQVLYR | 3 | 1 | y6 | 21.5 | 621.34 | 779.44 | 26.3 | 2000 |
| 80 | LGVALIDTADNTQVLYR | 3 | 1 | y5 | 21.5 | 621.34 | 678.39 | 26.3 | 2000 |
| 81 | LGVALIDTADNTQVLYR | 3 | 1 | y4 | 21.5 | 621.34 | 550.34 | 26.3 | 2000 |
| 82 | LGVALIDTADNTQVLYR | 3 | 1 | y3 | 21.4 | 621.34 | 451.27 | 26.3 | 2000 |
| 83 | LGVALINTADNSQILYR | 3 | 1 | y6 | 21.4 | 621.01 | 779.44 | 26.3 | 2000 |
| 84 | LGVALINTADNSQILYR | 3 | 1 | y5 | 21.4 | 621.01 | 692.41 | 26.3 | 2000 |
| 85 | LGVALINTADNSQILYR | 3 | 1 | y4 | 21.4 | 621.01 | 564.35 | 26.3 | 2000 |
| 86 | LGVALINTADNSQILYR | 3 | 1 | y3 | 21.4 | 621.01 | 461.27 | 26.3 | 2000 |
| 87 | LIAHLGGPDK | 3 | 1 | y6 | 13.2 | 340.87 | 586.32 | 17.6 | 2000 |
| 88 | LIAHLGGPDK | 3 | 2 | y9 | 13.2 | 340.87 | 454.25 | 17.6 | 2000 |
| 89 | LIAHLGGPDK | 3 | 2 | y8 | 13.2 | 340.87 | 397.71 | 17.6 | 2000 |
| 90 | LIAHVGGPASVTAFAR | 3 | 1 | y5 | 17.7 | 522.96 | 565.31 | 23.3 | 2000 |
| 91 | LIAHVGGPASVTAFAR | 3 | 1 | y4 | 17.7 | 522.96 | 464.26 | 23.3 | 2000 |
| 92 | LIAHVGGPASVTAFAR | 3 | 1 | y3 | 17.7 | 522.96 | 393.22 | 23.3 | 2000 |
| 93 | LIAQLGGPGGVTAFAR | 2 | 1 | y11 | 20.3 | 764.44 | 989.52 | 39.3 | 2000 |
| 94 | LIAQLGGPGGVTAFAR | 2 | 1 | y9 | 20.3 | 764.44 | 875.47 | 39.3 | 2000 |
| 95 | LIAQLGGPGGVTAFAR | 3 | 1 | y5 | 20.3 | 509.96 | 565.31 | 22.9 | 2000 |
| 96 | NLTLGK | 2 | 1 | y5 | 12.3 | 323.2 | 531.35 | 14.2 | 2000 |
| 97 | NLTLGK | 2 | 1 | y4 | 12.3 | 323.2 | 418.27 | 14.2 | 2000 |
| 98 | NLTLGK | 2 | 1 | y3 | 12.3 | 323.2 | 317.22 | 14.2 | 2000 |
| 99 | QLGDETFR | 2 | 1 | y6 | 13.6 | 483.24 | 724.33 | 23.3 | 2000 |
| 100 | QLGDETFR | 2 | 1 | y4 | 13.6 | 483.24 | 552.28 | 23.3 | 2000 |
| 101 | QLGDETFR | 2 | 1 | y3 | 13.6 | 483.24 | 423.24 | 23.3 | 2000 |
| 102 | QLTLGHALGETQR | 3 | 2 | y11 | 15.6 | 475.26 | 591.82 | 21.8 | 2000 |
| 103 | QLTLGHALGETQR | 3 | 1 | y5 | 15.6 | 475.26 | 590.29 | 21.8 | 2000 |
| 104 | QLTLGHALGETQR | 3 | 2 | y10 | 15.6 | 475.26 | 541.29 | 21.8 | 2000 |
| 105 | QSESDK | 2 | 1 | y5 | 0.8 | 347.16 | 565.25 | 15.5 | 2000 |
| 106 | QSESDK | 2 | 1 | y4 | 0.8 | 347.16 | 478.21 | 15.5 | 2000 |
| 107 | QSESDK | 2 | 1 | y3 | 0.8 | 347.16 | 349.17 | 15.5 | 2000 |
| 108 | QSETQK | 2 | 1 | y5 | 0.8 | 360.68 | 592.29 | 16.3 | 2000 |
| 109 | QSETQK | 2 | 1 | y4 | 0.8 | 360.68 | 505.26 | 16.3 | 2000 |
| 110 | QSETQK | 2 | 1 | y3 | 0.8 | 360.68 | 376.22 | 16.3 | 2000 |
| 111 | QSGGR | 2 | 1 | y4 | 0.7 | 252.63 | 376.19 | 10.1 | 2000 |
| 112 | QSGGR | 2 | 1 | y3 | 0.7 | 252.63 | 289.16 | 10.1 | 2000 |
| 113 | QSGGR | 2 | 2 | y4 | 0.7 | 252.63 | 188.6 | 10.1 | 2000 |

TABLE 38-continued

| Transition number | Peptide | Charge state of the precursor | Charge state of the fragment | Fragment ion | Retention time (minutes) | (m/z) filtered in Q1 | (m/z) filtered in Q3 | Collision energy (eV) | Positivity threshold |
|---|---|---|---|---|---|---|---|---|---|
| 114 | SDLVNYNPIAEK | 2 | 1 | y8 | 17.3 | 681.85 | 948.48 | 34.6 | 2000 |
| 115 | SDLVNYNPIAEK | 2 | 1 | y6 | 17.4 | 681.85 | 671.37 | 34.6 | 2000 |
| 116 | SDLVNYNPIAEK | 2 | 1 | y5 | 17.4 | 681.85 | 557.33 | 34.6 | 2000 |
| 117 | SESEPNLLNQR | 2 | 1 | y7 | 14.6 | 643.82 | 854.48 | 32.4 | 2000 |
| 118 | SESEPNLLNQR | 2 | 2 | y7 | 14.6 | 643.82 | 427.75 | 32.4 | 2000 |
| 119 | SESEPNLLNQR | 3 | 1 | y3 | 14.6 | 429.55 | 417.22 | 20.4 | 2000 |
| 120 | SLGDETFR | 2 | 1 | y6 | 13.9 | 462.73 | 724.33 | 22.1 | 2000 |
| 121 | SLGDETFR | 2 | 1 | y5 | 13.8 | 462.73 | 667.31 | 22.1 | 2000 |
| 122 | SLGDETFR | 2 | 1 | y4 | 13.9 | 462.73 | 552.28 | 22.1 | 2000 |
| 123 | SSGGR | 2 | 1 | y4 | 0.7 | 232.12 | 376.19 | 9 | 2000 |
| 124 | SSGGR | 2 | 1 | y3 | 0.7 | 232.12 | 289.16 | 9 | 2000 |
| 125 | SSGGR | 2 | 2 | y4 | 0.7 | 232.12 | 188.6 | 9 | 2000 |
| 126 | SWVVGDK | 2 | 1 | y5 | 13.9 | 395.71 | 517.3 | 18.3 | 2000 |
| 127 | SWVVGDK | 2 | 1 | y4 | 13.9 | 395.71 | 418.23 | 18.3 | 2000 |
| 128 | SWVVGDK | 2 | 1 | y3 | 13.9 | 395.71 | 319.16 | 18.3 | 2000 |
| 129 | TEPTLNTAIPGDPR | 2 | 2 | y12 | 16.3 | 741.38 | 626.34 | 38 | 2000 |
| 130 | TEPTLNTAIPGDPR | 2 | 1 | y5 | 16.3 | 741.38 | 541.27 | 38 | 2000 |
| 131 | TEPTLNTAIPGDPR | 3 | 1 | y5 | 16.3 | 494.59 | 541.27 | 22.4 | 2000 |
| 132 | TGSGDYGTTNDIAVIWPK | 2 | 1 | y8 | 20.9 | 947.96 | 941.55 | 49.8 | 2000 |
| 133 | TGSGDYGTTNDIAVIWPK | 3 | 2 | y6 | 21 | 632.31 | 357.22 | 26.7 | 2000 |
| 134 | TGSGDYGTTNDIAVIWPK | 3 | 2 | y5 | 20.9 | 632.31 | 321.7 | 26.7 | 2000 |
| 135 | TGSGDYGTTNDIAVIWPQGR | 3 | 1 | y6 | 20.5 | 703.34 | 756.42 | 28.9 | 2000 |
| 136 | TGSGDYGTTNDIAVIWPQGR | 3 | 1 | y5 | 20.5 | 703.34 | 643.33 | 28.9 | 2000 |
| 137 | TGSGDYGTTNDIAVIWPQGR | 3 | 1 | y4 | 20.5 | 703.34 | 457.25 | 28.9 | 2000 |
| 138 | TGSGGYGTTNDIAVIWPK | 2 | 1 | y3 | 20.9 | 918.96 | 430.25 | 48.1 | 2000 |
| 139 | TGSGGYGTTNDIAVIWPK | 3 | 1 | y6 | 20.9 | 612.98 | 713.43 | 26.1 | 2000 |
| 140 | TGSGGYGTTNDIAVIWPK | 3 | 1 | y5 | 20.9 | 612.98 | 642.4 | 26.1 | 2000 |
| 141 | VMAAAAVLK | 2 | 1 | y8 | 15.7 | 437.27 | 774.45 | 20.7 | 2000 |
| 142 | VMAAAAVLK | 2 | 1 | y7 | 15.7 | 437.27 | 643.41 | 20.7 | 2000 |
| 143 | VMAAAAVLK | 2 | 1 | y6 | 15.7 | 437.27 | 572.38 | 20.7 | 2000 |
| 144 | VMAVAAVLK | 2 | 1 | y7 | 18.2 | 451.28 | 671.45 | 21.5 | 2000 |
| 145 | VMAVAAVLK | 2 | 1 | y6 | 18.2 | 451.28 | 600.41 | 21.5 | 2000 |
| 146 | VMAVAAVLK | 2 | 1 | y5 | 18.2 | 451.28 | 501.34 | 21.5 | 2000 |
| 147 | VTAFAR | 2 | 1 | y5 | 11 | 332.69 | 565.31 | 14.7 | 2000 |
| 148 | VTAFAR | 2 | 1 | y4 | 11 | 332.69 | 464.26 | 14.7 | 2000 |
| 149 | VTAFAR | 2 | 1 | y3 | 11 | 332.69 | 393.22 | 14.7 | 2000 |

The other machine parameters used are as follows:
Scan type: MRM
MRM planned: yes
Polarity: Positive
Ionising source: Turbo V™ (Applied BioSystems)
Q1 setting: Filtering with unit resolution
Q3 setting: Filtering with unit resolution
Inter-scan pause: 5.00 msec
Scanning speed: 10 Da/s
Curtain gas: 50.00 psi
Cone voltage: 5500.00 V
Source temperature: 500.00° C.
Nebulising gas: 50.00 psi
Heating gas: 50.00 psi
Collision gas which induces dissociation: 9.00 psi
Dynamic filling: activated
Declustering potential (DP): 100.00 V
Entry potential before Q0 (EP): 6.00 V
Collision cell exit potential (CXP): 15 V
Total cycle time: 0.04 sec
Detection window: 120 sec The areas obtained for each of the transitions and for each of the microorganisms studied were measured. When the areas of the transitions are greater than or equal to the positivity threshold described in TABLE 38, the detection of the transition is considered to be positive and is labelled "1" in TABLE 39. When a transition has an area less than the positivity threshold described in TABLE 38, the transition is considered non-detected and is labelled "0" in TABLE 39.

For a given peptide, when at least 3 transitions are labelled "1", the peptide is considered as being detected.

TABLE 39

| Transition number | Sam109 | Sam110 | Sam111 | Sam112 | Sam113 | Sam114 | Sam115 | Sam116 | Sam117 | Sam118 |
|---|---|---|---|---|---|---|---|---|---|---|
| 1 | 0 | 0 | 0 | 0 | 0 | 0 | 0 | 0 | 1 | 0 |
| 2 | 1 | 1 | 0 | 0 | 1 | 0 | 0 | 0 | 1 | 1 |
| 3 | 1 | 1 | 0 | 0 | 1 | 0 | 0 | 0 | 1 | 1 |
| 4 | 0 | 0 | 0 | 0 | 0 | 0 | 0 | 1 | 0 | 0 |
| 5 | 0 | 0 | 0 | 0 | 0 | 0 | 0 | 0 | 0 | 0 |
| 6 | 0 | 0 | 0 | 0 | 0 | 0 | 0 | 1 | 0 | 0 |
| 7 | 0 | 1 | 0 | 0 | 1 | 0 | 0 | 0 | 0 | 0 |
| 8 | 0 | 0 | 0 | 0 | 0 | 0 | 0 | 0 | 0 | 0 |
| 9 | 0 | 0 | 0 | 0 | 0 | 0 | 0 | 0 | 0 | 0 |
| 10 | 0 | 0 | 0 | 0 | 0 | 0 | 0 | 0 | 0 | 0 |
| 11 | 0 | 0 | 0 | 0 | 0 | 0 | 0 | 0 | 0 | 0 |
| 12 | 0 | 0 | 0 | 0 | 0 | 0 | 0 | 0 | 0 | 0 |
| 13 | 0 | 0 | 0 | 0 | 0 | 0 | 0 | 0 | 0 | 0 |
| 14 | 0 | 0 | 0 | 0 | 0 | 0 | 0 | 0 | 0 | 0 |
| 15 | 0 | 0 | 0 | 0 | 0 | 0 | 0 | 0 | 0 | 0 |
| 16 | 1 | 1 | 1 | 1 | 1 | 0 | 1 | 1 | 0 | 1 |
| 17 | 1 | 1 | 1 | 1 | 1 | 0 | 1 | 1 | 0 | 1 |
| 18 | 1 | 1 | 1 | 1 | 1 | 0 | 1 | 1 | 0 | 1 |
| 19 | 0 | 0 | 0 | 0 | 0 | 0 | 0 | 0 | 0 | 0 |
| 20 | 0 | 0 | 0 | 0 | 0 | 0 | 0 | 0 | 0 | 0 |
| 21 | 0 | 0 | 0 | 0 | 0 | 0 | 0 | 0 | 0 | 0 |
| 22 | 0 | 0 | 0 | 0 | 0 | 0 | 0 | 0 | 0 | 0 |
| 23 | 0 | 0 | 0 | 0 | 0 | 0 | 0 | 0 | 0 | 0 |
| 24 | 0 | 0 | 0 | 0 | 0 | 0 | 0 | 0 | 0 | 0 |
| 25 | 1 | 1 | 0 | 0 | 1 | 0 | 1 | 0 | 1 | 0 |
| 26 | 1 | 1 | 1 | 0 | 1 | 1 | 1 | 1 | 1 | 0 |
| 27 | 1 | 1 | 0 | 0 | 1 | 0 | 1 | 0 | 1 | 0 |
| 28 | 0 | 0 | 0 | 0 | 0 | 0 | 0 | 0 | 0 | 0 |
| 29 | 0 | 0 | 0 | 0 | 0 | 0 | 0 | 0 | 0 | 0 |
| 30 | 1 | 1 | 0 | 0 | 1 | 0 | 1 | 0 | 0 | 0 |
| 31 | 0 | 1 | 1 | 0 | 1 | 0 | 0 | 0 | 1 | 1 |
| 32 | 0 | 0 | 0 | 0 | 0 | 0 | 0 | 0 | 0 | 0 |
| 33 | 0 | 0 | 0 | 0 | 0 | 0 | 0 | 0 | 0 | 0 |
| 34 | 0 | 0 | 0 | 0 | 0 | 0 | 0 | 0 | 0 | 0 |
| 35 | 0 | 0 | 0 | 0 | 0 | 0 | 0 | 0 | 0 | 0 |
| 36 | 0 | 0 | 0 | 0 | 0 | 0 | 0 | 0 | 0 | 0 |
| 37 | 0 | 0 | 0 | 0 | 0 | 0 | 0 | 1 | 1 | 0 |
| 38 | 0 | 0 | 0 | 0 | 0 | 0 | 0 | 1 | 1 | 0 |
| 39 | 0 | 0 | 0 | 0 | 0 | 0 | 0 | 0 | 1 | 0 |
| 40 | 0 | 0 | 0 | 0 | 1 | 0 | 0 | 0 | 0 | 0 |
| 41 | 0 | 0 | 0 | 0 | 1 | 0 | 1 | 0 | 0 | 1 |
| 42 | 0 | 0 | 0 | 0 | 0 | 0 | 0 | 0 | 0 | 1 |
| 43 | 1 | 0 | 0 | 0 | 0 | 0 | 0 | 0 | 1 | 0 |
| 44 | 1 | 0 | 0 | 0 | 0 | 0 | 0 | 0 | 1 | 0 |
| 45 | 1 | 0 | 0 | 0 | 0 | 0 | 0 | 0 | 1 | 0 |
| 46 | 1 | 0 | 0 | 0 | 0 | 0 | 0 | 0 | 0 | 1 |
| 47 | 1 | 0 | 0 | 0 | 0 | 0 | 0 | 0 | 0 | 1 |
| 48 | 0 | 0 | 0 | 0 | 1 | 0 | 0 | 0 | 0 | 1 |
| 49 | 0 | 1 | 0 | 0 | 1 | 0 | 1 | 0 | 0 | 0 |
| 50 | 0 | 1 | 0 | 0 | 1 | 0 | 1 | 0 | 0 | 0 |
| 51 | 0 | 1 | 0 | 0 | 1 | 0 | 1 | 0 | 0 | 0 |
| 52 | 1 | 0 | 1 | 1 | 0 | 1 | 0 | 1 | 1 | 1 |
| 53 | 1 | 0 | 1 | 1 | 0 | 1 | 0 | 1 | 1 | 1 |
| 54 | 1 | 0 | 1 | 1 | 1 | 1 | 1 | 1 | 1 | 1 |
| 55 | 0 | 0 | 0 | 0 | 1 | 0 | 0 | 0 | 0 | 0 |
| 56 | 0 | 0 | 0 | 0 | 1 | 0 | 0 | 0 | 0 | 0 |

TABLE 39-continued

| Transition number | Sam109 | Sam110 | Sam111 | Sam112 | Sam113 | Sam114 | Sam115 | Sam116 | Sam117 | Sam118 |
|---|---|---|---|---|---|---|---|---|---|---|
| 57 | 0 | 0 | 0 | 0 | 1 | 0 | 0 | 0 | 0 | 0 |
| 58 | 0 | 0 | 0 | 0 | 0 | 0 | 0 | 0 | 0 | 1 |
| 59 | 0 | 0 | 0 | 0 | 0 | 0 | 0 | 0 | 0 | 0 |
| 60 | 0 | 0 | 0 | 0 | 0 | 0 | 0 | 0 | 0 | 1 |
| 61 | 1 | 0 | 0 | 0 | 0 | 0 | 0 | 0 | 0 | 0 |
| 62 | 1 | 0 | 0 | 0 | 0 | 0 | 0 | 0 | 0 | 0 |
| 63 | 1 | 0 | 0 | 0 | 0 | 0 | 0 | 0 | 0 | 0 |
| 64 | 0 | 1 | 0 | 0 | 1 | 1 | 1 | 0 | 0 | 0 |
| 65 | 0 | 1 | 0 | 0 | 1 | 1 | 1 | 0 | 0 | 0 |
| 66 | 0 | 1 | 0 | 0 | 1 | 1 | 1 | 0 | 0 | 0 |
| 67 | 0 | 0 | 0 | 0 | 0 | 0 | 0 | 0 | 1 | 0 |
| 68 | 0 | 0 | 0 | 0 | 0 | 0 | 0 | 0 | 1 | 0 |
| 69 | 0 | 0 | 0 | 0 | 0 | 0 | 0 | 0 | 1 | 0 |
| 70 | 0 | 0 | 0 | 0 | 0 | 0 | 0 | 0 | 0 | 0 |
| 71 | 0 | 0 | 0 | 0 | 0 | 1 | 0 | 0 | 1 | 0 |
| 72 | 0 | 0 | 0 | 0 | 0 | 0 | 0 | 0 | 1 | 0 |
| 73 | 1 | 1 | 0 | 0 | 1 | 1 | 0 | 0 | 0 | 1 |
| 74 | 1 | 1 | 0 | 1 | 1 | 1 | 1 | 0 | 0 | 1 |
| 75 | 1 | 1 | 0 | 0 | 1 | 1 | 1 | 0 | 0 | 1 |
| 76 | 0 | 0 | 1 | 1 | 0 | 0 | 0 | 1 | 0 | 1 |
| 77 | 0 | 0 | 1 | 1 | 0 | 0 | 0 | 1 | 0 | 1 |
| 78 | 0 | 0 | 1 | 1 | 0 | 0 | 0 | 1 | 0 | 1 |
| 79 | 0 | 0 | 0 | 0 | 0 | 0 | 0 | 0 | 0 | 0 |
| 80 | 0 | 0 | 0 | 0 | 0 | 0 | 0 | 0 | 0 | 0 |
| 81 | 0 | 0 | 0 | 0 | 0 | 0 | 0 | 0 | 0 | 0 |
| 82 | 0 | 0 | 0 | 0 | 0 | 0 | 0 | 0 | 0 | 0 |
| 83 | 0 | 0 | 0 | 0 | 0 | 0 | 0 | 0 | 0 | 0 |
| 84 | 0 | 0 | 0 | 0 | 0 | 0 | 0 | 0 | 0 | 0 |
| 85 | 0 | 0 | 0 | 0 | 0 | 0 | 0 | 0 | 0 | 0 |
| 86 | 0 | 0 | 0 | 0 | 0 | 0 | 0 | 0 | 0 | 0 |
| 87 | 1 | 0 | 0 | 0 | 0 | 1 | 0 | 0 | 1 | 0 |
| 88 | 1 | 0 | 0 | 0 | 0 | 1 | 0 | 0 | 1 | 0 |
| 89 | 1 | 0 | 0 | 0 | 0 | 1 | 1 | 0 | 1 | 0 |
| 90 | 0 | 0 | 0 | 0 | 0 | 1 | 0 | 0 | 0 | 0 |
| 91 | 0 | 0 | 0 | 0 | 0 | 1 | 1 | 0 | 0 | 0 |
| 92 | 0 | 0 | 0 | 0 | 0 | 1 | 1 | 0 | 0 | 0 |
| 93 | 0 | 0 | 0 | 0 | 0 | 0 | 0 | 0 | 0 | 0 |
| 94 | 0 | 0 | 0 | 0 | 0 | 0 | 0 | 1 | 0 | 0 |
| 95 | 0 | 0 | 0 | 0 | 0 | 0 | 0 | 0 | 0 | 0 |
| 96 | 0 | 0 | 0 | 0 | 0 | 0 | 0 | 0 | 0 | 0 |
| 97 | 0 | 0 | 0 | 0 | 0 | 0 | 0 | 0 | 0 | 0 |
| 98 | 0 | 0 | 0 | 0 | 0 | 0 | 0 | 0 | 0 | 0 |
| 99 | 0 | 0 | 0 | 0 | 0 | 0 | 0 | 0 | 0 | 0 |
| 100 | 0 | 0 | 0 | 0 | 0 | 0 | 0 | 0 | 1 | 0 |
| 101 | 0 | 0 | 0 | 0 | 0 | 0 | 0 | 0 | 0 | 0 |
| 102 | 0 | 1 | 0 | 0 | 1 | 0 | 1 | 0 | 0 | 0 |
| 103 | 0 | 1 | 0 | 0 | 1 | 1 | 1 | 1 | 0 | 1 |
| 104 | 0 | 1 | 0 | 0 | 1 | 1 | 1 | 0 | 0 | 0 |
| 105 | 0 | 0 | 0 | 0 | 0 | 0 | 0 | 0 | 0 | 0 |
| 106 | 0 | 0 | 0 | 0 | 0 | 0 | 0 | 0 | 0 | 0 |
| 107 | 0 | 0 | 0 | 0 | 0 | 0 | 0 | 0 | 0 | 0 |
| 108 | 0 | 0 | 0 | 0 | 0 | 0 | 0 | 0 | 0 | 0 |
| 109 | 0 | 0 | 0 | 0 | 0 | 0 | 0 | 0 | 0 | 0 |
| 110 | 0 | 0 | 0 | 0 | 0 | 0 | 0 | 0 | 0 | 0 |
| 111 | 0 | 0 | 0 | 0 | 0 | 0 | 0 | 0 | 0 | 0 |
| 112 | 0 | 0 | 0 | 0 | 0 | 0 | 0 | 0 | 0 | 0 |
| 113 | 0 | 0 | 0 | 0 | 0 | 0 | 0 | 0 | 0 | 0 |
| 114 | 0 | 0 | 1 | 1 | 0 | 0 | 0 | 1 | 1 | 1 |
| 115 | 0 | 1 | 1 | 1 | 0 | 0 | 0 | 1 | 1 | 1 |
| 116 | 0 | 0 | 1 | 1 | 0 | 0 | 0 | 1 | 1 | 1 |
| 117 | 0 | 0 | 0 | 0 | 0 | 0 | 0 | 0 | 0 | 1 |
| 118 | 0 | 0 | 0 | 0 | 0 | 0 | 0 | 0 | 0 | 1 |
| 119 | 0 | 0 | 0 | 1 | 0 | 0 | 0 | 0 | 0 | 1 |
| 120 | 0 | 0 | 0 | 0 | 0 | 0 | 0 | 0 | 0 | 0 |
| 121 | 0 | 0 | 0 | 0 | 0 | 0 | 0 | 0 | 0 | 0 |
| 122 | 0 | 0 | 0 | 0 | 0 | 0 | 0 | 0 | 0 | 0 |
| 123 | 0 | 0 | 0 | 0 | 0 | 0 | 0 | 0 | 0 | 0 |
| 124 | 0 | 0 | 0 | 0 | 0 | 0 | 0 | 0 | 0 | 0 |
| 125 | 0 | 0 | 0 | 0 | 0 | 0 | 0 | 0 | 0 | 0 |
| 126 | 0 | 0 | 0 | 0 | 0 | 0 | 0 | 0 | 0 | 0 |
| 127 | 0 | 0 | 0 | 0 | 0 | 0 | 0 | 0 | 0 | 0 |
| 128 | 0 | 0 | 0 | 0 | 0 | 0 | 0 | 0 | 0 | 0 |
| 129 | 1 | 1 | 0 | 1 | 1 | 1 | 1 | 1 | 1 | 1 |
| 130 | 1 | 1 | 0 | 1 | 1 | 1 | 1 | 1 | 1 | 1 |
| 131 | 1 | 1 | 0 | 1 | 1 | 1 | 1 | 1 | 1 | 1 |
| 132 | 0 | 0 | 0 | 0 | 0 | 0 | 0 | 0 | 0 | 0 |
| 133 | 0 | 0 | 0 | 0 | 0 | 0 | 0 | 0 | 0 | 0 |

TABLE 39-continued

| Transition number | Sam109 | Sam110 | Sam111 | Sam112 | Sam113 | Sam114 | Sam115 | Sam116 | Sam117 | Sam118 |
|---|---|---|---|---|---|---|---|---|---|---|
| 134 | 0 | 0 | 0 | 0 | 0 | 0 | 0 | 0 | 0 | 0 |
| 135 | 1 | 1 | 0 | 0 | 1 | 0 | 1 | 0 | 0 | 0 |
| 136 | 1 | 1 | 1 | 0 | 1 | 0 | 1 | 0 | 0 | 0 |
| 137 | 0 | 1 | 0 | 0 | 1 | 0 | 1 | 0 | 0 | 0 |
| 138 | 0 | 0 | 0 | 1 | 0 | 0 | 0 | 0 | 0 | 1 |
| 139 | 1 | 0 | 0 | 1 | 0 | 0 | 0 | 0 | 0 | 1 |
| 140 | 1 | 0 | 0 | 0 | 0 | 0 | 0 | 0 | 0 | 1 |
| 141 | 1 | 1 | 0 | 1 | 1 | 1 | 1 | 1 | 1 | 1 |
| 142 | 1 | 1 | 0 | 1 | 1 | 1 | 1 | 1 | 1 | 1 |
| 143 | 1 | 1 | 0 | 1 | 1 | 1 | 1 | 1 | 1 | 1 |
| 144 | 0 | 0 | 1 | 0 | 0 | 0 | 0 | 0 | 0 | 0 |
| 145 | 0 | 0 | 1 | 0 | 0 | 0 | 0 | 0 | 0 | 0 |
| 146 | 0 | 0 | 1 | 0 | 0 | 0 | 0 | 0 | 0 | 0 |
| 147 | 0 | 0 | 0 | 0 | 0 | 0 | 0 | 0 | 0 | 0 |
| 148 | 0 | 0 | 0 | 0 | 0 | 0 | 0 | 0 | 0 | 0 |
| 149 | 0 | 0 | 0 | 0 | 0 | 0 | 0 | 0 | 0 | 0 |

Samples Sam109 to Sam118 comprise at least one peptide which is characteristic of the CTX-M proteins. The bacteria present in samples Sam109 to Sam118 therefore express a beta-lactamase which confers on them a resistance to penicillins, to cephalosporins and to monobactams.

EXAMPLE 28

Identification of a Resistance to DHA Beta-Lactams

Samples Sam119 to Sam124 are identified according to one of the methods described in examples 1, 3 or 4. The identification of the species is set out in TABLE 40.

TABLE 40

| Names | Species |
|---|---|
| Sam119 | E. coli |
| Sam120 | K. oxytoca |
| Sam121 | K. pneumoniae |
| Sam122 | K. pneumoniae |
| Sam123 | K. pneumoniae |
| Sam124 | K. pneumoniae |

Samples Sam119 to Sam124 correspond to a species able to comprise a DHA resistance mechanism. Each sample is treated according to example 5, then analysed according to example 6 by detecting the peptides from TABLE 41 instead of the peptides from TABLE 3.

TABLE 41

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 1 | AAQAILSALEMK | 2 | y8 monocharged | 21.45 | 623.35 | 904.52 | 31.3 | 2500 |
| 2 | AAQAILSALEMK | 2 | y7 monocharged | 21.45 | 623.35 | 791.43 | 31.3 | 2500 |
| 3 | AAQAILSALEMK | 2 | y6 monocharged | 21.45 | 623.35 | 678.35 | 31.3 | 2500 |
| 4 | ADLLNFYQQWQPSR | 2 | y3 monocharged | 22.92 | 883.44 | 359.2 | 46.1 | 2500 |
| 5 | ADLLNFYQQWQPSR | 3 | y5 monocharged | 22.92 | 589.29 | 673.34 | 25.4 | 2500 |
| 6 | ADLLNFYQQWQPSR | 3 | y3 monocharged | 22.92 | 589.29 | 359.2 | 25.4 | 2500 |
| 7 | AGNADLEMAMYLAQTR | 3 | y6 monocharged | 21.53 | 585.61 | 751.41 | 25.2 | 2500 |
| 8 | AGNADLEMAMYLAQTR | 3 | y5 monocharged | 21.53 | 585.61 | 588.35 | 25.2 | 2500 |
| 9 | AGNADLEMAMYLAQTR | 3 | y4 monocharged | 21.53 | 585.61 | 475.26 | 25.2 | 2500 |
| 10 | EMALNDPAAK | 2 | y8 monocharged | 13.12 | 530.26 | 799.43 | 26 | 2500 |
| 11 | EMALNDPAAK | 2 | y6 monocharged | 13.12 | 530.26 | 615.31 | 26 | 2500 |
| 12 | EMALNDPAAK | 2 | y4 monocharged | 13.12 | 530.26 | 386.24 | 26 | 2500 |
| 13 | GKPYYFNYGFADIQAK | 3 | y8 monocharged | 19.85 | 627.98 | 849.45 | 26.5 | 2500 |
| 14 | GKPYYFNYGFADIQAK | 3 | y6 monocharged | 19.85 | 627.98 | 645.36 | 26.5 | 2500 |
| 15 | GKPYYFNYGFADIQAK | 3 | y5 monocharged | 19.85 | 627.98 | 574.32 | 26.5 | 2500 |
| 16 | NYPNTER | 2 | y5 monocharged | 7.63 | 447.21 | 616.31 | 21.2 | 2500 |

TABLE 41-continued

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 17 | NYPNTER | 2 | y3 monocharged | 7.63 | 447.21 | 405.21 | 21.2 | 2500 |
| 18 | NYPNTER | 2 | y5 dicharged | 7.63 | 447.21 | 308.66 | 21.2 | 2500 |
| 19 | QPVTENTLFELGSVSK | 2 | y8 monocharged | 20.9 | 874.96 | 866.46 | 45.6 | 2500 |
| 20 | QPVTENTLFELGSVSK | 3 | y8 monocharged | 20.9 | 583.64 | 866.46 | 25.2 | 2500 |
| 21 | QPVTENTLFELGSVSK | 3 | y5 monocharged | 20.9 | 583.64 | 477.27 | 25.2 | 2500 |
| 22 | QVAIVILANK | 2 | y8 monocharged | 18.75 | 534.84 | 841.55 | 26.2 | 2500 |
| 23 | QVAIVILANK | 2 | y6 monocharged | 18.75 | 534.84 | 657.43 | 26.2 | 2500 |
| 24 | QVAIVILANK | 2 | y5 monocharged | 18.75 | 534.84 | 558.36 | 26.2 | 2500 |
| 25 | TFTGVLGAVSVAK | 2 | y11 monocharged | 20.03 | 625.36 | 1001.6 | 31.4 | 2500 |
| 26 | TFTGVLGAVSVAK | 2 | y8 monocharged | 20.03 | 625.36 | 744.46 | 31.4 | 2500 |
| 27 | TFTGVLGAVSVAK | 2 | y7 monocharged | 20.03 | 625.36 | 631.38 | 31.4 | 2500 |
| 28 | TGATTGFGAYVAFIPEK | 2 | y3 monocharged | 22.12 | 865.44 | 373.21 | 45.1 | 2500 |
| 29 | TGATTGFGAYVAFIPEK | 3 | y6 monocharged | 22.12 | 577.3 | 704.4 | 25 | 2500 |
| 30 | TGATTGFGAYVAFIPEK | 3 | y3 monocharged | 22.12 | 577.3 | 373.21 | 25 | 2500 |
| 31 | VSPGQLDAESYGVK | 2 | y8 monocharged | 15.43 | 725.37 | 868.41 | 37.1 | 2500 |
| 32 | VSPGQLDAESYGVK | 2 | y13 dicharged | 15.43 | 725.37 | 675.83 | 37.1 | 2500 |
| 33 | VSPGQLDAESYGVK | 2 | y12 dicharged | 15.43 | 725.37 | 632.31 | 37.1 | 2500 |
| 34 | WAEMNMEPSR | 2 | y8 monocharged | 15.78 | 625.77 | 993.41 | 31.4 | 2500 |
| 35 | WAEMNMEPSR | 2 | y6 monocharged | 15.78 | 625.77 | 733.33 | 31.4 | 2500 |
| 36 | WAEMNMEPSR | 2 | y3 monocharged | 15.78 | 625.77 | 359.2 | 31.4 | 2500 |
| 37 | YQPELALPQWK | 2 | y4 monocharged | 20.97 | 686.87 | 558.3 | 34.9 | 2500 |
| 38 | YQPELALPQWK | 2 | y9 dicharged | 20.97 | 686.87 | 541.31 | 34.9 | 2500 |
| 39 | YQPELALPQWK | 3 | y4 monocharged | 20.97 | 458.25 | 558.3 | 21.3 | 2500 |

The other machine parameters used are as follows:
Scan type: MRM
MRM planned: no
Polarity: Positive
Ionising source: Turbo V™ (Applied BioSystems)
Q1 setting: Filtering with unit resolution
Q3 setting: Filtering with unit resolution
Inter-scan pause: 5.00 msec
Scanning speed: 10 Da/s
Curtain gas: 50.00 psi
Cone voltage: 5500.00 V
Source temperature: 500.00° C.
Nebulising gas: 50.00 psi
Heating gas: 50.00 psi
Collision gas which induces dissociation: 9.00 psi
Dynamic filling: activated
Declustering potential (DP): 100.00 V
Entry potential before Q0 (EP): 6.00 V
Collision cell exit potential (CXP): 15 V
Total cycle time: 1.17 sec
The areas obtained for each of the transitions and for each of the microorganisms studied were measured. When the areas of the transitions are greater than or equal to the positivity threshold described in TABLE 41, the detection of the transition is considered to be positive and is labelled "1" in TABLE 42. When a transition has an area less than the positivity threshold described in TABLE 41, the transition is considered non-detected and is labelled "0" in TABLE 42.

For a given peptide, when at least 3 transitions are labelled "1", the peptide is considered as being detected.

TABLE 42

| Transition number | Sam119 | Sam120 | Sam121 | Sam122 | Sam123 | Sam124 |
|---|---|---|---|---|---|---|
| 1 | 1 | 0 | 1 | 1 | 0 | 0 |
| 2 | 0 | 0 | 0 | 0 | 0 | 0 |
| 3 | 0 | 0 | 0 | 0 | 0 | 0 |
| 4 | 0 | 0 | 1 | 0 | 1 | 0 |
| 5 | 0 | 1 | 1 | 0 | 0 | 0 |
| 6 | 0 | 1 | 1 | 0 | 0 | 0 |
| 7 | 0 | 0 | 0 | 1 | 0 | 0 |
| 8 | 0 | 0 | 0 | 1 | 0 | 0 |
| 9 | 0 | 0 | 0 | 1 | 0 | 0 |
| 10 | 1 | 1 | 1 | 1 | 1 | 1 |
| 11 | 1 | 1 | 1 | 1 | 1 | 1 |

TABLE 42-continued

| Transition number | Sam119 | Sam120 | Sam121 | Sam122 | Sam123 | Sam124 |
|---|---|---|---|---|---|---|
| 12 | 1 | 1 | 1 | 0 | 1 | 1 |
| 13 | 1 | 1 | 1 | 0 | 1 | 0 |
| 14 | 1 | 1 | 1 | 0 | 1 | 0 |
| 15 | 1 | 0 | 1 | 0 | 0 | 0 |
| 16 | 0 | 0 | 1 | 1 | 0 | 1 |
| 17 | 0 | 0 | 1 | 1 | 0 | 1 |
| 18 | 0 | 0 | 1 | 1 | 1 | 1 |
| 19 | 1 | 1 | 1 | 1 | 1 | 1 |
| 20 | 1 | 0 | 1 | 1 | 1 | 1 |
| 21 | 1 | 1 | 1 | 1 | 1 | 1 |
| 22 | 0 | 1 | 1 | 1 | 1 | 1 |
| 23 | 0 | 0 | 1 | 1 | 1 | 1 |
| 24 | 1 | 1 | 1 | 1 | 1 | 1 |
| 25 | 1 | 1 | 1 | 1 | 1 | 1 |
| 26 | 1 | 1 | 1 | 1 | 1 | 1 |
| 27 | 1 | 1 | 1 | 1 | 1 | 1 |
| 28 | 0 | 0 | 1 | 1 | 0 | 0 |
| 29 | 0 | 0 | 1 | 1 | 1 | 0 |
| 30 | 0 | 0 | 1 | 1 | 0 | 0 |
| 31 | 1 | 1 | 1 | 1 | 1 | 1 |
| 32 | 0 | 1 | 1 | 1 | 1 | 1 |
| 33 | 0 | 1 | 1 | 1 | 1 | 1 |
| 34 | 1 | 1 | 1 | 1 | 1 | 1 |
| 35 | 0 | 1 | 1 | 1 | 1 | 1 |
| 36 | 1 | 0 | 1 | 1 | 1 | 1 |
| 37 | 1 | 0 | 1 | 1 | 0 | 1 |
| 38 | 1 | 1 | 1 | 1 | 1 | 1 |
| 39 | 1 | 1 | 1 | 1 | 1 | 1 |

Samples 119 to Sam124 comprise at least one peptide which is characteristic of the DHA proteins. The bacteria present in samples Sam119 to Sam124 therefore express a beta-lactamase which confers on them a resistance to penicillins and to cephalosporins, with the exception of fourth-generation cephalosporins.

EXAMPLE 29

Identification of a Resistance to FOX Beta-Lactams

Samples Sam125 to Sam130 are identified according to one of the methods described in examples 1, 3 or 4. The identification of the species is set out in TABLE 43.

TABLE 43

| Names | Species |
|---|---|
| Sam125 | E. coli |
| Sam126 | E. coli |
| Sam127 | K. oxytoca |
| Sam128 | K. oxytoca |
| Sam129 | K. pneumoniae |
| Sam13 | K. pneumoniae |

Samples Sam125 to Sam130 correspond to a species able to comprise a FOX resistance mechanism. Each sample is treated according to example 5, then analysed according to example 6 by detecting the peptides from TABLE 44 instead of the peptides from TABLE 3.

TABLE 44

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 1 | AHYFNYGVANR | 3 | y3 monocharged | 14.08 | 437.88 | 360.2 | 20.7 | 2500 |
| 2 | AHYFNYGVANR | 3 | y4 monocharged | 14.08 | 437.88 | 459.27 | 20.7 | 2500 |
| 3 | AHYFNYGVANR | 3 | y5 monocharged | 14.08 | 437.88 | 516.29 | 20.7 | 2500 |
| 4 | AMGEQR | 2 | y5 dicharged | 1.08 | 346.16 | 310.65 | 15.5 | 2500 |
| 5 | AMGEQR | 2 | y4 monocharged | 1.08 | 346.16 | 489.24 | 15.5 | 2500 |
| 6 | AMGEQR | 2 | y5 monocharged | 1.08 | 346.16 | 620.28 | 15.5 | 2500 |
| 7 | ESGQR | 2 | y3 dicharged | 0.8 | 288.64 | 180.6 | 12.2 | 2500 |
| 8 | ESGQR | 2 | y3 monocharged | 0.76 | 288.64 | 360.2 | 12.2 | 2500 |
| 9 | ESGQR | 2 | y4 monocharged | 0.82 | 288.64 | 447.23 | 12.2 | 2500 |
| 10 | FAVPK | 3 | y4 monocharged | 12.95 | 187.79 | 414.27 | 12.9 | 2500 |
| 11 | FAVPK | 2 | y3 monocharged | 12.95 | 281.17 | 343.23 | 11.8 | 2500 |
| 12 | FAVPK | 2 | y4 monocharged | 12.93 | 281.17 | 414.27 | 11.8 | 2500 |
| 13 | GGFELDDK | 2 | y6 dicharged | 14.31 | 440.71 | 383.69 | 20.9 | 2500 |
| 14 | GGFELDDK | 2 | y4 monocharged | 14.34 | 440.71 | 490.25 | 20.9 | 2500 |
| 15 | GGFELDDK | 2 | y5 monocharged | 14.31 | 440.71 | 619.29 | 20.9 | 2500 |
| 16 | GIAIVMLANR | 2 | y4 monocharged | 20.15 | 529.31 | 473.28 | 25.9 | 2500 |
| 17 | GIAIVMLANR | 2 | y5 monocharged | 20.13 | 529.31 | 604.32 | 25.9 | 2500 |
| 18 | GIAIVMLANR | 2 | y6 monocharged | 20.13 | 529.31 | 703.39 | 25.9 | 2500 |
| 19 | IPGMAVAVLK | 2 | y9 dicharged | 19.17 | 499.81 | 443.27 | 24.2 | 2500 |
| 20 | IPGMAVAVLK | 2 | y8 monocharged | 19.17 | 499.81 | 788.47 | 24.2 | 2500 |

TABLE 44-continued

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 21 | IPGMAVAVLK | 2 | y9 monocharged | 19.15 | 499.81 | 885.52 | 24.2 | 2500 |
| 22 | NYPIEAR | 2 | y3 monocharged | 12.04 | 431.73 | 375.2 | 20.3 | 2500 |
| 23 | NYPIEAR | 2 | y4 monocharged | 12.04 | 431.73 | 488.28 | 20.3 | 2500 |
| 24 | NYPIEAR | 2 | y5 monocharged | 12.06 | 431.73 | 585.34 | 20.3 | 2500 |
| 25 | SWSPVYPAGTHR | 3 | y9 dicharged | 14.97 | 453.23 | 499.26 | 21.1 | 2500 |
| 26 | SWSPVYPAGTHR | 3 | y10 dicharged | 14.97 | 453.23 | 542.78 | 21.1 | 2500 |
| 27 | SWSPVYPAGTHR | 3 | y6 monocharged | 14.97 | 453.23 | 638.34 | 21.1 | 2500 |
| 28 | TGSADLLK | 2 | y5 monocharged | 12.97 | 402.73 | 559.35 | 18.7 | 2500 |
| 29 | TGSADLLK | 2 | y6 monocharged | 12.95 | 402.73 | 646.38 | 18.7 | 2500 |
| 30 | TGSADLLK | 2 | y7 monocharged | 12.97 | 402.73 | 703.4 | 18.7 | 2500 |
| 31 | TGSTGGFGAYVAFVPAR | 3 | y5 monocharged | 21.03 | 553.28 | 589.35 | 24.2 | 2500 |
| 32 | TGSTGGFGAYVAFVPAR | 3 | y6 monocharged | 21.03 | 553.28 | 660.38 | 24.2 | 2500 |
| 33 | TGSTGGFGAYVAFVPAR | 2 | y3 monocharged | 21.03 | 829.42 | 343.21 | 43 | 2500 |
| 34 | TGSTGGFGAYVAFVPAR | 2 | y6 monocharged | 21.03 | 829.42 | 660.38 | 43 | 2500 |
| 35 | TLTATLGAYAAVK | 2 | y7 monocharged | 18.68 | 640.37 | 679.38 | 32.2 | 2500 |
| 36 | TLTATLGAYAAVK | 2 | y8 monocharged | 18.68 | 640.37 | 792.46 | 32.2 | 2500 |
| 37 | TLTATLGAYAAVK | 2 | y9 monocharged | 18.66 | 640.37 | 893.51 | 32.2 | 2500 |
| 38 | VSEQTLFEIGSVSK | 2 | y5 monocharged | 20.34 | 762.4 | 477.27 | 39.2 | 2500 |
| 39 | VSEQTLFEIGSVSK | 2 | y7 monocharged | 20.34 | 762.4 | 719.39 | 39.2 | 2500 |
| 40 | VSEQTLFEIGSVSK | 2 | y8 monocharged | 20.34 | 762.4 | 866.46 | 39.2 | 2500 |
| 41 | VSQHAPWLK | 3 | y6 dicharged | 14.1 | 355.87 | 376.22 | 18.1 | 2500 |
| 42 | VSQHAPWLK | 3 | y8 dicharged | 14.1 | 355.87 | 483.76 | 18.1 | 2500 |
| 43 | VSQHAPWLK | 3 | y4 monocharged | 14.1 | 355.87 | 543.33 | 18.1 | 2500 |
| 44 | VTPGVLAAEAYGIK | 2 | y12 dicharged | 19.37 | 694.89 | 594.84 | 35.3 | 2500 |
| 45 | VTPGVLAAEAYGIK | 2 | y7 monocharged | 19.37 | 694.89 | 751.4 | 35.3 | 2500 |
| 46 | VTPGVLAAEAYGIK | 2 | y8 monocharged | 19.37 | 694.89 | 822.44 | 35.3 | 2500 |

The other machine parameters used are as follows:
Scan type: MRM
MRM planned: no
Polarity: Positive
Ionising source: Turbo V™ (Applied BioSystems)
Q1 setting: Filtering with unit resolution
Q3 setting: Filtering with unit resolution
Inter-scan pause: 5.00 msec
Scanning speed: 10 Da/s
Curtain gas: 50.00 psi
Cone voltage: 5500.00 V
Source temperature: 500.00° C.
Nebulising gas: 50.00 psi
Heating gas: 50.00 psi
Collision gas which induces dissociation: 9.00 psi
Dynamic filling: activated
Declustering potential (DP): 100.00 V
Entry potential before Q0 (EP): 6.00 V
Collision cell exit potential (CXP): 15 V
Total cycle time: 1.38 sec The areas obtained for each of the transitions and for each of the microorganisms studied were measured. When the areas of the transitions are greater than or equal to the positivity threshold described in TABLE 44, the detection of the transition is considered to be positive and is labelled "1" in TABLE 45, When a transition has an area less than the positivity threshold described in TABLE 44, the transition is considered non-detected and is labelled "0" in TABLE 45.

For a given peptide, when at least 2 transitions are labelled "1", the peptide is considered as being detected.

TABLE 45

| transition number | Sam125 | Sam126 | Sam127 | Sam128 | Sam129 | Sam130 |
|---|---|---|---|---|---|---|
| 1 | 0 | 0 | 1 | 1 | 0 | 0 |
| 2 | 1 | 0 | 1 | 1 | 0 | 0 |
| 3 | 1 | 1 | 1 | 1 | 0 | 1 |
| 4 | 1 | 1 | 0 | 1 | 1 | 1 |
| 5 | 1 | 1 | 0 | 1 | 1 | 1 |
| 6 | 1 | 1 | 1 | 1 | 1 | 1 |
| 7 | 0 | 0 | 0 | 0 | 0 | 0 |
| 8 | 0 | 0 | 1 | 0 | 0 | 0 |
| 9 | 0 | 0 | 0 | 0 | 0 | 0 |
| 10 | 0 | 0 | 0 | 0 | 0 | 0 |
| 11 | 0 | 0 | 0 | 0 | 0 | 0 |
| 12 | 0 | 0 | 0 | 0 | 0 | 0 |
| 13 | 1 | 1 | 1 | 1 | 1 | 1 |
| 14 | 1 | 0 | 0 | 1 | 0 | 1 |
| 15 | 1 | 0 | 0 | 1 | 0 | 1 |
| 16 | 1 | 0 | 1 | 1 | 1 | 1 |
| 17 | 1 | 1 | 1 | 1 | 1 | 1 |
| 18 | 1 | 1 | 1 | 1 | 1 | 1 |
| 19 | 1 | 1 | 1 | 1 | 1 | 1 |
| 20 | 1 | 1 | 1 | 1 | 1 | 1 |
| 21 | 1 | 1 | 1 | 1 | 1 | 1 |
| 22 | 1 | 1 | 1 | 1 | 1 | 1 |
| 23 | 1 | 1 | 1 | 1 | 1 | 1 |
| 24 | 1 | 1 | 1 | 1 | 1 | 1 |
| 25 | 1 | 1 | 1 | 1 | 1 | 1 |
| 26 | 1 | 1 | 1 | 1 | 1 | 1 |
| 27 | 1 | 1 | 1 | 1 | 1 | 1 |
| 28 | 1 | 1 | 1 | 1 | 1 | 1 |
| 29 | 1 | 1 | 1 | 1 | 1 | 1 |
| 30 | 1 | 1 | 1 | 1 | 1 | 1 |
| 31 | 1 | 0 | 1 | 1 | 1 | 1 |
| 32 | 0 | 1 | 1 | 1 | 1 | 1 |
| 33 | 0 | 1 | 1 | 0 | 1 | 1 |
| 34 | 0 | 1 | 1 | 1 | 1 | 1 |
| 35 | 0 | 0 | 0 | 0 | 0 | 1 |
| 36 | 1 | 1 | 1 | 0 | 1 | 1 |
| 37 | 1 | 0 | 1 | 0 | 1 | 1 |
| 38 | 1 | 1 | 1 | 1 | 1 | 1 |
| 39 | 1 | 1 | 1 | 1 | 1 | 1 |
| 40 | 1 | 1 | 1 | 1 | 1 | 1 |
| 41 | 1 | 1 | 1 | 1 | 1 | 1 |
| 42 | 1 | 1 | 0 | 0 | 1 | 1 |
| 43 | 1 | 1 | 1 | 1 | 1 | 1 |
| 44 | 0 | 0 | 0 | 0 | 0 | 0 |
| 45 | 0 | 0 | 0 | 0 | 0 | 0 |
| 46 | 0 | 0 | 0 | 0 | 0 | 0 |

Samples Sam125 to Sam130 comprise at least one peptide which is characteristic of the FOX proteins. The bacteria present in samples Sam125 to Sam130 therefore express a beta-lactamase which confers on them a resistance to penicillins and to cephalosporins, with the exception of fourth-generation cephalosporins.

EXAMPLE 30

Identification of a Resistance to SHV Beta-Lactams

Samples Sam131 to Sam144 are identified according to one of the methods described in examples 1, 3 or 4. The identification of the species is set out in TABLE 46.

TABLE 46

| Names | Species |
|---|---|
| Sam131 | *E. aerogenes* |
| Sam132 | *E. coli* |
| Sam133 | *E. coli* |
| Sam134 | *E. coli* |
| Sam135 | *E. coli* |
| Sam136 | *K. pneumoniae* |
| Sam137 | *K. pneumoniae* |
| Sam138 | *K. pneumoniae* |
| Sam139 | *K. pneumoniae* |
| Sam140 | *K. pneumoniae* |
| Sam141 | *K. pneumoniae* |
| Sam142 | *K. pneumoniae* |
| Sam143 | *K. pneumoniae* |
| Sam144 | *K. pneumoniae* |

Samples Sam131 to Sam144 correspond to a species able to comprise an SHV resistance mechanism. Each sample is treated according to example 5, then analysed according to example 6 by detecting the peptides from TABLE 47 instead of the peptides from TABLE 3.

TABLE 47

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 1 | AGAGER | 2 | y3 monocharged | 0.9 | 280.64 | 361.18 | 11.7 | 2000 |
| 2 | AGAGER | 2 | y4 monocharged | 0.9 | 280.64 | 432.22 | 11.7 | 2000 |
| 3 | AGAGER | 2 | y5 monocharged | 0.9 | 250.64 | 489.24 | 11.7 | 2000 |
| 4 | ATTTPASMAATLR | 3 | y5 monocharged | 16.2 | 431.23 | 531.33 | 20.5 | 2000 |
| 5 | ATTTPASMAATLR | 2 | y9 dicharged | 16.2 | 646.34 | 459.25 | 32.6 | 2000 |
| 6 | ATTTPASMAATLR | 2 | y9 monocharged | 16.2 | 646.34 | 917.49 | 32.6 | 2000 |
| 7 | CIISLLATLPLAVHASPQPLEQIK | 3 | y18 dicharged | 27.4 | 871.5 | 957.05 | 34.1 | 2000 |
| 8 | CIISLLATLPLAVHASPQPLEQIK | 3 | y21 dicharged | 27.4 | 871.5 | 1113.65 | 34.1 | 2000 |
| 9 | CIISLLATLPLAVHASPQPLEQIK | 3 | y22 dicharged | 27.3 | 571.5 | 1170.19 | 34.1 | 2000 |
| 10 | DMPASMAER | 2 | y7 dicharged | 12.4 | 504.22 | 381.18 | 24.5 | 2000 |
| 11 | DMPASMAER | 2 | y5 monocharged | 12.4 | 504.22 | 593.27 | 24.5 | 2000 |

TABLE 47-continued

| Tran-sition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 12 | DMPASMAER | 2 | y7 monocharged | 12.4 | 504.22 | 761.36 | 24.5 | 2000 |
| 13 | DSPASMAER | 2 | y7 dicharged | 10.5 | 482.21 | 381.18 | 23.2 | 2000 |
| 14 | DSPASMAER | 2 | y5 monocharged | 10.5 | 482.21 | 593.27 | 23.2 | 2000 |
| 15 | DSPASMAER | 2 | y6 monocharged | 10.5 | 482.21 | 664.31 | 23.2 | 2000 |
| 16 | DTLASMAER | 2 | y5 monocharged | 14 | 497.24 | 593.27 | 24.1 | 2000 |
| 17 | DTLASMAER | 2 | y6 monocharged | 14 | 497.24 | 664.31 | 24.1 | 2000 |
| 18 | DTLASMAER | 2 | y7 monocharged | 14 | 497.24 | 777.39 | 24.1 | 2000 |
| 19 | DTPASMAER | 2 | y7 dicharged | 10.5 | 489.22 | 381.18 | 23.6 | 2000 |
| 20 | DTPASMAER | 2 | y5 monocharged | 10.5 | 489.22 | 593.27 | 23.6 | 2000 |
| 21 | DTPASMAER | 2 | y7 monocharged | 10.5 | 489.22 | 761.36 | 23.6 | 2000 |
| 22 | DTPASMAK | 2 | y6 dicharged | 9.1 | 410.7 | 302.66 | 19.1 | 2000 |
| 23 | DTPASMAK | 2 | y5 monocharged | 9.1 | 410.7 | 507.26 | 19.1 | 2000 |
| 24 | DTPASMAK | 2 | y6 monocharged | 9.1 | 410.7 | 604.31 | 19.1 | 2000 |
| 25 | DTTTPASMAATLR | 3 | y5 monocharged | 16.5 | 445.89 | 531.33 | 20.9 | 2000 |
| 26 | DTTTPASMAATLR | 2 | y9 dicharged | 16.5 | 668.33 | 459.25 | 33.8 | 2000 |
| 27 | DTTTPASMAATLR | 2 | y9 monocharged | 16.5 | 668.33 | 917.49 | 33.8 | 2000 |
| 28 | DTTTPASMAGTLR | 3 | y4 monocharged | 15.3 | 441.22 | 446.27 | 20.8 | 2000 |
| 29 | DTTTPASMAGTLR | 2 | y9 dicharged | 15.3 | 661.32 | 452.24 | 33.4 | 2000 |
| 30 | DTTTPASMAGTLR | 2 | y9 monocharged | 15.3 | 661.32 | 903.47 | 33.4 | 2000 |
| 31 | DTTTPASMTATLR | 2 | y9 dicharged | 15.9 | 683.34 | 474.25 | 34.7 | 2000 |
| 32 | DTTTPASMTATLR | 2 | y7 monocharged | 15.9 | 683.34 | 779.41 | 34.7 | 2000 |
| 33 | DTTTPASMTATLR | 2 | y9 monocharged | 15.9 | 683.34 | 947.5 | 34.7 | 2000 |
| 34 | FPMISTFK | 2 | y7 dicharged | 20.2 | 485.76 | 412.22 | 23.4 | 2000 |
| 35 | FPMISTFK | 2 | y6 monocharged | 20.2 | 485.76 | 595.35 | 23.4 | 2000 |
| 36 | FPMISTFK | 2 | y6 monocharged | 20.2 | 485.76 | 726.39 | 23.4 | 2000 |
| 37 | FPMMSTFK | 2 | y7 dicharged | 19.3 | 494.74 | 421.2 | 23.9 | 2000 |
| 38 | FPMMSTFK | 2 | y5 monocharged | 19.3 | 494.74 | 613.3 | 23.9 | 2000 |
| 39 | FPMMSTFK | 2 | y6 monocharged | 19.3 | 494.74 | 744.34 | 23.9 | 2000 |
| 40 | GIVALLGGNIK | 2 | y5 monocharged | 21.1 | 527.84 | 488.28 | 25.5 | 2000 |
| 41 | GIVALLGGNIK | 2 | y6 monocharged | 21.1 | 527.84 | 601.37 | 25.8 | 2000 |
| 42 | GIVALLGGNIK | 2 | y8 monocharged | 21.1 | 527.84 | 785.49 | 25.8 | 2000 |
| 43 | GIVALLGPDNK | 2 | y5 monocharged | 18.9 | 548.82 | 530.26 | 27 | 2000 |
| 44 | GIVALLGPDNK | 2 | y6 monocharged | 19 | 548.82 | 643.34 | 27 | 2000 |
| 45 | GIVALLGPDNK | 2 | y8 monocharged | 18.9 | 548.82 | 827.46 | 27 | 2000 |
| 46 | GIVALLGPNHK | 3 | y9 dicharged | 17.6 | 373.56 | 474.79 | 18.7 | 2000 |
| 47 | GIVALLGPNHK | 3 | y5 monocharged | 17.6 | 373.56 | 552.29 | 18.7 | 2000 |
| 48 | GIVALLGPNHK | 3 | y6 monocharged | 17.6 | 373.56 | 665.37 | 18.7 | 2000 |
| 49 | GIVALLGPNNK | 2 | y5 monocharged | 18.6 | 548.33 | 529.27 | 27 | 2000 |

TABLE 47-continued

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 50 | GIVALLGPNNK | 2 | y6 monocharged | 16.6 | 548.33 | 642.36 | 27 | 2000 |
| 51 | GIVALLGPNNK | 2 | y7 monocharged | 18.6 | 548.33 | 755.44 | 27 | 2000 |
| 52 | GIVALLGPNNNAER | 3 | y8 dicharged | 18.8 | 479.93 | 436.2 | 22 | 2000 |
| 53 | GIVALLGPNNNAER | 2 | y7 monocharged | 18.8 | 719.39 | 814.38 | 36.7 | 2000 |
| 54 | GIVALLGPNNNAER | 2 | y8 monocharged | 18.7 | 719.39 | 871.4 | 36.7 | 2000 |
| 55 | GIVALR | 2 | y4 dicharged | 14.1 | 314.71 | 229.66 | 13.7 | 2000 |
| 56 | GIVALR | 2 | y3 monocharged | 14.1 | 314.71 | 359.24 | 13.7 | 2000 |
| 57 | GIVALR | 2 | y4 monocharged | 14.1 | 314.71 | 458.31 | 13.7 | 2000 |
| 58 | GPNNK | 2 | y4 dicharged | 0.8 | 265.14 | 236.63 | 10.8 | 2000 |
| 59 | GPNNK | 2 | y3 monocharged | 0.8 | 265.14 | 375.2 | 10.8 | 2000 |
| 60 | GPNNK | 2 | y4 monocharged | 0.8 | 265.14 | 472.25 | 10.8 | 2000 |
| 61 | GTTTPASMAATLR | 2 | y9 dicharged | 16 | 639.33 | 459.25 | 32.2 | 2000 |
| 62 | GTTTPASMAATLR | 2 | y7 monocharged | 16 | 639.33 | 749.4 | 32.2 | 2000 |
| 63 | GTTTPASMAATLR | 2 | y9 monocharged | 16 | 639.33 | 917.49 | 32.2 | 2000 |
| 64 | HLADGMTVGELCAAAITMSDNSAAK | 3 | y6 monocharged | 21.3 | 845.39 | 605.29 | 33.3 | 2000 |
| 65 | HLADGMTVGELCAAAITMSDNSAAK | 3 | y7 monocharged | 21.3 | 845.39 | 692.32 | 33.3 | 2000 |
| 66 | HLADGMTVGELCAAAITMSDNSAAK | 3 | y9 monocharged | 21.3 | 845.39 | 924.41 | 33.3 | 2000 |
| 67 | HLLQWMVDDR | 3 | y3 monocharged | 19.6 | 438.22 | 405.17 | 20.7 | 2000 |
| 68 | HLLQWMVDDR | 3 | y4 monocharged | 19.6 | 438.22 | 504.24 | 20.7 | 2000 |
| 69 | HLLQWMVDDR | 3 | y5 monocharged | 19.6 | 438.22 | 635.28 | 20.7 | 2000 |
| 70 | IHYLQQDLVDYSPVSEK | 3 | y6 monocharged | 19 | 678.68 | 646.34 | 28.1 | 2000 |
| 71 | IHYLQQDLVDYSPVSEK | 3 | y7 monocharged | 19 | 678.68 | 809.4 | 28.1 | 2000 |
| 72 | IHYLQQDLVDYSPVSEK | 3 | y8 monocharged | 18.9 | 678.68 | 924.43 | 28.1 | 2000 |
| 73 | IVVIYLR | 2 | y3 monocharged | 19.3 | 438.29 | 451.27 | 20.7 | 2000 |
| 74 | IVVIYLR | 2 | y4 monocharged | 19.3 | 438.29 | 564.35 | 20.7 | 2000 |
| 75 | IVVIYLR | 2 | y5 monocharged | 19.3 | 438.29 | 663.42 | 20.7 | 2000 |
| 76 | LCIISLLAALPLAVHASPQPLEQIK | 3 | y17 dicharged | 30.7 | 899.19 | 906.52 | 35 | 2000 |
| 77 | LCIISLLAALPLAVHASPQPLEQIK | 3 | y18 dicharged | 30.7 | 899.19 | 942.04 | 35 | 2000 |
| 78 | LCIISLLAALPLAVHASPQPLEQIK | 3 | y22 dicharged | 30.7 | 899.19 | 1155.18 | 35 | 2000 |
| 79 | LCIISLLATLPLAVHASPQPLDQIK | 3 | y19 dicharged | 30.2 | 904.52 | 1006.58 | 35.1 | 2000 |
| 80 | LCIISLLATLPLAVHASPQPLDQIK | 3 | y22 dicharged | 30.2 | 904.52 | 1183.18 | 35.1 | 2000 |
| 81 | LCIISLLATLPLAVHASPQPLDQIK | 3 | y23 dicharged | 30.3 | 904.52 | 1219.72 | 35.1 | 2000 |
| 82 | LCIISLLATLPLAVHASPQPLEQIK | 3 | y15 dicharged | 30.2 | 909.19 | 814.46 | 35.3 | 2000 |
| 83 | LCIISLLATLPLAVHASPQPLEQIK | 3 | y17 dicharged | 30.2 | 909.19 | 921.53 | 35.3 | 2000 |
| 84 | LCIISLLATLPLAVHASPQPLEQIK | 3 | y19 dicharged | 30.2 | 909.19 | 1013.59 | 35.3 | 2000 |
| 85 | LCIISLLATLPLAVHSSPQPLEQIK | 3 | y15 dicharged | 29.3 | 914.53 | 822.46 | 35.4 | 2000 |
| 86 | LCIISLLATLPLAVHSSPQPLEQIK | 3 | y18 dicharged | 29.3 | 914.53 | 965.04 | 35.4 | 2000 |

TABLE 47-continued

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 87 | LCIISLLATLPLAVHSSPQPLEQIK | 3 | y21 dicharged | 29.3 | 914.53 | 1121.64 | 35.4 | 2000 |
| 88 | LCIISLLATLPLAVHTSPQPLEQIK | 3 | y15 dicharged | 29.4 | 919.2 | 829.47 | 35.6 | 2000 |
| 89 | LCIISLLATLPLAVHTSPQPLEQIK | 3 | y21 dicharged | 29.5 | 919.2 | 1128.65 | 35.6 | 2000 |
| 90 | LCIISLLATLPLAVHTSPQPLEQIK | 3 | y23 dicharged | 29.4 | 919.2 | 1241.74 | 35.6 | 2000 |
| 91 | LCIISLLATLPLTVHASPQPLEQIK | 3 | y16 dicharged | 29.8 | 919.2 | 829.47 | 35.6 | 2000 |
| 92 | LCIISLLATLPLTVHASPQPLEQIK | 3 | y17 dicharged | 29.8 | 919.2 | 936.53 | 35.6 | 2000 |
| 93 | LCIISLLATLPLTVHASPQPLEQIK | 3 | y22 dicharged | 29.8 | 919.2 | 1185.19 | 35.6 | 2000 |
| 94 | LCIISLLATLPLVVHASPQPLEQIK | 3 | y19 dicharged | 31.3 | 918.54 | 1027.6 | 35.6 | 2000 |
| 95 | LCIISLLATLPLVVHASPQPLEQIK | 3 | y21 dicharged | 31.3 | 918.54 | 1127.66 | 35.6 | 2000 |
| 96 | LCIISLLATLPLVVHASPQPLEQIK | 3 | y23 dicharged | 31.3 | 918.54 | 1240.75 | 35.6 | 2000 |
| 97 | LCIISLLATLSLAVHASPQPLEQIK | 3 | y18 dicharged | 31.2 | 905.85 | 952.04 | 35.2 | 2000 |
| 98 | LCIISLLATLSLAVHASPQPLEQIK | 3 | y22 dicharged | 31.3 | 905.85 | 1165.18 | 35.2 | 2000 |
| 99 | LCIISLLATLSLAVHASPQPLEQIK | 3 | y23 dicharged | 31.2 | 905.85 | 1221.72 | 35.2 | 2000 |
| 100 | LCIISLLATMPLAVHASPQPLEQIK | 3 | y18 dicharged | 28.9 | 915.18 | 966.03 | 35.5 | 2000 |
| 101 | LCIISLLATMPLAVHASPQPLEQIK | 3 | y19 dicharged | 28.9 | 916.18 | 1022.57 | 35.5 | 2000 |
| 102 | LCIISLLATMPLAVHASPQPLEQIK | 3 | y23 dicharged | 28.9 | 915.18 | 1235.71 | 35.5 | 2000 |
| 103 | LCIISLLAVLPLAVHASPQPLEQIK | 3 | y17 dicharged | 31 | 908.54 | 920.54 | 35.2 | 2000 |
| 104 | LCIISLLAVLPLAVHASPQPLEQIK | 3 | y22 dicharged | 31.1 | 908.54 | 1169.2 | 35.2 | 2000 |
| 105 | LCIISLLAVLPLAVHASPQPLEQIK | 3 | y23 dicharged | 31.1 | 908.54 | 1225.74 | 35.2 | 2000 |
| 106 | LLISQR | 2 | y3 monocharged | 13.4 | 365.24 | 390.21 | 16.6 | 2000 |
| 107 | LLISQR | 2 | y4 monocharged | 13.4 | 365.24 | 503.29 | 16.6 | 2000 |
| 108 | LLISQR | 2 | y5 monocharged | 13.4 | 365.24 | 616.38 | 16.6 | 2000 |
| 109 | LLLATVGGPAGLTAFLR | 3 | y4 monocharged | 26.9 | 557.34 | 506.31 | 24.4 | 2000 |
| 110 | LLLATVGGPAGLTAFLR | 3 | y5 monocharged | 26.9 | 557.34 | 607.36 | 24.4 | 2000 |
| 111 | LLLATVGGPAGLTAFLR | 2 | y11 monocharged | 26.9 | 835.5 | 1059.6 | 43.4 | 2000 |
| 112 | LLNSQR | 2 | y3 monocharged | 8.4 | 365.71 | 390.21 | 16.6 | 2000 |
| 113 | LLNSQR | 2 | y4 monocharged | 8.4 | 365.71 | 504.25 | 16.6 | 2000 |
| 114 | LLNSQR | 2 | y5 monocharged | 8.4 | 365.71 | 617.34 | 16.6 | 2000 |
| 115 | LLTNQR | 2 | y3 monocharged | 9.3 | 372.72 | 417.22 | 17 | 2000 |
| 116 | LLTNQR | 2 | y4 monocharged | 9.3 | 372.72 | 518.27 | 17 | 2000 |
| 117 | LLTNQR | 2 | y5 monocharged | 9.3 | 372.72 | 631.35 | 17 | 2000 |
| 118 | LLTSQR | 2 | y3 monocharged | 9.5 | 359.22 | 390.21 | 16.2 | 2000 |
| 119 | LLTSQR | 2 | y4 monocharged | 9.5 | 359.22 | 491.26 | 16.2 | 2000 |
| 120 | LLTSQR | 2 | y5 monocharged | 9.5 | 359.22 | 604.34 | 16.2 | 2000 |
| 121 | LNIISLLATLPLAVHASPQPLEQIK | 3 | y17 dicharged | 30.8 | 893.87 | 921.53 | 34.8 | 2000 |
| 122 | LNIISLLATLPLAVHASPQPLEQIK | 3 | y18 dicharged | 30.7 | 893.87 | 957.05 | 34.8 | 2000 |
| 123 | LNIISLLATLPLAVHASPQPLEQIK | 3 | y21 dicharged | 30.8 | 893.87 | 1113.65 | 34.8 | 2000 |
| 124 | LSASSQR | 2 | y4 monocharged | 1.2 | 374.7 | 477.24 | 17.1 | 2000 |

TABLE 47-continued

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 125 | LSASSQR | 2 | y5 monocharged | 1.2 | 374.7 | 548.28 | 17.1 | 2000 |
| 126 | LSASSQR | 2 | y6 monocharged | 1.2 | 374.7 | 635.31 | 17.1 | 2000 |
| 127 | LSESQLSGR | 2 | y8 dicharged | 11.6 | 488.76 | 432.22 | 23.6 | 2000 |
| 128 | LSESQLSGR | 2 | y6 monocharged | 11.6 | 488.76 | 647.35 | 23.6 | 2000 |
| 129 | LSESQLSGR | 2 | y7 monocharged | 11.6 | 488.76 | 776.39 | 23.6 | 2000 |
| 130 | LSESQLSGSVGMIEMDLASGR | 3 | y3 monocharged | 23.7 | 723.02 | 319.17 | 29.5 | 2000 |
| 131 | LSESQLSGSVGMIEMDLASGR | 3 | y4 monocharged | 23.7 | 723.02 | 390.21 | 29.5 | 2000 |
| 132 | LSESQLSGSVGMIEMDLASGR | 3 | y6 monocharged | 23.7 | 723.02 | 618.32 | 29.5 | 3000 |
| 133 | MWIYLR | 2 | y3 monocharged | 19.5 | 447.27 | 451.27 | 21.2 | 3000 |
| 134 | MWIYLR | 2 | y4 monocharged | 19.5 | 447.27 | 564.35 | 21.2 | 3000 |
| 135 | MWIYLR | 2 | y5 monocharged | 19.5 | 447.27 | 663.42 | 21.2 | 2000 |
| 136 | NEALPGDAR | 2 | y5 monocharged | 10.9 | 471.74 | 515.26 | 22.6 | 2000 |
| 137 | NEALPGDAR | 2 | y6 monocharged | 10.9 | 471.74 | 628.34 | 22.6 | 2000 |
| 138 | NEALPGDAR | 2 | y7 monocharged | 10.9 | 471.74 | 699.38 | 22.6 | 2000 |
| 139 | NQHIAGIGAALIEHWQR | 3 | y13 dicharged | 20.1 | 638.68 | 711.39 | 26.9 | 2000 |
| 140 | NQHIAGIGAALIEHWQR | 3 | y14 dicharged | 20.1 | 638.68 | 767.93 | 26.9 | 2000 |
| 141 | NQHIAGIGAALIEHWQR | 3 | y15 dicharged | 20.1 | 638.68 | 836.46 | 26.9 | 2000 |
| 142 | NQQIAGIGAALIEHWQR | 3 | y13 dicharged | 22.3 | 635.67 | 711.39 | 26.8 | 2000 |
| 143 | NQQIAGIGAALIEHWQR | 3 | y14 dicharged | 22.3 | 635.67 | 767.93 | 26.8 | 2000 |
| 144 | NQQIAGIGAALIEHWQR | 3 | y15 dicharged | 22.3 | 635.67 | 831.96 | 26.8 | 2000 |
| 145 | NQQIAGLGAALIEHWQR | 3 | y13 dicharged | 22.7 | 635.67 | 711.39 | 26.8 | 2000 |
| 146 | NQQIAGLGAALIEHWQR | 3 | y14 dicharged | 22.7 | 635.67 | 767.93 | 26.8 | 2000 |
| 147 | NQQIAGLGAALIEHWQR | 3 | y15 dicharged | 22.6 | 635.67 | 831.96 | 26.8 | 2000 |
| 148 | NTTTPASMAATLR | 3 | y4 monocharged | 16 | 445.56 | 460.29 | 20.9 | 2000 |
| 149 | NTTTPASMAATLR | 3 | y5 monocharged | 16 | 445.56 | 531.33 | 20.9 | 2000 |
| 150 | NTTTPASMAATLR | 2 | y9 monocharged | 16 | 667.84 | 917.49 | 33.8 | 2000 |
| 151 | NVLTSQR | 2 | y3 monocharged | 10.2 | 409.23 | 390.21 | 19.1 | 2000 |
| 152 | NVLTSQR | 2 | y4 monocharged | 10.2 | 409.23 | 491.26 | 19.1 | 2000 |
| 153 | NVLTSQR | 2 | y5 monocharged | 10.2 | 409.23 | 504.34 | 19.1 | 2000 |
| 154 | QIDDNVTR | 2 | y4 monocharged | 10 | 480.74 | 489.28 | 23.1 | 2000 |
| 155 | QIDDNVTR | 2 | y5 monocharged | 10 | 480.74 | 504.31 | 23.1 | 2000 |
| 156 | QIDDNVTR | 2 | y6 monocharged | 10 | 480.74 | 719.33 | 23.1 | 2000 |
| 157 | QIGDK | 3 | y4 monocharged | 1.1 | 187.44 | 432.25 | 12.9 | 2000 |
| 158 | QIGDK | 2 | y3 monocharged | 1.1 | 280.66 | 319.16 | 11.7 | 2000 |
| 159 | QIGDK | 2 | y4 monocharged | 1.1 | 280.66 | 432.25 | 11.7 | 2000 |
| 160 | QIGDNVTR | 2 | y3 monocharged | 10.2 | 451.74 | 375.24 | 21.5 | 2000 |
| 161 | QIGDNVTR | 2 | y4 monocharged | 10.2 | 451.74 | 489.28 | 21.5 | 2000 |

TABLE 47-continued

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 162 | QIGDNVTR | 2 | y6 monocharged | 10.2 | 451.74 | 661.33 | 21.5 | 2000 |
| 163 | QIGENVTR | 2 | y3 monocharged | 10.3 | 458.75 | 375.24 | 21.9 | 2000 |
| 164 | QIGENVTR | 2 | y4 monocharged | 10.3 | 458.75 | 489.28 | 21.9 | 2000 |
| 165 | QIGENVTR | 2 | y6 monocharged | 10.3 | 458.75 | 675.34 | 21.9 | 2000 |
| 166 | QLLQWMVDAR | 2 | y5 monocharged | 22.1 | 630.33 | 591.29 | 31.7 | 2000 |
| 167 | QLLQWMVDAR | 2 | y6 monocharged | 22.1 | 630.33 | 777.37 | 31.7 | 2000 |
| 168 | QLLQWMVDAR | 2 | y7 monocharged | 22.1 | 630.33 | 905.43 | 31.7 | 2000 |
| 169 | QLLQWMVDDGVAGPLIR | 3 | y4 monocharged | 25.7 | 637.68 | 498.34 | 26.8 | 2000 |
| 170 | QLLQWMVDDGVAGPLIR | 3 | y5 monocharged | 25.8 | 637.68 | 555.36 | 26.8 | 2000 |
| 171 | QLLQWMVDDGVAGPLIR | 3 | y6 monocharged | 25.7 | 637.68 | 626.4 | 26.8 | 2000 |
| 172 | QLLQWMVDDR | 2 | y4 monocharged | 21.7 | 652.33 | 504.24 | 32.9 | 2000 |
| 173 | QLLQWMVDDR | 2 | y5 monocharged | 21.7 | 652.33 | 635.28 | 32.9 | 2000 |
| 174 | QLLQWMVDDR | 2 | y6 monocharged | 21.7 | 652.33 | 821.36 | 32.9 | 2000 |
| 175 | QLLQWMVDGR | 2 | y4 monocharged | 21.4 | 623.32 | 446.24 | 31.3 | 2000 |
| 176 | QLLQWMVDGR | 2 | y5 monocharged | 21.4 | 623.32 | 577.28 | 31.3 | 2000 |
| 177 | QLLQWMVDGR | 2 | y6 monocharged | 21.4 | 623.32 | 763.36 | 31.3 | 2000 |
| 178 | QLLQWMVEDR | 3 | y4 monocharged | 21.7 | 439.89 | 518.26 | 20.7 | 2000 |
| 179 | QLLQWMVEDR | 2 | y5 monocharged | 21.7 | 659.34 | 649.3 | 33.3 | 2000 |
| 180 | QLLQWMVEDR | 2 | y6 monocharged | 21.7 | 659.34 | 835.38 | 33.3 | 2000 |
| 181 | QQDLVDYSPVSEK | 3 | y5 monocharged | 16 | 503.25 | 559.31 | 22.7 | 2000 |
| 182 | QQDLVDYSPVSEK | 2 | y5 monocharged | 16 | 754.37 | 569.31 | 38.7 | 2000 |
| 183 | QQDLVDYSPVSEK | 2 | y8 monocharged | 16 | 754.37 | 924.43 | 38.7 | 2000 |
| 184 | QQHLVDYSPVSEK | 3 | y6 dicharged | 14.2 | 510.59 | 323.67 | 22.9 | 2000 |
| 185 | QQHLVDYSPVSEK | 3 | y5 monocharged | 14.2 | 510.59 | 559.31 | 22.9 | 2000 |
| 186 | QQHLVDYSPVSEK | 3 | y6 monocharged | 14.3 | 510.59 | 646.34 | 22.9 | 2000 |
| 187 | QSESQLSGR | 2 | y3 monocharged | 7.2 | 496.24 | 319.17 | 24 | 2000 |
| 188 | QSESQLSGR | 2 | y8 dicharged | 7.2 | 496.24 | 432.22 | 24 | 2000 |
| 189 | QSESQLSGR | 2 | y4 monocharged | 7.2 | 496.24 | 432.26 | 24 | 2000 |
| 190 | QSESQLSGSVGMIEMDLASGR | 3 | y3 monocharged | 22.3 | 728.01 | 319.17 | 29.7 | 2000 |
| 191 | QSESQLSGSVGMIEMDLASGR | 3 | y6 monocharged | 22.3 | 728.01 | 618.32 | 29.7 | 2000 |
| 192 | QSESQLSGSVGMIEMDLASGR | 3 | y8 monocharged | 22.3 | 728.01 | 878.4 | 29.7 | 2000 |
| 193 | SQLQLLQWMVDDR | 3 | y4 monocharged | 24.9 | 544.61 | 504.24 | 24 | 2000 |
| 194 | SQLQLLQWMVDDR | 3 | y5 monocharged | 24.9 | 544.61 | 635.28 | 24 | 2000 |
| 195 | SQLQLLQWMVDDR | 3 | y6 monocharged | 24.9 | 544.61 | 821.36 | 24 | 2000 |
| 196 | SVLPAGWFIADK | 2 | y9 dicharged | 23.1 | 652.36 | 502.76 | 32.9 | 2000 |
| 197 | SVLPAGWFIADK | 2 | y10 dicharged | 23.1 | 652.36 | 559.31 | 32.9 | 2000 |
| 198 | SVLPAGWFIADK | 2 | y9 monocharged | 23.1 | 652.36 | 1004.52 | 32.9 | 2000 |
| 199 | SVLPAGWFIADR | 2 | y9 dicharged | 23.4 | 666.36 | 516.77 | 33.7 | 2000 |

TABLE 47-continued

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 200 | SVLPAGWFIADR | 2 | y10 dicharged | 23.4 | 666.36 | 573.31 | 33.7 | 2000 |
| 201 | SVLPAGWFIADR | 2 | y9 monocharged | 23.4 | 666.36 | 1032.53 | 33.7 | 2000 |
| 202 | SVLSAGWFIADK | 2 | y7 monocharged | 22.3 | 647.35 | 836.43 | 32.6 | 2000 |
| 203 | SVLSAGWFIADK | 2 | y8 monocharged | 22.3 | 647.35 | 907.47 | 32.6 | 2000 |
| 204 | SVLSAGWFIADK | 2 | y9 monocharged | 22.3 | 647.35 | 994.5 | 32.6 | 2000 |
| 205 | TGAAER | 2 | y3 monocharged | 1 | 302.66 | 375.2 | 13 | 2000 |
| 206 | TGAAER | 2 | y4 monocharged | 1 | 302.66 | 446.24 | 13 | 2000 |
| 207 | TGAAER | 2 | y5 monocharged | 1 | 302.66 | 503.26 | 13 | 2000 |
| 208 | TGAAK | 2 | y4 dicharged | 0.8 | 224.13 | 173.61 | 8.5 | 2000 |
| 209 | TGAAK | 2 | y3 monocharged | 0.8 | 224.13 | 289.19 | 8.5 | 2000 |
| 210 | TGAAK | 2 | y4 monocharged | 0.8 | 224.13 | 346.21 | 8.5 | 2000 |
| 211 | TGAGER | 2 | y3 monocharged | 1 | 295.65 | 361.18 | 12.6 | 2000 |
| 212 | TGAGER | 2 | y4 monocharged | 1 | 295.65 | 432.22 | 12.6 | 2000 |
| 213 | TGAGER | 2 | y5 monocharged | 1 | 205.65 | 489.24 | 12.6 | 2000 |
| 214 | TGAGK | 3 | y4 monocharged | 0.7 | 145.09 | 332.19 | 11.6 | 2000 |
| 215 | TGAGK | 2 | y3 monocharged | 0.7 | 217.12 | 275.17 | 8.1 | 2000 |
| 216 | TGAGK | 2 | y4 monocharged | 0.7 | 217.12 | 332.19 | 8.1 | 2000 |
| 217 | TGASER | 2 | y3 monocharged | 1 | 310.65 | 391.19 | 13.4 | 2000 |
| 218 | TGASER | 2 | y4 monocharged | 1 | 310.65 | 462.23 | 13.4 | 2000 |
| 219 | TGASER | 2 | y5 monocharged | 1 | 310.65 | 519.25 | 13.4 | 2000 |
| 220 | TGASK | 2 | y4 dicharged | 0.8 | 232.13 | 181.61 | 9 | 2000 |
| 221 | TGASK | 2 | y3 monocharged | 0.8 | 232.13 | 305.18 | 9 | 2000 |
| 222 | TGASK | 2 | y4 monocharged | 0.8 | 232.13 | 362.2 | 9 | 2000 |
| 223 | TGASR | 3 | y4 monocharged | 0.8 | 164.42 | 390.21 | 12.2 | 2000 |
| 224 | TGASR | 2 | y3 monocharged | 0.8 | 246.13 | 333.19 | 9.8 | 2000 |
| 225 | TGASR | 2 | y4 monocharged | 0.8 | 246.13 | 390.21 | 9.8 | 2000 |
| 226 | TLTAWCADER | 2 | y5 monocharged | 15.5 | 611.76 | 650.26 | 30.6 | 5200 |
| 227 | TLTAWCADER | 2 | y6 monocharged | 15.5 | 611.78 | 836.34 | 30.6 | 5200 |
| 228 | TLTAWCADER | 2 | y8 monocharged | 15.5 | 611.78 | 1008.42 | 30.6 | 5200 |
| 229 | TLTAWHADER | 3 | y6 dicharged | 13.1 | 400.53 | 407.19 | 19.5 | 2000 |
| 230 | TLTAWHADER | 3 | y8 dicharged | 13.1 | 400.53 | 493.23 | 19.5 | 2000 |
| 231 | TLTAWHADER | 3 | y5 monocharged | 13.1 | 400.53 | 627.28 | 19.5 | 2000 |
| 232 | TLTAWR | 2 | y3 monocharged | 14.6 | 374.21 | 432.24 | 17.1 | 2000 |
| 233 | TLTAWR | 2 | y4 monocharged | 14.6 | 374.21 | 533.28 | 17.1 | 2000 |
| 234 | TLTAWR | 2 | y5 monocharged | 14.6 | 374.21 | 646.37 | 17.1 | 2000 |
| 235 | TVGGPAGLTAFLR | 2 | y5 monocharged | 22 | 630.36 | 607.36 | 31.7 | 2000 |
| 236 | TVGGPAGLTAFLR | 2 | y7 monocharged | 22 | 630.36 | 777.46 | 31.7 | 2000 |

TABLE 47-continued

| Tran-sition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 237 | TVGGPAGLTAFLR | 2 | y11 monocharged | 22 | 630.36 | 1059.6 | 31.7 | 2000 |
| 238 | TVVIYLR | 2 | y3 monocharged | 17.5 | 432.27 | 451.27 | 20.4 | 2000 |
| 239 | TVVIYLR | 2 | y4 monocharged | 17.5 | 432.27 | 564.35 | 20.4 | 2000 |
| 240 | TVVIYLR | 2 | y5 monocharged | 17.4 | 432.27 | 663.42 | 20.4 | 2000 |
| 241 | VAGPLIR | 2 | y4 monocharged | 13.8 | 363.24 | 498.34 | 16.4 | 2000 |
| 242 | VAGPLIR | 2 | y5 monocharged | 13.8 | 363.24 | 555.36 | 16.4 | 2000 |
| 243 | VAGPLIR | 2 | y6 monocharged | 13.8 | 363.24 | 626.4 | 16.4 | 2000 |
| 244 | VALCGAVLAR | 2 | y8 dicharged | 16.4 | 515.3 | 430.25 | 25.1 | 2000 |
| 245 | VALCGAVLAR | 2 | y6 monocharged | 16.4 | 615.3 | 586.37 | 25.1 | 2000 |
| 246 | VALCGAVLAR | 2 | y7 monocharged | 16.4 | 515.3 | 746.4 | 25.1 | 2000 |
| 247 | VDAGDEQLER | 2 | y5 monocharged | 11 | 566.27 | 674.35 | 28 | 2000 |
| 248 | VDAGDEQLER | 2 | y7 monocharged | 11 | 566.27 | 846.4 | 28 | 2000 |
| 249 | VDAGDEQLER | 2 | y8 monocharged | 11 | 566.27 | 917.43 | 28 | 2000 |
| 250 | VDAGDK | 2 | y3 monocharged | 1 | 302.65 | 319.16 | 13 | 2000 |
| 251 | VDAGDK | 2 | y4 monocharged | 1 | 302.65 | 390.2 | 13 | 2000 |
| 252 | VDAGDK | 2 | y5 monocharged | 1 | 302.65 | 505.23 | 13 | 2000 |
| 253 | VGMIEMDLASGR | 2 | y6 monocharged | 19.3 | 639.81 | 618.32 | 32.2 | 2000 |
| 254 | VGMIEMDLASGR | 2 | y7 monocharged | 19.3 | 639.81 | 749.36 | 32.2 | 2000 |
| 255 | VGMIEMDLASGR | 2 | y8 monocharged | 19.3 | 639.81 | 878.4 | 32.2 | 2000 |
| 256 | VGMIEMDLASR | 2 | y6 monocharged | 19.2 | 611.3 | 692.34 | 30.6 | 2000 |
| 257 | VGMIEMDLASR | 2 | y7 monocharged | 19.2 | 611.3 | 821.38 | 30.6 | 2000 |
| 258 | VGMIEMDLASR | 2 | y8 monocharged | 19.2 | 611.3 | 934.47 | 30.6 | 2000 |
| 259 | VGMIEMDLASSR | 2 | y6 monocharged | 18.8 | 654.82 | 648.33 | 33.1 | 2000 |
| 260 | VGMIEMDLASSR | 2 | y7 monocharged | 18.8 | 654.82 | 779.37 | 33.1 | 2000 |
| 261 | VGMIEMDLASSR | 2 | y8 monocharged | 18.8 | 654.82 | 908.41 | 33.1 | 2000 |
| 262 | VLLCGAVLAR | 2 | y6 monocharged | 18.2 | 536.32 | 586.37 | 26.3 | 5400 |
| 263 | VLLCGAVLAR | 2 | y7 monocharged | 18.3 | 536.32 | 746.4 | 26.3 | 5400 |
| 264 | VLLCGAVLAR | 2 | y8 monocharged | 18.3 | 536.32 | 859.48 | 26.3 | 5400 |
| 265 | VVLCGAMLAR | 2 | y6 monocharged | 17.7 | 545.3 | 618.34 | 26.8 | 2000 |
| 266 | VVLCGAMLAR | 2 | y7 monocharged | 17.7 | 545.3 | 778.37 | 26.8 | 2000 |
| 267 | VVLCGAMLAR | 2 | y8 monocharged | 17.7 | 545.3 | 891.45 | 26.8 | 2000 |
| 268 | VVLCGAVLAR | 2 | y6 monocharged | 17.2 | 529.31 | 586.37 | 25.9 | 2000 |
| 269 | VVLCGAVLAR | 2 | y7 monocharged | 17.2 | 529.31 | 746.4 | 25.9 | 2000 |
| 270 | VVLCGAVLAR | 2 | y8 monocharged | 17.2 | 529.31 | 859.48 | 25.9 | 2000 |
| 271 | VVLCGTVLAR | 2 | y6 monocharged | 16.9 | 544.32 | 616.38 | 26.8 | 2000 |
| 272 | VVLCGTVLAR | 2 | y7 monocharged | 16.9 | 544.32 | 776.41 | 26.8 | 2000 |
| 273 | VVLCGTVLAR | 2 | y8 monocharged | 16.9 | 544.32 | 669.49 | 26.8 | 2000 |
| 274 | WETDR | 3 | y4 monocharged | 8.2 | 236.11 | 520.24 | 14.4 | 2000 |

TABLE 47-continued

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 275 | WETDR | 2 | y3 monocharged | 8.2 | 353.66 | 391.19 | 15.9 | 2000 |
| 276 | WETDR | 2 | y4 monocharged | 8.2 | 353.66 | 520.24 | 15.9 | 2000 |
| 277 | WETELNEAFPGDAR | 3 | y5 monocharged | 19.1 | 545.59 | 515.26 | 24 | 2000 |
| 278 | WETELNEAFPGDAR | 3 | y6 monocharged | 19.1 | 545.59 | 662.33 | 24 | 2000 |
| 279 | WETELNEAFPGDAR | 2 | y5 monocharged | 19.1 | 817.88 | 515.26 | 42.4 | 2000 |
| 280 | WETELNEALPADAR | 3 | y5 monocharged | 18.5 | 538.93 | 529.27 | 23.8 | 2000 |
| 281 | WETELNEALPADAR | 2 | y5 monocharged | 18.5 | 807.89 | 529.27 | 41.8 | 2000 |
| 282 | WETELNEALPADAR | 2 | y7 monocharged | 18.5 | 807.89 | 713.39 | 41.8 | 2000 |
| 283 | WETELNEALPGDAR | 3 | y5 monocharged | 18.2 | 534.26 | 515.26 | 23.6 | 2000 |
| 284 | WETELNEALPGDAR | 2 | y5 monocharged | 18.2 | 500.88 | 515.26 | 41.4 | 2000 |
| 285 | WETELNEALPGDAR | 2 | y7 monocharged | 18.2 | 800.88 | 699.38 | 41.4 | 2000 |
| 286 | WETELNEALSGDAR | 3 | y5 monocharged | 16.9 | 530.92 | 505.24 | 23.5 | 2000 |
| 287 | WETELNEALSGDAR | 3 | y6 monocharged | 18.9 | 530.92 | 618.32 | 23.5 | 2000 |
| 288 | WETELNEALSGDAR | 2 | y5 monocharged | 18.9 | 795.87 | 505.24 | 41.1 | 2000 |
| 289 | WETELNEVLPGDAR | 3 | y5 monocharged | 20.1 | 543.6 | 515.26 | 23.9 | 2000 |
| 290 | WETELNEVLPGDAR | 2 | y5 monocharged | 20.1 | 814.9 | 515.26 | 42.2 | 2000 |
| 291 | WETELNEVLPGDAR | 2 | y6 monocharged | 20.1 | 814.9 | 628.34 | 42.2 | 2000 |
| 292 | WETER | 3 | y4 monocharged | 9 | 240.78 | 534.25 | 14.5 | 2000 |
| 293 | WETER | 2 | y3 monocharged | 8.9 | 360.67 | 405.21 | 16.3 | 2000 |
| 294 | WETER | 2 | y4 monocharged | 8.9 | 360.67 | 534.25 | 16.3 | 2000 |

The other machine parameters used are as follows:
Scan type: MRM
MRM planned: yes
Polarity: Positive
Ionising source: Turbo V™ (Applied BioSystems)
Q1 setting: Filtering with unit resolution
Q3 setting: Filtering with unit resolution
Inter-scan pause: 5.00 msec
Scanning speed: 10 Da/s
Curtain gas: 50.00 psi
Cone voltage: 5500.00 V
Source temperature: 500.00° C.
Nebulising gas: 50.00 psi
Heating gas: 50.00 psi
Collision gas which induces dissociation: 9.00 psi
Dynamic filling: activated
Declustering potential (DP): 100.00 V
Entry potential before Q0 (EP): 6.00 V
Collision cell exit potential (CXP): 15 V
Total cycle time: 1 sec
Detection window: 120 sec The areas obtained for each of the transitions and for each of the microorganisms studied were measured. When the areas of the transitions are greater than or equal to the positivity threshold described in TABLE 47, the detection of the transition is considered to be positive and is labelled "1" in TABLE 48. When a transition has an area less than the positivity threshold described in TABLE 47, the transition is considered non-detected and is labelled "0" in TABLE 48.

For a given peptide, when at least 3 transitions are labelled "1", the peptide is considered as being detected.

TABLE 48

| transition number | Sam131 | Sam132 | Sam133 | Sam134 | Sam135 | Sam136 | Sam137 | Sam138 | Sam139 | Sam140 | Sam141 | Sam142 | Sam143 | Sam144 |
|---|---|---|---|---|---|---|---|---|---|---|---|---|---|---|
| 1 | 0 | 0 | 0 | 0 | 0 | 0 | 0 | 0 | 0 | 0 | 0 | 0 | 0 | 0 |
| 2 | 0 | 0 | 0 | 0 | 0 | 0 | 0 | 0 | 1 | 0 | 0 | 0 | 1 | 0 |
| 3 | 0 | 0 | 0 | 0 | 0 | 0 | 0 | 0 | 0 | 0 | 0 | 0 | 1 | 0 |
| 4 | 0 | 0 | 0 | 0 | 0 | 0 | 0 | 0 | 0 | 0 | 0 | 0 | 0 | 0 |
| 5 | 0 | 0 | 0 | 0 | 0 | 0 | 0 | 0 | 0 | 0 | 0 | 0 | 0 | 0 |
| 6 | 0 | 0 | 0 | 0 | 0 | 0 | 0 | 0 | 0 | 0 | 0 | 0 | 0 | 0 |

TABLE 48-continued

| transition number | Sam131 | Sam132 | Sam133 | Sam134 | Sam135 | Sam136 | Sam137 | Sam138 | Sam139 | Sam140 | Sam141 | Sam142 | Sam143 | Sam144 |
|---|---|---|---|---|---|---|---|---|---|---|---|---|---|---|
| 7 | 0 | 0 | 0 | 0 | 0 | 0 | 0 | 0 | 0 | 0 | 0 | 0 | 0 | 0 |
| 8 | 0 | 0 | 0 | 0 | 0 | 0 | 0 | 0 | 0 | 0 | 0 | 0 | 0 | 0 |
| 9 | 0 | 0 | 0 | 0 | 0 | 0 | 0 | 0 | 0 | 0 | 0 | 0 | 0 | 0 |
| 10 | 0 | 0 | 0 | 0 | 0 | 0 | 0 | 0 | 0 | 0 | 0 | 0 | 0 | 0 |
| 11 | 0 | 0 | 0 | 0 | 1 | 0 | 0 | 0 | 0 | 0 | 0 | 0 | 0 | 0 |
| 12 | 0 | 0 | 0 | 0 | 1 | 0 | 0 | 0 | 0 | 0 | 0 | 0 | 0 | 0 |
| 13 | 0 | 0 | 0 | 0 | 0 | 0 | 0 | 0 | 0 | 0 | 0 | 0 | 0 | 0 |
| 14 | 0 | 0 | 0 | 0 | 0 | 0 | 0 | 1 | 0 | 0 | 0 | 0 | 1 | 0 |
| 15 | 0 | 0 | 0 | 0 | 0 | 0 | 0 | 0 | 0 | 0 | 0 | 0 | 0 | 0 |
| 16 | 0 | 0 | 0 | 0 | 0 | 0 | 0 | 0 | 0 | 0 | 0 | 0 | 0 | 0 |
| 17 | 1 | 0 | 0 | 0 | 0 | 1 | 1 | 1 | 1 | 1 | 1 | 1 | 1 | 1 |
| 18 | 0 | 0 | 0 | 0 | 0 | 0 | 0 | 0 | 0 | 0 | 0 | 0 | 0 | 0 |
| 19 | 1 | 0 | 0 | 0 | 1 | 1 | 1 | 1 | 1 | 0 | 0 | 1 | 1 | 1 |
| 20 | 1 | 0 | 0 | 0 | 1 | 1 | 1 | 0 | 1 | 0 | 0 | 1 | 1 | 1 |
| 21 | 1 | 0 | 1 | 0 | 1 | 1 | 1 | 0 | 1 | 0 | 0 | 1 | 1 | 0 |
| 22 | 0 | 0 | 0 | 0 | 0 | 0 | 0 | 0 | 0 | 0 | 0 | 0 | 0 | 0 |
| 23 | 0 | 0 | 0 | 0 | 0 | 0 | 0 | 0 | 0 | 0 | 0 | 0 | 0 | 0 |
| 24 | 0 | 0 | 0 | 0 | 0 | 0 | 0 | 0 | 0 | 0 | 0 | 0 | 0 | 0 |
| 25 | 1 | 1 | 1 | 0 | 1 | 1 | 1 | 0 | 1 | 0 | 1 | 1 | 1 | 0 |
| 26 | 1 | 1 | 1 | 0 | 1 | 1 | 1 | 0 | 1 | 1 | 1 | 1 | 1 | 0 |
| 27 | 0 | 1 | 1 | 0 | 1 | 1 | 1 | 0 | 1 | 0 | 1 | 1 | 1 | 0 |
| 28 | 0 | 0 | 0 | 0 | 0 | 0 | 0 | 0 | 0 | 0 | 0 | 0 | 0 | 0 |
| 29 | 0 | 0 | 0 | 0 | 0 | 0 | 0 | 0 | 0 | 0 | 0 | 0 | 0 | 0 |
| 30 | 0 | 0 | 0 | 0 | 0 | 0 | 0 | 0 | 0 | 0 | 0 | 0 | 0 | 0 |
| 31 | 0 | 0 | 0 | 0 | 0 | 1 | 0 | 0 | 0 | 0 | 0 | 0 | 0 | 0 |
| 32 | 0 | 0 | 0 | 0 | 0 | 0 | 0 | 0 | 0 | 0 | 0 | 0 | 0 | 0 |
| 33 | 0 | 0 | 0 | 0 | 0 | 0 | 0 | 0 | 0 | 0 | 0 | 0 | 0 | 0 |
| 34 | 0 | 0 | 0 | 0 | 0 | 0 | 0 | 0 | 0 | 0 | 0 | 0 | 0 | 0 |
| 35 | 0 | 0 | 0 | 0 | 0 | 0 | 0 | 0 | 0 | 0 | 0 | 0 | 0 | 0 |
| 36 | 0 | 0 | 0 | 0 | 0 | 0 | 0 | 0 | 0 | 0 | 0 | 0 | 0 | 0 |
| 37 | 0 | 0 | 0 | 0 | 0 | 0 | 0 | 0 | 0 | 0 | 0 | 0 | 0 | 0 |
| 38 | 0 | 0 | 0 | 0 | 1 | 0 | 0 | 1 | 0 | 0 | 0 | 0 | 1 | 0 |
| 39 | 0 | 0 | 0 | 0 | 0 | 0 | 0 | 0 | 0 | 0 | 0 | 0 | 0 | 0 |
| 40 | 0 | 0 | 0 | 0 | 0 | 0 | 0 | 0 | 0 | 0 | 0 | 0 | 0 | 0 |
| 41 | 0 | 0 | 0 | 0 | 0 | 0 | 0 | 0 | 0 | 0 | 0 | 0 | 0 | 0 |
| 42 | 0 | 0 | 0 | 0 | 0 | 0 | 0 | 0 | 0 | 0 | 0 | 0 | 0 | 0 |
| 43 | 0 | 0 | 0 | 0 | 1 | 1 | 1 | 0 | 1 | 0 | 0 | 1 | 1 | 0 |
| 44 | 0 | 0 | 0 | 0 | 1 | 1 | 1 | 0 | 1 | 0 | 0 | 1 | 1 | 0 |
| 45 | 0 | 0 | 1 | 1 | 1 | 1 | 1 | 0 | 0 | 0 | 0 | 1 | 1 | 0 |
| 46 | 0 | 0 | 0 | 0 | 0 | 0 | 0 | 0 | 0 | 0 | 0 | 0 | 0 | 0 |
| 47 | 0 | 0 | 0 | 0 | 0 | 0 | 0 | 0 | 0 | 0 | 0 | 0 | 0 | 0 |
| 48 | 0 | 0 | 0 | 0 | 0 | 0 | 0 | 0 | 0 | 0 | 0 | 0 | 0 | 0 |
| 49 | 1 | 1 | 1 | 1 | 1 | 1 | 1 | 1 | 1 | 1 | 1 | 1 | 1 | 1 |
| 50 | 1 | 1 | 1 | 1 | 1 | 1 | 1 | 1 | 1 | 1 | 1 | 1 | 1 | 1 |
| 51 | 1 | 1 | 1 | 1 | 1 | 1 | 1 | 1 | 1 | 1 | 1 | 1 | 1 | 1 |
| 52 | 1 | 0 | 0 | 0 | 0 | 0 | 0 | 0 | 0 | 0 | 0 | 0 | 0 | 0 |
| 53 | 0 | 0 | 0 | 0 | 0 | 0 | 0 | 0 | 0 | 0 | 0 | 0 | 0 | 0 |
| 54 | 1 | 0 | 0 | 0 | 0 | 0 | 0 | 0 | 0 | 0 | 0 | 0 | 0 | 0 |
| 55 | 1 | 1 | 1 | 1 | 1 | 1 | 1 | 1 | 1 | 1 | 1 | 1 | 1 | 1 |
| 56 | 1 | 1 | 1 | 1 | 1 | 1 | 1 | 1 | 1 | 1 | 1 | 1 | 1 | 1 |
| 57 | 1 | 1 | 1 | 1 | 1 | 1 | 1 | 1 | 1 | 1 | 1 | 1 | 1 | 1 |
| 58 | 0 | 0 | 0 | 0 | 0 | 0 | 0 | 0 | 0 | 0 | 0 | 0 | 0 | 0 |
| 59 | 0 | 0 | 0 | 0 | 0 | 0 | 0 | 0 | 0 | 0 | 0 | 0 | 0 | 0 |
| 60 | 0 | 0 | 0 | 0 | 0 | 0 | 0 | 0 | 0 | 0 | 0 | 0 | 0 | 0 |
| 61 | 0 | 0 | 0 | 0 | 0 | 0 | 0 | 0 | 0 | 0 | 0 | 0 | 0 | 0 |
| 62 | 0 | 0 | 0 | 0 | 0 | 0 | 0 | 0 | 0 | 0 | 0 | 0 | 0 | 0 |
| 63 | 0 | 0 | 0 | 0 | 0 | 0 | 0 | 0 | 0 | 0 | 0 | 0 | 0 | 0 |
| 64 | 0 | 0 | 0 | 0 | 0 | 0 | 0 | 0 | 0 | 0 | 0 | 0 | 0 | 0 |
| 65 | 0 | 0 | 0 | 0 | 0 | 0 | 0 | 0 | 0 | 0 | 0 | 0 | 0 | 0 |
| 66 | 0 | 0 | 0 | 0 | 0 | 0 | 0 | 0 | 0 | 0 | 0 | 0 | 0 | 0 |
| 67 | 0 | 0 | 0 | 0 | 0 | 0 | 0 | 0 | 0 | 0 | 0 | 0 | 0 | 0 |
| 68 | 0 | 0 | 0 | 0 | 1 | 0 | 0 | 0 | 0 | 0 | 0 | 0 | 0 | 0 |
| 69 | 0 | 0 | 0 | 0 | 0 | 0 | 0 | 0 | 0 | 0 | 0 | 0 | 0 | 0 |
| 70 | 0 | 0 | 0 | 0 | 0 | 0 | 0 | 0 | 0 | 0 | 0 | 0 | 0 | 0 |
| 71 | 0 | 0 | 0 | 0 | 0 | 0 | 0 | 0 | 1 | 0 | 0 | 0 | 0 | 0 |
| 72 | 0 | 0 | 0 | 0 | 0 | 0 | 0 | 0 | 0 | 0 | 0 | 0 | 0 | 0 |
| 73 | 0 | 0 | 0 | 0 | 0 | 0 | 0 | 0 | 1 | 0 | 0 | 0 | 0 | 0 |
| 74 | 0 | 0 | 0 | 0 | 0 | 0 | 0 | 0 | 0 | 0 | 0 | 0 | 0 | 0 |
| 75 | 0 | 0 | 0 | 0 | 0 | 0 | 0 | 0 | 0 | 0 | 0 | 0 | 0 | 0 |
| 76 | 0 | 0 | 0 | 0 | 0 | 0 | 0 | 0 | 0 | 0 | 0 | 0 | 0 | 0 |
| 77 | 0 | 0 | 0 | 0 | 0 | 0 | 0 | 0 | 0 | 0 | 0 | 0 | 0 | 0 |
| 78 | 0 | 0 | 0 | 0 | 0 | 0 | 0 | 0 | 0 | 0 | 0 | 0 | 0 | 0 |
| 79 | 0 | 0 | 0 | 0 | 0 | 0 | 0 | 0 | 0 | 0 | 0 | 0 | 0 | 0 |
| 80 | 0 | 0 | 0 | 0 | 0 | 0 | 0 | 0 | 0 | 0 | 0 | 0 | 0 | 0 |
| 81 | 0 | 0 | 0 | 0 | 0 | 0 | 0 | 0 | 0 | 0 | 0 | 0 | 0 | 0 |
| 82 | 0 | 0 | 0 | 0 | 0 | 0 | 0 | 0 | 0 | 0 | 0 | 0 | 0 | 0 |
| 83 | 0 | 0 | 0 | 0 | 0 | 0 | 0 | 0 | 0 | 0 | 0 | 0 | 0 | 0 |

TABLE 48-continued

| transition number | Sam131 | Sam132 | Sam133 | Sam134 | Sam135 | Sam136 | Sam137 | Sam138 | Sam139 | Sam140 | Sam141 | Sam142 | Sam143 | Sam144 |
|---|---|---|---|---|---|---|---|---|---|---|---|---|---|---|
| 84 | 0 | 0 | 0 | 0 | 0 | 0 | 0 | 0 | 0 | 0 | 0 | 0 | 0 | 0 |
| 85 | 0 | 0 | 0 | 0 | 0 | 0 | 0 | 0 | 0 | 0 | 0 | 0 | 0 | 0 |
| 86 | 0 | 0 | 0 | 0 | 0 | 0 | 0 | 0 | 0 | 0 | 0 | 0 | 0 | 0 |
| 87 | 0 | 0 | 0 | 0 | 0 | 0 | 0 | 0 | 0 | 0 | 0 | 0 | 0 | 0 |
| 88 | 0 | 0 | 0 | 0 | 0 | 0 | 0 | 0 | 0 | 0 | 0 | 0 | 0 | 0 |
| 89 | 0 | 0 | 0 | 0 | 0 | 0 | 0 | 0 | 0 | 0 | 0 | 0 | 0 | 0 |
| 90 | 0 | 0 | 0 | 0 | 0 | 0 | 0 | 0 | 0 | 0 | 0 | 0 | 0 | 0 |
| 91 | 0 | 0 | 0 | 0 | 0 | 0 | 0 | 0 | 0 | 0 | 0 | 0 | 0 | 0 |
| 92 | 0 | 0 | 0 | 0 | 0 | 0 | 0 | 0 | 0 | 0 | 0 | 0 | 0 | 0 |
| 93 | 0 | 0 | 0 | 0 | 0 | 0 | 0 | 0 | 0 | 0 | 0 | 0 | 0 | 0 |
| 94 | 0 | 0 | 0 | 0 | 0 | 0 | 0 | 0 | 0 | 0 | 0 | 0 | 0 | 0 |
| 95 | 0 | 0 | 0 | 0 | 0 | 0 | 0 | 0 | 0 | 0 | 0 | 0 | 0 | 0 |
| 96 | 0 | 0 | 0 | 0 | 0 | 0 | 0 | 0 | 0 | 0 | 0 | 0 | 0 | 0 |
| 97 | 0 | 0 | 0 | 0 | 0 | 0 | 0 | 0 | 0 | 0 | 0 | 0 | 0 | 0 |
| 98 | 0 | 0 | 0 | 0 | 0 | 0 | 0 | 0 | 0 | 0 | 0 | 0 | 0 | 0 |
| 99 | 0 | 0 | 0 | 0 | 0 | 0 | 0 | 0 | 0 | 0 | 0 | 0 | 0 | 0 |
| 100 | 0 | 0 | 0 | 0 | 0 | 0 | 0 | 0 | 0 | 0 | 0 | 0 | 0 | 0 |
| 101 | 0 | 0 | 0 | 0 | 0 | 0 | 0 | 0 | 0 | 0 | 0 | 0 | 0 | 0 |
| 102 | 0 | 0 | 0 | 0 | 0 | 0 | 0 | 0 | 0 | 0 | 0 | 0 | 0 | 0 |
| 103 | 0 | 0 | 0 | 0 | 0 | 0 | 0 | 0 | 0 | 0 | 0 | 0 | 0 | 0 |
| 104 | 0 | 0 | 0 | 0 | 0 | 0 | 0 | 0 | 0 | 0 | 0 | 0 | 0 | 0 |
| 105 | 0 | 0 | 0 | 0 | 0 | 0 | 0 | 0 | 0 | 0 | 0 | 0 | 0 | 0 |
| 106 | 0 | 0 | 0 | 0 | 0 | 0 | 0 | 0 | 0 | 0 | 1 | 0 | 0 | 0 |
| 107 | 0 | 0 | 0 | 0 | 0 | 0 | 0 | 0 | 0 | 0 | 0 | 0 | 0 | 0 |
| 108 | 0 | 0 | 0 | 0 | 0 | 0 | 0 | 0 | 0 | 0 | 0 | 0 | 0 | 0 |
| 109 | 0 | 0 | 0 | 0 | 0 | 0 | 0 | 0 | 0 | 0 | 0 | 0 | 0 | 0 |
| 110 | 0 | 0 | 0 | 0 | 0 | 0 | 0 | 0 | 0 | 0 | 0 | 0 | 0 | 0 |
| 111 | 0 | 0 | 0 | 0 | 0 | 0 | 0 | 0 | 0 | 0 | 0 | 0 | 0 | 0 |
| 112 | 0 | 0 | 0 | 0 | 0 | 0 | 0 | 0 | 0 | 0 | 0 | 1 | 1 | 1 | 0 |
| 113 | 0 | 0 | 0 | 0 | 0 | 0 | 0 | 0 | 0 | 0 | 0 | 1 | 0 | 0 |
| 114 | 0 | 0 | 0 | 0 | 0 | 0 | 0 | 0 | 0 | 0 | 0 | 0 | 0 | 0 |
| 115 | 0 | 0 | 0 | 0 | 0 | 0 | 0 | 0 | 0 | 0 | 0 | 0 | 0 | 0 |
| 116 | 0 | 0 | 0 | 0 | 0 | 0 | 0 | 0 | 0 | 0 | 0 | 0 | 0 | 0 |
| 117 | 1 | 0 | 0 | 0 | 0 | 0 | 0 | 0 | 0 | 0 | 0 | 0 | 0 | 0 |
| 118 | 0 | 1 | 1 | 1 | 0 | 0 | 0 | 0 | 0 | 0 | 0 | 1 | 0 | 0 |
| 119 | 0 | 0 | 0 | 0 | 0 | 0 | 0 | 0 | 0 | 0 | 0 | 1 | 0 | 0 |
| 120 | 0 | 0 | 0 | 0 | 0 | 0 | 0 | 0 | 0 | 0 | 0 | 1 | 0 | 0 |
| 121 | 0 | 0 | 0 | 0 | 0 | 0 | 0 | 0 | 0 | 0 | 0 | 0 | 0 | 0 |
| 122 | 0 | 0 | 0 | 0 | 0 | 0 | 0 | 0 | 0 | 0 | 0 | 0 | 0 | 0 |
| 123 | 0 | 0 | 0 | 0 | 0 | 0 | 0 | 0 | 0 | 0 | 0 | 0 | 0 | 0 |
| 124 | 0 | 0 | 0 | 0 | 0 | 0 | 0 | 1 | 0 | 0 | 0 | 0 | 0 | 0 |
| 125 | 0 | 0 | 0 | 0 | 0 | 0 | 0 | 1 | 0 | 0 | 0 | 0 | 1 | 0 |
| 126 | 0 | 0 | 0 | 0 | 0 | 0 | 0 | 1 | 0 | 0 | 0 | 0 | 0 | 0 |
| 127 | 1 | 0 | 0 | 0 | 1 | 0 | 0 | 0 | 0 | 0 | 0 | 1 | 1 | 0 |
| 128 | 1 | 0 | 0 | 0 | 1 | 0 | 0 | 0 | 0 | 0 | 0 | 1 | 1 | 0 |
| 129 | 1 | 0 | 0 | 0 | 1 | 0 | 0 | 0 | 0 | 0 | 0 | 1 | 1 | 0 |
| 130 | 0 | 0 | 0 | 0 | 0 | 0 | 0 | 0 | 0 | 0 | 0 | 0 | 0 | 0 |
| 131 | 0 | 0 | 0 | 0 | 0 | 0 | 0 | 0 | 0 | 0 | 0 | 0 | 0 | 0 |
| 132 | 0 | 0 | 1 | 0 | 0 | 0 | 0 | 0 | 0 | 0 | 0 | 0 | 0 | 0 |
| 133 | 0 | 0 | 0 | 1 | 0 | 0 | 1 | 0 | 0 | 0 | 0 | 0 | 0 | 0 |
| 134 | 0 | 1 | 0 | 0 | 0 | 0 | 0 | 0 | 0 | 0 | 1 | 1 | 0 | 1 |
| 135 | 0 | 0 | 0 | 1 | 0 | 0 | 1 | 0 | 1 | 1 | 1 | 1 | 1 | 1 |
| 136 | 0 | 0 | 0 | 0 | 0 | 0 | 0 | 0 | 0 | 0 | 0 | 0 | 0 | 0 |
| 137 | 0 | 0 | 0 | 0 | 0 | 0 | 0 | 0 | 0 | 0 | 0 | 0 | 0 | 0 |
| 138 | 1 | 0 | 0 | 0 | 1 | 1 | 1 | 0 | 1 | 1 | 1 | 1 | 1 | 1 |
| 139 | 0 | 0 | 0 | 0 | 0 | 1 | 0 | 0 | 0 | 0 | 0 | 0 | 0 | 0 |
| 140 | 0 | 0 | 0 | 0 | 0 | 1 | 1 | 1 | 1 | 1 | 1 | 1 | 0 | 1 |
| 141 | 0 | 0 | 0 | 0 | 0 | 0 | 0 | 0 | 0 | 0 | 0 | 0 | 0 | 0 |
| 142 | 0 | 1 | 1 | 1 | 1 | 1 | 1 | 0 | 1 | 1 | 1 | 1 | 1 | 0 |
| 143 | 0 | 1 | 1 | 1 | 1 | 1 | 1 | 0 | 1 | 1 | 1 | 1 | 1 | 0 |
| 144 | 0 | 1 | 1 | 1 | 1 | 1 | 1 | 0 | 1 | 1 | 1 | 1 | 1 | 0 |
| 145 | 0 | 1 | 1 | 1 | 1 | 1 | 1 | 1 | 1 | 1 | 1 | 1 | 1 | 1 |
| 146 | 0 | 1 | 1 | 1 | 1 | 1 | 1 | 1 | 1 | 1 | 1 | 1 | 1 | 1 |
| 147 | 0 | 1 | 1 | 1 | 1 | 1 | 1 | 1 | 1 | 1 | 1 | 1 | 1 | 1 |
| 148 | 0 | 0 | 0 | 0 | 0 | 0 | 0 | 0 | 0 | 0 | 0 | 1 | 0 | 0 |
| 149 | 1 | 1 | 1 | 1 | 1 | 1 | 1 | 1 | 1 | 1 | 1 | 1 | 0 | 1 |
| 150 | 0 | 0 | 0 | 0 | 0 | 0 | 0 | 0 | 0 | 0 | 0 | 1 | 0 | 0 |
| 151 | 0 | 0 | 0 | 0 | 0 | 0 | 0 | 0 | 0 | 0 | 0 | 0 | 0 | 1 |
| 152 | 0 | 0 | 0 | 0 | 0 | 1 | 0 | 0 | 0 | 0 | 0 | 0 | 0 | 1 |
| 153 | 0 | 0 | 0 | 0 | 0 | 0 | 0 | 0 | 0 | 0 | 0 | 0 | 0 | 1 |
| 154 | 0 | 0 | 0 | 0 | 0 | 0 | 0 | 0 | 0 | 0 | 0 | 0 | 0 | 0 |
| 155 | 0 | 0 | 0 | 0 | 0 | 0 | 0 | 0 | 0 | 0 | 0 | 0 | 0 | 0 |
| 156 | 0 | 0 | 0 | 0 | 0 | 0 | 0 | 0 | 0 | 0 | 0 | 0 | 0 | 0 |
| 157 | 0 | 0 | 0 | 0 | 0 | 0 | 0 | 0 | 0 | 0 | 0 | 0 | 0 | 0 |
| 158 | 0 | 0 | 0 | 0 | 0 | 0 | 0 | 0 | 1 | 0 | 0 | 0 | 1 | 0 |
| 159 | 0 | 0 | 0 | 0 | 0 | 0 | 0 | 0 | 1 | 0 | 0 | 0 | 1 | 0 |
| 160 | 1 | 0 | 0 | 0 | 1 | 1 | 1 | 0 | 1 | 0 | 0 | 1 | 1 | 0 |

TABLE 48-continued

| transition number | Sam131 | Sam132 | Sam133 | Sam134 | Sam135 | Sam136 | Sam137 | Sam138 | Sam139 | Sam140 | Sam141 | Sam142 | Sam143 | Sam144 |
|---|---|---|---|---|---|---|---|---|---|---|---|---|---|---|
| 161 | 1 | 1 | 1 | 0 | 1 | 1 | 1 | 1 | 1 | 0 | 0 | 1 | 1 | 0 |
| 162 | 0 | 0 | 0 | 0 | 1 | 1 | 1 | 0 | 0 | 0 | 0 | 1 | 1 | 0 |
| 163 | 0 | 0 | 0 | 0 | 1 | 0 | 0 | 0 | 0 | 0 | 0 | 0 | 0 | 0 |
| 164 | 0 | 0 | 0 | 0 | 0 | 0 | 0 | 0 | 0 | 0 | 0 | 0 | 0 | 0 |
| 165 | 1 | 0 | 0 | 0 | 0 | 0 | 0 | 0 | 0 | 0 | 0 | 0 | 0 | 0 |
| 166 | 0 | 0 | 0 | 0 | 0 | 0 | 0 | 0 | 0 | 0 | 0 | 0 | 0 | 0 |
| 167 | 0 | 0 | 0 | 0 | 0 | 0 | 0 | 0 | 0 | 0 | 0 | 0 | 0 | 0 |
| 168 | 0 | 0 | 0 | 0 | 0 | 0 | 0 | 0 | 0 | 0 | 0 | 0 | 0 | 0 |
| 169 | 0 | 0 | 0 | 0 | 0 | 0 | 0 | 0 | 0 | 0 | 0 | 0 | 0 | 0 |
| 170 | 0 | 0 | 0 | 0 | 0 | 0 | 0 | 0 | 0 | 0 | 0 | 0 | 0 | 0 |
| 171 | 0 | 0 | 0 | 0 | 0 | 0 | 0 | 0 | 0 | 0 | 0 | 0 | 0 | 0 |
| 172 | 0 | 0 | 0 | 0 | 0 | 0 | 0 | 1 | 0 | 0 | 0 | 0 | 0 | 0 |
| 173 | 0 | 0 | 0 | 0 | 0 | 0 | 0 | 0 | 1 | 0 | 0 | 0 | 0 | 0 |
| 174 | 0 | 0 | 0 | 0 | 0 | 1 | 0 | 0 | 1 | 0 | 1 | 0 | 0 | 1 |
| 175 | 0 | 0 | 0 | 0 | 0 | 0 | 0 | 0 | 0 | 0 | 0 | 0 | 0 | 0 |
| 176 | 0 | 0 | 1 | 0 | 0 | 0 | 0 | 0 | 0 | 0 | 0 | 0 | 0 | 0 |
| 177 | 0 | 0 | 0 | 0 | 0 | 0 | 0 | 0 | 0 | 0 | 0 | 0 | 0 | 0 |
| 178 | 0 | 0 | 0 | 0 | 0 | 0 | 0 | 0 | 0 | 0 | 0 | 0 | 0 | 0 |
| 179 | 0 | 0 | 0 | 0 | 0 | 0 | 0 | 0 | 0 | 0 | 0 | 0 | 0 | 0 |
| 180 | 0 | 0 | 0 | 0 | 0 | 0 | 0 | 0 | 0 | 0 | 0 | 0 | 0 | 0 |
| 181 | 0 | 0 | 0 | 0 | 0 | 0 | 1 | 0 | 0 | 0 | 0 | 1 | 1 | 0 |
| 182 | 1 | 0 | 0 | 0 | 1 | 1 | 1 | 0 | 1 | 0 | 0 | 1 | 1 | 0 |
| 183 | 0 | 0 | 0 | 0 | 1 | 1 | 1 | 0 | 0 | 0 | 0 | 1 | 1 | 0 |
| 184 | 0 | 0 | 0 | 0 | 0 | 0 | 0 | 0 | 0 | 0 | 0 | 0 | 0 | 0 |
| 185 | 0 | 0 | 0 | 0 | 0 | 0 | 0 | 0 | 0 | 0 | 0 | 0 | 0 | 0 |
| 186 | 0 | 0 | 0 | 0 | 0 | 0 | 0 | 0 | 0 | 0 | 0 | 0 | 0 | 0 |
| 187 | 0 | 0 | 0 | 0 | 0 | 0 | 0 | 0 | 0 | 0 | 0 | 0 | 0 | 0 |
| 188 | 0 | 0 | 0 | 0 | 0 | 0 | 0 | 0 | 0 | 0 | 0 | 0 | 0 | 0 |
| 189 | 0 | 0 | 0 | 0 | 0 | 0 | 0 | 0 | 0 | 0 | 0 | 0 | 0 | 0 |
| 190 | 0 | 0 | 0 | 0 | 0 | 0 | 0 | 0 | 0 | 0 | 0 | 0 | 0 | 0 |
| 191 | 0 | 0 | 0 | 0 | 0 | 0 | 0 | 0 | 0 | 0 | 0 | 0 | 0 | 0 |
| 192 | 0 | 0 | 0 | 0 | 0 | 0 | 0 | 0 | 0 | 0 | 0 | 0 | 0 | 0 |
| 193 | 0 | 0 | 0 | 0 | 0 | 0 | 0 | 0 | 0 | 0 | 0 | 0 | 0 | 0 |
| 194 | 0 | 0 | 0 | 0 | 0 | 0 | 0 | 0 | 0 | 0 | 0 | 0 | 0 | 0 |
| 195 | 0 | 0 | 0 | 0 | 0 | 0 | 0 | 0 | 0 | 0 | 0 | 0 | 0 | 0 |
| 196 | 0 | 0 | 0 | 0 | 0 | 0 | 0 | 0 | 0 | 0 | 0 | 0 | 0 | 0 |
| 197 | 0 | 0 | 0 | 0 | 0 | 0 | 0 | 0 | 0 | 0 | 0 | 0 | 0 | 0 |
| 198 | 0 | 0 | 0 | 0 | 0 | 0 | 0 | 0 | 0 | 0 | 0 | 0 | 0 | 0 |
| 199 | 0 | 0 | 0 | 0 | 0 | 0 | 0 | 0 | 0 | 0 | 0 | 0 | 0 | 0 |
| 200 | 0 | 0 | 0 | 0 | 0 | 0 | 0 | 0 | 0 | 0 | 0 | 0 | 0 | 0 |
| 201 | 0 | 0 | 0 | 0 | 0 | 0 | 0 | 0 | 0 | 0 | 0 | 0 | 0 | 0 |
| 202 | 0 | 0 | 0 | 0 | 0 | 0 | 0 | 0 | 0 | 0 | 0 | 0 | 0 | 0 |
| 203 | 0 | 0 | 0 | 0 | 0 | 0 | 0 | 0 | 0 | 0 | 0 | 0 | 0 | 0 |
| 204 | 0 | 0 | 0 | 0 | 0 | 0 | 0 | 0 | 0 | 0 | 0 | 0 | 0 | 0 |
| 205 | 1 | 1 | 1 | 1 | 1 | 0 | 1 | 1 | 0 | 0 | 0 | 0 | 0 | 0 |
| 206 | 1 | 1 | 1 | 1 | 1 | 0 | 1 | 1 | 0 | 1 | 1 | 1 | 0 | 0 |
| 207 | 1 | 1 | 1 | 1 | 1 | 1 | 0 | 1 | 0 | 1 | 1 | 1 | 0 | 1 |
| 208 | 0 | 0 | 0 | 0 | 0 | 0 | 0 | 0 | 0 | 0 | 0 | 0 | 0 | 0 |
| 209 | 0 | 0 | 0 | 0 | 0 | 0 | 0 | 0 | 0 | 0 | 0 | 0 | 0 | 0 |
| 210 | 0 | 0 | 0 | 0 | 0 | 0 | 0 | 0 | 0 | 0 | 0 | 0 | 0 | 0 |
| 211 | 0 | 0 | 0 | 0 | 0 | 0 | 0 | 0 | 0 | 0 | 0 | 0 | 0 | 0 |
| 212 | 0 | 0 | 0 | 0 | 0 | 0 | 0 | 0 | 0 | 0 | 0 | 0 | 1 | 0 |
| 213 | 0 | 0 | 0 | 0 | 0 | 0 | 0 | 0 | 1 | 0 | 0 | 0 | 1 | 0 |
| 214 | 0 | 0 | 0 | 0 | 0 | 0 | 0 | 0 | 0 | 0 | 0 | 0 | 0 | 0 |
| 215 | 0 | 0 | 0 | 0 | 0 | 0 | 0 | 0 | 0 | 0 | 0 | 0 | 0 | 0 |
| 216 | 0 | 0 | 0 | 0 | 0 | 0 | 0 | 0 | 0 | 0 | 0 | 0 | 0 | 0 |
| 217 | 0 | 0 | 0 | 0 | 0 | 0 | 0 | 0 | 0 | 0 | 0 | 0 | 1 | 0 |
| 218 | 0 | 1 | 0 | 0 | 0 | 1 | 0 | 0 | 0 | 0 | 1 | 1 | 0 | 0 |
| 219 | 0 | 0 | 1 | 1 | 0 | 0 | 0 | 0 | 0 | 0 | 0 | 0 | 0 | 0 |
| 220 | 0 | 0 | 0 | 0 | 0 | 0 | 0 | 0 | 0 | 0 | 0 | 0 | 0 | 0 |
| 221 | 0 | 0 | 0 | 0 | 0 | 0 | 0 | 0 | 0 | 0 | 0 | 0 | 0 | 0 |
| 222 | 0 | 0 | 0 | 0 | 0 | 0 | 0 | 0 | 0 | 0 | 0 | 0 | 0 | 0 |
| 223 | 0 | 0 | 0 | 0 | 0 | 0 | 0 | 0 | 0 | 0 | 0 | 0 | 0 | 0 |
| 224 | 0 | 0 | 0 | 0 | 0 | 0 | 0 | 0 | 0 | 0 | 0 | 0 | 0 | 0 |
| 225 | 0 | 0 | 0 | 0 | 0 | 0 | 0 | 0 | 0 | 0 | 0 | 0 | 0 | 0 |
| 226 | 1 | 0 | 0 | 0 | 0 | 0 | 1 | 1 | 0 | 0 | 0 | 0 | 0 | 0 |
| 227 | 0 | 0 | 0 | 0 | 0 | 0 | 0 | 0 | 0 | 0 | 0 | 0 | 0 | 0 |
| 228 | 1 | 0 | 0 | 0 | 0 | 0 | 1 | 0 | 0 | 0 | 1 | 0 | 0 | 0 |
| 229 | 0 | 0 | 0 | 0 | 0 | 0 | 0 | 0 | 0 | 0 | 0 | 0 | 0 | 0 |
| 230 | 0 | 0 | 0 | 0 | 0 | 0 | 0 | 0 | 0 | 0 | 0 | 0 | 0 | 0 |
| 231 | 0 | 0 | 0 | 0 | 0 | 0 | 0 | 0 | 0 | 0 | 0 | 0 | 0 | 0 |
| 232 | 0 | 0 | 1 | 0 | 1 | 1 | 1 | 0 | 0 | 0 | 0 | 1 | 1 | 0 |
| 233 | 0 | 0 | 1 | 0 | 1 | 1 | 1 | 0 | 0 | 0 | 0 | 1 | 1 | 0 |
| 234 | 0 | 0 | 0 | 0 | 1 | 1 | 1 | 0 | 0 | 0 | 0 | 1 | 1 | 0 |
| 235 | 0 | 0 | 0 | 0 | 0 | 0 | 0 | 0 | 0 | 0 | 0 | 0 | 0 | 0 |
| 236 | 0 | 0 | 0 | 0 | 0 | 0 | 0 | 0 | 0 | 0 | 0 | 0 | 0 | 0 |
| 237 | 0 | 0 | 0 | 0 | 0 | 0 | 0 | 0 | 0 | 0 | 0 | 0 | 0 | 0 |

TABLE 48-continued

| transition number | Sam131 | Sam132 | Sam133 | Sam134 | Sam135 | Sam136 | Sam137 | Sam138 | Sam139 | Sam140 | Sam141 | Sam142 | Sam143 | Sam144 |
|---|---|---|---|---|---|---|---|---|---|---|---|---|---|---|
| 238 | 0 | 0 | 0 | 0 | 0 | 0 | 0 | 0 | 0 | 0 | 0 | 0 | 0 | 0 |
| 239 | 0 | 0 | 0 | 0 | 0 | 0 | 0 | 0 | 0 | 0 | 0 | 0 | 0 | 0 |
| 240 | 0 | 0 | 0 | 0 | 0 | 0 | 0 | 0 | 0 | 0 | 0 | 0 | 0 | 0 |
| 241 | 1 | 1 | 1 | 1 | 1 | 1 | 1 | 1 | 1 | 1 | 1 | 1 | 1 | 1 |
| 242 | 1 | 1 | 1 | 1 | 1 | 1 | 1 | 0 | 1 | 0 | 1 | 1 | 1 | 1 |
| 243 | 1 | 1 | 1 | 1 | 1 | 1 | 1 | 0 | 1 | 0 | 1 | 1 | 1 | 1 |
| 244 | 0 | 0 | 0 | 0 | 0 | 0 | 0 | 0 | 1 | 0 | 0 | 0 | 0 | 0 |
| 245 | 0 | 0 | 0 | 0 | 1 | 0 | 0 | 0 | 0 | 0 | 0 | 0 | 0 | 0 |
| 246 | 0 | 0 | 0 | 0 | 0 | 0 | 0 | 0 | 0 | 0 | 0 | 0 | 0 | 0 |
| 247 | 1 | 0 | 1 | 0 | 1 | 1 | 1 | 0 | 1 | 0 | 1 | 1 | 1 | 0 |
| 248 | 1 | 1 | 1 | 1 | 1 | 1 | 1 | 1 | 1 | 1 | 1 | 1 | 1 | 1 |
| 249 | 1 | 1 | 1 | 1 | 1 | 1 | 1 | 0 | 1 | 1 | 1 | 1 | 1 | 1 |
| 250 | 0 | 0 | 0 | 0 | 0 | 0 | 0 | 0 | 0 | 0 | 0 | 0 | 0 | 0 |
| 251 | 0 | 1 | 1 | 1 | 0 | 0 | 0 | 0 | 0 | 0 | 0 | 0 | 0 | 0 |
| 252 | 0 | 0 | 0 | 0 | 0 | 0 | 0 | 0 | 0 | 0 | 0 | 0 | 0 | 0 |
| 253 | 0 | 0 | 0 | 0 | 1 | 0 | 1 | 0 | 1 | 0 | 0 | 1 | 1 | 0 |
| 254 | 0 | 0 | 0 | 0 | 1 | 0 | 1 | 0 | 1 | 0 | 0 | 1 | 1 | 0 |
| 255 | 0 | 0 | 0 | 0 | 1 | 0 | 1 | 0 | 1 | 0 | 0 | 1 | 1 | 0 |
| 256 | 0 | 0 | 0 | 0 | 0 | 0 | 0 | 0 | 0 | 0 | 0 | 0 | 0 | 0 |
| 257 | 0 | 0 | 0 | 0 | 0 | 0 | 0 | 0 | 0 | 0 | 0 | 0 | 0 | 0 |
| 258 | 0 | 0 | 0 | 0 | 0 | 0 | 0 | 0 | 0 | 0 | 0 | 0 | 0 | 0 |
| 259 | 0 | 0 | 0 | 0 | 0 | 0 | 0 | 0 | 0 | 0 | 0 | 0 | 0 | 0 |
| 260 | 0 | 0 | 0 | 0 | 0 | 0 | 0 | 0 | 0 | 0 | 0 | 0 | 0 | 0 |
| 261 | 0 | 0 | 0 | 0 | 0 | 0 | 0 | 0 | 0 | 0 | 0 | 0 | 0 | 0 |
| 262 | 0 | 0 | 0 | 0 | 0 | 0 | 0 | 0 | 0 | 0 | 0 | 1 | 1 | 0 |
| 263 | 0 | 0 | 0 | 0 | 0 | 0 | 0 | 0 | 0 | 0 | 1 | 0 | 1 | 0 |
| 264 | 0 | 0 | 0 | 0 | 0 | 0 | 0 | 0 | 0 | 0 | 0 | 1 | 0 | 0 |
| 265 | 0 | 0 | 0 | 0 | 0 | 0 | 0 | 0 | 0 | 0 | 0 | 0 | 0 | 0 |
| 266 | 0 | 0 | 0 | 0 | 0 | 0 | 0 | 0 | 0 | 0 | 0 | 0 | 0 | 0 |
| 267 | 0 | 0 | 0 | 0 | 0 | 1 | 0 | 0 | 0 | 0 | 0 | 0 | 0 | 0 |
| 268 | 0 | 0 | 0 | 0 | 0 | 0 | 0 | 0 | 0 | 0 | 0 | 0 | 0 | 0 |
| 269 | 0 | 0 | 0 | 0 | 0 | 0 | 0 | 0 | 0 | 0 | 0 | 0 | 0 | 0 |
| 270 | 0 | 0 | 0 | 0 | 0 | 0 | 0 | 0 | 0 | 0 | 0 | 0 | 0 | 0 |
| 271 | 0 | 0 | 0 | 0 | 0 | 0 | 0 | 0 | 0 | 0 | 0 | 0 | 0 | 0 |
| 272 | 0 | 0 | 0 | 0 | 0 | 0 | 0 | 0 | 0 | 1 | 0 | 0 | 0 | 0 |
| 273 | 0 | 0 | 0 | 0 | 0 | 0 | 0 | 0 | 1 | 0 | 0 | 0 | 0 | 0 |
| 274 | 0 | 0 | 0 | 0 | 0 | 0 | 0 | 0 | 0 | 0 | 0 | 0 | 0 | 0 |
| 275 | 0 | 0 | 0 | 0 | 0 | 0 | 0 | 0 | 0 | 0 | 0 | 0 | 0 | 0 |
| 276 | 0 | 0 | 0 | 0 | 0 | 0 | 0 | 0 | 0 | 0 | 0 | 0 | 0 | 0 |
| 277 | 0 | 0 | 0 | 0 | 0 | 0 | 0 | 0 | 0 | 0 | 0 | 0 | 0 | 0 |
| 278 | 0 | 0 | 0 | 0 | 0 | 0 | 0 | 0 | 0 | 0 | 0 | 0 | 0 | 0 |
| 279 | 0 | 0 | 0 | 0 | 0 | 0 | 0 | 0 | 0 | 0 | 0 | 0 | 0 | 0 |
| 280 | 0 | 0 | 0 | 0 | 1 | 0 | 0 | 0 | 0 | 0 | 0 | 0 | 0 | 0 |
| 281 | 0 | 0 | 0 | 0 | 0 | 0 | 0 | 0 | 0 | 0 | 0 | 0 | 0 | 0 |
| 282 | 0 | 0 | 0 | 0 | 1 | 0 | 0 | 0 | 0 | 0 | 0 | 0 | 0 | 0 |
| 283 | 0 | 0 | 0 | 0 | 1 | 1 | 1 | 0 | 0 | 0 | 0 | 1 | 1 | 0 |
| 284 | 0 | 1 | 1 | 0 | 0 | 1 | 1 | 0 | 0 | 0 | 0 | 1 | 1 | 0 |
| 285 | 0 | 0 | 0 | 0 | 0 | 1 | 1 | 0 | 0 | 0 | 0 | 1 | 1 | 0 |
| 286 | 0 | 0 | 0 | 0 | 0 | 0 | 0 | 0 | 0 | 0 | 0 | 0 | 0 | 0 |
| 287 | 0 | 0 | 0 | 0 | 0 | 0 | 0 | 0 | 0 | 0 | 0 | 0 | 0 | 0 |
| 288 | 0 | 0 | 0 | 0 | 0 | 0 | 0 | 0 | 0 | 0 | 0 | 0 | 0 | 0 |
| 289 | 0 | 0 | 0 | 0 | 0 | 0 | 0 | 0 | 0 | 0 | 0 | 0 | 0 | 0 |
| 290 | 0 | 0 | 0 | 0 | 0 | 0 | 0 | 0 | 0 | 0 | 0 | 0 | 0 | 0 |
| 291 | 0 | 0 | 0 | 0 | 0 | 0 | 0 | 0 | 0 | 0 | 0 | 0 | 0 | 0 |
| 292 | 0 | 0 | 0 | 0 | 0 | 0 | 0 | 0 | 0 | 0 | 0 | 0 | 0 | 0 |
| 293 | 0 | 0 | 0 | 0 | 0 | 0 | 0 | 0 | 0 | 0 | 0 | 0 | 0 | 0 |
| 294 | 0 | 0 | 0 | 0 | 0 | 0 | 0 | 0 | 0 | 0 | 0 | 0 | 0 | 0 |

Samples Sam131 to Sam144 comprise at least one peptide which is characteristic of the SHV proteins. The bacteria present in samples Sam131 to Sam144 therefore express a beta-lactamase which confers on them a resistance to penicillins.

Sample Sam142 comprises a peptide specific to phenotype 2be. Therefore sample Sam142 is resistant to penicillins, to cephalosporins and to monobactams.

No peptide specific to phenotypes 2b and 2br is observed, no sample tested is identified as belonging only to these phenotypes.

The detection methods described in examples 6 to 30 are particularly advantageous because they make it possible to assay a large number of peptides and at the same time to detect the presence of one or more resistance mechanisms induced by one or more beta-lactamases.

Furthermore, the detection is performed in a short time, less than one hour. In fact, only the part of the gradient between 3 and 34 minutes is useful to the analysis. Furthermore, the retention times of the assayed peptides are all below 34 minutes.

In addition, the detection methods described in examples 6 to 30 are more advantageous than the molecular biology methods because they detect the product of the expression of the genes, and not the genes themselves. The detection of a resistance may not have any clinical meaning if this gene is not expressed, or it if is expressed too weakly to lead to an effective resistance. The detection of a peptide characterising a protein characteristic of a resistance mechanism does not have this disadvantage.

Surprisingly, the above examples show that it is possible to attain by mass spectrometry the sensitivity necessary for the specific detection of the existence of a mechanism of resistance to at least one antimicrobial of a microorganism contained in a sample, without employing an amplification method as is usually the case when molecular biology methods are used.

BIBLIOGRAPHIC REFERENCES

[1] J. Anhalt & C. Fenselau, 1975, Anal. Chem., 47(2):219-225.
[2] A. Fox et al., ed., 1990, Analytical microbiology methods: chromatography and mass spectrometry, Plenum Press, New York, N.Y.
[3] M. Claydon et al., 1996, Nature Biotech. 14:1584-1586.
[4] T. Krishnamurthy & P. Ross, 1996, Rapid Com. Mass Spec., 10:1992-1996.
[5] P. Seng et al. 2009, Clin. Infect. Dis., 49:543-551.
[6] C. Fenselau et al., 2008, Appl. Environ. Microbiol., 904-906.
[7] S. Hofstadler et al., 2005, Int. J Mass Spectrom., 242: 23-41.
[8] D. Ecker, 2008, Nat. Rev. Microbiol., 6(7):553-558.
[9] Bush and Jacoby, 2010, Antimicrobial Agents and Chemotherapy; 54 (3): 969-976
[10] W.-J. Chen et al., 2008, Anal. Chem., 80: 9612-9621
[11] D. Lopez-Ferrer et al., 2008, Anal. Chem., 80:8930-8936
[12] D. Lopez-Ferrer et al., 2005, J. Proteome res., 4(5): 1569-1574
[13] T. Fortin et al., 2009, Mol. Cell Proteomics, 8(5): 1006-1015.
[14] H. Keshishian et al., 2007, Mol. Cell Proteomics, 2212-2229.
[15] J. Stal-Zeng et al., 2007, Mol. Cell Proteomics, 1809-1817.
[16] Gaskell, Electrospray: principles and practise, 1997, J. Mass Spectrom., 32, 677-688).
[17] V. Fusaro et al., 2009, Nature Biotech. 27, 190-198.
[18] J. Mead et al., 15 Nov. 2008, Mol. Cell Proteomics, E-pub.
[19] F. Desiere et al., 2006, Nucleic Acids Res., 34 (database issue): D655-8).
[20] L. Anderson & C. Hunter, 2006, Mol. Cell Proteomics, 573-588).
[21] B. Han & R. Higgs, 2008, Brief Funct Genomic Proteomic., 7(5):340-54).
[22] K.-Y. Wang et al., 2008, Anal. Chem, 80(16) 6159-6167).
[23] J. Bundy & C. Fenselau, 1999, Anal. Chem. 71: 1460-1463.
[24] K-C Ho et al., 2004, Anal. Chem. 76: 7162-7268.
[25] Y. S. Lin et al., 2005, Anal. Chem., 77: 1753-1760.
[26] S. Vaidyanathan et al., 2001, Anal. Chem., 73:4134-4144.
[27] R. Everley et al., 2009, J. Microbiol. Methods, 77:152-158.
[28] P. Seng et al., 2009, Clin. Infect. Dis., 49:543-551.
[29] Manes N. et al., 2007, Mol. & Cell. Proteomics, 6(4): 717-727.
[30] R. Nandakumar et al., 2009, Oral Microbiology Immunology, 24:347-352).
[31] L. Hernychova et al., 2008, Anal. Chem., 80:7097-7104.
[32] J.-M. Pratt et al., 2006, Nat. Protoc., 1:1029-1043.
[33] V. Brun et al., 2007, Mol. Cell Proteomics, 2139-2149.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09506932B2). An electronic copy of the "Sequence Listing" will also be available from the USPTO upon request and payment of the fee set forth in 37 CFR 1.19(b)(3).

The invention claimed is:

1. A method of detecting a CTX-M protein in a sample from a microorganism, the method comprising:
    subjecting the sample to MRM mass spectrometry and detecting whether one or more CTX-M fragments selected from the group consisting of in SEQ ID NOS: 446-478, 480-495, 2009-2013, 2015, 2017, 2019, 2021-2027, 2029, 2030, 2032, 2034-2039, 2042-2051, 2054, 2055, 2057-2063, 2065-2067, 2069-2074, 2076-2078, and 2081-2092 is present, wherein detection of any of the CTX-M fragments by the MRM mass spectrometry indicates the presence of CTX-M protein in the sample.

2. The detection method according to claim 1, further comprising, before performing mass spectrometry, digesting proteins to produce peptides in the sample.

3. The detection method according to claim 2, wherein the digestion is performed by an enzyme.

4. The detection method according to claim 3, wherein the enzyme is trypsin.

5. The detection method according to claim 1, wherein the one or more CTX-M fragments is selected from the group consisting of SEQ ID NOS: 446, 451, 454, 458, 460-464, 467, 468, 470, 471, 474, 480, 484, 485, 489, and 491.

* * * * *